(12) United States Patent
Subramanyam et al.

(10) Patent No.: US 9,764,040 B2
(45) Date of Patent: *Sep. 19, 2017

(54) SPLICEOSTATIN ANALOGS AND METHODS FOR THEIR PREPARATION

(71) Applicant: PFIZER INC., New York, NY (US)

(72) Inventors: Chakrapani Subramanyam, South Glastonbury, CT (US); Frank Erich Koehn, Mystic, CT (US); Kenneth John Dirico, Gales Ferry, CT (US); Alessandra S. Eustaquio, Old Saybrook, CT (US); Michael Eric Green, Boston, MA (US); Haiyin He, Mahwah, NJ (US); Min He, North Potomac, MD (US); Christopher John O'Donnell, Mystic, CT (US); Sujiet Puthenveetil, North Attleboro, MA (US); Anokha Ratnayake, Mystic, CT (US); Jesse Alexander Teske, Westerly, RI (US); Hui Yu Yang, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/280,563

(22) Filed: Sep. 29, 2016

(65) Prior Publication Data

US 2017/0014523 A1 Jan. 19, 2017

Related U.S. Application Data

(60) Continuation of application No. 14/818,455, filed on Aug. 5, 2015, now Pat. No. 9,504,669, which is a division of application No. 14/069,057, filed on Oct. 31, 2013, now Pat. No. 9,169,264.

(60) Provisional application No. 61/829,409, filed on May 31, 2013, provisional application No. 61/723,645, filed on Nov. 7, 2012, provisional application No. 61/722,769, filed on Nov. 5, 2012.

(51) Int. Cl.
| | |
|---|---|
| *A61K 38/00* | (2006.01) |
| *A61K 47/48* | (2006.01) |
| *C07D 309/10* | (2006.01) |
| *C07D 405/12* | (2006.01) |
| *C07D 493/20* | (2006.01) |
| *A61K 45/06* | (2006.01) |
| *C07D 309/14* | (2006.01) |
| *C07D 405/14* | (2006.01) |
| *C07D 493/10* | (2006.01) |
| *A61K 31/351* | (2006.01) |
| *A61K 31/397* | (2006.01) |
| *A61K 31/453* | (2006.01) |
| *A61K 31/496* | (2006.01) |
| *A61K 31/501* | (2006.01) |
| *A61K 31/35* | (2006.01) |
| *A61K 31/4025* | (2006.01) |

(52) U.S. Cl.
CPC ........ *A61K 47/48384* (2013.01); *A61K 31/35* (2013.01); *A61K 31/351* (2013.01); *A61K 31/397* (2013.01); *A61K 31/4025* (2013.01); *A61K 31/453* (2013.01); *A61K 31/496* (2013.01); *A61K 31/501* (2013.01); *A61K 45/06* (2013.01); *A61K 47/48584* (2013.01); *A61K 47/48638* (2013.01); *A61K 47/48715* (2013.01); *C07D 309/10* (2013.01); *C07D 309/14* (2013.01); *C07D 405/12* (2013.01); *C07D 405/14* (2013.01); *C07D 493/10* (2013.01); *C07D 493/20* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,225,539 A | 7/1993 | Winter | |
| 5,545,806 A | 8/1996 | Lonberg et al. | |
| 5,569,825 A | 10/1996 | Lonberg et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 2006/0205670 A1 | 9/2006 | Bradshaw et al. | |

FOREIGN PATENT DOCUMENTS

| | | |
|---|---|---|
| EP | 0 012 023 | 6/1980 |
| EP | 0 171 496 | 2/1986 |
| EP | 0 173 494 | 3/1986 |
| EP | 0 184 187 | 6/1986 |
| EP | 0 404 097 | 12/1990 |
| WO | WO 86/01533 | 3/1986 |
| WO | WO 87/02671 | 5/1987 |
| WO | WO 93/11161 | 6/1993 |

(Continued)

OTHER PUBLICATIONS

Beidler, C., et al., "Cloning and High Level Expression of a Chimeric Antibody With Specificity for Human Carcinoembryonic Antigen", Journal of Immunology, 1988, vol. 141:4053-4060.

(Continued)

*Primary Examiner* — Jeanette Lieb
(74) *Attorney, Agent, or Firm* — David Rubin

(57) ABSTRACT

The present invention is directed to novel cytotoxic spliceostatin analogs and derivatives, to antibody drug conjugates thereof, and to methods for using the same to treat medical conditions including cancer.

2 Claims, 4 Drawing Sheets

(56) References Cited

FOREIGN PATENT DOCUMENTS

| WO | WO 97/34631 | 9/1997 |
|---|---|---|
| WO | WO 2011/106491 | 9/2011 |
| WO | WO 2012/049882 | 4/2012 |
| WO | WO 2013/068946 | 5/2013 |

OTHER PUBLICATIONS

Better, M., et al., "*Escherichia coli* Secretion of an Active Chimeric Antibody Fragment," Science, 1988, vol. 240:1041-1043.
Challis G., "Genome Mining for Novel natural Product Discovery," Journal of Medicinal Chemistry, 2008, vol. 51:2618-2628.
Chothia, C. et al. "Canonical Structures for the Hypervariable Regions of Immunoglobulins," Journal of Molecular Biology, 1987, vol. 196:901-917.
Datsenko, K., et al., "One-step inactivation of chromosomal genes in *Escherichia coli* K-12 using PCR products," Proceedings of the National Academy of Sciences of the United States of America, vol. 97:6640-6645.
Fan, L, et. al., "Sudemycins, Novel Small Molecule Analogues of FR901464, Induce Alternative Gene Splicing", ACS Chemical Biology, Jun. 17, 2011, vol. 6:582-589.
Furumai, R., et. al., "Spliceostatin A blocks angiogenesis by inhibiting gloabl gene expression including VEGF", Cancer Anger Science, Nov. 23, 2010, vol. 101:2483-2489.
Goodson, J., "Dental Applications," Medical Applications of Controlled Release, supra, 1984, vol. 2:115-138.
Hoang, T., et al., "A broad-hot-range Flp-FRT recombination system for site-specific excision of chromosomally-located DNA sequences: application for isolation of unmarked Pseudomonas aeruginosa mutants," Gene 1998, vol. 212:77-86.
Hoang, T., et al., "Integration-Proficient Plasmids for Pseudomonas aeruginosa: Site-Specific Integration and Use for Engineering of reporter and Expression Strains," Plasmid, 2000, vol. 43:59-72.
Holliger, P., et al., ""Diabodies": Small bivalent and bispecific antibody fragments," Proc. Natl. Acad. Sci., 1993, vol. 90:6444-64480
Hoogenboom, H., el al., "By-passing Immunisation Human Antibodies from Synthetic Repertoires of Germline VH Gene Segments Rearranged in Vitro," Journal of Molecular Biology, 1991, vol. 227:381-388.
International Search Report dated Apr. 7, 2014 for Intentional Application No. PCT/IB2013/059553, published as WO2014/068443.
Jespers, L., et al., "Guiding the Selection of Human Antibodies from Phage Display Repertoires to a Single Epitope of an Antigen," Bio/technology. 1994, vol. 12:899-903.
Jones, P., et al., "Replacing the complementarity-determining regions in a human antibody with those from a mouse," Letters to Nature, 1986, vol. 321:522-525.
Kabat E., "Origins of Antibody Complementarity and Specificity-Hypervariable Regions and the Minigen Hypothesis 1,2," The Journal of Immunology, 1980, vol. 125(3):961-969.
Kaida, D., et al., "U1 snRNP protexts pre-mRNAs from premature cleavage and polyadenylation," Nature, 2010, vol. 468:664-668.
Kaida, D., et. al., "Spliceostatin a targets 3F3b and inhibits both splicing and nuclear retention of pre-mRNA," Nature Chemical Biology, 2007, vol. 3(9):576-583.
Kozbor, D., et al., "The production of monocolonal antibodies from human lymphocytes," Immunology Today, 1983, vol. 4:72-79.
Langer, R., "New Methods of Drug Delivery," Science, 1990, vol. 249:1527-1533.
Liu A., et. al., "Chimeric mouse-human IgG1 antibody that can mediate lysis of cancer cells," Proc. Natl. Acad. Sci., 1987, vol. 84:3439-3443.
Liu A., et.al. "Production of a Mouse-Human Chimeric Monoclonal Antibody to CD20 With Potent Fc-Dependent Biologic Activity,"The Journal of Immunology, 1987, vol. 139:3521-3526.
Lonberg, N., et al., "Human Antibodies from Transgenic Mice," Intern. Rev. Immunol., 1995, vol. 13:65-93.
Marks, J., et al., "Human Antibodies from V-gene Libraries Displayed on Phage," Journal of Molecular Biology, 1991, vol. 222:581-597.
Morrison, S., "Transfectomas Provide Novel Chimeric Antibodies," Science, 1985, vol. 229:1202-1207.
Nakajima, H., et al., "Activities against Experimental Tumors in Mice and Mechanism of Action," The Journal of Antibiotics, 1996, vol. 49(12):1204-1211.
Nishimura, Y., et. al., "Recombinant Human-Mouse Chimeric Monoclonal Antibody Specific for Common Acute Lymphocytic Leukemia Antigen," Cancer Research, 1987, vol. 47:999-1005.
Oi, V.T., et. al., "Chimeric Antibodies," BioTechniques, 1986, vol. 4:214-221.
Olsson, L., et. al., "Human-Human Monoclonal Antibody-Producing Hybridomas: Technical Aspects," et al., Methods in Enzymology, 1983, vol. 92:3-16.
Osman, S., et. al., "Evaluation of FR901464 analogues in vitro and in vivo", MEDCHEMCOMM, Jan. 1, 2011, vol. 2:38.
Piel, J., "Biosynthesis of polyketides by trans-AT polyketide synthases," Natural Product Reports, 2010, vol. 27:996-1047.
Plückthun, A., "Antibodies from *Escherichia coli*," The Pharmacology of Monocolona Antibodies, 1994, vol. 113:269-315.
Presta, L., "Antibody engineering," Current Opinion in Structural Biology, 1992, vol. 2:593-596.
Quan, M. et. al., "The Rise of Antibodies as Therapeutics," n Anti-IgE and Allergic Disease, 2002, Chapter 20, pp. 427-469.
Riechmann, L. et. al., "Reshaping human antibodies for therapy," Nature, 1988, vol. 332:323-329.
Schroder, et. al., "The Peptides—Formation of the Peptide Bond," Academic Press, 1965, vol. 1:76-136.
Schweizer, H., "An improved system for gene replacement and xylE fusion analysis in Pseudomonas aeruginosa," Gene, 1995, vol. 158(1):15-22.
Shaw, D., et. al., "Mouse/Human Chimeric Antibodies to a Tumopr-Associated Antigen: Biologic Activity of the Four Human IgG Subclasses," J. Natl. Cancer Inst. , 1988, vol. 80:1553-1559.
Sun, L., et al., "Chimerica antibody with human constant regions and mouse variable regions directed against carcinoma-associated antigen 17-1A," Proceedings of the National Acadmeny of Sciens of the United States of America, 1987, vol. 84:214-218.
Teng, N., et. al., "Construction and testing of mouse-human heteromyelomas for human monoclonal antibody production," Proc. Natl. Acad. Sci., 1983, vol. 80:7308-7312.
Thompson C., et al. "FR901464: Total synthesis, proof of structure, and evaluation of synthetic analogues", Journal of the American Chemical Society, Jan. 2, 2001, vol. 123: 9974-9983.
Verhoeyen, M., et. al., "Reshaping Human Antibodies: Grafting an Antilysozyme Activity," Science, 1988, vol. 239:1534-1536.
Wood, C., et. al., "The synthesis and in vivo assembly of functional antibodies in yeast," Letters to Nature, 1985, vol. 314:446-449.
Mang, F., et al., "Cloning and Elucidation of FR901464 Gene cluster Revealing a Complex Acyltransferase-less Polyketide Synthase Using Glycerate as Starter Unites," 2011, Journal of the American Chemical Society, 2011, vol. 133(8):2452-2462.

PKS Domain Key
A. adenylation. C. condensation. CR. crotonase. DH. dehydratase. ER. enoyl reductase. FMO. flavin-dependent monooxygenase. GT.P. gylceryl transferase phosphatase. KR. ketoreductase. KS. ketosynthase. T. thiolation. TE. thioesterase. X. KS lacks active site cysteine.

SPLICEOSTATIN ANALOGS AND METHODS FOR THEIR PREPARATION

CROSS-REFERENCE TO RELATED APPLICATIONS

This application is a continuation application of U.S. Non-provisional application Ser. No. 14/818,455 filed on Aug. 5, 2015 which is a divisional application of U.S. Non-provisional Ser. No. 14/069,057 filed on Oct. 31, 2013, now U.S. Pat. No. 9,169,264, which claims the benefit of U.S. Provisional Application Nos. 61/829,409 filed May 31, 2013, 61/723,645 filed Nov. 7, 2012 and 61/722,769 filed Nov. 5, 2012, all of which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC71885A_SEQLISTING_ST25.txt" created on Oct. 8, 2013 and having a size of 10 KB. The sequence listing contained in this .txt file is part of the specification and is herein incorporated by reference in its entirety.

FIELD OF THE INVENTION

The present invention is directed to novel natural product-derived and/or spliceostin-based compounds useful as payloads in antibody-drug-conjugates (ADCs), and payload-linker compounds useful in connection with ADCs. The present invention further relates to compositions including the aforementioned payloads, payload-linkers and ADCs, and methods for using these payloads, payload-linkers and ADCs, to treat pathological conditions including cancer.

BACKGROUND

Conjugation of drugs to antibodies, either directly or via linkers, involves a consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

While a number of different drug classes have been tried for delivery via antibodies, only a few drug classes have proved efficacious as antibody drug conjugates, while having a suitable toxicity profile.

Natural products FR901463, FR901464, and FR901465 were reported to have potent inhibitory activities against human cancer cell lines and efficacies in several xenograft tumor models. (Journal of Antibiotics (1996), 49(12), 1204-1211.) The natural product FR901464 and its methyl ketal, designated spliceostatin A, were recently reported to inhibit the spliceosome by interaction with SF3b, which is a component of the essential subcomplex, U2 snRNA. (Nature Chemical Biology (2007), 3(9), 576-583; Nature (London, United Kingdom) (2010), 468(7324), 664-668.)

SUMMARY OF THE INVENTION

The present invention relates to compounds and pharmaceutical compositions containing them, to their preparation and to uses for the compounds, primarily but not exclusively anti-cancer agents.

According to one aspect, the present invention relates to a compound or compounds of formula (I):

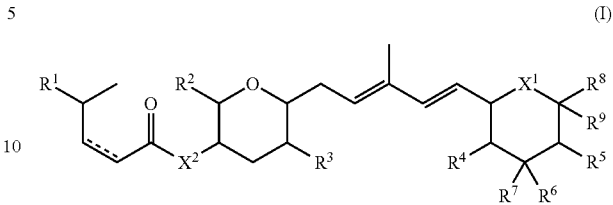

(I)

wherein:
a dashed line represents an optional bond;
each $X^1$ is independently selected from the group consisting of: —O—, —S— and —NR—;
each $X^2$ is independently selected from the group consisting of: —O—, —S— and —NR—;
$R^1$ is selected from the group consisting of: —R, —OR, —OCOR$^{13}$, —OCONR$^{14}$R$^{15}$, —OCON(R$^{14}$)NR(R$^{15}$), =O (double bond to oxygen) and —NR$^{14}$R$^{15}$;
$R^2$ and $R^3$ are independently selected from the group consisting of: hydrogen and $C_{1-6}$alkyl;
$R^4$ and $R^5$ are independently selected from the group consisting of: hydrogen, —OR, —NR$^{14}$R$^{15}$ and oxo;
$R^6$ and $R^7$ are independently selected from the group consisting of: hydrogen, halogen, hydroxyl and $C_{1-6}$alkyl optionally substituted with 1-3 substituents independently selected from hydroxyl and halogen,
$R^6$ and $R^7$, together with the carbon atom to which they are bound, form a $C_{2-5}$alkylidene optionally substituted with 1-3 substituents independently selected from R,
$R^6$ and $R^7$ together are oxo, or
$R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;
$R^8$ is hydrogen, $C_{1-6}$alkyl or —OR;
$R^9$ is independently selected from hydrogen, —$C_{1-6}$alkyl, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)—SR, —(C(R)$_2$)$_m$—C(O)NR$^{14}$N(R)R$^{15}$, —(C(R)$_2$)$_m$—NR—C(O)—NR$^{14}$R$^{15}$, —(C(R)$_2$)$_m$—N(R)COR$^{13}$ and —(C(R)$_2$)$_m$—NR$^{14}$N(R)R$^{15}$;
$R^{13}$ is selected from the group consisting of hydrogen, $C_{1-6}$alkyl, $C_{3-8}$carbocyclyl, $C_{3-8}$heterocyclyl, $C_{1-6}$alkyl-$C_{6-14}$aryl, $C_{1-6}$alkyl-$C_{5-14}$heteroaryl, wherein $R^{13}$ is optionally substituted with —NRR or —SO$_2$NRR;
each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;
or $R^{14}$ and $R^{15}$, together with the atom or atoms to which they are joined, form a $C_{3-10}$heterocyclyl ring,
wherein $R^{14}$, $R^{15}$, or both, or a ring formed with $R^{14}$ and $R^{15}$, are optionally substituted with —(C(R)$_2$)$_m$—R$^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, —(C(R)$_2$)$_m$—O—NRR and —S—S—$C_{1-6}$alkyl-NRR;
each R is independently selected from the group consisting of: hydrogen and —$C_{1-6}$alkyl; and
each m is independently 0, 1, 2 or 3;
or a pharmaceutically acceptable salt thereof.

According to another aspect, the present invention relates to a compound or compounds of formula (II):

$$L-P \qquad (II)$$

or a pharmaceutically acceptable salt thereof, wherein:
L is the linker moiety $L^1$-$L^2$-$L^3$, where $L^3$ is bound to P;
P is a radical of formula (I):

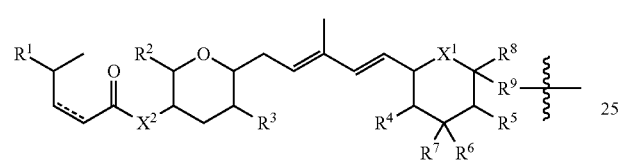

(I)

wherein:
a dashed line represents an optional bond;
each $X^1$ is independently selected from the group consisting of: —O—, —S— and —NR—;
each $X^2$ is independently selected from the group consisting of: —O—, —S— and —NR—;
each X' is CR or N;
each X'' is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X'' binds to $L^2$ or an additional $L^3$, or otherwise is O, S, CRR, CR—(C(R)$_2$)$_m$—NRR or NRR;
each X''' is —(C(R)$_2$)$_m$—NR— or CR—(C(R)$_2$)$_m$—O— if X''' binds to $L^2$, or otherwise is R;
Y is C(R)$_2$—, —O—, —NR— or —S—;
$R^1$ is selected from the group consisting of: —R, —OR, —OCOR$^{13}$, —OCONR$^{14}$R$^{15}$, —OCON(R$^4$)NR(R$^{15}$), =O (double bond to oxygen) and —NR$^{14}$R$^{15}$;
$R^2$ and $R^3$ are independently selected from the group consisting of: hydrogen and $C_{1-6}$alkyl;
$R^4$ and $R^5$ are independently selected from the group consisting of: hydrogen, —OR, —NR$^{14}$R$^{15}$ and oxo;
$R^6$ and $R^7$ are independently selected from the group consisting of: hydrogen, halogen, hydroxyl and $C_{1-6}$alkyl optionally substituted with 1-3 substituents independently selected from hydroxyl and halogen,
$R^6$ and $R^7$, together with the carbon atom to which they are bound, form a $C_{2-5}$alkylidene optionally substituted with 1-3 substituents independently selected from R,
$R^6$ and $R^7$ together are oxo, or
$R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;
$R^8$ is hydrogen, $C_{1-6}$alkyl or —OR;

$R^9$ is —(C(R)$_2$)$_m$—C(O)— or —(C(R)$_2$)$_m$—;
$L^1$ is selected from: -halogen, —NR$_2$,

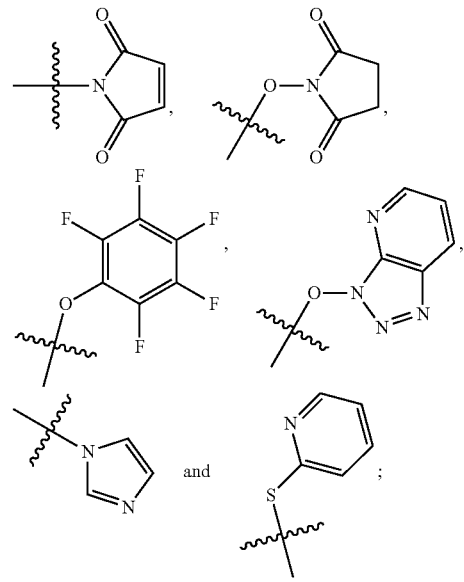

$L^2$ is $L^{2A}$-$L^{2B}$-$L^{2C}$ or $L^{2C}$-$L^{2B}$-$L^{2A}$ where:
$L^{2A}$ comprises one or more components selected from: —O—, —C(O)—, —C(O)NR—, —C(O)—$C_{1-6}$alkyl, —C(O)NRC$_{1-6}$alkyl-, —$C_{1-6}$alkyl(OCH$_2$CH$_2$)$_{1-6}$—, —C(O)—$C_{1-6}$alkyl-NRC(O)—, —C(O)—$C_{1-6}$alkyl (OCH$_2$CH$_2$)$_{1-6}$—, —$C_{1-6}$alkyl(OCH$_2$CH$_2$)$_{1-6}$—C(O)—, —$C_{1-6}$alkyl-S—S—$C_{1-6}$alkyl-NRC(O)CH$_2$—, —$C_{1-6}$alkyl-(OCH$_2$CH$_2$)$_{1-6}$—NRC(O)CH$_2$—, —C(O)—$C_{1-6}$alkyl-NRC(O)$C_{1-6}$alkyl-, —N=CR-phenyl-O—$C_{1-6}$alkyl-, —N=CR-phenyl-O—$C_{1-6}$alkyl-C(O)—, —C(O)—$C_{1-6}$alkyl (OCH$_2$CH$_2$)$_{1-6}$—NRC(O)—, —C(O)—$C_{1-6}$alkyl-phenyl-(NR—C(O)—$C_{1-6}$alkyl)$_{1-4}$-, —C(O)—$C_{1-6}$alkyl-(OCH$_2$CH$_2$)$_{1-6}$—NRC(O)$C_{1-6}$alkyl-, —S—, —C(O)—$C_{1-6}$alkyl-phenyl-NR—, —C(O)—O—$C_{1-6}$alkyl-S— and (—CH$_2$—CH$_2$—O—)$_{1-20}$, or $L^{2A}$ is absent;
$L^{2B}$ is selected from AA$_{0-aa}$, where AA is a natural or non-natural amino acid and aa is 12; and
$L^{2C}$ comprises one or more components selected from: —PABA- and —PABC—, or $L^{2C}$ is absent;
$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$-alkyl-NR—, —NR—$C_{1-6}$-alkyl-, —S—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

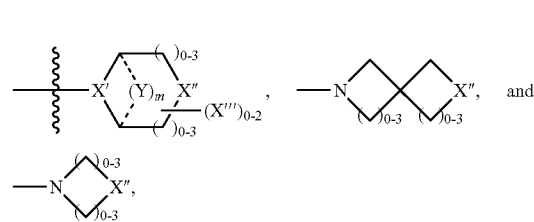

or $L^3$ is absent;
$R^{13}$ is selected from the group consisting of hydrogen, $C_{1-6}$alkyl, $C_{3-8}$carbocyclyl, $C_{3-8}$heterocyclyl, $C_{1-6}$alkyl- $C_{6-14}$aryl, $C_{1-6}$alkyl-$C_{5-14}$heteroaryl, wherein $R^{13}$ is optionally substituted with —NRR or —SO$_2$NRR;

each $R^{14}$ and $R^{15}$ is independently selected from the group consisting of: hydrogen, hydroxyl, —NRR, —NRNR$_2$, —C$_{3-10}$carbocyclyl, —C$_{1-6}$alkylene-C$_{3-10}$carbocyclyl, —C$_{3-10}$heterocyclyl, —C$_{1-6}$alkylene-C$_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —C$_{1-6}$alkyl, C$_{6-14}$aryl, —C$_{1-6}$alkylene-C$_{6-14}$aryl and —C$_{5-14}$heteroaryl;

or $R^{14}$ and $R^{15}$, together with the atom or atoms to which they are joined, form a C$_{3-10}$heterocyclyl ring, wherein $R^{14}$, $R^{15}$, or both, or a ring formed with $R^{14}$ and $R^{15}$, are optionally substituted with —(C(R)$_2$)$_m$—R$^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—C$_{1-6}$alkyl-C(O)OR, (vii) —SO$_2$NRR, (viii) —C(O)NRR, (ix) —C(O)OR, (x) —C$_{4-6}$cycloalkyl optionally substituted with —NRR, —SO$_2$NRR or —NR—C(O) (CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—C$_{1-6}$alkyl-NRR;

each R is independently selected from the group consisting of: hydrogen and —C$_{1-6}$alkyl; and each m is independently 0, 1, 2 or 3.

According to another aspect, the present invention relates to a compound or compounds of formula (II'):

L-P'  (II')

or a pharmaceutically acceptable salt thereof, wherein:
L is the linker moiety $L^1$-$L^2$-$L^3$, where $L^3$ is bound to P';
P' is a radical of formula (F):

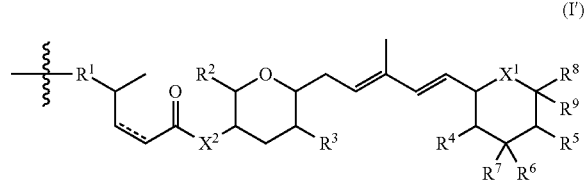

(I')

wherein:
a dashed line represents an optional bond;
each $X^1$ is independently selected from the group consisting of: —O—, —S— and —NR—;
each $X^2$ is independently selected from the group consisting of: —O—, —S— and —NR—;
each X' is CR or N;
each X" is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X" binds to $L^2$ or an additional $L^3$, or otherwise is O, S, CRR, CR—(C(R)$_2$)$_m$—NRR or NRR;
each X''' is —(C(R)$_2$)$_m$—NR— or CR—(C(R)$_2$)$_m$—O— if X''' binds to $L^2$, or otherwise is R;
Y is —C(R)$_2$—, —O—, —NR— or —S—;
$R^1$ is selected from the group consisting of: —(C(R)$_2$)$_m$—, —OR", —OCOR$^{13'}$, —OC(O)NRR$^{14'}$, —OCON(R)N(R)—, and —NR—
$R^2$ and $R^3$ are independently selected from the group consisting of: hydrogen and C$_{1-6}$alkyl;
$R^4$ and $R^5$ are independently selected from the group consisting of: hydrogen, —OR, —NR$^{14}$R$^{15}$ and oxo;

$R^6$ and $R^7$ are independently selected from the group consisting of: hydrogen, halogen, hydroxyl and C$_{1-6}$alkyl optionally substituted with 1-3 substituents independently selected from hydroxyl and halogen, $R^6$ and $R^7$, together with the carbon atom to which they are bound, form a C$_{2-5}$alkylidene optionally substituted with 1-3 substituents independently selected from R, $R^6$ and $R^7$ together are oxo, or $R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;

$R^8$ is hydrogen, C$_{1-6}$alkyl or —OR;
$R^9$ is independently selected from hydrogen, —C$_{1-6}$alkyl, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)—SR, —(C(R)$_2$)$_m$—C(O)NR$^{14}$N(R)R$^{15}$, —(C(R)$_2$)$_m$—NR—C(O)—NR$^{14}$R$^{15}$, —(C(R)$_2$)$_m$—N(R)COR$^{13}$ and (C(R)$_2$)$_m$—NR$^{14}$N(R)R$^{15}$;
$L^1$ is selected from: -halogen, —NR$_2$,

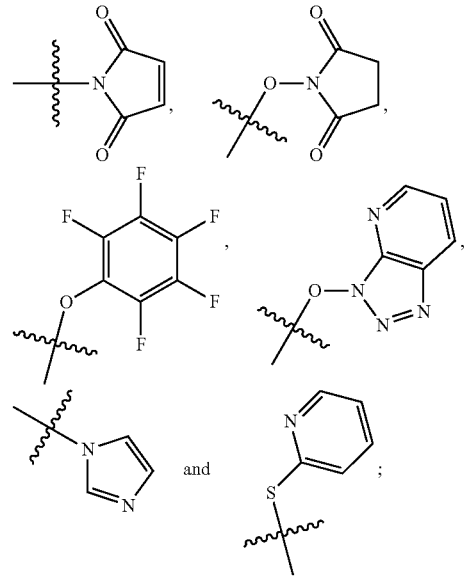

$L^2$ is $L^{2A}$-$L^{2B}$-$L^{2C}$ or $L^{2C}$-$L^{2B}$-$L^{2A}$ where
$L^{2A}$ comprises one or more components selected from: —O—, —C(O)—, —C(O)NR—, —C(O)—C$_{1-6}$alkyl-, —C(O)NRC$_{1-6}$alkyl-, —C$_{1-6}$alkyl(OCH$_2$CH$_2$)$_{1-6}$—, —C(O)—C$_{1-6}$alkyl-NRC(O)—, —C(O)—C$_{1-6}$alkyl(OCH$_2$CH$_2$)$_{1-6}$—, —C$_{1-6}$alkyl(OCH$_2$CH$_2$)$_{1-6}$—C(O)—, —C$_{1-6}$alkyl-S—S—C$_{1-6}$alkyl-NRC(O)CH$_2$—, —C$_{1-6}$alkyl-(OCH$_2$CH$_2$)$_{1-6}$—NRC(O)CH$_2$—, —C(O)—C$_{1-6}$alkyl-NRC(O)C$_{1-6}$alkyl-, —N=CR-phenyl-O—C$_{1-6}$alkyl-, —N=CR-phenyl-O—C$_{1-6}$alkyl-C(O)—, —C(O)—C$_{1-6}$alkyl(OCH$_2$CH$_2$)$_{1-6}$—NRC(O)—, —C(O)—C$_{1-6}$alkyl-phenyl-(NR—C(O)—C$_{1-6}$alkyl)$_{1-4}$-, —C(O)—C$_{1-6}$alkyl-(OCH$_2$CH$_2$)$_{1-6}$—NRC(O)C$_{1-6}$alkyl-, —C$_{1-6}$alkyl-, —S—, —C(O)—C$_{1-6}$alkyl-phenyl-NR—, —O—C$_{1-6}$alkyl-S—, —C(O)—O—C$_{1-6}$alkyl-S— and (—CH$_2$—CH$_2$—O—)$_{1-20}$, or $L^{2A}$ is absent;

$L^{2B}$ is selected from AA$_{0-aa}$, where AA is a natural or non-natural amino acid and aa is 12; and $L^{2C}$ comprises one or more components selected from: —PABA- and —PABC—, or $L^{2C}$ is absent;

$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

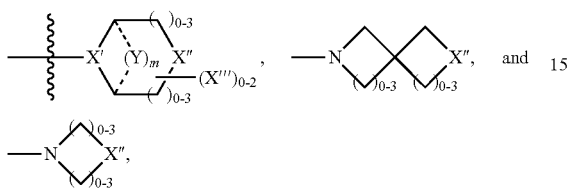

or $L^3$ is absent;

$R^{13'}$ is selected from the group consisting of a bond, —$C_{1-6}$alkylene-, —$C_{3-8}$carbocyclyl-, —$C_{3-8}$heterocyclyl-, —$C_{1-6}$alkyl-$C_{5-14}$heteroaryl-;

each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —(C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$alkyl-NRR;

each $R^{14'}$ is independently selected from the group consisting of: a bond, —NR—, —$C_{3-10}$carbocyclyl-, —$C_{3-10}$heterocyclyl-, —(CH$_2$CH$_2$O)$_{1-6}$CH$_2$CH$_2$C(O)OR', —(CH$_2$CH$_2$O)$_{1-6}$CH$_2$CH$_2$NR—, and —$C_{1-6}$alkylene-, wherein $R^{14'}$ is optionally substituted with —(C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —NRR or —SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) cycloalkyl optionally substituted with NRR, —SO$_2$NRR or NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$—NRR;

each R is independently selected from the group consisting of: hydrogen and —$C_{1-6}$alkyl;

each R' is independently selected from —H, $C_1$-$C_8$ alkyl, $C_1$-$C_8$ heteroalkyl and aryl;

each R'' is independently selected from the group consisting of: a bond and —$C_{1-6}$alkylene-; and each m is independently 0, 1, 2 or 3.

According to still another aspect, the present invention relates to a compound or compounds of formula (III):

or a pharmaceutically acceptable salt thereof, wherein:
L is the linker moiety $L^1$-$L^2$-$L^3$, where $L^3$ is bound to P;
P is a radical of formula (I):

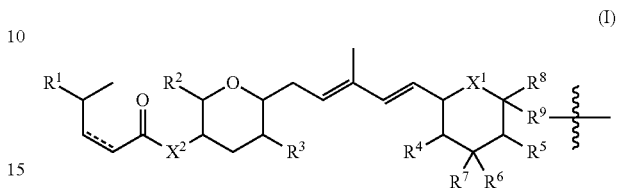

wherein:
a dashed line represents an optional bond;
AB is an antibody;
each $X^1$ is independently selected from the group consisting of: —O—, —S— and —NR—;
each $X^2$ is independently selected from the group consisting of: —O—, —S— and —NR—;
each X' is CR or N;
each X'' is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X'' binds to $L^2$ or an additional $L^3$, or otherwise is O, S, CRR, CR—(C(R)$_2$)$_m$—NRR or NRR;

each X''' is —(C(R)$_2$)$_m$—NR— or CR—(C(R)$_2$)$_m$—O— if X''' binds to $L^2$, or otherwise is R;
Y is —C(R)$_2$—, —O—, —NR— or —S—;
$R^1$ is selected from the group consisting of: —R, —OR, —OCOR$^{13}$, —OCONR$^{14}$R$^{15}$, —OCON($\tilde{R}^{14}$)NR(R$^{15}$), =O (double bond to oxygen) and —NR$^{14}$R$^{15}$;
$R^2$ and $R^3$ are independently selected from the group consisting of: hydrogen and $C_{1-6}$alkyl;
$R^4$ and $R^5$ are independently selected from the group consisting of: hydrogen, —OR, —NR$^{14}$R$^{15}$ and oxo;
$R^6$ and $R^7$ are independently selected from the group consisting of: hydrogen, halogen, hydroxyl and $C_{1-6}$alkyl optionally substituted with 1-3 substituents independently selected from hydroxyl and halogen,
$R^6$ and $R^7$, together with the carbon atom to which they are bound, form a $C_{2-5}$alkylidene optionally substituted with 1-3 substituents independently selected from R,
$R^6$ and $R^7$ together are oxo, or
$R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;
$R^8$ is hydrogen, $C_{1-6}$alkyl or —OR;
$R^9$ is —(C(R)$_2$)$_m$—C(O)— or —(C(R)$_2$)$_m$—;
$L^1$ is selected from: a bond to AB, —NR— (bond to AB) and

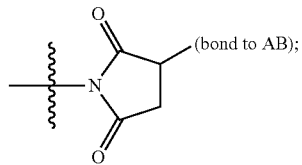

$L^2$ is $L^{2A}$-$L^{2B}$-$L^{2C}$ or $L^{2C}$-$L^{2B}$-$L^{2A}$ where:

$L^{2A}$ comprises one or more components selected from: —O—, —C(O)—, —C(O)NR—, —C(O)—$C_{1-6}$alkyl-, —C(O)NR$C_{1-6}$alkyl-, —$C_{1-6}$alkyl(OCH$_2$CH$_2$)$_{1-6}$—, —C(O)—$C_{1-6}$alkyl-NRC(O)—, —C(O)—$C_{1-6}$alkyl(OCH$_2$CH$_2$)$_{1-6}$—, —$C_{1-6}$alkyl(OCH$_2$CH$_2$)$_{1-6}$—C(O)—, —$C_{1-6}$alkyl-S—S—$C_{1-6}$alkyl-NRC(O)CH$_2$—, —$C_{1-6}$alkyl-(OCH$_2$CH$_2$)$_{1-6}$—NRC(O)CH$_2$—, —C(O)—$C_{1-6}$alkyl-NRC(O)$C_{1-6}$alkyl-, —N=CR-phenyl-O—$C_{1-6}$alkyl-, —N=CR-phenyl-O—$C_{1-6}$alkyl-C(O)—, —C(O)—$C_{1-6}$alkyl(OCH$_2$CH$_2$)$_{1-6}$—NRC(O)—, —C(O)—$C_{1-6}$alkyl-phenyl-(NR—C(O)—$C_{1-6}$alkyl)$_{1-4}$-, —C(O)—$C_{1-6}$alkyl-(OCH$_2$CH$_2$)$_{1-6}$—NRC(O)$C_{1-6}$alkyl-, —$C_{1-6}$alkyl-, —S—, —C(O)—$C_{1-6}$alkyl-phenyl-NR—, —O—$C_{1-6}$alkyl-S—, —C(O)—O—$C_{1-6}$alkyl-S— and (—CH$_2$—CH$_2$—O—)$_{1-20}$, or $L^{2A}$ is absent;

$L^{2B}$ is selected from AA$_{0-aa}$, where AA is a natural or non-natural amino acid and aa is 12; and $L^{2C}$ comprises one or more components selected from: —PABA- and —PABC—, or $L^{2C}$ is absent;

$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

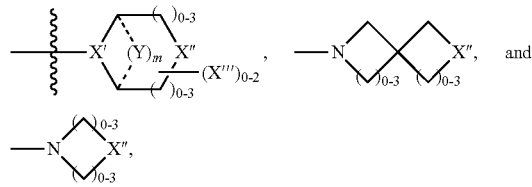

or $L^3$ is absent;

$R^{13}$ is selected from the group consisting of hydrogen, $C_{1-6}$alkyl, $C_{3-8}$carbocyclyl, $C_{3-8}$heterocyclyl, $C_{1-6}$alkyl-$C_{6-14}$aryl, $C_{1-6}$alkyl-$C_{5-14}$heteroaryl, wherein $R^{13}$ is optionally substituted with —NRR or —SO$_2$NRR;

each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —(C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$alkyl-NRR;

each R is independently selected from the group consisting of: hydrogen and —$C_{1-6}$alkyl; and b is 1-20; and each m is independently 0, 1, 2 or 3.

According to yet another aspect, the present invention relates to a compound or compounds of formula (III'):

$$(AB)-(L-P')_b \qquad (III')$$

or a pharmaceutically acceptable salt thereof, wherein:

L is the linker moiety $L^1$-$L^2$-$L^3$, where $L^3$ is bound to P';

P' is a radical of formula (I'):

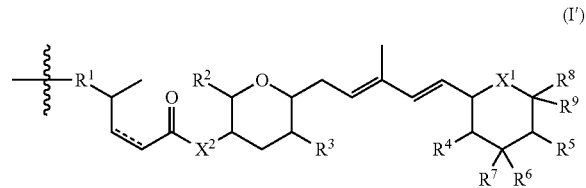

wherein:

a dashed line represents an optional bond;

AB is an antibody;

each $X^1$ is independently selected from the group consisting of: —O—, —S— and —NR—;

each $X^2$ is independently selected from the group consisting of: —O—, —S— and —NR—;

each X' is CR or N;

each X" is CH—, CR—(C(R)$_2$)$_m$—NR—, CR—(C(R)$_2$)$_m$—O—, CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X" binds to $L^2$ or an additional $L^3$, or otherwise is O, S, CRR, CR—(C(R)$_2$)$_m$—NRR or NRR;

each X'" is —(C(R)$_2$)$_m$—NR— or CR—(C(R)$_2$)$_m$—O— if X'" binds to $L^2$, or otherwise is R;

Y is C(R)$_2$—, —O—, —NR— or —S—;

$R^1$ is selected from the group consisting of: —(C(R)$_2$)$_m$—C(O)—, —(C(R)$_2$)$_m$—, —OR", —OCOR$^{13'}$, —OCONRR$^{14'}$, —OCON(R$^{14}$)N(R$^{15}$)—, and —NR$^{14}$—

$R^2$ and $R^3$ are independently selected from the group consisting of: hydrogen and $C_{1-6}$alkyl;

$R^4$ and $R^5$ are independently selected from the group consisting of: hydrogen, —OR, —NR$^{14}$R$^{15}$ and oxo;

$R^6$ and $R^7$ are independently selected from the group consisting of: hydrogen, halogen, hydroxyl and $C_{1-6}$alkyl optionally substituted with 1-3 substituents independently selected from hydroxyl and halogen, $R^6$ and $R^7$, together with the carbon atom to which they are bound, form a $C_{2-5}$alkylidene optionally substituted with 1-3 substituents independently selected from R, $R^6$ and $R^7$ together are oxo, or $R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;

$R^8$ is hydrogen, $C_{1-6}$alkyl or —OR;

$R^9$ is independently selected from hydrogen, —$C_{1-6}$alkyl, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)—SR, —(C(R)$_2$)$_m$—C(O)NR$^{14}$N(R)R$^{15}$, —(C(R)$_2$)$_m$—NR—C(O)—NR$^{14}$R$^{15}$, —(C(R)$_2$)$_m$—N(R)COR$^{13}$ and (C(R)$_2$)$_m$—NR$^{14}$N(R)R$^{15}$;

$L^1$ is selected from: a bond to AB, —NR— (bond to AB) and

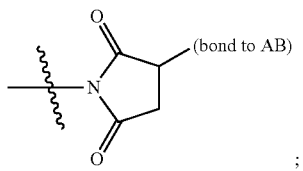

$L^2$ is $L^{2A}$-$L^{2B}$-$L^{2C}$ or $L^{2C}$-$L^{2B}$-$L^{2A}$ where:

$L^{2A}$ comprises one or more components selected from: —O—, —C(O)—, —C(O)NR—, —C(O)—$C_{1-6}$alkyl-, —C(O)NR$C_{1-6}$alkyl-, —$C_{1-6}$alkyl(OCH$_2$CH$_2$)$_{1-6}$—, —C(O)—$C_{1-6}$alkyl-NRC(O)—, —C(O)—$C_{1-6}$alkyl(OCH$_2$CH$_2$)$_{1-6}$—, —$C_{1-6}$alkyl(OCH$_2$CH$_2$)$_{1-6}$—C(O)—, —$C_{1-6}$alkyl-S—S—$C_{1-6}$alkyl-NRC(O)CH$_2$—, —$C_{1-6}$alkyl-(OCH$_2$CH$_2$)$_{1-6}$—NRC(O)CH$_2$—, —C(O)—$C_{1-6}$alkyl-NRC(O)$C_{1-6}$alkyl-, —N═CR-phenyl-O—$C_{1-6}$alkyl-, —N═CR-phenyl-O—$C_{1-6}$alkyl-C(O)—, —C(O)—$C_{1-6}$alkyl(OCH$_2$CH$_2$)$_{1-6}$—NRC(O)—, —C(O)—$C_{1-6}$alkyl-phenyl-(NR—C(O)—$C_{1-6}$alkyl)$_{1-4}$-, —C(O)—$C_{1-6}$alkyl-(OCH$_2$CH$_2$)$_{1-6}$—NRC(O)$C_{1-6}$alkyl-, —$C_{1-6}$alkyl-, —S—, —C(O)—$C_{1-6}$alkyl-phenyl-NR—, —O—$C_{1-6}$alkyl-S—, —C(O)—O—$C_{1-6}$alkyl-S— and (—CH$_2$—CH$_2$—O—)$_{1-20}$, or $L^{2A}$ is absent;

$L^{2B}$ is selected from AA$_{0-aa}$, where AA is a natural or non-natural amino acid and aa is 12; and $L^{2C}$ comprises one or more components selected from: —PABA- and —PABC—, or $L^{2C}$ is absent;

$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

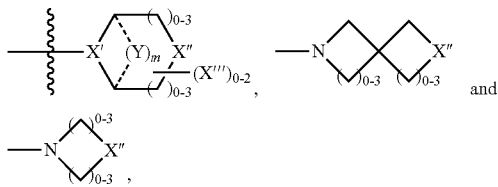

or $L^3$ is absent;

$R^{13'}$ is selected from the group consisting of a bond, —$C_{1-6}$alkylene-, —$C_{3-8}$carbocyclyl-, —$C_{3-8}$heterocyclyl-, —$C_{1-6}$alkyl-$C_{6-14}$aryl-, —$C_{1-6}$alkyl-$C_{5-14}$heteroaryl-;

each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —(C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$alkyl-NRR;

each $R^{14'}$ is independently selected from the group consisting of: a bond, —NR—, —$C_{3-10}$carbocyclyl-, —$C_{3-10}$heterocyclyl-, —(CH$_2$CH$_2$O)$_{1-6}$CH$_2$CH$_2$C(O)OR', —(CH$_2$CH$_2$O)$_{1-6}$CH$_2$CH$_2$NR—, and —$C_{1-6}$alkylene-, wherein $R^{14'}$ is optionally substituted with (C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —NRR or —SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or NR—C(O)(CH$_2$)$_{0-6}$NRR, (xi) —R, (xii) —OR, (xiii) —N(R)NRR, (xiv) —C(O)N(R)NRR, (xv) (C(R)$_2$)$_m$—O—NRR and (xiv) —S—S—$C_{1-6}$alkyl-NRR;

each R is independently selected from the group consisting of: hydrogen and —$C_{1-6}$alkyl;

each R' is independently selected from —H, $C_1$-$C_8$ alkyl, $C_1$-$C_8$ heteroalkyl and aryl;

each R" is independently selected from the group consisting of: a bond and —$C_{1-6}$alkylene-; and b is 1-20; and each m is independently 0, 1, 2 or 3.

In another aspect, the present invention relates to an antibody drug conjugate compound of formulae III or III' wherein the antibody AB is selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha_v\beta_3$), alemtuzumab, a humanized anti-HLA-DR antibody for the treatment of non-Hodgkin's lymphoma, 131I Lym-1, a murine anti-HLA-Dr10 antibody for the treatment of non-Hodgkin's lymphoma, a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, gemtuzumab, humanized monoclonal antibody to the oncofecal protein receptor 5T4 and M1/70 (antibody to CD11b receptor) and other antibodies.

Trastuzumab refers to: (INN; trade names Herclon, Herceptin) refers to a monoclonal antibody that interferes with the HER2/neu receptor.

In another aspect, the present invention relates to a compound or compounds of formulas II, II', III or III' wherein L comprises one or more independently selected amino acid di-radicals, preferably one or more independently selected amino acid diradicals selected from the group consisting of valine, citrulline, phenylalanine, lysine, alanine and glycine.

According to another aspect, the present invention relates to a compound or compounds of formulae III or III' wherein L is capable of being cleaved from P, or a radical comprising P, by an intracellular protease.

According to an additional aspect, the present invention relates to a compound or compounds of formulae III or III' wherein the antibody is attached to an amino acid di-radical via a cysteine residue of the antibody via a sulphur or sulphur-sulphur bond, a lysine residue of there antibody via an amide bond, or a glutamine residue via an amide bond. Preferably, the antibody is a monoclonal antibody, a chimeric antibody, a humanized antibody, a bispecific antibody or an antibody fragment.

According to still another aspect, the present invention relates to a pharmaceutical composition of a compound or compounds of formulae I, I', II, II', III or III', and/or a salt or salts thereof, comprising an effective amount of the compound(s) or salt(s) and a pharmaceutically acceptable diluent, carrier or excipient. Such pharmaceutical compositions may additionally include a therapeutically effective amount of a chemotherapeutic agent selected from the group consisting of a tubulin-forming inhibitor, a topoisomerase inhibitor, and a DNA binder.

According to another aspect, the present invention relates to a method for killing or inhibiting the proliferation of tumor cells or cancer cells comprising treating tumor cells or cancer cells in a patient with an amount of the compound of formulae I, I', II, II', III or III', and/or a salt or salts thereof, said amount being effective to kill or inhibit the proliferation of the tumor cells or cancer cells.

Another aspect of the invention relates to a method of using an effective amount of any one of the aforementioned compounds and/or any one of the aforementioned antibody drug conjugates to treat cancer by administering to a patient in need thereof an effective amount of said compound and/or conjugate.

DETAILED DESCRIPTION

Figure 1:
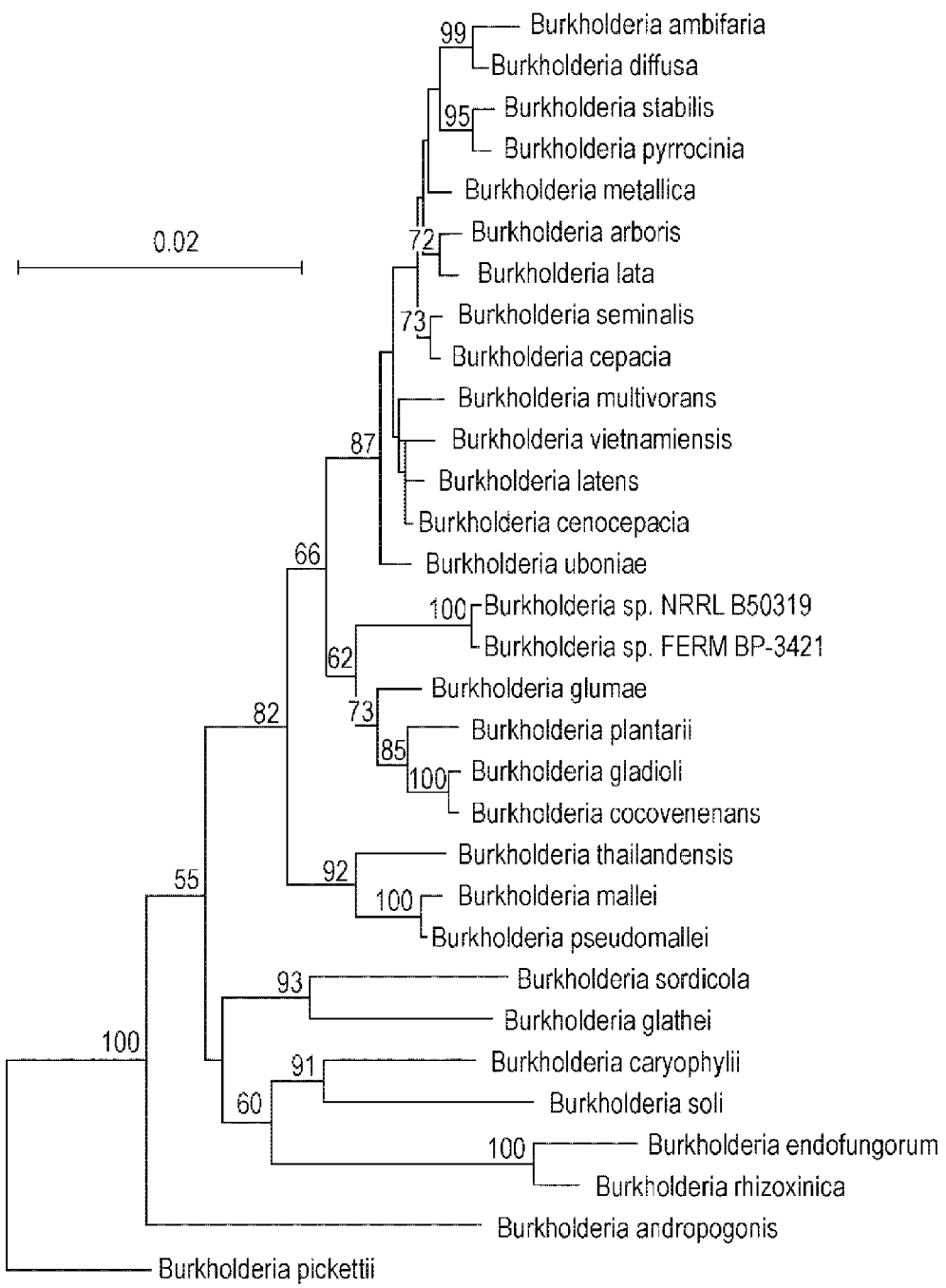
FIG. 1 is a schematic representation of the phylogenetic relationship determined with nearly complete 16S rRNA sequences of FERM BP-3421 to other *Burkholderia* spp.

The present invention is directed to cytotoxic natural products including cytotoxic spliceostatin analogs, to antibody drug conjugates comprising said cytotoxic natural products including cytotoxic spliceostatin analogs, and to methods for using the same to treat cancer and other pathological conditions. The invention also relates to methods of using such compounds and/or conjugates in vitro, in situ, and in vivo for the detection, diagnosis, or treatment of mammalian cells, or associated pathological conditions.

Definitions and Abbreviations

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" (or "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. An intact antibody has primarily two regions: a variable region and a constant region. The variable region binds to and interacts with a target antigen. The variable region includes a complementary determining region (CDR) that recognizes and binds to a specific binding site on a particular antigen. The constant region may be recognized by and interact with the immune system (see, e.g., Janeway et al., 2001, Immuno. Biology, 5th Ed., Garland Publishing, New York). An antibody can be of any type or class (e.g., IgG, IgE, IgM, IgD, and IgA) or subclass (e.g., IgG1, IgG2, IgG3, IgG4, IgA1 and IgA2). The antibody can be derived from any suitable species. In some embodiments, the antibody is of human or murine origin. An antibody can be, for example, human, humanized or chimeric.

The terms "specifically binds" and "specific binding" refer to antibody binding to a predetermined antigen. Typically, the antibody binds with an affinity of at least about $1 \times 10^7$ $M^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "monoclonal antibodies" specifically includes "chimeric" antibodies in which a portion of the heavy and/or light chain is identical to or homologous with the corresponding sequence of antibodies derived from a particular species or belonging to a particular antibody class or subclass, while the remainder of the chain(s) is identical to or homologous with the corresponding sequences of antibodies derived from another species or belonging to another antibody class or subclass, as well as fragments of such antibodies, so long as they exhibit the desired biological activity.

An "intact antibody" is one which comprises an antigen-binding variable region as well as a light chain constant domain ($C_L$) and heavy chain constant domains, $C_{H1}$, $C_{H2}$, $C_{H3}$ and $C_{H4}$, as appropriate for the antibody class. The constant domains may be native sequence constant domains (e.g., human native sequence constant domains) or amino acid sequence variants thereof An intact antibody may have one or more "effector functions", which refers to those biological activities attributable to the Fc region (e.g., a native sequence Fc region or amino acid sequence variant Fc region) of an antibody. Examples of antibody effector functions include complement dependent cytotoxicity, antibody-dependent cell-mediated cytotoxicity (ADCC) and antibody-dependent cell-mediated phagocytosis.

An "antibody fragment" comprises a portion of an intact antibody, preferably comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immuno specifically bind to a target antigen (e.g., a cancer cell antigen, a viral antigen or a microbial antigen).

The term "variable" in the context of an antibody refers to certain portions of the variable domains of the antibody that differ extensively in sequence and are used in the binding and specificity of each particular antibody for its particular antigen. This variability is concentrated in three segments called "hypervariable regions" in the light chain and the heavy chain variable domains. The more highly conserved portions of variable domains are called the framework regions (FRs). The variable domains of native heavy and light chains each comprise four FRs connected by three hypervariable regions.

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (L3) in the heavy chain variable domain; Kabat et al. (Sequences of Proteins of Immunological Interest, 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (142) and 96-101 (H3) in the heavy chain variable domain; Chothia and Lesk, 1987, J. Mol. Biol. 196:901-917). FR residues are those variable domain residues other than the hypervariable region residues as herein defined.

A "single-chain Fv" or "scFv" antibody fragment comprises the V.sub.H and V.sub.L domains of an antibody, wherein these domains are present in a single polypeptide chain. Typically, the Fv polypeptide further comprises a polypeptide linker between the V.sub.H and V.sub.L domains which enables the scFv to form the desired structure for antigen binding. For a review of scFv, see Pluckthun in The Pharmacology of Monoclonal Antibodies, vol. 113, Rosenburg and Moore eds., Springer-Verlag, New York, pp. 269-315 (1994).

The term "diabody" refers to small antibody fragments with two antigen-binding sites, which fragments comprise a variable heavy domain (V$_H$) connected to a variable light domain (V$_L$) in the same polypeptide chain. By using a linker that is too short to allow pairing between the two domains on the same chain, the domains are forced to pair with the complementary domains of another chain and create two antigen-binding sites. Diabodies are described more fully in, for example, EP 0 404 097; WO 93/11161; and Hollinger et al., 1993, Proc. Natl. Acad. Sci. USA 90:6444-6448.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., 1986, Nature 321:522-525; Riechmann et al., 1988, Nature 332:323-329; and Presta, 1992, Curr. Op. Struct. Biol. 2:593-596.

As used herein, "isolated" means separated from other components of (a) a natural source, such as a plant or animal cell or cell culture, or (b) a synthetic organic chemical reaction mixture. As used herein, "purified" means that when isolated, the isolate contains at least 95%, and in another aspect at least 98%, of a compound (e.g., a conjugate) by weight of the isolate.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is a tumor cell, e.g., a breast, ovarian, stomach, endometrial, salivary gland, lung, kidney, colon, thyroid, pancreatic or bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit the growth of and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. greater than 50% of a population, of a mixture or a sample.

The term "intracellular metabolite" refers to a compound resulting from a metabolic process or reaction inside a cell on an antibody-drug conjugate (ADC). The metabolic process or reaction may be an enzymatic process such as proteolytic cleavage of a peptide linker of the ADC. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on an ADC or the like, whereby the covalent attachment, e.g., the linker, between the drug moiety and the antibody is broken, resulting in the free drug, or other metabolite of the conjugate dissociated from the antibody inside the cell. The cleaved moieties of the ADC are thus intracellular metabolites.

The term "bioavailability" refers to the systemic availability (i.e., blood/plasma levels) of a given amount of a drug administered to a patient. Bioavailability is an absolute term that indicates measurement of both the time (rate) and total amount (extent) of drug that reaches the general circulation from an administered dosage form.

The term "cytotoxic activity" refers to a cell-killing, a cytostatic or an anti-proliferative effect of a ADC or an intracellular metabolite of said ADC. Cytotoxic activity may be expressed as the $IC_{50}$ value, which is the concentration (molar or mass) per unit volume at which half the cells survive.

A "disorder" is any condition that would benefit from treatment with a drug or antibody-drug conjugate. This includes chronic and acute disorders or diseases including those pathological conditions which predispose a mammal to the disorder in question. Non-limiting examples of disorders to be treated herein include benign and malignant cancers; leukemia and lymphoid malignancies, neuronal, glial, astrocytal, hypothalamic and other glandular, macrophagal, epithelial, stromal and blastocoelic disorders; and inflammatory, angiogenic and immunologic disorders.

The terms "cancer" and "cancerous" refer to or describe the physiological condition or disorder in mammals that is typically characterized by unregulated cell growth. A "tumor" comprises one or more cancerous cells.

Examples of a "patient" include, but are not limited to, a human, rat, mouse, guinea pig, monkey, pig, goat, cow, horse, dog, cat, bird and fowl. In an exemplary embodiment, the patient is a human.

The terms "treat" or "treatment," unless otherwise indicated by context, refer to therapeutic treatment and prophylactic measures to prevent relapse, wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of inhibiting replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: inhibiting the growth, multiplication or replication of the pathogen that causes the infectious disease and ameliorating one or more symptoms of an infectious disease.

The term "package insert" is used to refer to instructions customarily included in commercial packages of therapeutic products, that contain information about the indication(s), usage, dosage, administration, contraindications and/or warnings concerning the use of such therapeutic products.

As used herein, the terms "cell," "cell line," and "cell culture" are used interchangeably and all such designations include progeny. The words "transformants" and "transformed cells" include the primary subject cell and cultures or progeny derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Unless otherwise indicated, the term "alkyl" by itself or as part of another term refers to a straight chain or branched, saturated hydrocarbon having the indicated number of carbon atoms (e.g., "$C_1$-$C_8$" alkyl refer to an alkyl group having from 1 to 8 carbon atoms). When the number of carbon atoms is not indicated, the alkyl group has from 1 to 8 carbon atoms, preferably from 1 to 6 carbon atoms. Representative straight chain $C_1$-$C_8$ alkyls include, but are not limited to, methyl, ethyl, n-propyl, n-butyl, n-pentyl, n-hexyl, n-heptyl and n-octyl; while branched $C_1$-$C_8$ alkyls include, but are not limited to, -isopropyl, -sec-butyl, -isobutyl, -tert-butyl, -isopentyl, and -2-methylbutyl; unsaturated $C_2$-$C_8$ alkyls include, but are not limited to, vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexyl, 2-hexyl, 3-hexyl, acetylenyl, propynyl, 1-butynyl, 2-butynyl, 1-pentynyl, 2-pentynyl and 3-methyl-1-butynyl.

Unless otherwise indicated, "alkylene," by itself of as part of another term, refers to a saturated, branched or straight chain or cyclic hydrocarbon radical of the stated number of carbon atoms, typically 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene (—$CH_2CH_2$—), 1,3-propylene (—$CH_2CH_2CH_2$—), 1,4-butylene (—$CH_2CH_2CH_2CH_2$—), and the like. A "$C_1$-$C_{10}$" straight chain alkylene is a straight chain, saturated hydrocarbon group of the formula —$(CH_2)_{1\text{-}10}$—. Examples of a $C_1$-$C_{10}$ alkylene include methylene, ethylene, propylene, butylene, pentylene, hexylene, heptylene, ocytylene, nonylene and decalene. In certain embodiments of the invention, alkylenes have from 1 to 9, from 1 to 8, from 1 to 7, and from 1 to 6 carbons.

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si, S and/or P, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive.

"Halo" or "halogen" refers to fluoro, chloro, bromo and iodo.

"Halo($C_{1-6}$-alkyl)" refers to $C_{1-6}$-alkyl groups substituted with 1 to 3 or 1 to 2 halo groups, wherein $C_{1-6}$-alkyl and halo are as defined herein. The term includes, for example, $CF_3$.

The term "epoxy", or "epoxy group" or "epoxy residue" with be known to those skilled in the art to refer to a three member ring comprising to carbon atoms and an oxygen atom linked by single bonds as follows:

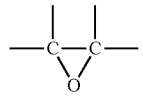

Accordingly, the term "epoxide" refers to a compound that comprise at least one epoxy group as herein before defined.

Unless otherwise indicated, the term "heteroalkylene" by itself or as part of another substituent means a divalent group derived from heteroalkyl (as discussed above). For heteroalkylene groups, heteroatoms can also occupy either or both of the chain termini.

Unless otherwise indicated, "aryl," by itself or an part of another term, means a substituted or unsubstituted monovalent aromatic hydrocarbon radical of 6 to 20 carbon atoms, preferably from 6 to 14 carbon atoms, derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. A substituted aromatic group (e.g., an aryl group) can be substituted with one or more, preferably 1 to 5, of the following groups: $C_1$-$C_8$ alkyl, —O—($C_1$-$C_8$ alkyl), —C(O)R', —OC(O)R', —C(O)OR', —C(O)NH$_2$, —C(O)NHR', —C(O)N(R)$_2$, —NHC(O)R', —S(O)$_2$R', —S(O)R', —OH, halogen, —N$_3$, —NH$_2$, —NH(R'), —N(R')$_2$ and —CN; wherein each R' is independently selected from —H, $C_1$-$C_8$ alkyl, $C_1$-$C_8$ heteroalkyl and aryl, preferably unsubstituted aryl. In some embodiments, a substituted aromatic group can further include one or more of: —NHC(=NH)NH$_2$, —NHCONH$_2$, —S(=O)$_2$R' and —SR'.

The term "heteroaryl" as used herein refers to an aromatic heterocycle ring of 5 to 14 members, such as 5 to 6 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl. Heteroaryls are optionally substituted. Typical substituents include, but are not limited to, —X, —R, —O—, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3^{2-}$, PO$_3$H$_2$, —AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each R is independently —H or $C_1$-$C_6$ alkyl.

The terms "arylene", "heteroarylene" refer to divalent versions of "aryl" and "heteroaryl" respectively, and other terms incorporating "aryl" and "heteroaryl".

"Hydroxy" refers to the group —OH.

"Substituted alkyl" means an alkyl in which one or more hydrogen atoms are each independently replaced with a substituent. Typical substituents include, but are not limited to, —X, —R, —O—, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_3^{2-}$, PO$_3$H$_2$, —AsO$_2$H$_2$, —C(=O)R, —C(O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, $C_1$-$C_{20}$ heteroalkyl, $C_6$-$C_{20}$ aryl, $C_3$-$C_8$ heterocyclyl, a protecting group or a prodrug moiety, where each X is independently a halogen: —F, —Cl, —Br, or —I; and each R is independently —H or $C_1$-$C_6$ alkyl. A substituted alkyl substituted with a halogen is sometimes referred to herein as a haloalkyl. Aryl, alkylene, heteroalkylene and other groups containing or not containing an alkyl or alkylene moiety as described herein may also be similarly substituted.

Unless otherwise indicated, "aralkyl" by itself or part of another term, means an alkyl group, as defined above, substituted with an aryl group, as defined above.

Unless otherwise indicated, "$C_3$-$C_8$heterocyclyl" by itself or as part of another term, refers to a monovalent or divalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. Similarly, unless otherwise indicated, "$C_3$-$C_{10}$heterocyclyl" by itself or as part of another term, refers to a monovalent or divalent substituted or unsubstituted aromatic or non-aromatic monocyclic or bicyclic ring system having from 3 to 10 carbon atoms (also referred to as ring members) and one to four heteroatom ring members independently selected from N, O, P or S, and derived by removal of one hydrogen atom from a ring atom of a parent ring system. One or more N, C or S atoms in the heterocyclyl can be oxidized. The ring that includes the heteroatom can be aromatic or nonaromatic. Heterocyclyl groups with more than 10 carbons, for instance rings or ring systems with 11, 12, 13, 14, 15, 16, 17, 18, 19 or 20 carbons, are also possible and are encompassed, along with $C_3$-$C_{10}$heterocyclyls, when the term "heterocyclyl" is employed without reference to a specific number of carbons. Similarly, heterocyclyl groups with less than 3 carbons, for instance rings with 1 or 2, are possible and are encompassed when the term "heterocyclyl" is employed without reference to a specific number of carbons. The term "heterocycloalkyl" refers to non-aromatic heterocyclyl rings or ring systems where all carbon atoms are saturated (i.e., bonded to a hydrogen or another substituent as noted below, with no double or triple bonds). In certain embodiments heterocycloalkyl groups typically have 3 to 5 members and 1 to 2 heteroatoms. In certain embodiments heterocycloalkyl can be epoxy.

Unless otherwise noted, the heterocyclyl is attached to its pendant group at any heteroatom or carbon atom that results in a stable structure. Representative examples of a $C_3$-$C_8$ heterocyclyl include, but are not limited to, tetrahydrofuranyl, oxetanyl, pyranyl, pyrrolidinyl, piperidinyl, benzofuranyl, benzothiophene, indolyl, benzopyrazolyl, pyrrolyl, thiophenyl (thiopene), furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocyclyl, or a $C_3$-$C_{10}$ heterocyclyl, can be substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O)NH$_2$, —C(O)NHR', —C(O)N(R')$_2$, —NHC(O)R', —S(=O)$_2$R', —S(O)R', halogen, —N$_3$, —NH$_2$, —NH(R'), —N(R')$_2$ and —CN; wherein each R' is independently selected from —H, $C_1$-$C_8$ alkyl, $C_1$-$C_8$ heteroalkyl and aryl. In some embodiments, a substituted heterocyclyl can also include one or more of: —NHC(=NH)NH$_2$, —NHCONH$_2$, —S(=O)$_2$R' and —SR'.

Unless otherwise indicated, "heteroaralkyl" by itself or part of another term, means an alkyl group, as defined above, substituted with an aromatic heterocyclyl group, as defined above.

Unless otherwise indicated, "$C_3$-$C_8$ carbocyclyl" by itself or as part of another term, is a 3-, 4-, 5-, 6-, 7- or 8-membered monovalent or divalent, substituted or unsubstituted, saturated or unsaturated non-aromatic monocyclic or bicyclic carbocyclic ring derived by the removal of one hydrogen atom or two hydrogen atoms from a ring atom of a parent ring system. Similarly, unless otherwise indicated, "$C_3$-$C_{10}$ carbocyclyl" by itself or as part of another term, is a 3-, 4-, 5-, 6-, 7-, 8-, 9- or 10-membered monovalent or divalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(111)pentane, and bicyclo(222)octane. A $C_3$-$C_8$ carbocyclyl group, or a $C_3$-$C_{10}$ carbocyclyl group, can be unsubstituted or substituted with up to seven groups including, but not limited to, $C_1$-$C_8$ alkyl, $C_1$-$C_8$ heteroalkyl, —OR', aryl, —C(O)R', —OC(O)R', —C(O)OR', —C(O)NH$_2$, —C(O)NHR', —C(O)N(R)$_2$, —NHC(O)R', —S(=O)$_2$R', —S(=O)R', —OH, -halogen, —N$_3$, —NH$_2$, —NH(R'), —N(R')$_2$ and —CN; where each R' is independently selected from —H, $C_1$-$C_8$ alkyl, $C_1$-$C_8$ heteroalkyl and aryl. Carbocyclyl groups with more than 10 carbons, for instance ring systems with 11, 12, 13, 14, 15, 16, 17, 18, 19 or 20 carbons, are also possible and are encompassed, along with $C_3$-$C_{10}$ carbocyclyls, when the term "carbocyclyl" is employed without reference to a specific number of carbons. The term "cycloalkyl" refers to carbocyclyl rings or ring systems where all carbon atoms are saturated (i.e., bonded to a hydrogen or another substituent as noted below, with no double or triple bonds).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

Stereochemical definitions and conventions used herein generally follow S. P. Parker, Ed., McGraw-Hill Dictionary of Chemical Terms, McGraw-Hill Book Company, New York (1984); and Eliel and Wilen, Stereochemistry of Organic Compounds, John Wiley & Sons, Inc., New York (1994). Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

An amino acid "derivative" includes an amino acid having substitutions or modifications by covalent attachment of a parent amino acid, such as, e.g., by alkylation, glycosylation, acetylation, phosphorylation, and the like. Further included within the definition of "derivative" is, for example, one or more analogs of an amino acid with substituted linkages, as well as other modifications known in the art.

A "natural amino acid" refers to arginine, glutamine, phenylalanine, tyrosine, tryptophan, lysine, glycine, alanine, histidine, serine, proline, glutamic acid, aspartic acid, threonine, cysteine, methionine, leucine, asparagine, isoleucine, and valine, unless otherwise indicated by context.

The phrase "pharmaceutically acceptable salt," as used herein, refers to pharmaceutically acceptable organic or inorganic salts of a compound. The compound typically contains at least one amino group, and accordingly acid addition salts can be formed with this amino group. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The terms "loading" or "drug loading" or "payload loading" represent or refer to the average number of payloads ("payload" and "payloads" are used interchangeable herein with "drug" and "drugs") per antibody in an ADC molecule. Drug loading may range from 1 to 20 drugs per antibody. This is sometimes referred to as the DAR, or drug to antibody ratio. Compositions of the ADCs described herein typically have DAR's of from 1-20, and in certain embodiments from 1-8, from 2-8, from 2-6, from 2-5 and from 2-4. Typical DAR values are 2, 4, 6 and 8. The average number of drugs per antibody, or DAR value, may be characterized by conventional means such as UV/visible spectroscopy, mass spectrometry, ELISA assay, and HPLC. The quantitative DAR value may also be determined. In some instances, separation, purification, and characterization of homogeneous ADCs having a particular DAR value may be achieved by means such as reverse phase HPLC or electrophoresis. DAR may be limited by the number of attachment sites on the antibody. For example, where the attachment is a cysteine thiol, an antibody may have only one or several cysteine thiol groups, or may have only one or several sufficiently reactive thiol groups through which a Linker unit may be attached. In some embodiments, the cysteine thiol is a thiol group of a cysteine residue that forms an interchain disulfide bond. In some embodiments, the cysteine thiol is a thiol group of a cysteine residue that does not form an interchain disulfide bond. Typically, fewer than the theoretical maximum of drug moieties are conjugated to an antibody during a conjugation reaction. An antibody may contain, for example, many lysine residues that do not react with a linker or linker intermediate. Only the most reactive lysine groups may react with a reactive linker reagent.

Generally, antibodies do not contain many, if any, free and reactive cysteine thiol groups which may be linked to a drug via a linker. Most cysteine thiol residues in the antibodies exist as disulfide bridges and must be reduced with a reducing agent such as dithiothreitol (DTT). The antibody may be subjected to denaturing conditions to reveal reactive nucleophilic groups such as lysine or cysteine. The loading (drug/antibody ratio) of an ADC may be controlled in several different manners, including: (i) limiting the molar excess of drug-linker relative to the antibody, (ii) limiting the conjugation reaction time or temperature, and (iii) partial or limiting reductive conditions for cysteine thiol modification. Where more than one nucleophilic group reacts with a drug-linker then the resulting product is a mixture of ADCs with a distribution of one or more drugs moieties per antibody. The average number of drugs per antibody may be calculated from the mixture by, for example, dual ELISA antibody assay, specific for antibody and specific for the drug. Individual ADCs may be identified in the mixture by mass spectroscopy, and separated by HPLC, e. g, hydrophobic interaction chromatography.

Below is a list of abbreviations and definitions that may not otherwise be defined or described in this application: DMSO (refers to dimethyl sulfoxide), HRMS (refers to high resolution mass spectrometry), DAD (refers to diode array detection), TFA (refers to 2,2,2-trifluoroacetic acid or trifluoroacetic acid), TFF (refers to tangential flow filtration), EtOH (refers to ethanol), MW (refers to molecular weight), HPLC (refers to high performance liquid chromatography), prep HPLC (refers to preparative high performance liquid chromatography), etc. (refers to and so forth), trityl (refers 1,1',1"-ethane-1,1,1-triyltribenzene), THF (refers to tetrahydrofuran), NHS (refers to 1-Hydroxy-2,5-pyrrolidinedione), Cbz (refers to carboxybenzyl), eq. (refers to equivalent), n-BuLi (refers to n-butyllithium), OAc (refers to acetate), MeOH (refers to methanol), i-Pr (refers to isopropyl or propan-2-yl), NMM (refers to 4-methylmorpholine), and "-" (in a table refers to no data available at this time).

As used herein, "H/C" refers to trastuzumab (trade name HERCEPTIN®) which is a monoclonal antibody that interferes with the HER2/neu receptor, bound through one of its cysteine residues (to a linker or a compound of the invention).

As used herein, "H/K" refers to trastuzumab which is a monoclonal antibody that interferes with the HER2/neu receptor, bound through one of its lysine residues (to a linker or a compound of the invention).

As used throughout this application, the amino acid residue numbering (for example: Alanine at position 114) is based on EU index of Kabat method.

As used herein, "H/TG1-(Q)" refers to engineered trastuzumab which is a monoclonal antibody that interferes with the HER2/neu receptor, bound through one of its natural or engineered glutamine residues which is in the transglutaminase peptide (TG1) substrate tag embedded in the antibody (to a linker or a compound of the invention).

As used herein, "H-A114C/C114" refers to engineered trastuzumab which is a monoclonal antibody that interferes with the HER2/neu receptor, bound through one of its engineered cysteine which was substituted for alanine at position 114 of heavy chain (to a linker or a compound of the invention).

As used herein, "H-K392C+L443C/C392+C443" refers to engineered trastuzumab which is a monoclonal antibody that interferes with the HER2/neu receptor, bound through one or both of its engineered cysteine residues that were substituted for lysine at position 392 of the heavy chain and leucine at position 443 of the heavy chain (to a linker or a compound of the invention).

As used herein, "H-E388C+N421C/C388+C421" refers to engineered trastuzumab which is a monoclonal antibody that interferes with the HER2/neu receptor, bound through one or both of its engineered cysteine residues that were substituted for glutamic acid at position 388 and asparigine at position 421 of heavy chain (to a linker or a compound of the invention).

As used herein, "H-Q347C+K392C/C347+C392" refers to engineered trastuzumab which is a monoclonal antibody that interferes with the HER2/neu receptor, bound through one or both of its engineered cysteine residues that were substituted for glutamine at position 347 and lysine at position 392 of heavy chain (to a linker or a compound of the invention).

As used herein, "H-L443C+kK183C/C443+kC183" refers to engineered trastuzumab which is a monoclonal antibody that interferes with the HER2/neu receptor, bound through one or both of its engineered cysteine which was substituted for leucine at position 443 at the heavy chain and lysine at position 183 of light (kappa) chain (to a linker or a compound of the invention).

As used herein, "H-Q347C+L443C/C347+C443" refers to engineered trastuzumab which is a monoclonal antibody that interferes with the HER2/neu receptor, bound through one or both of its engineered cysteine which were substituted for glutamine at position 347 and leucine at position 443 of heavy chain (to a linker or a compound of the invention).

As used herein, "H-kK183C/kC183" refers to engineered trastuzumab which is a monoclonal antibody that interferes with the HER2/neu receptor, bound through its engineered cysteine which was substituted at lysine at position 183 of light (kappa) chain (to a linker or a compound of the invention).

As used herein, "H-N421C/C421" refers to engineered trastuzumab which is a monoclonal antibody that interferes with the HER2/neu receptor, bound through its engineered cysteine which was substituted at asparigine at position 421 of heavy chain (to a linker or a compound of the invention).

Generally, as used herein, "H-(AA1)###(AA2)/(AA2)###" (where (AA1) and (AA2) are a first and a second amino acid) refers to engineered trastuzumab which is a monoclonal antibody that interferes with the HER2/neu receptor, bound through its engineered (AA2) which was substituted at (AA1) at position ### of heavy chain to compound of the invention, where ### represents the position of the relevant amino acid(s). Similar notation referencing "k" or kappa" would indicate a substitution on the light chain.

Similarly, as used herein, "H-(AA1)###(AA2)±(AA3)####(AA4)/(AA2)###+(AA4)####" (where (AA1), (AA2), (AA3) and (AA4) are first, second, third and fourth amino acids) refers to engineered trastuzumab which is a monoclonal antibody that interferes with the HER2/neu receptor, bound through its engineered (AA2) which was substituted at (AA1) at position ### of heavy chain to compound of the invention, where ### represents the position of the relevant amino acid(s), and also bound through its engineered (AA4) which was substituted at (AA3) at position #### of heavy chain to compound of the invention, where #### represents the position of the relevant amino acid(s). Similar notation referencing "k" or kappa" would indicate a substitution on the light chain.

As used herein, "—PABC—" or "PABC" refers to the structure:

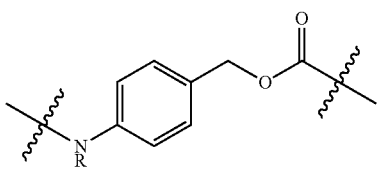

or variants thereof

As used herein, "—PABA-" or "PABA" refers to the structure:

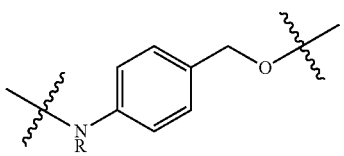

or variants thereof

Compounds and Antibody Drug Conjugates Thereof

According to one aspect, the present invention relates to a compound or compounds of formula (I):

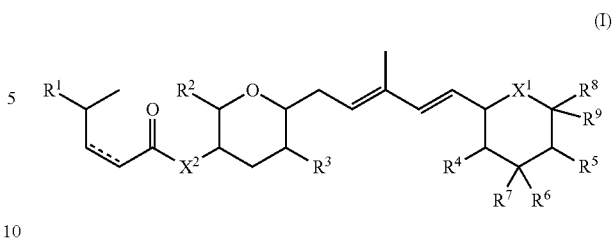

wherein:
a dashed line represents an optional bond;
each $X^1$ is independently selected from the group consisting of: —O—, —S— and —NR—;
each $X^2$ is independently selected from the group consisting of: —O—, —S— and —NR—;
$R^1$ is selected from the group consisting of: —R, —OR, —OCOR$^{13}$, —OCONR$^{14}$R$^{15}$, —OCON(R$^{14}$)NR(R$^{15}$), =O (double bond to oxygen) and —NR$^{14}$R$^{15}$;
$R^2$ and $R^3$ are independently selected from the group consisting of: hydrogen and $C_{1-6}$alkyl;
$R^4$ and $R^5$ are independently selected from the group consisting of: hydrogen, —OR, —NR$^{14}$R$^{15}$ and oxo;
$R^6$ and $R^7$ are independently selected from the group consisting of: hydrogen, halogen, hydroxyl and $C_{1-6}$alkyl optionally substituted with 1-3 substituents independently selected from hydroxyl and halogen,
$R^6$ and $R^7$, together with the carbon atom to which they are bound, form a $C_{2-5}$alkylidene optionally substituted with 1-3 substituents independently selected from R,
$R^6$ and $R^7$ together are oxo, or
$R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;
$R^8$ is hydrogen, $C_{1-6}$alkyl or —OR;
$R^9$ is independently selected from hydrogen, —$C_{1-6}$alkyl, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)—SR, —(C(R)$_2$)$_m$—C(O)NR$^{14}$N(R)R$^{15}$, —(C(R)$_2$)$_m$—NR—C(O)—NR$^{14}$R$^{15}$, —(C(R)$_2$)$_m$—N(R)COR$^{13}$ and —(C(R)$_2$)$_m$—NR$^{14}$N(R)R$^{15}$;
$R^{13}$ is selected from the group consisting of hydrogen, $C_{1-6}$alkyl, $C_{3-8}$carbocyclyl, $C_{3-8}$heterocyclyl, $C_{1-6}$alkyl-$C_{6-14}$aryl, $C_{1-6}$alkyl-$C_{5-14}$heteroaryl, wherein $R^{13}$ is optionally substituted with —NRR or —SO$_2$NRR;
each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;
or $R^{14}$ and $R^{15}$, together with the atom or atoms to which they are joined, form a $C_{3-10}$heterocyclyl ring,
wherein $R^{14}$, $R^{15}$, or both, or a ring formed with $R^{14}$ and $R^{15}$, are optionally substituted with —(C(R)$_2$)$_m$—R$^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)

(CH$_2$)$_{0-6}$NRR, (xi) —R, (xii) —OR, (xiii) —N(R)NRR, (xiv) —C(O)N(R)NRR, —(C(R)$_2$)$_m$—O—NRR and —S—S—C$_{1-6}$alkyl-NRR;

each R is independently selected from the group consisting of: hydrogen and —C$_{1-6}$alkyl; and each m is independently 0, 1, 2 or 3;

or a pharmaceutically acceptable salt thereof

According to another aspect, the present invention relates to a compound or compounds of formula (II):

L-P    (II)

or a pharmaceutically acceptable salt thereof, wherein:
L is the linker moiety L$^1$-L$^2$-L$^3$, where L$^3$ is bound to P;
P is a radical of formula (I):

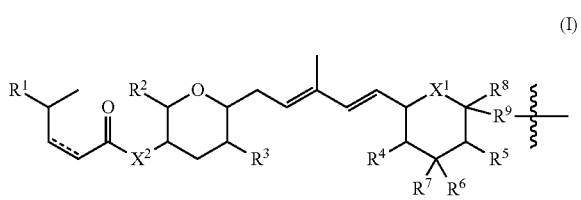

(I)

wherein:
a dashed line represents an optional bond;
each X$^1$ is independently selected from the group consisting of: —O—, —S— and —NR—;
each X$^2$ is independently selected from the group consisting of: —O—, —S— and —NR—;
each X' is CR or N;
each X" is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X" binds to L$^2$ or an additional L$^3$, or otherwise is O, S, CRR, CR—(C(R)$_2$)$_m$—NRR or NRR;
each X''' is —(C(R)$_2$)$_m$—NR— or CR—(C(R)$_2$)$_m$—O— if X''' binds to L$^2$, or otherwise is R;
Y is C(R)$_2$—, —O—, —NR— or —S—;
R$^1$ is selected from the group consisting of: —R, —OR, —OCOR$^{13}$, —OCONR$^{14}$R$^{15}$, —OCON(R$^{14}$)NR(R$^{15}$), =O (double bond to oxygen) and —NR$^{14}$R$^{15}$;
R$^2$ and R$^3$ are independently selected from the group consisting of: hydrogen and C$_{1-6}$alkyl;
R$^4$ and R$^5$ are independently selected from the group consisting of: hydrogen, —OR, —NR$^{14}$R$^{15}$ and oxo;
R$^6$ and R$^7$ are independently selected from the group consisting of: hydrogen, halogen, hydroxyl and C$_{1-6}$alkyl optionally substituted with 1-3 substituents independently selected from hydroxyl and halogen,
R$^6$ and R$^7$, together with the carbon atom to which they are bound, form a C$_{2-5}$alkylidene optionally substituted with 1-3 substituents independently selected from R,
R$^6$ and R$^7$ together are oxo, or
R$^6$ and R$^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;
R$^8$ is hydrogen, C$_{1-6}$alkyl or —OR;
R$^9$ is —(C(R)$_2$)$_m$—C(O)— or —(C(R)$_2$)$_m$—;
L$^1$ is selected from: -halogen, —NR$_2$,

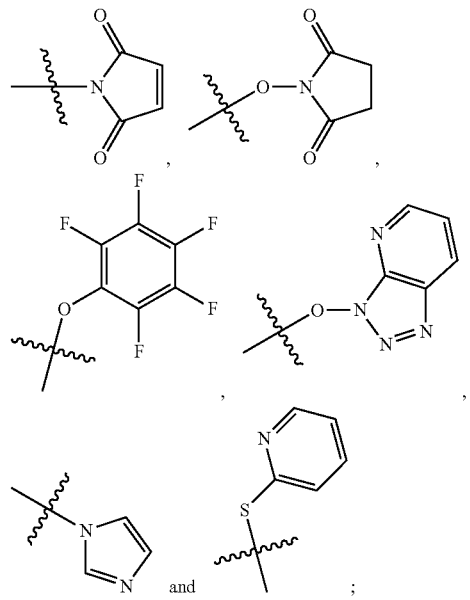

L$^2$ is L$^{2A}$-L$^{2B}$-L$^{2C}$ or L$^{2C}$-L$^{2B}$-L$^{2A}$ where:
L$^{2A}$ comprises one or more components selected from: —O—, —C(O)—, —C(O)NR—, —C(O)—C$_{1-6}$alkyl-, —C(O)NRC$_{1-6}$alkyl-, —C$_{1-6}$alkyl(OCH$_2$CH$_2$)$_{1-6}$—, alkyl-NRC(O)—, —C(O)—C$_{1-6}$alkyl(OCH$_2$CH$_2$)$_{1-6}$—, —C$_{1-6}$alkyl(OCH$_2$CH$_2$)$_{1-6}$—C(O)—, —C$_{1-6}$alkyl-S—S—C$_{1-6}$alkyl-NRC(O)—, —CH$_2$—, —C$_{1-6}$alkyl-(OCH$_2$CH$_2$)$_{1-6}$—NRC(O)CH$_2$—, —C(O)—C$_{1-6}$alkyl-NRC(O)C$_{1-6}$alkyl-, —N=CR-phenyl-O—C$_{1-6}$alkyl-, —N=CR-phenyl-O—C$_{1-6}$alkyl-C(O)—, —C(O)—C$_{1-6}$alkyl(OCH$_2$CH$_2$)$_{1-6}$—NRC(O)—, —C(O)—C$_{1-6}$alkyl-phenyl-(NR—C(O)—C$_{1-6}$alkyl)$_{1-4}$-, —C(O)—C$_{1-6}$alkyl-(OCH$_2$CH$_2$)$_{1-6}$—NRC(O)C$_{1-6}$alkyl-, —C$_{1-6}$alkyl-, —S—, —C(O)—C$_{1-6}$alkyl-phenyl-NR—, —O—C$_{1-6}$alkyl-S—, —C(O)—O—C$_{1-6}$alkyl-S— and (—CH$_2$—CH$_2$—O—)$_{1-20}$, or L$^{2A}$ is absent;

L$^B$ is selected from AA$_{0-aa}$, where AA is a natural or non-natural amino acid and aa is 12; and L$^{2C}$ comprises one or more components selected from: —PABA- and —PABC—, or L$^{2C}$ is absent;

L$^3$ is selected from one or more of: —C$_{1-6}$alkyl-, —NR—C$_3$-C$_8$heterocyclyl-NR—, —NR—C$_3$-C$_8$carbocyclyl-NR—, —NR—C$_{1-6}$alkyl-NR—, —NR—C$_{1-6}$alkyl-, —S—, —NR—, —NR—NR— and —NR—C(O)—NR— where the two R groups optionally join to form a 4-10 membered ring, —NR—C$_{1-6}$alkyl-phenyl-NR—, —NR—C$_{1-6}$alkyl-phenyl-SO$_2$—NR—, —SO$_2$—, —NR—C$_{1-6}$alkyl-phenyl-C(O)—,

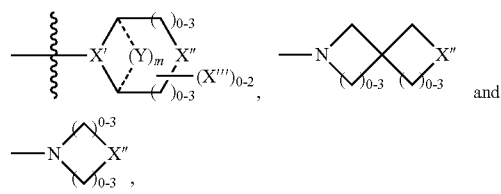

or L$^3$ is absent;
R$^{13}$ is selected from the group consisting of hydrogen, C$_{1-6}$alkyl, C$_{3-8}$carbocyclyl, C$_{3-8}$heterocyclyl, C$_{1-6}$alkyl- $C_{6-14}$aryl, $C_{1-6}$alkyl-$C_{5-14}$heteroaryl, wherein $R^{13}$ is optionally substituted with —NRR or —SO$_2$NRR;

each $R^{14}$ and $R^{15}$ is independently selected from the group consisting of: hydrogen, hydroxyl, —NRR, —NRNR$_2$, —C$_{3-10}$carbocyclyl, —C$_{1-6}$alkylene-C$_{3-10}$carbocyclyl, —C$_{3-10}$heterocyclyl, —C$_{1-6}$alkylene-C$_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —C$_{1-6}$alkyl, C$_{6-14}$aryl, —C$_{1-6}$alkylene-C$_{6-14}$aryl and —C$_{5-14}$heteroaryl;

or $R^{14}$ and $R^{15}$, together with the atom or atoms to which they are joined, form a C$_{3-10}$heterocyclyl ring, wherein $R^{14}$, $R^{15}$, or both, or a ring formed with $R^{14}$ and $R^{15}$, are optionally substituted with $(C(R)_2)_m$—R$^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—C$_{1-6}$alkyl-C(O)OR, (vii) —SO$_2$NRR, (viii) —C(O)NRR, (ix) —C(O)OR, (x) —C$_{4-6}$cycloalkyl optionally substituted with NRR, —SO$_2$NRR or NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—C$_{1-6}$alkyl-NRR;

each R is independently selected from the group consisting of: hydrogen and —C$_{1-6}$alkyl; and
each m is independently 0, 1, 2 or 3.

According to another aspect, the present invention relates to a compound or compounds of formula (II'):

L-P'  (II')

or a pharmaceutically acceptable salt thereof, wherein:
L is the linker moiety $L^1$-$L^2$-$L^3$, where $L^3$ is bound to P';
P' is a radical of formula (I'):

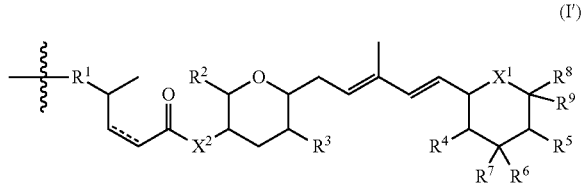

(I')

wherein:
a dashed line represents an optional bond;
each $X^1$ is independently selected from the group consisting of: —O—, —S— and —NR—;
each $X^2$ is independently selected from the group consisting of: —O—, —S— and —NR—;
each X' is CR or N;
each X" is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—CR—(C(R)$_2$)$_m$—SO$_2$NR—, CR—(C(R)$_2$)$_m$—NR—NR—, CR—(C(R)$_2$)$_m$—NR—C(O)— or N— if X" binds to $L^2$ or an additional $L^3$, or otherwise is O, S, CRR, CR(C(R)$_2$)$_m$—NRR or NRR;
each X''' is —(C(R)$_2$)$_m$—NR— or CR—(C(R)$_2$)$_m$—O— if X''' binds to $L^2$, or otherwise is R;
Y is —C(R)$_2$—, —O—, —NR— or —S—;
$R^1$ is selected from the group consisting of: —(C(R)$_2$)$_m$—, —OR", —OCOR$^{13'}$, —OC(O)NRR$^{14'}$, —OCON(R)N(R)—, and —NR—
$R^2$ and $R^3$ are independently selected from the group consisting of: hydrogen and C$_{1-6}$alkyl;
$R^4$ and $R^5$ are independently selected from the group consisting of: hydrogen, —OR, —NR$^{14}$R$^{15}$ and oxo;

$R^6$ and $R^7$ are independently selected from the group consisting of: hydrogen, halogen, hydroxyl and C$_{1-6}$alkyl optionally substituted with 1-3 substituents independently selected from hydroxyl and halogen, $R^6$ and $R^7$, together with the carbon atom to which they are bound, form a C$_{2-5}$alkylidene optionally substituted with 1-3 substituents independently selected from R, $R^6$ and $R^7$ together are oxo, or $R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;

$R^8$ is hydrogen, C$_{1-6}$alkyl or —OR;
$R^9$ is independently selected from hydrogen, —C$_{1-6}$alkyl, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)—SR, —(C(R)$_2$)$_m$—C(O)NR$^{14}$N(R)R$^{15}$, —(C(R)$_2$)$_m$—NR—C(O)—NR$^{14}$R$^{15}$, —(C(R)$_2$)$_m$—N(R)COR$^{13}$ and —(C(R)$_2$)$_m$—NR$^{14}$N(R)R$^{15}$;
$L^1$ is selected from: -halogen, —NR$_2$,

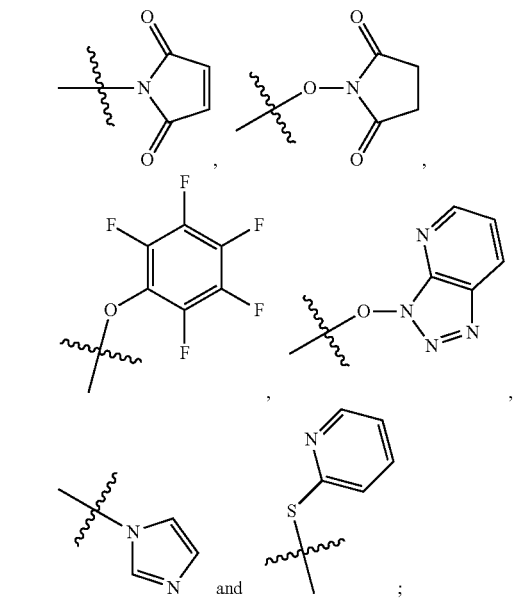

$L^2$ is $L^{2A}$-$L^{2B}$-$L^{2C}$ or $L^{2C}$-$L^{2B}$-$L^{2A}$ where:
$L^{2A}$ comprises one or more components selected from:
—O—, —C(O)—, —C(O)NR—, —C(O)—C$_{1-6}$alkyl-, —C(O)NRC$_{1-6}$alkyl-, —C$_{1-6}$alkyl(OCH$_2$CH$_2$)$_{1-6}$—, —C(O)—C$_{1-6}$alkyl-NRC(O)—, —C(O)—C$_{1-6}$alkyl(OCH$_2$CH$_2$)$_{1-6}$—, —C$_{1-6}$alkyl(OCH$_2$CH$_2$)$_{1-6}$—C(O)—, —C$_{1-6}$alkyl-S—S—C$_{1-6}$alkyl-NRC(O)CH$_2$—, —C$_{1-6}$alkyl-(OCH$_2$CH$_2$)$_{1-6}$—NRC(O)CH$_2$—, —C(O)—C$_{1-6}$alkyl-NRC(O)C$_{1-6}$alkyl-, —N═CR-phenyl-O—C$_{1-6}$alkyl-, —N═CR-phenyl-O—C$_{1-6}$alkyl-C(O)—, —C(O)—C$_{1-6}$alkyl(OCH$_2$CH$_2$)$_{1-6}$—NRC(O)—, —C(O)—C$_{1-6}$alkyl-phenyl-(NR—C(O)—C$_{1-6}$alkyl)$_{1-4}$-, —C(O)—C$_{1-6}$alkyl-(OCH$_2$CH$_2$)$_{1-6}$—NRC(C)C$_{1-6}$alkyl-, —C$_{1-6}$alkyl-, —S—, —C(O)—C$_{1-6}$alkyl-phenyl-NR—, —O—C$_{1-6}$alkyl-S—, —C(O)—O—C$_{1-6}$alkyl-S— and (—CH$_2$—CH$_2$—O—)$_{1-20}$, or $L^{2A}$ is absent;

$L^{2B}$ is selected from AA$_{0-aa}$, where AA is a natural or non-natural amino acid and aa is 12; and $L^{2C}$ comprises one or more components selected from: —PABA- and —PABC—, or $L^{2C}$ is absent;

$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

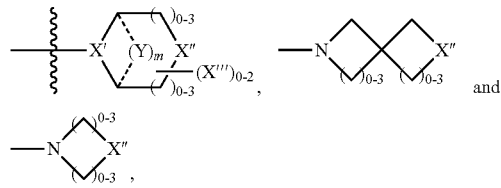

or $L^3$ is absent;

$R^{13'}$ is selected from the group consisting of a bond, —$C_{1-6}$alkylene-, —$C_{3-8}$carbocyclyl-, —$C_{3-8}$heterocyclyl-, —$C_{1-6}$alkyl-$C_{6-14}$aryl-, —$C_{1-6}$alkyl-$C_{5-14}$heteroaryl-;

each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —(C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$alkyl-NRR;

each $R^{14'}$ is independently selected from the group consisting of: a bond, —NR—, —$C_{3-10}$carbocyclyl-, —$C_{3-10}$heterocyclyl-, —(CH$_2$CH$_2$O)$_{1-6}$CH$_2$CH$_2$C(O)OR', —(CH$_2$CH$_2$O)$_{1-6}$CH$_2$CH$_2$NR—, and —$C_{1-6}$alkylene-, wherein $R^{14'}$ is optionally substituted with —(C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —NRR or —SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$alkyl-NRR;

each R is independently selected from the group consisting of: hydrogen and —$C_{1-6}$alkyl;

each R' is independently selected from —H, $C_1$-$C_8$ alkyl, $C_1$-$C_8$ heteroalkyl and aryl;

each R" is independently selected from the group consisting of: a bond and —$C_{1-6}$alkylene-; and each m is independently 0, 1, 2 or 3.

According to still another aspect, the present invention relates to a compound or compounds of formula (III):

or a pharmaceutically acceptable salt thereof, wherein:

L is the linker moiety $L^1$-$L^2$-$L^3$, where $L^3$ is bound to P;

P is a radical of formula (I):

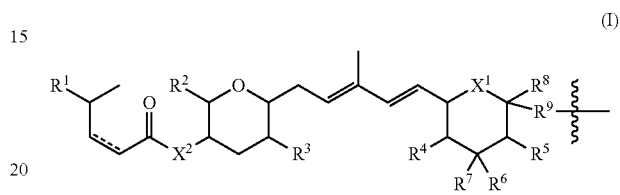

wherein:

a dashed line represents an optional bond;

AB is an antibody;

each $X^1$ is independently selected from the group consisting of: —O—, —S— and —NR—;

each $X^2$ is independently selected from the group consisting of: —O—, —S— and —NR—;

each X' is CR or N;

each X" is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X" binds to $L^2$ or an additional $L^3$, or otherwise is O, S, CRR, CR—(C(R)$_2$)$_m$—NRR or NRR;

each X'" is —(C(R)$_2$)$_m$—NR— or CR—(C(R)$_2$)$_m$—O— if X'" binds to $L^2$, or otherwise is R;

Y is —C(R)$_2$—, —O—, —NR— or —S—;

$R^1$ is selected from the group consisting of: —R, —OR, —OCOR$^{13}$, —OCONR$^{14}$R$^{15}$, —OCON(R$^{14}$)NR(R$^{15}$), =O (double bond to oxygen) and —NR$^{14}$R$^{15}$;

$R^2$ and $R^3$ are independently selected from the group consisting of: hydrogen and $C_{1-6}$alkyl;

$R^4$ and $R^5$ are independently selected from the group consisting of: hydrogen, —OR, —NR$^{14}$R$^{15}$ and oxo;

$R^6$ and $R^7$ are independently selected from the group consisting of: hydrogen, halogen, hydroxyl and $C_{1-6}$alkyl optionally substituted with 1-3 substituents independently selected from hydroxyl and halogen, $R^6$ and $R^7$, together with the carbon atom to which they are bound, form a $C_{2-5}$alkylidene optionally substituted with 1-3 substituents independently selected from R, $R^6$ and $R^7$ together are oxo, or $R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;

$R^8$ is hydrogen, $C_{1-6}$alkyl or —OR;

$R^9$ is —(C(R)$_2$)$_m$—C(O)— or —(C(R)$_2$)$_m$—;

L¹ is selected from: a bond to AB, —NR— (bond to AB) and

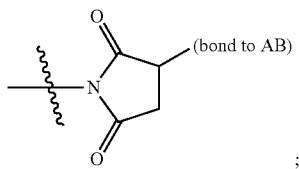

L² is L²ᴬ-L²ᴮ-L²ᶜ or L²ᶜ-L²ᴮ-L²ᴬ where:
L²ᴬ comprises one or more components selected from:
—O—, —C(O)—, —C(O)NR—, —C(O)—C$_{1-6}$alkyl-,
—C(O)NRC$_{1-6}$alkyl-, —C$_{1-6}$alkyl(OCH$_2$CH$_2$)$_{1-6}$—,
—C(O)—C$_{1-6}$alkyl-NRC(O)—, —C(O)—C$_{1-6}$alkyl(OCH$_2$CH$_2$)$_{1-6}$—, —C$_{1-6}$alkyl(OCH$_2$CH$_2$)$_{1-6}$—C(O)—,
—C$_{1-6}$alkyl-S—S—C$_{1-6}$alkyl-NRC(O)CH$_2$—, —C$_{1-6}$alkyl-(OCH$_2$CH$_2$)$_{1-6}$—NRC(O)CH$_2$—, —C(O)—C$_{1-6}$alkyl-NRC(O)C$_{1-6}$alkyl-, —N=CR-phenyl-O—C$_{1-6}$alkyl-, —N=CR-phenyl-O—C$_{1-6}$alkyl-C(O)—, —C(O)—C$_{1-6}$alkyl(OCH$_2$CH$_2$)$_{1-6}$—NRC(O)—, —C(O)—C$_{1-6}$alkyl-phenyl-(NR—C(O)—C$_{1-6}$alkyl)$_{1-4}$-, —C(O)—C$_{1-6}$alkyl-(OCH$_2$CH$_2$)$_{1-6}$—NRC(O)C$_{1-6}$alkyl-, —C$_{1-6}$alkyl-, —S—,
—C(O)—C$_{1-6}$alkyl-phenyl-NR—, —O—C$_{1-6}$alkyl-S—,
—C(O)—O—C$_{1-6}$alkyl-S— and (—CH$_2$—CH$_2$—O—)$_{1-20}$, or L²ᴬ is absent;
L²ᴮ is selected from AA$_{0-aa}$, where AA is a natural or non-natural amino acid and aa is 12; and
L²ᶜ comprises one or more components selected from: —PABA- and —PABC—, or L²ᶜ is absent;
L³ is selected from one or more of: —C$_{1-6}$alkyl-, —NR—C$_3$-C$_8$heterocyclyl-NR—, —NR—C$_3$-C$_8$carbocyclyl-NR—, —NR—C$_{1-6}$alkyl-NR—, —NR—C$_{1-6}$alkyl-, —S—, —NR—, —NR—NR— and —NR—C(O)—NR— where the two R groups optionally join to form a 4-10 membered ring, —NR—C$_{1-6}$alkyl-phenyl-NR—, —NR—C$_{1-6}$alkyl-phenyl-SO$_2$—NR—, —SO$_2$—, —NR—C$_{1-6}$alkyl-phenyl-C(O)—,

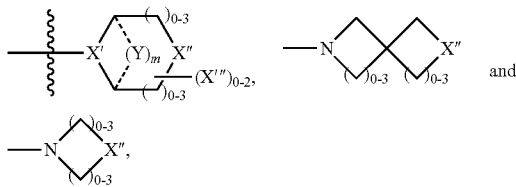

or L³ is absent;
R¹³ is selected from the group consisting of hydrogen, C$_{1-6}$alkyl, C$_{3-8}$carbocyclyl, C$_{3-8}$heterocyclyl, C$_{1-6}$alkyl-C$_{6-14}$aryl, C$_{1-6}$alkyl-C$_{5-14}$heteroaryl, wherein R¹³ is optionally substituted with —NRR or —SO$_2$NRR;
each R¹⁴ and R¹⁵ is independently selected from the group consisting of: hydrogen, hydroxyl, —NRR, —NRNR$_2$, —C$_{3-10}$carbocyclyl, —C$_{1-6}$alkylene-C$_{3-10}$carbocyclyl, —C$_{3-10}$heterocyclyl, —C$_{1-6}$alkylene-C$_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —C$_{1-6}$alkyl, C$_{6-14}$aryl, —C$_{1-6}$alkylene-C$_{6-14}$aryl and —C$_{5-14}$heteroaryl;
or R¹⁴ and R¹⁵, together with the atom or atoms to which they are joined, form a C$_{3-10}$heterocyclyl ring, wherein R¹⁴, R¹⁵, or both, or a ring formed with R¹⁴ and R¹⁵, are optionally substituted with —(C(R)$_2$)$_m$—R¹⁸ where each R¹⁸ is independently selected from (i) —NRR, (ii)

—C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—C$_{1-6}$alkyl-C(O)OR, (vii) —SO$_2$NRR, (viii) —C(O)NRR, (ix) —C(O)OR, (x) —C$_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—C$_{1-6}$alkyl-NRR;
each R is independently selected from the group consisting of: hydrogen and —C$_{1-6}$alkyl; and
b is 1-20; and
each m is independently 0, 1, 2 or 3.
According to yet another aspect, the present invention relates to a compound or compounds of formula (III'):

(AB)-(L-P)$_b$    (III')

or a pharmaceutically acceptable salt thereof, wherein:
L is the linker moiety L¹-L²-L³, where L³ is bound to P';
P' is a radical of formula (F):

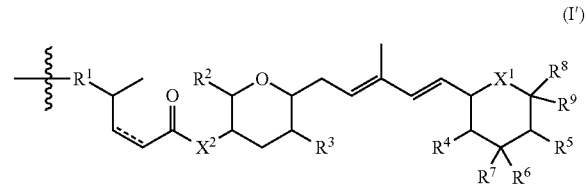

wherein:
a dashed line represents an optional bond;
AB is an antibody;
each X¹ is independently selected from the group consisting of: —O—, —S— and —NR—;
each X² is independently selected from the group consisting of: —O—, —S— and —NR—;
each X' is CR or N;
each X" is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X" binds to L² or an additional L³, or otherwise is O, S, CRR, CR—(C(R)$_2$)$_m$—NRR or NRR;
each X''' is —(C(R)$_2$)$_m$—NR— or CR—(C(R)$_2$)$_m$—O— if X''' binds to L², or otherwise is R;
Y is C(R)$_2$—, —O—, —NR— or —S—;
R¹ is selected from the group consisting of: —(C(R)$_2$)$_m$—C(O)—, —(C(R)$_2$)$_m$—, —OR", —OCOR¹³', —OCONRR¹⁴', —OCON(R¹⁴)N(R¹⁵)—, and —NR¹⁴—
R² and R³ are independently selected from the group consisting of: hydrogen and C$_{1-6}$alkyl;
R⁴ and R⁵ are independently selected from the group consisting of: hydrogen, —OR, —NR¹⁴R¹⁵ and oxo;
R⁶ and R⁷ are independently selected from the group consisting of: hydrogen, halogen, hydroxyl and C$_{1-6}$alkyl optionally substituted with 1-3 substituents independently selected from hydroxyl and halogen,
R⁶ and R⁷, together with the carbon atom to which they are bound, form a C$_{2-5}$alkylidene optionally substituted with 1-3 substituents independently selected from R,
R⁶ and R⁷ together are oxo, or
R⁶ and R⁷, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;

$R^8$ is hydrogen, $C_{1-6}$alkyl or —OR;

$R^9$ is independently selected from hydrogen, —$C_{1-6}$alkyl, —$(C(R)_2)_m$—C(O)OR, —$(C(R)_2)_m$—C(O)NR$^{14}$R$^{15}$, —$(C(R)_2)_m$—NR$^{14}$R$^{15}$, —$(C(R)_2)_m$—C(O)—SR, —$(C(R)_2)_m$—C(O)NR$^{14}$N(R)R$^{15}$, —$(C(R)_2)_m$—NR—C(O)—NR$^{14}$R$^{15}$, —$(C(R)_2)_m$—N(R)COR$^{13}$ and $(C(R)_2)_m$—NR$^{14}$N(R)R$^{15}$;

$L^1$ is selected from: a bond to AB, —NR— (bond to AB) and

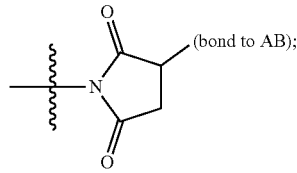

$L^2$ is $L^{2A}$-$L^{2B}$-$L^{2C}$ or $L^{2C}$-$L^{2B}$-$L^{2A}$ where:

$L_2^A$ comprises one or more components selected from: —O—, —C(O)—, —C(O)NR—, —C(O)—$C_{1-6}$alkyl-, —C(O)NR$C_{1-6}$alkyl-, —$C_{1-6}$alkyl(OCH$_2$CH$_2$)$_{1-6}$—, —C(O)—$C_{1-6}$alkyl-NRC(O)—, —C(O)—$C_{1-6}$alkyl(OCH$_2$CH$_2$)$_{1-6}$—, —$C_{1-6}$alkyl(OCH$_2$CH$_2$)$_{1-6}$—C(O)—, —$C_{1-6}$alkyl-S—S—$C_{1-6}$alkyl-NRC(O)CH$_2$—, —$C_{1-6}$alkyl-(OCH$_2$CH$_2$)$_{1-6}$—NRC(O)CH$_2$—, —C(O)—$C_{1-6}$alkyl-NRC(O)$C_{1-6}$alkyl-, —N=CR-phenyl-O—$C_{1-6}$alkyl-, —N=CR-phenyl-O—$C_{1-6}$alkyl-C(O)—, —C(O)—$C_{1-6}$alkyl(OCH$_2$CH$_2$)$_{1-6}$—NRC(O)—, —C(O)—$C_{1-6}$alkyl-phenyl-(NR—C(O)—$C_{1-6}$alkyl)$_{1-4}$-, —C(O)—$C_{1-6}$alkyl-(OCH$_2$CH$_2$)$_{1-6}$—NRC(O)$C_{1-6}$alkyl-, —S—, —C(O)—$C_{1-6}$alkyl-phenyl-NR—, —C(O)—O—$C_{1-6}$alkyl-S— and (—CH$_2$—CH$_2$—O—)$_{1-20}$, or $L^{2A}$ is absent;

$L^{2B}$ is selected from $AA_{0-aa}$, where AA is a natural or non-natural amino acid and aa is 12; and $L^{2C}$ comprises one or more components selected from: —PABA- and —PABC—, or $L^{2C}$ is absent;

$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

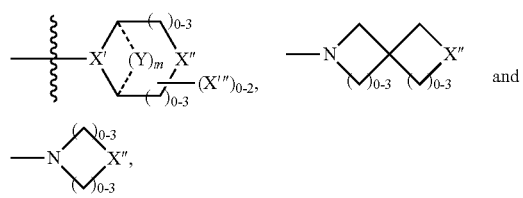

or $L^3$ is absent;

$R^{13'}$ is selected from the group consisting of a bond, —$C_{1-6}$alkylene-, —$C_{3-8}$carbocyclyl-, —$C_{3-8}$heterocyclyl-, —$C_{1-6}$alkyl-$C_{6-14}$aryl-, —$C_{1-6}$alkyl-$C_{5-14}$heteroaryl-;

each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —$(C(R)_2)_m$—R$^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —$(C(R)_2)_m$—NRR or —$(C(R)_2)_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —$(C(R)_2)_m$—O—NRR and (xiv) —S—S—$C_{1-6}$alkyl-NRR;

each $R^{14'}$ is independently selected from the group consisting of: a bond, —NR—, —$C_{3-10}$carbocyclyl-, —$C_{3-10}$heterocyclyl-, —(CH$_2$CH$_2$O)$_{1-6}$CH$_2$CH$_2$C(O)OR', —(CH$_2$CH$_2$O)$_{1-6}$CH$_2$CH$_2$NR—, and —$C_{1-6}$alkylene-, wherein $R^{14'}$ is optionally substituted with —$(C(R)_2)_m$—R$^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —NRR or —SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —$(C(R)_2)_m$—O—NRR and (xiv) —S—S—$C_{1-6}$alkyl-NRR;

each R is independently selected from the group consisting of: hydrogen and —$C_{1-6}$alkyl;

each R' is independently selected from —H, $C_1$-$C_5$ alkyl, $C_1$-$C_8$heteroalkyl and aryl;

each R" is independently selected from the group consisting of: a bond and —$C_{1-6}$alkylene-; and b is 1-20; and each m is independently 0, 1, 2 or 3.

It is to be noted that divalent variables recited in the above are meant to depict, where appropriate, the positioning of such radicals in multiple orientations within the molecule. Thus, for instance, to cite but a single example, the $L^2$ moiety "—PABC-Cit-Val-C(O)—$C_{1-6}$alkyl-" between $L^1$ and $L^3$ can be positioned as $L^1$-PABC-Cit-Val-C(O)—$C_{1-6}$alkyl-$L^3$ or as $L^1$-$C_{1-6}$alkyl-C(O)-Val-Cit-PABC-$L^3$. Similarly, L2 is defined herein as comprising L2A-L2B-L2C, which construct may likewise be positioned in multiple orientations.

Thus, in certain embodiments there is provided an ADC of the formula III or III' having the following sequence of components:

AB-$L^1$-$L^2$-$L^3$-P;

AB-$L^1$-$L^2$-$L^3$-P';

AB-$L^1$-$L^{2A}$-$L^{2B}$-$L^{2C}$-$L^3$-P; or

AB-$L^1$-$L^{2C}$-$L^{2B}$-$L^{2A}$-$L^3$-P.

Certain chemical groups and moieties described herein are preferred, depending on circumstances. Thus, in certain embodiments of the invention, including with respect to the various payloads, linker-payloads and ADCs described and claimed herein, one or more (or all, or none) of the following may apply:

In certain embodiments of the invention $X^1$ is preferably —O—.

In certain embodiments of the invention $X^2$ is preferably —NR—.

In certain embodiments of the invention $R^1$ is preferably selected from the group consisting of: —OR, —OCOR$^{13}$, —OCONR$^{14}$R$^{15}$ and —NR$^{14}$R$^{15}$.

In certain embodiments of the invention $R^2$ is preferably $C_{1-6}$alkyl, and is more preferably is methyl.

In certain embodiments of the invention $R^3$ is preferably $C_{1-6}$alkyl, and is more preferably is methyl.

In certain embodiments of the invention $R^4$ is preferably hydrogen or —OR.

In certain embodiments of the invention $R^5$ is preferably hydrogen or —OR.

In certain embodiments of the invention it is preferred that $R^6$ and $R^7$ are each independently selected from the group consisting of: hydroxyl and $C_{1-6}$alkyl optionally substituted with 1-3 substituents independently selected from and halogen, or $R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R.

In certain embodiments of the invention $R^8$ is preferably hydrogen or —OR.

In certain embodiments of the invention $R^9$ is independently selected from, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)NR$^{14}$N(R)R$^{15}$, —(C(R)$_2$)$_m$—NR—C(O)—NR$^{14}$R$^{15}$ and (C(R)$_2$)$_m$—N(R)COR$^{13}$.

In certain embodiments of the invention $R^{13}$ is preferably selected from the group consisting of hydrogen, $C_{1-6}$alkyl.

In certain embodiments of the invention it is preferred that each $R^{14}$ and $R^{15}$ is independently selected from the group consisting of: hydrogen, —NRR, —NRNR$_2$, —C$_{3-10}$carbocyclyl, —C$_{3-10}$heterocyclyl, —C$_{1-6}$alkyl, C$_{6-14}$aryl, —C$_{1-6}$alkylene-C$_{6-14}$aryl and —C$_{5-14}$heteroaryl; or $R^{14}$ and $R^{15}$, together with the atom or atoms to which they are joined, form a C$_{3-10}$heterocyclyl ring; wherein $R^{14}$, $R^{15}$, or both, or a ring formed with $R^{14}$ and $R^{15}$, are optionally substituted with (C(R)$_2$)$_m$—R$^{18}$ where each R$^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or (C(R)$_2$)$_m$—SO$_2$NRR, (v) —SO$_2$R, (vi) —S—S—C$_{1-6}$alkyl-C(O)OR, (vii) —SO$_2$NRR, (viii) —C(O)NRR, (ix) —C(O)OR, (x) —C$_{4-6}$cycloalkyl optionally substituted with NRR, —SO$_2$NRR or NR—C(O)(CH$_2$)$_{0-6}$NRR, (xi) —R, (xii) —OR, (xiii) —N(R)NRR, (xiv) —C(O)N(R)NRR, —(C(R)$_2$)$_m$—O—NRR and —S—S—C$_{1-6}$alkyl-NRR.

In certain embodiments of the invention it is preferred that m is 0. In certain embodiments of the invention it is preferred that m is 1. In certain embodiments of the invention it is preferred that m is 2. In certain embodiments of the invention it is preferred that m is 3.

In certain embodiments of the invention it is preferred that $X^2$ is NH—, $X^1$ is —O—, $R^1$ is —OCOR$^{13}$, OH or —OCONR$^{14}$R$^{15}$, $R^2$ is methyl, $R^3$ is methyl, $R^4$ is —OH, $R^5$ is hydrogen, $R^8$ is hydrogen, $R^6$ and $R^7$ together form epoxide, $R^9$ is —(C(R)$_2$)$_m$—C(O)—, $R^{13}$ is C$_{1-6}$ alkyl (more preferably methyl), $R^{14}$ and $R^{15}$, together with the atom or atoms to which they are joined, form a C$_{3-10}$heterocyclyl ring, $L^1$ is

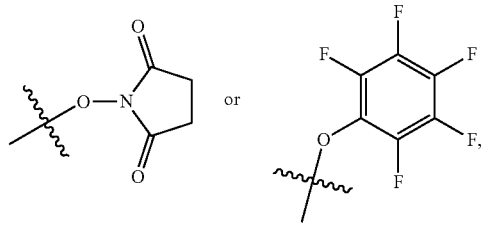 [SMILES: *ON1C(=O)CCC1=O ; *Oc1c(F)c(F)c(F)c(F)c1F]

and $L^{2A}$, $L^{2B}$, $L^{2C}$ and $L^3$ are all absent. Alternatively $R^6$ is —OH and $R^7$ is $C_{1-6}$alkyl optionally substituted with 1-3 substituents independently selected from a halogen, with chlorine being more preferable.

In certain embodiments of the invention it is preferred that $X^2$ is NH—, $X^1$ is —O—, $R^1$ is —OCOR$^{13}$, OH or —OCONR$^{14}$R$^{15}$, $R^2$ is methyl, $R^3$ is methyl, $R^4$ is —OH, $R^5$ is hydrogen, $R^8$ is hydrogen, $R^6$ and $R^7$ together form epoxide, $R^9$ is —(C(R)$_2$)$_m$—C(O)—, $R^{13}$ is C$_{1-6}$ alkyl (more preferably methyl), $R^{14}$ and $R^{15}$, together with the atom or atoms to which they are joined, form a C$_{3-10}$heterocyclyl ring, $L^1$ is a halogen, $L^3$ is —NR—C$_{1-6}$alkyl-NR with R more preferably being hydrogen and the alkyl group more preferably being ethyl, $L^{2A}$ is —C(O)—C$_{1-6}$alkyl- and $L^{2B}$ and $L^{2C}$ are absent.

In certain embodiments of the invention it is preferred that $X^2$ is NH—, $X^1$ is —O—, $R^1$ is —OCOR$^{13}$ where R13 is more preferably hydrogen, $R^2$ is methyl, $R^3$ is methyl, $R^4$ is —OH, $R^5$ is hydrogen, $R^8$ is hydrogen, $R^6$ and $R^7$ together form epoxide, $R^9$ is —(C(R)$_2$)$_m$—C(O)—, $R^{13}$ is C$_{1-6}$ alkyl (more preferably methyl), $R^{14}$ and $R^{15}$, together with the atom or atoms to which they are joined, form a C$_{3-10}$heterocyclyl ring, $L^1$ is a halogen, $L^3$ is —NR—C$_{1-6}$alkyl-NR with R more preferably being hydrogen and the alkyl group more preferably being ethyl, $L^{2A}$ is —C(O)—C$_{1-6}$alkyl- and $L^{2B}$ and $L^{2C}$ are absent.

In certain embodiments of the invention it is preferred that R1 is —OCOR$^{13}$ or —OR where R is more preferably hydrogen, $R^2$ is methyl, $R^3$ is methyl, $R^4$ is —OH, $R^5$ is hydrogen, $R^8$ is hydrogen, $R^6$ and $R^7$ form an epoxide, $R^9$ is —(C(R)$_2$)$_m$—C(O)—, $L^3$ is —NR—NR— where each R is more preferably hydrogen or methyl or the two R substituents together form a 6 membered ring, $L^1$ is a halogen, —NR$^2$ or

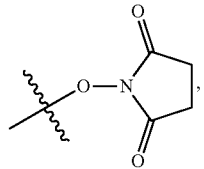 [SMILES: *ON1C(=O)CCC1=O]

$L^{2C}$ is PABC, $L^{2B}$ is -Cit-Val-, $L^{2A}$ is —C(O)—C$_{1-6}$alkyl-NRC(O)C$_{1-6}$alkyl-.

In certain embodiments of the invention it is preferred that R1 is —OCOR$^{13}$ or —OR where R is more preferably hydrogen, $R^2$ is methyl, $R^3$ is methyl, $R^4$ is —OH, $R^5$ is hydrogen, $R^8$ is hydrogen, $R^6$ and $R^7$ form an epoxide, $R^9$ is —(C(R)$_2$)$_m$—C(O)—, $L^3$ is —NR—NR— where each R is more preferably hydrogen or methyl or the two R substituents together form a 6 membered ring, $L^1$ is a halogen, —NR$^2$ or

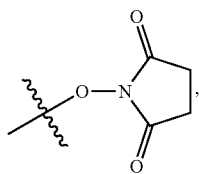

$L^{2C}$ is absent; $L^{2B}$ is -Ala-Val- and $L^{2A}$ is —C(O)—$C_{1-6}$alkyl-NRC(O)$C_{1-6}$alkyl- or —C(O)$C_{1-6}$alkyl-.

In certain embodiments of the invention it is preferred that $L^1$ is selected from: -halogen, —$NR_2$,

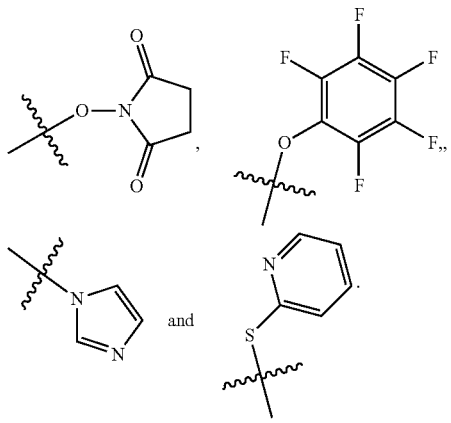

In certain embodiments of the invention it is preferred that $R^1$ is —$OCOR^{13'}$, $R^2$ is methyl, $R^3$ is methyl, $R^4$ is —OH, $R^5$ is hydrogen, $R^8$ is hydrogen, $R^9$ is —$(C(R)_2)_m$—$C(O)NR^{14}R^{15}$ where $R^{14}$ and $R^{15}$ are more preferably hydrogen, $R^{13'}$ is a bond, $L^3$ is

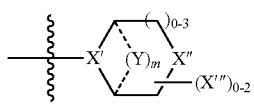

where m is 0, X' is N, X" is —N— and X'" is absent, $L^1$ is a halogen, $L^{2C}$ is PABC, $L^{2B}$ is -Cit-Val- and $L^{2A}$ is —C(O)—$C_{1-6}$alkyl-NRC(O)$C_{1-6}$alkyl-.

In certain embodiments of the invention it is preferred that $X^2$ is NH—, $X^1$ is —O—, $R^1$ is —$OCOR^{13}$, OH or —$OCONR^{14}R^{15}$, $R^2$ is methyl, $R^3$ is methyl, $R^4$ is —OH, $R^5$ is hydrogen, $R^8$ is hydrogen, $R^6$ and $R^7$ together form epoxide, $R^9$ is —$(C(R)_2)_m$—C(O)—, $R^{13}$ is $C_{1-6}$ alkyl (more preferably methyl), $R^{14}$ and $R^{15}$, together with the atom or atoms to which they are joined, form a $C_{3-10}$heterocyclyl ring, $L^1$ is selected from: a bond to AB, —NR— (bond to AB) and

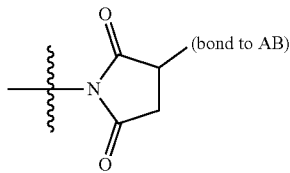

and $L^{2A}$, $L^{2B}$, $L^{2C}$ and $L^3$ are all absent. Alternatively $R^6$ is —OH and $R^7$ is $C_{1-6}$alkyl optionally substituted with 1-3 substituents independently selected from a halogen, with chlorine being more preferable.

In certain embodiments of the invention it is preferred that $X^2$ is —NH—, $X^1$ is —O—, $R^1$ is —$OCOR^{13}$, OH or —$OCONR^{14}R^{15}$, $R^2$ is methyl, $R^3$ is methyl, $R^4$ is —OH, $R^5$ is hydrogen, $R^8$ is hydrogen, $R^6$ and $R^7$ together form epoxide, $R^9$ is —$(C(R)_2)_m$—C(O)—, $R^{13}$ is $C_{1-6}$ alkyl (more preferably methyl), $R^{14}$ and $R^{15}$, together with the atom or atoms to which they are joined, form a $C_{3-10}$heterocyclyl ring, $L^1$ is selected from: a bond to AB, —NR— (bond to AB) and

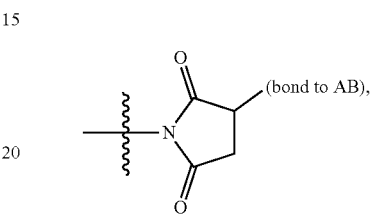

$L^3$ is —NR—$C_{1-6}$alkyl-NR with R more preferably being hydrogen and the alkyl group more preferably being ethyl, $L^{2A}$ is —C(O)—$C_{1-6}$alkyl- and $L^{2B}$ and $L^{2C}$ are absent.

In certain embodiments of the invention it is preferred that $X^2$ is —NH—, $X^1$ is —O—, $R^1$ is —$OCOR^{13}$ where R13 is more preferably hydrogen, $R^2$ is methyl, $R^3$ is methyl, $R^4$ is —OH, $R^5$ is hydrogen, $R^8$ is hydrogen, $R^6$ and $R^7$ together form epoxide, $R^9$ is —$(C(R)_2)_m$—C(O)—, $R^{13}$ is $C_{1-6}$ alkyl (more preferably methyl), $R^{14}$ and $R^{15}$, together with the atom or atoms to which they are joined, form a $C_{3-10}$heterocyclyl ring, $L^1$ is selected from: a bond to AB, —NR— (bond to AB) and

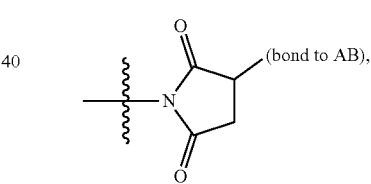

$L^3$ is —NR—$C_{1-6}$alkyl-NR with R more preferably being hydrogen and the alkyl group more preferably being ethyl, $L^{2A}$ is —C(O)—$C_{1-6}$alkyl- and $L^{2B}$ and $L^{2C}$ are absent.

In certain embodiments of the invention it is preferred that R1 is —$OCOR^{13}$ or —OR where R is more preferably hydrogen, $R^2$ is methyl, $R^3$ is methyl, $R^4$ is —OH, $R^5$ is hydrogen, $R^8$ is hydrogen, $R^6$ and $R^7$ form an epoxide, $R^9$ is —$(C(R)_2)_m$—C(O)—, $L^3$ is —NR—NR— where each R is more preferably hydrogen or methyl or the two R substituents together form a 6 membered ring, $L^1$ is selected from: a bond to AB, —NR— (bond to AB) and

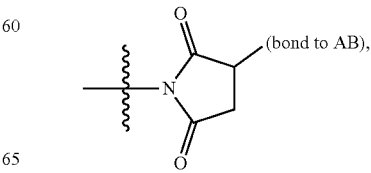

$L^{2C}$ is PABC, $L^{2B}$ is -Cit-Val-, $L^{2A}$ is —C(O)—$C_{1-6}$alkyl-NRC(O)$C_{1-6}$alkyl-.

In certain embodiments of the invention it is preferred that R1 is —OCOR$^{13}$ or —OR where R is more preferably hydrogen, $R^2$ is methyl, $R^3$ is methyl, $R^4$ is —OH, $R^5$ is hydrogen, $R^8$ is hydrogen, $R^6$ and $R^7$ form an epoxide, $R^9$ is —(C(R)$_2$)$_m$—C(O)—, $L^3$ is —NR—NR— where each R is more preferably hydrogen or methyl or the two R substituents together form a 6 membered ring, $L^1$ is selected from: a bond to AB, —NR— (bond to AB) and

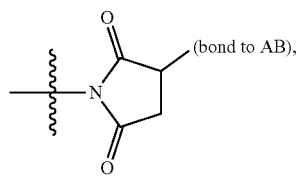

$L^{2C}$ is absent; $L^{2B}$ is -Ala-Val- and $L^{2A}$ is —C(O)—$C_{1-6}$alkyl-NRC(O)$C_{1-6}$alkyl-.

In certain embodiments of the invention it is preferred that $L^1$ is selected from: a bond to AB, —NR— (bond to AB) and

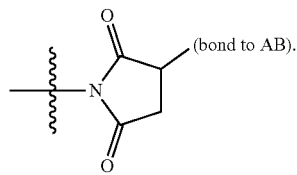

In certain embodiments of the invention it is preferred that the antibody is selected from trastuzumab, the (C392+L443) trastuzumab mutant, and the (C392+C443) trastuzumab mutant.

In certain embodiments of the invention it is preferred that the antibody bound via an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase.

In certain embodiments, the present invention relates to any of the aforementioned antibody drug conjugates and attendant definitions, wherein the antibody drug conjugate comprises between 2, 3, 4, 5, 6, 7, 8, 9 or 10 compounds of the invention.

In certain embodiments, the present invention relates to any of the aforementioned antibody drug conjugates and attendant definitions, wherein the antibody drug conjugate comprises 3 or 4 compounds of the invention.

The typically carboxyl- and/or amino-containing compounds of the present invention bear distinct and unique advantages over non-carboxyl containing compounds. One such advantage lies in improved water solubility. Another advantage is improved chemical stability in water and in biological fluids such as serum, blood, cerebral spinal fluid and in drug formulations. Yet another advantage is the ability to readily prepare salt forms of carboxylate compounds by pairing them with an appropriate anion such as chloride, acetate, and other counter-ion. Moreover, the carboxylate compounds of the present invention can readily be used to prepare amide and ester derivatives with have potent and improved cytotoxicity against cancer cell lines and cancers. Carboxylate containing compounds additionally have an advantage in their ability to be linked to antibodies, as the carboxylic acid group can be reacted with appropriately modified linker molecules bearing amine, alcohol and other groups to obtain payload-linkers. The carboxylic acid compounds can also be directly functionalized to obtain activated carboxylic acid derivatives, which can subsequently be conjugated to antibodies without appending additional linkers. For example, the inventive carboxylic acid containing compounds may be reacted with N-hydroxysuccinimide to obtain activated carboxyl-NHS esters. The carboxyl-NHS esters and payload-linkers made therefore can then be reacted with antibodies to produce antibody drug conjugates.

The Antibody Unit (Ab or AB)

As noted above, the term "antibody" (or "Ab" or "AB") herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. In addition, while certain aspects of the invention described herein refer to antibody drug conjugates, it is further envisioned that the antibody portion of the conjugate might be replaced with anything that specifically binds or reactively associates or complexes with a receptor, antigen or other receptive moiety associated with a given target-cell population. For example, instead of containing an antibody a conjugates of the invention could contain a targeting molecule that binds to, complexes with, or reacts with a receptor, antigen or other receptive moiety of a cell population sought to be therapeutically or otherwise biologically modified. Example of such molecules include smaller molecular weight proteins, polypeptide or peptides, lectins, glycoproteins, non-peptides, vitamins, nutrient-transport molecules (such as, but not limited to, transferrin), or any other cell binding molecule or substances. In certain aspects, the antibody or other such targeting molecule acts to deliver a drug to the particular target cell population with which the antibody or other targeting molecule interacts.

In another aspect, the present invention relates to an antibody drug conjugate compound of formulae III or III' wherein the antibody AB is selected from: trastuzumab, trastuzumab mutants (for instance the trastuzumab mutants disclosed herein or in international patent application PCT/IB2012/056234), oregovomab, edrecolomab, cetuximab, a humanized monoclonal antibody to the vitronectin receptor ($\alpha_v\beta_3$), alemtuzumab, anti-HLA-DR antibodies including a humanized anti-HLA-DR antibody for the treatment of non-Hodgkin's lymphoma, 131I Lym-1, anti-HLA-Dr10 antibodies including a murine anti-HLA-Dr10 antibody for the treatment of non-Hodgkin's lymphoma, anti-cd33 antibodies, anti-cd22 antibodies including a humanized anti-CD22 mAb for the treatment of Hodgkin's Disease or non-Hodgkin's lymphoma, labetuzumab, bevacizumab, ibritumomab tiuxetan, ofatumumab, panitumumab, rituximab, tositumomab, ipilimumab, and gemtuzumab.

Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These hetero atoms can be present on the antibody in the antibody's natural state, for example a naturally-occurring antibody, or can be introduced into the antibody via chemical modification.

In one embodiment, an antibody unit has a sulfhydryl group and the antibody unit bonds via the sulfhydryl group's sulfur atom.

In another embodiment, the antibody has lysine residues that can react with activated esters (such esters include, but are not limited to, N-hydroxysuccinimide, pentafluorophenyl, and p-nitrophenyl esters) and thus form an amide bond consisting of the nitrogen atom of the antibody unit and a carbonyl.

In yet another aspect, the antibody unit has one or more lysine residues that can be chemically modified to introduce one or more sulfhydryl groups. The reagents that can be used to modify lysines include, but are not limited to, N-succinimidyl S-acetylthioacetate (SATA) and 2-Iminothiolane hydrochloride (Traut's Reagent).

In another embodiment, the antibody unit can have one or more carbohydrate groups that can be chemically modified to have one or more sulfhydryl groups.

In yet another embodiment, the antibody unit can have one or more carbohydrate groups that can be oxidized to provide an aldehyde group (see, e.g., Laguzza, et al., 1989, J. Med. Chem. 32(3):548-55). The corresponding aldehyde can form a bond with a reactive site such as, for example, hydrazine and hydroxylamine. Other protocols for the modification of proteins for the attachment or association of drugs are described in Coligan et al., Current Protocols in Protein Science, vol. 2, John Wiley & Sons (2002) (incorporated herein by reference).

When the conjugates comprise non-immunoreactive protein, polypeptide, or peptide units instead of an antibody, useful non-immunoreactive protein, polypeptide, or peptide units include, but are not limited to, transferrin, epidermal growth factors ("EGF"), bombesin, gastrin, gastrin-releasing peptide, platelet-derived growth factor, IL-2, IL-6, transforming growth factors ("TOP"), such as TGF-α and TGF-β, vaccinia growth factor ("VGF"), insulin and insulin-like growth factors I and II, somatostatin, lectins and apoprotein from low density lipoprotein.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, antibody fragments, or chimeric monoclonal antibodies. Human monoclonal antibodies may be made by any of numerous techniques known in the art (e.g., Teng et al., 1983, Proc. Natl. Acad. Sci. USA. 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art and are discussed infra.

The antibody can be a functionally active fragment, derivative or analog of an antibody that immunospecifically binds to target cells (e.g., cancer cell antigens, viral antigens, or microbial antigens) or other antibodies that bind to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (for location of the CDR sequences, see, e.g., Kabat et al., 1991, Sequences of Proteins of Immunological Interest, Fifth Edition, National Institute of Health, Bethesda, Md.; Kabat E et al., 1980, J. Immunology 125(3):961-969).

Other useful antibodies include fragments of antibodies such as, but not limited to, $F(ab')_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. No. 4,816,567; and U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239: 1534; and Beidler et al., 1988, J. Immunol. 141:4053-4060; each of which is incorporated herein by reference in its entirety.

Completely human antibodies are particularly desirable and can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (now Amgen, Freemont, Calif.) and Medarex (Princeton, N.J.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903). Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, The rise of monoclonal antibodies as therapeutics, In Anti-IgE and Allergic Disease, Jardieu and Fick, eds., Marcel Dekker, New York, N.Y., Chapter 20, pp. 427-469).

In other embodiments, the antibody is a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, preferably at least 10, 20 or 50 amino acid portion of the protein) that is not from an antibody. Preferably, the antibody or fragment thereof is covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, literature publications, or by routine cloning and sequencing.

In a specific embodiment, known antibodies for the treatment of cancer can be used. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, OVAREX which is a murine antibody for the treatment of ovarian cancer; PANOREX (Glaxo Wellcome, NC) which is a murine $IgG_{2a}$ antibody for the treatment of colorectal cancer; Cetuximab ERBITUX (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; CAMPATH I/H (Leukosite, MA) which is a humanized $IgG_1$ antibody for the treatment of chronic lymphocytic leukemia (CLL); SMART ID10 (Protein Design Labs, Inc., CA) which is a humanized anti-HLA-DR antibody for the treatment of non-Hodgkin's lymphoma; ONCOLYM (Techniclone, Inc., CA) which is a radiolabeled murine anti-HLA-Dr10 antibody for the treatment of non-Hodgkin's lymphoma; ALLOMUNE (BioTransplant, CA) which is a humanized anti-CD2 mAb for the treatment of Hodgkin's Disease or non-Hodgkin's lymphoma; and CEACIDE (Immunomedics, NJ) which is a humanized anti-CEA antibody for the treatment of colorectal cancer.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

The Linker Unit (L)

A linker (sometimes referred to as "[linker]" herein) is a bifunctional compound which can be used to link a drug and an antibody to form an antibody drug conjugate (ADC). Such conjugates are useful, for example, in the formation of immunoconjugates directed against tumor associated antigens. Such conjugates allow the selective delivery of cytotoxic drugs to tumor cells.

In an ADC the linker serves to attach the payload to the antibody.

In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

In the context of the invention, particularly but not limited to linker components such as $L^1$, $L^2$ (including $L^{2A}$, $L^{2B}$ and $L^{2C}$) and $L^3$, the language "selected from one or more of" or "one or more of" indicates that multiple components, which may be the same or different, are or may be arranged sequentially. Thus, for example, $L^3$ may be $C_{1-6}$alkyl-, —NR— or the other individually listed components, but also $C_{1-6}$alkyl-NR—, or any other combination of 2 or more listed components.

Synthesis of Compounds and Antibody Drug Conjugates Thereof

The compounds and conjugates of the invention can be made using the synthetic procedures outlined below in the Exemplification. As described in more detail below, the compounds and conjugates of the invention can be prepared using a section of a linker unit having a reactive site for binding to the compound. In one aspect, a second section of the linker unit is introduced which has a second reactive site e.g., an electrophilic group that is reactive to a nucleophilic group present on an antibody unit (e.g., an antibody). Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups. The electrophilic group provides a convenient site for antibody attachment.

In another embodiment, a linker unit has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide. The electrophilic group on an antibody provides a convenient site for attachment to a linker unit.

Amino functional groups are also useful reactive sites for a linker unit because they can react with carboxylic acid, or activated esters of a compound to form an amide linkage. Typically, the peptide-based compounds of the invention can be prepared by forming a peptide bond between two or more amino acids and/or peptide fragments. Such peptide bonds can be prepared, for example, according to the liquid phase synthesis method (see, e.g., Schroder and Lubke, "The Peptides", volume 1, pp 76-136, 1965, Academic Press) that is well known in the field of peptide chemistry.

As described in more detail below, the conjugates can be prepared using a section of the linker having a reactive site for binding to a compound of the invention and introducing another section of the linker unit having a reactive site for an antibody. In one aspect, a linker unit has a reactive site which has an electrophilic group that is reactive with a nucleophilic group present on an antibody unit, such as an antibody. The electrophilic group provides a convenient site for antibody attachment. Useful nucleophilic groups on an antibody include but are not limited to, sulfhydryl, hydroxyl and amino groups. The heteroatom of the nucleophilic group of an antibody is reactive to an electrophilic group on a linker unit and forms a covalent bond to a linker unit. Useful electrophilic groups include, but are not limited to, maleimide and haloacetamide groups.

In another embodiment, a linker unit has a reactive site which has a nucleophilic group that is reactive with an electrophilic group present on an antibody unit. The electrophilic group on an antibody provides a convenient site for attachment to a linker unit. Useful electrophilic groups on an antibody include, but are not limited to, aldehyde and ketone carbonyl groups. The heteroatom of a nucleophilic group of a linker unit can react with an electrophilic group on an antibody and form a covalent bond to the antibody. Useful nucleophilic groups on a linker unit include, but are not limited to, hydrazide, oxime, amino, hydrazine, thiosemicarbazone, hydrazine carboxylate, and arylhydrazide.

Conjugation with Transglutaminase

In certain embodiments, a compound of the invention may be covalently crosslinked to an Fc-containing or Fab-containing polypeptide engineered with an acyl donor glutamine-containing tag (e.g., Gln-containing peptide tags or Q-tags) or an endogenous glutamine made reactive (i.e., the ability to form a covalent bond as an acyl donor in the presence of an amine and a transglutaminase) by polypeptide engineering (e.g., via amino acid deletion, insertion, substitution, mutation, or any combination thereof on the polypeptide), in the presence of transglutaminase, provided that the compound of the invention comprises an amine donor agent (e.g., small molecule comprising or attached to a reactive amine), thereby forming a stable and homogenous population of an engineered Fc-containing polypeptide conjugate with the amine donor agent being site-specifically conjugated to the Fc-containing or Fab-containing polypeptide through the acyl donor glutamine-containing tag or the exposed/accessible/reactive endogenous glutamine. For example, compounds of the invention may be conjugated as described in International Patent Application Serial No. PCT/IB2011/054899, whose entire contents are incorporated herein by reference. In certain embodiments, to facilitate conjugation of the compound of the invention to an Fc-containing or Fab-containing polypeptide engineered with an acyl donor glutamine-containing tag or an endogenous glutamine made reactive by polypeptide engineering in the presence of transglutaminase, Z is $NH_2$.

Conjugation to the Human Light Chain Kappa Domain Constant Region

In certain embodiments, a compound of the invention may be covalently attached to the side chain of $K^{188}$ of the human light chain kappa domain constant region (CLκ) (full light chain numbering according to Kabat). For example, compounds of the invention may be conjugated as described in U.S. patent application Ser. No. 13/180,204, whose entire contents are incorporated herein by reference. In certain embodiments, to facilitate conjugation to K188 CLκ, Z is

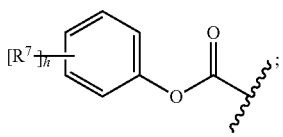

$R^7$ is independently selected for each occurrence from the group consisting of F, Cl, I, Br, $NO_2$, CN and $CF_3$; and h is 1, 2, 3, 4 or 5.

In certain embodiments, the invention provides for a composition comprising a compound of the invention covalently conjugated to an antibody (or antigen binding portion thereof), wherein at least about 50%, or at least about 60%, or at least about 70%, or at least about 80%, or at least about 90% of the compound of the invention in the composition is conjugated to the antibody or antigen binding portion thereof at $K^{188}$ CLκ.

In certain embodiments, the compounds of the invention may be conjugated to the combining site of a catalytic antibody, such as aldolase antibodies, or antigen binding portion thereof. Aldolase antibodies contain combining site portions that, when unencumbered (for example by conjugation), catalyze an aldol addition reaction between an aliphatic ketone donor and an aldehyde acceptor. The contents of US Patent Application Publication No. US 2006/205670 are incorporated herein by reference, in particular pages 78-118 describing linkers, and paragraphs [0153]-[0233] describing antibodies, useful fragments, variants and modifications thereof, h38C2, combining sites and complimentary determining regions (CDRs), and related antibody technology. The term "combining site" includes the CDRs and the adjacent framework residues that are involved in antigen binding.

Compositions and Methods of Administration

In other embodiments, another aspect of the invention relates to pharmaceutical compositions including an effective amount of a compound of the invention and/or antibody drug conjugate thereof and a pharmaceutically acceptable carrier or vehicle. In certain embodiments, the compositions are suitable for veterinary or human administration.

The present pharmaceutical compositions can be in any form that allows for the composition to be administered to a patient. For example, the composition can be in the form of a solid or liquid. Typical routes of administration include, without limitation, parenteral, ocular and intra-tumor. Parenteral administration includes subcutaneous injections, intravenous, intramuscular or intrasternal injection or infusion techniques. In one aspect, the compositions are administered parenterally. In a specific embodiment, the compositions are administered intravenously.

Pharmaceutical compositions can be formulated so as to allow a compound of the invention and/or antibody drug conjugate thereof to be bioavailable upon administration of the composition to a patient. Compositions can take the form of one or more dosage units, where for example, a tablet can be a single dosage unit, and a container of a compound of the invention and/or antibody drug conjugate thereof in liquid form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the a compound of the invention and/or antibody drug conjugate thereof, the manner of administration, and the composition employed.

The pharmaceutically acceptable carrier or vehicle can be solid or particulate, so that the compositions are, for example, in tablet or powder form. The carrier(s) can be liquid. In addition, the carrier(s) can be particulate.

The composition can be in the form of a liquid, e.g., a solution, emulsion or suspension. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of a compound of the invention and/or antibody drug conjugate thereof that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound of the invention and/or antibody drug conjugate thereof such that a suitable dosage will be obtained. Typically, this amount is at least about 0.01% of a compound of the invention and/or antibody drug conjugate thereof by weight of the composition. In an exemplary embodiment, pharmaceutical compositions are prepared so that a parenteral dosage unit contains from about 0.01% to about 2% by weight of the amount of a compound of the invention and/or antibody drug conjugate thereof For intravenous administration, the composition can comprise from about 0.01 to about 100 mg of a compound of the invention and/or antibody drug conjugate thereof per kg of the patient's body weight. In one aspect, the composition can include from about 1 to about 100 mg of a compound of the invention and/or antibody drug conjugate thereof per kg of the patient's body weight. In another aspect, the amount administered will be in the range from about 0.1 to about 25 mg/kg of body weight of a compound of the invention and/or antibody drug conjugate thereof.

Generally, the dosage of a compound of the invention and/or antibody drug conjugate thereof administered to a patient is typically about 0.01 mg/kg to about 20 mg/kg of the patient's body weight. In one aspect, the dosage administered to a patient is between about 0.01 mg/kg to about 10 mg/kg of the patient's body weight. In another aspect, the dosage administered to a patient is between about 0.1 mg/kg and about 10 mg/kg of the patient's body weight. In yet another aspect, the dosage administered to a patient is between about 0.1 mg/kg and about 5 mg/kg of the patient's body weight. In yet another aspect the dosage administered is between about 0.1 mg/kg to about 3 mg/kg of the patient's body weight. In yet another aspect, the dosage administered is between about 1 mg/kg to about 3 mg/kg of the patient's body weight.

A compound of the invention and/or antibody drug conjugate thereof can be administered by any convenient route, for example by infusion or bolus injection. Administration can be systemic or local. Various delivery systems are known, e.g., encapsulation in liposomes, microparticles, microcapsules, capsules, etc., and can be used to administer a compound of the invention and/or antibody drug conjugate thereof. In certain embodiments, more than one compound of the invention and/or antibody drug conjugate thereof is administered to a patient.

In specific embodiments, it can be desirable to administer one or more compounds of the invention and/or antibody drug conjugates thereof locally to the area in need of treatment. This can be achieved, for example, and not by way of limitation, by local infusion during surgery; topical application, e.g., in conjunction with a wound dressing after surgery; by injection; by means of a catheter; or by means of an implant, the implant being of a porous, non-porous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In yet another embodiment, the compound of the invention and/or antibody drug conjugate thereof can be delivered in a controlled release system, such as but not limited to, a pump or various polymeric materials can be used. In yet another embodiment, a controlled-release system can be placed in proximity of the target of the compound of the invention and/or antibody drug conjugate thereof, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a compound or antibody drug conjugate thereof is administered. Such pharmaceutical carriers can be liquids, such as water and oils, including those of petroleum, animal, vegetable or synthetic origin. The carriers can be saline, and the like. In addition, auxiliary, stabilizing and other agents can be used. In one embodiment, when administered to a patient, the compound or conjugate and pharmaceutically acceptable carriers are sterile. Water is an exemplary carrier when the compound or conjugate are administered intravenously. Saline solutions and aqueous dextrose and glycerol solutions can also be employed as liquid carriers, particularly for injectable solutions. The present compositions, if desired, can also contain minor amounts of wetting or emulsifying agents, or pH buffering agents.

The present compositions can take the form of solutions, pellets, powders, sustained-release formulations, or any other form suitable for use. Other examples of suitable pharmaceutical carriers are described in "Remington's Pharmaceutical Sciences" by E. W. Martin.

In an embodiment, the compound of the invention and/or antibody drug conjugate thereof are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a compound of the invention and/or antibody drug conjugate thereof is to be administered by infusion, it can be dispensed, for example, with an infusion bottle containing sterile pharmaceutical grade water or saline. Where the compound of the invention and/or antibody drug conjugate thereof is administered by injection, an ampoule of sterile water for injection or saline can be provided so that the ingredients can be mixed prior to administration.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

Whether in solid or liquid form, the present compositions can include a pharmacological agent used in the treatment of cancer.

Therapeutics Uses of Compounds and Antibody Drug Conjugates Thereof

Another aspect of the invention relates to a method of using the compounds of the invention and antibody drug conjugates thereof for treating cancer.

The compounds of the invention and/or antibody drug conjugates thereof are useful for inhibiting the multiplication of a tumor cell or cancer cell, causing apoptosis in a tumor or cancer cell, or for treating cancer in a patient. The compounds of the invention and/or antibody drug conjugates thereof can be used accordingly in a variety of settings for the treatment of animal cancers. Said conjugates can be used to deliver a compound of the invention to a tumor cell or cancer cell. Without being bound by theory, in one embodiment, the antibody of the conjugate binds to or associates with a cancer-cell or a tumor-cell-associated antigen, and the conjugate can be taken up (internalized) inside a tumor cell or cancer cell through receptor-mediated endocytosis or other internalization mechanism. The antigen can be attached to a tumor cell or cancer cell or can be an extracellular matrix protein associated with the tumor cell or cancer cell. In certain embodiments, once inside the cell, one or more specific peptide sequences are enzymatically or hydrolytically cleaved by one or more tumor cell or cancer cell-associated proteases, resulting in release of a compound of the invention from the conjugate. The released compound of the invention is then free to migrate within the cell and induce cytotoxic or cytostatic activities. The conjugate also can be cleaved by an intracellular protease to release a compound of the invention. In an alternative embodiment, the compound of the invention is cleaved from conjugate outside the tumor cell or cancer cell, and the compound of the invention subsequently penetrates the cell.

In certain embodiments, the conjugates provide conjugation-specific tumor or cancer drug targeting, thus reducing general toxicity of the compounds of the invention.

In another embodiment, the antibody unit binds to the tumor cell or cancer cell.

In another embodiment, the antibody unit binds to a tumor cell or cancer cell antigen which is on the surface of the tumor cell or cancer cell.

In another embodiment, the antibody unit binds to a tumor cell or cancer cell antigen which is an extracellular matrix protein associated with the tumor cell or cancer cell.

The specificity of the antibody unit for a particular tumor cell or cancer cell can be important for determining those tumors or cancers that are most effectively treated.

Particular types of cancers that can be treated with a compound of the invention and/or antibody drug conjugate thereof, include but are not limited to, carcinomas of the bladder, breast, cervix, colon, endometrium, kidney, lung, esophagus, ovary, prostate, pancreas, skin, stomach, and testes; and blood born cancers including but not limited to leukemias and lymphomas.

Multi-Modality Therapy for Cancer.

Cancers, including, but not limited to, a tumor, metastasis, or other disease or disorder characterized by uncontrolled cell growth, can be treated or inhibited by administration of a compound of the invention and/or antibody drug conjugate thereof.

In other embodiments, methods for treating cancer are provided, including administering to a patient in need thereof an effective amount of a compound of the invention and/or antibody drug conjugate thereof and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. A compound of the invention and/or antibody drug conjugate thereof can be administered to a patient that has also undergone surgery as treatment for the cancer.

In some embodiments, the patient also receives an additional treatment, such as radiation therapy. In a specific embodiment, the compound of the invention and/or antibody drug conjugate thereof is administered concurrently with the chemotherapeutic agent or with radiation therapy. In another specific embodiment, the chemotherapeutic agent or radiation therapy is administered prior or subsequent to administration of a compound of the invention and/or antibody drug conjugate thereof A chemotherapeutic agent can be administered over a series of sessions. Any one or a combination of the chemotherapeutic agents, such a standard of care chemotherapeutic agent(s), can be administered.

Additionally, methods of treatment of cancer with a compound of the invention and/or antibody drug conjugate thereof are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

The compounds of the invention and/or antibody drug conjugates thereof can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stein cells are harvested and purged of all cancer cells, the animal's remaining bone-marrow cell population is then eradicated via the administration of a high dose of a compound of the invention and/or antibody drug conjugate thereof with or without accompanying high dose radiation therapy, and the stem cell graft is infused back into the animal. Supportive care is then provided while bone marrow function is restored and the patient recovers.

The invention is further described in the following examples, which are in not intended to limit the scope of the invention.

Released Species

Further embodiments of the invention include the chemical species released, inside or in the vicinity of the cancer cell or tumor cell by what is believed to be enzymatic and/or hydrolytic cleavage by one or more cancer cell or tumor cell-associated proteases. Such compounds include the species described herein, and also include compounds such as those described in the structure:

A compound or compounds of formula (II):

$$L\text{-}P \qquad (II)$$

or a pharmaceutically acceptable salt thereof, wherein:

L is the linker moiety $L^1\text{-}L^2\text{-}L^3$, where $L^3$ is bound to P;

P is a radical of formula (I):

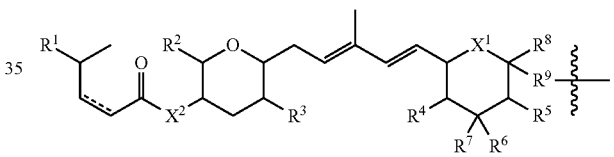

wherein:

a dashed line represents an optional bond;

each $X^1$ is independently selected from the group consisting of: —O—, —S— and —NR—;

each $X^2$ is independently selected from the group consisting of: —O—, —S— and —NR—;

each X' is CR or N;

each X" is CH—, CR—$(C(R)_2)_m$—NR—, CR—$(C(R)_2)_m$—O—; CR—$(C(R)_2)_m$—C(O)NR—, CR—$(C(R)_2)_m$—C(O)NR—NR—, CR—$(C(R)_2)_m$—SO$_2$NR—, CR—$(C(R)_2)_m$—NR—NR—, CR—$(C(R)_2)_m$—NR—C(O)— or N— if X" binds to $L^2$ or an additional $L^3$, or otherwise is O, S, CRR, CR—$(C(R)_2)_m$—NRR or NRR;

each X'" is —$(C(R)_2)_m$—NR— or CR—$(C(R)_2)_m$—O— if X'" binds to $L^2$, or otherwise is R;

Y is $C(R)_2$—, —O—, —NR— or —S—;

$R^1$ is selected from the group consisting of: —R, —OR, —OCOR$^{13}$, —OCONR$^{14}$R$^{15}$, —OCON(R$^{14}$)NR(R$^{15}$), =O (double bond to oxygen) and —NR$^{14}$R$^{15}$;

$R^2$ and $R^3$ are independently selected from the group consisting of: hydrogen and $C_{1\text{-}6}$alkyl;

$R^4$ and $R^5$ are independently selected from the group consisting of: hydrogen, —OR, —NR$^{14}$R$^{15}$ and oxo;

$R^6$ and $R^7$ are independently selected from the group consisting of: hydrogen, halogen, hydroxyl and $C_{1\text{-}6}$alkyl optionally substituted with 1-3 substituents independently selected from hydroxyl and halogen, $R^6$ and $R^7$, together with the carbon atom to which they are bound, form a $C_{2-5}$alkylidene optionally substituted with 1-3 substituents independently selected from R, $R^6$ and $R^7$ together are oxo, or $R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;

$R^8$ is hydrogen, $C_{1-6}$alkyl or —OR;

$R^9$ is —$(C(R)_2)_m$—C(O)— or $(C(R)_2)_m$—;

$L^1$ is selected from: -acid, —NR-acid and

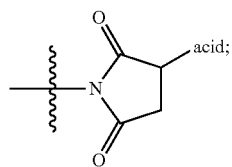

$L^2$ is $L^{2A}$-$L^{2B}$-$L^{2C}$ or $L^{2C}$-$L^{2B}$-$L^{2A}$ where $L^{2A}$ comprises one or more components selected from: —O—, —C(O)—, —C(O)NR—, —C(O)—$C_{1-6}$alkyl-, —C(O)NR$C_{1-6}$alkyl-, —$C_{1-6}$alkyl(OCH$_2$CH$_2$)$_{1-6}$—, —C(O)—$C_{1-6}$alkyl-NRC(O)—, —C(O)—$C_{1-6}$alkyl(OCH$_2$CH$_2$)$_{1-6}$—, —$C_{1-6}$alkyl(OCH$_2$CH$_2$)$_{1-6}$—C(O)—, —$C_{1-6}$alkyl-S—S—$C_{1-6}$alkyl-NRC(O)CH$_2$—, —$C_{1-6}$alkyl-(OCH$_2$CH$_2$)$_{1-6}$—NRC(O)CH$_2$—, —C(O)—$C_{1-6}$alkyl-NRC(O)$C_{1-6}$alkyl-, —N=CR-phenyl-O—$C_{1-6}$alkyl-, —N=CR-phenyl-O—$C_{1-6}$alkyl-C(O)—, —C(O)—$C_{1-6}$alkyl(OCH$_2$CH$_2$)$_{1-6}$—NRC(O)—, —C(O)—$C_{1-6}$alkyl-phenyl-(NR—C(O)—$C_{1-6}$alkyl)$_{1-4}$-, —C(O)—$C_{1-6}$alkyl-(OCH$_2$CH$_2$)$_{1-6}$—NRC(O)$C_{1-6}$alkyl-, —$C_{1-6}$alkyl-, —S—, —C(O)—$C_{1-6}$alkyl-phenyl-NR—, —O—$C_{1-6}$alkyl-S—, —C(O)—O—$C_{1-6}$alkyl-S— and (—CH$_2$—CH$_2$—O—)$_{1-20}$, or $L^{2A}$ is absent;

$L^{2B}$ is selected from AA$_{0-aa}$, where AA is a natural or non-natural amino acid and aa is 12; and $L^{2C}$ comprises one or more components selected from: —PABA- and —PABC—, or $L^{2C}$ is absent;

$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

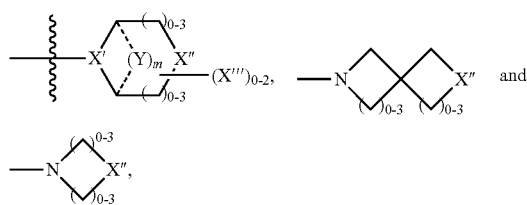

or $L^3$ is absent;

$R^{13}$ is selected from the group consisting of hydrogen, $C_{1-6}$alkyl, $C_{3-8}$carbocyclyl, $C_{3-8}$heterocyclyl, $C_{1-6}$alkyl-$C_{6-14}$aryl, $C_{1-6}$alkyl-$C_{5-14}$heteroaryl, wherein $R^{13}$ is optionally substituted with —NRR or —SO$_2$NRR;

each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —(C(R)$_2$)$_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with NRR, —SO$_2$NRR or NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$alkyl-NRR;

acid is an amino acid residue selected from SCH$_2$CH(COOH)(NH$_2$), —NH(CH$_2$)$_4$CH(COOH)(NH$_2$) and —C(O)(CH$_2$)$_2$CH(COOH)(NH$_2$);

each R is independently selected from the group consisting of: hydrogen and —$C_{1-6}$alkyl; and each m is independently 0, 1, 2 or 3.

Additionally, a compound or compounds of formula (II'):

L-P'     (II')

or a pharmaceutically acceptable salt thereof, wherein:

L is the linker moiety $L^1$-$L^2$-$L^3$, where $L^3$ is bound to P';

P' is a radical of formula (I'):

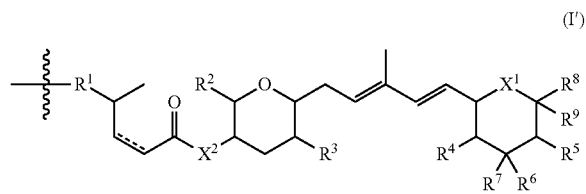

wherein:

a dashed line represents an optional bond;

each $X^1$ is independently selected from the group consisting of: —O—, —S— and —NR—;

each $X^2$ is independently selected from the group consisting of: —O—, —S— and —NR—;

each X' is CR or N;

each X''' is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X''' binds to $L^2$ or an additional $L^3$, or otherwise is O, S, CRR, CR—(C(R)$_2$)$_m$—NRR or NRR;

each X''' is —(C(R)$_2$)$_m$—NR— or CR—(C(R)$_2$)$_m$—O— if X''' binds to $L^2$, or otherwise is R;

Y is —C(R)$_2$—, —O—, —NR— or —S—;

$R^1$ is selected from the group consisting of: —(C(R)$_2$)$_m$—, —OR'', —OCOR$^{13'}$, —OC(O)NRR$^{14'}$, —OCON(R)N(R)—, and —NR—

$R^2$ and $R^3$ are independently selected from the group consisting of: hydrogen and $C_{1-6}$alkyl;

$R^4$ and $R^5$ are independently selected from the group consisting of: hydrogen, —OR, —NR$^{14}$R$^{15}$ and oxo;

$R^6$ and $R^7$ are independently selected from the group consisting of: hydrogen, halogen, hydroxyl and C$_{1-6}$alkyl optionally substituted with 1-3 substituents independently selected from hydroxyl and halogen, $R^6$ and $R^7$, together with the carbon atom to which they are bound, form a C$_{2-5}$alkylidene optionally substituted with 1-3 substituents independently selected from R, $R^6$ and $R^7$ together are oxo, or $R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;

$R^8$ is hydrogen, C$_{1-6}$alkyl or —OR;

$R^9$ is independently selected from hydrogen, —C$_{1-6}$alkyl, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)—SR, —(C(R)$_2$)$_m$—C(O)NR$^{14}$N(R)R$^{15}$, —(C(R)$_2$)$_m$—NR—C(O)—NR$^{14}$R$^{15}$, —(C(R)$_2$)$_m$—N(R)COR$^{13}$ and (C(R)$_2$)$_m$—NR$^{14}$N(R)R$^{15}$;

L$^1$ is selected from: -acid, —NR-acid and

[structure: succinimide with acid label]

L$^2$ is L$^{2A}$-L$^{2B}$-L$^{2C}$ or L$^{2C}$-L$^{2B}$-L$^{2A}$ where:

L$^{2A}$ comprises one or more components selected from: —O—, —C(O)—, —C(O)NR—, —C(O)—C$_{1-6}$alkyl-, —C(O)NRC$_{1-6}$alkyl-, —C$_{1-6}$alkyl(OCH$_2$CH$_2$)$_{1-6}$—, —C(O)—C$_{1-6}$alkyl-NRC(O)—, —C(O)—C$_{1-6}$alkyl(OCH$_2$CH$_2$)$_{1-6}$—, —C$_{1-6}$alkyl(OCH$_2$CH$_2$)$_{1-6}$—C(O)—, —C$_{1-6}$alkyl-S—S—C$_{1-6}$alkyl-NRC(O)CH$_2$—, —C$_{1-6}$alkyl-(OCH$_2$CH$_2$)$_{1-6}$—NRC(O)CH$_2$—, —C(O)—C$_{1-6}$alkyl-NRC(O)C$_{1-6}$alkyl-, —N=CR-phenyl-O—C$_{1-6}$alkyl-, —N=CR-phenyl-O—C$_{1-6}$alkyl-C(O)—, —C(O)—C$_{1-6}$alkyl(OCH$_2$CH$_2$)$_{1-6}$—NRC(O)—, —C(O)—C$_{1-6}$alkyl-phenyl-(NR—C(O)—C$_{1-6}$alkyl)$_{1-4}$-, —C(O)—C$_{1-6}$alkyl-(OCH$_2$CH$_2$)$_{1-6}$—NRC(O)C$_{1-6}$alkyl-, —C$_{1-6}$alkyl-, —S—, —C(O)—C$_{1-6}$alkyl-phenyl-NR—, —O—C$_{1-6}$alkyl-S—, —C(O)—O—C$_{1-6}$alkyl-S— and (—CH$_2$—CH$_2$—O—)$_{1-20}$, or L$^{2A}$ is absent;

L$^{2B}$ is selected from AA$_{0-aa}$, where AA is a natural or non-natural amino acid and aa is 12; and L$^{2C}$ comprises one or more components selected from: —PABA- and —PABC—, or L$^{2C}$ is absent;

L$^3$ is selected from one or more of: —C$_{1-6}$alkyl-, —NR—C$_3$-C$_8$heterocyclyl-NR—, —NR—C$_3$-C$_8$carbocyclyl-NR—, —NR—C$_{1-6}$alkyl-NR—, —NR—C$_{1-6}$alkyl-, —S—, —NR—NR— and —NR—C(O)—NR— where the two R groups optionally join to form a 4-10 membered ring, —NR—C$_{1-6}$alkyl-phenyl-NR—, —NR—C$_{1-6}$alkyl-phenyl-SO$_2$—NR—, —SO$_2$—, —NR—C$_{1-6}$alkyl-phenyl-C(O)—,

[structures]

or L$^3$ is absent;

R$^{13'}$ is selected from the group consisting of a bond, —C$_{1-6}$alkylene-, —C$_{3-8}$carbocyclyl-, —C$_{3-8}$heterocyclyl-, —C$_{1-6}$alkyl-C$_{6-14}$aryl-, —C$_{1-6}$alkyl-C$_{5-14}$heteroaryl-;

each R$^{14}$ and R$^{15}$ is independently selected from the group consisting of: hydrogen, hydroxyl, —NRR, —NRNR$_2$, —C$_{3-10}$carbocyclyl, —C$_{1-6}$alkylene-C$_{3-10}$carbocyclyl, —C$_{3-10}$heterocyclyl, —C$_{1-6}$alkylene-C$_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —C$_{1-6}$alkyl, C$_{6-14}$aryl, —C$_{1-6}$alkylene-C$_{6-14}$aryl and —C$_{5-14}$heteroaryl;

or R$^{14}$ and R$^{15}$, together with the atom or atoms to which they are joined, form a C$_{3-10}$heterocyclyl ring, wherein R$^{14}$, R$^{15}$, or both, or a ring formed with R$^{14}$ and R$^{15}$, are optionally substituted with —(C(R)$_2$)$_m$—R$^{18}$ where each R$^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—C$_{1-6}$alkyl-C(O)OR, (vii) —SO$_2$NRR, (viii) —C(O)NRR, (ix) —C(O)OR, (x) —C$_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—C$_{1-6}$alkyl-NRR;

each R$^{14'}$ is independently selected from the group consisting of: a bond, —NR—, —C$_{3-10}$carbocyclyl-, —C$_{3-10}$heterocyclyl-, —(CH$_2$CH$_2$O)$_{1-6}$CH$_2$CH$_2$C(O)OR'-, —(CH$_2$CH$_2$O)$_{1-6}$CH$_2$CH$_2$NR—, and —C$_{1-6}$alkylene-, wherein R$^{14'}$ is optionally substituted with (C(R)$_2$)$_m$—R$^{18}$ where each R$^{18}$ is independently selected from (i) —NRR, (ii) —C(NRR)(C(O)OR), (iii) —S—R, (iv) aryl or heteroaryl optionally substituted with one or more of halogen, —CF$_3$, NRR or SO$_2$NRR, (v) SO$_2$R, (vi) —S—S—C$_{1-6}$alkyl-C(O)OR, (vii) —SO$_2$NRR, (viii) —C(O)NRR, (ix) —C(O)OR, (x) —C$_{4-6}$cycloalkyl optionally substituted with NRR, —SO$_2$NRR or NR—C(O)(CH$_2$)$_{0-6}$NRR, (xi) —R, (xii) —OR, (xiii) N(R)NRR, (xiv) —C(O)N(R)NRR, (xv) —(C(R)$_2$)$_m$—O—NRR and (xiv) —S—S—C$_{1-6}$alkyl-NRR;

acid is an amino acid residue selected from —SCH$_2$CH(COOH)(NH$_2$), —NH(CH$_2$)$_4$CH(COOH)(NH$_2$) and —C(O)(CH$_2$)$_2$CH(COOH)(NH$_2$);

each R is independently selected from the group consisting of: hydrogen and —C$_{1-6}$alkyl;

each R' is independently selected from —H, C$_1$-C$_8$ alkyl, C$_1$-C$_8$ heteroalkyl and aryl;

each R" is independently selected from the group consisting of: a bond and —C$_{1-6}$alkylene-; and each m is independently 0, 1, 2 or 3.

EXAMPLES

Natural Product Production

The following procedures outline the production of "natural products" useful as payloads in the current invention. The term "natural product" denotes that the product is produced via a fermentation process, but does not suggest that these products are known or could be found in nature. Natural products are notes below with the prefix "NP".

Example 1

Fermentation, Extraction and Isolation of: [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetic Acid (#NP1); [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetic acid (#NP2); [(2S,5S,6R)-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-5-hydroxy-4-methylidenetetrahydro-2H-pyran-2-yl]acetic acid (#NP3); [(2S,6S)-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-methylidenetetrahydro-2H-pyran-2-yl]acetic acid (#NP4)

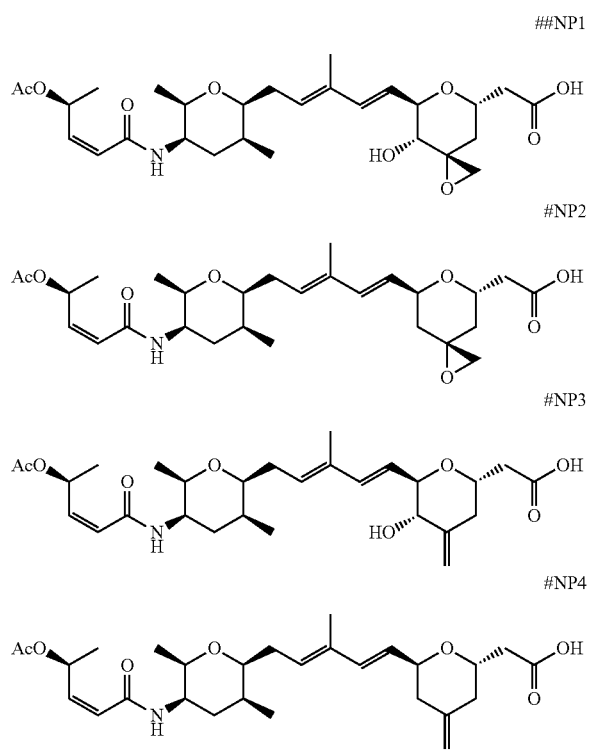

Step 1:
Fermentation Using *Pseudomonas* sp. No. 2663, (Strain FERM BP-3421)

*Pseudomonas* sp. No. 2663, (Strain FERM BP-3421), was acquired from the International Patent Organism Depositary (IPOD) at the National Institute of Advanced Industrial Science and Technology (AIST Tsukuba, Central 6, 1-1-1, Higashi, Tsukuba, Ibaraki 305-8566, Japan). Subsequent taxonomical studies performed by biochemical (BBL Crystal Kit) and 16S rRNA sequence analysis revealed that FERM BP-3421 was a *Burkholderia* sp.

Single colony isolates were cultured by dilution plating a frozen culture of FERM BP-3421 wild-type onto nutrient agar plates. Several 250 ml Erlenmeyer flasks containing 50 ml of seed medium (1% polypeptone, 0.5% yeast extract, 0.5% NaCl) were inoculated with agar grown culture and incubated at 30° C. with shaking at 220 rpm for 18-20 hours. The seed culture was inoculated into 500 ml of production medium (1% soluble starch, 1% glycerine, 0.5% glucose, 1% HySoy Soypeptone, 0.5% corn steep liquor, 0.2% ammonium sulfate, 0.006% magnesium sulfate. $6H_2O$, 0.2% $CaCO_3$, pH 7.0) per 2.8 L Fernbach flask with no baffles at 2.5% (v/v). The fermentation was incubated at 25° C. with shaking at 200 rpm for 72 hours.

Step 2:
Extraction of fermentation broth: At the end of fermentation from step 1 of example 1, 50 g/L of wet DIAION HP-20 resin was added to the supernatant of the production fermentation and the mixture was shaken at 100 rpm for 30 minutes. The HP-20 was collected by centrifugation and then extracted with ethyl acetate at ambient temperature. In more detail, a 13 L fermentation of FERM BP-3421 was performed at 25° C. for 72 hours according to step 1 of Example 1. The whole broth was centrifuged at 3800 rpm for 30 minutes. The cells were discarded and the supernatant was mixed with pre-washed wet HP20 resin (260 g dry weight). The resulting suspension was shaken on a shaker at ambient temperature for 1 hour. The compound-bound HP20 resin was extracted twice with ethyl acetate (1 L each time) and the ethyl acetate solution was filtered over Celite followed by evaporation under reduced pressure to afford a light-colored crude extract (2.4 g).

Step 3:
Isolation and Characterization of [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetic acid (#NP1); [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetic acid (#NP2): The crude extract from step 2 of example 1 was dissolved in a mixture of 1:1 acetonitrile/dimethyl sulfoxide (14 mL total). The viscous solution was filtered and then purified by preparative HPLC: (Column: Waters C18 DELTA PAK (WAT011801), 300×50 mm, 15 µm, 100 A; Mobile Phase A: 0.02% acetic acid (vv) n 1:1 acetonitrile/$H_2O$; Mobile Phase B: 0.02% acetic acid (v/v) in 3:1 acetonitrile/$H_2O$ and Mobile Phase C: 0.02% acetic acid (v/v) in acetonitrile. Gradient: 100% A for 5 min, 0% A to 100% B over 18 min and 100%, B to 100% C over 2 min, and 100% C for 2 min. Flow rate: 50 mL/min.). The fractions with retention times of 13.5 and 18.0 min were collected and freeze-dried to afford #NP1 (172.5 mg) and #NP2 (227.2 mg) respectively as white powders. The fractions with retentions times of 14.8 min and 20.5 min were also collected and freeze dried to yield two semi-purified grayish powders I and II.

NP1; HPLC (Protocol N): retention time=9.36 minutes (purity 92.5%); HRESIMS (protocol O) m/z 536.2837 [M+H]+; 1H NMR (400 MHz, DMSO-d6, mult, J in Hz) δ 12.20 (br s, D2O exchangeable), 7.80 (d, J=7.9, 1H, D2O exchangeable), 6.35 (dq, J=6.0, 6.0, 1H), 6.32 (br d, J=15.6, 1H), 6.10 (d, J=11.2, 1H), 5.85 (dd, J=11.8, 7.4, 1H), 5.58 (dd, J=15.5, 5.8, 1H), 5.49 (br dd, J=7.0, 7.0, 1H), 4.24 (m, 2H), 3.63 (m, 2H), 3.49 (ddd, J=5.5, 5.5, 2.5, 1H), 3.24 (d, J=6.0, 1H), 2.74 (d, J=3.5, 1H), 2.57 (d, J=3.5, 1H), 2.55 (dd, J=16.4, 8.5, 1H), 2.46 (m, 1H), 2.28 (m, 1H), 2.18 (m, 1H), 1.97 (s, 3H), 1.82 (m, 1H), 1.79 (m, 2H), 1.68 (s, 3H), 1.65 (m, 1H), 1.56 (m), 1.23 (d, J=6.4, 3H), 1.06 (d, J=6.5, 3H), 0.93 (d, J=7.0, 3H). 13C NMR (100 MHz, DMSO-d6) δ172.15, 169.66, 164.55, 142.76, 136.22, 133.88, 128.84, 123.73, 122.83, 79.90, 76.93, 74.88, 70.35, 68.10, 67.93, 57.36, 49.63, 46.39, 39.09, 35.21, 33.91, 31.71, 28.67, 21.02, 19.96, 17.79, 14.22, 12.41.

NP2. HPLC (Protocol N): retention time=10.93 minutes (purity 90.4%); HRESIMS (Protocol O) m/z 520.2895 [M+H]+; 1H NMR (400 MHz, DMSO-d6, mult, J in Hz) δ 12.13 (br s, 1H, D2O exchangeable), 7.80 (d, J=7.9, 1H, D2O exchangeable), 6.35 (dq, J=6.0, 6.0, 1H), 6.27 (br d, J=15.8, 1H), 6.10 (d, J=11.2, 1H), 5.85 (dd, J=11.8, 7.3, 1H), 5.57 (dd, J=15.6, 5.8, 1H), 5.50 (br dd, J=7.0, 7.0, 1H), 4.50 (ddd, J=5.5, 5.5, 5.5, 1H), 4.29 (m, 1H), 3.63 (m, 2H), 3.48 (m, 1H), 2.61 (s, 2H), 2.58 (dd, J=16.0, 8.5, 1H), 2.49 (m, 1H), 2.28 (m, 1H), 2.18 (m, 1H), 1.96 (s, 3H), 1.79 (m, 2H), 1.76 (m, 1H), 1.68 (s, 3H), 1.65 (m, 1H), 1.63 (m, 1H), 1.40 (dd, J=11.5, 7.2, 1H), 1.24 (d, J=6.4, 3H), 1.06 (d, J=6.4, 3H), 0.94 (d, J=7.0, 3H). $^{13}$C NMR (100 MHz, DMSO-$d_6$) δ 172.88, 169.64, 164.56, 142.75, 135.37, 133.74, 128.99, 126.57, 122.84, 79.97, 74.90, 70.36, 68.16, 68.11, 54.71, 52.25, 46.40, 39.08, 37.22, 36.46, 35.23, 31.72, 28.71, 21.01, 19.95, 17.78, 14.23, 12.40.

Step 4:

Isolation of [(2S,5S,6R)-6-{(1E,3E)-5-[(2S,3S,5R,6R)-5-{[(2Z,4S)-4-(acetyloxy)pent-2-enoyl]amino}-3,6-dimethyl-tetrahydro-2H-pyran-2-yl]-3-methylpenta-1,3-dien-1-yl}-5-hydroxy-4-methylidenetetrahydro-2H-pyran-2-yl]acetic acid (#NP3).

The semi-purified power I isolated in step 2 of example 1 was further purified by reverse phase HPLC (Column: YMC-Pack-ODS-A, 250×30 mm, S-10 μm, 12 nm.: Mobile Phase A: 0.02% acetic acid in water; Mobile Phase B: 0.02% acetic acid in acetonitrile: Gradient system: 30% to 100% B over 23 min and hold 100% B for 1 min. Flow rate: 20 mL/min) to afford #NP3 (7.6 mg) as a white powder.

NP3: HPLC (Protocol N): retention time=10.9 minutes (purity 94.2%); HRESIMS (Protocol O) m/z 520.2910 [M+H]+; $^1$H NMR (400 MHz, DMSO-$d_6$, mult, J in Hz) δ 7.76 (d, J=7.9, 1H, D$_2$O exchangeable), 6.35 (dq, J=6.4, 6.4, 1H), 6.22 (br d, J=15.8, 1H), 6.10 (d, J=11.0, 1H), 5.85 (dd, J=11.8, 7.4, 1H), 5.57 (dd, J=15.5, 5.8, 1H), 5.48 (br dd, J=7.0, 7.0, 1H), 5.04 (br s, 1H), 4.80 (br s, 1H), 4.18 (m, 1H), 3.88 (dd, J=5.8, 5.8, 1H), 3.63 (m, 2H), 3.49 (ddd, J=6.0, 6.0, 2.5, 1H), 2.37 (m, 2H), 2.33 (m, 1H), 2.27 (m, 1H), 2.23 (m, 1H), 2.17 (m, 1H), 1.97 (s, 3H), 1.79 (m, 2H), 1.68 (s, 3H), 1.65 (m, 1H), 1.24 (d, J=6.4, 3H), 1.06 (d, J=6.5, 3H), 0.94 (d, J=7.0, 3H). $^{13}$C NMR (100 MHz, DMSO-$d_6$) δ 172.35, 169.57, 164.50, 144.64, 142.64, 136.08, 133.77, 128.74, 125.24, 122.81, 108.88, 79.95, 76.97, 74.84, 72.37, 69.47, 68.02, 46.34, 38.09, 36.97, 35.17, 31.67, 28.70, 20.95, 19.91, 17.72, 14.20, 12.34.

Step 5:

Isolation of [(2S,6S)-6-{(1E,3E)-5-[(2S,3S,5R,6R)-5-{[(2Z,4S)-4-(acetyloxy)pent-2-enoyl]amino}-3,6-dimethyl-tetrahydro-2H-pyran-2-yl]-3-methylpenta-1,3-dien-1-yl}-4-methylidenetetrahydro-2H-pyran-2-yl]acetic acid (#NP4).

The semi-purified powder II isolated in step 2 of example 1 was further purified by reverse phase HPLC (Column: YMC-Pack-ODS-A, 250×30 mm, S-10 μm, 12 nm.: Mobile Phase A: 0.02% acetic acid in water; Mobile Phase B: 0.02% acetic acid in acetonitrile: Gradient system: 30% to 100% B over 23 min and hold 100% B for 1 min. Flow rate: 20 mL/min) to afford #NP4 (12.2 mg) as a white powder.

NP4: HPLC (Protocol N): retention time=12.7 minutes (purity 96.5%); HRESIMS (Protocol O) m/z 504.2959 [M+H]$^+$. $^1$H NMR (400 MHz, DMSO-$d_6$, mult, J in Hz) δ 7.75 (d, J=7.9, 1H, D$_2$O exchangeable), 6.37 (dq, J=7.5, 6.4, 1H), 6.23 (br d, J=16.0, 1H), 6.10 (d, J=11.8, 1H), 5.85 (dd, J=11.8, 7.5, 1H), 5.53 (dd, J=16.0, 5.6, 1H), 5.51 (dd, J=6.5, 6.5, 1H), 4.80 (br s, 1H), 4.76 (br s, 1H), 4.32 (ddd, J=5.6, 5.5, 5.5, 1H), 4.13 (m, 1H), 3.63 (m, 2H), 3.49 (ddd, J=6.0, 6.0, 2.5, 1H), 2.38 (m, 2H), 2.36 (dd, J=11.5, 5.0, 1H), 2.32 (m, 1H), 2.29 (m, 1H), 2.18 (br dd, J=11.9, 6.5, 1H), 2.13 (dd, J=11.5, 5.9, 1H), 2.00 (dd, J=10.5, 7.0, 1H), 1.97 (s, 3H), 1.79 (m, 2H), 1.67 (s, 3H), 1.65 (m, 1H), 1.24 (d, J=6.4, 3H), 1.05 (d, J=6.3, 3H), 0.94 (d, J=7.0, 3H). $^{13}$C NMR (100 MHz, DMSO-$d_6$) δ172.11, 169.61, 164.54, 142.69, 141.40, 135.72, 133.71, 129.01, 126.48, 122.83, 110.53, 79.94, 74.86, 71.99, 68.76, 68.06, 46.37, 38.97, 38.92, 38.70, 35.19, 31.70, 28.71, 20.97, 19.92, 17.74, 14.21, 12.36.

Example 2

Fermentation, Extraction and Isolation of Natural Product Analogs: (5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methyl-penta-1,3-dien-1-yl}-1,5-anhydro-1-(carboxymethyl)-3-C-(chloromethyl)-2-deoxypentitol (#NP5); (6R)-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1-deoxy-4-C-(hydroxymethyl)hex-2-ulopyranose (#NP6); (4-[(acetyloxy)methyl]-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-hydroxytetrahydro-2H-pyran-2-yl)acetic acid (#NP7); [6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-(chloromethyl)-4-hydroxytetrahydro-2H-pyran-2-yl]acetic acid (#NP8); 4-C-[(acetyloxy)methyl]-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1-deoxyhex-2-ulopyranose (#NP9); 6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-C-[({6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-(chloromethyl)-4-hydroxytetrahydro-2H-pyran-2-yl]acetyl}oxy)methyl]-1-deoxyhex-2-ulopyranose (#NP10); (2S,3Z)-5-{[(2R,3R,5S,6S)-2,5-dimethyl-6-{(2E,4E)-3-methyl-5-[(2S)-4-methyl-6-oxo-3,6-dihydro-2H-pyran-2-yl]penta-2,4-dien-1-yl}tetrahydro-2H-pyran-3-yl]amino}-5-oxopent-3-en-2-yl acetate (#NP11)

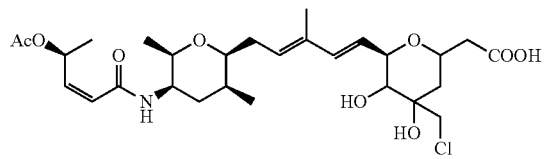

NP5

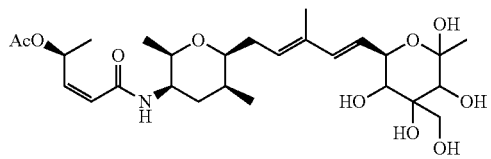

NP6

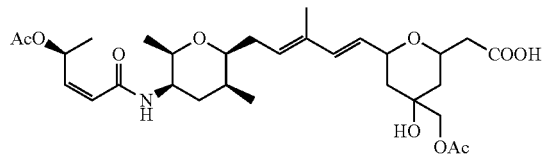
NP7

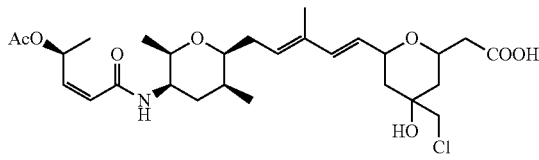
NP8

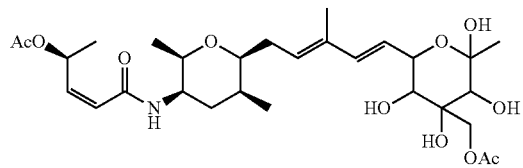
NP9

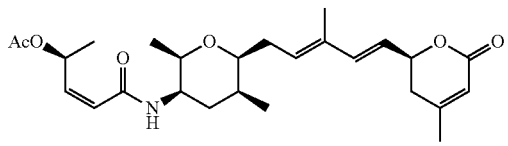
NP11

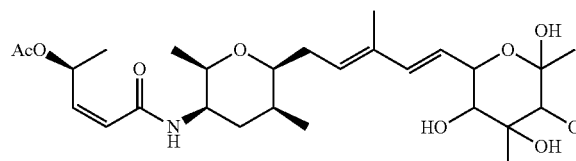
NP10

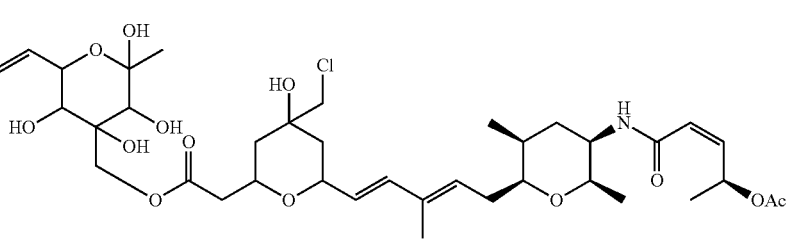

Step 1:

Crude solid extract (3.7 g) prepared as in step 2, Example 1 was dissolved in methanol and fractionated on a Sephadex LH20 column using methanol, with eluents collected at 15 minute intervals using an automated fraction collector for a period of 15.0 hours (Total of 65 fractions collected). Fraction-19 from this was further purified by reverse phase HPLC (Column: YMC-Pack-ODS-A, 250×30 mm, S-10 um, 12 nm; Mobile Phase A: 0.2% ammonium acetate (W/v); Mobile Phase B: 0.02% acetic acid in acetonitrile; Gradient: 30% B to 60% B over 20 minutes, to 100% B over 5 minutes and hold at 100% B for 4 minutes and 100% B to 30% B over 2 minutes; Flow rate: 20 mL/min.) to yield thirteen fractions: Fraction A (4.3-6.4 min), B (10.8-11.9 min), C (12.5-13.5 min), D (13.5-14.6 min), E (15.0-16.1 min), F (16.5-17.8 min), G (19.0-19.8 min), H (19.8-21.0 min), I (21.8-23.0 min), J (23.3-25.4 min), J1 (25.4-26.2 min), K (27.9-28.5 min), L (28.7-29.5 min)

Step 2:

Isolation of (5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,5-anhydro-1-(carboxymethyl)-3-C-(chloromethyl)-2-deoxypentitol (#NP5): (6R)-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1-deoxy-4-C-(hydroxymethyl)hex-2-ulopyranose (#NP6); (4-[(acetyloxy)methyl]-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-hydroxytetrahydro-2H-pyran-2-yl)acetic acid (#NP7)

Fraction D from step 1 of Example 2 was further purified by reverse phase HPLC (Column, Column: C18-Phenomenex; Luna 10 μM; 250×10 mm; Mobile Phase A: 0.2% Ammonium acetate in water (W/v); Mobile Phase B: 0.02% acetic acid in acetonitrile; Gradient: 25% B to 35% B over 5 minutes, to 45% B over 17 minutes, to 70% B over 2 minutes: Flow rate: 2.5 mL/minute) and fractions eluting at 13, 14 and 15 minutes were collected and freeze dried.

Fraction eluting at 13 minutes yielded #NP5: Yield: 1.0 mg: HRESIMS (Protocol 0) m/z 572.2614 (M+H)$^+$, m/z 594.2438 (M+Na)$^+$; $^1$H NMR (500 MHz, DMSO-d$_6$, mult, J in Hz) δ 7.80 (d, J=8.0, 1H), 6.36 (m, 1H), 6.23 (d, J=15.8, 1H), 6.11 (dd, J=1.3, 11.7, 1H), 5.86 (dd, J=7.5, 11.6, 1H), 5.63 (dd, J=5.6, 15.8, 4H), 5.47 (m, 1H), 4.21 (m, 1H), 4.10 (dd, J=5.6, 8.3, 1H), 3.64 (m, 2H), 3.62 (d, J=10.6, 1H), 3.49 (m, 1H), 3.42 (d, J=10.6, 1H), 3.16 (d, J=8.3, 1H), 2.68 (m, 1H), 2.57 (m, 1H), 2.30 (m, 1H), 2.19 (m, 1H), 1.98 (s, 3H), 1.83 (m, 2H), 1.80 (m, 2H), 1.69 (s, 3H), 1.65 (m, 1H), 1.24 (d, J=6.5, 3H), 1.06 (d, J=6.3, 3H), 0.95 (d, J=7.3, 2H). $^{13}$C NMR (126 MHz, DMSO-d$_6$) δ173.3, 170.1, 165.0, 143.1, 135.6, 134.4, 128.5, 126.8, 123.2, 80.2, 75.1, 71.7, 71.3, 70.0, 68.6, 68.2, 50.4, 46.6, 39.9, 35.2, 35.0, 31.9, 29.0, 21.0, 20.1, 17.9, 14.4, 12.5.

Step 3:

Isolation of 6R)-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1-deoxy-4-C-(hydroxymethyl)hex-2-ulopyranose (#NP6): Fraction collected at retention time 14.0 minutes above from step 2 of Example 2 was further purified using reverse phase HPLC (Column: Chromolith: RP 18e, 100-10 mm: Mobile Phase A: 0.2% Ammonium acetate in water (W/v); Mobile Phase B: 0.02% acetic acid in acetonitrile; Gradient: 25% B to 33% B over 20 minutes; flow rate: 2.5 mL/min) to afford #NP6: Yield 4.0 mg, HRESIMS (Protocol 0) m/z 542.2948 (M+H)$^+$; $^1$H NMR (400 MHz, DMSO-d$_6$, mult, J in Hz) δ7.77 (d, J=8.0, 1H), 6.32 (m, 1H), 6.17 (d, J=15.8, 1H), 6.05 (dd, J=1.3, 11.6, 1H), 5.82 (dd, J=7.5, 11.6, 1H), 5.57 (dd, J=5.9, 15.8, 1H), 5.42 (m, 1H), 4.09 (m, 1H), 3.60 (m, 2H), 3.46 (m, 1H), 3.38 (d, J=10.1, 1H), 3.28 (d, J=10.1, 1H), 3.21 (br s, 1H), 3.17 (br s, 1H), 2.25 (m, 1H), 2.16 (m, 1H), 1.94 (s, 3H), 1.76 (m, 2H), 1.66 (s, 3H), 1.62 (m, 1H), 1.21 (d, J=6.3, 3H), 1.17 (d, J=8.5, 3H), 1.02 (d, J=6.3, 3H), 0.91 (d, J=7.3, 3H). $^{13}$C NMR (126 MHz, DMSO-d$_6$) δ

174.1, 165.2, 143.5, 135.9, 134.6, 128.9, 127.4, 123.6, 98.8, 80.0, 77.3, 75.5, 69.7, 69.4, 69.2, 68.8, 59.6, 47.0, 35.8, 32.6, 29.5, 26.5, 21.7, 20.7, 18.5, 14.9, 13.1.

Step 4:

Isolation of (4-[(acetyloxy)methyl]-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-hydroxytetrahydro-2H-pyran-2-yl)acetic acid (#NP7): Fraction collected at retention time 15.0 minutes above from step 2 of Example 2 was further purified using reverse phase HPLC (YMC-Pack-ODS-A; 250×10 mm, S-5 um, 12 nm. Mobile Phase A: 0.2% Ammonium acetate in water (W/v); Mobile Phase B: 0.02% acetic acid in acetonitrile; Gradient: 30% B to 50% B over 20 minutes, to 95% B over 5 minutes: Flow rate: 2.5 mL/min) to yield #NP7: HRESIMS (Protocol 0) m/z 580.3112 (M+H)$^+$, m/z 602.2928 (M+Na)$^+$; $^1$H NMR (500 MHz, DMSO-d$_6$, mult, J in Hz) δ 7.80 (d, J=8.0, 1H), 6.36 (m, 1H), 6.19 (d, J=15.8, 1H), 6.11 (d, J=11.6, 1H), 5.87 (dd, J=7.5, 11.6, 1H), 5.49 (m, 1H), 5.48 (m, 1H), 4.41 (dd, J=7.2, 12.8, 1H), 4.28 (d, J=5.8, 1H), 3.79 (m, 2H), 3.65 (m, 1H), 3.64 (m, 1H), 3.49 (m, 1H), 2.60 (m, 1H), 2.56 (m, 1H), 2.29 (m, 1H), 2.19 (m, 1H), 2.02 (s, 3H), 1.97 (s, 3H), 1.80 (m, 2H), 1.67 (br s, 3H), 1.68-1.65 (br m, 2H), 1.51 (m, 1H), 1.45 (m, 1H), 1.40 (m, 1H), 1.24 (d, J=6.5, 3H), 1.06 (d, J=6.3, 3H), 0.94 (d, J=7.3, 3H). $^{13}$C NMR (126 MHz, DMSO-d$_6$) δ 173.4, 170.8, 170.1, 165.0, 143.2, 134.4, 134.2, 129.0, 128.9, 123.3, 80.3, 75.1, 68.3, 68.2, 68.0, 66.3, 71.1, 46.5, 39.4, 38.6, 35.4, 35.3, 31.8, 28.9, 21.1, 20.8, 20.0, 17.9, 14.4, 12.5.

Step 5:

Isolation [6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-(chloromethyl)-4-hydroxytetrahydro-2H-pyran-2-yl]acetic acid (#NP8), 4-C-[(acetyloxy)methyl]-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1-deoxyhex-2-ulopyranose (#NP9), and 6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-C-[({[6-{(1E,3E)-5-[(2S,3S,5R,6R)-5-{[(2Z,4S)-4-(acetyloxy) pent-2-enoyl]amino}-3,6-dimethyltetrahydro-2H-pyran-2-yl]-3-methylpenta-1,3-dien-1-yl}-4-(chloromethyl)-4-hydroxytetrahydro-2H-pyran-2-yl]acetyl}oxy)methyl]-1-deoxyhex-2-ulopyranose (#NP10):

Fraction F from step 1 of Example 2 was further purified by reverse phase HPLC (C18-Phenomenex; Luna 250×10 mm. 10 uM; Mobile Phase A: 0.2% Ammonium acetate in water (W/v); Mobile Phase B: 0.02% acetic acid in acetonitrile; Gradient: 40% B to 45% B over 20 min, to 95% B over 5 min; flow rate: 2.5 mL/min: The fractions eluting at 8, 13 and 28 minutes were collected and freeze dried to give:

NP8 (fraction eluting at 8.0 min): Yield: 1.0 mg; HRESIMS (Protocol 0) m/z 556.2671 (M+H)$^+$, m/z 578.2489 (M+Na)$^+$; $^1$H NMR (500 MHz, DMSO-d$_6$, mult, J in Hz) δ 7.80 (d, J=8.0, 1H), 6.37 (m, 1H), 6.21 (d, J=15.9, 1H), 6.11 (dd, J=1.3, 11.6, 1H), 5.87 (dd, J=7.5, 11.6, 1H), 5.50 (m, 1H), 5.48 (m, 1H), 4.39 (m, 1H), 4.30 (m, 1H), 3.65 (m, 2H), 3.50 (m, 1H), 3.48 (br s, 2H), 2.91 (dd, J=8.9, 15.0, 1H), 2.60 (dd, J=6.0, 15.0, 1H), 2.30 (m, 1H), 2.19 (m, 1H), 1.98 (s, 3H), 1.80 (m, 2H), 1.73 (m, 1H), 1.69 (br s, 3H), 1.65 (m, 1H), 1.58 (m, 1H), 1.55 (m, 1H), 1.43 (br dd, J=13.1, 10.4, 1H), 1.25 (d, J=6.5, 3H), 1.07 (d, J=6.3, 3H), 0.95 (d, J=7.3, 3H). $^{13}$C NMR (126 MHz, DMSO-d$_6$) δ 173.4, 170.1, 165.0, 143.2, 134.5, 134.2, 128.9 (×2), 123.2, 80.2, 75.2, 68.7, 68.5, 68.2, 66.5, 54.6, 46.5, 39.9, 38.7, 35.6, 35.4, 31.9, 28.9, 21.1, 20.1, 17.9, 14.4, 12.5.

NP9 (fraction eluting at 13 minutes): Yield: 1.0 mg: HRESIMS (Protocol 0) m/z 584.3066 (M+H)$^+$, m/z 606.2887 (M+Na)$^+$; $^1$H NMR (500 MHz, DMSO-d$_6$, mult, J in Hz) δ 7.80 (d, J=7.9, 1H), 6.36 (m, 1H), 6.25 (d, J=15.7, 1H), 6.11 (dd, J=1.0, 11.6, 1H), 5.87 (dd, J=7.5, 11.6, 1H), 5.63 (dd, J=6.1, 15.8, 1H), 5.48 (m, 1H), 4.19 (dd, J=6.1, 9.6, 1H), 3.97 (d, J=10.0, 1H), 3.88 (d, J=10.0, 1H), 3.65 (m, 2H), 3.50 (m, 1H), 3.17 (brs, 1H), 3.15 (brs, 1H), 2.30 (m, 1H), 2.19 (m, 1H), 2.00 (s, 3H), 1.98 (s, 3H), 1.80 (m, 2H), 1.70 (s, 3H), 1.65 (m, 1H), 1.26 (br d, J=1.6, 3H), 1.24 (br s, 3H), 1.06 (d, J=6.2, 3H), 0.96 (d, J=7.3, 3H). $^{13}$C NMR (126 MHz, DMSO-d$_6$) δ 170.4, 170.1, 165.0, 143.1, 136.1, 134.4, 128.9, 126.4, 123.2, 98.5, 80.4, 75.4, 75.2, 69.2 (×2), 69.0, 68.2, 60.7, 46.5, 35.4, 31.9, 28.9, 25.9, 21.1 (×2), 20.0, 17.9, 14.4, 12.6.

NP10 (fraction eluting at 23 minutes): Yield: 1.0 mg, HRESIMS (Protocol 0) m/z 562.2582 (M+2Na)$^{2+}$, m/z 1101.5263 (M+Na)$^+$; $^1$H NMR (500 MHz, DMSO-d$_6$, mult, J in Hz) δ 7.79 (d, J=7.9, 2H), 6.37 (m, 2H), 6.27 (d, J=16.2, 1H), 6.21 (d, J=15.6, 1H), 6.12 (d, J=11.6, 1H), 6.11 (d, J=15.3, 1H), 5.88 (dd, J=7.5, 11.6, 1H), 5.64 (dd, J=6.2, 15.8, 1H), 5.54-5.48 (m, 3H), 4.40-4.31 (m, 2H), 4.20 (dd, J=6.2, 9.4, 1H), 4.04 (m, 1H), 3.90 (d, J=10.0 Hz, 1H), 3.69-3.62 (m, 4H), 3.54-3.47 (m, 4H), 3.21-3.13 (m, 2H), 3.06 (dd, J=8.7, 15.6, 1H), 2.73 (dd, J=5.3, 15.7, 1H), 2.31 (m, 2H), 2.20 (m, 2H), 1.99 (s, 6H), 1.84-1.79 (m, 5H), 1.72 (s, 3H), 1.69 (s, 3H), 1.68-1.64 (m, 2H), 1.62 (m, 1H), 1.55 (d, J=13.8 Hz, 1H), 1.44 (m, 1H), 1.27 (brs, 3H), 1.26 (brs, 6H), 1.08 (m, 6H), 0.96 (m, 6H). $^{13}$C NMR (126 MHz, DMSO-d$_6$) δ 171.3, 170.0 (×2), 165.0 (×2), 143.2 (×2), 136.5, 134.6, 134.7, 134.4, 128.9 (×3), 126.6, 123.3 (×2), 98.4, 80.5 (×2), 75.4, 75.5 (×2), 69.5 (×2), 69.2, 68.6, 68.5 (×3), 66.5, 60.7, 54.8, 46.9 (×2), 40.0, 38.5, 35.9, 35.7 (×2), 32.3 (×2), 29.3, 29.2, 26.2, 21.5 (×2), 20.4 (×2), 18.2 (×2), 14.7 (×2), 12.9 (×2).

Step 6:

Isolation of (2S,3Z)-5-{[(2R,3R,5S,6S)-2,5-dimethyl-6-{(2E,4E)-3-methyl-5-[(2S)-4-methyl-6-oxo-3,6-dihydro-2H-pyran-2-yl]penta-2,4-dien-1-yl}tetrahydro-2H-pyran-3-yl]amino}-5-oxopent-3-en-2-yl acetate (#NP11).

Fraction K from step 1 of Example 2 was further purified by reverse phase HPLC (C18-Phenomenex; Luna 250×10 mm. 10 uM; Phenomenex; Luna 250×10 mm. 10 uM; Mobile Phase A: 0.2% Ammonium acetate in water (W/v); Mobile Phase B: 0.02% acetic acid in acetonitrile; Gradient: 40 to 95% B over 15 min. flow rate: 2.5 ml/min) to afford #NP11 Yield: 2.0 mg. HRESIMS (Protocol 0) m/z 460.2694 (M+H)$^+$, m/z 482.2514 (M+Na)$^+$; $^1$H NMR (500 MHz, DMSO-d$_6$) δ ppm $^1$H NMR (500 MHz, DMSO-d$_6$, mult, J in Hz) δ 7.82 (d, J=6.9 Hz, 1H), 6.37 (m, 1H), 6.38 (m, 1H), 6.13 (dd, J=1.2, 11.6, 1H), 5.88 (dd, J=7.5, 11.6, 1H), 5.78 (s, 1H), 5.68 (dd, J=6.7, 15.8, 1H), 5.62 (t, J=7.0, 1H), 4.97 (m, 1H), 3.67 (m, 1H), 3.66 (m, 1H), 3.52 (m, 1H), 2.47 (m, 1H), 2.44 (m, 1H), 2.33 (m, 1H), 2.23 (m, 1H), 2.00 (s, 3H), 1.97 (s, 3H), 1.82 (m, 2H), 1.74 (s, 3H), 1.67 (m, 1H), 1.26 (d, J=6.5, 3H), 1.08 (d, J=6.3, 3H), 0.97 (d, J=7.1, 3H). $^{13}$C NMR (126 MHz, DMSO-d$_6$) δ 170.1, 165.0, 164.4, 159.0, 143.1, 137.6, 133.9, 131.2, 124.4, 123.2, 115.6, 80.2, 75.2, 77.2, 68.0, 46.5, 35.3, 34.5, 32.1, 28.9, 22.3, 21.0, 20.1, 17.9, 14.3, 12.4.

Example 3

Molecular Phylogenetic Characterization of FERM BP-3421

Step 1: Genomic DNA was isolated from a pure culture of FERM BP-3421 and the nearly complete 16S rRNA gene was PCR amplified using primers 8FPL (5'AGAGTTT-GATCCTGGCTCAG3') (SEQ. ID NO. 1) and 1492RPL (5'GGTTACCTTGTTACGACTT3') (SEQ. ID NO. 2). PCR products were purified with the DNA Clean and Concentrator™-25 kit (Zymo Research) and directly sequenced to provide double stranded coverage with the following 16S rRNA primers: 8FPL, pC FWD (5'CTACGGGAGGCA-GCAGTGGG3') (SEQ. ID NO. 3), pC REV (5'CCCACT-GCTGCCTCCCGTAG3') (SEQ. ID NO. 4), pD FWD (5'CAGCAGCCGCGGTAATAC3') (SEQ. ID NO. 5), pD REV (5'GTATTACCGCGGCTGCTG3') (SEQ. ID NO. 6), pF FWD (5'CATGGCTGTCGTCAGCTCGT3') (SEQ. ID NO. 7), pF REV (5'ACGAGCTGACGACAGCCATG3') (SEQ. ID NO. 8) and 1492RPL. The fully double stranded 16S rRNA sequence (SEQ ID NO: 1) was searched against a public database (National Center for Biotechnology Information) to determine the taxonomic affiliation of FERM BP-3421 as a Burkholderia sp. The 16S rRNA sequences of the most closely related Burkholderia spp. type strains and the sequence of Burkholderia sp. NRRL B50319 (strain A396)(US20110207604A1 Asolkar et al., 2011), which shares 100% identity with FERM BP-3421, were extracted from GenBank. A multiple sequence alignment was performed using ClustalX (version 1.81) and the phylogenetic position of FERM BP-3421 relative to other Burkholderia spp. was determined with standard treeing methods such as TREECON (version 1.3b).

FERM BP-3421

(SEQ. ID NO. 9)
AGAGTTTGATCCTGGCTCAGATTGAACGCTGGCGGCATGCCTTACACATG

CAAGTCGAACGGCAGCACGGGTGCTTGCACCTGGTGGCGAGTGGCGAACG

GGTGAGTAATACATCGGAACATGTCCTGTAGTGGGGGATAGCCCGGCGAA

AGCCGGATTAATACCGCATACGATCTACGGATGAAAGCGGGGGATCTTCG

GACCTCGCGCTATAGGGTTGGCCGATGGCTGATTAGCTAGTTGGTGGGGT

AAAGGCCTACCAAGGCGACGATCAGTAGCTGGTCTGAGAGGACGATCAGC

CACACTGGGACTGAGACACGGCCCAGACTCCTACGGGAGGCAGCAGTGGG

GAATTTTGGACAATGGGGGAAACCCTGATCCAGCAATGCCGCGTGTGTGA

AGAAGGCCTTCGGGTTGTAAAGCACTTTTGTCCGGAAAGAAATCCTTTGG

GCTAATACCCCGGGGGATGACGGTACCGGAAGAATAAGCACCGGCTAAC

TACGTGCCAGCAGCCGCGGTAATACGTAGGGTGCGAGCGTTAATCGGAAT

TACTGGGCGTAAAGCGTGCGCAGGCGGTTTGTTAAGACAGATGTGAAATC

CCCGGGCTTAACCTGGGAACTGCATTTGTGACTGGCAAGCTAGAGTATGG

CAGAGGGGGGTAGAATTCCACGTGTAGCAGTGAAATGCGTAGAGATGTGG

AGGAATACCGATGGCGAAGGCAGCCCCCTGGGCCAATACTGACGCTCATG

CACGAAAGCGTGGGGAGCAAACAGGATTAGATACCCTGGTAGTCCACGCC

CTAAACGATGTCAACTAGTTGTTGGGGATTCATTTCCTTAGTAACGTAGC

TAACGCGTGAAGTTGACCGCCTGGGGAGTACGGTCGCAAGATTAAAACTC

AAAGGAATTGACGGGGACCCGCACAAGCGGTGGATGATGTGGATTAATTC

GATGCAACGCGAAAAACCTTACCTACCCTTGACATGGTCGGAATCCTGAA

GAGATTCGGGAGTGCTCGAAAGAGAACCGATACACAGGTGCTGCATGGCT

GTCGTCAGCTCGTGTCGTGAGATGTTGGGTTAAGTCCCGCAACGAGCGCA

-continued
ACCCTTGTCCTTAGTTGCTACGCAAGAGCACTCTAAGGAGACTGCCGGTG

ACAAACCGGAGGAAGGTGGGGATGACGTCAAGTCCTCATGGCCCTTATGG

GTAGGGCTTCACACGTCATACAATGGTCGGAACAGAGGGTTGCCAACCCG

CGAGGGGGAGCTAATCCCAGAAAACCGATCGTAGTCCGGATTGCACTCTG

CAACTCGAGTGCATGAAGCTGGAATCGCTAGTAATCGCGGATCAGCATGC

CGCGGTGAATACGTTCCCGGGTCTTGTACACACCGCCCGTCACACCATGG

GAGTGGGTTTTACCAGAAGTGGCTAGTCTAACCGCAAGGAGGACGGTCAC

CACGGTAGGATTCATGACTGGGGTGAAGTCGTAACAAGGTAACC

FIG. 1 illustrates the phylogenetic relationship determined with nearly complete 16S rRNA sequences of FERM BP-3421 to other Burkholderia spp. The neighbor-joining phylogenetic tree was rooted with Burkholderia pickettii and shows bootstrap values (based on 100 replicates and greater than 50%) at their respective nodes. The scale bar represents 0.02 substitutions per nucleotide.

Example 4

Fermentation, Extraction and Isolation of: [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetic Acid (#NP1); and [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl] acetic acid (#NP2) with engineered strain #1 of FERM BP-3421

Step 1:
Genome mining for spliceostatin biosynthetic gene cluster:
The genome of FERM BP-3421 was sequenced using next-generation technologies (454 and Illumina). The biosynthetic gene cluster for spliceostatins (FIG. 2) was inferred from the DNA sequence by genome mining (for a review see Challis GL 2008 J Med Chem 51: 2618-2628) which led us to identify a trans-acyltransferase (AT) polyketide synthase (PKS)/non-ribosomal peptide synthetase (NRPS) hybrid pathway (for a review see J Piel 2010 Nat Prod Rep 27:996-1047 and references therein). PKS and NRPS gene knockout mutants showed no detectable spliceostatin production, confirming the involvement of these genes in spliceostatin biosynthesis. Our findings are in agreement with those reported by Zhang F et al. (2011 J Am Chem Soc 133: 2452-62) and the gene terminology introduced in this JACS paper is used hereafter.

Figure 2:
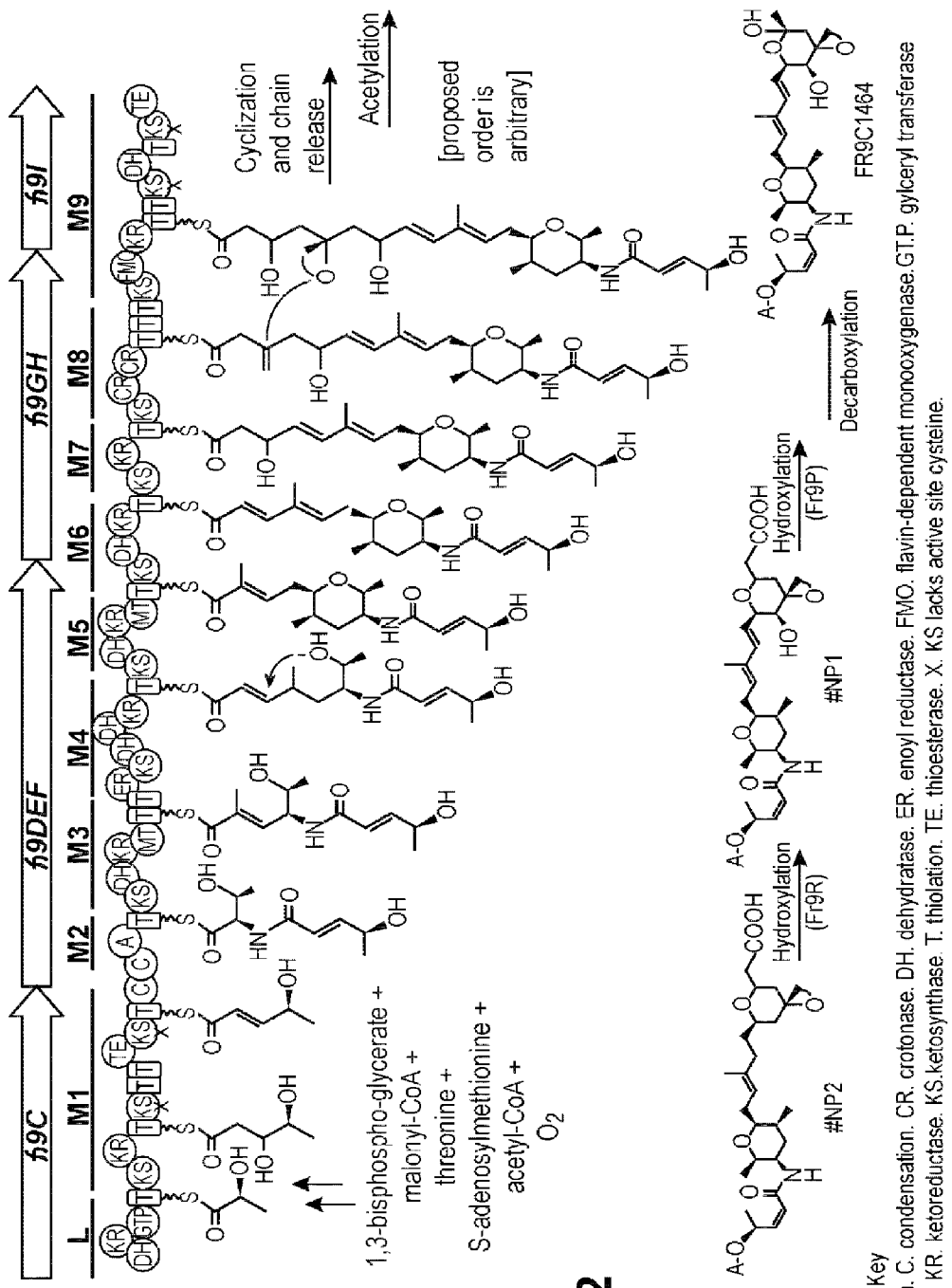
FIG. 2 is a biosynthetic gene cluster for spliceostatins and proposed biosynthetic pathway highlighting hydroxylation steps catalyzed by cytochrome P450 Fr9R and Fe(II)/α-ketoglutarate-dependent dioxygenase Fr9P. Arrows at the top represent coding DNA sequences of PKS-NRPS genes; auxiliary genes are not shown.

FIG. 2 is a biosynthetic gene cluster for spliceostatins and proposed biosynthetic pathway highlighting hydroxylation steps catalyzed by cytochrome P450 Fr9R and Fe(II)/α-ketoglutarate-dependent dioxygenase Fr9P. Arrows at the top represent coding DNA sequences of PKS-NRPS genes; auxiliary genes are not shown.

Step 2:
Generation of the dioxygenase (fr9P) knockout mutant strain of FERM BP-3421 (Strain #1)
Two ~700-bp long DNA fragments upstream and downstream of the point of gene replacement were amplified by PCR (Pfu Ultra™ Polymerase, Promega) using FERM BP-3421 genomic DNA as template and primer pairs

```
P1_dox
                                            (SEQ. ID NO. 10)
(TGG CGA ACA GAT CGA GTT TG)
and P2_diox
                                            (SEQ. ID NO. 11)
(CTT GCG GAG AAC TGT GAA TGC GCA ATA GAA GCG CTG TCA TGG AAT G),
and P3_diox
                                            (SEQ. ID NO. 12)
(CCG AAA AGT GCC ACC TGA CGT CTA AGA TAA CTC GTG GAT ATT CGG CAA G)
and P4_diox
                                            (SEQ. ID NO. 13)
(AGA ATC CCG CGA TCC CAA C);
``` underlined bases represent homology regions to the tetracycline resistance (tet) marker. The tet marker was amplified by PCR using pEX18Tc (Schweizer H P 1998 *Gene* 212: 77-86) as template and primer pair Ptet_f (TTG CGC ATT CAC AGT TCT C) (SEQ. ID NO. 14) and Ptet_r (TCT TAG ACG TCA GGT GGC AC) (SEQ. ID NO. 15). The three fragments were assembled by SOE-PCR (using Pfu Ultra™ Polymerase, Promega) and ligated into the SmaI site of pEX100T (Schweizer H P & Hoang T T 1995 *Gene* 158: 15-22) to generate plasmid pAE-PF12. pAE-PF12 was transferred into FERM BP-3421 by conjugation from *E. coli* S17.1. Tetracycline (25 μg/ml) was used for selection of mutants; sucrose 5% for counter-selection of the vector backbone; and gentamycin (10 μg/ml) to remove *E. coli* after conjugation. Mutants were confirmed by colony PCR (RED Taq®, Sigma) in three separate reactions using primer pairs P1_diox/P4_diox, P1_diox/Ptet_r, and TP1_pEX100T (GGA CGA ATC GAA CTC AGG AAC TTG) (SEQ. ID NO. 16)/TP2_pEX100T (CGA AGA GCG ATT GAG GAA AAG G) (SEQ. ID NO. 17), providing strain #1.

Step 3:

Fermentation using engineered strain #1: Engineered strain #1 was cultured in seed medium (1% polypeptone, 0.5% yeast extract, 0.5% NaCl) containing tetracycline (25 mg/L) at 30° C. and 220 rpm for ~24 hours. A second seed culture was generated by inoculating fresh seed medium containing tetracycline (25 mg/L) with the first seed culture at 10% (v/v) and incubated at 30° C. with shaking at 220 rpm for ~24 hours. 850 ml of the seed culture was used to inoculate 29 L of production medium (4% glycerine, 2% HySoy soypeptone, 0.2% ammonium sulfate, 0.01% magnesium sulfate. 6H$_2$O, 0.2% CaCO$_3$) contained in a 30-L Bioreactor (BIOSTAT® C plus, Sartorius BBI Systems). The fermentation was carried out at 25° C. for 5 days. Initial agitation was set at 344 rpm; initial airflow at 1.3 slpm; DO was controlled at 3% with increased agitation.

Step 4:

Extraction of fermentation broth: At the end of fermentation from step 3 of example 4, 1.5 kg of wet DIAION HP-20 resin was added to the whole broth and the mixture was shaken overnight. The HP-20 was collected by filtration through a 50 μm-150 μm stainless steel wedge wire mesh. The compound-bound HP-20 resin was extracted four times with ethyl acetate (3 L each time, with shaking for 45 min). The resin was then washed (once with 2 L methanol and 3 times with abundant DI water) and reused for recapture of compound still remaining in the aqueous filtrate, following the same procedure described above. Solvent from the combined ethyl acetate extracts was removed by evaporation under reduced pressure to afford a light-yellow powder (137 g).

Step 5:

Isolation of [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetic acid (#NP1); and [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetic acid (#NP2): 1.7 g of extract from step 4 of Example 4 was dissolved in a mixed solvent of 2:1 DMF/ACN (22 ml total), filtered, and then purified by reversed phase HPLC (Waters ODS-A 50×300 mm, 15 um, 120 A, Mobile Phase A: 0.02% AcOH in water, Mobile Phase B: 0.02% AcOH in acetonitrile solvent system, Gradient: 50% B for 2 min, to 75% B over 18 min; 100% B for 2 min. Flow rate: 50 mL/min; 5 repeated injections). The fractions with retention times of 13.5 and 18.0 min were collected and freeze-dried to afford #NP1 (191 mg) and #NP2 (466 mg) respectively as white powders.

NP1; HPLC (Protocol N): retention time=9.38 minutes (purity 98.5%)

NP2; HPLC (Protocol N): retention time=10.97 minutes (purity 96.5%)

Example 5

Fermentation, Extraction and Isolation of: [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetic Acid (#NP1) with engineered strain #2 of Ferm FERM BP-3421

Step 1:

Generation of engineered strain #2: Firstly, the tet marker in vector mini-CTX1 (Hoang T T et al. 2000 Plasmid 43:59-72) was replaced by neo (kanamycin and neomycin resistance) from pCR2.1 (Invitrogen) by λ-Red-mediated recombination (Datsenko K A & Wanner B L. 2000 *Proc Natl Acad Sci USA* 97:6640-5). Primers used were

```
P1_neo_pCR2.1
                                            (SEQ. ID NO. 18)
(GTT GGT TTG CGC ATT CAC AGT TCT CCG CAA GAA TTG ATT GCA AGG GCT GCT AAA GGA AG)
and P2_neo_tet_CTX1_pCR2.1
                                            (SEQ. ID NO. 19)
(TCT TCC GCT TCC TCG CTC ACT GAC TCG CTG CGC TCG

GTC ACG AAA ATG TTG AAT ACT CAT ACT C);
``` underlined sequences represent homology regions for λ-Red-mediated recombination. The obtained vector was named pAE-PF24.

A P$_{BAD}$/araC arabinose-inducible system was amplified by PCR (Phusion® Hot Start polymerase, Finnzymes) using pKD46 as template and primer pair

```
P1_BADp_f
                                    (SEQ. ID NO. 20)
(GCT CTA GAC ATC GAT TTA TTA TGA CAA CTT GAC,

XbaI site underlined)
and

P2_BADp_r
                                    (SEQ. ID NO. 21)
(CCC AAA AAA ACG GGT AT G).
```

The gene (including the putative RBS but no promoter) coding for the cytochrome P450 gene (fr9R) contained in the spliceostatin biosynthetic gene cluster was amplified by PCR (Phusion® Hot Start polymerase, Finnzymes) using genomic DNA from

```
FERM BP-3421 and primer pair P3_P450_BAD_f
                                    (SEQ. ID NO. 22)
(CTA CTG TTT CTC CAT ACC CGT TTT TTT GGG GGG TTG TTG GTT TTT GAA ATT GC, extension for SOE-PCR underlined)
and P4_P450_r
                                    (SEQ. ID NO. 23)
(ATG GTG AAG CTT AAG TCG ACA ACC GGC ATT CC, HindIII site underlined).
```

The two fragments so obtained were assembled by SOE-PCR (Phusion® Hot Start polymerase, Finnzymes) and subsequently ligated into the SpeI and HindIII sites of pAE-PF24, generating pAE-PF29. pAE-PF29 was transferred into engineered strain #1 by conjugation from E. coli S17.1. Kanamycin (500 µg/ml) was used for selection of mutants; and gentamycin (10 ug/ml) to remove E. coli after conjugation. Mutants were confirmed by two colony PCR reactions (RED Taq® Sigma) using primer sets TP1_CTX1_marker (GCA TTC ACA GTT CTC CGC AAG) (SEQ. ID NO. 24) and TP2_CTX1_marker (CTC GCT CAC TGA CTC GCT G) (SEQ. ID NO. 25), and T3_mini-CTX1_f (GCA ATT AAC CCT CAC TAA AGG) (SEQ. ID NO. 26) and MCS_mini-CTX1_r (CTA TAG GGC GAA TTG GGT AC) (SEQ. ID NO. 27), providing engineered strain #2.

Step 2:
Fermentation using engineered strain #2: Engineered strain #2 was cultured in seed medium (1% polypeptone, 0.5% yeast extract, 0.5% NaCl) containing tetracycline (25 mg/L) at 30° C. and 220 rpm for ~24 hours. A second seed culture was generated by inoculating fresh seed medium containing tetracycline (25 mg/L) with the first seed culture at 10% (v/v) and incubated at 30° C. with shaking at 220 rpm for ~24 hours. The seed culture was used to inoculate 550 ml of production medium (4% glycerine, 2% HySoy soypeptone, 1.5% L-arabinose, 0.2% ammonium sulfate, 0.01% magnesium sulfate. 6H$_2$O, 0.2% CaCO$_3$) per 2.8 L Fernbach flask with no baffles at 2.5% (v/v). The fermentation was incubated at 25° C. with shaking at 200 rpm for 4 days.

Step 3:
Extraction of fermentation broth: At the end of the fermentation from step 2 of example 5, 100 g/L of wet DIAION HP-20 resin was added to 6 L of production fermentation and the mixture was shaken for 3 hours. The HP-20 was collected by filtration through a 50 µm-150 µm stainless steel wedge wire mesh. The compound-bound HP-20 resin was extracted three times with ethyl acetate (2 L each time).

In more detail, each extraction was performed by transferring the resin to a carboy, adding 2 L ethylacetate, shaking for 1 hour and filtering through a 50 µm-150 µm stainless steel wedge wire mesh. Solvent from the combined ethyl acetate extracts was removed by evaporation under reduced pressure to afford a light-yellow crude extract (17.25 g).

Step 4:
Isolation of [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetic acid (#NP1), 0.12 g of extract from step 3 of Example 5 was dissolved in a mixed solvent of 2:1 DMF/ACN (22 ml total), filtered, and then purified by reversed phase HPLC (YMC ODS-A 30×250 mm, 10 um, 120 A, Mobile Phase A: 0.02% AcOH in water, Mobile Phase B: 0.02% AcOH in acetonitrile. Gradient: 30% B for 2 min, to 100% B over 18 min; 100% B for 2 min. Flow rate: 20 mL/min). The fraction with retention time of 15.0 min was collected and freeze-dried to afford #NP1 (73.6 mg) as a white powder.

NP1; HPLC (Protocol N): retention time=9.36 minutes (purity 92.5%)

Example 6

Fermentation, Extraction and Isolation of (2S,3Z)-5-{[(2R,3R,5S,6S)-6-{(2E,4E)-5-[(3R,5S,7S)-7-hydroxy-7-methyl-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#NP12); and [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl] acetic acid (#NP2) with engineered strain #3 of FERM BP-3421

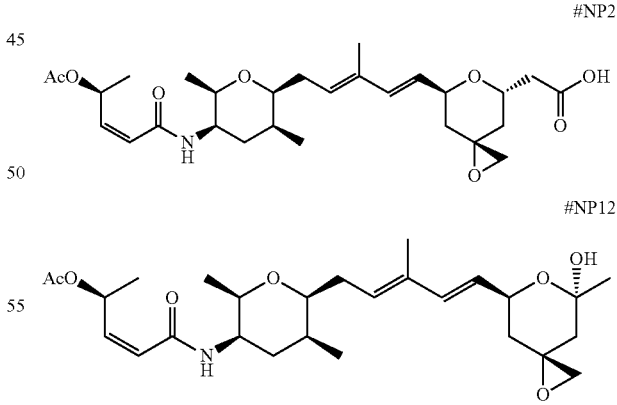

Step 1:
Generation of engineered strain #3: Two ~700-bp long DNA fragments upstream and downstream of the point of gene replacement were amplified by PCR (Pfu Ultra™ Polymerase, Promega) using FERM BP-3421 genomic DNA as template and primer pairs P1_P450
(GCA TCC AAT CAC TTG AAC AGG) (SEQ. ID NO. 28)
and P2_P450
(CTT GCG GAG AAC TGT GAA TGC GCA AGC CAT CAT TCT CGA CAT TTC C), (SEQ. ID NO. 29)
and P3_P450
(CCG AAA AGT GCC ACC TGA CGT CTA AGA AGA TTG TGA CGG TAC TGA AGC) (SEQ. ID NO. 30)
and

P4_P450
(AGA GAA CGA TCG CTC CAC AG); (SEQ. ID NO. 31)

underlined bases represent homology regions to the tetracycline resistance (tet) marker. The tet marker was amplified by PCR using pEX18Tc (Schweizer H P 1998 *Gene* 212: 77-86) as template and primer pair Ptet_f (TTG CGC ATT CAC AGT TCT C) (SEQ. ID NO. 32) and Ptet_r (TCT TAG ACG TCA GGT GGC AC) (SEQ. ID NO. 33). The three fragments were assembled by SOE-PCR (using Pfu Ultra™ Polymerase, Promega) and ligated into the SmaI site of pEX100T (Schweizer H P & Hoang T T 1995 *Gene* 158: 15-22) to generate plasmid pAE-PF11. pAE-PF11 was transferred into FERM BP-3421 by conjugation from *E. coli* S17.1. Tetracycline (25 µg/ml) was used for selection of mutants; sucrose 5% for counter-selection of the vector backbone; and gentamycin (10 µg/ml) to remove *E. coli* after conjugation. Mutants were confirmed in two colony PCR (RED Taq®, Sigma) reactions using primer pairs P1_P450/Ptet_r and TP1_pEX100T (GGA CGA ATC GAA CTC AGG AAC TTG) (SEQ. ID NO. 34)/TP2_pEX100T (CGA AGA GCG ATT GAG GAA AAG G) (SEQ. ID NO. 35), providing strain #3.

Step 2:
Fermentation using engineered strain #3: Engineered strain #3 was cultured in seed medium (1% polypeptone, 0.5% yeast extract, 0.5% NaCl) containing tetracycline (25 mg/L) at 30° C. and 220 rpm for ~24 hours. A second seed culture was generated by inoculating fresh seed medium containing tetracycline (25 mg/L) with the first seed culture at 10% (v/v) and incubated at 30° C. with shaking at 220 rpm for ~24 hours. The seed culture was used to inoculate 400 ml of production medium (4% glycerine, 2% HySoy soypeptone, 0.2% ammonium sulfate, 0.01% magnesium sulfate. 6H$_2$O, 0.2% CaCO$_3$) at 2.5% (v/v) contained in a 2.8-L Fernbach flask without baffles. The fermentation was incubated at 25° C. with shaking at 200 rpm for 5 days.

Step 3:
Extraction of fermentation broth: The production culture from step 2 of example 6 was centrifuged for 30 min at 4,200 rpm to remove cells. 50 g of wet DIAION HP-20 resin was added to the supernatant (12.5% w/v) and the mixture was shaken at 200 rpm for 1 h. The compound-bound HP-20 was collected by centrifugation and then extracted twice with ethyl acetate (250 ml for each extraction). After drying the combined extracts with MgSO$_4$ (which was then removed by filtration with Whatman paper), the solvent was removed by evaporation under reduced pressure to afford a light-colored crude extract.

Step 4:
Isolation of [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetic acid (#NP2) and (2S,3Z)-5-{[(2R,3R,5S,6S)-6-{(2E,4E)-5-[(3R,5S,7S)-7-hydroxy-7-methyl-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#NP12): Half of the crude extract from step 3 of Example 6 was purified by preparative, normal phase HPLC: (Column: Princeton SFC 2-ethylpyridine, 250×21.2 mm, 5 µm; Mobile Phase A: heptane; Mobile Phase B: ethanol (denatured). Gradient: 5% B for 1.5 min, to 100% B over 8.5 min, 100% B for 2 min, to 5% B over 0.5 min and 5% B for 2.5 min. Flow rate: 27 mL/min). The fractions with retention times of 6.58 min and 8.18 min were collected and freeze-dried to afford #NP12 (163 mg, 89% pure as a very light, yellowish powder), and #NP2 (205 mg, 89% pure by UV), respectively.

NP12: HPLC (Protocol P): retention time=12.65 min (purity 89%); LC/MS: m/z 474.2 [M+H$^+$—H$_2$O]$^+$ and 514.2 [M+Na$^+$]$^+$

NP2: HPLC (Protocol P): retention time=12.46 min (purity 89%); LC/MS: m/z 520.2 [M+H$^+$]$^+$ Step 5:
Isolation of (2S,3Z)-5-{[(2R,3R,5S,6S)-6-{(2E,4E)-5-[(3R,5S,7S)-7-hydroxy-7-methyl-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#NP12): One half of the 6.58-min fraction from step 4 of example 6 was purified by reverse-phase HPLC: (Column: Phenomenex Luna C18, 150×21.2 mm, 5 µm; Mobile Phase A: water; Mobile Phase B: acetonitrile. Gradient: 20% B for 1.5 min, to 70% B over 8.5 min, to 100% B over 2 min, to 20% B over 0.5 min. Flow rate: 27 mL/min). The fraction with retention time 8.25 min was collected and freeze-dried to afford #NP12 (28 mg) as a white powder. #NP12; HPLC (Protocol N): retention time=12.6 min ((purity 98.5%); HRESIMS (protocol 0) m/z 492.296 [M+H]$^+$; $^1$H NMR (400 MHz, DMSO-d$_6$, mult, J in Hz) δ 7.78 (d, J=8.0 Hz, 1H), 6.35 (m, 1H), 6.21 (d, J=15.8, 1H), 6.11 (dd, J=0.9, 11.7, 1H), 5.85 (dd, J=11.6, 7.5 Hz, 1H), 5.53 (m, 1H), 5.49 (m, 1H), 5.41 (d, J=1.6 Hz, OH), 4.64 (m, 1H), 3.65 (m, 1H), 3.64 (m, 1H), 3.49 (m, 1H), 2.45 (m, 2H), 2.30 (m, 1H), 2.20 (m, 1H), 1.98 (s, 3H), 1.96 (m, 1H), 1.81 (m, 3H), 1.69 (s, 3H), 1.65 (m, 1H), 1.31 (s, 3H), 1.25 (m, 1H), 1.25 (d, J=6.3 Hz, 3H), 1.14 (m, 1H), 1.07 (d, J=6.5 Hz, 3H), 0.95 (d, J=7.3 Hz, 3H). $^{13}$C NMR (100 MHz, DMSO-d$_6$) δ 169.6, 164.6, 142.1, 134.1, 133.7, 128.2, 127.1, 122.6, 95.3, 79.5, 74.3, 67.6, 66.7, 54.5, 48.4, 46.1, 41.4, 37.5, 35.0, 31.1, 29.6, 28.5, 20.8, 19.5, 17.8, 13.9, 12.2.

Example 7

Fermentation, Extraction and establishing production of: [(3R,5S,7R,8R)-7-{(1E,3E)-5-[(2S,3S,5R, 6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetic Acid (#NP1); [(3S, 5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1, 3-dien-1-yl}-1,6-dioxaspiro[2.5]oct-5-yl]acetic acid (#NP2) using *Burkholderia* sp. MSMB 43

Step 1:
Fermentation using *Burkholderia* sp. MSMB 43: *Burkholderia* sp. (proposed name "*Burkholderia humptydooensis*") MSMB 43 was acquired from the Centers for Disease Control and Prevention (CDC) and Menzies School of Health Research. MSMB 43 was cultured on nutrient agar plates from a cryopreserve and incubated at 30° C. for 48 hours. The agar grown culture was inoculated into a 25×150 mm culture tube containing 10 ml of seed medium (1% polypeptone, 0.5% yeast extract, 0.5% NaCl). The seed culture was incubated at 30° C. with shaking at 220 rpm for 18-20 hours. The seed culture was inoculated into 50 ml of production medium (1% soluble starch, 1% glycerine, 0.5% glucose, 1% HySoy Soypeptone, 0.5% corn steep liquor, 0.2% ammonium sulfate, 0.006% magnesium sulfate. $6H_2O$, 0.2% $CaCO_3$, pH 7.0) per 250 ml Erlenmeyer flask at 2.5% (volume/volume). The fermentations were incubated at 25° C. with shaking at 200 rpm for 72 hours.

Step 2:

LC-MS analysis of fermentations.

Fermentations were centrifuged to pellet the cells, and the supernatants filtered through 0.22 μm polyvinylidene fluoride membranes. A portion of each supernatant was mixed with dimethyl sulfoxide (10:1) and analyzed by LC-MS using an Acuity UPLC (Waters) instrument: Column: XBridge C18, 4.6×150 mm, 3.5 uM Mobile phase A: 0.1% formic acid in water (v/v); Mobile phase B: 0.1% formic acid in acetonitrile (v/v); Gradient 5% to 100% B over 12.0 minutes; 100% B for 3.0 minutes (Inj. Volume: 5.0 uL. On day five of the fermentations, MSMB43 produced NP1 and NP2 at a titre of 150 mg/L of and 50 mg/L respectively as evident by retention time and mass spec data.

NP1: m/z: 535.9 $(M+H)^+$, Retention time: 13.31 min.

NP2: m/z: 519.9 $(M+H)^+$ Retention time: 14.58 min

Synthetic Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS) or atmospheric pressure chemical ionization (APCI). Chemical shifts for nuclear magnetic resonance (NMR) data are expressed in parts per million (ppm, δ) referenced to residual peaks from the deuterated solvents employed For syntheses referencing procedures in other Examples or Methods, reaction Protocol (length of reaction and temperature) may vary. In general, reactions were followed by thin layer chromatography, LCMS or HPLC, and subjected to work-up when appropriate. Purifications may vary between experiments: in general, solvents and the solvent ratios used for eluents/gradients were chosen to provide appropriate retention times. Unless otherwise specified, reverse phase HPLC fractions were concentrated via lyophilization/Freeze-drying. Intermediate and final compounds were stored at (0° C.) or room temperature in closed vials or flasks under nitrogen.

Compound names were generated with ACD Labs software.

HPLC Conditions Used for Analysis

Protocol $A^A$ and $A^B$:

Column: Phenomenex Luna C18 (2), 150×3.0 mm, 5 μm; Mobile phase A: 0.02% trifluoroacetic acid in water (v/v); Mobile phase B: 0.02% trifluoroacetic acid in acetonitrile (v/v); Gradient: 5% to 100% B (over 10 minutes)' or (over 20 minutes)$^B$; Flow Rate: 0.75 mL/minute. Temperature: not controlled; Detection: DAD 215, 254 nm; Injection volume 10 μL; Instrument: HP 1100.

Protocol B:

Column: Waters Sunfire C18, 50×4.6 mm, 5 μm; Mobile phase A: 0.05% formic acid in water (v/v); Mobile phase B: 0.05% formic acid in acetonitrile (v/v); Gradient: 5% to 95% B over 4 minutes, Hold at 95% B for 1 minute. Flow Rate: 2.0 mL/min. Temperature: room temperature; Detection: DAD 215 nm; Injection volume 4 μL; Instrument: Waters LC and ZQ Mass Spectrometer.

Protocol C:

Column: Waters Acquity UPLC HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 2.5 minutes, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol D:

Column: Waters Acquity UPLC HSS T3, C18, 2.1×50 mm, 1.7 μm; Mobile phase A: 0.1% formic acid in water (v/v); Mobile phase B: 0.1% formic acid in acetonitrile (v/v); Gradient: 5% B over 0.1 minute, 5% to 95% B over 1.5 minute, 95% B over 0.35 minute; Flow rate: 1.25 mL/minute. Temperature: 60° C.; Detection: 200-450 nm; MS (+) range 100-2000 daltons; Injection volume: 5 μL; Instrument: Waters Acquity.

Protocol E:

Column: Phenomenex Luna C18 (2), 150×3.0 mm, 5 μm; Mobile phase A: 0.02% trifluoroacetic acid in water (v/v); Mobile phase B: 0.02% trifluoroacetic acid in acetonitrile (v/v); Gradient: 0% to 100% B over 23.5 minutes; Flow rate: 1.5 mL/minute. Temperature: not controlled; Detection: DAD 210 nm; Injection Volume: 10 μL; Instrument: Agilent 1100 HPLC Protocol F:

Column: Phenomenex Luna C18 (2), 150×3.0 mm, 5 μm; Mobile phase A: 0.1% formic acid in water (v/v); Mobile phase B: 0.1% formic acid in acetonitrile (v/v); Gradient: 5% B over 1.5 minutes, 5% to 100% B over 8.5 minutes, then 100% B for 1 minute; Flow rate: 0.75 mL/minute. Temperature: 45° C.; Detection: DAD 215 nm, 254 nm; MS (+) range 150-2000 daltons; Injection volume: 10 μL; Instrument: Agilent 1200 LCMS.

Protocol G:

Column: Atlantis dC18, 50×4.6 mm, 5 μm; Mobile phase A: 0.05% trifluoroacetic acid in water (v/v); Mobile phase B: 0.05% trifluoroacetic acid in acetonitrile (v/v); Gradient: 5% to 95% B over 4.0 minutes, linear; then hold at 95% B over 1 minute. Flow rate: 2 mL/minute. Temperature: room temperature; Detection: DAD 215 nm; MS (+) range 160-1000 daltons; Injection volume 4 uL; Instrument: Waters 996 PDA.

Protocol H:

Column: Phenomenex Luna C18 (2), 150×3.0 mm, 5 μm; Mobile phase A: water; Mobile phase B: acetonitrile; Gradient: 5% B over 1.5 minutes, 5% to 100% B over 8.5 minutes, then 100% B for 1 minute; Flow rate: 0.75 mL/minute. Temperature: 25° C.; Detection: DAD 215 nm, 254 nm; MS (+) range 150-2000 daltons; Injection volume: 10 μL; Instrument: Agilent 1200 LCMS.

Protocol I:

Column: Xtimate C18, 2.1×30 mm, 3 □m; Mobile phase A: 0.1% trifluoroacetic acid in water (v/v); Mobile phase B: 0.1% trifluoroacetic acid in acetonitrile (v/v); Gradient 0% to 60% B over 0.9 minutes, 60% B over 0.6 minutes; 100% B for 0.5 minutes; Flow rate: 1.2 mL/minute. Detection: DAD 220 nM; Temperature: 25° C.; Injection volume: 1 μL; Instrument: Agilent Protocol J:
Column: Xtimate C18, 2.1×30 mm, 3 µm; Mobile phase A: 0.1% trifluoroacetic acid in water (v/v); Mobile phase B: 0.1% trifluoroacetic acid in acetonitrile (v/v); Gradient: 10% to 80% B over 0.9 minutes, 80% B over 0.6 minutes; 100% B for 0.5 minutes; Flow rate: 1.2 mL/minute. Detection: DAD 220 nM; Temperature: 25° C.; Injection volume: 1 µL; Instrument: Agilent.

Protocol K:
Column: Phenomenex Luna PFP, 100×3 mm, 5 µm; Mobile phase A: 0.05% formic acid in water (v/v); Mobile phase B: 0.05% formic acid in acetonitrile (v/v); Gradient: 5% to 95% B over 9 minutes, Hold at 95% B for 1 minute. Flow Rate: 1.0 mL/min. Temperature: room temperature; Detection: DAD 215 nm; Injection volume: 4 µL; Instrument: Waters LC and ZQ Mass Spectrometer.

Protocol L:
Column: Phenomenex Gemini-NX, C18, 4.6 mm×50 mm, 110 A, 3 µm, Mobile phase A: 0.1% formic acid in water (v/v); Mobile phase B: 0.1% formic acid in acetonitrile (v/v); Gradient 5%; to 100% B over 0.0-4.10 min; hold at 100% B from 4.10-4.50 min; Flow rate: 1.25 mL/minute. Temperature: 60° C.; Detection: 200-450 nm; MS (+) range 100-2000 daltons; Injection volume: 5 µL; Instrument: Waters Acquity.

Protocol M:
Column: Phenomenex Gemini-NX, 4.6 mm×50 mm, C18, 3 µm, 110 A; Mobile phase A: 0.1% formic acid in water (v/v); Mobile phase B: 0.1% formic acid in acetonitrile (v/v); Gradient: 5% to 100% B over 4.10 minutes, hold at 100% B for 0.4 minutes, then 100% to 5% B over 0.5 minutes; Flow rate: 1.5 mL/minute. Temperature: 60° C.; Detection: HP1100 DAD (1315A), 200-450 nm scan; 1 nm interval; MS ESI(+/−), 100-1200 m/z scan, 0.5 sec scan time, Centroid; Injection volume: 5 µL; Instrument: HPLC Pump, DAD Detector, Column Oven from Agilent Technologies, Wilmington, Del.; Autosampler and MS detector from Waters Corporation, Milford, Mass.; ELS Detector from Varian medical devices, Palo Alto, Calif.

Protocol N:
Column: YMC ODS-A, 4.6×150 mm, 5 µm; Mobile phase A: 0.01% trifluoroacetic acid in water (v/v); Mobile phase B: 0.01% trifluoroacetic acid in acetonitrile (v/v); Gradient: 10% to 100% B over 15 minutes; Flow rate: 1.0 mL/minute. Temperature: not controlled; Detection: DAD 230 nm; Injection volume: 5 µL; Instrument: Agilent 1100 HPLC.

Protocol O:
High resolution electrospray ionization mass spectra (HRESIMS) were obtained using a Bruker (Billerica, Mass.) APEXII FTICR mass spectrometer equipped with an actively shielded 9.4 Tesla superconducting magnet (Magnex Scientific Ltd., UK), an external Bruker APOLLO ESI source, and a Synrad 50W $CO_2$ CW laser. The sample was flow injected into the mass spectrometer with carrier solvent consisting of 1:1 (v:v) water:acetonitrile (0.25% formic acid) at a flow rate of 50 µL/min. Bruker Xmass software was used for data acquisition and analysis. The mass spectrum was externally calibrated using HP tuning mix.

Protocol P:
Column: YMC ODS-A, 4.6×150 mm, 5 m; Mobile phase A: 0.01% trifluoroacetic acid in water (v/v); Mobile phase B: 0.01% trifluoroacetic acid in acetonitrile (v/v); Gradient: 10% to 100% B over 19 minutes; Flow rate: 1.0 mL/minute. Temperature: not controlled; Detection: DAD 230 nm; Injection volume: 5 µL; Instrument: Agilent 1100 HPLC.

Protocol Q:
Column: Column: Agilent Poroshell 300SB-C8, 75×2.1 mm, 2.6 µm; Mobile phase A: 0.1% formic acid in water (v/v); Mobile phase B: 0.1% formic acid in acetonitrile (v/v); Gradient: 20% B to 45% B over 4 minutes; Flow rate: 1.0 mL/minute. Temperature: 60° C.; Detection: 220 nm; MS (+) range 400-2000 Da; Injection volume: 10 µL; Instrument: Agilent 1100 LC, Waters MicromassZQ MS. Deconvolution was performed using MaxEnt1.

HPLC Conditions Used for Purification

Method A:
Column: Phenomenex Gemini, C18, 30×100 mm, 5 µm; Mobile phase A: 0.02% acetic acid in water (v/v); Mobile phase B: 0.02% acetic acid in acetonitrile (v/v); Gradient: variable, increasing gradient of B in A over 15-20 minutes; Flow rate: 20 mL/minute. Temperature: not controlled; Detection: DAD 215 nm, 254 nm; Injection Volume: variable; Instrument: Gilson.

Method B*:
Column: YMC ODS-A, 30×250 mm, 10 µm; Mobile phase A: 0.02% acetic acid in water (v/v); Mobile phase B: 0.02% acetic acid in acetonitrile (v/v); Gradient: variable, increasing gradient of B in A over 15-20 minutes; Flow rate: 20 mL/minute. Temperature: not controlled; Detection: DAD 230 nm; Injection volume: variable, 0.5-2 mL; Instrument: Varian ProStar Model 330 preparative HPLC.

Method C*:
Column: Phenomenex Luna C18(2), 150×21.2 mm, 5 µm; Mobile phase A: water; Mobile phase B: acetonitrile; Gradient: variable, increasing gradient of B in A over 10 minutes; Flow rate: 27 mL/minute. Temperature: room temperature; Detection: DAD 210-360 nm; MS (+) range 150-2000 daltons; Instrument: Waters Fraction Lynx LCMS.

Method D*:
Column: Waters Sunfire, C18, 19×100 mm, 5 µm; Mobile phase A: 0.05% formic acid in water (v/v); Mobile phase B: 0.05% formic acid in acetonitrile (v/v); Gradient: variable, increasing gradient of B in A over 10-20 minutes; Flow rate: 25 mL/minute. Detection: DAD 215 nm MS (+) range 160-1000 daltons; Instrument: Waters FractionLynx.

Method E:
Column: Waters Sunfire, C18, 19×100 mm, 5 µm; Mobile phase A: 0.05% trifluoroacetic acid in water (v/v); Mobile phase B: 0.05% trifluoroacetic acid in acetonitrile (v/v); Gradient: 10 to 50% B over 8.5 minutes, 50 to 100% B over 0.5 minutes, hold at 100% B for 1 minute. Flow rate: 25 mL/minute. Detection: DAD 215 nm MS (+) range 160-1000 daltons; Instrument: Waters FractionLynx.

Method F*:
Column: Waters C18 DELTA PAK (WAT011801), 300× 50 mm, 15 µm; Mobile phase A: 0.02% acetic acid in water (v/v); Mobile phase B: 0.02% acetic acid in acetonitrile (v/v); Gradient: variable, increasing gradient of B in A over 15-20 minutes; Flow rate: 50 mL/minute. Temperature: not controlled; Detection: DAD 230 nm; Injection volume: variable, 0.5-5 mL; Instrument: Varian ProStar Model 330 preparative HPLC.

Method G*:
Column: YMC ODS-A, 50×300 mm, 12 µm, 120 A. Mobile phase A: 0.02% acetic acid in water (v/v); Mobile phase B: 0.02% acetic acid in acetonitrile (v/v); Gradient: 40% B for 3 minutes, 40-100% B over 20 minutes and 100% B for 3 minutes. Flow rate; 20 mL/minute. Temperature: not controlled; Detection: DAD 230 nm; Injection volume: variable, 0.5-5 mL; Instrument: Varian ProStar Model 330 preparative HPLC.

Method H:

Column: Cromolith RP-18e 100-10 mm. Mobile phase A: 0.02% acetic acid in water (v/v); Mobile phase B: 0.02% acetic acid in acetonitrile (v/v); Gradient: 20-55% B over 30 minutes, 55-100% B over 4 min, 100-20% B over 2 min and 20% B for 2 minutes. Flow rate; 2.5 mL/minute. Temperature: not controlled; Detection: DAD 230 nm; Injection volume: variable, 0.025-0.1 mL; Instrument: Agilent 1100 analytical HPLC.

Method I:

Column: C18 semiprep YMC-Pack ODS-A 250×10 mm (5-5 µm, 12 nm). Mobile phase A: 0.02% acetic acid in water (v/v); Mobile phase B: 0.02% acetic acid in acetonitrile (v/v); Gradient: 18-25% B over 22 minutes, 25-95% B over 1 min, 95% B for 4 min, 95-18% B over 1 min and 18% B for 6 minutes. Flow rate: 2.5 mL/minute. Temperature: not controlled. Detection: DAD 230 nm. Injection volume: variable, 0.025-0.1 mL. Instrument: Agilent 1200 analytical HPLC.

Method J:

Column: C18 semiprep YMC-Pack ODS-A 250×10 mm (S-5 µm, 12 nm). Mobile phase A: 0.02% acetic acid in water (v/v); Mobile phase B: 0.02% acetic acid in acetonitrile (v/v); Gradient: 20-30% B over 30 minutes, 30-95% B over 1 min, 95% B for 4 min, 95-20% B over 2 min and 20% B for 6 minutes. Flow rate: 2.5 mL/minute. Temperature: not controlled. Detection: DAD 230 nm. Injection volume: variable, 0.025-0.1 mL. Instrument: Agilent 1200 analytical HPLC.

Method K:

Column: Cromolith RP-18e 100-10 mm. Mobile phase A: water (v/v); Mobile phase B: acetonitrile (v/v); Gradient: 30-65% B over 20 minutes, 65-95% B over 1 min, 95-30% B over 2 min. Flow rate; 2.5 mL/minute. Temperature: not controlled; Detection: DAD 230 nm; Injection volume: variable, 0.025-0.1 mL; Instrument: Agilent 1200 analytical HPLC.

In some instances some minor alterations to purification HPLC conditions were made such as but not limited to a change in gradient, gradient length and flow rate which is indicated by the symbol *.

General Procedures

General Procedure A:

Preparation of activated N-hydroxysuccinimide (NHS) ester.

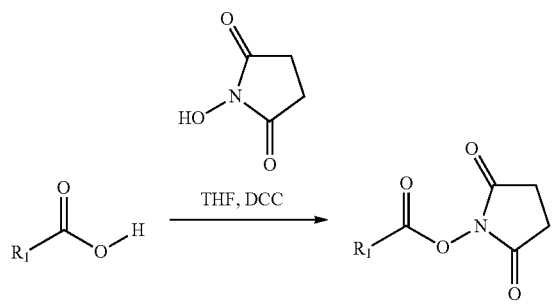

To a 0.1 M solution of the acid in tetrahydrofuran at 0° C. was added N,N'-dicyclohexylcarbodiimide (DCC) (2.2 eq.) followed by N-hydroxy succinimide (2.2 eq.) and the reaction was allowed to warm to room temperature and stirred. Reaction progress was monitored by LC-MS (or HPLC or TLC); the reaction was usually completed within 1-72 hours. The solvents were removed under reduced pressure and the residue was purified by reverse phase chromatography to afford the desired N-hydroxysuccinimide ester.

General Procedure B:

Preparation of amides from NHS esters.

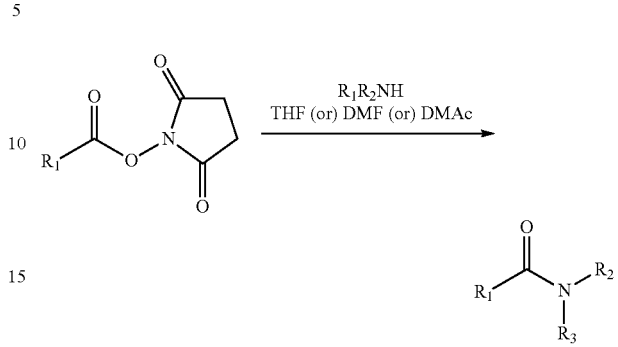

To a (0.1M) of the N-hydroxysuccinimide ester (1 eq.) in either tetrahydrofuran, N,N-dimethylformamide, or N,N-Dimethylacetamide at 0° C. was added the amine (1 to 10 eq.). Reaction progress was monitored by LC-MS (or HPLC or TLC); the reaction was usually completed within 1-72 hours. The reaction mixture was concentrated in vacuo and the residue was purified by reverse phase chromatography to give the desired amide product.

General Procedure C:

Preparation of pentafluorophenyl (PFP) ester

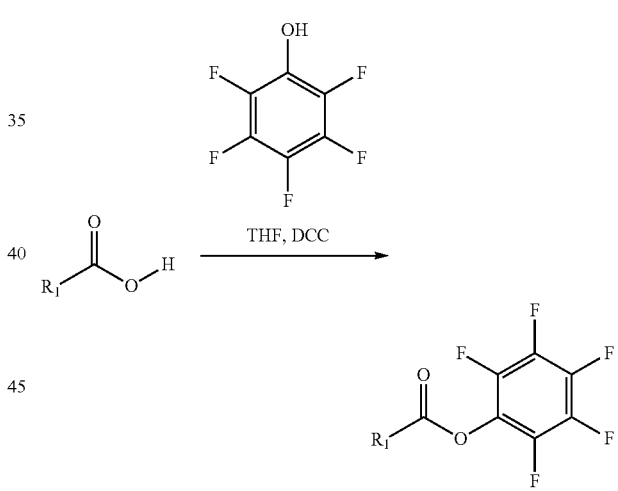

To a 0.05M solution of the acid in tetrahydrofuran at 0° C. was added DCC (1 eq.) followed by a solution of pentafluorophenol (2 to 4 eq.) dissolved in tetrahydrofuran (0.3 M). The reaction was warmed to room temperature and stirred. Reaction progress was monitored by LC-MS (or HPLC or TLC); the reaction was usually completed within 1-48 hours. The reaction was concentrated under reduced pressure and the residue was purified by reverse phase chromatography to provide desired pentafluorophenyl (PFP) ester.

General Procedure D:

Library Protocol for Preparation of amides from NHS ester. The amine (1 eq.) was dissolved into tetrahydrofuran (1 mL, 0.04 M) and N,N-diisopropylethylamine (5 eq.) was added followed by methanol (0.2 mL). The entire solution was then added drop-wise to a cooled solution (0° C.) of the N-hydroxy succinimide ester (1 eq.) dissolved into tetrahydrofuran (1 mL, 0.04 M). The reaction was stirred at (0° C.) for 30 minutes and then allowed to warm to room temperature and stirred up to 72 hours. Reaction progress was monitored by LC-MS (or HPLC or TLC); the reaction was usually completed within 1-72 hours. Solvents were removed in vacuo and the residue was purified by reverse phase chromatography and the fractions that pertained to the desired product were combined and lyophilized to give the target amides.

General Procedure E:

Preparation of amides via in situ formation of NHS esters.

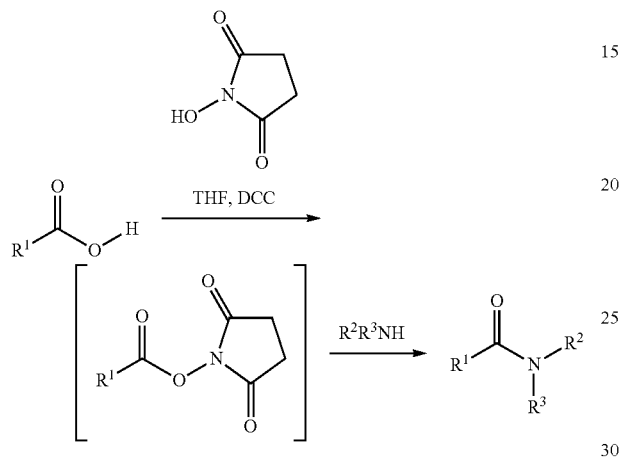

TLC); the reaction was usually completed within 1-72 hours. The reaction mixture was concentrated in vacuo and the residue was purified by reverse phase chromatography to give the desired amide.

General Procedure F:

Preparation of amides from NHS esters. A mixture of amine (or amine-acid salt) (1.0 eq.) and N,N'-Diisopropylethylamine (5 eq) in methanol (0.2 mL) was stirred for 15 minutes and the resulting solution transferred to a solution of the NHS ester (1.0 eq.) in tetrahydrofuran (1.0 mL). The reaction was stirred at room temperature with addition of more amine (1-3 eq.) until analysis by LC/MS indicated majority of the NHS-ester starting material has been consumed. The reaction mixture was concentrated in vacuo and the residue was purified by reverse phase chromatography to give the desired amide product Example A1

Preparation of (2S,3Z)-5-{[(2R,3R,5S,6S)-6-{(2E,4E)-5-[(3R,4R,5R,7S)-7-{2-[(2,5-dioxopyrrolidin-1-yl)oxy]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate #B1

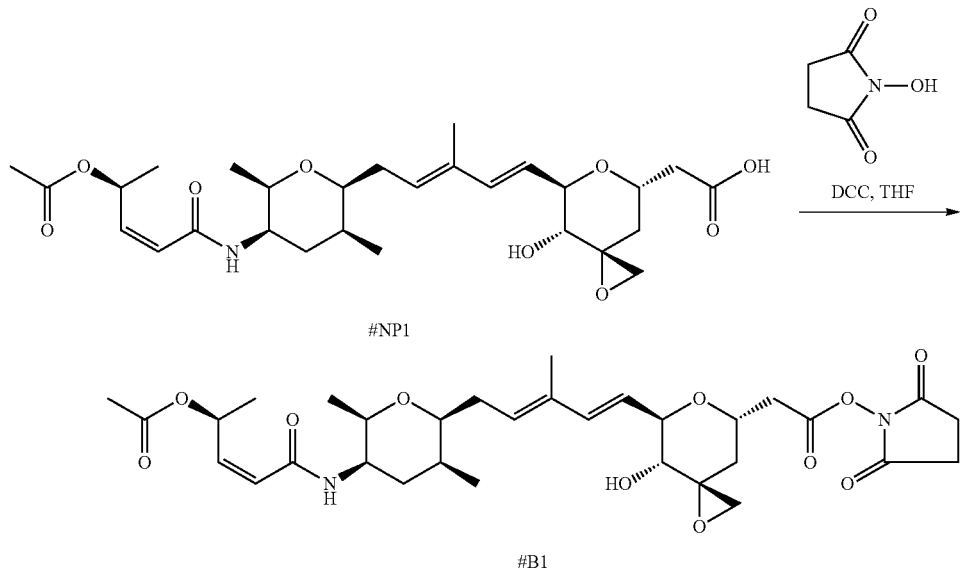

To a solution (0.08 M) of the acid (1 eq.) (0° C. or room temperature) in tetrahydrofuran or N,N-dimethylformamide, or N,N-Dimethylacetamide was added DCC (2.2 eq.) followed by N-hydroxysuccinimide (2.2 eq.) and the reaction was either stirred at 0° C. or allowed to warm to room temperature and stirred until analysis by LC/MS indicated majority of the acid starting acid has been consumed. The reaction mixture was recooled to 0° C. and the amine (1 to 20 eq.) was added, warmed to room temperature and stirred. Reaction progress was monitored by LC-MS (or HPLC or Step 1:

Synthesis of (2S,3Z)-5-{[(2R,3R,5S,6S)-6-{(2E,4E)-5-[(3R,4R,5R,7S)-7-{2-[(2,5-dioxopyrrolidin-1-yl)oxy]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate #B1. To a cooled (0° C.) solution of #NP1 (103 mg, 0.192 mmol, 1 eq.) in tetrahydrofuran (2 mL, 0.096 M) was added DCC (87.1 mg, 0.422 mmol, 2.2 eq.) and the reaction was stirred for 15 minutes. N-hydroxysuccinimide (48.6 mg, 0.422 mmol, 2.2 eq.) was added and the reaction was stirred at (0° C.) for 15 minutes, warmed to room temperature and stirred for 72 hours. The reaction was concentrated in vacuo, and the residue was purified by medium pressure reverse phase C18 chromatography (Gradient: 5% to 90% water in acetonitrile with 0.02% acetic acid in each phase). The fractions that pertained to the desired product were lyophilized to give #B1 as a solid. Yield: 66.6 mg, 0.103 mmol, 54%. HPLC (Protocol A[A]) retention time=8.170 minutes (purity 91%). LCMS (Protocol D): m/z 633.3 [M+H]$^+$, retention time=0.81 minutes. $^1$H NMR (400 MHz, DMSO-d$_6$) δ ppm 7.78 (d, J=8.02 Hz, 1H) 6.37-6.30 (m, 2H) 6.09 (m, 1H) 5.85 (dd, J=11.54, 7.43 Hz, 1H) 5.59 (dd, J=16.04, 5.28 Hz, 1H) 5.50 (t, J=7.04 Hz, 1H) 5.07 (d, J=6.06 Hz, 1H, D$_2$O exchangeable) 4.34-4.25 (m, 2H) 3.63 (d, J=5.48 Hz, 2H) 3.48 (td, J=7.09, 2.64 Hz, 1H) 3.27 (d, J=5.28 Hz, 1H) 2.97 (d, J=6.85 Hz, 2H) 2.82-2.77 (m, 4H) 2.59 (d, J=5.09 Hz, 1H) 2.33-2.11 (m, 2H) 1.96 (s, 3H) 1.92 (d, J=8.22 Hz, 1H) 1.82-1.77 (m, 2H) 1.68 (s, 3H) 1.66-1.6 (br. s., 1H) 1.59-1.55 (m, 1H) 1.23 (d, J=6.46 Hz, 3H) 1.05 (d, J=6.26 Hz, 3H) 0.93 (d, J=7.24 Hz, 3H)

Example A2

Preparation of (2S,3Z)-5-{[(2R,3R,5S,6S)-6-{(2E,4E)-5-[(3S,5S,7S)-7-{2-[(2,5-dioxopyrrolidin-1-yl)oxy]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B2)

Step 1.

Synthesis of (2S,3Z)-5-{[(2R,3R,5S,6S)-6-{(2E,4E)-5-[(3S,5S,7S)-7-{2-[(2,5-dioxopyrrolidin-1-yl)oxy]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B2). To a cooled (0° C.) solution of #NP2 (430 mg, 0.828 mmol, 1 eq.) in tetrahydrofuran (6 mL, 0.13 M) was added DCC (376 mg, 1.82 mmol, 2.2 eq.) followed by N-hydroxysuccinimide (210 mg, 1.82 mmol, 2.2 eq.). The reaction was allowed to warm to room temperature. After 18 hours, filtered off white solid and concentrated filtrate to yellow residue. The residue was purified by reverse phase chromatography (Method A) to afford #B2 as a white solid. Yield: 204 mg, 0.331 mmol, 40%. HPLC (Protocol A[A]): retention time=9.463 minutes (purity 77%). LCMS (Protocol D): m/z 617.3 [M+H]$^+$ retention time=0.91 minutes. 1H NMR (400 MHz, DMSO-d$_6$) δ ppm 7.72 (d, J=7.81 Hz, 1H) 6.32-6.21 (m, 2H) 6.04 (m, 1H) 5.85 (dd, J=11.48, 7.21 Hz, 1H) 5.57 (dd, J=15.80, 4.90 Hz, 1H) 5.47 (t, J=7.04 Hz, 1H) 4.53-4.47 (m, 1H) 4.32-4.25 (m, 1H) 3.62-3.55 (m, 2H) 3.45-3.41 (m, 1H) 2.95 (d, J=6.60 Hz, 2H) 2.74 (s, 3H) 2.59 (dd, J=16.00, 4.68 Hz, 2H) 2.30-2.07 (m, 2H) 1.91 (s, 3H) 1.77-1.65 (m, 4H) 1.63 (br s, 4H) 1.61-1.57 (m, 1H) 1.48 (dd, J=13.27, 7.02 Hz, 1H) 1.19 (d, J=6.24 Hz, 3H) 1.050 (d, J=6.24 Hz, 3H) 0.89 (d, J=7.41 Hz, 3H)

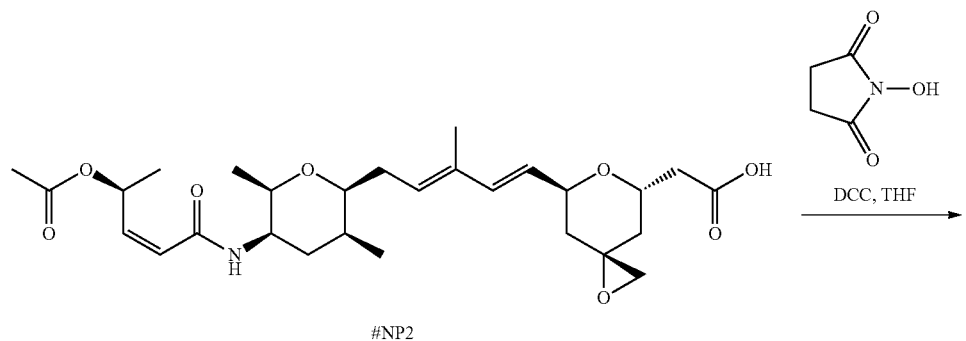

NP2

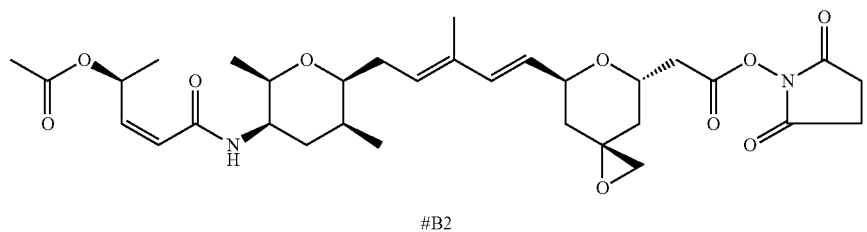

B2

Example A3

Synthesis of pentafluorophenyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetate (#B3)

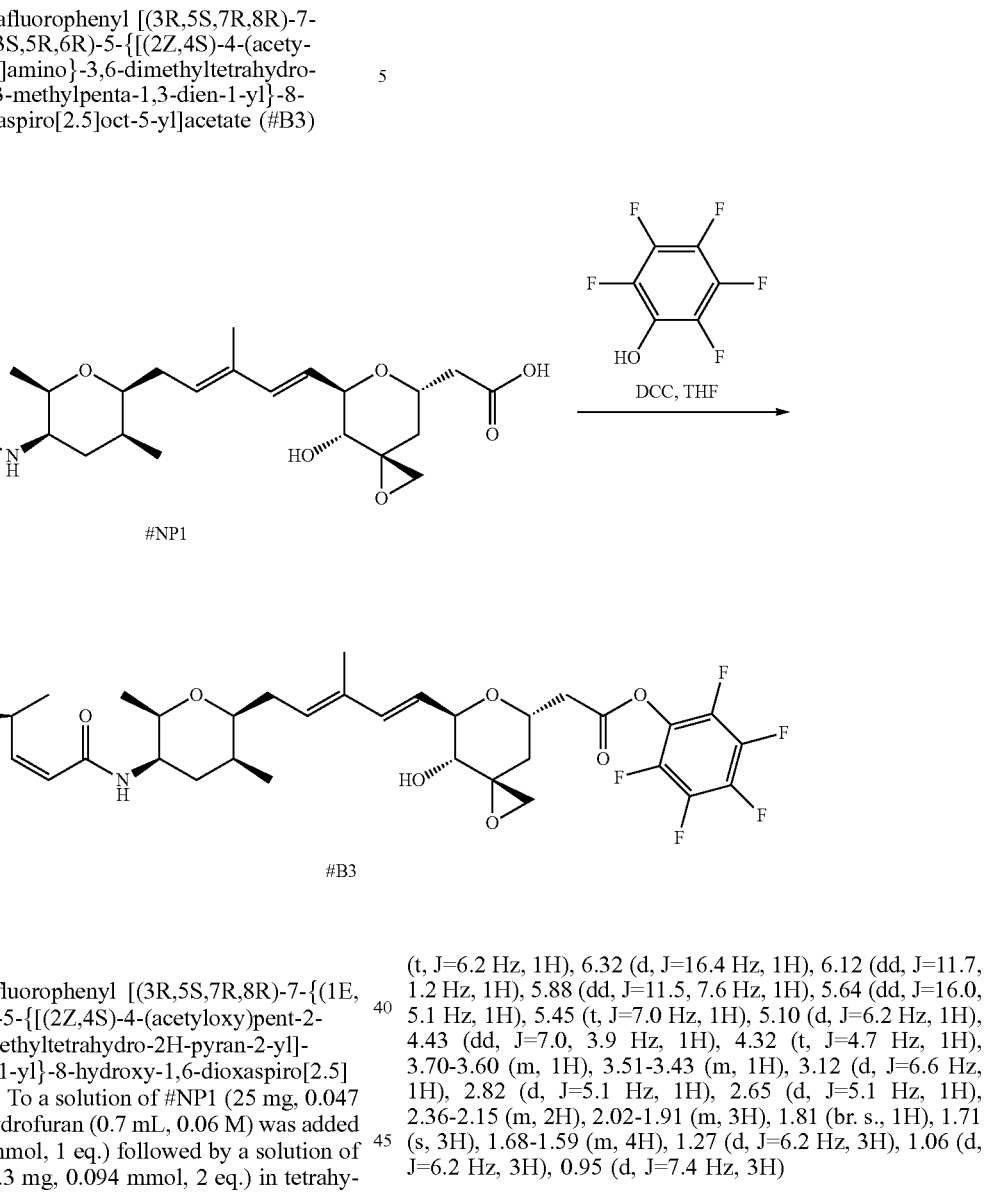

Step 1:

Synthesis of pentafluorophenyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-methylpenta-1,3-dien-1-yl}-8-hydroxy-1,6-dioxaspiro[2.5]oct-5-yl]acetate (#B3). To a solution of #NP1 (25 mg, 0.047 mmol, 1 eq.) in tetrahydrofuran (0.7 mL, 0.06 M) was added DCC (9.7 mg, 0.047 mmol, 1 eq.) followed by a solution of pentafluorophenol (17.3 mg, 0.094 mmol, 2 eq.) in tetrahydrofuran (0.3 mL, 0.3M). The reaction was stirred at room temperature for 18 hours, filtered and filter cake rinsed with acetonitrile. The combined filtrates were concentrated in vacuo and the crude material was purified by reverse phase chromatography (Method A) to yield #B3 as a white solid. Yield: 21.6 mg, 0.030 mmol, 65%. HPLC (Protocol $A^B$): retention time=15.617 minutes (purity 87%). LCMS (Protocol D): m/z 702.2 [M+H]$^+$ retention time=1.0 minutes. $^1$H NMR ((400 MHz, DMSO-$d_6$) δ: 7.79 (d, J=7.8 Hz, 1H), 6.38 (t, J=6.2 Hz, 1H), 6.32 (d, J=16.4 Hz, 1H), 6.12 (dd, J=11.7, 1.2 Hz, 1H), 5.88 (dd, J=11.5, 7.6 Hz, 1H), 5.64 (dd, J=16.0, 5.1 Hz, 1H), 5.45 (t, J=7.0 Hz, 1H), 5.10 (d, J=6.2 Hz, 1H), 4.43 (dd, J=7.0, 3.9 Hz, 1H), 4.32 (t, J=4.7 Hz, 1H), 3.70-3.60 (m, 1H), 3.51-3.43 (m, 1H), 3.12 (d, J=6.6 Hz, 1H), 2.82 (d, J=5.1 Hz, 1H), 2.65 (d, J=5.1 Hz, 1H), 2.36-2.15 (m, 2H), 2.02-1.91 (m, 3H), 1.81 (br. s., 1H), 1.71 (s, 3H), 1.68-1.59 (m, 4H), 1.27 (d, J=6.2 Hz, 3H), 1.06 (d, J=6.2 Hz, 3H), 0.95 (d, J=7.4 Hz, 3H)

Example A4

Preparation of (2Z,4S)—N-[(2R,3R,5S,6S)-6-{(2E,4E)-5-[(3R,4R,5R,7S)-7-{2-[(2,5-dioxopyrrolidin-1-yl)oxy]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B5)

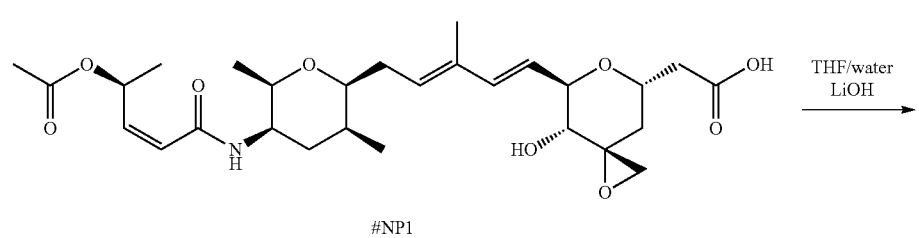

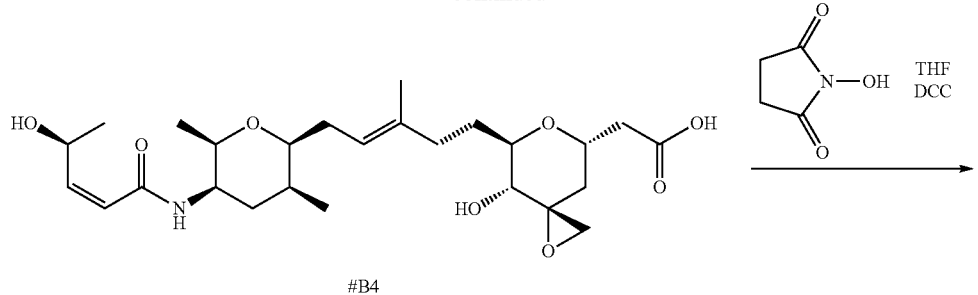

B4

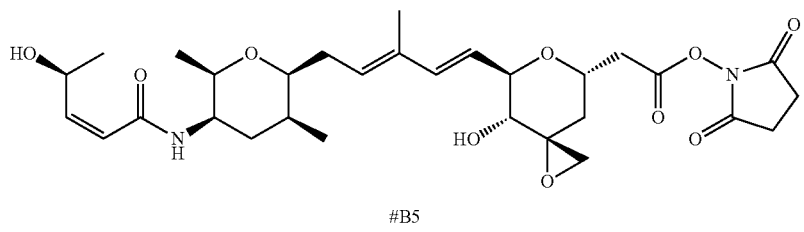

B5

Step 1:

Synthesis of [(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetic acid (#B4). To a solution of #NP1 (10.2 mg, 0.019 mmol, 1 eq.) dissolved in a 1:1 mixture of tetrahydrofuran/water (1.5 mL, 0.012 M) was added lithium hydroxide (6 mg, 0.25 mmol, 13 eq.). The reaction was stirred at room temperature for 1½ hours and the solvents were removed in vacuo. The crude residue was purified by reverse phase chromatography (Method A) to afford #B4 as a solid. Yield: 2 mg, 0.004 mmol, 20%. HPLC (Protocol A): retention time=7.850 minutes (purity 93%). LCMS (Protocol D); m/z 494.1[M+H]+ retention time=0.68 minutes. $^1$H NMR (400 MHz, CDCl$_3$) δ 6.46 (d, J=8.6 Hz, 1H), 6.28 (d, J=16 Hz, 1H), 6.09 (dd, J=11.9 and 5.3 Hz, 1H), 5.73, (dd, J=12.1 and 1.6 Hz, 1H), 5.57 (dd, J=15.6 and 5.9 Hz, 1H), 5.39-5.32 (m, 1H), 4.75-4.66 (m, 1H), 4.50-4.41 (m, 1H), 4.19-4.13 (m, 1H), 3.89-3.82 (m, 1H), 3.68-3.59 (m, 1H), 3.52-3.43 (m, 2H), 2.99 (dd, J=15.2 and 9.4 Hz, 1H), 2.94 (d, J=4.3 Hz, 1H), 2.59-2.49 (m, 2H), 2.36-2.25 (m, 1H), 2.20-2.09 (m, 2H), 1.94-1.79 (m, 2H), 1.76-1.68 (m, 1H), 1.66 (s, 3H), 1.63 (d, J=3.9 Hz, 1H), 1.27 (d, J=6.6 Hz, 3H), 1.08 (d, J=6.2 Hz, 3H), 0.93 (d, J=7.4 Hz, 3H).

Step 2:

Synthesis of (2Z,4S)—N-[(2R,3R,5S,6S)-6-{(2E,4E)-5-[(3R,4R,5R,7S)-7-{2-[(2,5-dioxopyrrolidin-1-yl)oxy]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B5). Was prepared according to the general procedure for the synthesis of #B1 in Example A1 except that #B4 was used instead of #NP1. The crude reaction was concentrated in vacuo and was then purified by reverse phase chromatography (Method A) to afford #B5 as a solid. Yield: 16.2 mg, 0.027 mmol, 64%. LCMS (Protocol D): m/z 591.3[M+H]+ retention time=0.71 minutes. $^1$H NMR (500 MHz, DMSO-d$_6$, mult, J in Hz) δ 7.78 (d, J=8.0 Hz, 1H), 6.35 (d, J=15.6 Hz, 1H), 5.97 (dd, J=11.9 and 1.2 Hz, 1H), 5.87 (dd, J=11.7 and 7.1 Hz, 1H), 5.61 (dd, J=15.6 and 5.1 Hz, 1H), 5.55-5.49 (m, 1H), 5.22-5.14 (m, 1H), 5.11 (d, J=4.7 Hz, 1H), 5.08 (d, J=6.0 Hz, 1H), 4.36-4.25 (m, 2H), 3.69-3.60 (m, 2H), 3.53-3.45 (m, 1H), 3.31-3.27 (m, 1H), 2.99 (d, J=6.7 Hz, 2H), 2.84-2.76 (m, 4H), 2.61 (d, J=5.0 Hz, 1H), 2.34-2.26 (m, 1H), 2.24-2.15 (m, 1H), 1.95 (dd, J=13.0 and 8.2 Hz, 1H), 1.87-1.73 (m, 2H), 1.72-1.62 (m, 4H), 1.59 (dd, J=13.0 and 3.6 Hz, 1H), 1.11 (d, J=6.4 Hz, 3H), 1.06 (d, J=6.4 Hz, 3H), 0.95 (d, J=7.3 Hz, 3H).

Example A5

Preparation of (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B6)

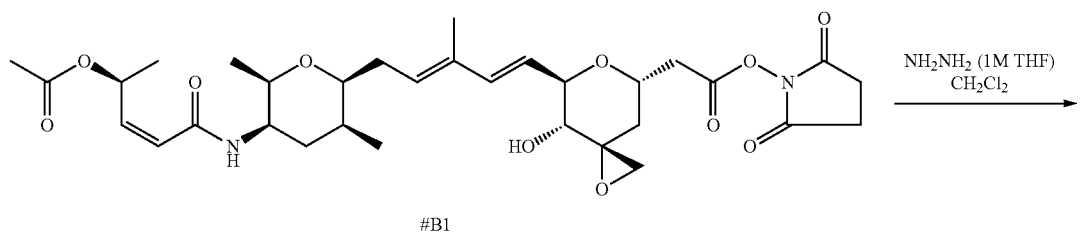

B1

B6

Step 1:

Synthesis of (2S,3Z)-5-{[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B6). Hydrazine (0.615 mL of a 1M solution in tetrahydrofuran, 0.615 mmol, 5 eq.) was added to a solution of #B1 (78 mg, 0.12 mmol, 1 eq.) dissolved in dichloromethane (3 mL, 0.04M) and stirred at room temperature for 1 hour and then additional hydrazine (0.615 mL of a 1M solution in tetrahydrofuran, 0.615 mmol, 5 eq.) was added. After 1 hour, the reaction was diluted with water and extracted with dichloromethane (3×), the organic layers were combined, dried over sodium sulfate, filtered and concentrated in vacuo. The crude residue was purified by reverse phase chromatography (Method A) to afford #B6 as a solid. Yield: 43 mg, 58%. HPLC (Protocol A) retention time=6.870 minutes (purity=72%). LCMS (Protocol C): m/z 550.4 [M+H]$^+$, retention time=1.15 minutes. $^1$H NMR (400 MHz, DMSO-d$_6$) δ 8.99 (s, 1H), 7.78 (d, J=8.2 Hz, 1H), 6.42-6.25 (m, 2H), 6.11 (dd, J=11.5 and 1.4 Hz, 1H), 5.86 (dd, J=11.7 and 7.4 Hz, 1H), 5.60 (dd, J=16 and 5.9 Hz, 1H), 5.55-5.49 (m, 1H), 5.02 (d, J=5.5 Hz, 1H), 4.32-4.07 (m, 4H), 3.70-3.60 (m, 2H), 3.54-3.45 (m, 1H), 3.22 (app t, J=4.9 Hz, 1H), 2.74 (d, J=5.1 Hz, 1H), 2.58 (d, J=5.1 Hz, 1H), 2.44 (dd, J=14.2 and 8.4 Hz, 1H), 2.35-2.25 (m, 1H), 2.24-2.14 (m, 2H), 1.97 (s, 3H), 1.91-1.77 (m, 3H), 1.70-1.60 (m, 4H), 1.46 (dd, J=12.9 and 3.5 Hz, 1H), 1.25 (d, J=6.2 Hz, 3H), 1.07 (d, J=6.6 Hz, 3H), 0.95 (d, J=7.4 Hz, 3H).

Example A6

Preparation of (2S,3Z)-5-{[(2R,3R,5S,6S)-6-{(2E,4E)-5-[(3S,5S,7S)-7-(2-hydrazinyl-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B7)

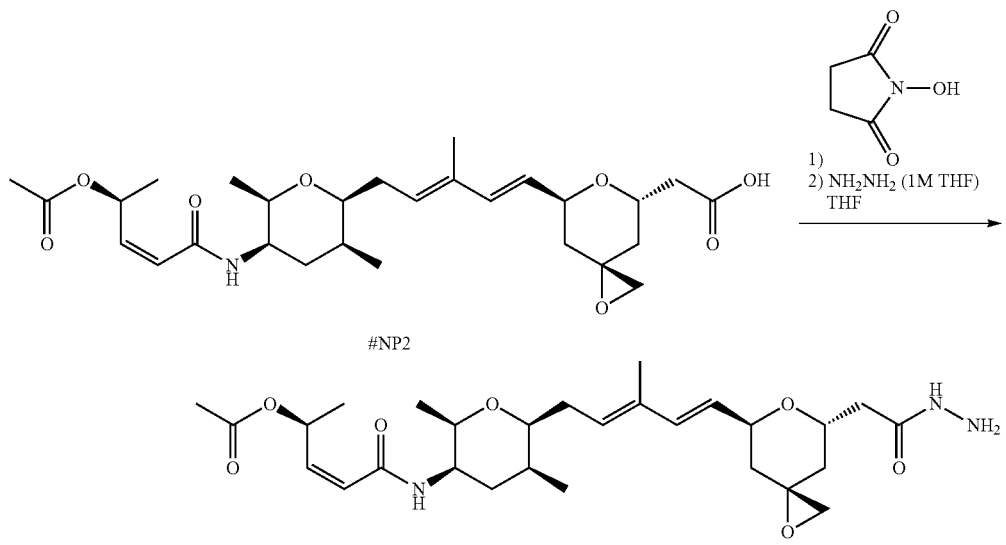

Step 1:

Synthesis of (2S,3Z)-5-{[(2R,3R,5S,6S)-6-{(2E,4E)-5-[(3S,5S,7S)-7-(2-hydrazinyl-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B7). To a solution of #NP2 (140 mg, 0.269 mmol, 1 eq.) in tetrahydrofuran (4 mL, 0.07 M) was added DCC (122 mg, 0.592 mmol, 2.2 eq.), followed by N-Hydroxysuccinimide (68.1 mg, 0.592 mmol, 2.2 eq). After 18 hours hydrazine (0.576 mL of a 1M solution in tetrahydrofuran, 0.576 mmol, 2.1 eq.) was added. After 30 minutes, additional hydrazine (1 mL of a 1M solution in tetrahydrofuran, 1 mmol, 3.7 eq.) was added. After 10 minutes the reaction was concentrated in vacuo and the crude desired material was purified by reverse phase chromatography (Method C*) to afford #B7 as a solid. Yield: 78 mg, 0.145 mmol, 54%. HPLC (Protocol F): m/z 534.4 [M+H]$^+$, retention time=8.143 minutes (purity 100%).

Example A7

Preparation of (2S,3Z)-5-{[(2R,3R,5S,6S)-6-{(2E,4E)-5-[(3R,4R,5R,7S)-4-hydroxy-7-{2-[(2-hydroxyethyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B8). and (2S,3Z)-5-{[(2R,3R,5S,6S)-6-{(2E,4E)-5-[(3R,4R,5R,7S)-7-(2-amino-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B9). and (2S,3Z)-5-{[(2R,3R,5S,6S)-6-{(2E,4E)-5-[(3R,4R,5R,7S)-4-hydroxy-7-{2-oxo-2-[(4-sulfamoylbenzyl)amino]ethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B10). and (2S,3Z)-5-{[(2R,3R,5S,6S)-6-{(2E,4E)-5-[(3R,4R,5R,7S)-7-{2-[(4-aminobenzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B11). and (2S,3Z)-5-({(2R,3R,5S,6S)-6-[(2E,4E)-5-{(3R,4R,5R,7S)-4-hydroxy-7-[2-oxo-2-(piperazin-1-yl)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate, acetate salt (#B12). and (2S,3Z)-5-({(2R,3R,5S,6S)-6-[(2E,4E)-5-{(3R,4R,5R,7S)-4-hydroxy-7-[2-(4-methylpiperazin-1-yl)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate, acetate salt (#B13). and (2S,3Z)-5-({(2R,3R,5S,6S)-6-[(2E,4E)-5-{(3R,4R,5R,7S)-4-hydroxy-7-[2-(hydroxyamino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B14)

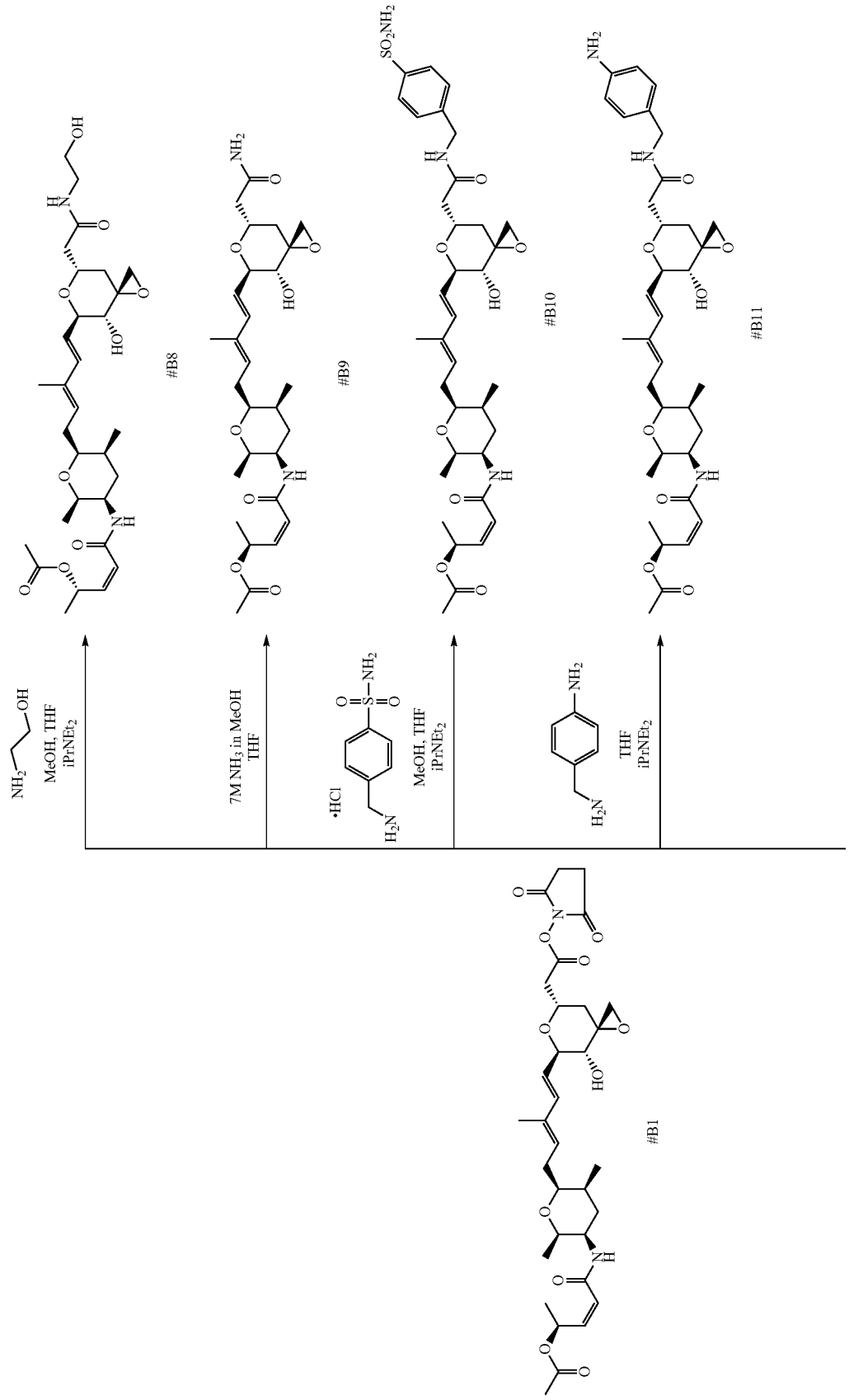

-continued
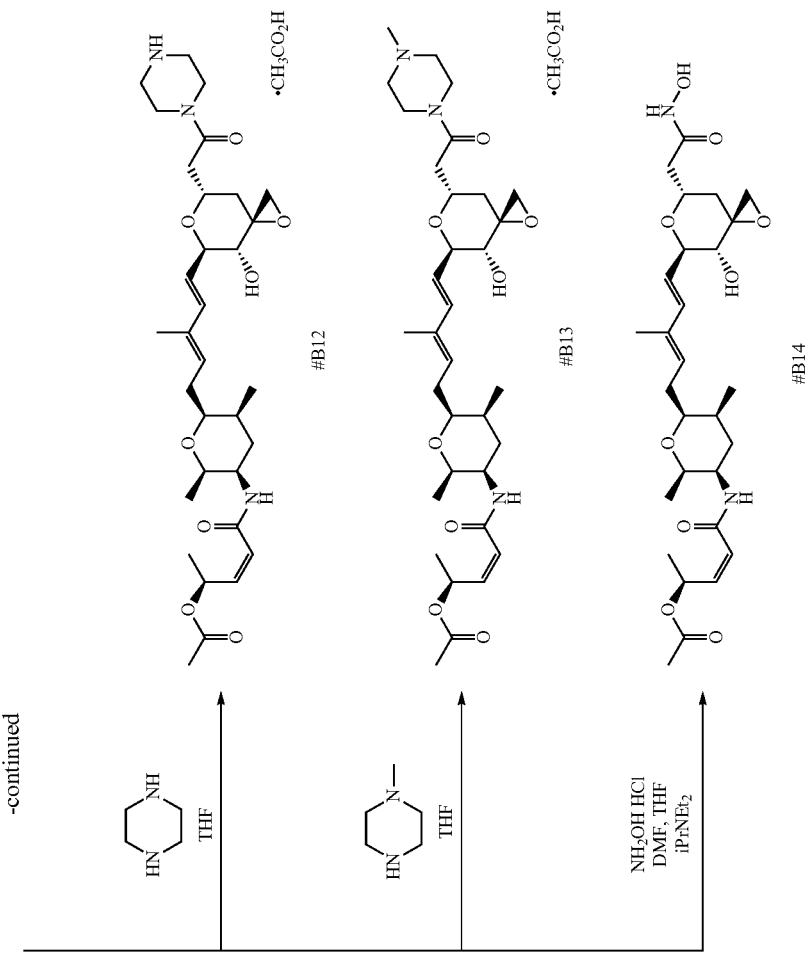

Step 1a.

Synthesis of (2S,3Z)-5-{[(2R,3R,5S,6S)-6-{(2E,4E)-5-[(3R,4R,5R,7S)-4-hydroxy-7-{2-[(2-hydroxyethyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B8). According to General Procedure D, from 2-aminoethanol (2.0 mg, 0.033 mmol, 1.03 eq.) tetrahydrofuran (1 mL), N,N-diisopropylethylamine (0.028 mL, 0.160 mmol, 5 eq.), methanol (0.2 mL), and #B1 (20 mg, 0.032 mmol, 1 eq.), was synthesized the crude desired material, which was purified by reverse phase chromatography (Method D*) to afford #B8 as a solid. Yield: 17.6 mg, 0.031 mmol, 97%. HPLC (Protocol B): m/z 579.6 [M+H]$^+$, retention time=2.00 minutes (purity 100%).

Step 1b.

Synthesis of (2S,3Z)-5-{[(2R,3R,5S,6S)-6-{(2E,4E)-5-[(3R,4R,5R,7S)-7-(2-amino-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B9). To a solution of #B1 (15 mg, 0.024 mmol, 1 eq.) dissolved in tetrahydrofuran (1 mL, 0.024 M) was added ammonia (0.069 mL of a 7 M solution in methanol, 0.480 mmol, 20 eq.) After stirring for 3½ hours, the solvents were removed in vacuo, and the crude desired material was purified by reverse phase chromatography (Method C*) to give #B9 as a solid. Yield: 6 mg, 0.012 mmol, 50%. HPLC (Protocol F) m/z 535.3 [M+H]$^+$, retention time=7.796 minutes (purity 100%). $^1$H NMR (400 MHz, DMSO-d$_6$) δ 7.78 (d, J=8.2 Hz, 1H), 7.30 (s, 1H), 6.77 (s, 1H), 6.40-6.28 (m, 2H), 6.10 (d, J=11.7 Hz, 1H), 5.87 (dd, J=11.5 and 7.6 Hz, 1H), 5.61 (dd, J=15.8 and 5.7 Hz, 1H), 5.54-5.47 (m, 1H), 4.99 (d, J=5.9 Hz, 1H), 4.29-4.20 (m, 2H), 3.69-3.61 (m, 2H), 3.53-3.46 (m, 1H), 3.23 (app t, J=5.1 Hz, 1H), 2.74 (d, J=5.1 Hz, 1H), 2.57 (d, J=5.1 Hz, 1H), 2.48-2.44 (m, 1H), 2.36-2.25 (m, 1H), 2.25-2.16 (m, 2H), 1.97 (s, 3H), 1.87-1.77 (m, 2H), 1.69 (s, 3H), 1.68-1.60 (m, 2H), 1.49 (dd, J=13.1 and 3.7 Hz, 1H), 1.25 (d, J=6.6 Hz, 3H), 1.07 (d, J=6.2 Hz, 3H), 0.95 (d, J=7.4 Hz, 3H).

Step 1c.

Synthesis of (2S,3Z)-5-{[(2R,3R,5S,6S)-6-{(2E,4E)-5-[(3R,4R,5R,7S)-4-hydroxy-7-{2-oxo-2-[(4-sulfamoylbenzyl)amino]ethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B10). According to General Procedure D, from 4-(aminomethyl)benzenesulfonamide, hydrochloride salt (9.2 mg, 0.041 mmol, 1 eq.) tetrahydrofuran (1 mL), N,N-diisopropylethylamine (0.035 mL, 0.200 mmol, 5 eq.), methanol (0.2 mL), and #B1 (25 mg, 0.040 mmol, 1 eq.), was synthesized the crude desired material, which was purified by reverse phase chromatography (Method D*) to afford #B10 as a solid. Yield: 15.5 mg, 0.022 mmol, 55%. HPLC (Protocol B): m/z 704.4 [M+H]$^+$, retention time=2.36 minutes (purity 100%). $^1$H NMR (400 MHz, METHANOL-d$_4$) δ: 8.58 (br. s., 1H), 7.80 (d, J=8.2 Hz, 1H), 7.63 (d, J=8.6 Hz, 2H), 7.45 (d, J=8.2 Hz, 2H), 6.42-6.32 (m, 2H), 6.02-5.90 (m, 2H), 5.67 (dd, J=15.8, 6.0 Hz, 1H), 5.53 (t, J=7.0 Hz, 1H), 4.62-4.54 (m, 1H), 4.46 (d, J=4.3 Hz, 1H), 4.42-4.32 (m, 2H), 3.78-3.65 (m, 2H), 3.58 (t, J=5.8 Hz, 1H), 3.43 (d, J=5.8 Hz, 1H), 2.92-2.81 (m, 2H), 2.66 (d, J=5.1 Hz, 1H), 2.40 (m, 2H), 2.24 (m, 1H), 2.02-2.02 (m, 3H), 1.98 (s, 1H), 1.98-1.67 (m, 2H), 1.90-1.85 (m, 1H), 1.83-1.80 (m, 1H), 1.77 (s, 2H), 1.41-1.32 (m, 4H), 1.13-0.98 (m, 3H).

Step 1d.

Synthesis of (2S,3Z)-5-{[(2R,3R,5S,6S)-6-{(2E,4E)-5-[(3R,4R,5R,7S)-7-{2-[(4-aminobenzyl)amino]-2-oxoethyl}-4-hydroxy- 1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B11). According to General Procedure D, from 4-(aminomethyl)aniline (3.9 mg, 0.032 mmol, 1 eq.) tetrahydrofuran (1 mL), N,N-diisopropylethylamine (0.011 mL, 0.064 mmol, 2 eq.), methanol (0.2 mL), and #B1 (20 mg, 0.032 mmol, 1 eq.), was synthesized the crude desired material, which was purified by reverse phase chromatography (Method A) to afford #B11 as a solid. Yield: 17.6 mg, 0.027 mmol, 86%. HPLC (Protocol A$^4$):retention time=6.748 minutes (purity 91%). $^1$H NMR (400 MHz, DMSO-d$_6$) δ ppm 8.14 (t, J=5.77 Hz, 1H) 7.78 (d, J=8.02 Hz, 1H) 6.90-6.84 (m, 2H) 6.48-6.43 (m, 2H) 6.39-6.30 (m, 1H) 6.27 (s, 1H) 6.09 (m, 1H) 5.88-5.80 (m, 1H) 5.59 (dd, J=15.85, 5.48 Hz, 1H) 5.51 (t, J=6.94 Hz, 1H) 5.01 (d, J=5.28 Hz, 1H) 4.89 (s, 2H) 4.30-4.22 (m, 1H) 4.12-3.99 (m, 1H) 3.63 (d, J=5.87 Hz, 2H) 3.49 (td, J=7.04, 2.54 Hz, 1H) 3.22 (t, J=4.40 Hz, 1H) 2.73 (d, J=5.09 Hz, 1H) 2.59-2.50 (m, 2H) 2.35-2.13 (m, 3H) 1.96 (s, 3H) 1.88-1.75 (m, 3H) 1.69 (s, 3H) 1.64 (td, J=4.89, 2.54 Hz, 1H) 1.44 (dd, J=12.81, 3.62 Hz, 1H) 1.23 (d, J=6.46 Hz, 3H) 1.04 (d, J=6.46 Hz, 3H) 0.93 (d, J=7.43 Hz, 3H)

Step 1e.

(2S,3Z)-5-({(2R,3R,5S,6S)-6-[(2E,4E)-5-{(3R,4R,5R,7S)-4-hydroxy-7-[2-oxo-2-(piperazin-1-yl)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate, acetate salt (#B12). To a solution of #B1 (15.5 mg, 0.024 mmol, 1 eq.) dissolved in tetrahydrofuran (0.24 mL, 0.048 M) was added piperazine (2.5 mg, 0.029 mmol, 1.2 eq.) After stirring for 30 minutes, the reaction was diluted with water, extracted with dichloromethane, the combined organics were dried over sodium sulfate, filtered and the solvents were removed in vacuo. The crude desired material was purified by reverse phase chromatography (Method A) to give #B12 as a white solid. Yield: 8.2 mg, 0.012 mmol, 52%. HPLC (Protocol A$^4$) retention time=6.795 minutes (purity 80%). LCMS (Protocol C): m/z 604.3 [M+H]$^+$, retention time=1.01 minutes. $^1$H NMR (400 MHz, DMSO-d$_6$) δ 7.79 (d, J=8.2 Hz, 1H), 6.41-6.28 (m, 2H), 6.11 (d, J=10.5 Hz, 1H), 5.87 (dd, J=11.5 and 7.6 Hz, 1H), 5.60 (dd, J=16 and 5.1 Hz, 1H), 5.55-5.48 (m, 1H), 4.97 (d, J=5.9 Hz, 1H), 4.31-4.20 (m, 2H), 3.70-3.60 (m, 2H), 3.55-3.35 (m, 6H), 3.27-3.22 (m, 1H), 2.75 (d, J=5.1 Hz, 1H), 2.69-2.54 (m, 5H), 2.36-2.13 (m, 4H), 1.98 (s, 3H), 1.88-1.76 (m, 3H), 1.72-1.61 (m, 4H), 1.58-1.51 (m, 1H), 1.25 (d, J=6.2 Hz, 3H), 1.07 (d, J=6.2 Hz, 3H), 0.95 (d, J=7.4 Hz, 3H).

Step 1f.

(2S,3Z)-5-({(2R,3R,5S,6S)-6-[(2E,4E)-5-{(3R,4R,5R,7S)-4-hydroxy-7-[2-(4-methylpiperazin-1-yl)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate, acetate salt (#B13). To a solution of #B1 (18.8 mg, 0.03 mmol, 1 eq.) dissolved in tetrahydrofuran (0.500 mL, 0.06 M) was added 1-methylpiperazine (3.6 mg, 0.036 mmol, 1.2 eq.) After stirring for 30 minutes, the reaction was diluted with water, extracted with dichloromethane, the combined organics were dried over sodium sulfate, filtered and the solvents were removed in vacuo. The crude desired material was purified by reverse phase chromatography (Method A) to give #B13 as a white solid. Yield: 11.6 mg, 0.017 mmol, 57%. HPLC (Protocol A[4]) retention time=6.422 minutes (purity 94%). LCMS (Protocol C): m/z 618.4 [M+H]+, retention time=0.97 minutes. 1H NMR (400 MHz, DMSO-$d_6$) δ 7.79 (d, J=7.8 Hz, 1H), 6.42-6.27 (m, 2H), 6.11 (d, J=10.5 Hz, 1H), 5.87 (dd, J=11.3 and 7.4 Hz, 1H), 5.60 (dd, J=15.8 and 5.3 Hz, 1H), 5.55-5.48 (m, 1H), 4.97 (d, J=6.2 Hz, 1H), 4.30-4.21 (m, 2H), 3.70-3.61 (m, 2H), 3.56-3.33 (m, 5H), 3.25 (app t, J=5.5 Hz, 1H), 2.79-2.65 (m, 2H), 2.60-2.53 (m, 2H), 2.35-2.12 (m, 9H), 1.98 (s, 3H), 1.88-1.78 (m, 3H), 1.72-1.61 (m, 4H), 1.56 (dd, J=12.9 and 3.5 Hz, 1H), 1.25 (d, J=6.2 Hz, 3H), 1.07 (d, J=6.2 Hz, 3H), 0.95 (d, J=7.4 Hz, 3H).

Step 1g.

(2S,3Z)-5-({(2R,3R,5S,6S)-6-[(2E,4E)-5-{(3R,4R,5R,7S)-4-hydroxy-7-[2-(hydroxyamino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B14). To a solution of #B1 (30.7 mg, 0.049 mmol, 1 eq.) dissolved in tetrahydrofuran (0.450 mL) and N,N-dimethylformamide (0.175 mL) was added N,N-diisopropylethylamine (32 mg, 0.245 mmol, 5 eq.) and hydroxylamine hydrochloride (10.6 mg, 0.152 mmol, 3 eq.) After stirring for 30 minutes, the reaction was diluted with water, extracted with ethyl acetate (3×), the combined organics were washed again with water, dried over sodium sulfate, filtered and concentrated in vacuo. The crude desired material was purified by reverse phase chromatography (Method A) to give #B14 as a white solid. Yield: 11.8 mg, 0.021 mmol, 43%. HPLC (Protocol A[4]) retention time=7.189 minutes (purity 96%). LCMS (Protocol C): m/z 551.2 [M+H]+, retention time=1.18 minutes. 1H NMR (400 MHz, DMSO-$d_6$) δ 10.42 (s, 1H), 8.74 (s, 1H) 7.80 (d, J=7.8 Hz, 1H), 6.43-6.29 (m, 2H), 6.16-6.10 (m, 1H), 5.88 (dd, J=11.7 and 7.4 Hz, 1H), 5.61 (dd, J=16 and 5.5 Hz, 1H), 5.57-5.51 (m, 1H), 5.04 (d, J=5.5 Hz, 1H), 4.32-4.23 (m, 2H), 3.72-3.62 (m, 2H), 3.57-3.48 (m, 1H), 3.27-3.21 (m, 1H), 2.76 (d, J=5.1 Hz, 1H), 2.60 (d, J=5.1 Hz, 1H), 2.44-2.27 (m, 2H), 2.26-2.11 (m, 2H), 2.00 (s, 3H), 1.92-1.80 (m, 3H), 1.74-1.63 (m, 4H), 1.49 (dd, J=12.7 and 3.3 Hz, 1H), 1.27 (d, J=6.6 Hz, 3H), 1.09 (d, J=6.2 Hz, 3H), 0.97 (d, J=7.4 Hz, 3H).

Example A8

Preparation of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B15)

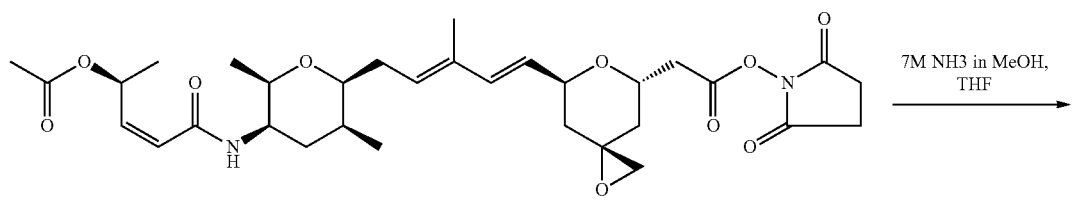

B2

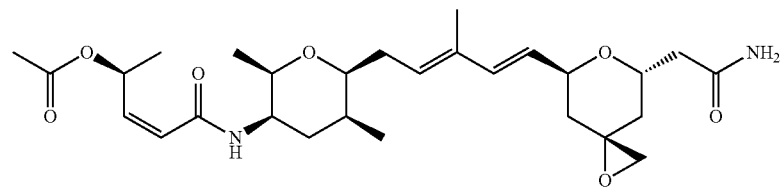

B15

Step 1:

Synthesis of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B15). To a solution of #B2 (108 mg, 0.175 mmol, 1 eq.) dissolved in tetrahydrofuran (3 mL, 0.06 M) was added ammonia (0.500 mL of a 7 M solution in methanol, 3.5 mmol, 20 eq.) After stirring for 1 hour, the solvents were removed in vacuo, and the crude desired material was purified by medium pressure reverse phase C18 chromatography (Gradient: 0% to 90% water in acetonitrile with 0.02% acetic acid in each phase) to give #B15 as a solid. Yield: 23.9 mg, 0.045 mmol, 26%. HPLC (Protocol A[4]) retention time=8.231 minutes (purity 89%). LCMS (Protocol C): m/z 519.3 [M+H]+, retention time=1.41 minutes. 1H NMR (400 MHz, DMSO-$d_6$) δ 7.80 (d, J=7.8 Hz, 1H), 7.33 (s, 1H), 6.78 (s, 1H), 6.42-6.33 (m, 1H), 6.28 (d, J=16 Hz, 1H), 6.16-6.10 (m, 1H), 5.88 (dd, J=11.7 and 7.4 Hz, 1H), 5.61 (dd, J=15.8 and 5.7 Hz, 1H), 5.56-5.50 (m, 1H), 4.60-4.51 (m, 1H), 4.38-4.27 (m, 1H), 3.72-3.62 (m, 2H), 3.56-3.48 (m, 1H), 2.71-2.54 (m, 4H), 2.38-2.27 (m, 1H), 2.26-2.16 (m, 2H), 2.00 (s, 3H), 1.89-1.74 (m, 3H), 1.71 (s, 3H), 1.69-1.61 (m, 2H), 1.39 (dd, J=13.5 and 6.4 Hz, 1H), 1.27 (d, J=6.2 Hz, 3H), 1.09 (d, J=6.6 Hz, 3H), 0.97 (d, J=7.4 Hz, 3H).

Example A9

Preparation of [(3S,5S,7S)-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methyl-penta-1,3-dien-1-yl}-1,6-dioxaspiro[2.5]oct-5-yl] acetic acid (#B16). and (2Z,4S)—N-[(2R,3R,5S,6S)-6-{(2E,4E)-5-[(3S,5S,7S)-7-{2-[(2,5-dioxopyrrolidin-1-yl)oxy]-2-oxoethyl}-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B17)

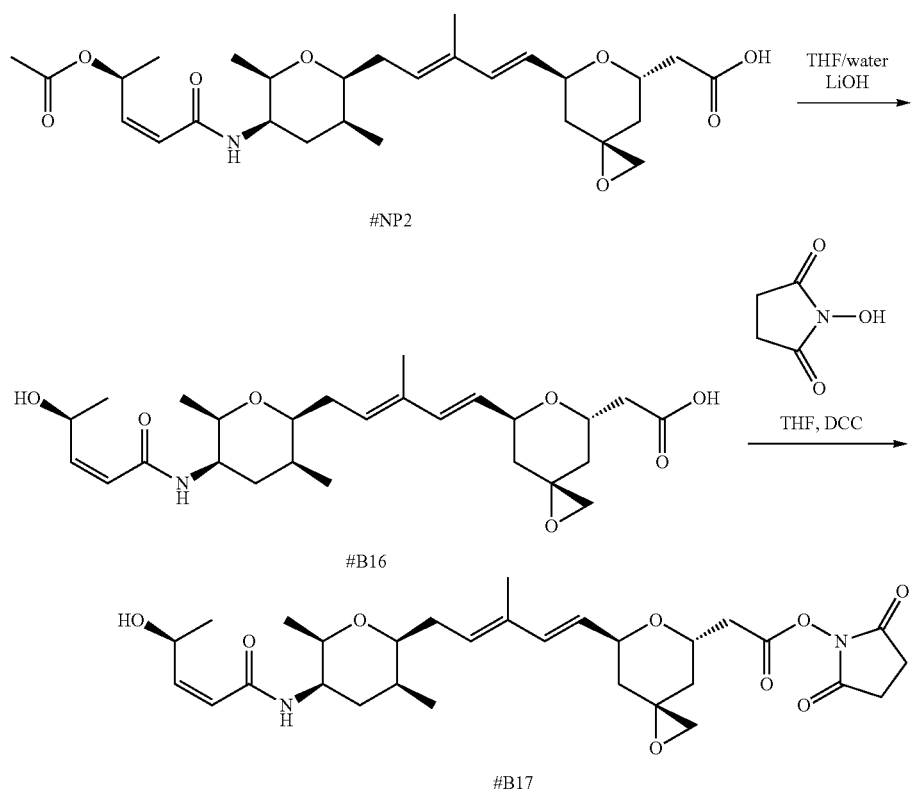

Step 1.

Synthesis of [(3S,5S,7S)-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetic acid (#B16). To a solution of #NP2 (25 mg, 0.048 mmol, 1 eq.) dissolved in a 1:1 mixture of tetrahydrofuran/water (3 mL, 0.016 M) was added lithium hydroxide (15 mg, 0.63 mmol, 13 eq.). The reaction was stirred at room temperature for 1 hour and the solvents were removed in vacuo. The crude residue was purified by reverse phase chromatography (Method A) to afford #B16 as a solid. Yield: 17 mg, 0.035 mmol, 74%. LCMS (Protocol D); m/z 478.1 [M+H]$^+$, retention time=0.75 minutes. $^1$H NMR (400 MHz, CDCl3-d) δ 6.27 (d, J=8.98 Hz, 1H) 6.09 (d, J=15.61 Hz, 1H) 6.00 (dd, J=12.10, 5.46 Hz, 1H) 5.62 (dd, J=12.10, 1.17 Hz, 1H) 5.40 (dd, J=15.61, 5.85 Hz, 2H) 5.25 (t, J=6.63 Hz, 1H) 4.61 (t, J=6.63 Hz, 1H) 4.48-4.32 (m, 2H) 3.79-3.73 (m, 1H) 3.57-3.48 (m, 2H) 3.42-3.33 (m, 2H) 2.85 (dd, J=15.22, 8.98 Hz, 2H) 2.52-2.44 (m, 2H) 2.42 (d, J=5.07 Hz, 1H) 2.25-2.00 (m, 1H) 1.94-1.87 (m, 2H) 1.80-1.74 (m, 2H) 1.68-1.59 (m, 2H) 1.55 (s, 3H) 1.46 (dd, J=13.46, 3.71 Hz, 1H) 1.27 (dd, J=13.66, 4.29 Hz, 1H) 1.17 (d, J=6.63 Hz, 3H) 0.98 (d, J=6.24 Hz, 3H) 0.83 (d, J=7.02 Hz, 3H).

Step 2:

Synthesis of (2Z,4S)—N-[(2R,3R,5S,6S)-6-{(2E,4E)-5-[(3S,5S,7S)-7-{2-[(2,5-dioxopyrrolidin-1-yl)oxy]-2-oxoethyl}-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B17). Was prepared according to the general procedure for the synthesis of #B1 in Example A1 except that #B16 was used instead of #NP1. The crude reaction was concentrated in vacuo and was then purified by reverse phase chromatography (Method A) to afford #B17 as a solid. Yield: 28 mg, 0.043 mmol, 43% LCMS (Protocol D); m/z 575.1 [M+H]$^+$, retention time=0.82 minutes. $^1$H NMR (400 MHz, DMSO-d$_6$) δ 7.76 (d, J=7.8 Hz, 1H), 6.30 (d, J=16 Hz, 1H), 5.97 (d, J=12.1 Hz, 1H), 5.86 (dd, J=11.7 and 7.0 Hz, 1H), 5.63 (dd, J=16 and 5.1 Hz, 1H), 5.56-5.48 (m, 1H), 5.22-5.06 (m, 2H), 4.60-4.53 (m, 1H), 4.39-4.30 (m, 1H), 3.70-3.60 (m, 2H), 3.54-3.45 (m, 1H), 3.03-2.98 (m, 2H), 2.80 (s, 4H), 2.70-2.60 (m, 2H), 2.59 (s, 1H), 2.37-2.13 (m, 3H), 1.87-1.60 (m, 7H), 1.54 (dd, J=13.3 and 7 Hz, 1H), 1.11 (d, J=6.2 Hz, 3H), 1.06 (d, J=6.2 Hz, 3H), 0.95 (d, J=7.4 Hz, 3H).

Example A10

Preparation of 4-{4-[(1E)-1-(2-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinylidene)ethyl]phenoxy}butanoic acid (#B18). and (2S,3Z)-5-{[(2R,3R,5S,6S)-6-{(2E,4E)-5-[(3S,5S,7S)-7-(2-{(2E)-2-[1-(4-{4-[(2,5-dioxopyrrolidin-1-yl)oxy]-4-oxobutoxy}phenyl)ethylidene]hydrazinyl}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B19)

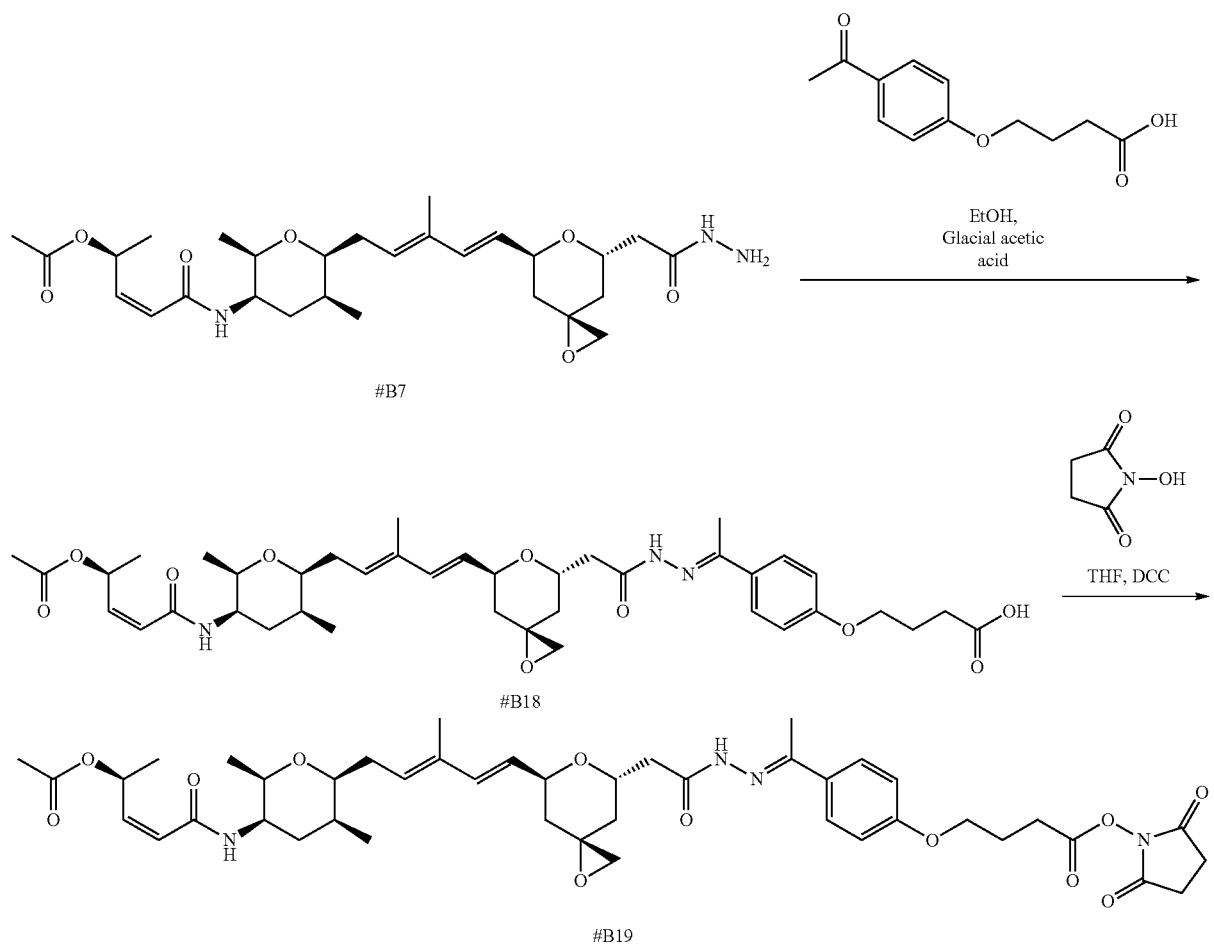

Step 1:

Synthesis of 4-{4-[(1E)-1-(2-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinylidene)ethyl]phenoxy}butanoic acid (#B18). To a solution of #B7 (35 mg, 0.066 mmol, 1 eq.) in ethanol (1 mL, 0.06 M) was added 4-(4-acetylphenoxy)butanoic acid (73.3 mg, 0.330 mmol, 5 eq.) followed by glacial acetic acid (0.250 mL) and the reaction was heated to 37° C. After 3½ hours the reaction was filtered and purified by reverse phase chromatography (Method A) to afford #B18 as a white solid. Yield: 25.5 mg, 0.034 mmol, 52%. LCMS (Protocol D); m/z 737.38 [M+H]$^+$, retention time=0.88 minutes.

Step 2:

Synthesis of (2S,3Z)-5-{[(2R,3R,5S,6S)-6-{(2E,4E)-5-[(3S,5S,7S)-7-(2-{(2E)-2-[1-(4-{4-[(2,5-dioxopyrrolidin-1-yl)oxy]-4-oxobutoxy}phenyl)ethylidene]hydrazinyl}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B19). To a solution of #B18 (25 mg, 0.034 mmol, 1 eq.) dissolved in tetrahydrofuran (0.7 mL, 0.049 M) was added DCC (15.5 mg, 0.075 mmol, 2.2 eq.) followed by N-Hydroxy succinimide (8.60 mg, 0.075 mmol, 2.2 eq.). The reaction was stirred for 4 hours. Solvents were removed in vacuo and the residue was purified by reverse phase chromatography (Method A) to afford #B19 as a white solid. Yield: 13 mg, 0.015 mmol, 46%. LCMS (Protocol D); m/z 835.8 [M+H]$^+$, retention time=0.92 minutes.

Example A11

Preparation of 4-{4-[(1E)-1-(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinylidene)ethyl]phenoxy}butanoic acid (#B20). and (2S,3Z)-5-{[(2R,3R,5S,6S)-6-{(2E,4E)-5-[(3R,4R,5R,7S)-7-(2-{(2E)-2-[1-(4-{4-[(2,5-dioxopyrrolidin-1-yl)oxy]-4-oxobutoxy}phenyl)ethylidene]hydrazinyl}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B21)

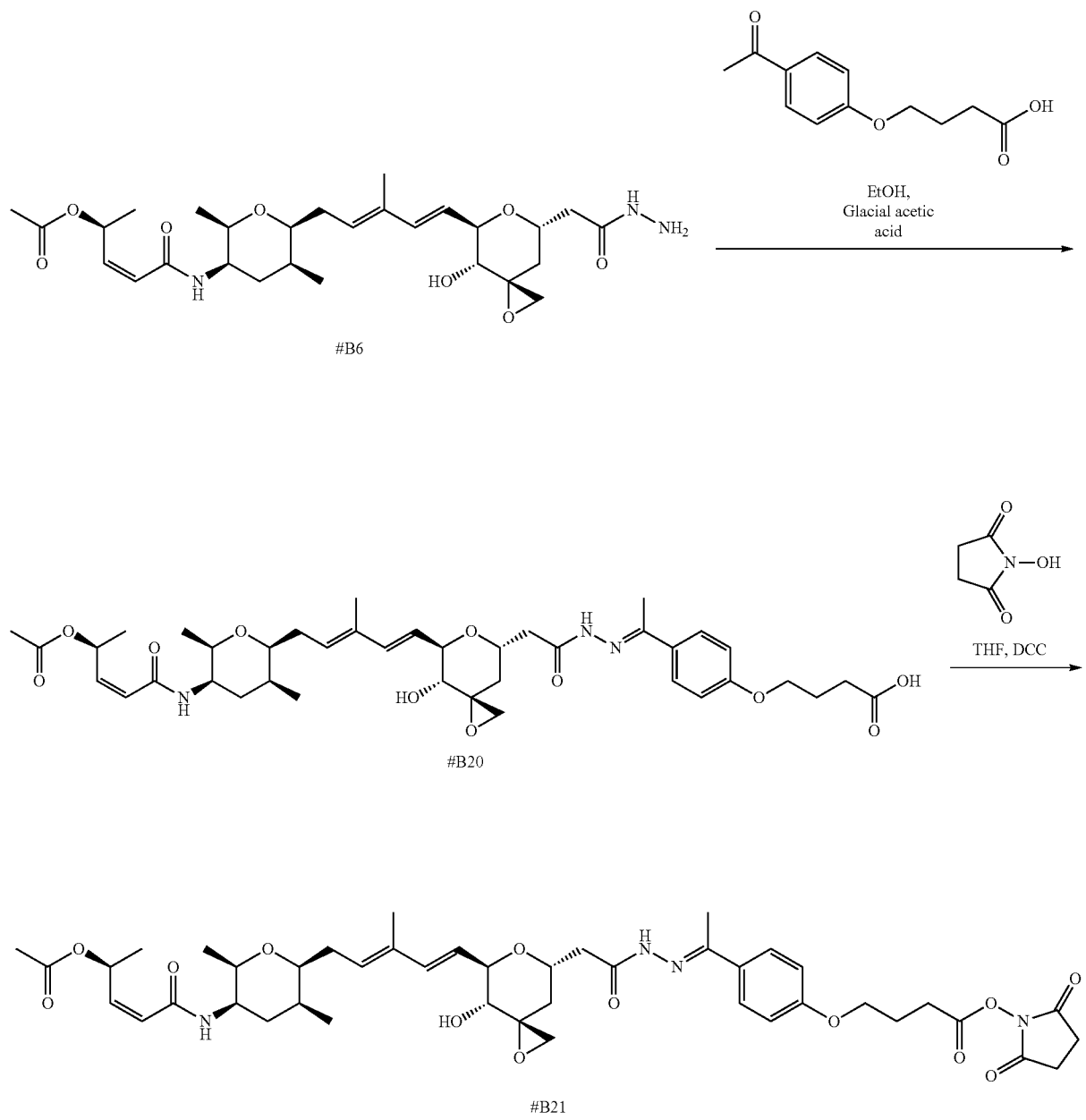

Step 1:

Synthesis of 4-{4-[(1E)-1-(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl]-8-hydroxy-1,6-dioxaspiro[2.5]oct-5-yl]acetyl}hydrazinylidene)ethyl]phenoxy}butanoic acid (#B20). To a solution of #B6 (18.1 mg, 0.033 mmol, 1 eq.) in ethanol (0.500 mL, 0.06 M) was added 4-(4-acetylphenoxy)butanoic acid (36.7 mg, 0.165 mmol, 5 eq.) followed by glacial acetic acid (0.125 mL) and the reaction was heated to 37° C. After 1 hour the reaction was filtered and purified by reverse phase chromatography (Method A). to afford #B20 as a white solid. Yield: 24.9 mg, 0.028 mmol, 85%. LCMS (Protocol C); m/z 754.5 [M+H]+, retention time=1.47 minutes.

Step 2:

Synthesis of (2S,3Z)-5-{[(2R,3R,5S,6S)-6-{(2E,4E)-5-[(3R,4R,5R,7S)-7-(2-{(2E)-2-[1-(4-{4-[(2,5-dioxopyrrolidin-1-yl)oxy]-4-oxobutoxy}phenyl)ethylidene]hydrazinyl}-2-oxoethyl)-4-hydroxy-1,6-dioxaspiro[2.5]oct-5-yl]-3-methylpenta-2,4-dien-1-yl]-2,5-dimethyltetrahydro-2H-pyran-3-yl]amino}-5-oxopent-3-en-2-yl acetate (#B21). To a solution of #B20 (21.3 mg, 0.028 mmol, 1 eq.) dissolved in tetrahydrofuran (0.550 mL, 0.05 M) was added DCC (13.5 mg, 0.062 mmol, 2.2 eq.) followed by N-Hydroxy succinimide (7.3 mg, 0.062 mmol, 2.2 eq.). The reaction was stirred for 5 hours and additional DCC (5 mg, 0.022 mmol, 0.8 eq.) followed by N-Hydroxy succinimide (5 mg, 0.042 mmol, 1.5 eq.). After 18 hours, solvents were removed in vacuo and the residue was purified by reverse phase chromatography (Method A) to afford #B21 as a white solid. Yield: 11 mg, 0.013 mmol, 47%. HPLC (Protocol H): m/z 851.3 [M+H]+, retention time=9.074 minutes (purity 88%). LCMS (Protocol C); m/z 851.5 [M+H]+, retention time=1.58 minutes. 1H NMR (400 MHz, DMSO-d6, mult, J in Hz) δ 10.42-10.25 (m, 1H), 7.83-7.66 (m, 3H), 7.02-6.92 (m, 2H), 6.43-6.22 (m, 2H), 6.1-6.05 (m, 1H), 5.93-5.81 (m, 1H), 5.68-5.37 (m, 2H), 5.08-4.90 (m, 1H), 4.52-4.25 (m, 3H), 4.13-4.04 (m, 2H), 3.71-3.55 (m, 2H), 3.52-3.40 (m, 1H), 2.94-2.55 (m, 9H), 2.35-2.03 (m, 7H), 1.98 (s, 3H), 1.95-1.85 (m, 1H), 1.84-1.73 (m, 2H), 1.72-1.54 (m, 5H), 1.30-1.20 (m, 3H), 1.12-1.00 (m, 3H), 0.98-0.87 (m, 3H).

Preparation of (2S,3Z)-5-({(2R,3R,5S,6S)-6-[(2E,4E)-5-{(3S,5S,7S)-7-[2-(hydroxyamino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B22)

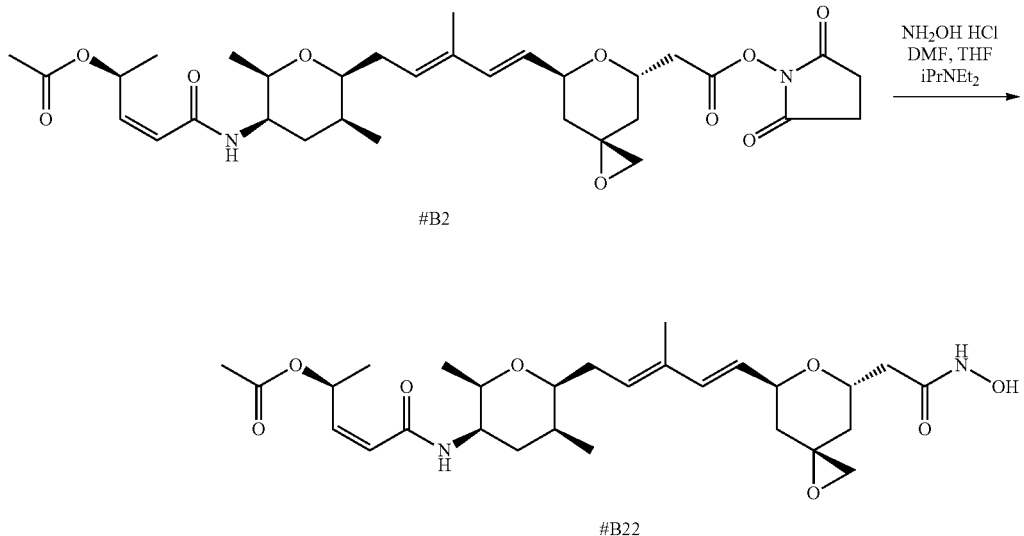

Step 1:

Synthesis of (2S,3Z)-5-({(2R,3R,5S,6S)-6-[(2E,4E)-5-{(3S,5S,7S)-7-[2-(hydroxyamino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B22). To a solution of #B2 (100.8 mg, 0.175 mmol, 1 eq.) dissolved in tetrahydrofuran (1.8 mL) and N,N-dimethylformamide (0.600 mL) was added N,N-diisopropylethylamine (114 mg, 0.875 mmol, 5 eq.) and hydroxylamine hydrochloride (10.6 mg, 0.152 mmol, 3 eq.) After stirring for 1 hour, the reaction was diluted with water, extracted with ethyl acetate ((3×)), the combined organics were washed again with water, dried over sodium sulfate, filtered and concentrated in vacuo. The crude desired material was purified by medium pressure reverse phase C18 chromatography (Gradient: 10% to 100% water in acetonitrile with 0.02% acetic acid in each phase) to give #B22 as a white solid. Yield: 68 mg, 0.127 mmol, 73%. LCMS (Protocol C): m/z 535.4 [M+H]+, retention time=1.36 minutes. 1H NMR (400 MHz, DMSO-d6) δ 10.40 (s, 1H), 8.73 (d, J=2 Hz, 1H), 7.79 (d, J=8.2 Hz, 1H), 6.41-6.32 (m, 1H), 6.26 (d, J=15.6 Hz, 1H), 6.12 (d, J=11.3 Hz, 1H), 5.87 (dd, J=11.5 and 7.6 Hz, 1H), 5.59 (dd, J=16 and 5.5 Hz, 1H), 5.55-5.49 (m, 1H), 4.56-4.49 (m, 1H), 4.36-4.27 (m, 1H), 3.70-3.61 (m, 2H), 3.54-3.47 (m, 1H), 2.65-2.60 (m, 2H), 2.48-2.41 (m, 1H), 2.36-2.17 (m, 2H), 2.16-2.09 (m, 1H), 1.98 (s, 3H), 1.85-1.72 (m, 3H), 1.72-1.61 (m, 6H), 1.43-1.35 (m, 1H), 1.25 (d, J=6.6 Hz, 3H), 1.07 (d, J=6.2 Hz, 3H), 0.95 (d, J=7.4 Hz, 3H).

Example A12

Preparation of N-[3-(2-{2-[(bromoacetyl)amino]ethoxy}ethoxy)propanoyl]-D-valyl-N-(4-{[({4-[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]phenyl}carbamoyl)oxy]methyl}phenyl)-N~5~-carbamoyl-D-ornithinamide (#B27)

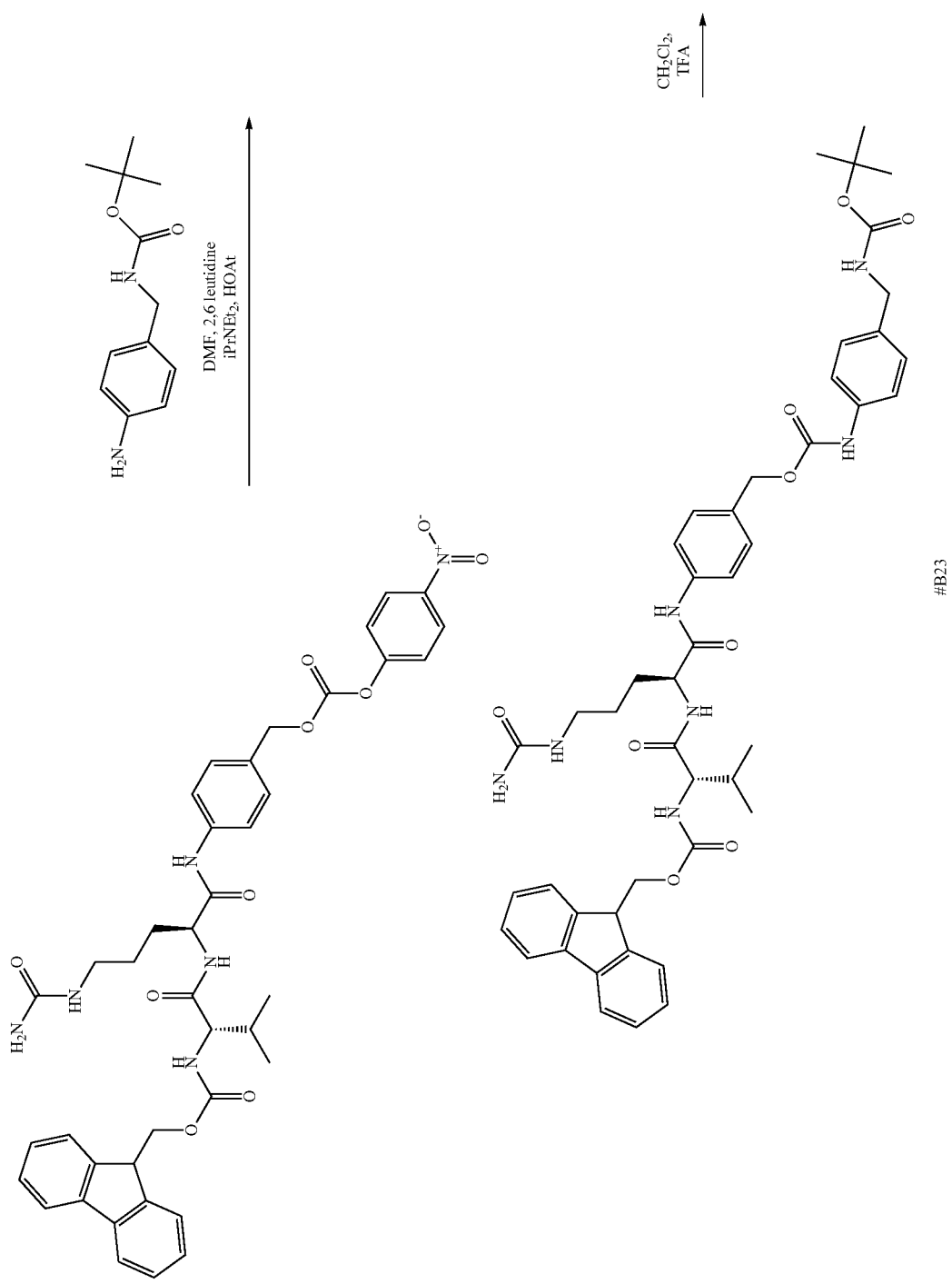

-continued
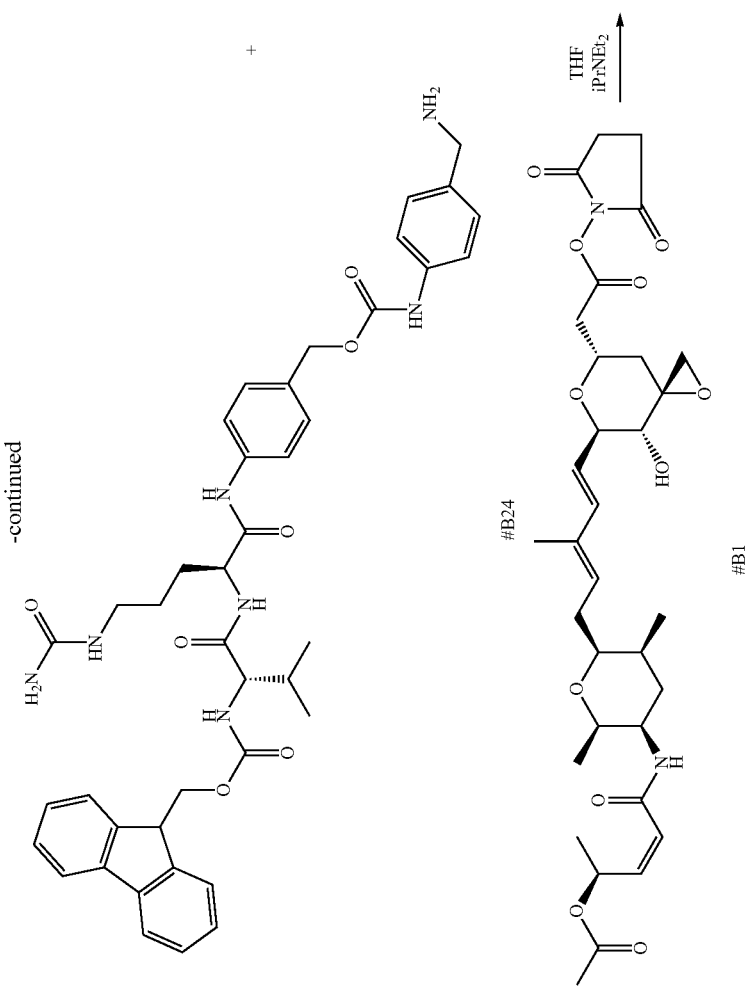

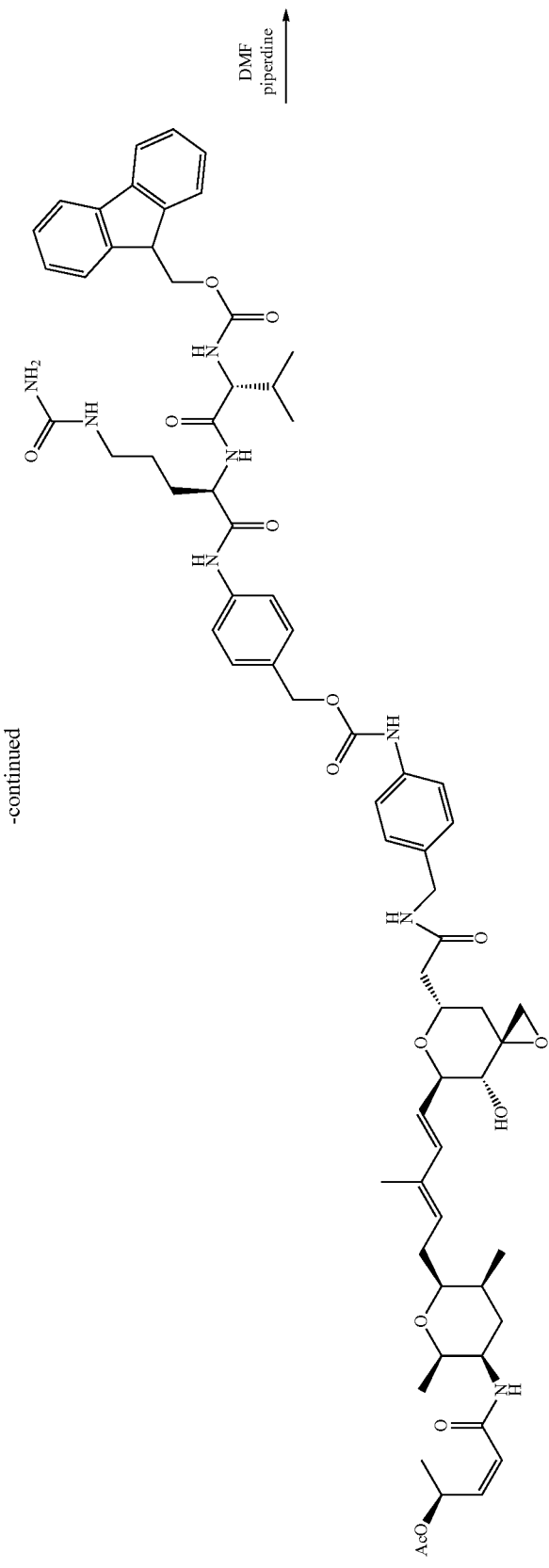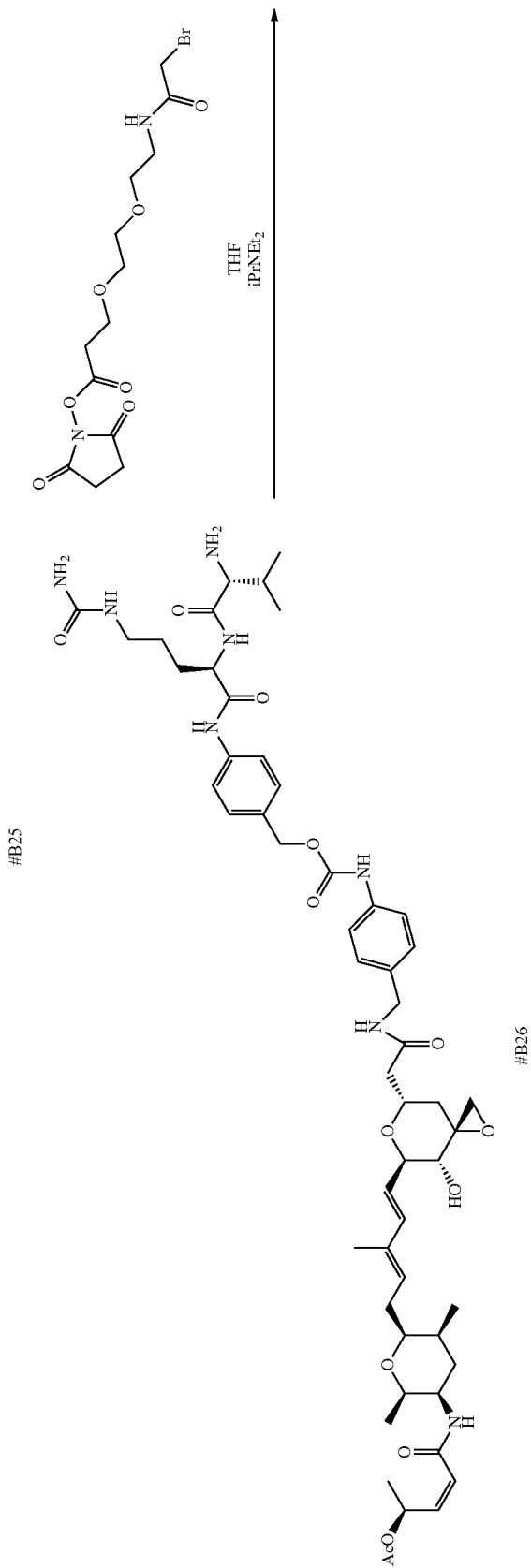

-continued
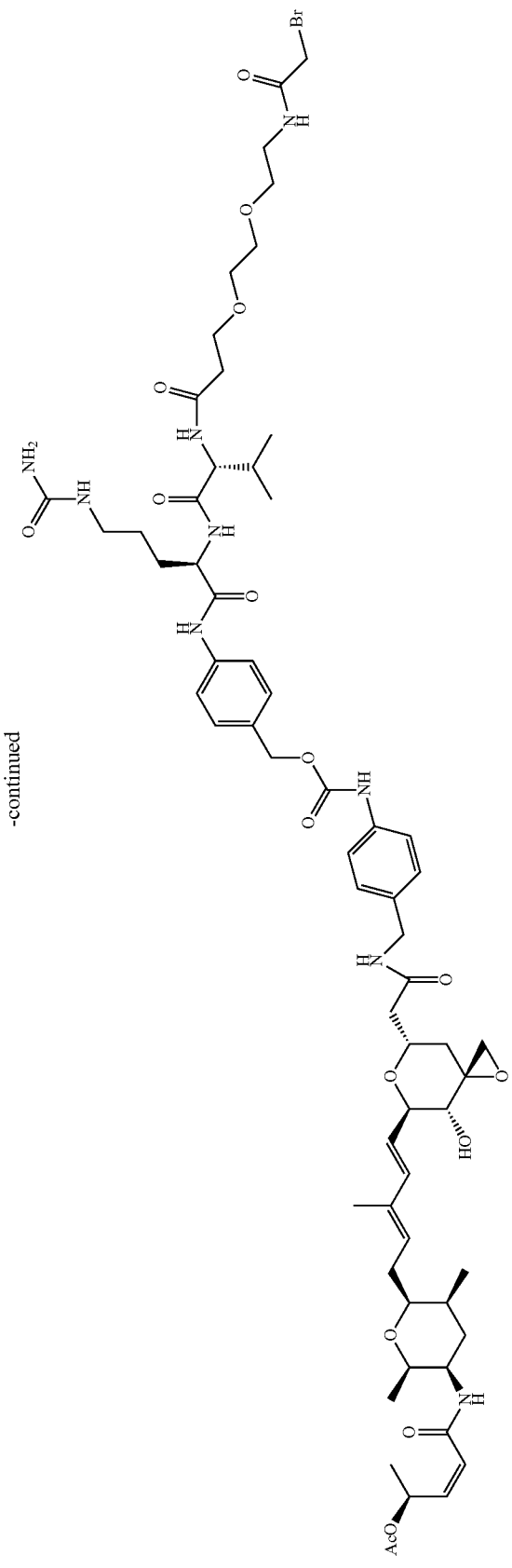
B27

Step 1:
Synthesis of N-[(9H-fluoren-9-ylmethoxy)carbonyl]-L-valyl-N-[4-({[(4-{[(tert-butoxycarbonyl)amino]methyl}phenyl)carbamoyl]oxy}methyl)phenyl]-N~5~-carbamoyl-L-ornithinamide (#B23). To a solution of tert-butyl (4-aminobenzyl)carbamate (75.4 mg, 0.339 mmol, 1.3 eq.) in N,N-dimethylformamide (2 mL, 0.16 M) was added 2,6-dimethylpyridine (140 mg, 1.3 mmol, 5 eq.), N,N-diisopropylethylamine (169 mg, 1.3 mmol, 5 eq.) and 3H-[1,2,3]triazolo[4,5-b]pyridin-3-ol (HOAt, 71.1 mg, 0.522 mmol, 2 eq.) was stirred for 5 minutes. The entire reaction mixture was added to a solution of N-[(9H-fluoren-9-ylmethoxy)carbonyl]-L-valyl-N~5~-carbamoyl-N-[4-({[(4-nitrophenoxy)carbonyl]oxy}methyl)phenyl]-L-ornithinamide (200 mg, 0.261 mmol, 1 eq.) in N,N-dimethylformamide (2 mL, 0.13 M) and the reaction was heated to 50° C. for 5 hours and concentrated in vacuo. The crude desired material was purified by medium pressure reverse phase C18 chromatography (Gradient: 10% to 100% water in acetonitrile with 0.02% trifluoroacetic acid in each phase) to give #B23 as a solid. Yield: 40 mg, 0.047 mmol, 18%.

Step 2:
Synthesis N-[(9H-fluoren-9-ylmethoxy)carbonyl]-L-valyl-N-{4-[({[4-(aminomethyl)phenyl]carbamoyl}oxy)methyl]phenyl}-N~5~-carbamoyl-L-ornithinamide, di trifluoroacetic acid salt. (#B24). To a suspension of #B23 (40 mg, 0.047 mmol, 1 eq.) in dichloromethane (2 mL, 0.023 M) was added a 1:1 solution of dichloromethane/trifluoroacetic acid (2 mL). After 45 minutes the reaction was concentrated in vacuo to an orange gum #B24 which was used without further purification. Yield: 46 mg (assumed quantitative yield). LCMS (Protocol D): m/z 750.4 [M+H]+, retention time=0.73 minutes.

Step 3:
Synthesis of N-[(9H-fluoren-9-ylmethoxy)carbonyl]-D-valyl-N-(4-{[({4-[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]phenyl}carbamoyl)oxy]methyl}phenyl)-N~5~-carbamoyl-D-ornithinamide (#B25). To a solution of #B24 (46 mg, 0.047 mmol, 1 eq.) in tetrahydrofuran (1 mL, 0.047 M) was added N,N-diisopropylethylamine (12.8 mg, 0.017 mmol, 2.1 eq.). The entire mixture was then added dropwise to a solution of #B1 (29.7 mg, 0.047 mmol, 1 eq.) in tetrahydrofuran (1 mL). After 18 hours methanol (0.4 mL) was added. After 48 hours, the reaction was concentrated in vacuo and the crude product was purified by reverse phase chromatography (Method A) to afford #B25 as a white solid. Yield: 12.2 mg, 0.009 mmol, 20%. HPLC (Protocol $A^4$): retention time=9.140 (purity=89%). LCMS (Protocol D): m/z 1268.7 [M+H]+, retention time=0.92 minutes.

Step 4:
Synthesis of D-valyl-N-(4-{[({4-[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]phenyl}carbamoyl)oxy]methyl}phenyl)-N5-carbamoyl-D-ornithinamide (#B26). To a solution of #B25 (12 mg, 0.009 mmol, 1 eq.) in N,N-dimethylformamide (0.3 mL, 0.3 M) was added piperadine (0.2 mL of a stock solution 0.050 mL in 1 mL of N,N-dimethylformamide). After 30 minutes, reaction was concentrated in vacuo and purified by reverse phase chromatography (Method A) and the fractions that pertained to the desired product were lyophilized to afford #B26 as a solid. Yield: 6.6 mg, 0.006 mmol, 70%. HPLC (Protocol $A^4$): retention time=6.957 (purity=89%). LCMS (Protocol D): m/z 1045.8 [M+H]+, retention time=0.69 minutes.

Step 5:
Synthesis of N-[3-(2-{2-[(bromoacetyl)amino]ethoxy}ethoxy)propanoyl]-D-valyl-N-(4-{[({4-[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]phenyl}carbamoyl)oxy]methyl}phenyl)-N~5~-carbamoyl-D-ornithinamide (#B27). To a solution of #B26 (6 mg, 0.006 mmol, 1 eq.) in tetrahydrofuran (0.6 mL, 0.01 M) was added N,N-diisopropylethylamine (0.25 mL of a stock solution [prepared by dissolving 0.01 mL N,N-diisopropylethylamine in 1 mL tetrahydrofuran], 0.012 mmol, 2 eq.) and was stirred at room temperature for 5 minutes. The entire mixture was added dropwise to a cooled (0° C.) solution of 2-bromo-N-[2-(2-{3-[(2,5-dioxopyrrolidin-1-yl)oxy]-3-oxopropoxy}ethoxy)ethyl]acetamide (2.4 mg, 0.006 mmol, 1 eq.). The reaction was stirred at (0° C.) for 5 minutes and then allowed to warm to room temperature. After 16 hours, the reaction was concentrated in vacuo and purified by reverse phase chromatography (Method A) to afford #B27 as a white solid. Yield: 1.4 mg, 0.001 mmol, 20%. LCMS (Protocol D): m/z 1348.7 [M+Na]+, retention time=0.77 minutes.

Example A13

Preparation of (2S,3Z)-5-({(2R,3R,5S,6S)-6-[(2E,4E)-5-{(3R,4R,5R,7S)-7-[2-({4-[(3-{2-[(N-{6-[(bromoacetyl)amino]hexanoyl}glycyl)amino]phenyl}propanoyl)sulfamoyl]benzyl}amino)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B37)

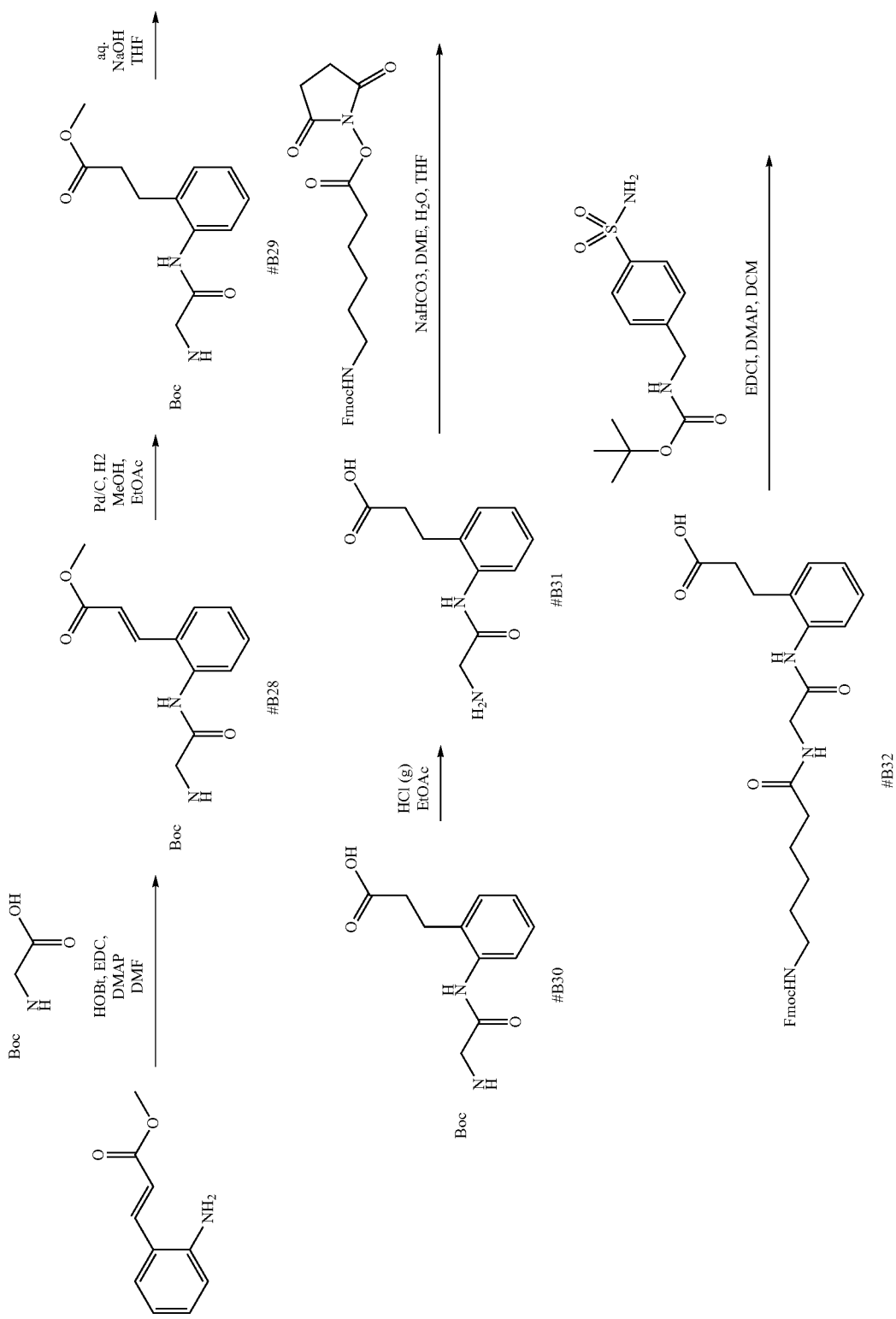

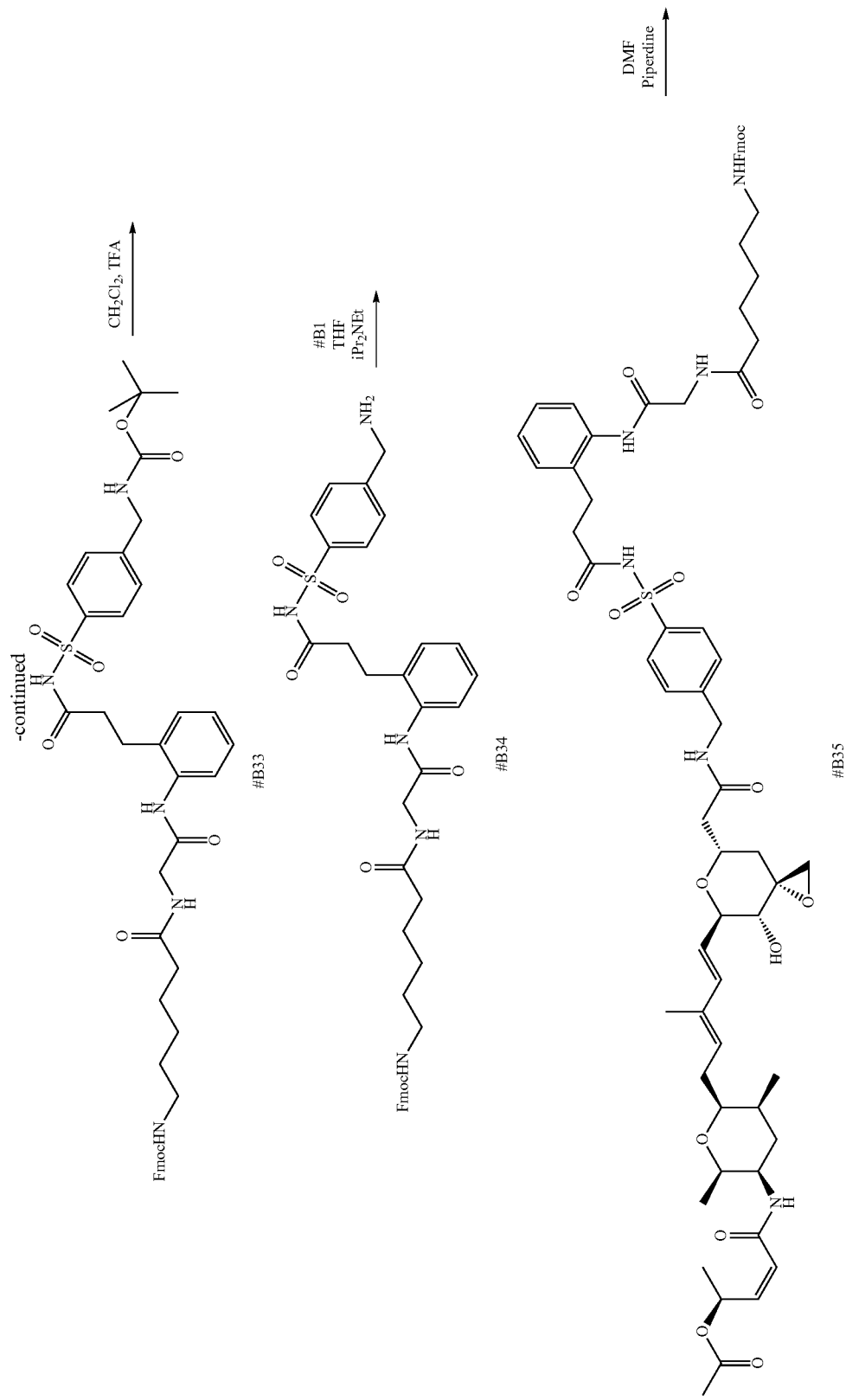

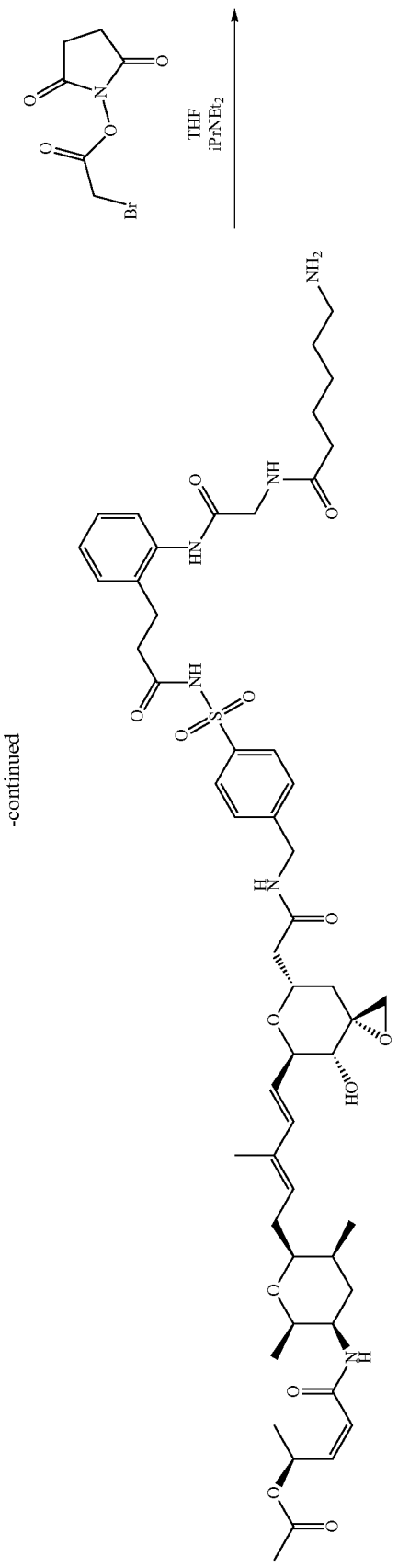
B36
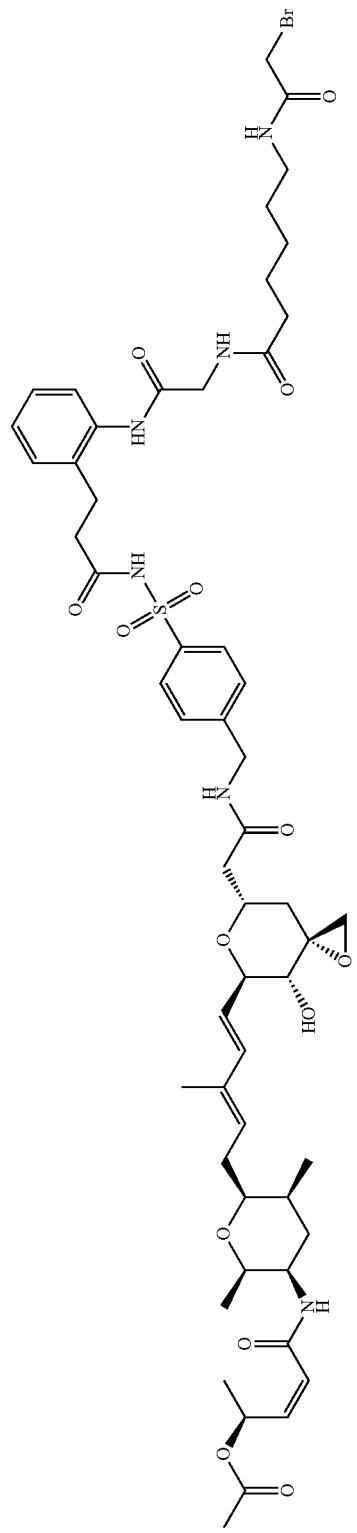
B37

Step 1:

Synthesis of methyl (2E)-3-(2-{[N-(tert-butoxycarbonyl) glycyl]amino}phenyl)prop-2-enoate (#B28). To a solution of N-(tert-butoxycarbonyl)glycine (13.4 g, 77.1 mmol, 1 eq.), 1-[3-(dimethylamino)propyl]-3-ethylcarbodiimide hydrochloride (22.1 g, 115.7 mmol, 1.5 eq.), 1-Hydroxybenzotriazole (11.4 g, 84.8 mmol, 1.1 eq.), 4-(dimethylamino)pyridine (0.9 g, 7.4 mmol, 0.10 eq.) in N,N-dimethylformamide (350 mL) was added methyl (2E)-3-(2-aminophenyl)prop-2-enoate (15 g, 84.7 mmol, 1.1 eq.) at room temperature. The reaction was warmed to 50° C., stirred for 18 hours. The reaction was diluted with water (400 mL), washed with citric acid (200 mL), extracted with ethyl acetate (300 mL×3). The organic layer was washed with brine (150 mL), dried over sodium sulfate, filtered and filtrate concentrated in vacuo. The crude product was purified by silica gel chromatography eluted with petroleum ether: ethyl acetate from 8:1 to 1:1 to afford compound #B28 (20 g, 71%) as a solid. $^1$H NMR (400 MHz, CDCl$_3$): δ 8.29 (br, 1H), 7.84 (d, 2H), 7.55 (t, 1H), 7.40 (t, 1H), 7.22 (t, 1H), 6.41 (d, 2H), 5.37 (br, 1H), 4.00 (d, 2H), 3.79 (s, 3H), 1.46 (s, 9H).

Step 2:

Synthesis of methyl 3-(2-{[N-(tert-butoxycarbonyl)glycyl]amino}phenyl)propanoate (#B29). A suspension of compound #B28 (20 g, 59.8 mmol, 1 eq.) and Pd/C (2.0 g) in ethyl acetate (350 mL) and methanol (300 mL) was degassed under vacuum and purged with H$_2$ several times. The reaction mixture was stirred at room temperature under H$_2$ (30 Psi) for 9 hours. The reaction mixture was filtered, and the filer cake was washed with ethyl acetate (100 mL). The filtrate was evaporated to dryness to afford compound #B29 as an oil which was used in next step without further purification: Yield (20.75 g, assume quantitative). $^1$H NMR (400 MHz, CDCl$_3$): δ 9.13 (br, 1H), 7.75 (d, 1H), 7.22 (d, 1H), 7.17 (m, 2H), 5.34 (br, 1H), 4.04 (d, 2H), 3.64 (s, 3H), 2.95 (t, 2H), 2.72 (t, 2H), 1.46 (s, 9H).

Step 3:

Synthesis of 3-(2-{[N-(tertbutoxycarbonyl)glycyl] amino}-phenyl)propanoic acid (#B30). To a solution of #B29 (20.75 g, 59.8 mmol, 1 eq.) in tetrahydrofuran (200 mL) was added a solution of sodium hydroxide (12.24 g, 0.306 mmol) in water (155 mL). The reaction mixture was stirred at room temperature for 3 hours. The reaction mixture pH was adjusted to pH 5~6 by citric acid, extracted with ethyl acetate (400 mL×2). The organic layer was washed with brine (150 mL×2), dried over sodium sulfate, concentrated to dryness to afford #B30 as solid which was used without further purification in the next step Yield: 21.5 g (assume quantitative). $^1$H NMR (400 MHz, CD$_3$OD) δ 7.29 (m, 1H), 7.23 (m, 3H), 3.90 (s, 2H), 2.91 (m, 2H), 2.66 (m, 2H), 1.49 (m, 9H). LCMS (Protocol I): m/z 345 [M+Na]$^+$, retention time=1.034 minutes.

Step 4:

Synthesis of 3-[2-(glycylamino)phenyl]propanoic acid (#B31). To a solution of #B30 (10 g, 31.1 mmol, 1 eq.) in ethyl acetate (100 mL) was added HCl/dioxane (70 mL). The reaction was stirred at room temperature for 3 hours, and then concentrated to dryness. The residue was re-crystallized from tert-butyl methyl ether (50 mL) to afford #B31 as solid (5.9 g, 26.5 mmol, 85.5% over three steps). $^1$H NMR (400 MHz, DMSO-d$_6$): δ 10.06 (br, 1H), 8.31 (br, 3H), 7.41 (d, 1H), 7.28 (m, 3H), 3.84 (s, 2H), 2.88 (m, 2H), 2.52 (m, 2H).

Step 5:

Synthesis of 3-(2-{[N-(6-{[(9H-fluoren-9-ylmethoxy)carbonyl]amino} hexanoyl)glycyl]amino}phenyl)propanoic acid (#B32). To a solution of #B31 (1.11 g, 4.98 mmol, 1 eq.) and sodium bicarbonate (528 mg, 7.47 mmol, 1.5 eq.) in tetrahydrofuran (25 mL) and water (10 mL) was added dropwise a solution of 9H-fluoren-9-ylmethyl {6-[(2,5-dioxopyrrolidin-1-yl)oxy]-6-oxohexyl}carbamate (2.7 g, 5.98 mmol, 1.2 eq.) in tetrahydrofuran (45 mL) and 1,2-Dimethoxyethane (10 mL). The reaction mixture was stirred at room temperature for 16 hours. The reaction mixture pH was adjusted to pH 5~6 by citric acid, extracted with dichloromethane (100 mL×2). The organic layer was washed with brine (100 mL), dried over sodium sulfate, concentrated to dryness. The crude product was purified by silica gel chromatography eluted with dichloromethane: methanol from 100:1 to 10:1 to afford #B32. (1.1 g, 1.97 mmol, 39.7%) as solid. $^1$H NMR (400 MHz, DMSO-d$_6$), δ 9.31 (s, 1H), 8.18 (s, 1H), 7.89 (d, 2H), 7.70 (d, 2H), 7.40 (m, 6H), 7.13 (m, 5H), 4.30 (m, 2H), 4.21 (m, 1H), 3.90 (m, 2H), 2.98 (m, 2H), 2.80 (m, 2H), 2.77 (m, 1H), 2.48 (m, 1H), 2.20 (m, 2H), 1.54 (m, 2H), 1.42 (m, 2H), 1.25 (m, 2H). LCMS (Protocol I): m/z 580.1 [M+Na]$^+$, retention time=1.315 minutes.

Step 6:

Synthesis of 9H-fluoren-9-ylmethyl {6-[(2-{[2-(3-{[(4-{[(tert-butoxycarbonyl)amino]methyl}phenyl)sulfonyl]amino}-3-oxopropyl)phenyl]amino}-2-oxoethyl) amino]-6-oxohexyl}carbamate (#B33). The mixture of #B32 (900 mg, 1.62 mmol, 1 eq.) and tert-butyl (4-sulfamoylbenzyl)carbamate (787 mg, 2.59 mmol, 1.6 eq.), 4-(dimethylamino)pyridine (198 mg, 1.62 mmol, 1 eq.), 1-[3-(dimethylamino)propyl]-3-ethylcarbodiimide hydrochloride (369 mg, 1.2 mmol, 0.7 eq.) in dichloromethane (30 mL) was stirred at room temperature for 3.5 hours. The reaction mixture pH was adjusted to pH 5~6 by citric acid, extracted with dichloromethane (30 mL×2). The organic layer was washed with brine (100 mL), dried over sodium sulfate, concentrated to dryness. The crude product was purified by silica gel chromatography eluted with dichloromethane: methanol from 100:1 to 20:1 to afford #B33 as a solid (800 mg, 0.972 mmol, 60.0%). $^1$H NMR (400 MHz, DMSO-d$_6$), δ 12.09 (br, 1H), 9.30 (s, 1H), 8.19 (m, 1H), 7.89 (m, 4H), 7.70 (m, 2H), 7.46 (m, 1H), 7.44 (m, 4H), 7.42 (m, 3H), 7.35 (m, 1H), 7.16 (m, 1H), 7.08 (m, 2H), 4.23 (m, 2H), 3.88 (m, 3H), 3.87 (m, 2H), 2.70 (m, 2H), 2.68 (m, 2H), 2.50 (m 2H), 2.17 (m, 2H), 1.53 (m, 2H), 1.51 (s, 9H), 1.25 (m, 4H). LCMS (Protocol J): m/z 726.1 [M-Boc]$^+$, retention time=1.211 minutes.

Step 7:

Synthesis of 9H-fluoren-9-ylmethyl (6-{[2-({2-[3-({[4-(aminomethyl)phenyl]sulfonyl}amino)-3-oxopropyl] phenyl}amino)-2-oxoethyl]amino}-6-oxohexyl)carbamate (#B34). To a suspension of (#B33) (52.6 mg, 0.063 mmol, 1 eq.), in dichloromethane (3 mL, 0.02 M) was added trifluoroacetic acid (0.6 mL) and was stirred for 2 hours and then concentrated in vacuo. The residue was azeotroped with acetonitrile (3×) to afford #B34 (45.7 mg, 0.063 mmol, assume quantitative) which was used as is in the next step without further purification. LCMS (Protocol D): m/z 726.3 [M+H]$^+$, retention time=0.73 minutes.

Step 8:

Synthesis of (2S,3Z)-5-{[(2R,3R,5S,6S)-6-{(2E,4E)-5-[(3R,4R,5R,7S)-7-{2-[(4-{[3-(2-{[N-(6-{[(9H-fluoren-9-ylmethoxy)carbonyl]amino}hexanoyl)glycyl]amino}phenyl) propanoyl]sulfamoyl}benzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B35). To a solution of #B34 (45.7 mg, 0.063 mmol, 1 eq.) in tetrahydrofuran (0.5 mL, 0.12 M) was added N,N-diisopropylethylamine (24.4 mg, 0.189 mmol, 3 eq.). The entire reaction mixture was added to a cooled (0° C.) solution of #B1 (40 mg, 0.063 mmol, 1 eq.) in tetrahydrofuran (0.5 mL) and the reaction was allowed to warm to room temperature. After one hour the reaction was concentrated in vacuo to afford #B35 (55 mg, 0.053 mmol, 70%) which was used as is, in the next step, without further purification. LCMS (Protocol D): m/z 1243.6 [M+H]$^+$, retention time=0.95 minutes.

Step 9:

Synthesis of (2S,3Z)-5-{[(2R,3R,5S,6S)-6-{(2E,4E)-5-[(3R,4R,5R,7S)-7-{2-[(4-{[3-(2-{[N-(6-aminohexanoyl)glycyl]amino}phenyl)propanoyl]sulfamoyl}benzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate, formate salt (#B36). To a solution of #B35 (55 mg, 0.053 mmol, 1 eq.) in N,N-dimethylformamide was added piperidine (0.2 mL of a stock solution [prepared by dissolving 0.05 mL in 1 mL N,N-dimethylformamide], 0.106 mmol, 2 eq.). After 30 minutes reaction was concentrated in vacuo and purified by reverse phase chromatography (Method A) to afford #B36 as a white solid. Yield: 30 mg, 0.027 mmol, 52%. HPLC (Protocol A$^A$): retention time=7.143 minutes (purity=92%). LCMS (Protocol D): m/z 1021.4 [M+H]$^+$ retention time=0.67 minutes. $^1$H NMR (DMSO-d$_6$) δ: 10.23-10.21 (b.s., 1H D$_2$O exchangeable) 8.36-8.31 (m, 1H), 8.25-8.20 (m, 1H), 7.76-7.68 (m, 1H), 7.53-7.42 (m, 3H), 7.14-7.02 (m, 3H), 6.99-6.93 (m, 1H), 6.35-6.21 (m, 2H), 6.08-6.01 (m, 1H), 5.82-5.76 (m, 1H), 5.61-5.52 (m, 1H), 5.50-5.42 (m, 1H), 4.28-4.16 (m, 4H), 3.82 (d, J=5.9 Hz, 2H), 3.57 (d, J=6.2 Hz, 2H), 3.49-3.42 (m, 1H), 3.21-3.18 (m, 1H), 2.74-2.66 (m, 3H), 2.62-2.49 (m, 3H), 2.31-2.11 (m, 6H), 1.91 (s, 3H), 1.84-1.69 (m, 3H), 1.64 (s, 3H), 1.60-1.41 (m, 6H), 1.32-1.22 (m., 2H), 1.18 (d, J=6.6 Hz, 3H), 0.99 (d, J=6.21 Hz, 3H) –0.88 (d, J=6.21 Hz, 3H)

Step 10:

Synthesis of (2S,3Z)-5-({(2R,3R,5S,6S)-6-[(2E,4E)-5-{(3R,4R,5R,7S)-7-[2-({4-[(3-{2-[(N-{6-[(bromoacetyl)amino]hexanoyl}glycyl)amino]phenyl}propanoyl)sulfamoyl]benzyl}amino)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B37). To a solution of #B36 (20 mg, 0.018 mmol, 1 eq.) in tetrahydrofuran was added N,N-diisopropylethylamine (9.8 mg, 0.076 mmol, 4.2 eq.) and methanol (0.1 mL). The entire mixture was added to a cooled (0° C.) solution of 1-[(bromoacetyl)oxy]pyrrolidine-2,5-dione (4.2 mg, 0.018 mmol, 1 eq) and was stirred at 0° C. for 5 minutes and then allow to warm to room temperature. After 18 hours, reaction was concentrated in vacuo and purified by reverse phase chromatography (Method A) to afford #B37 as a white solid. Yield: 3.8 mg, 0.003 mmol, 18%. HPLC (Protocol A$^A$): retention time=7.554 and 7.77 minutes (purity 91%). LCMS (Protocol D): m/z 1141.4 [M+H]$^+$ retention time=0.8 minutes. $^1$H NMR (400 MHz, METHANOL-d$_4$) □ 7.66 (d, J=8.2 Hz, 2H), 7.56-7.49 (m, 1H), 7.33-7.26 (m, 2H), 7.03 (m, 3H), 6.32-6.23 (m, 1H), 5.94-5.81 (m, 2H), 5.58 (dd, J=16.0, 8.0 Hz, 1H), 5.47-5.39 (m, 1H), 4.46 (s, 2H), 4.43-4.34 (m, 1H), 4.3 (m, 2H), 3.88 (s, 2H), 3.68 (s, 2H), 3.67-3.62 (m, 2H), 3.61-3.55 (m, 1H), 3.52-3.44 (m, 1H), 3.36-3.32 (m, 1H), 3.11 (t, J=16 Hz, 1H), 2.8 (d, J=8.0, 1H), 2.78-2.72 (m, 2H), 2.68 (t, J=8.0, 2H), 2.57 (d, J=4.0 Hz, 1H), 2.45-2.39 (m, 2H), 2.36 (dd, J=16.0, 8.0 Hz, 1H), 2.30 (d, J=8.0 Hz, 1H), 2.25 (t, J=8.0 Hz, 2H), 2.20-2.09 (m, 1H), 1.9 (s, 1H), 1.85-1.78 (m, 2H), 1.75-1.71, (m, 1H), 1.68 (s, 3H), 1.64-1.54 (m, 3H), 1.50-1.43 (m, 2H), 1.27-1.35 (m, 2H), 1.25 (d, J=8.0 Hz, 3H), 1.00 (d, J=8.0 Hz, 3H), 1.05-0.87 (d, J=8.0 Hz, 3H).

Example A14

Preparation of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperidine-1-carboxylate (#B40)

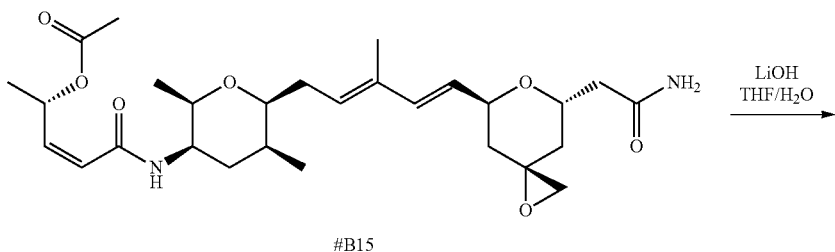

B15

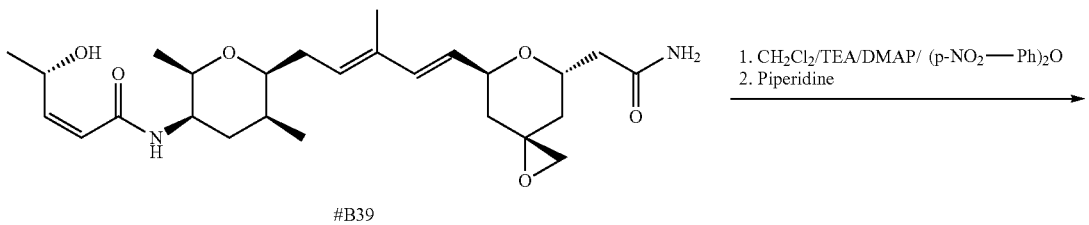

B39

1. CH$_2$Cl$_2$/TEA/DMAP/ (p-NO$_2$—Ph)$_2$O
2. Piperidine

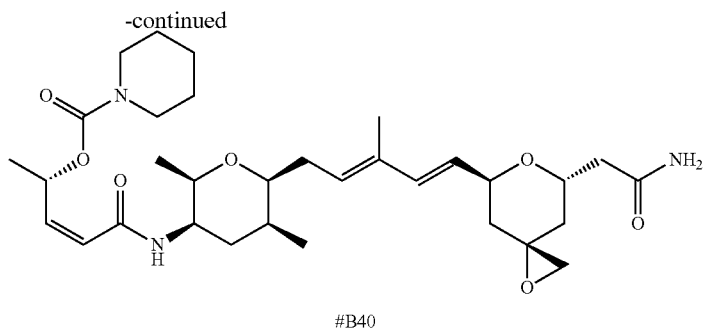

B40

Step 1:

Synthesis of (2Z,4S)—N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B39). To a solution of #B15 (38 mg, 0.075 mmol, 1 eq.) in 4:1 tetrahydrofuran:water (2.2 mL) was added lithium hydroxide (15.6 mg, 0.652 mmol, 8.7 eq.) and the mixture stirred at room temperature for 12 hours. The reaction was diluted with ethyl acetate and washed with water. The aqueous layer was extracted with ethyl acetate (3×) and the combined organic layers were dried over anhydrous sodium sulfate and concentrated in vacuo. Purification by reverse phase chromatography (Method A) provided # B39 as a solid. Yield: 16.7 mg, 0.035 mol, 47%. $^1$H NMR (400 MHz, DMSO-d$_6$, mult, J in Hz) δ 7.76 (d, J=8.2 Hz, 1H), 7.31 (s, 1H), 6.77 (s, 1H), 6.27 (d, J=16.0 Hz, 1H), 5.97 (d, J=11 Hz, 1H), 5.86 (dd, J=11.7 and 7.0 Hz, 1H), 5.59 (dd, J=16.0 and 5.5 Hz, 1H), 5.54-5.47 (m, 1H), 5.22-5.12 (m, 1H), 5.10 (d, J=4.7 Hz, 1H), 4.58-4.48 (m, 1H), 4.35-4.25 (m, 1H), 3.69-3.59 (m, 2H), 3.54-3.46 (m, 1H), 2.64-2.52 (m, 3H), 2.37-2.14 (m, 3H), 1.87-1.73 (m, 3H), 1.72-1.60 (m, 6H), 1.37 (dd, J=13.3 and 6.2 Hz, 1H), 1.11 (d, J=6.2 Hz, 3H), 1.06 (d, J=6.2 Hz, 3H), 0.95 (d, J=7.4 Hz, 3H). HPLC (Protocol A$^A$) retention time=7.15 minutes (purity=100%). LCMS (Protocol C): m/z 499.3 [M+Na]$^+$, retention time=1.18 minutes.

Step 2:

Synthesis of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperidine-1-carboxylate #B40: To a solution of #B39 (106 mg, 0.222 mmol, 1 eq.) in dichloromethane (3 mL) was added triethylamine (79 mg, 0.777 mmol, 3.5 eq), 4-N,N'-dimethylamino Pyridine (18.9 mg, 0.155 mmol, 0.7 eq.) and bis(4-nitrophenyl) carbonate (207 mg, 0.666 mmol, 3 eq.) and the reaction stirred at room temperature for 2 hours. To ⅓ of this mixture was added piperidine (18.9 mg, 0.222 mmol, 1 eq.) and the mixture stirred at room temperature for 3.5 hours, concentrated in vacuo and the residue purified by reverse phase chromatography (Method D*) to provide #B40. Yield 2.7 mg, 0.021 mmol, 9.5%. HPLC (Protocol B) m/z 588.4 [M+H]$^+$, retention time=2.82 minutes (purity=100%).

Example A15

Preparation of N-[3-(2-{2-[(bromoacetyl)amino]ethoxy}ethoxy)propanoyl]-L-valyl-N-[4-({[(2-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-N~5~-carbamoyl-L-ornithinamide (#B43)

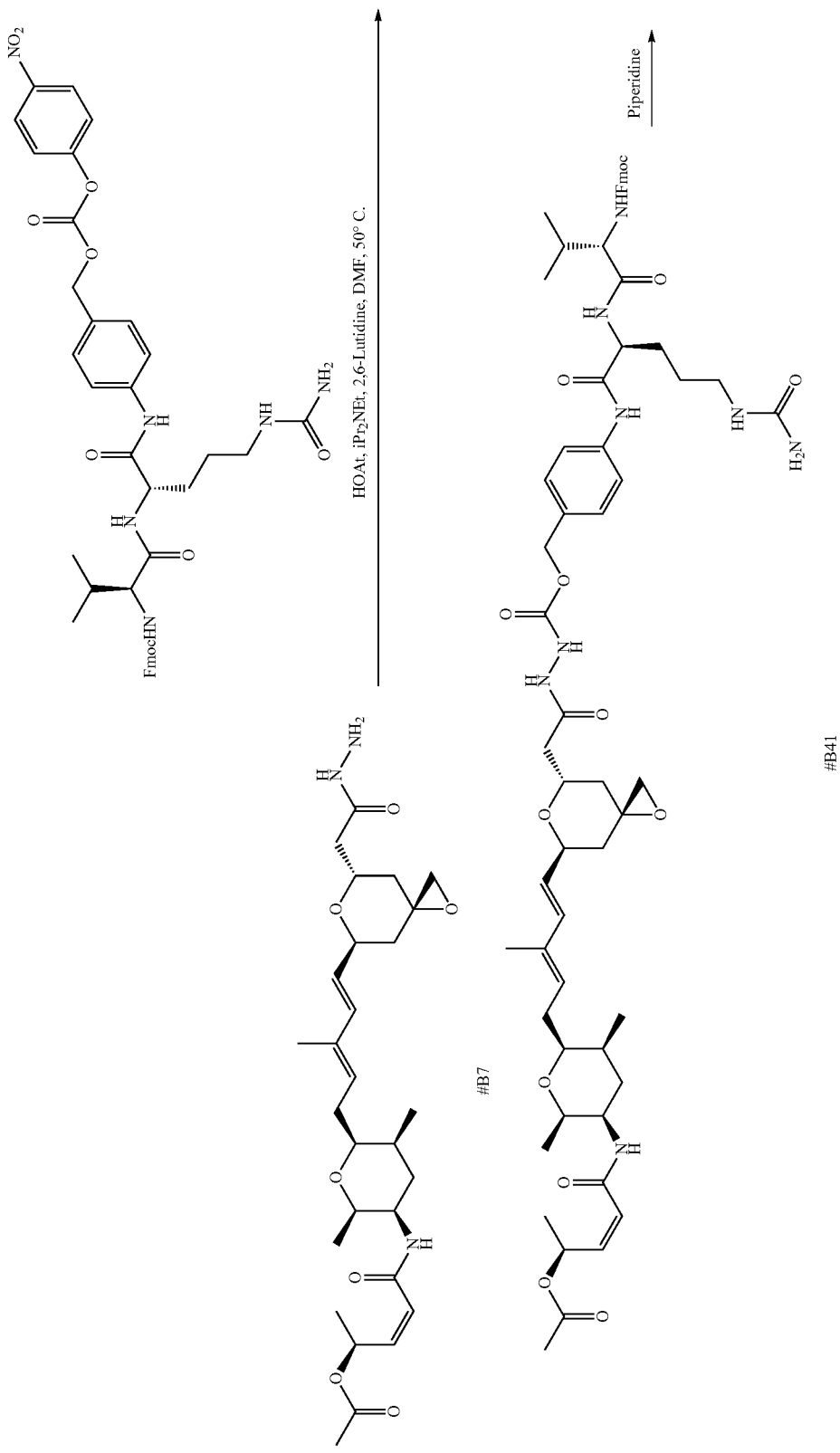

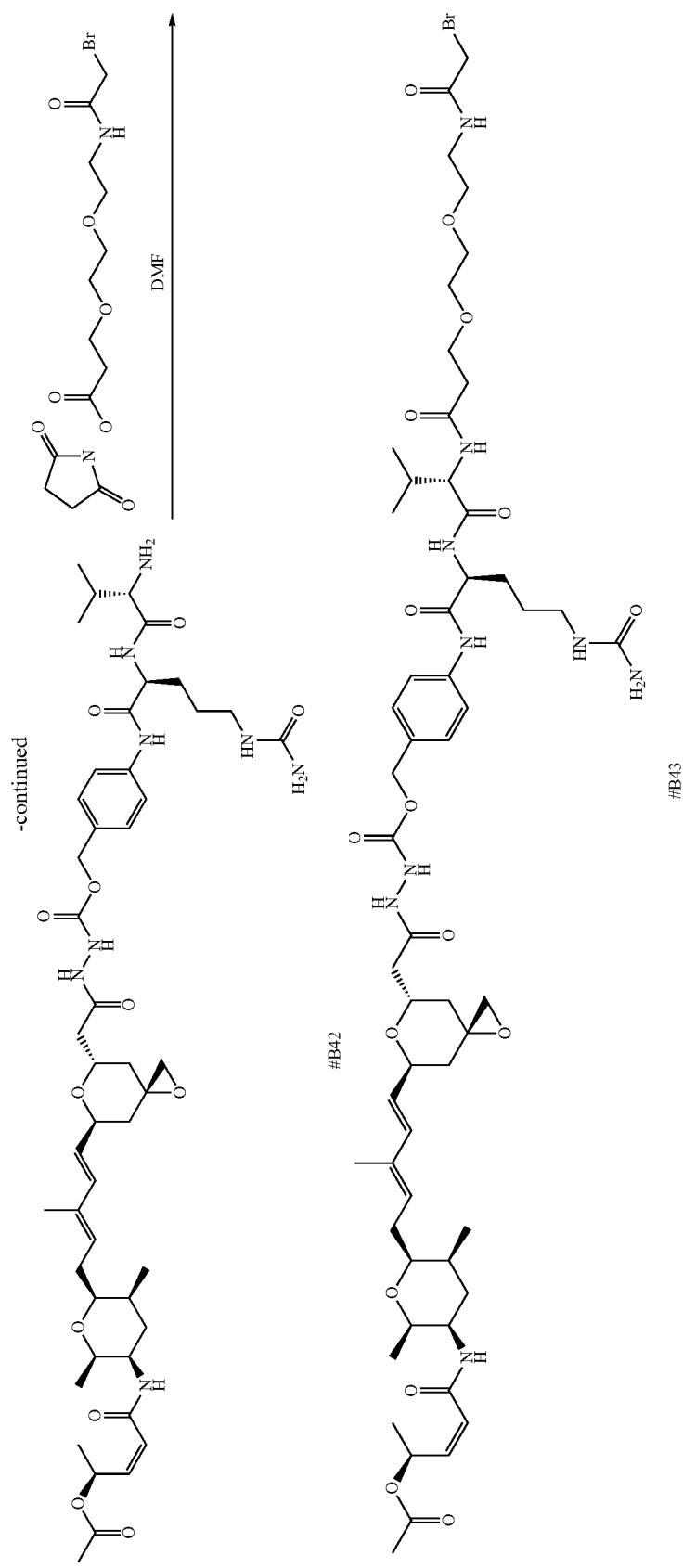

Step 1:

Synthesis of N-[(9H-fluoren-9-ylmethoxy)carbonyl]-L-valyl-N-[4-({[(2-{[(3S,5S,7S) 7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-N~5~-carbamoyl-L-ornithinamide (#B41). To a solution of #B7 of (56 mg, 0.1 mmol, 1 eq.) in N,N-dimethylformamide (2.6 mL) was added N-[(9H-fluoren-9-ylmethoxy)carbonyl]-L-valyl-N~5~-carbamoyl-N-[4-({[(4-nitrophenoxy)carbonyl]oxy}methyl)phenyl]-L-ornithinamide (FMocValCitPABC-PNP, WO04010957, 121 mg, 0.15 mmol, 1.5 eq.) N,N'-diisopropylethylamine (56 mg, 0.4 mmol, 4.0 eq.), 2,6-Dimethylpyridine (45 mg, 0.4 mmol, 4.0 eq.) and 3H-[1,2,3]triazolo[4,5-b]pyridin-3-ol (14.3 mg, 0.105 mmol, 1.05 eq.,). After stirring at 50° C. for 1.5 hours, the reaction mixture was concentrated in vacuo and the crude material was purified by reverse phase chromatography (Method A) to provide #B41 as a solid. Yield: 72 mg, 0.06 mmol, 59%. LCMS (Protocol D): m/z 1183.5 [M+Na]$^+$, retention time=0.95 minutes.

Step 2:

Synthesis of L-valyl-N-[4-({[(2-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-N~5~-carbamoyl-L-ornithinamide (#B42). To a solution of #B41 (50 mg, 0.043 mmol, 1 eq.) in N,N-dimethylformamide (0.7 mL) was added piperidine (66 mg, 0.78 mmol, 20 eq.) and the mixture stirred for 20 minutes. The reaction mixture was concentrated in vacuo and the crude material was purified by reverse phase chromatography (Method A) to provide #B42. Yield: 31 mg, 0.033 mmol, 76%. LCMS (Protocol D): m/z 939.3 [M+H]$^+$, retention time=0.66 minutes.

Step 3:

Synthesis of N-[3-(2-{2-[(bromoacetyl)amino]ethoxy}ethoxy)propanoyl]-L-valyl-N-[4-({[(2-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5 yl]acetyl}hydrazinyl)carbonyl]oxy}methyl)phenyl]-N5-carbamoyl-L-ornithinamide (#B43). To a solution of #B42 (10 mg, 0.011 mmol, 1 eq.) in N,N-dimethylformamide (0.2 mL) was added 2-bromo-N-[2-(2-{3-[(2,5-dioxopyrrolidin-1-yl)oxy]-3-oxopropoxy}ethoxy)ethyl]acetamide (4.3 mg, 0.011 mmol, 1 eq.) and the mixture stirred at room temperature for 30 minutes. The reaction was diluted with dimethylsulfoxide (0.2 mL) and purified by reverse phase chromatography (Method A) to provide #B43 as a solid. Yield: 8.8 mg, 0.007 mmol, 66%. HPLC (Protocol A$^A$) retention time=7.69 minutes (purity=71%). LCMS (Protocol A): m/z 1220.4 [M+H]$^+$, retention time=0.77 minutes.

Example A16

Preparation of N-(6-aminohexanoyl)-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N~5~-carbamoyl-L-ornithinamide (#B47)

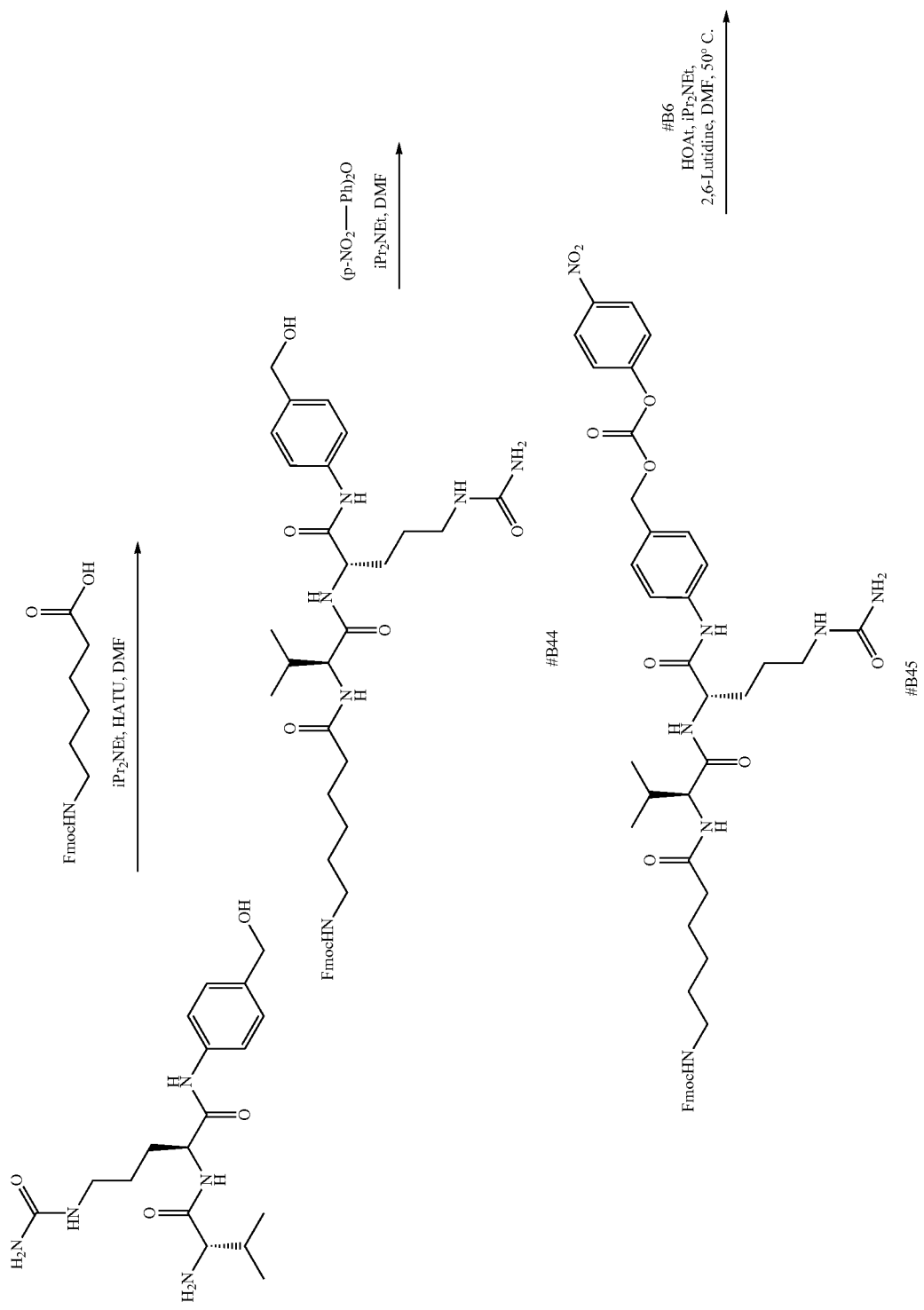

-continued
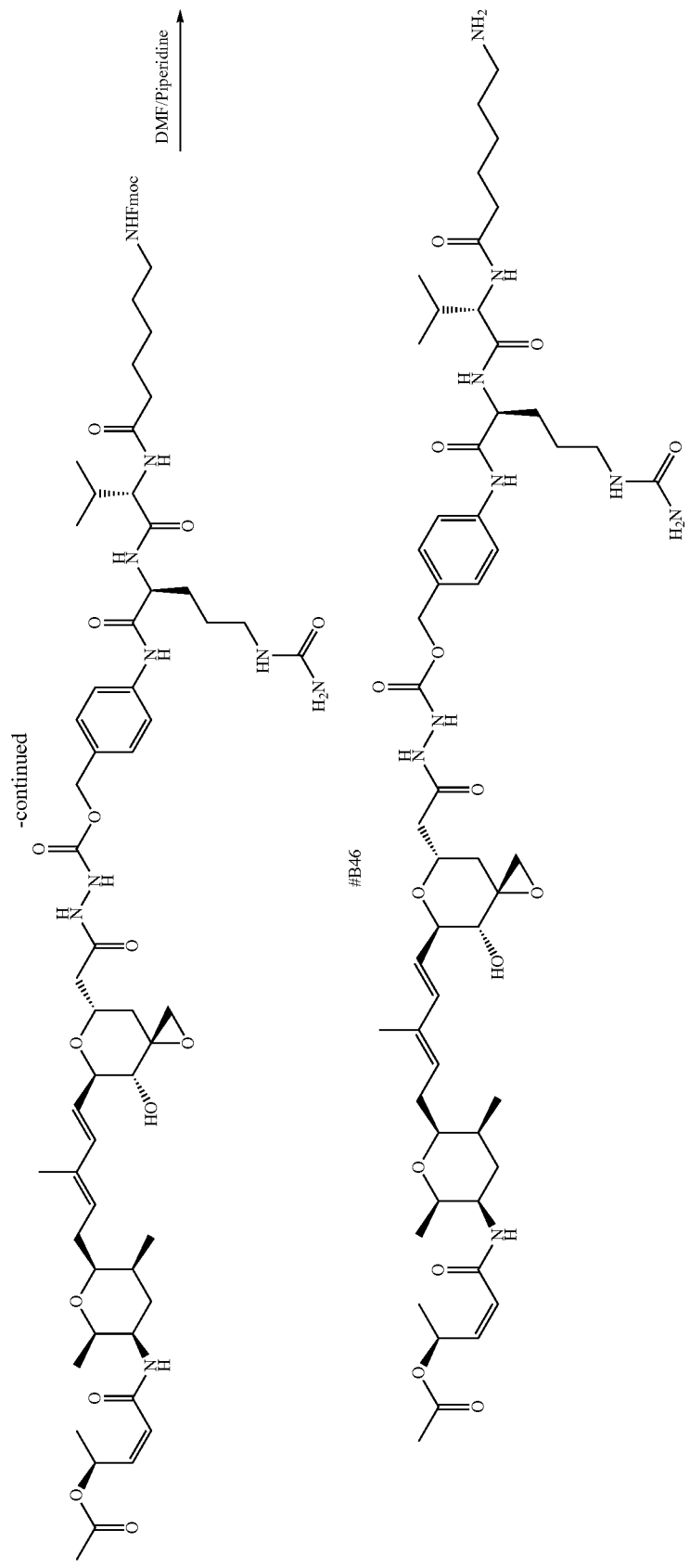

Step 1:

Synthesis of N-(6-{[(9H-fluoren-9-ylmethoxy)carbonyl]amino}hexanoyl)-L-valyl-N~5~-carbamoyl-N-[4-(hydroxymethyl)phenyl]-L-ornithinamide (#B44). N,N-diisopropylethylamine (3.8 mL, 22.12 mmol, 1.9 eq.) was added to a solution of 6-{[(9H-fluoren-9-ylmethoxy)carbonyl]amino}hexanoic acid (4.2 g, 11.80 mmol, 1 eq.) and N,N,N',N'-tetramethyl-O-(7-azabenzotriazol-1-yl)uronium hexafluorophosphate (HATU, 5.6 g, 14.75 mmol, 1.25 eq.) in N,N-dimethylformamide (50 mL, 0.24 M) at room temperature and stirred for ten minutes. Then L-valyl-N~5~-carbamoyl-N-[4-(hydroxymethyl)phenyl]-L-ornithinamide (From WO04010957, 5.6 g, 14.75 mmol, 1.25 eq.) was added to the mixture. After 15 hours, the reaction mixture was precipitated by adding dichloromethane and filtered to obtain #B44 as an off-white solid. Yield: 6.9 g, 9.6 mmol, 82%. LCMS 715.6 (M+H)$^+$ Step 2:

Synthesis of 4-[(N~5~-carbamoyl-N~2~-{(3S)-3-[(6-{[(9H-fluoren-9-ylmethoxy)carbonyl]amino}hexanoyl)amino]-4-methylpent-1-en-2-yl}-L-ornithyl)amino]benzyl 4-nitrophenyl carbonate (#B45) A solution of #B44 (500 mg, 0.7 mmol, 1 eq.) and 4-nitrophenyl carbonate (638 mg, 2.1 mmol, 3 eq.) in N,N-dimethylformamide (3 mL, 0.2 M) was treated with N,N-diisopropylethylamine (365 µL, 2.1 mmol, 3 eq.). The reaction was stirred at room temperature overnight. The reaction mixture was concentrated in vacuo, absorbed onto SiO$_2$ and purified by silica gel chromatography (Gradient: 0 to 25% methanol in dichloromethane) to give #B45 as a solid. Yield: 402 mg, 0.476 mmol, 68%. LCMS (Protocol L): m z 880.7 [M+H]$^+$ retention time 3.39.

Step 3:

Synthesis of N-(6-{[(9H-fluoren-9-ylmethoxy)carbonyl]amino}hexanoyl)-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N~5~-carbamoyl-L-ornithinamide (#B46). The title compound was prepared in 10% yield from 71 mg (0.13 mmol) of #B6 and 171 mg (0.194 mmol) of #B45 using the procedure described for preparation of compound #B41. LCMS (Protocol D): m z 1290.5 [M+H]$^+$, retention time=0.91 minutes.

Step 4:

Synthesis of N-(6-aminohexanoyl)-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N~5~-carbamoyl-L-ornithinamide (#B47). To a solution of #B46 (19 mg, 0.015 mmol, 1 eq.) in N,N-dimethylformamide (0.35 mL) was added piperidine (25 mg, 0.3 mmol, 20 eq.) and the mixture was stirred at room temperature for 30 minutes. The reaction was diluted with dimethylsulfoxide (0.7 mL) and purified by reverse phase chromatography (Method A) to provide #B47 as a solid. Yield: 3 mg, 0.0028 mmol, 18%. HPLC (Protocol A$^A$) retention time=6.65, 6.69 minutes (purity=91%). LCMS (Protocol D): m/z 1069.9 [M+H]$^+$, retention time=0.61 minutes.

Example A17

Preparation of N-(6-aminohexanoyl)-L-valyl-N-[4-({[(2-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-N~5~-carbamoyl-L-ornithinamide (#B48)

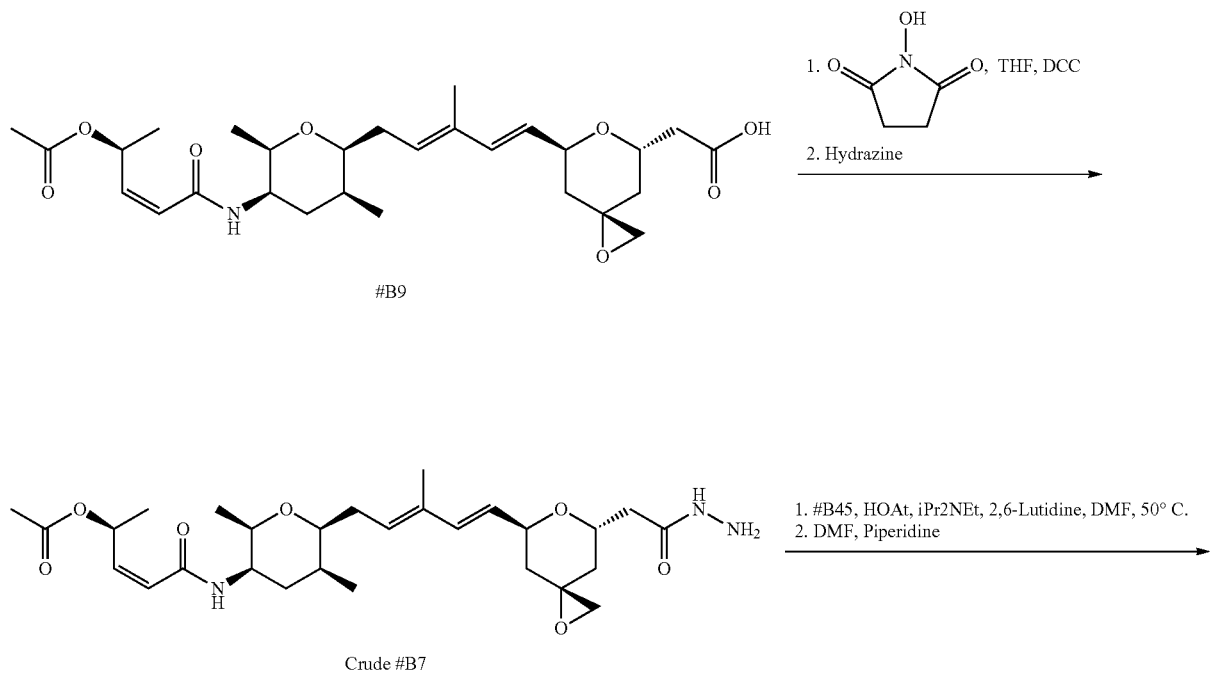

-continued

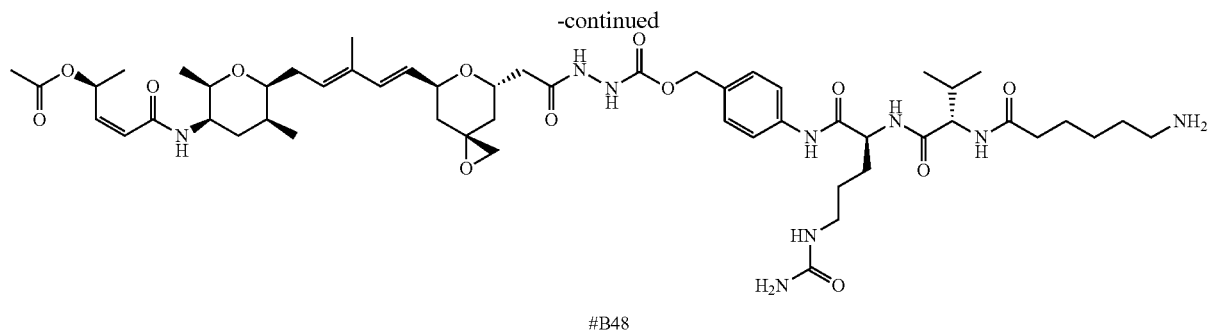

B48

Step 1:
Compound #B9 (113 mg, 0.217 mmol) was converted to crude #B7 as in general procedure E. LCMS (protocol D): m/z 534.1 [M+H]$^+$, retention time=0.77 min. The crude material was used in next step without further purification Step 2:
Synthesis of N-(6-aminohexanoyl)-L-valyl-N-[4-({[(2-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl]-1,6-dioxaspiro[2.5]oct-5-yl]acetyl}hydrazinyl)carbonyl]oxy}methyl)phenyl]-N~5~-carbamoyl-L-ornithinamide (#B48). To a solution of crude #B7 (60 mg, 0.11 mmol, 1 eq.) in N,N-dimethylformamide (2.8 mL) was added 2,6-dimethylpyridine (48 mg, 0.448 mmol, 4 eq.), N,N'-Diisopropylethylamine (57.9 mg, 0.448 mmol, 4 eq.) and HOAt (15.2 mg, 0.112 mmol, 1 eq.). The reaction was warmed to 50° C. and stirred for 1.5 hours. The reaction was cooled to room temperature and piperidine (191 mg, 2.24 mmol, 20 eq.) was added slowly and stirred for 2.0 hours. The reaction was concentrated in vacuo and purified by reverse phase chromatography (Method C) to yield #B48 as a solid. Yield 6.4 mg, 0.005 mmol, 5.2%. HPLC (Protocol F): m/z 1052.6 [M+H]$^+$, retention time=7.114 minutes (purity 100%).

Example A18

Preparation of (2S,3Z)-5-({(2R,3R,5S,6S)-6-[(2E,4E)-5-{(3R,4R,5R,7S)-4-hydroxy-7-[2-oxo-2-(3H-[1,2,3]triazolo[4,5-b]pyridin-3-yloxy)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B49)

Step 1.
Synthesis of (2S,3Z)-5-({(2R,3R,5S,6S)-6-[(2E,4E)-5-{(3R,4R,5R,7S)-4-hydroxy-7-[2-oxo-2-(3H-[1,2,3]triazolo[4,5-b]pyridin-3-yloxy)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B49). A mixture of #NP1 (1.5 g, ~50% purity, 2.8 mmol, 1.0 eq.), O-(7-azabenzotriazol-1-yl)-N,N,N'N'-tetramethyluronium hexafluorophosphate (HATU, 1.07 g, 4.5 mmol, 1.6 eq.), and N,N'-Diisopropylethylamine (Hunig's base, 1.0 mL) in N,N-dimethylformamide (7.0 mL) was stirred at ambient temperature for 40 minutes. The reaction mixture was filtered and then purified using reverse phase chromatography (Method F*) to afford #B49 as a white powder. Yield: 730.7 mg, 80% yield. HPLC (Protocol N): retention time=11.15 minutes (purity 92%). HRESIMS (Protocol O) m/z 654.313 [M+H]$^+$. $^1$H NMR (400 MHz, DMSO-d$_6$, mult, J in Hz) δ 8.84 (dd, J=4.4, 1.2, 1H), 8.74 (dd, J=8.3, 1.2, 1H), 7.77 (d, J=8.2, 1H, D$_2$O exchangeable), 7.66 (dd, J=8.3, 4.4, 1H), 6.45 (br d, J=15.8, 1H), 6.36 (ddq, J=1.5, 6.5, 6.5, 1H), 6.09 (dd, J=1.3, 11.7, 1H), 5.86 (dd, J=11.7, 7.4, 1H), 5.62 (dd, J=16.0, 5.0, 1H), 5.38 (br dd, J=7.4, 7.4, 1H), 5.18 (d, J=6.0, D$_2$O exchangeable), 4.48 (m, 1H), 4.37 (dd, J=4.0, 4.0, 1H), 3.61 (m, 1H), 3.54 (dq, 2.1, 6.5, 1H), 3.37 (ddd, J=6.9, 6.9, 3.1, 1H), 3.34 (m, 2H), 3.26 (dd, J=16.0, 9.7, 1 H), 2.21 (m, 1H), 2.14 (m, 1H), 2.10 (dd, J=12.7, 8.9, 1H), 1.99 (s, 3H), 1.74 (m, 2H), 1.68 (s, 3H), 1.59 (dd, J=13.0, 3.3, 1H), 1.50 (m, 1H), 1.25 (d, J=6.4, 3H), 0.95 (d, J=6.5, 3H), 0.86 (d, J=7.0, 3H).

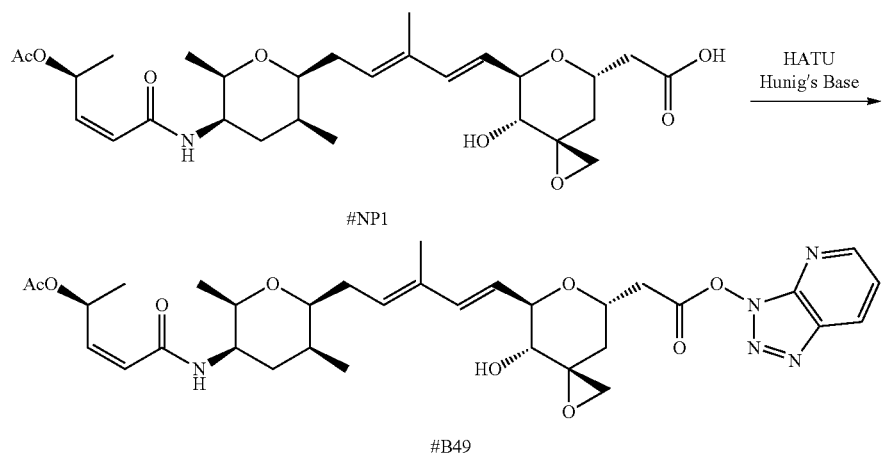

Example A19

Preparation of (2S,3Z)-5-({(2R,3R,5S,6S)-2,5-dimethyl-6-[(2E,4E)-3-methyl-{(3S,5S,7S)-7-[2-oxo-2-(3H-[[1,2,3]triazolo[4,5-b]pyridin-3-yloxy)ethyl]-1,6-dioxaspiro[2.5]oct-5-yl}penta-2,4-dien-1-yl]tetrahydro-2H-pyran-3-yl}amino)-5-oxopent-3-en-2-yl acetate (#B50)

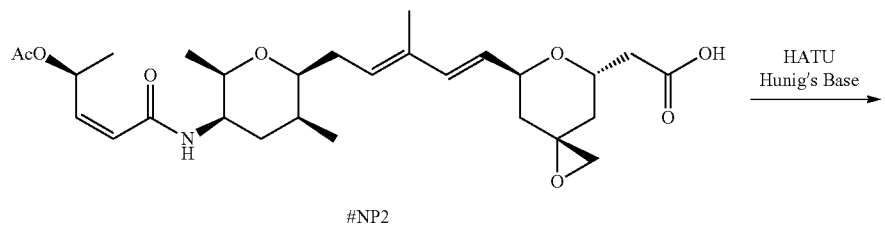

NP2

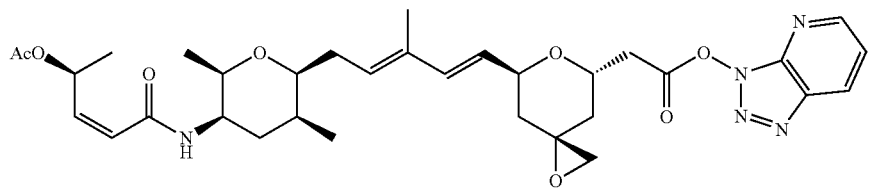

B50

Step 1.

Synthesis of (2S,3Z)-5-({(2R,3R,5S,6S)-2,5-dimethyl-6-[(2E,4E)-3-methyl-5-{(3 S,5S,7S)-7-[2-oxo-2-(3H-[1,2,3]triazolo[4,5-b]pyridin-3-yloxy)ethyl]-1,6-dioxaspiro[2.5]oct-5-yl}penta-2,4-dien-1-yl]tetrahydro-2H-pyran-3-yl}amino)-5-oxopent-3-en-2-yl acetate (#B50). A mixture of #NP2 (284 mg, 92% pure, 0.47 mmol, 1.0 eq), O-(7-azabenzotriazol-1-yl)-N,N,N',N'-tetramethyluronium hexafluorophosphate (HATU, 220 mg, 0.58 mmol, 1.2 eq) and N,N'-Diisopropylethylamine (Hunig's base, 0.1 mL) in N,N-dimethylformamide (2 mL) was stirred at ambient temperature for 60 minutes. The reaction mixture was filtered and then purified using reverse phase chromatography (Method F*) to afford #B50 as a white powder. Yield: 307.0 mg, 88% yield HPLC (Protocol N): retention time=13.12 minutes (purity 94%). HRESIMS (Protocol O) m/z 638.320 [M+H]+. 1H NMR (400 MHz, DMSO-d6, mult, J in Hz) δ 8.83 (dd, J=4.4, 1.2, 1H), 8.73 (dd, J=8.5, 1.2, 1H), 7.76 (d, J=8.1, 1H, D2O exchangeable), 7.66 (dd, J=8.5, 4.4, 1H), 6.39 (br d, J=15.8, 1H), 6.36 (ddq, J=1.5, 6.5, 6.5, 1H), 6.09 (dd, J=1.5, 11.7, 1H), 5.87 (dd, J=11.7, 7.5, 1H), 5.66 (dd, J=16.1, 4.9, 1H), 5.44 (br dd, J=7.1, 7.1, 1H), 4.71 (ddd, J=4.4, 4.4, 4.4, 1H), 4.51 (m, 1H), 3.63 (m, 1H), 3.57 (dq, J=2.3, 6.6, 1H), 3.41 (ddd, J=6.9, 6.9, 3.1, 1H), 3.36 (dd, J=16.0, 4.1, 1H), 3.33 (dd, J=16.1, 10.0, 1H), 2.74 (d, J=4.8, 1H), 2.70 (d, J=4.8, 1H), 2.24 (m, 1H), 2.15 (m, 1H), 1.98 (s, 3H), 1.85 (m, 1H), 1.83 (m, 1H), 1.70 (dd, J=13.0, 7.5, 1H), 1.66 (dd, J=13.5, 7.9, 1H), 1.52 (m, 1H), 1.25 (d, J=6.8, 3H), 1.00 (d, J=6.5, 3H), 0.89 (d, J=7.5, 3H).

Example A20

Preparation of (2S,3Z)-5-({(2R,3R,5S,6S)-6-[(2E,4E)-5-{(3R,4R,5R,7S)-4-hydroxy-7-[2-({2-[(iodoacetyl)amino]ethyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B52)

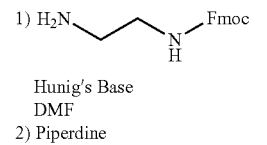

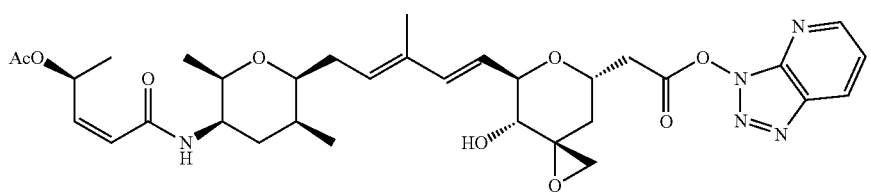

B49

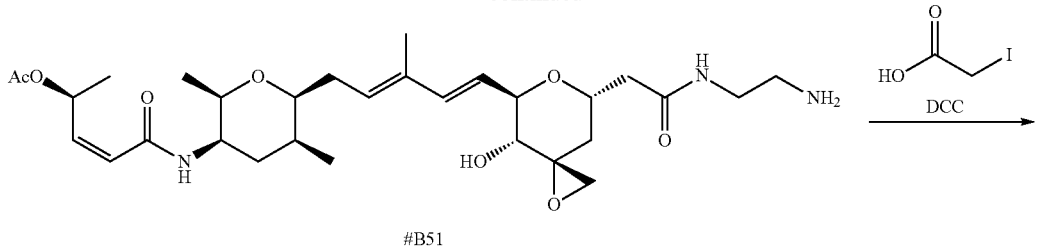

B51

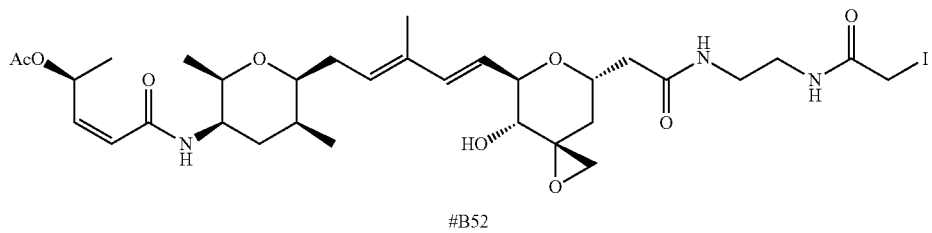

B52

Step 1:

Synthesis of (2S,3Z)-5-{[(2R,3R,5S,6S)-6-{(2E,4E)-5-[(3R,4R,5R,7S)-7-{2-[(2-aminoethyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B51). To a solution of #B49 (50.5 mg, 92% purity, 0.08 mmol, 1.0 eq.) and 9H-fluoren-9-ylmethyl (2-aminoethyl)carbamate (32.1 mg, 0.11 mmol, 1.4 eq.) in N,N-dimethylformamide (1.0 mL) was added N,N'-Diisopropylethylamine (Hunig's base, 20 μL) with stirring. The resulting mixture was then stirred at room temperature for 10 minutes. To the reaction solution was slowly added piperidine (30 μL, 0.35 mmol, 4.4 eq.) and the solution was stirred at ambient temperature for 1 hour. The reaction mixture was then purified using reverse phase chromatography (Method B*) to afford #B51 as a white powder. Yield: 38.8 mg, 86% yield HPLC (Protocol N): retention time=6.61 minutes (purity 97%). LCMS (Protocol M): m/z 578.8 [M+H]$^+$.

Step 2:

Synthesis of (2S,3Z)-5-({(2R,3R,5S,6S)-6-[(2E,4E)-5-{(3R,4R,5R,7S)-4-hydroxy-7-[2-({2-[(iodoacetyl)amino]ethyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B52). A solution of iodoacetic acid (40.3 mg, 0.22 mmol, 7.3 eq.) and N,N'-dicyclohexylcarbodiimide (DCC, 61.6 mg, 0.3 mmol, 10.0 eq.) in N,N-dimethylformamide (2.5 mL) was stirred at room temperature for 10 minutes and the light yellow solution was added to #B51 (21.1 mg, 85.0% purity, 0.031 mmol, 1.0 eq.) in N,N-dimethylformamide (0.2 mL). The resulting solution was stirred at room temperature for 20 minutes. The reaction mixture was then purified using reverse phase chromatography (Method B*) to afford #B52 as a white powder. Yield: 10.3 mg, 37% yield HPLC (Protocol N): retention time=8.96 minutes (purity 37%). LCMS (Protocol M): m/z 746.3 [M+H]$^+$. $^1$H NMR (400 MHz, DMSO-d$_6$, mult, J in Hz) δ 8.22 (m, 1H, D$_2$O exchangeable), 7.91 (m, 1H, D$_2$O exchangeable), 7.80 (d, J=7.8, 1H, D$_2$O exchangeable), 6.36 (dq, J=6.0, 6.0, 1H), 6.29 (br d, J=16.0, 1H), 6.11 (d, J=11.7, 1H), 5.86 (dd, J=11.7, 7.8, 1H), 5.60 (dd, J=16.0, 5.5, 1H), 5.51 (br dd, J=6.6, 6.6, 1H), 5.02 (d, J=5.0, D$_2$O exchangeable, 1H), 4.26 (m, 2H), 3.65 (m, 2H), 3.60 (s, 2H), 3.51 (br dd, J=6.2, 6.2, 1H), 3.24 (m, 1H), 3.08 (br s, 4H), 2.76 (d, J=5.1, 1H), 2.60 (d, J=5.1, 1H), 2.51 (m, 1H), 2.47 (m, 1H), 2.28 (m, 1H), 2.18 (m, 1H), 1.98 (s, 3H), 1.86 (m, 1H), 1.80 (m, 2H), 1.70 (s, 3H), 1.65 (m, 1H), 1.49 (dd, J=12.5, 2.7, 1H), 1.25 (d, J=6.6, 3H), 1.07 (d, J=6.5, 3H), 0.95 (d, J=7.0, 3H).

Example A21

Preparation of (2Z,4S)-4-hydroxy-N-{(2R,3R,5S,6S)-6-[(2E,4E)-5-{(3R,4R,5R,7S)-4-hydroxy-7-[2-({2-[(iodoacetyl)amino]ethyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}pent-2-enamide (#B54)

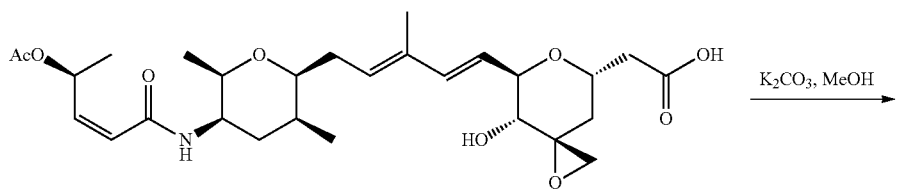

NP1

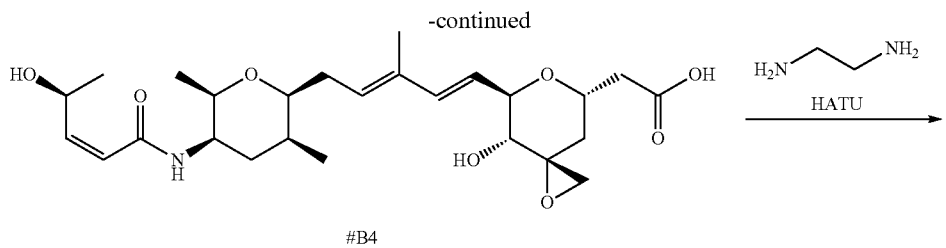

B4

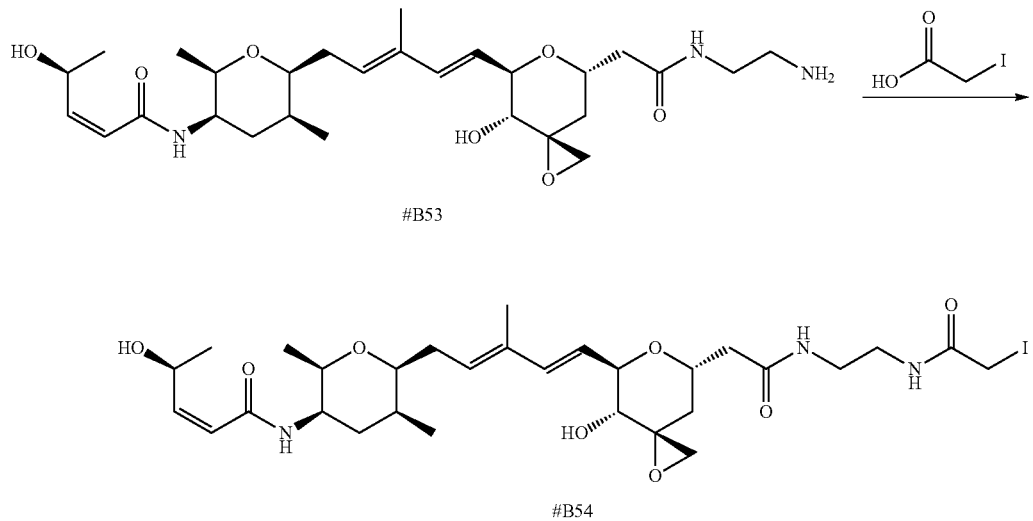

B53

B54

Step 1:

Synthesis of [(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetic acid (#B4). A mixture of #NP1 (192 mg, ~50% purity, 0.18 mmol, 1.0 eq.), potassium carbonate (300 mg, 2.4 mmol, 13.5 eq.), and methanol (5 mL) was stirred at room temperature for 2 hours. The reaction mixture was neutralized with acetic acid, filtered, and then purified using reverse phase chromatography (Method G) to afford #B4 as a white powder. Yield: 50.2 mg, HPLC (Protocol N): retention time=7.39 minutes (purity 96%). LCMS (Protocol M): m/z 494.3 [M+H]$^+$.

Step 2:

Synthesis of (2Z,4S)—N-[(2R,3R,5S,6S)-6-{(2E,4E)-5-[(3R,4R,5R,7S)-7-{2-[(2-aminoethyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B53). A solution of #B4 (23.4 mg, 0.047 mmol, 1.0 eq.), O-(7-Azabenzotriazol-1-yl)-N,N,N',N-tetramethyluronium hexafluorophosphate (HATU, 34.0 mg, 0.09 mmol, 2.0 eq.), and N,N'-Diisopropylethylamine (20.0 µL) in N,N-dimethylformamide (1.0 mL) was stirred at room temperature for 30 minutes. To this solution was added ethane-1,2-diamine (80 µl, 1.3 mmol, ~30 eq.) and the resulting solution was stirred for 1 hour. The reaction mixture was filtered and then purified using reverse phase chromatography (Method B*) to afford #B53 as a white powder. Yield: 31 mg. HPLC (Protocol N): retention time=5.58 minutes (purity 50%). LCMS (Protocol M): m z 536.4 [M+H]$^+$ Step 3:

Synthesis of (2Z,4S)-4-hydroxy-N-{(2R,3R,5S,6S)-6-[(2E,4E)-5-{(3R,4R,5R,7S)-4-hydroxy-7-[2-({2-[(iodoacetyl)amino]ethyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}pent-2-enamide (#B54). A solution of iodoacetic acid (35 mg, 0.18 mmol, 6 eq.) and N,N'-dicyclohexylcarbodiimide (DCC, 49.8 mg, 0.24 mmol, 8 eq.) in N,N-dimethylformamide (2 ml) was stirred at room temperature for 10 minutes and then added to #B53 (31.0 mg, ~50% purity, ~0.03 mmol, 1.0 eq.) in N,N-dimethylformamide (0.2 mL). The resulting solution was stirred at room temperature for 0.5 hour. The reaction mixture was purified using reverse phase chromatography (Method B*) to afford crude #B54 as a white powder (23.0 mg). This material was re-purified with a different gradient system, which afforded #B54 as a white powder. Yield: 15.9 mg, 27% yield, over three steps. HPLC (Protocol N): retention time=7.10 minutes (purity 92%). LCMS (Protocol M) m/z 704.2 [M+H]$^+$. $^1$H NMR (400 MHz, DMSO-d$_6$, mult, J in Hz) δ 8.22 (m, 1H, D$_2$O exchangeable), 7.91 (m, 1H, D$_2$O exchangeable), 7.77 (d, J=7.8, 1H, D$_2$O exchangeable), 6.28 (br d, J=16.0, 1H), 5.98 (d, J=11.7, 1H), 5.86 (dd, J=11.7, 7.0, 1H), 5.60 (dd, J=16.0, 5.5, 1H), 5.51 (br dd, J=6.6, 6.6, 1H), 5.16 (dq, J=6.2, 6.2, 1H), 5.11 (d, J=3.9, 1H, D$_2$O exchangeable), 5.03 (d, J=4.5, D$_2$O exchangeable, 1H), 4.26 (m, 2H), 3.65 (m, 2H), 3.60 (s, 2H), 3.51 (br dd, J=6.5, 6.5, 1H), 3.25 (m, 1H), 3.08 (br s, 4H), 2.75 (d, J=4.7, 1H), 2.60 (d, J=4.7, 1H), 2.51 (m, 1H), 2.47 (m, 1H), 2.27 (m, 1H), 2.22 (m, 1H), 1.86 (m, 1H), 1.80 (m, 2H), 1.70 (s, 3H), 1.65 (m, 1H), 1.49 (dd, J=12.5, 2.3, 1H), 1.11 (d, J=6.6, 3H), 1.07 (d, J=6.0, 3H), 0.95 (d, J=7.4, 3H).

Example A22

Preparation of methyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetate (#B55)

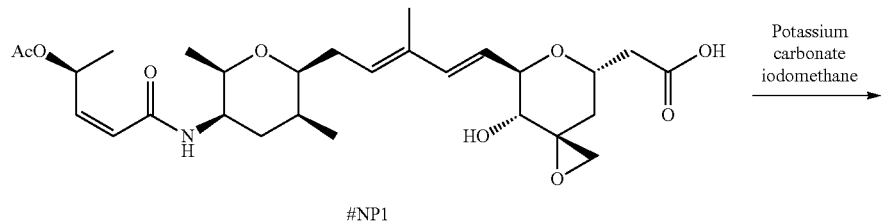

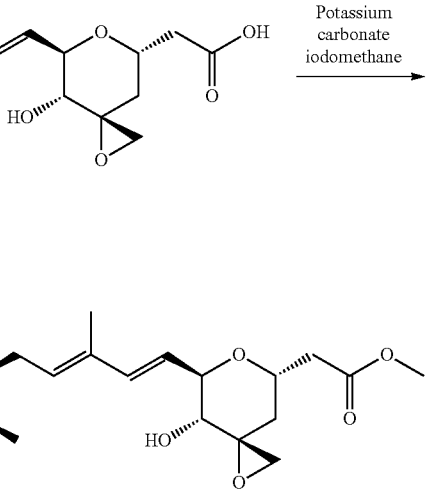

Step 1:

Synthesis of methyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetate (#B55). A mixture of #NP1 (9.9 mg, 92% purity, 0.018 mmol, 1.0 eq.), potassium carbonate (40 mg, 0.33 mmol, 18 eq.), and iodomethane (30 µL, 0.31 mmol, 17 eq.) in N,N-dimethylformamide (500 µL) was stirred at room temperature for 2 hours. The reaction mixture was neutralized with acetic acid, filtered, and then purified using reverse phase chromatography (Method B*) to afford #B55 as a white powder. Yield: 7.8 mg, 77% yield. HPLC (Protocol N): retention time=10.7 minutes (purity 94%). LCMS (Protocol M) m/z 550.5 [M+H]+. $^1$H NMR (400 MHz, DMSO-d$_6$, mult, J in Hz) δ 7.80 (d, J=8.1, 1H, D$_2$O exchangeable), 6.36 (ddq, J=1.2, 6.8, 6.8, 1H), 6.28 (br d, J=15.9, 1H), 6.11 (dd, J=1.2, 11.7, 1H), 5.87 (dd, J=11.7, 7.7, 1H), 5.58 (dd, J=16.1, 5.0, 1H), 5.52 (br dd, J=7.4, 7.4, 1H), 5.02 (d, J=5.8, D$_2$O exchangeable), 4.29 (m, 1H), 4.27 (dd, J=5.3, 5.3, 1H), 3.65 (m, 2H), 3.60 (s, 3H), 3.51 (ddd, J=7.0, 7.0, 2.5, 1H), 3.25 (dd, J=5.8, 5.3, 1H), 2.76 (d, J=5.0, 1H), 2.65 (dd, 15.4, 8.7, 1H), 2.58 (d, J=5.0, 1H), 2.57 (dd, J=15.4, 5.0), 2.30 (m, 1H), 2.21 (m, 1H), 1.98 (s, 3H), 1.86 (dd, J=13.2, 7.6, 1H), 1.69 (s, 3H), 1.66 (m, 1H), 1.53 (dd, 13.2, 3.9, 1H), 1.25 (d, J=6.1, 3H), 1.07 (d, J=6.4, 3H), 0.95 (d, J=7.4, 3H).

Example A23

Preparation of [(3R,5S,7R,8R)-7-{(1E,3E)-5-[(2S,3S,5R,6R)-3,6-dimethyl-5-({(2Z,4S)-4-[(piperidin-1-ylcarbonyl)oxy]pent-2-enoyl}amino)tetrahydro-2H-pyran-2-yl]-3-methylpenta-1,3-dien-1-yl}-8-hydroxy-1,6-dioxaspiro[2.5]oct-5-yl]acetic acid (#B60) and (2S,3Z)-5-({(2R,3R,5S,6S)-6-[(2E,4E)-5-{(3R,4R,5R,7S)-4-hydroxy-7-[2-({2-[(iodoacetyl)amino]ethyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl piperidine-1-carboxylate (#B62)

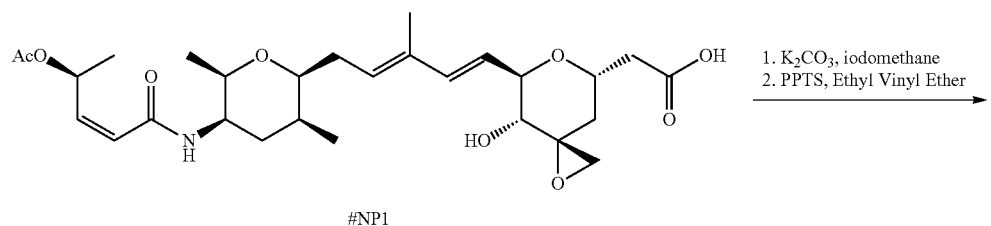

1. K$_2$CO$_3$, iodomethane
2. PPTS, Ethyl Vinyl Ether

-continued
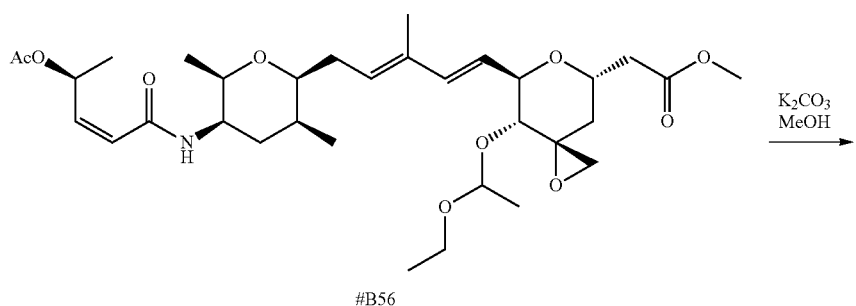
B56
K₂CO₃
MeOH
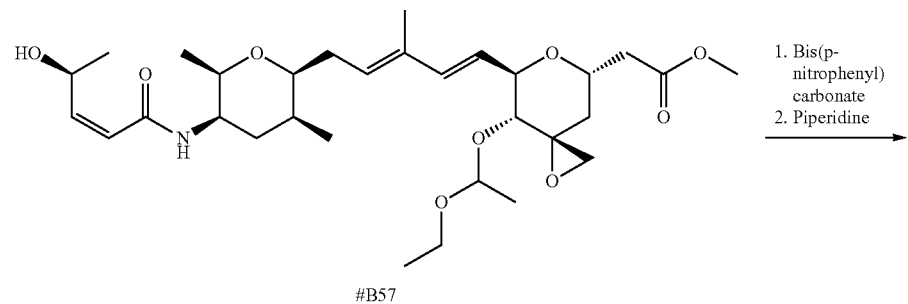
B57
1. Bis(p-nitrophenyl) carbonate
2. Piperidine
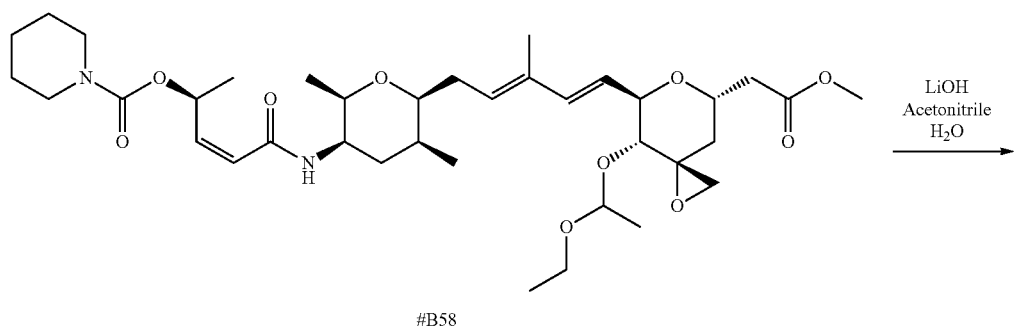
B58
LiOH
Acetonitrile
H₂O
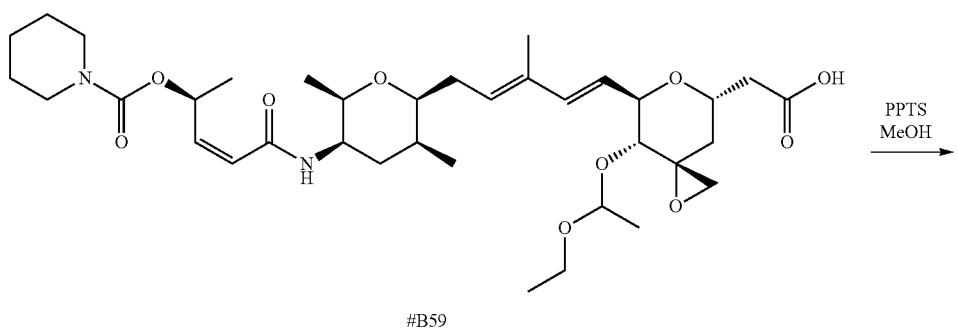
B59
PPTS
MeOH
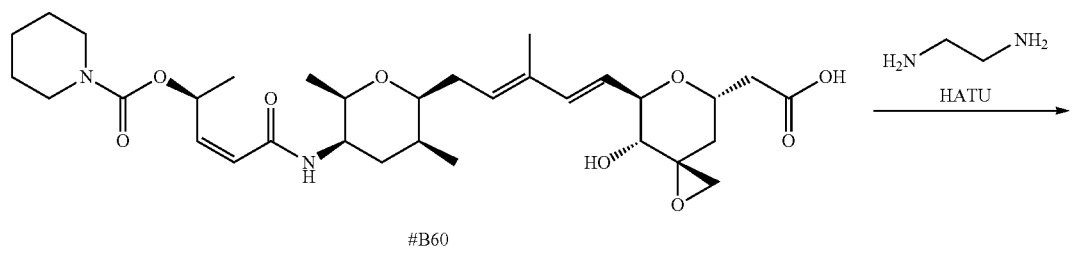
B60
H₂N—CH₂CH₂—NH₂
HATU -continued

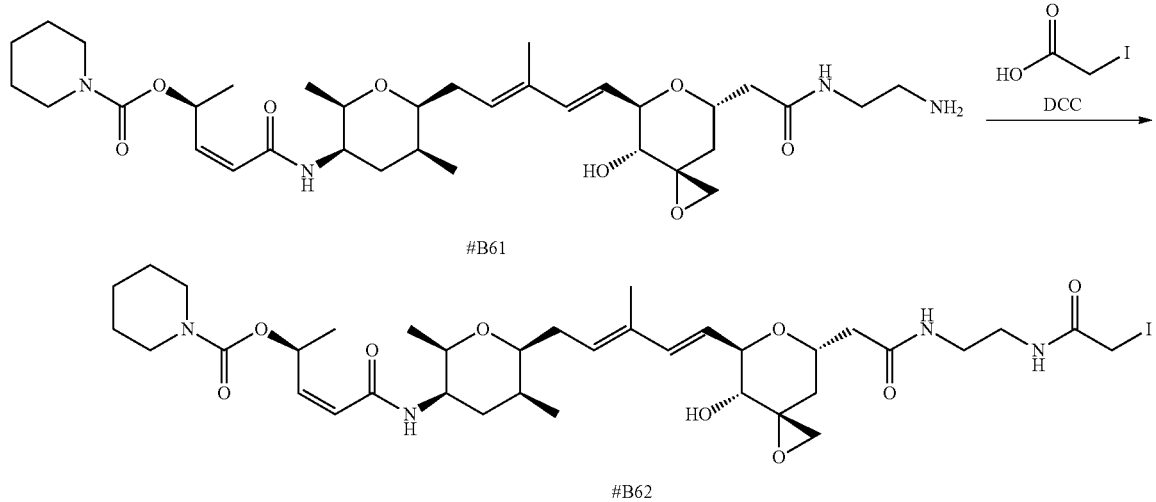

B61

B62

Step 1:

Synthesis of methyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-(1-ethoxyethoxy)-1,6-dioxaspiro[2.5]oct-5-yl] acetate (#B56). To a mixture of #NP1 (195 mg, ~50% purity, 0.18 mmol, 1.0 eq.) and potassium carbonate (200 mg, 1.6 mmol, 9 eq.) in N,N-dimethylformamide (4.0 mL) was added iodomethane (500 µL, 18 eq.). The resulting solution was stirred for 120 minutes. The reaction mixture was filtered and the filtrate partitioned between water and ethyl acetate (10 mL each phase). The organic layer was dried over anhydrous magnesium sulfate and evaporated under reduced pressure to afford #B55 as a film (191.2 mg, ~50% purity). Next, crude #B55 (191.0 mg, 0.18 mmol, 1.0 eq.) was mixed with pyridinium p-toluenesulfonate (PPTS, 56.1 mg, 0.22 mmol, 1.2 eq.), and ethyl vinyl ether (2.5 ml, 43 mmol) in anhydrous dichloromethane (2.0 ml) was stirred at room temperature for 1 hour. The reaction mixture was partially evaporated under reduced pressure and then partitioned between ethyl acetate (10 mL)/sodium bicarbonate aqueous solution (saturated, 10 mL). The organic layer was dried over anhydrous magnesium sulfate and then evaporated under reduced pressure to afford #B56 (187.1 mg) HPLC (Protocol N): retention time=13.2 minutes (purity 50%). LCMS (Protocol M): m/z 549.5 [M+H—CHCH$_3$OCH$_2$CH$_3$]$^+$. which was used as is in the next reaction.

Step 2:

Synthesis of methyl [(3R,5S,7R,8R)-8-(1-ethoxyethoxy)-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl] acetate (#B57). A suspension of #B56 (187.1 mg, ~50% purity, 0.15 mmol, 1.0 eq.), potassium carbonate (120 mg, 0.98 mmol, 6.5 eq.) in methanol (4 ml) was stirred at room temperature for 1 hour. The reaction mixture was then filtered and evaporated to dryness under reduced pressure to afford #B57 (171.5 mg) which was used as is in the next reaction. HPLC (Protocol N): retention time=9.9 minutes (purity 50%). LCMS (Protocol M): m/z 507.5 [M+H—CHCH$_3$OCH$_2$CH$_3$]$^+$.

Step 3:

Synthesis of (2S,3Z)-5-{[(2R,3R,5S,6S)-6-{(2E,4E)-5-[(3R,4R,5R,7S)-4-(1-ethoxyethoxy)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperidine-1-carboxylate (#B58). A solution of #B57 (171 mg, 50% purity, 0.15 mmol, 1.0 eq.), bis(p-nitrophenyl)carbonate (320.1 mg, 1.0 mmol, 7 eq.), 4-(dimethylamino)pyridine (9.8 mg, 0.08 mmol, 0.5 eq.), and N,N'-Diisopropylethylamine (Hunig's base, 150 µL) in dichloromethane (4.0 mL) was stirred at room temperature for 6 hours. To the reaction solution was slowly added piperidine (500 µL, 5.8 mmol, 38 eq.) and the resulting yellow solution was stirred at room temperature for 15 minutes. Ice cold water (20 mL) was added and the organic solvent was removed by evaporation under reduced pressure. The precipitate thus formed was collected by filtration and then dried under vacuum to afford #B58 (347.0 mg), which was used as is in the next reaction HPLC (Protocol N): retention time=13.20 minutes (purity 25%). LCMS (Protocol M): m/z 691.7 [M+H]$^+$.

Step 4:

Synthesis of [(3R,5S,7R,8R)-7-{(1E,3E)-5-[(2S,3S,5R,6R)-3,6-dimethyl-5-({(2Z,4S)-4-[(piperidin-1-ylcarbonyl)oxy]pent-2-enoyl}amino)tetrahydro-2H-pyran-2-yl]-3-methylpenta-1,3-dien-1-yl}-8-(1-ethoxyethoxy)-1,6-dioxaspiro[2.5]oct-5-yl]acetic acid (#B59). To a solution of #B58 (347 mg, ~25% purity, 0.13 mmol, 1.0 eq.) in acetonitrile (10 ml) was added 1M lithium hydroxide (1 mL) and water (1 mL). The resulting murky solution was stirred at room temperature for 1 hour and it gradually became clear. Additional 1M lithium hydroxide (1.0 mL) was added and the solution was further stirred for 2 hours. The reaction mixture was partitioned between n-butanol (30 mL) and water (30 mL). The top layer was washed with H$_2$O (20 mL), and then evaporated to dryness under reduced pressure to afford #B59 (280.2 mg) which was used as is in the next reaction HPLC (Protocol N): retention time=7.43 minutes (purity 30%). LCMS (Protocol M): m/z 677.4 [M+H]$^+$.

Step 5.

Synthesis of [(3R,5S,7R,8R)-7-{(1E,3E)-5-[(2S,3S,5R,6R)-3,6-dimethyl-5-({(2Z,4S)-4-[(piperidin-1-ylcarbonyl)oxy]pent-2-enoyl}amino)tetrahydro-2H-pyran-2-yl]-3-methylpenta-1,3-dien-1-yl}-8-hydroxy-1,6-dioxaspiro[2.5]oct-5-yl]acetic acid (#B60) A solution of #B59 (280.2 mg, ~30% purity, 0.12 mmol, 1.0 eq.) and pyridinium p-toluenesulfonate (PPTS, 250.4 mg, 1 mmol, 8.0 eq.) in methanol (5 mL) was stirred at room temperature for 4 hours and then allowed to stand at 4° C. for 18 hours. The reaction mixture was then purified using reverse phase chromatography (Method B*) to afford #B60 as a white powder. Yield: 78.4 mg, (40% yield, over steps 1-5) HPLC (Protocol N): retention time=10.84 minutes (purity 96.7%). LCMS (Protocol M): m/z 605.4 [M+H]$^+$.

Step 6.

Synthesis of (2S,3Z)-5-{[(2R,3R,5S,6S)-6-{(2E,4E)-5-[(3R,4R,5R,7S)-7-{2-[(2-aminoethyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperidine-1-carboxylate (#B61). A solution of #B60 (38.2 mg, 0.06 mmol, 1.0 eq.), O-(7-azabenzotriazol-1-yl)-N,N,N',N'-tetramethyluronium hexafluorophosphate (HATU, 40.1 mg, 0.1 mmol, 1.7 eq.), and N,N'-Diisopropylethylamine (Hunig's base, 20.0 μL) in N,N-dimethylformamide (1.0 mL) was stirred at room temperature for 20 minutes. To this solution was added 1,2-ethylenediamine (120 μL, 2 mmol, 33 eq.) and the resulting solution was stirred for 20 minutes. The reaction mixture was filtered and then purified using reverse phase chromatography (Method B*) to afford #B61 as a white powder. Yield: 14.2 mg, xx %) HPLC (Protocol N): retention time=7.86 minutes (purity 70%). LCMS (Protocol M): m/z 647.8 [M+H]$^+$.

Step 7.

Synthesis of (2S,3Z)-5-({(2R,3R,5S,6S)-6-[(2E,4E)-5-{(3R,4R,5R,7S)-4-hydroxy-7-[2-({2-[(iodoacetyl)amino]ethyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl piperidine-1-carboxylate (#B62). A solution of iodoacetic acid (20.3 mg, 0.1 mmol, 7 eq.) and N,N'-dicyclohexylcarbodiimide (DCC, 31.6 mg, 0.15 mmol, 10 eq.) in N,N-dimethylformamide (2 mL) was stirred at room temperature for 10 minutes and then added to a vial containing #B61 (14.0 mg, ~70% pure, 0.015 mmol, 1.0 eq.) in N,N-dimethylformamide (0.2 ml). The resulting solution was stirred at room temperature for 30 minutes. The reaction mixture was purified using reverse phase chromatography (Method B*) to afford #B62 as a white powder. Yield: 3.7 mg, (11%, over steps 6-7) HPLC (Protocol N): retention time=10.48 minutes (purity 94%). LCMS (Protocol M): m/z 815.4 [M+H]$^+$, 837.4 [M+Na]+.

$^1$H NMR (400 MHz, DMSO-d$_6$, mult, J in Hz) δ 8.22 (m, 1H, D$_2$O exchangeable), 7.91 (m, 1H, D$_2$O exchangeable), 7.78 (d, J=7.8, 1H, D$_2$O exchangeable), 6.29 (br d, J=16.1, 1H), 6.22 (dq, J=7.0, 7.0, 1H), 6.09 (d, J=11.7, 1H), 5.89 (dd, J=11.3, 7.4, 1H), 5.61 (dd, J=16.0, 5.1, 1H), 5.51 (br dd, J=6.2, 6.2, 1H), 5.03 (d, J=5.5, D$_2$O exchangeable), 4.26 (m, 2H), 3.65 (m, 2H), 3.60 (s, 2H), 3.51 (br dd, J=6.2, 6.2, 1H), 3.30 (m, 4H), 3.24 (dd, J=5.0, 5.0, 1H), 3.12-3.08 (m, 4H), 3.00 (d, 1H), 2.80 (s, 4H), 2.75 (d, J=5.1, 1H), 2.60 (d, J=5.1, 1H), 2.49 (m, 2H), 2.28 (m, 1H), 2.21 (m, 1H), 1.89 (dd, J=13.2, 8.6, 1H), 1.80 (m, 2H), 1.70 (s, 3H), 1.64 (m, 1H), 1.50 (dq, J=13.2, 3.1, 1H), 1.52 (m, 2H), 1.42 (m, 4H), 1.25 (d, J=6.2, 3H), 1.07 (d, J=6.0, 3H), 0.95 (d, J=7.4, 3H).

Example A24

Preparation of (2S,3Z)-5-({(2R,3R,5S,6S)-6-[(2E,4E)-5-{(3R,4R,5R,7S)-4-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B63)

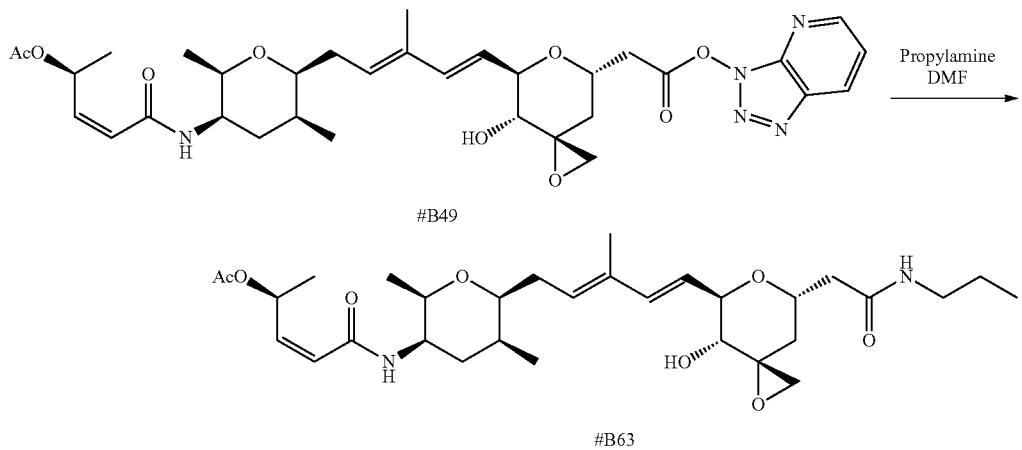

Step 1.

Synthesis of (2S,3Z)-5-({(2R,3R,5S,6S)-6-[(2E,4E)-5-{(3R,4R,5R,7S)-4-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B63). To a solution of #B49 (43.2 mg, 92.1% purity, 0.065 mmol, 1.0 eq.) in N,N-dimethylformamide (1.0 mL) was added neat propylamine (30 μL, 0.5 mmol, 7.0 eq.). The resulting solution was stirred for 10 minutes. The reaction mixture was partitioned between H$_2$O and ethyl acetate (10 ml each). The organic layer was dried over anhydrous magnesium sulfate and evaporated under reduced pressure to afford #B63 Yield: 40.4 mg, 100%. HPLC (Protocol N): retention time=9.73 minutes (purity 89%). HRESIMS (Protocol O) m/z 577.3478 [M+H]$^+$. $^1$H NMR (400 MHz, DMSO-d$_6$, mult, J in Hz) δ 7.83 (t, J=6.0, 1H, D$_2$O exchangeable), 7.81 (d, J=8.1, 1H, D$_2$O exchangeable), 6.36 (ddq, J=1.4, 6.5, 6.5, 1H), 6.28 (br d, J=15.9, 1H), 6.11 (dd, J=1.4, 11.7, 1H), 5.87 (dd, J=11.7, 7.5, 1H), 5.59 (dd, J=15.9, 5.4, 1H), 5.51 (br dd, J=7.1, 7.1, 1H), 5.02 (d, J=5.4, D$_2$O exchangeable), 4.26 (dd, J=5.0, 5.0, 1H), 4.24 (m, 1H), 3.65 (m, 1H), 3.64 (m, 1H), 3.49 (ddd, J=7.0, 7.0, 2.6, 1H), 3.24 (dd, J=5.0, 5.0, 1H), 3.01 (m, 1H), 2.96 (m, 1H), 2.75 (d, J=5.2, 1H), 2.58 (d, J=5.2, 1H), 2.52 (m, 1H), 2.29 (ddd, J=15.5, 7.1, 7.1, 1H), 2.21 (m, 1H), 2.20 (dd, J=14.0, 4.8, 1H), 1.98 (s, 3H), 1.83 (dd, J=13.4, 5.0, 1H), 1.80 (m, 2H), 1.69 (s, 3H), 1.65 (m, 1H), 1.48 (dd, 12.7, 3.9, 1H), 1.38 (dq, J=7.5, 7.5, 2H), 1.25 (d, J=6.6, 3H), 1.07 (d, J=6.8, 3H), 0.95 (d, J=7.5, 3H), 0.82 (t, J=7.5, 3H).

Example A25

Preparation of (2S,3Z)-5-({(2R,3R,5S,6S)-2,5-dimethyl-6-[(2E,4E)-3-methyl-5-{(3S,5S,7S)-7-[2-oxo-2-(propylamino)ethyl]-1,6-dioxaspiro[2.5]oct-5-yl}penta-2,4-dien-1-yl]tetrahydro-2H-pyran-3-yl}amino)-5-oxopent-3-en-2-yl acetate (#B64)

then purified using reverse phase chromatography (Method B*) to afford #B64 as a white powder. Yield: 34.1 mg, 86%. HPLC (Protocol N): retention time=13.11 minutes (purity 100%). LCMS (Protocol M): m/z 561.6 [M+H]$^+$. $^1$H NMR (400 MHz, DMSO-d$_6$, mult, J in Hz) δ 7.83 (t, J=6.0, 1H, D$_2$O exchangeable), 7.81 (d, J=8.0, 1H, D$_2$O exchangeable), 6.36 (ddq, J=1.6, 7.4, 6.6, 1H), 6.24 (br d, J=16.0, 1H), 6.10 (dd, J=1.6, 12.0, 1H), 5.87 (dd, J=11.8, 7.6, 1H), 5.58 (dd, J=15.9, 5.4, 1H), 5.50 (br dd, J=7.3, 7.3, 1H), 4.55 (ddd, J=5.3, 5.3, 5.3, 1H), 4.29 (dddd, J=9.5, 5.3, 5.3, 5.3, 1H), 3.65 (m, 1H), 3.64 (m, 1H), 3.48 (ddd, J=7.1, 7.1, 2.6, 1H), 3.01 (m, 1H), 2.96 (m, 1H), 2.63 (d, J=5.0, 1H), 2.61 (d, J=5.0, 1H), 2.59 (dd, J=14.2, 8.8, 1H), 2.31 (ddd, J=16.1, 7.5, 7.0, 1H), 2.21 (dd, J=14.1, 5.0, 1H), 2.19 (m, 1H), 1.96

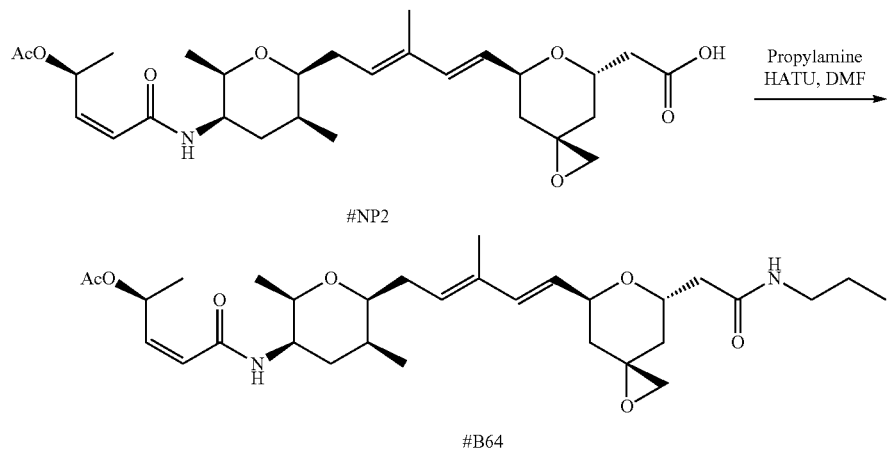

NP2

B64

Step 1:

Synthesis of (2S,3Z)-5-({(2R,3R,5S,6S)-2,5-dimethyl-6-[(2E,4E)-3-methyl-5-{(3S,5S,7S)-7-[2-oxo-2-(propylamino)ethyl]-1,6-dioxaspiro[2.5]oct-5-yl}penta-2,4-dien-1-yl]tetrahydro-2H-pyran-3-yl}amino)-5-oxopent-3-en-2-yl acetate (#B64). A solution of #NP2 (28.7 mg, 91% purity, 0.055 mmol, 1.0 eq.), O-(7-azabenzotriazol-1-yl)-N,N,N',N'-tetramethyluronium hexafluorophosphate (HATU, 24.8 mg, 0.065 mmol, 1.2 eq.), and N,N'-Diisopropylethylamine (Hunig's base, 30 µL) in N,N-dimethylformamide (0.5 mL) was stirred at room temperature for 30 minutes. To this solution was added neat propylamine (30 µL, 0.5 mmol, 7.0 eq.) and the resulting reaction mixture was stirred at room temperature for 1 hour. The reaction mixture was filtered and (s, 3H), 1.81 (m, 1H), 1.79 (m, 1H), 1.77 (dd, J=13.0, 4.0, 1H), 1.69 (s, 3H), 1.66 (m, 2H), 1.37 (dq, J=7.5, 7.5, 2H), 1.36 (m, 1H), 1.25 (d, J=6.6, 3H), 1.07 (d, J=6.8, 3H), 0.95 (d, J=7.5, 3H), 0.82 (t, J=7.5, 3H).

Example A26

Preparation of (2S,3Z)-5-({(2R,3R,5S,6S)-6-[(2E,4E)-5-{(3R,4R,5R,7S)-4-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl piperidine-1-carboxylate (#B66)

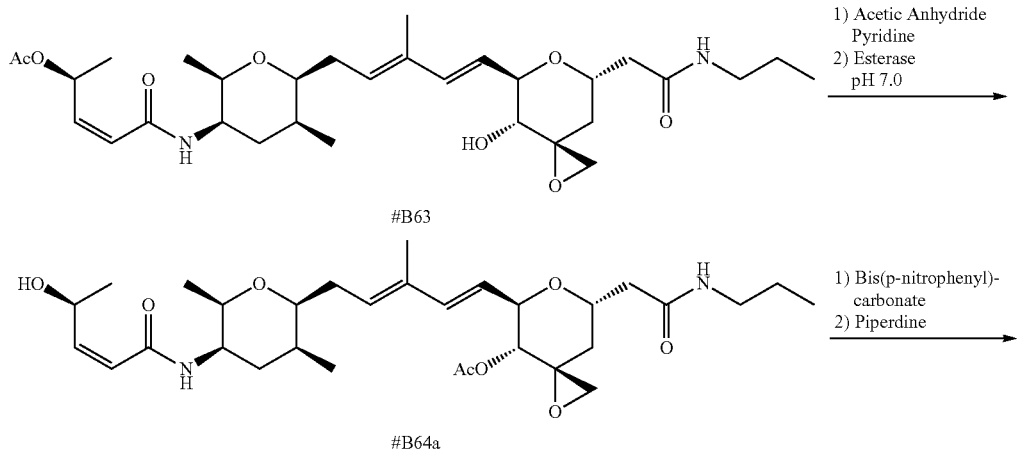

B63

B64a

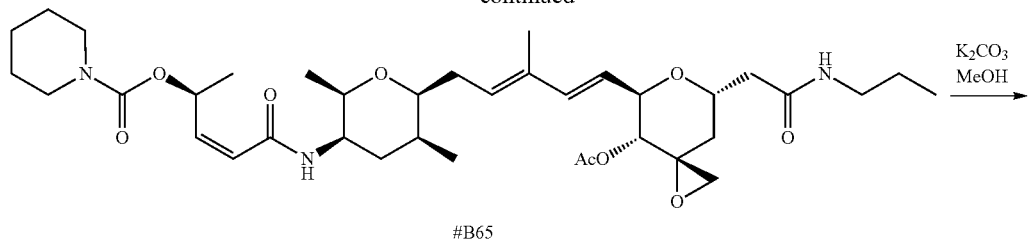

B65

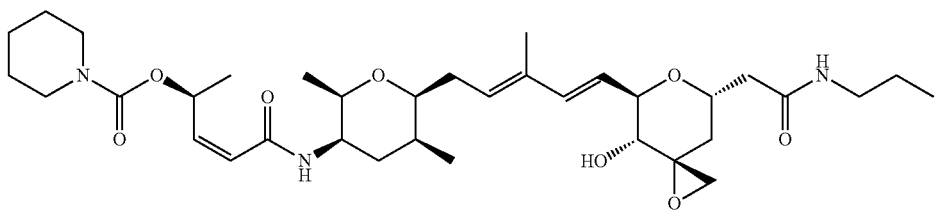

B66

Step 1:

Synthesis of (3R,4R,5R,7S)-5-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-7-[2-oxo-2-(propylamino)ethyl]-1,6-dioxaspiro[2.5]oct-4-yl acetate (#B64a). To a solution of #B63 (44.0 mg, ~90% purity, 0.076 mmol, 1.0 eq.) in pyridine (0.5 mL) was added acetic anhydride (150 μL, 1.6 mmol, 21.0 eq.)). The resulting mixture was then stirred at room temperature for 3 hours. The reaction mixture was transferred to ice cold water (10 mL), stirred for 20 minutes, and then partitioned between ethyl acetate (30 mL) and water (30 mL). The organic layer was washed with water (3×20 mL) and evaporated to dryness. The residue was dissolved in dimethyl sulfoxide (150 μL) and the solution was slowly added to 1M Tris buffer solution (pH 7.0) that contained an esterase produced by *Bucillus stearothermorphillus* (Sigma 69509, 0.5 mg/mL, 15 mL total). The reaction was stirred for one hour and then partitioned between ethyl acetate (2×20 mL) and water (20 mL). The combined organic layers were washed with water (2×20 mL) and then evaporated under reduced pressure to afford #B64a as an off-white powder Yield: 44.9 mg, (assume quantitative) HPLC (Protocol N): retention time=9.51 minutes (purity 88%). LCMS (Protocol M): m/z 577.6 [M+H]⁺.

Step 2:

Synthesis of (2S,3Z)-5-({(2R,3R,5S,6S)-6-[(2E,4E)-5-{(3R,4R,5R,7S)-4-(acetyloxy)-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl piperidine-1-carboxylate (#B65). A solution of #B64a (14.7 mg, 0.025 mmol, 1.0 eq.), bis(p-nitrophenyl)carbonate (38.4 mg, 0.13 mmol, 5 eq.), p-dimethylaminopyridine (1.6 mg, 0.013 mmol, 0.5 eq.), and N,N'-Diisopropylethylamine (Hunig's base, 30 μL) in dichloromethane (1 mL) was stirred at room temperature for 16 hours. To this reaction solution was slowly added piperidine (60 μL, 0.7 mmol, 28 eq.) and the solution was stirred at room temperature for 15 minutes. Ice cold water (10 mL) was added and the organic solvent was removed by evaporation under reduced pressure. The precipitate was collected by filtration, washed with water, and then evaporated under reduced pressure to afford #B65. Yield 26.2 mg, (assume quantitative) HPLC (Protocol N): retention time=13.1 minutes (purity 45%). LCMS (Protocol M): m/z 688.5 [M+H]⁺, Step 3.

Synthesis of (2S,3Z)-5-({(2R,3R,5S,6S)-6-[(2E,4E)-5-{(3R,4R,5R,7S)-4-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl piperidine-1-carboxylate (#B66). A solution of #B65 (26.1 mg, ~45% purity, 0.017 mmol, 1.0 eq.), potassium carbonate (51 mg, 0.41 mmol, 24 eq.) in methanol (1.5 mL) was stirred at room temperature for 1 hour. The reaction mixture was filtered and the filtrate partitioned between ethyl acetate and water (10 mL each phase). The organic layer was dried over anhydrous magnesium sulfate and evaporated under reduced pressure to dryness, which was then purified using reverse phase chromatography (Method B*) to afford #B66 as a white powder. Yield: 7.3 mg, (44% over steps 1-3). HPLC (Protocol N): retention time=11.44 minutes (purity 96.7%). LCMS (Protocol M): m/z 646.4 [M+H]⁺. ¹H NMR (400 MHz, DMSO-d₆, mult, J in Hz) δ 7.83 (t, J=5.6, 1H, D₂O exchangeable), 7.79 (d, J=8.0, 1H, D₂O exchangeable), 6.28 (br d, J=16.1, 1H), 6.22 (ddq, J=1.4, 6.8, 6.8, 1H), 6.08 (dd, J=1.4, 11.8, 1H), 5.88 (dd, J=11.7, 7.4, 1H), 5.59 (dd, J=15.7, 5.3, 1H), 5.51 (br dd, J=7.0, 7.0, 1H), 5.02 (d, J=5.3, D₂O exchangeable), 4.27 (dd, J=5.0, 5.0, 1H), 4.23 (m, 1H), 3.65 (m, 1H), 3.64 (m, 1H), 3.49 (ddd, J=7.0, 7.0, 2.6, 1H), 3.30 (m, 4H), 3.24 (dd, J=5.0, 5.0, 1H), 3.01 (m, 1H), 2.96 (m, 1H), 2.75 (d, J=5.2, 1H), 2.58 (d, J=5.2, 1H), 2.51 (m, 1H), 2.29 (m, 1H), 2.22 (m, 1H), 2.20 (dd, J=14.0, 4.8, 1H), 1.82 (dd, J=13.3, 8.2, 1H), 1.79 (m, 2H), 1.69 (s, 3H), 1.65 (m, 1H), 1.51 (m, 2H), 1.49 (dd, 13.3, 5.0, 1H), 1.42 (m, 4H), 1.38 (dq, J=7.5, 7.5, 2H), 1.25 (d, J=6.5, 3H), 1.07 (d, J=6.4, 3H), 0.95 (d, J=7.4, 3H), 0.82 (t, J=7.5, 3H).

Example A27

Preparation of (2S,3Z)-5-{[(2R,3R,5S,6S)-6-{(2E,4E)-5-[(3R,4R,5R,7S)-7-{2-[(2,5-dioxopyrrolidin-1-yl)oxy]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-ylpiperidine-1-carboxylate (#B67). and 2S,3Z)-5-({(2R,3R,5S,6S)-6-[(2E,4E)-5-{(3R,4R,5R,7S)-4-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl piperidine-1-carboxylate (#B67)

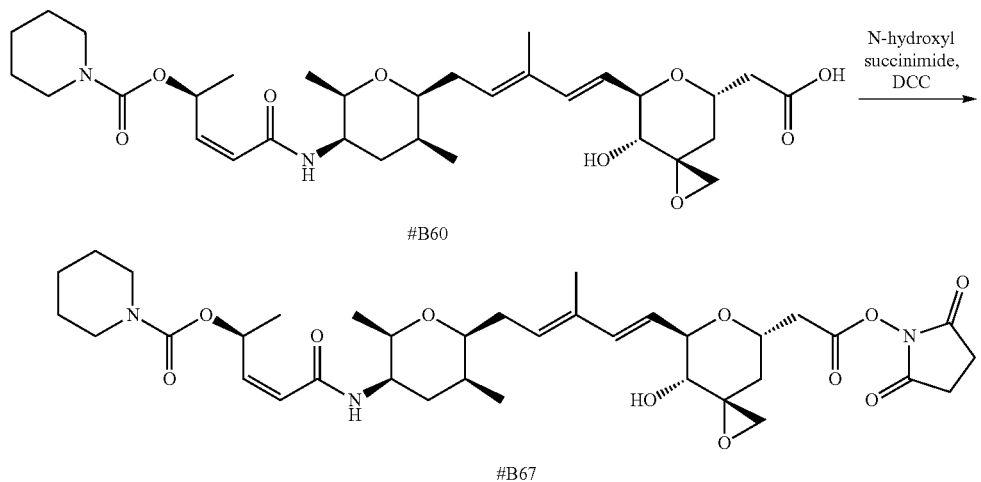

Step 1.

Synthesis of (2S,3Z)-5-{[(2R,3R,5S,6S)-6-{(2E,4E)-5-[(3R,4R,5R,7S)-7-{2-[(2,5-dioxopyrrolidin-1-yl)oxy]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-ylpiperidine-1-carboxylate (#B67). A mixture of #B60 (Example A23, 23.0 mg, 96.7% purity, 0.038 mmol, 1.0 eq.) and N,N'-dicyclohexylcarbodiimide (DCC, 13.1 mg, 0.06 mmol, 1.7 eq.) in N,N-dimethylformamide (0.8 mL) was stirred at room temperature for 20 minutes. To this solution was added N-hydroxyl succinimide (34.5 mg, 0.3 mmol, 7.7 eq.) in N,N-dimethylformamide (0.2 ml). The resulting solution was stirred at room temperature for 16 hours. The reaction mixture was filtered and then purified using reverse phase chromatography (Method B*) to afford #B67 as a white powder. Yield: 9.4 mg, 39%. HPLC (Protocol N): retention time=11.04 minutes (purity 100%). $^1$H NMR (400 MHz, DMSO-$d_6$, mult, J in Hz) δ 7.78 (d, J=8.0, 1H, $D_2O$ exchangeable), 6.35 (br d, J=16.1, 1H), 6.22 (dq, J=7.0, 7.0, 1H), 6.08 (d, J=11.7, 1H), 5.89 (dd, J=11.7, 7.4, 1H), 5.60 (dd, J=16.0, 5.1, 1H), 5.52 (br dd, J=7.0, 7.0, 1H), 5.08 (d, J=6.2, $D_2O$ exchangeable), 4.29 (m, 2H), 3.65 (m, 2H), 3.49 (br dd, J=7.0, 7.0, 1H), 3.29 (m, 5H), 3.00 (d, J=6.6, 2H), 2.80 (s, 4H), 2.79 (d, J=5.2, 1H), 2.60 (d, J=5.2, 1H), 2.28 (m, 1H), 2.21 (m, 1H), 1.95 (dd, J=13.2, 8.6, 1H), 1.81 (m, 2H), 1.69 (s, 3H), 1.64 (m, 1H), 1.58 (dq, J=13.2, 3.1, 1H), 1.52 (m, 2H), 1.43 (m, 4H), 1.25 (d, J=6.2, 3H), 1.07 (d, J=6.2, 3H), 0.95 (d, J=7.0, 3H).

Example A28

Preparation of (2S,3Z)-5-({(2R,3R,5S,6S)-6-[(2E,4E)-5-{(3R,4R,5R,7S)-4-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl 2-methylpropanoate (#B71)

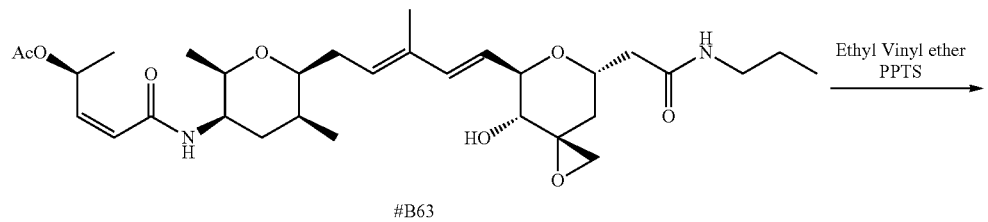

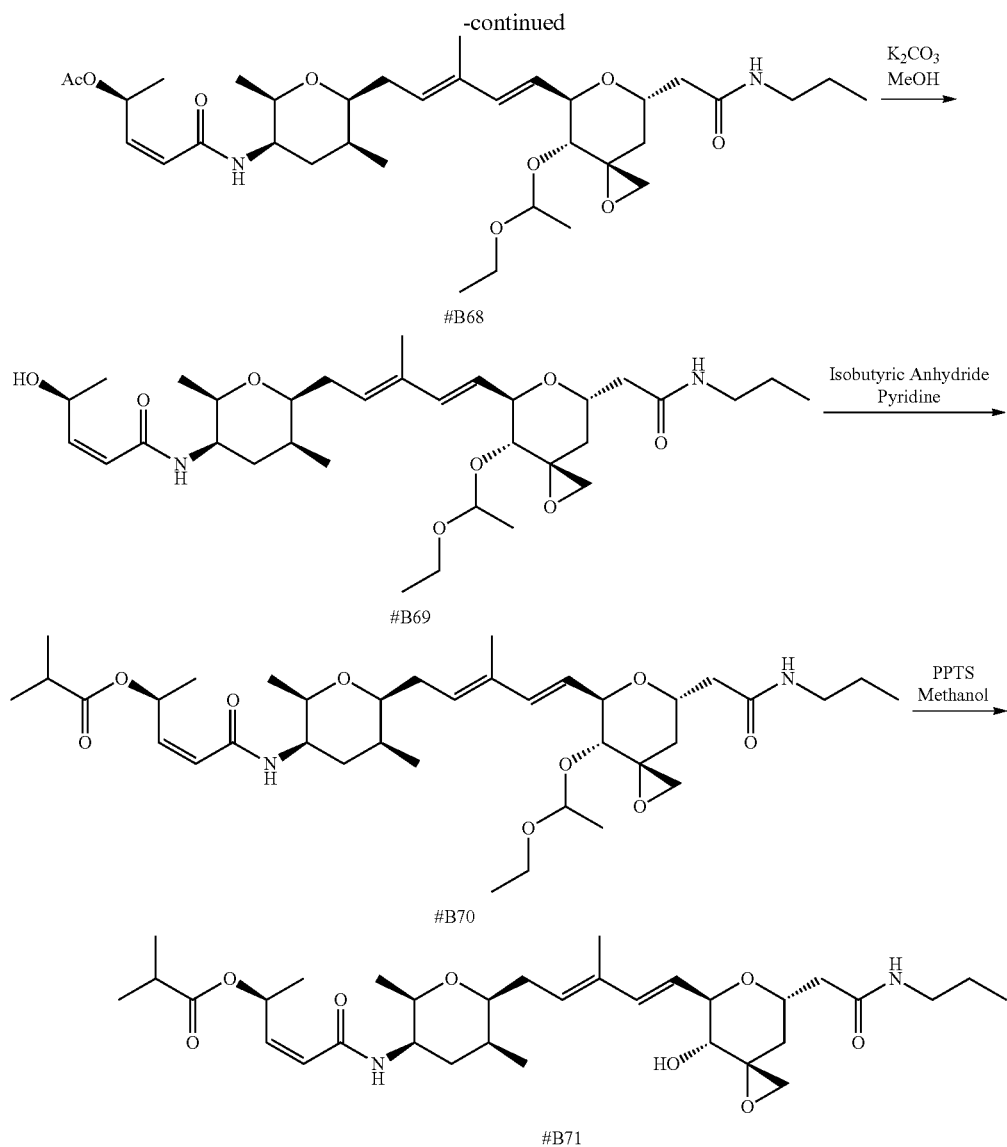

Step 1.

Synthesis of (2S,3Z)-5-({(2R,3R,5S,6S)-6-[(2E,4E)-5-{(3R,4R,5R,7S)-4-(1-ethoxyethoxy)-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B68). A solution of #B63 (Example A24, 35.0 mg, 92% purity, 0.06 mmol, 1.0 eq.), pyridinium p-toluenesulfonate (PPTS, 7.1 mg, 0.028 mmol, 0.4 eq.), and ethyl vinyl ether (0.5 mL, 8.6 mmol, large excess amount) in anhydrous dichloromethane (1.0 mL) was stirred at room temperature for 2 hours. The reaction mixture was partitioned between dichloromethane (10 mL)/water (10 mL). The organic layer was dried over anhydrous magnesium sulfate and then evaporated under reduced pressure to afford #B68. Yield: 36.1 mg, HPLC (Protocol N): retention time=12.33 minutes (purity 90%). LCMS (Protocol M): m/z 577.6 [M+H—CHCH₃OCH₂CH₃]⁺.

Step 2.

Synthesis of (2Z,4S)—N-{(2R,3R,5S,6S)-6-[(2E,4E)-5-{(3R,4R,5R,7S)-4-(1-ethoxyethoxy)-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}-4-hydroxypent-2-enamide (#B69). A suspension of #B68 (36.1 mg, 0.05 mmol, 1.0 eq.) and potassium carbonate (50 mg, 0.4 mmol, 8 eq.) in methanol (1.0 mL) was stirred at room temperature for 1 hour. The reaction mixture was then filtered and evaporated to dryness under reduced pressure to afford #B69. Yield: 33.4 mg. HPLC (Protocol N): retention time=10.458 and 10.459 minutes (purity 87.6%). LCMS (Protocol M): m/z 535.5 [M+H-CHCH₃OCH₂CH₃]⁺.

Step 3.

Synthesis of (2S,3Z)-5-({(2R,3R,5S,6S)-6-[(2E,4E)-5-{(3R,4R,5R,7S)-4-(1-ethoxyethoxy)-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl 2-methylpropanoate (#B70). A solution of #B69 (33.0 mg, 0.049 mmol, 1.0 eq.) and isobutyric anhydride (100 µL, 0.75 mmol, 15 eq.) in pyridine (500 µL) was stirred at 35° C. for 24 hours. The reaction mixture was then evaporated under reduced pressure to afforded #B70. Yield: 37.3 mg, HPLC (Protocol N):

retention time=14.06 (purity 88.3%). LCMS (Protocol M): m/z 605.6 [M+H-CHCH$_3$OCH$_2$CH$_3$]$^+$, Step 4.

Synthesis of (2S,3Z)-5-({(2R,3R,5S,6S)-6-[(2E,4E)-5-{(3R,4R,5R,7S)-4-hydroxy-7-[2-oxo-2-(propylamino) ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl 2-methylpropanoate (#B71). A solution of #B70 (17.8 mg, 0.023 mmol, 1.0 eq.), pyridinium p-toluenesulfonate (60 mg, 0.24 mmol, 10 eq.) in anhydrous methanol (2.0 ml) was stirred at room temperature for 60 minutes. The reaction mixture was then purified using reverse phase chromatography (Method B*) to afford #B71 as a white powder. Yield: 8 mg, (50% over steps 1-4). HPLC (Protocol N): retention time=11.50 minutes (purity 100%). HRESIMS (Protocol O) m/z 605.3798 (M+H)+. 1H NMR (400 MHz, DMSO-d6, mult, J in Hz) δ 7.83 (t, J=6.0, 1H, D2O exchangeable), 7.81 (d, J=8.1, 1H, D2O exchangeable), 6.35 (ddq, J=1.3, 6.5, 6.5, 1H), 6.28 (br d, J=15.9, 1H), 6.12 (dd, J=1.3, 11.7, 1H), 5.86 (dd, J=11.7, 7.5, 1H), 5.59 (dd, J=15.9, 5.4, 1H), 5.51 (br dd, J=7.1, 7.1, 1H), 5.02 (d, J=5.4, D2O exchangeable), 4.26 (dd, J=5.0, 5.0, 1H), 4.24 (m, 1H), 3.65 (m, 1H), 3.64 (m, 1H), 3.49 (ddd, J=7.0, 7.0, 2.6, 1H), 3.24 (dd, J=5.0, 5.0, 1H), 3.01 (m, 1H), 2.96 (m, 1H), 2.75 (d, J=5.2, 1H), 2.58 (d, J=5.2, 1H), 2.52 (m, 1H), 2.48 (sept, J=6.5, 1H), 2.29 (ddd, J=15.5, 7.1, 7.1, 1H), 2.21 (m, 1H), 2.20 (dd, J=14.0, 4.8, 1H), 1.83 (dd, J=13.4, 5.0, 1H), 1.80 (m, 2H), 1.69 (s, 3H), 1.65 (m, 1H), 1.48 (dd, 12.7, 3.9, 1H), 1.38 (dq, J=7.5, 7.5, 2H), 1.25 (d, J=6.6, 3H), 1.07 (d, J=6.8, 9H), 0.95 (d, J=7.5, 3H), 0.82 (t, J=7.5, 3H).

Example A29

Preparation of (2S,3Z)-5-({(2R,3R,5S,6S)-6-[(2E,4E)-5-{(3R,4R,5R,7S)-4-hydroxy-7-[2-oxo-2-(piperidin-1-yl)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B72)

Step 1:

Synthesis of (2S,3Z)-5-({(2R,3R,5S,6S)-6-[(2E,4E)-5-{(3R,4R,5R,7S)-4-hydroxy-7-[2-oxo-2-(piperidin-1-yl) ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B72). A mixture of #NP1 (163.0 mg, 92% purity, 0.27 mmol, 1.0 eq.), 1-hydroxybenzotriazole hydrate (HOBT, 160.0 mg, 1 mmol, 4 eq.), and 1-ethyl-3-(3-dimethylaminopropyl) carbodiimide-HCl (EDC, 195.0 mg, 1 mol, 4 eq.) in N,N-dimethylformamide (4.0 mL) was stirred at 0° C. for 30 min. To this solution were subsequently added triethylamine (50 µL) and piperidine (180 µL, 2.1 mmol, 7.5 eq.) at 0° C. The resulting reaction mixture was stirred at room temperature for 3 hours and at 0° C. for 16 hours. The reaction mixture was then partitioned between ethyl acetate (2×20 mL) and water (20 mL). The combined organic layer was washed with water (2×10 mL), dried over anhydrous magnesium sulfate, and then evaporated under reduced pressure to afford crude #B72 as an off-white glass (223.5 mg, 79.5% purity). A portion of this material (33.1 mg) was purified using reverse phase chromatography (Method B*) to afford #B72 as a white powder. Yield: 27.4 mg, 100% HPLC (Protocol N): retention time=10.58 minutes (purity 98%). LCMS (Protocol M): m/z 603.7 [M+H]$^+$. $^1$H NMR (400 MHz, DMSO-d$_6$, mult, J in Hz) δ 7.80 (d, J=7.8, 1H, D$_2$O exchangeable), 6.36 (dq, J=6.0, 6.0, 1H), 6.31 (br d, J=16.0, 1H), 6.11 (d, J=11.7, 1H), 5.87 (dd, J=11.7, 7.8, 1H), 5.60 (dd, J=16.0, 5.5, 1H), 5.52 (br dd, J=7.0, 7.0, 1H), 4.98 (d, J=5.8, 1H, D$_2$O exchangeable), 4.25 (m, 2H), 3.65 (m, 2H), 3.49 (br dd, J=6.2, 6.2, 1H), 3.40 (m, 4H), 3.25 (dd, 5.8, 5.1, 1H), 3.08 (br s, 4H), 2.76 (d, J=5.1, 1H), 2.68 (dd, J=15.2, 7.0, 1H), 2.58 (d, J=5.1, 1H), 2.50 (m, 1H), 2.29 (m, 1H), 2.20 (m, 1H), 1.98 (s, 3H), 1.86 (m, 1H), 1.80 (m, 2H), 1.70 (s, 3H), 1.65 (m, 1H), 1.56 (m, 3H), 1.48 (m, 2H), 1.40 (m, 2H), 1.25 (d, J=6.2, 3H), 1.07 (d, J=6.2, 3H), 0.95 (d, J=7.0, 3H).

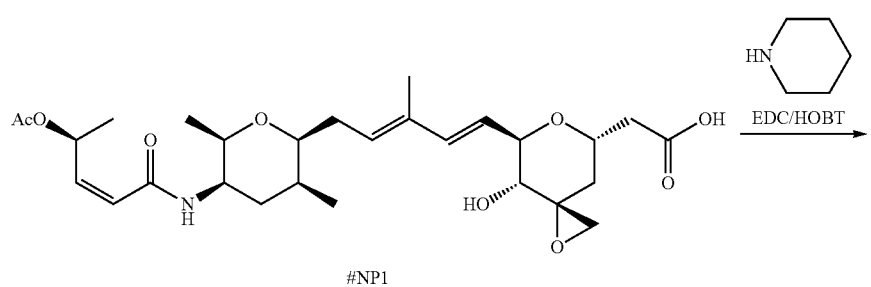

NP1

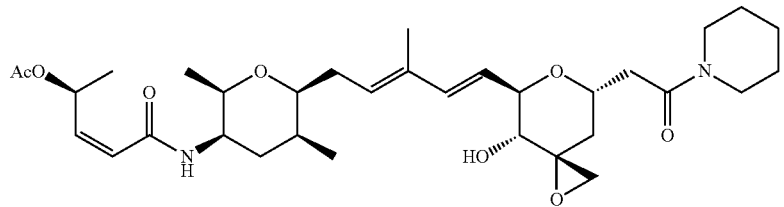

B72

Example A30

Preparation of (2S,3Z)-5-{[(2R,3R,5S,6S)-6-{(2E,4E)-5-[(3R,4R,5R,7S)-7-{2-[(trans-3-aminocyclobutyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B73)

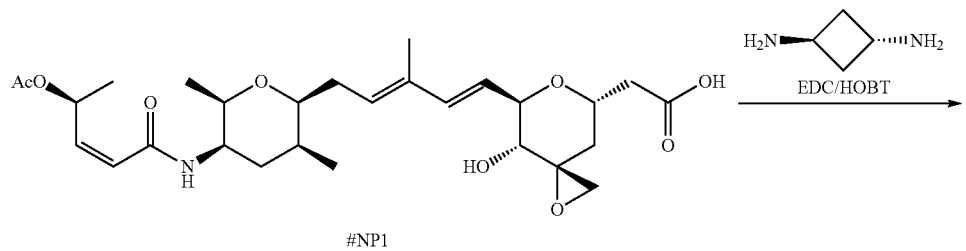

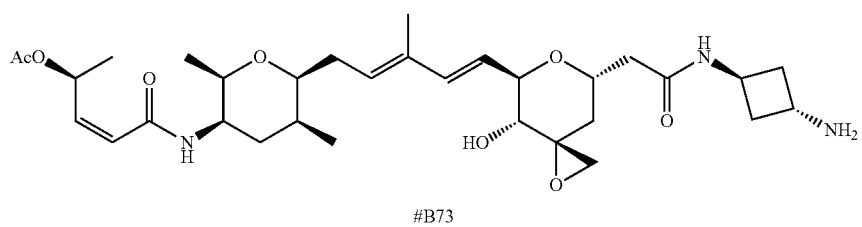

Step 1:

Synthesis of (2S,3Z)-5-{[(2R,3R,5S,6S)-6-{(2E,4E)-5-[(3R,4R,5R,7S)-7-{2-[(trans-3-aminocyclobutyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B73). A mixture of #NP1 (50.2 mg, 94% pure, 0.09 mmol, 1.0 eq), 1-hydroxybenzotriazole hydrate (HOBT, 65.5 mg, 0.43 mmol, 4.7 eq.), 1-ethyl-3-(3-dimethylaminopropyl) carbodiimide-HCl (EDC, 70 mg, 0.37 mmol, 4 eq.) in N,N-dimethylformamide (3.0 mL) was stirred at 0° C. for 30 minutes. To this solution were subsequently added trans-1,3-diaminocyclobutane (112 mg, 1.3 mmol, 14 eq.) in N,N-dimethylformamide (1.0 mL) and triethylamine (200 μL) at 0° C. The resulting reaction mixture was stirred at room temperature for 15 minutes. The reaction mixture was neutralized with acetic acid, filtered, and then purified using reverse phase chromatography (Method B*) to afford #B73 as a colorless glass. Yield: 64.3 mg, 100%. HPLC (Protocol N): retention time=6.66 minutes (purity 85.2%). LCMS (Protocol M): m/z 604.6 [M+H]$^+$. $^1$H NMR (400 MHz, DMSO-d$_6$, mult, J in Hz) δ 8.26 (d, J=7.0, 1H, D$_2$O exchangeable), 7.80 (d, J=7.9, 1H, D$_2$O exchangeable), 6.36 (dq, J=6.0, 6.0, 1H), 6.28 (br d, J=16.0, 1H), 6.11 (d, J=11.3, 1H), 5.88 (dd, J=11.7, 7.8, 1H), 5.60 (dd, J=16.0, 5.8, 1H), 5.49 (br dd, J=6.6, 6.6, 1H), 5.04 (m, 1H, D$_2$O exchangeable), 4.37 (m, 1H), 4.27-4.21 (m, 2H), 3.65 (m, 3H), 3.50 (br dd, J=5.5, 5.5, 1H), 3.26 (d, J=4.3, 1H), 2.76 (d, J=4.7, 1H), 2.58 (d, J=4.7, 1H), 2.48 (m, 1H), 2.29 (m, 1H), 2.22-2.11 (m, 6H), 1.98 (s, 3H), 1.82 (m, 1H), 1.80 (m, 2H), 1.70 (s, 3H), 1.65 (m, 1H), 1.49 (dd, J=12.5, 2.7, 1H), 1.25 (d, J=6.2, 3H), 1.07 (d, J=6.0, 3H), 0.95 (d, J=7.4, 3H).

Example A31

Preparation of (2S,3Z)-5-({(2R,3R,5S,6S)-6-[(2E,4E)-5-{(3R,4R,5R,7S)-4-hydroxy-7-[2-({trans-3-[(iodoacetyl)amino]cyclobutyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B74)

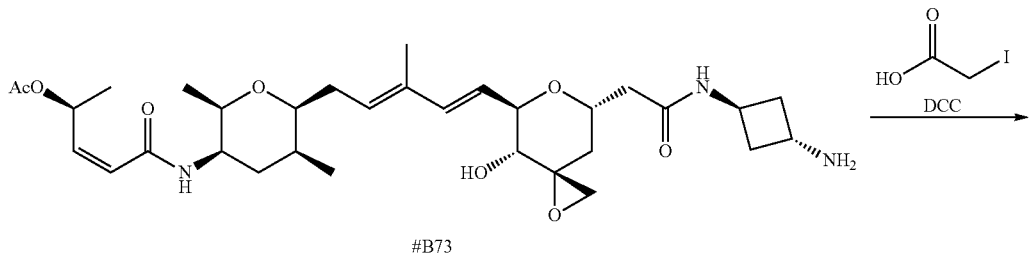

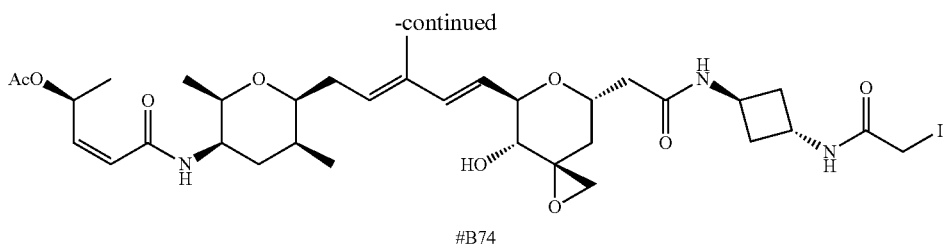

B74

Step 1:
Synthesis of (2S,3Z)-5-({(2R,3R,5S,6S)-6-[(2E,4E)-5-{(3R,4R,5R,7S)-4-hydroxy-7-[2-({trans-3-[(iodoacetyl) amino]cyclobutyl}amino)-2-oxoethyl]-1,6-dioxaspiro[2.5] oct-5-yl}-3-methylpenta-2,4-dien-1-yl]-2,5-dimethyltetrahydro-2H-pyran-3-yl}amino)-5-oxopent-3-en-2-yl acetate (#B74). A solution of iodoacetic acid (38.6 mg, 0.21 mmol, 5.9 eq.) and N,N'-dicyclohexylcarbodiimide (DCC, 64.2 mg, 0.31 mmol, 9 eq.) in anhydrous N,N-dimethylformamide (2.0 mL) was stirred at room temperature for 10 minutes. The resulting light yellow solution was slowly added to #B73 (Example A30, 27.1 mg, 0.035 mmol, 1.0 eq) in N,N-dimethylformamide (0.5 mL) and then stirred at room temperature for 15 minutes. The product was purified using reverse phase chromatography (Method B*) to afford #B74 as a white powder. Yield: 14.2 mg, 41%. HPLC (Protocol N): retention time=9.61 minutes (purity 100%). LCMS (Protocol M); m/z 772.4 [M+H]$^+$. $^1$H NMR (400 MHz, DMSO-d$_6$, mult, J in Hz) δ 8.60 (d, J=7.0, D$_2$O exchangeable), 8.28 (d, J=7.0, 1H, D$_2$O exchangeable), 7.80 (d, J=7.9, 1H, D$_2$O exchangeable), 6.36 (dq, J=6.0, 6.0, 1H), 6.29 (br d, J=16.0, 1H), 6.11 (d, J=11.7, 1H), 5.87 (dd, J=11.7, 7.8, 1H), 5.60 (dd, J=16.0, 5.8, 1H), 5.49 (br dd, J=7.0, 7.0, 1H), 5.01 (d, J=5.4, 1H, D$_2$O exchangeable), 4.27-4.23 (m, 3H), 4.19 (m, 1H), 3.65 (m, 2H), 3.59 (s, 2H), 3.49 (br dd, J=6.0, 6.0, 1H), 3.26 (dd, J=5.1, 5.1, 1H), 2.76 (d, J=5.1, 1H), 2.58 (d, J=5.1, 1H), 2.53 (m, 1H), 2.32 (m, 1H), 2.22-2.11 (m, 6H), 1.98 (s, 3H), 1.82 (m, 1H), 1.80 (m, 2H), 1.69 (s, 3H), 1.65 (m, 1H), 1.52 (dd, J=14.8, 2.7, 1H), 1.25 (d, J=6.2, 3H), 1.07 (d, J=6.0, 3H), 0.95 (d, J=7.0, 3H).

Example A32

Preparation of N-[6-(2,5-dioxo-2,5-dihydro-1H-pyrrol-1-yl)hexanoyl]-L-valyl-N-{4-[({[trans-3-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl] acetyl}amino)cyclobutyl]carbamoyl}oxy)methyl] phenyl}-N5-carbamoyl-L-ornithinamide (#B75)

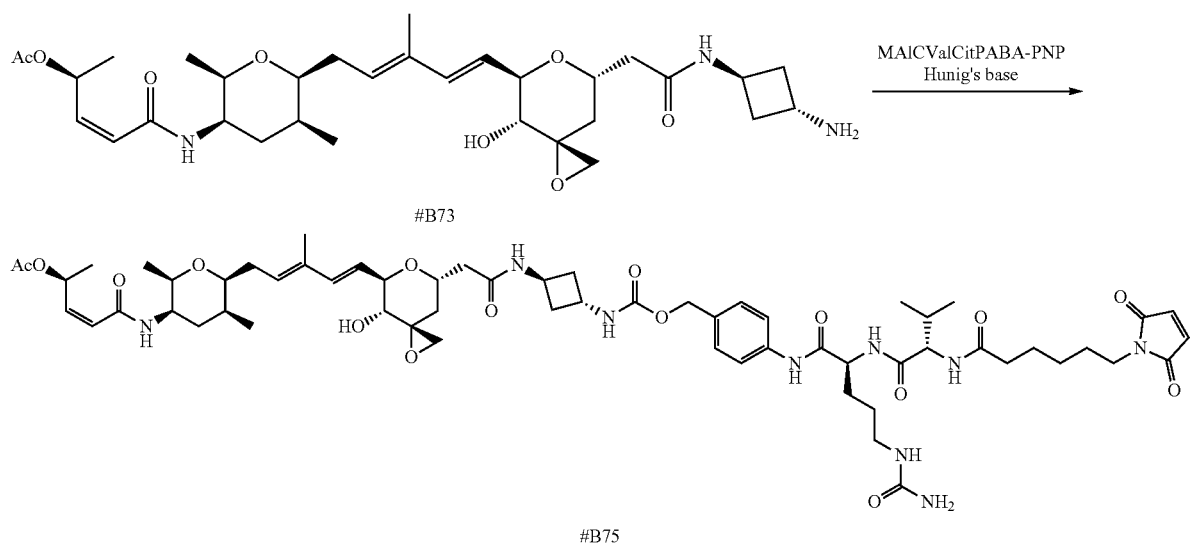

B73

B75

Step 1:
Synthesis of N-[6-(2,5-dioxo-2,5-dihydro-1H-pyrrol-1-yl)hexanoyl]-L-valyl-N-{4-[({[trans-3-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5] oct-5-yl]acetyl}amino)cyclobutyl]carbamoyl}oxy)methyl] phenyl}-N5-carbamoyl-L-ornithinamide (#B75). To a solution of N-[6-(2,5-dioxo-2,5-dihydro-1H-pyrrol-1-yl) hexanoyl]-L-valyl-N~5~-carbamoyl-N-{4-[({[(4 nitrobenzyl)oxy]carbonyl}oxy)methyl]phenyl}-L-ornithinamide (MalCValCitPABA-PNP, Eur. Pat. Appl. (1994), EP624377, 23.1 mg, 0.03 mmol, 1.3 eq.) and #B73 (15.5 mg, 85% purity, 0.022 mmol, 1.0 eq.) in anhydrous N,N-dimethylformamide (0.6 ml) was added N,N-diisopropylethylamine (Hunig's base, 30 μL). The resulting mixture was stirred at room temperature for 1 hour. The reaction mixture was purified using reverse phase chromatography (Method B*) to afford #B75 as a white powder. Yield: 12.6 mg, 28%. HPLC (Protocol N): retention time=9.3 minutes (purity 91%). LCMS (Protocol M): m/z 1202.5 [M+H]$^+$.

Example A33

Preparation of (2S,3Z)-5-{[(2R,3R,5S,6S)-6-{(2E,4E)-5-[(3R,4R,5R,7S)-7-{2-[(trans-4-aminocyclohexyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B76)

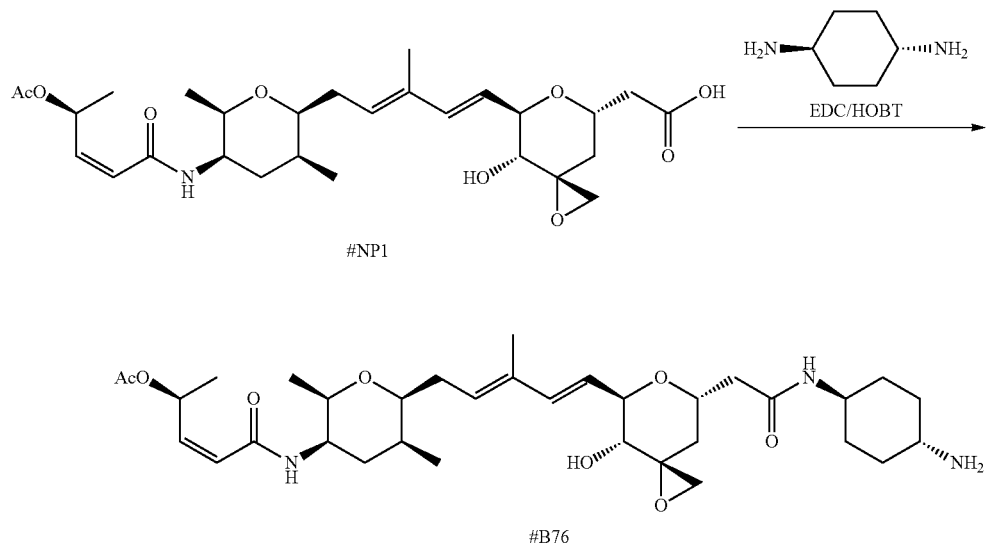

Step 1:

Synthesis of (2S,3Z)-5-{[(2R,3R,5S,6S)-6-{(2E,4E)-5-[(3R,4R,5R,7S)-7-{2-[(trans-4-aminocyclohexyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B76). A solution of #NP1 (40.2 mg, 92% purity, 0.07 mmol, 1.0 eq.), 1-hydroxybenzotriazole hydrate (HOBT, 62.5 mg, 0.4 mmol, 5.8 eq.), 1-ethyl-3-(3-dimethylaminopropyl) carbodiimide-HCl (EDC, 72.2 mg, 0.38 mmol, 5 eq.) in N,N-dimethylformamide (3.0 mL) was stirred at 0° C. for 30 minutes. To this solution were subsequently added trans-1,4-diaminocyclohexane (290.0 mg, 2.5 mmol, 30 eq.) in N,N-dimethylformamide (1.5 mL) and triethylamine (50 μL) at 0° C. The resulting mixture was then stirred at room temperature for 0.5 hour and 0° C. for 16 hours. The reaction mixture was neutralized with acetic acid, filtered, and then purified using reverse phase chromatography (Method B*) to afford #B76 as a white powder. Yield: 48.2 mg, 100%. HPLC (Protocol N): retention time=7.16 minutes (purity 87.5%). LCMS (Protocol M): m/z 632.2 [M+H]$^+$. $^1$H NMR (400 MHz, DMSO-d$_6$, mult, J in Hz) δ 7.81 (d, J=7.8, 1H, D$_2$O exchangeable), 7.72 (d, J=7.8, 1H, D$_2$O exchangeable), 6.36 (dq, J=6.0, 6.0, 1H), 6.28 (br d, J=15.6, 1H), 6.11 (d, J=11.7, 1H), 5.87 (dd, J=11.7, 7.8, 1H), 5.59 (dd, J=16.0, 5.5, 1H), 5.49 (br dd, J=6.6, 6.6, 1H), 5.02 (m, 1H, D$_2$O exchangeable), 4.26 (m, 1H), 4.22 (m, H), 3.65 (m, 2H), 3.49 (br dd, J=6.2, 6.2, 1H), 3.45-3.32 (m, 2H), 3.26 (d, J=3.9, 1H), 2.75 (d, J=5.1, 1H), 2.58 (d, J=5.1, 1H), 2.46 (m, 1H), 2.29 (m, 1H), 2.22 (m, 1H), 2.16 (dd, J=14.0, 4.7, 1H), 1.98 (s, 3H), 1.83 (m, 1H), 1.81 (m, 2H), 1.79-1.72 (m, 4H), 1.70 (s, 3H), 1.65 (m, 1H), 1.46 (dd, J=12.5, 3.0, 1H), 1.25 (d, J=6.2, 3H), 1.16-1.10 (m, 4H), 1.07 (d, J=6.0, 3H), 0.95 (d, J=7.0, 3H).

Example A34

Preparation of (2S,3Z)-5-{[(2R,3R,5S,6S)-6-{(2E,4E)-5-[(3R,4R,5R,7S)-7-{2-[(5-aminopentyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B77)

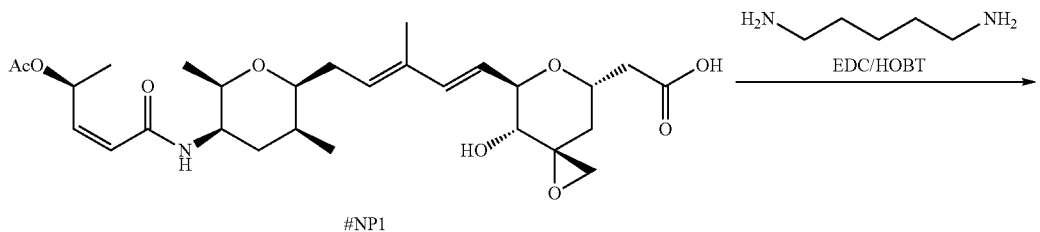

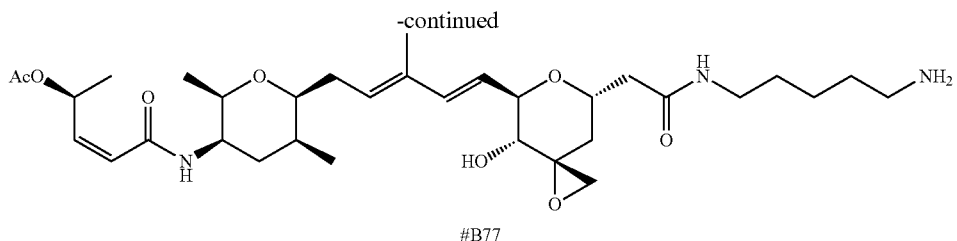

B77

Step 1:

Synthesis of (2S,3Z)-5-{[(2R,3R,5S,6S)-6-{(2E,4E)-5-[(3R,4R,5R,7S)-7-{2-[(5-aminopentyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B77). A solution of #NP1 (30.5 mg, 92% pure, 0.056 mmol, 1.0 eq.), 1-hydroxybenzotriazole hydrate (HOBT, 38.0 mg, 0.24 mmol, 4.4 eq.), 1-ethyl-3-(3-dimethylaminopropyl) carbodiimide-HCl (EDC, 54.0 mg, 0.28 mmol, 5 eq.) in N,N-dimethylformamide (3.0 mL) was stirred at 0° C. for 30 minutes. To this solution were subsequently added triethylamine (50 μL) and 1,5-pentanediamine (50 μL, 0.5 mmol, 9 eq.) at 0° C. The resulting mixture was stirred at room temperature for 1 hour. The reaction mixture was neutralized with acetic acid, filtered, and then purified using reverse phase chromatography (Method B*). The peak with retention time of 22.0 minutes was collected, neutralized with NH₄OH, and freeze dried to afford #B77 as a white powder. Yield 23.1 mg, 68% yield. HPLC (Protocol N): retention time=7.67 minutes (purity 91%). LCMS (Protocol M): m/z 620.6 [M+H]⁺.

Example A35

Preparation of N-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}-2-methylalanine (#B79)

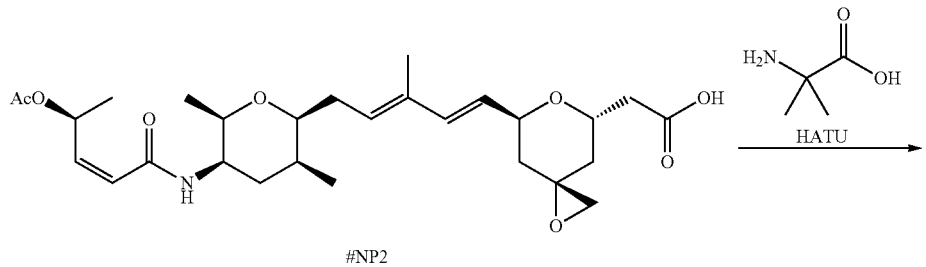

NP2

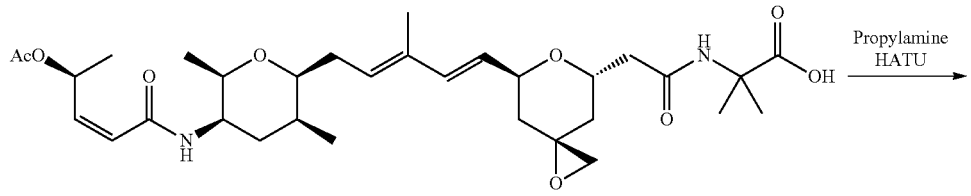

B78

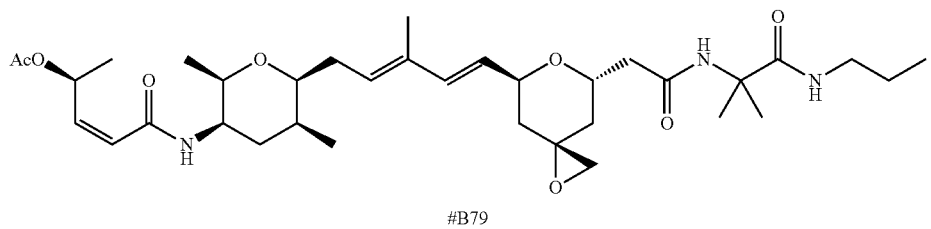

B79

Step 1:

Synthesis of N-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}-2-methylalanine (#B78). A mixture of #NP2 (118.3 mg, 94.0% purity, 0.2 mmol, 1.0 eq.), O-(7-azabenzotriazol-1-yl)-N,N,N',N'-tetramethyluronium hexafluorophosphate (HATU, 31.7 mg, 0.083 mmol, 0.4 eq.), and N,N-diisopropylethylamine (Hunig's base, 10 μL) in N,N-dimethylformamide (2.0 mL) was stirred at ambient temperature for 30 minutes. To this solution were subsequently added triethylamine (100 μL) and 2-methylalanine (32.5 mg, 0.3 mmol, 1.3 eq.) in 1:1

HPLC (Protocol N): retention time=12.31 minutes (purity 100%). LCMS (Protocol M): m/z 646.7 [M+H]$^+$; 668.7 [M+Na]$^+$.

Example A36

Preparation of (2S,3Z)-5-{[(2R,3R,5S,6S)-6-{(2E,4E)-5-[(3R,4R,5R,7S)-4-hydroxy-7-(2-{[2-methyl-1-oxo-1-(propylamino)propan-2-yl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B81)

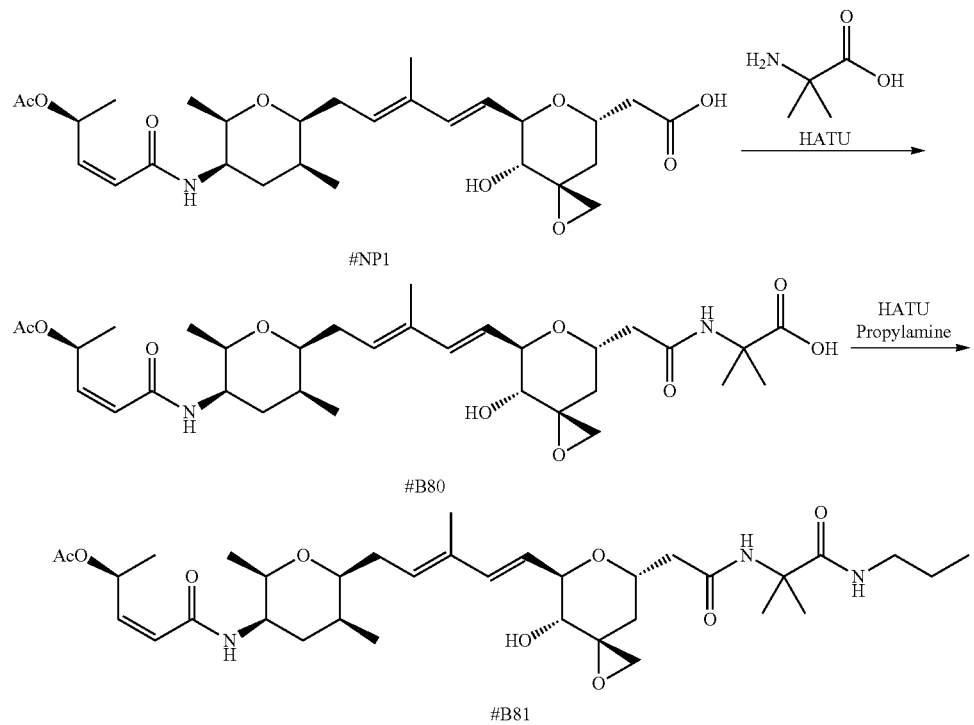

pyridine/dimethyl sulfoxide (1.0 mL). The resulting suspension was stirred at ambient temperature for 2.0 hours. The reaction mixture was purified using reverse phase chromatography (Method B*) to afford #B78 as a white powder. Yield: 54.3 mg, 45% yield. HPLC (Protocol N): retention time=11.29 minutes (purity 94.1%). LCMS (Protocol M); m/z 605.6 [M+H]$^+$.

Step 2:

Synthesis of N-{[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}-2-methylalanine (#B79). A solution of #B78 (6.6 mg, 0.011 mmol, 1.0 eq.), O-(7-azabenzotriazol-1-yl)-N,N,N',N'-tetramethyluronium hexafluorophosphate (HATU, 6.0 mg, 0.016 mmol, 1.5 eq.), and N,N-diisopropylethylamine (Hunig's base, 3.0 μL) in N,N-dimethylformamide (200 μL) was stirred at ambient temperature for 30 minutes. To this solution was added propylamine (3.6 μL, 0.06 mmol, 5 eq.) and the resulting solution was stirred for 1 hour. The reaction mixture was purified using reverse phase chromatography (Method B*) to afford #B79 as a white powder. Yield: 4.9 mg, 70% yield.

Step 1:

Synthesis of N-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}-2-methylalanine (#B80). A mixture of #NP1 (122.4 mg, 92.0% purity, 0.22 mmol, 1.0 eq.), O-(7-azabenzotriazol-1-yl)-N,N,N',N'-tetramethyluronium hexafluorophosphate (HATU, 33.2 mg, 0.087 mmol, 0.4 eq.), and N,N-diisopropylethylamine (Hunig's base, 10 μL) in N,N-dimethylformamide (2.0 mL) was stirred at ambient temperature for 30 minutes. To this solution were subsequently added triethylamine (100 μL) and 2-methylalanine (36.4 mg, 0.35 mmol, 1.2 eq.) in 1:1 pyridine/dimethyl sulfoxide (1.0 mL). The resulting suspension was stirred at ambient temperature for 2.0 hours. The reaction mixture was purified using reverse phase chromatography (Method B*) to afford #B80 as a white powder. Yield: 52.7 mg, 42% yield. HPLC (Protocol N): retention time=9.28 minutes (purity 90%). LCMS (Protocol M): m/z 621.6 [M+H]$^+$.

Step 2:

Preparation of (2S,3Z)-5-{[(2R,3R,5S,6S)-6-{(2E,4E)-5-[(3R,4R,5R,7S)-4- hydroxy-7-(2-{[2-methyl-1-oxo-1-(propylamino)propan-2-yl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B81). A solution of #B80 (6.0 mg, 90% purity, 0.01 mmol, 1.0 eq.), O-(7-azabenzotriazol-1-yl)-N,N,N',N'-tetramethyluronium hexafluorophosphate (HATU, 5.1 mg, 0.013 mmol, 1.3 eq.), and N,N-diisopropylethylamine (Hunig's base, 3.0 µL) in N,N-dimethylformamide (200 µL) was stirred at ambient temperature for 30 minutes. To this solution was added propylamine (3.6 µL, 0.06 mmol, 6 eq.) and the resulting solution was stirred for 1 hour. The reaction mixture was purified using reverse phase chromatography (Method B*) to afford #B81 as a white powder. Yield: 4.7 mg, 87% yield. HPLC (Protocol N): retention time=10.95 minutes (purity 99%). LCMS (Protocol M): m/z 662.7 [M+H]$^+$.

Example A37

Preparation of (2S,3Z)-5-{[(2R,3R,5S,6S)-6-{(2E,4E)-5-[(3R,4R,5R,7S)-7-{2-[(4-{[({4-[(N-{6-[(bromoacetyl)amino]hexanoyl}glycyl)amino]benzyl}oxy)carbonyl]amino}benzyl)-2-oxoethyl]-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B123)

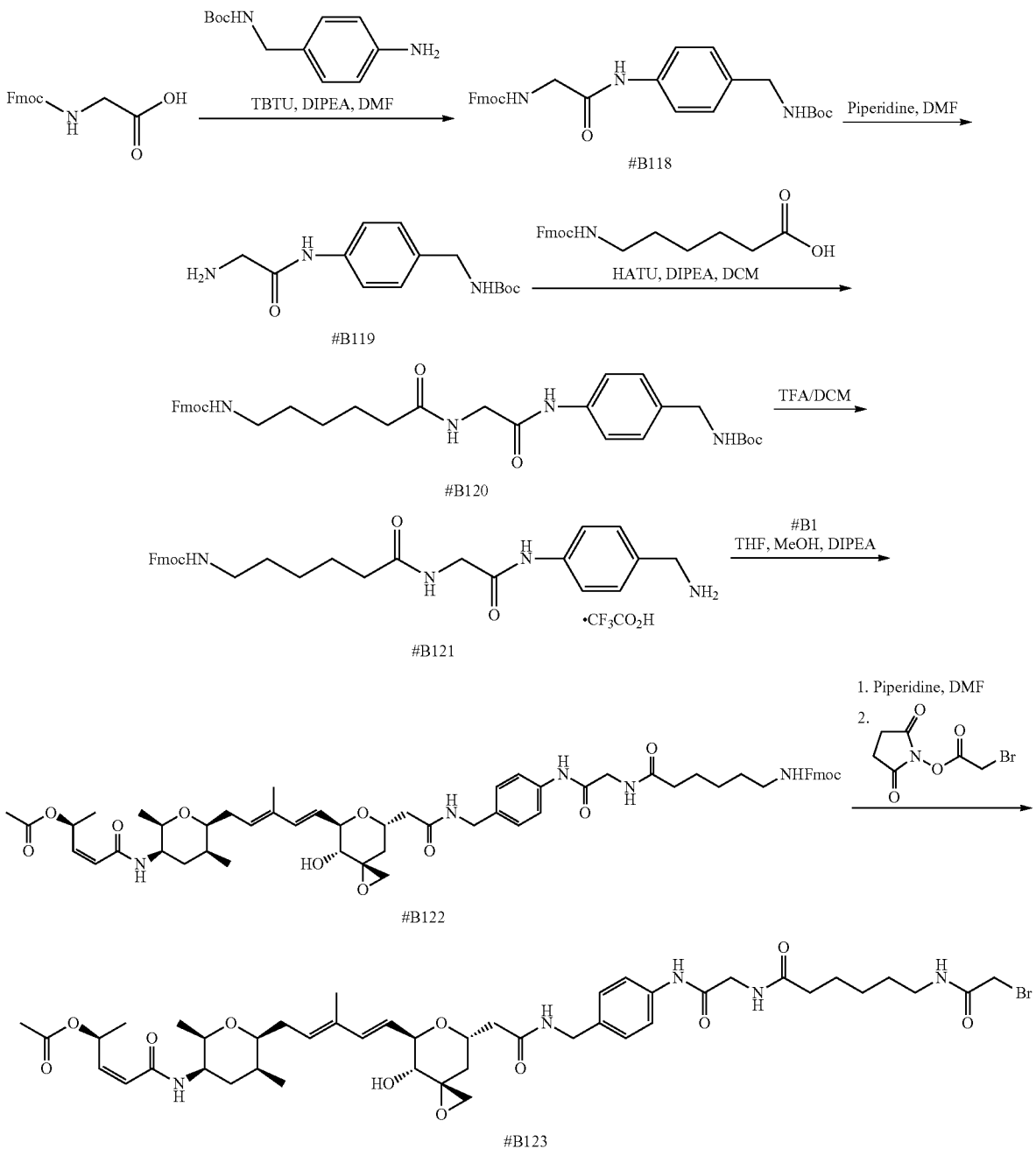

Step 1:

Synthesis of 9H-fluoren-9-ylmethyl {2-[(4-{[(tert-butoxycarbonyl)amino]methyl}phenyl)amino]-2-oxoethyl}carbamate (#B118): To a solution of Fmoc-Glycine (16 g, 54 mmol, 1.0 eq.) in dry DMF (160 mL) at 0° C. was added N,N-diisopropylethylamine (14 g, 108 mmol, 2.0 eq) and N,N,N',N'-Tetramethyl-O-(benzotriazol-1-yl)uronium tetrafluoroborate (16 g, 54 mmol, 1.0 eq). The mixture was stirred at 0° C. for 30 min and a solution of tert-butyl [4-(glycylamino)benzyl]carbamate (12 g, 54 mmol, 1.0 eq.) in dry DMF (50 mL) was added. The mixture was stirred at room temperature overnight poured into ice water (400 mL) and extracted with EtOAc (400 mL×2). The organic layer was washed with brine (200 mL×2), dried over Na2SO4 and concentrated in vacuum. The residue was re-crystallized from EtOAc (200 mL) and petroleum ether (400 mL) to afford #B118 (18 g, 66.6%) as a white solid. 1H NMR (400 Hz, DMSO-$d_6$): δ 9.93 (s, 1H), 7.91 (d, 2H), 7.75 (d, 2H), 7.61 (m, 1H), 7.52 (d, 2H), 7.43 (m, 2H), 7.36 (m, 3H), 7.18 (d, 3H), 4.32 (d, 2H), 4.26 (m, 1H), 4.07 (d, 2H), 3.80 (d, 2H), 1.39 (s, 9H)

Step 2:

Synthesis of tert-butyl [4-(glycylamino)benzyl]carbamate (#B119): To a solution of #B118 (7.0 g, 14.0 mmol, 1.0 eq) in DMF (70 mL) was added piperidine (4.7 mL, 47.5 mmol, 3.4 eq.) at room temperature. The mixture was stirred at room temperature for 30 min, evaporated in vacuo. The residue was washed with petroleum ether (100 mL×2) and re-crystallized from EtOAc (50 mL) and petroleum ether (200 mL) to gave #B119 (3.3 g, 84.6%) as a white solid. $^1$H NMR (400 Hz, CDCl$_3$): δ 9.37 (s, 1H), 7.57 (d, 2H), 7.25 (d, 2H), 4.80 (br, 1H), 4.27 (d, 2H), 3.47 (s, 2H), 1.45 (s, 9H)

Step 3:

Synthesis of 9H-fluoren-9-ylmethyl [6-({2-[(4-{[(tert-butoxycarbonyl)amino]methyl}phenyl)amino]-2-oxoethyl}amino)-6-oxohexyl]carbamate (#B120): To a solution of 6-{[(9H-fluoren-9-ylmethoxy)carbonyl]amino}hexanoic acid (2.66 g, 7.53 mmol, 1.0 eq.) in dry DCM (50 mL) at 0° C. was added N,N-diisopropylethylamine (1.93 g, 15.1 mmol, 2.0 eq) and 0-(7-azabenzotriazol-1-yl)-N,N,N',N'-tetramethyluronium hexafluorophosphate (HATU, 2.86 g, 7.53 mmol, 1.0 eq.). The mixture was stirred at 0° C. for 30 min and #B119 (2.1 g, 7.53 mmol, 1.0 eq.) was added in one portion. The mixture was stirred at room temperature overnight. The mixture was filtered and solid was washed with DCM and dried in vacuo to afford #B120 (4 g, 86.4%) as a white solid. 1H NMR (400 Hz, DMSO-$d_6$): δ 9.91 (s, 1H), 8.11 (br, 1H), 7.90 (d, 2H), 7.69 (d, 2H), 7.51 (d, 2H), 7.41 (m, 2H), 7.33 (m, 3H), 7.17 (d, 2H), 4.28 (m, 3H), 4.06 (d, 2H), 3.86 (br, 2H), 2.97 (m, 2H), 2.15 (m, 2H), 1.51 (m, 2H), 1.38 (m, 12H); LCMS (Protocol I): m/z 637.1 (M+Na)$^+$, retention time=1.18 minutes.

Step 4:

Synthesis of 9H-fluoren-9-ylmethyl {6-[(2-{[4-(aminomethyl)phenyl]amino}-2-oxoethyl)amino]-6-oxohexyl}carbamate trifluoroacetate salt (#B121): To a suspension of #B120 (1 g, 1.63 mmol, 1.0 eq) in dry DCM (20 mL) at 0° C. was added trifluoroacetic acid (6 mL, large excess). The mixture was stirred at room temperature for 2 hrs and concentrated in vacuo. The residue was suspended in water (30 mL) and lyophilized to afford #B121 (1.2 g, 100%) as a slight yellow solid. 1H NMR (400 Hz, DMSO-$d_6$): δ10.08 (s, 1H), 8.15 (br, 4H), 7.90 (d, 2H), 7.69 (d, 2H), 7.63 (d, 2H), 7.41 (m, 8H), 4.30 (m, 3H), 3.98 (m, 3H), 3.87 (d, 2H), 2.97 (m, 2H), 2.17 (m, 2H), 1.51 (m, 2H), 1.40 (m, 2H), 1.26 (m, 2H): LCMS (Protocol I): m/z 537.1 (M+Na)$^+$, retention time=1.10 minutes.

Step 5:

Synthesis of (2S,3Z)-5-{[(2R,3R,5S,6S)-6-{(2E,4E)-5-[(3R,4R,5R,7S)-7-{2-[(4-{[N-(6-{[(9H-fluoren-9-ylmethoxy)carbonyl]amino}hexanoyl)glycyl]amino}benzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B122): To a solution of #B121 (32.7 mg, 0.044 mmol, 1 eq.) in tetrahydrofuran (1.0 mL) and methanol (0.1 mL) was added N,N-diisopropylethylamine (26.0 mg, 0.2 mmol, 4.5 eq.). The entire reaction mixture was added to a cooled (0° C.) solution of #B1 (28 mg, 0.044 mmol, 1 eq.) in tetrahydrofuran (1.0 mL) and the reaction was allowed to warm to room temperature. After one hour the reaction was concentrated in vacuo and the residue was purified by reverse phase chromatography (Method A) to afford #B122 (12.4 mg, 0.011 mmol, 27%): LCMS (Protocol D): m/z 1032.6 [M+H]$^+$, retention time=0.92 minutes.

Step 6:

Synthesis of (2S,3Z)-5-{[(2R,3R,5S,6S)-6-{(2E,4E)-5-[(3R,4R,5R,7S)-7-{2-[(4-{[({4-[(N-{6-[(bromoacetyl)amino]hexanoyl}glycyl)amino]benzyl}oxy)carbonyl]amino}benzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B123): To a solution of #B122 (12.4 mg, 0.012 mmol, 1 eq.) in dimethylformamide (0.7 mL, 0.01 M) was added piperidine (11 uL of a stock solution [prepared by dissolving 100 uL piperidine in 1 ml DMF], 0.013 mmol, 1.1 eq.). The reaction was stirred for 16 hours and a solution of bromoacetic acid N-hydroxysuccinimide ester (2.8 mg, 0.012 mmol, 1 eq.) in tetrahydrofuran (0.5 mL) then added dropwise. The reaction was stirred for 16 hours, concentrated in vacuo and the residue was purified by reverse phase chromatography (Method A) to afford #B123 as a solid. Yield: 2.5 mg, 0.027 mmol, 22%. LCMS (Protocol D): m/z 932.2 [M+H]$^+$ retention time=0.76 minutes.

Example A38

Preparation of (2S,3Z)-5-{[(2R,3R,5S,6S)-6-{(2E,4E)-5-[(3R,4R,5R,7S)-7-(2-carbamimidamido-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B124) and (2S,3Z)-5-({(2R,3R,5S,6S)-6-[(2E,4E)-5-{(3R,4R,5R,7S)-7-[2-(N'-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}carbamimidamido)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B125)

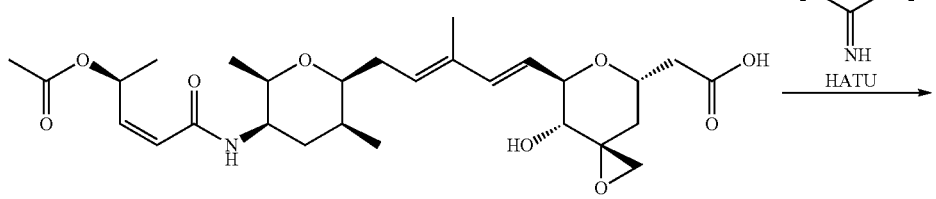

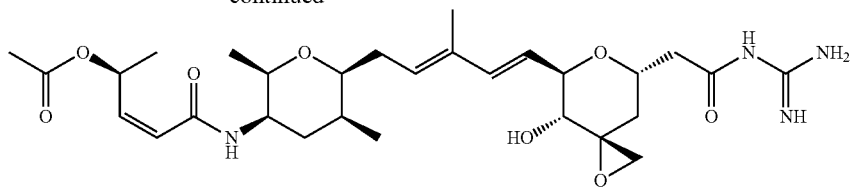

B124

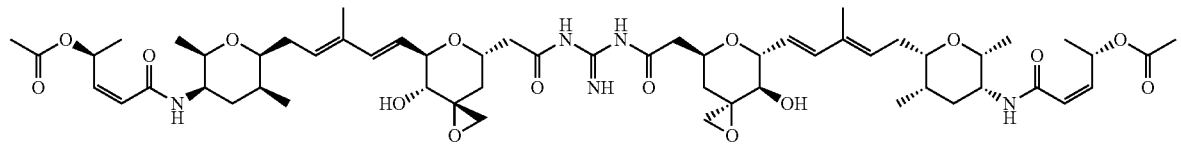

B125

Step 1:

Synthesis of (2S,3Z)-5-{[(2R,3R,5S,6S)-6-{(2E,4E)-5-[(3R,4R,5R,7S)-7-(2-carbamimidamido-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B124) and (2S,3Z)-5-({(2R,3R,5S,6S)-6-[(2E,4E)-5-{(3R,4R,5R,7S)-7-[2-(N'-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}carbamimidamido)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B125): To a mixture of #NP1 (135 mg, ~60% purity, ~0.15 mmol) and O-(7-azabenzotriazol-1-yl)-N,N,N'N'-tetramethyluronium hexafluorophosphate (HATU, 72 mg, 0.19 mmol, 1.2 eq.) in N,N-dimethylformamide (DMF, 1.0 mL) at 0° C. was added N,N'-diisopropylethylamine (30 uL, #eq). After stirring at ambient temperature for 10 minutes, the mixture was transferred to a solution of guanidine hydrochloride (400 mg, 4.1 mmol, 28 eq.) and N,N'-diisopropylethylamine (100 uL) in 1:1 methylsulfoxide/water (3.0 mL). The resulting solution was stirred for 20 minutes and purified using reversed phase chromatography (Method B*) to afford (#B124) and (#B125) as white powders.

B124: Yield: 55.6 mg, 38% yield HPLC (Protocol N): retention time=8.01 minutes (purity 87%). LCMS (Protocol M): m/z 577.44 [M+H]+. 1H NMR (400 MHz, DMSO-d6, mult, J in Hz) δ 7.80 (d, J=7.9, 1H, D2O exchangeable), 6.36 (dq, J=6.0, 6.0, 1H), 6.27 (br d, J=16.0, 1H), 6.11 (d, J=11.3, 1H), 5.87 (dd, J=11.3, 7.4, 1H), 5.60 (dd, J=15.6, 5.5, 1H), 5.51 (br dd, J=7.4, 7.4, 1H), 4.93 (d, J=5.8, 1H, D2O exchangeable), 4.29 (m, 1H), 4.22 (m, 1H), 3.65 (m, 2H), 3.50 (br dd, J=6.0, 6.0, 1H), 3.22 (dd, J=4.7, 4.7, 1H), 2.73 (d, J=5.1, 1H), 2.56 (d, J=5.1, 1H), 2.46 (m, 1H), 2.32 (m, 2H), 2.20 (m, 1H), 1.98 (s, 3H), 1.82 (m, 1H), 1.80 (m, 2H), 1.69 (s, 3H), 1.65 (m, 1H), 1.52 (dd, J=13.2, 3.5, 1H), 1.25 (d, J=6.2, 3H), 1.07 (d, J=6.0, 3H), 0.95 (d, J=7.4, 3H).

B125: Yield: 49.0 mg, 36% yield HPLC (Protocol N): retention time=10.14 minutes (purity 90%). LCMS (Protocol M): m/z 1094.76 [M+H]+. 1H NMR (400 MHz, DMSO-d6, mult, J in Hz) δ 7.78 (d, J=7.9, 2H, D2O exchangeable), 6.36 (dq, J=6.0, 6.0, 2H), 6.27 (br d, J=16.0, 2H), 6.11 (d, J=11.7, 2H), 5.87 (dd, J=11.7, 7.8, 2H), 5.60 (dd, J=16.0, 5.0, 2H), 5.49 (br dd, J=6.7, 6.7, 2H), 5.01 (br s, 2H, D2O exchangeable), 4.32 (m, 2H), 4.25 (m, 2H), 3.65 (m, 4H), 3.49 (br dd, J=6.6, 6.6, 2H), 3.28 (d, J=4.3, 2H), 2.76 (d, J=4.7, 2H), 2.59 (d, J=4.7, 2H), 2.54 (m, 2H), 2.30 (m, 2H), 2.28 (m, 2H), 2.21 (m, 2H), 1.98 (s, 6H), 1.83 (m, 2H), 1.80 (m, 4H), 1.69 (s, 6H), 1.65 (m, 2H), 1.52 (br d, J=12.8, 2H), 1.25 (d, J=6.2, 6H), 1.06 (d, J=6.2, 6H), 0.94 (d, J=7.0, 6H).

Similar dimeric compounds to those disclosed herein are also included within the scope of the present invention, for instance dimeric compounds having substitutions as described throughout this application.

Example A39

Preparation of (2S,3Z)-5-{[(2R,3R,5S,6S)-6-{(2E,4E)-5-[(3R,4R,5R,7S)-7-{2-[N'-(bromoacetyl)carbamimidamido]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B126)

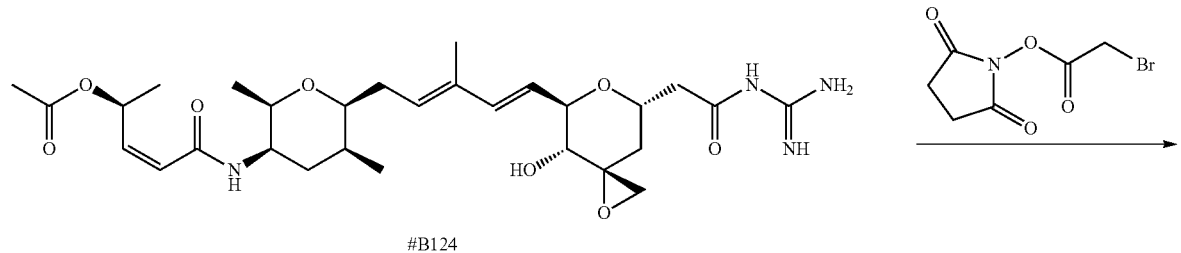

B124

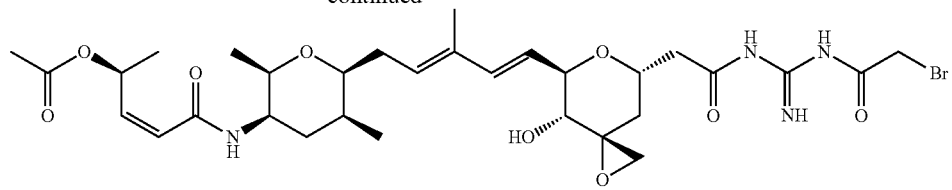

B126

Step 1:
Synthesis of (2S,3Z)-5-{[(2R,3R,5S,6S)-6-{(2E,4E)-5-[(3R,4R,5R,7S)-7-{2-[N'-(bromoacetyl)carbamimidamido]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B126) L
To a solution of #B124 (24.0 mg, 0.042 mmol, 1.0 eq.) and bromoacetic acid N-hydroxysuccinimide ester (24.1 mg, 0.092 mmol, 2.0 eq.) in N,N-dimethylformamide (1 ml) was added N,N'-diisopropylethylamine (10 uL). The resulting solution was stirred at ambient temperature for 30 minutes and purified using reverse phase chromatography (Method B*) to afford #B126 as a white powder. Yield: 5.7 mg, 20%. HPLC (Protocol N): retention time=10.01 minutes (purity 99%). LCMS (Protocol M): m/z 697.35, 699.35 (1:1) [M+H]$^+$. $^1$H NMR (400 MHz, DMSO-d$_6$, mult, J in Hz) δ 9.57 (br s, 1H, D$_2$O exchangeable), 9.41 (br s, 1H, D$_2$O exchangeable), 9.24 (br s, 1H, D$_2$O exchangeable), 9.08 (br s, 1H, D$_2$O exchangeable), 7.79 (d, J=7.5, 1H, D$_2$O exchangeable), 6.36 (dq, J=6.0, 6.0, 1H), 6.26 (br d, J=16.0, 1H), 6.11 (d, J=11.7, 1H), 5.87 (dd, J=11.3, 7.4, 1H), 5.60 (m, 1H), 5.49 (m, 1H), 4.35-4.28 (m, 2H), 3.65 (m, 2H), 3.50 (br dd, J=6.0, 6.0, 1H), 3.41 (s, 2H), 3.26 (d, J=4.7, 1H), 2.78 (d, J=4.3, 1H), 2.61 (d, J=4.3, 1H), 2.55 (m, 1H), 2.32 (m, 2H), 2.20 (m, 1H), 1.98 (s, 3H), 1.85 (m, 1H), 1.80 (m, 2H), 1.69 (s, 3H), 1.65 (m, 1H), 1.53 (dd, J=13.2, 3.5, 1H), 1.25 (d, J=6.2, 3H), 1.07 (d, J=6.2, 3H), 0.95 (d, J=6.6, 3H).

Example A40

Preparation of (2S,3Z)-5-{[(2R,3R,5S,6S)-6-{(2E,4E)-5-[(3R,4R,5R,7S)-4-hydroxy-7-{2-[{2-[(iodoacetyl)(methyl)amino]ethyl}(methyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B128)

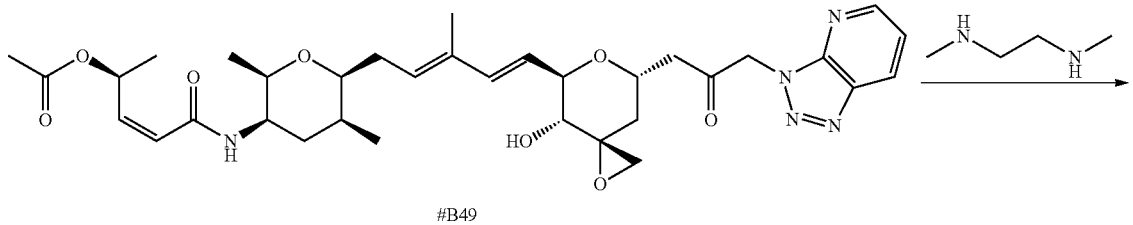

B49

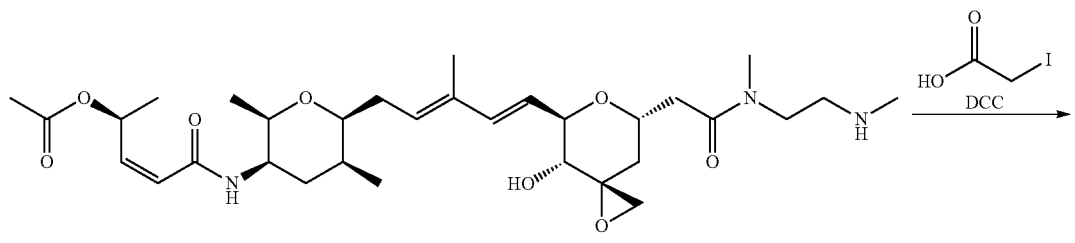

B127

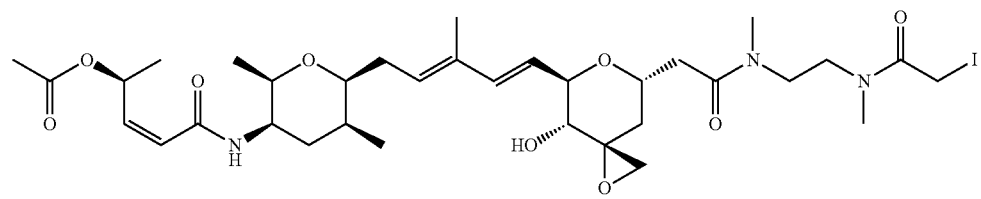

B128

Step 1:

Synthesis of (2S,3Z)-5-{[(2R,3R,5S,6S)-6-{(2E,4E)-5-[(3R,4R,5R,7S)-7-{2-[(methyl(2-(methylamino)ethyl)amino)]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate. (#B127): To a solution of #B49 (54.5 mg, 0.084 mmol, 1.0 eq.) in N,N-dimethylformamide (2.0 mL) was added N,N'-dimethyl-1,2-ethylenediamine (120 uL, 1.1 mmol, 12 eq.). The reaction mixture was stirred at ambient temperature for 5 minutes and the product was purified using reversed phase chromatography (Method B*) to afford. (#B127) Yield: 29.1 mg, 57%. HPLC (Protocol N): retention time=6.92 minutes (purity 76%). LCMS (Protocol M): m/z 606.3 [M+H]$^+$.

Step 2:

Synthesis of (2S,3Z)-5-{[(2R,3R,5S,6S)-6-{(2E,4E)-5-[(3R,4R,5R,7S)-4-hydroxy-7-{2-[{2-[(iodoacetyl)(methyl)amino]ethyl}(methyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate. (#B128). A solution of iodoacetic acid (43.1 mg, 0.23 mmol, 4.8 eq.) and N,N'-dicyclohexylcarbodiimide (DCC, 64.10 mg, 0.3 mmol, 6.3 eq.) in N,N-dimethylformamide (2.0 mL) was stirred at ambient temperature for 10 minutes and then transferred to a solution of. (#B127) (29.1 mg, 76.0% pure, 0.048 mmol, 1 eq.) in N,N-dimethylformamide (0.2 ml). The reaction mixture was stirred for 20 minutes and purified by reverse phase chromatography to afford. (#B128). as a white powder. Yield: 12.2 mg, 54%. HPLC analysis (Protocol N): retention time=9.57 minutes (purity 95.2%). LCMS (Protocol M): m/z 774.2 [M+H]$^+$. $^1$H NMR (400 MHz, DMSO-d$_6$, mult, J in Hz) δ 7.80 (d, J=7.4, 1H, D$_2$O exchangeable), 6.36 (dq, J=6.2, 6.2, 1H), 6.33 (br d, J=15.5, 1H), 6.11 (d, J=11.3, 1H), 5.86 (dd, J=11.7, 7.8, 1H), 5.60 (dd, J=16.0, 4.7, 1H), 5.52 (br dd, J=6.6, 6.6, 1H), 4.98 (m, 1H, D$_2$O exchangeable), 4.26 (m, 2H), 3.65 (m, 2H), 3.51 (br dd, J=6.2, 6.2, 1H), 3.46-3.35 (m, 6H), 3.24 (m, 1H), 3.02 (s, 1.5H), 2.97 (s, 1.5H), 2.95 (s, 1.5H), 2.82 (s, 1.5H), 2.76 (m, 1H), 2.65 (m, 1H), 2.59 (m, 1H), 2.55 (m, 1H), 2.30 (m, 1H), 2.22 (m, 1H), 1.98 (s, 3H), 1.86 (m, 1H), 1.80 (m, 2H), 1.70 (s, 3H), 1.65 (m, 1H), 1.49 (dd, J=12.5, 2.7, 1H), 1.25 (d, J=6.2, 3H), 1.07 (d, J=6.2, 3H), 0.95 (d, J=7.0, 3H).

Example A41

Preparation of (2Z)—N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]-4-oxopent-2-enamide (#B129)

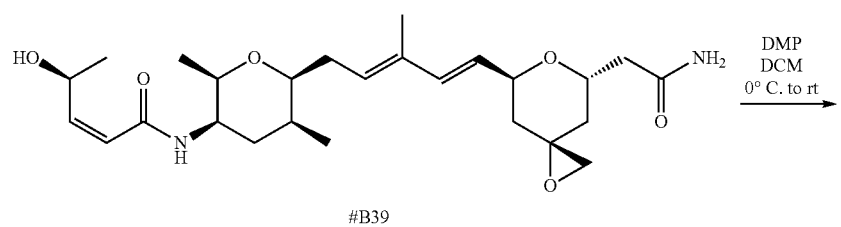

B39

B129

Step 1:

Synthesis of (2Z)—N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]-4-oxopent-2-enamide (#B129): To a solution of #B39 (60 mg, 0.13 mmol, 1 eq.) in dichloromethane (2 mL) at 0° C. was added Dess-Martin periodinane (119 mg, 0.27 mmol, 2 eq.), and the ice bath was removed. After 35 min saturated sodium bicarbonate and dichloromethane were added, and the aqueous layer was extracted with dichloromethane. The combined organic extracts were dried over sodium sulfate and filtered, and the solvents were removed in vacuo. The crude material was purified by reverse phase chromatography (Method A) to give #B129 as a white solid. Yield: 19.04 mg, 0.04 mmol, 32%. LCMS (Protocol D): m/z 475.3 [M+H]$^+$, retention time=0.70 minutes. $^1$H NMR (400 MHz, DMSO-d$_6$, mult, J in Hz) δ d, J=8.0 Hz, 1H), 7.32 (s, 1H), 6.77 (s, 1H), 6.32 (s, 2H), 6.27 (d, J=16.0 Hz, 1H), 5.60 (dd, J=16.0 and 5.5 Hz, 1H), 5.55-5.47 (m, 1H), 4.58-4.50 (m, 1H), 4.35-4.26 (m, 1H), 3.69-3.59 (m, 2H), 3.54-3.48 (m, 1H), 2.65-2.51 (m, 3H), 2.36-2.15 (m, 6H), 1.88-1.73 (m, 3H), 1.72-1.60 (m, 6H), 1.37 (dd, J=13.3 and 6.2 Hz, 1H), 1.08 (d, J=6.6 Hz, 3H), 0.96 (d, J=7.4 Hz, 3H).

Example A42

Preparation of (2S,3Z)-5-{[(2R,3R,5S,6S)-6-{(2E,4E)-5-[(3R,4R,5R,7S)-7-(2-amino-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl methyl[2-(methylsulfanyl)ethyl]carbamate (#B130)

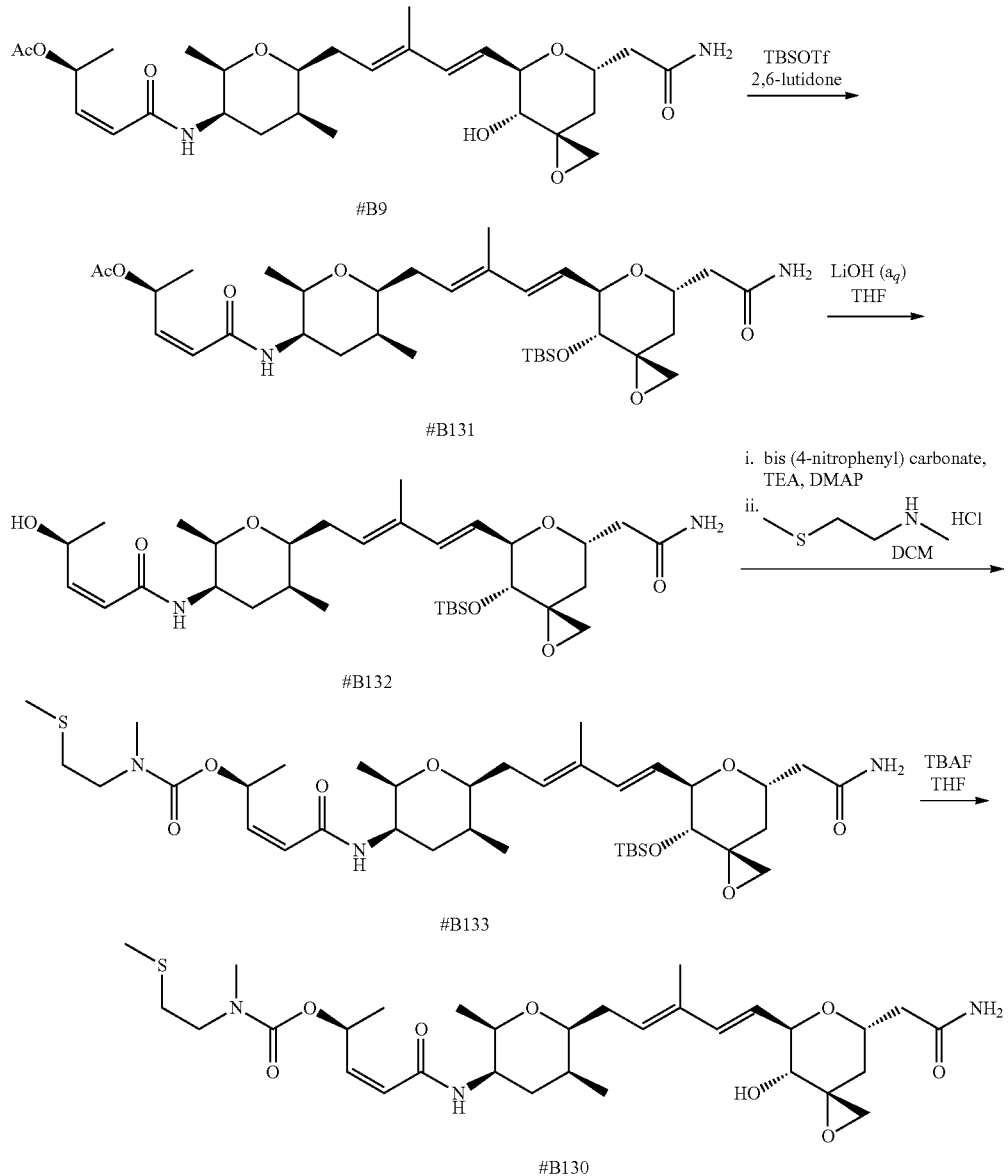

Step 1:

Synthesis of (2S,3Z)-5-{[(2R,3R,5S,6S)-6-{(2E,4E)-5-[(3R,4R,5R,7S)-7-(2-amino-2-oxoethyl)-4-{[tert-butyl(dimethyl)silyl]oxy}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (B131): To a solution of #B9 (119 mg, 0.22 mmol, 1 eq.) in dichloromethane (3 mL) at 0° C. was added 2,6-lutidine (104 µL, 0.89 mmol, 4 eq.) followed by tert-butyl-dimethylsilyl-trifluoromethanesulfonate (160 µL, 067 mmol, 3 eq.) dropwise. After 70 min, the reaction was diluted with saturated sodium bicarbonate and dichloromethane, extracted, filtered over a solvent separator tube and the solvents were removed in vacuo. The crude desired material was purified by reverse phase medium pressure liquid chromatography eluted with 0.02% acetic acid in water (v/v) and 0.02% acetic acid in acetonitrile (v/v) (5% to 100%) to afford #B131 as a white solid. Yield: 34 mg, 0.05 mmol, 23%. LCMS (Protocol C): m/z 671.3 [M+Na]+, retention time=2.08 minutes.

Step 2:

Synthesis of (2Z,4S)—N-[(2R,3R,5S,6S)-6-{(2E,4E)-5-[(3R,4R,5R,7S)-7-(2-amino-2-oxoethyl)-4-{[tert-butyl(dimethyl)silyl]oxy}-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B132). To a solution of #B131 (32 mg, 0.049 mmol, 1 eq.) in 4:1 tetrahydrofuran:water (1 mL) was added lithium hydroxide (11.7 mg, 0.49 mmol, 10 eq.), and the mixture stirred at room temperature for 21 hours. The reaction was concentrated in vacuo, and the residue was taken up in ethyl acetate and water. The aqueous layer was extracted with ethyl acetate (3×) and the combined organic layers were dried over anhydrous sodium sulfate and concentrated in vacuo. Purification by reverse phase medium pressure liquid chromatography eluted with 0.02% acetic acid in water (v/v) and 0.02% acetic acid in acetonitrile (v/v) (10% to 100%) provided #B132 as a white solid. Yield: 11.3 mg, 0.019 mol, 38%. LCMS (Protocol D): m/z 629.3 [M+Na]+, retention time=0.98 minutes.

Step 3:

Synthesis of (2S,3Z)-5-{[(2R,3R,5S,6S)-6-{(2E,4E)-5-[(3R,4R,5R,7S)-7-(2-amino-2-oxoethyl)-4-{[tert-butyl(dimethyl)silyl]oxy}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl methyl[2-(methylsulfanyl)ethyl]carbamate (#B133): To a solution of #B132 (63.2 mg, 0.104 mmol, 1 eq.) in dichloromethane (1.8 mL) was added triethylamine (73 µL, 0.520 mmol, 5 eq), 4-N,N-dimethylamino pyridine (8.9 mg, 0.073 mmol, 0.7 eq.) and bis-(4-nitrophenyl)-carbonate (106 mg, 0.343 mmol, 3.3 eq.) and the reaction stirred at room temperature for 2.5 hours. To ⅓ of this mixture was added N-methyl-2-(methylsulfanyl)ethanamine hydrochloride (24.6 mg, 0.174 mmol, 1.67 eq.), and the mixture was stirred at room temperature for 1 hour. The reaction was diluted with water, extracted with dichloromethane, filtered over a solvent separator tube, diluted with dimethyl sulfoxide (1 mL), and concentrated in vacuo.

The residue purified by reverse phase chromatography (Method A) to provide #B133. Yield: 15.2 mg, 0.021 mmol, 20%. LCMS (Protocol C): m/z 760.76 [M+Na], retention time=2.19 minutes.

Step 4:

Synthesis of (2S,3Z)-5-{[(2R,3R,5S,6S)-6-{(2E,4E)-5-[(3R,4R,5R,7S)-7-(2-amino-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl methyl[2-(methylsulfanyl)ethyl]carbamate (#B130): To a solution of #B133 (15.2 mg, 0.021 mmol, 1 eq.) in tetrahydrofuran (0.4 mL) cooled to 0° C. was added tetrabutylammonium fluoride (1 M in tetrahydrofuran, 53 µL, 0.053 mmol, 2.5 eq.), and the reaction was warmed to rt after 10 min. After 1.5 hours, the reaction was concentrated in vacuo, and the residue purified by reverse phase chromatography (Method A) to provide #B130. Yield: 8.5 mg, 0.014 mmol, 65%. LCMS (Protocol D): m/z 646.3 [M+Na]+, retention time=0.79 minutes. 1H NMR (400 MHz, DMSO-d6, mult, J in Hz) δ 7.77 (d, J=8.2 Hz, 1H), 7.31 (s, 1H), 6.77 (s, 1H), 6.32 (d, J=16.0 Hz, 1H), 6.26-6.18 (m, 1H), 6.09 (d, J=11.5 Hz, 1H), 5.89 (dd, J=11.5 and 7.0 Hz, 1H), 5.60 (dd, J=16.0 and 5.5 Hz, 1H), 5.54-5.47 (m, 1H), 5.00 (d, J=5.5 Hz, 1H), 4.29-4.21 (m, 2H), 3.69-3.61 (m, 2H), 3.54-3.47 (m, 1H), 3.42-3.33 (m, 2H), 3.26-3.21 (m, 1H), 2.89-2.78 (m, 3H), 2.74 (d, J=5.1 Hz, 1H), 2.64-2.56 (m, 3H), 2.36-2.17 (m, 4H), 2.07 (s, 3H), 1.90-1.78 (m, 3H), 1.72-1.61 (m, 4H), 1.54-1.46 (m, 1H), 1.26 (d, J=6.6 Hz, 3H), 1.07 (d, J=6.2 Hz, 3H), 0.96 (d, J=7.0 Hz, 3H).

Example A43

Preparation of (2S,3Z)-5-{[(2R,3R,5S,6S)-6-{(2E,4E)-5-[(3R,4R,5R,7S)-7-(2-amino-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperidine-1-carboxylate (#B134)

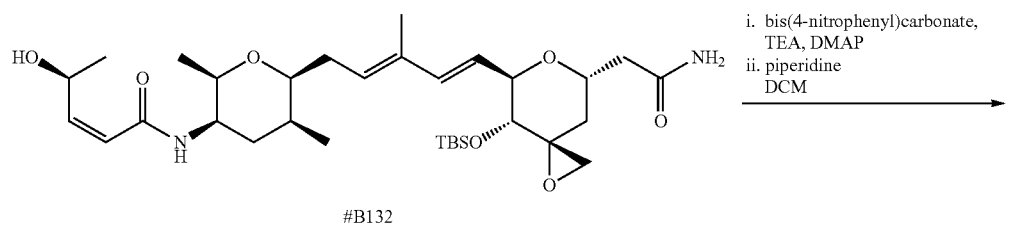

B132

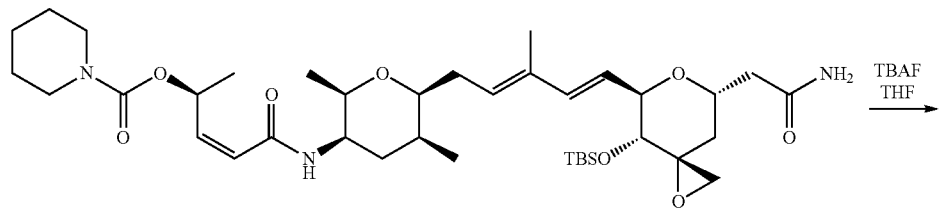

B135

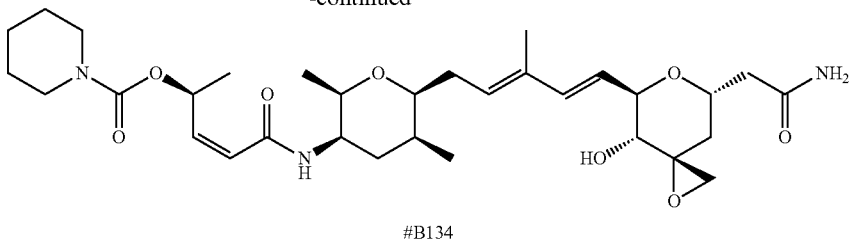

B134

Step 1:
Synthesis of (2S,3Z)-5-{[(2R,3R,5S,6S)-6-{(2E,4E)-5-[(3R,4R,5R,7S)-7-(2-amino-2-oxoethyl)-4-{[tert-butyl(dimethyl)silyl]oxy}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperidine-1-carboxylate (#B135): Using the procedure described in step 3 of example A42, the title compound was prepared in 18% yield from 63.2 mg (0.104 mmol, 1.0 eq) of #B132, triethylamine (73 μL, 0.520 mmol, 5 eq), 4-N,N-dimethylamino pyridine (8.9 mg, 0.073 mmol, 0.7 eq.) and bis-(4-nitrophenyl)-carbonate (106 mg, 0.343 mmol, 3.3 eq.) and piperidine (14.8 mg, 0.174 mmol, 1.7 eq.) using the procedure described for preparation of compound #B133. LCMS (Protocol D): m/z 740.5 [M+Na]+, retention time=1.13 minutes.

Step 2:
Synthesis of (2S,3Z)-5-{[(2R,3R,5S,6S)-6-{(2E,4E)-5-[(3R,4R,5R,7S)-7-(2-amino-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperidine-1-carboxylate (#B134): The title compound was prepared in 76% yield from 13.5 mg (0.019 mmol) of #B135 and 12.8 mg (53 μL of 1 M in tetrahydrofuran, 0.053 mmol, 2.5 eq.) of tetrabutylammonium fluoride using the procedure described for compound #B130. LCMS (Protocol D): m/z 626.60 [M+Na]+, retention time=0.81 minutes. 1H NMR (400 MHz, DMSO-d6, mult, J in Hz) δ 7.77 (d, J=7.80 Hz, 1H), 7.31 (s, 1H), 6.77 (s, 1H), 6.32 (d, J=15.6 Hz, 1H), 6.26-6.17 (m, 1H), 6.09 (d, J=11.7 Hz, 1H), 5.89 (dd, J=11.7 and 7.4 Hz, 1H), 5.60 (dd, J=16.0 and 5.5 Hz, 1H), 5.54-5.47 (m, 1H), 5.00 (d, J=5.5 Hz, 1H), 4.29-4.20 (m, 2H), 3.69-3.61 (m, 2H), 3.54-3.47 (m, 1H), 3.27-3.21 (m, 1H), 2.75 (d, J=5.1 Hz, 1H), 2.58 (d, J=5.1 Hz, 1H), 2.36-2.16 (m, 4H), 1.88-1.78 (m, 3H), 1.73-1.61 (m, 4H), 1.57-1.38 (m, 7H), 1.25 (d, J=6.2 Hz, 3H), 1.07 (d, J=6.2 Hz, 3H), 0.96 (d, J=7.4 Hz, 3H).

Example A44

Preparation of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperazine-1-carboxylate, acetate salt (#B136

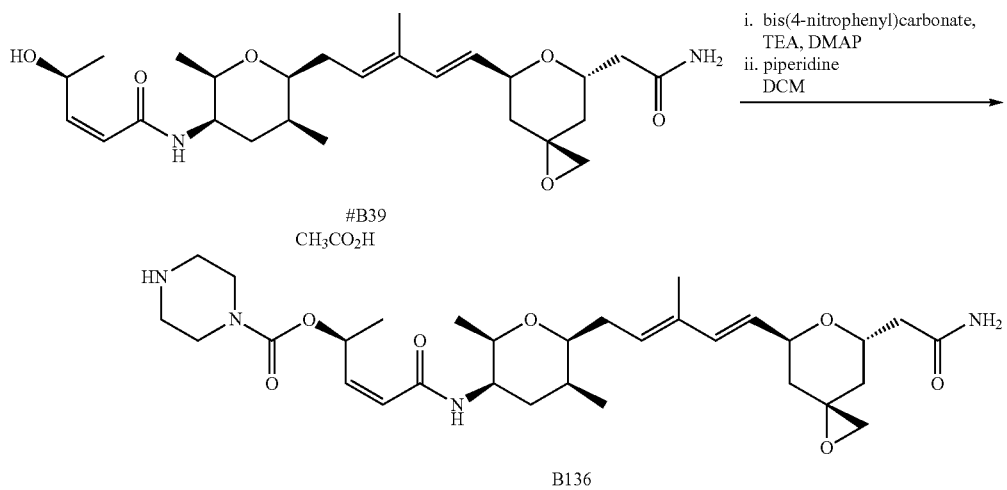

Step 1:
Synthesis of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl piperazine-1-carboxylate, acetate salt (#B136): The title compound was prepared in 27% yield from 37 mg (0.078 mmol) triethylamine (39.7 mg, 0.39 mmol, 5 eq), 4-N,N-dimethylamino pyridine (6.7 mg, 0.055 mmol, 0.7 eq.), bis-(4-nitrophenyl)-carbonate (84.7 mg, 0.273 mmol, 3.5 eq.) and piperazine (16.8 mg, 0.195 mmol, 2.5 eq.) using the procedure described for preparation of compound #B133.

HPLC (Protocol A$^A$): retention time=6.318 minutes (purity 95%). LCMS (Protocol C): m/z 589.4 [M+H]$^+$ retention time=0.97 minutes. $^1$H NMR (400 MHz, DMSO-d$_6$) δ7.77 (d, J=8.20 Hz, 1H), 7.31 (s, 1H), 6.77 (s, 1H), 6.31-6.17 (m, 2H), 6.09 (d, J=11.7 Hz, 1H), 5.89 (dd, J=11.7 and 7.4 Hz, 1H), 5.60 (dd, J=15.6 and 5.5 Hz, 1H), 5.55-5.45 (m, 1H), 4.57-4.50 (m, 1H), 4.35-4.25 (m, 1H), 3.69-3.60 (m, 2H), 3.54-3.46 (m, 2H), 2.65-2.53 (m, 4H) 2.36-2.14 (m, 4H), 1.88 (s, 3H), 1.85-1.73 (m, 3H), 1.72-1.61 (m, 5H), 1.41-1.33 (m, 1H), 1.25 (d, J=6.2 Hz, 3H), 1.07 (d, J=6.2 Hz, 3H), 0.95 (d, J=7.0 Hz, 3H).

Example A45

Preparation of (2S,3Z)-5-{[(2R,3R,5S,6S)-6-{(2E, 4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl -4-methylpiperazine-1-carboxylate (#B137)

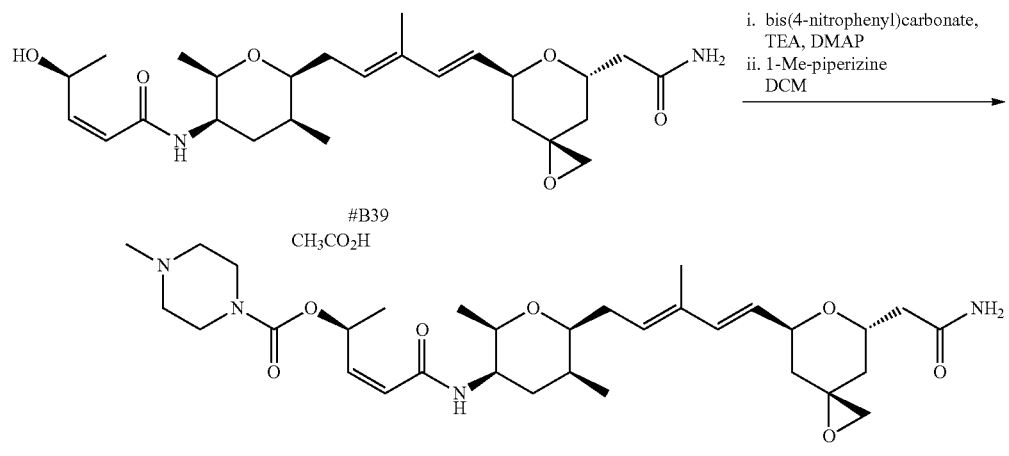

Step 1:
Synthesis of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl-4-methylpiperazine-1-carboxylate, acetate salt (#B137): The title compound was prepared in 27% yield from 37 mg (0.078 mmol) triethylamine (39.7 mg, 0.39 mmol, 5 eq), 4-N,N-dimethylamino pyridine (6.7 mg, 0.055 mmol, 0.7 eq.), bis-(4-nitrophenyl)-carbonate (84.7 mg, 0.273 mmol, 3.5 eq.) and 1-Me-piperazine (19.5 mg, 0.195 mmol, 2.5 eq.) using the procedure described for preparation of compound #B133. LCMS (Protocol C): m/z 603.4 [M+H]$^+$ retention time=1.29 minutes. $^1$H NMR (400 MHz, DMSO-d$_6$) δ 7.77 (d, J=7.8 Hz, 1H), 7.32 (s, 1H), 6.77 (s, 1H), 6.32-6.19 (m, 2H), 6.10 (d, J=11.7 Hz, 1H), 5.89 (dd, J=11.7 and 7.4 Hz, 1H), 5.60 (dd, J=16.0 and 5.9 Hz, 1H), 5.55-5.47 (m, 1H), 4.58-4.50 (m, 1H), 4.35-4.26 (m, 1H), 3.71-3.61 (m, 2H), 3.55-3.47 (m, 2H), 2.65-2.53 (m, 3H), 2.36-2.14 (m, 8H), 1.89 (s, 3H), 1.85-1.74 (m, 3H), 1.72-1.61 (m, 5H), 1.42-1.33 (m, 1H), 1.26 (d, J=6.2 Hz, 3H), 1.07 (d, J=6.2 Hz, 3H), 0.96 (d, J=7.4 Hz, 3H).

Example A46

Preparation of (2S,3Z)-5-{[(2R,3R,5S,6S)-6-{(2E, 4E)-5-[(3R,5S,7S)-7-{[(1H-imidazol-1-ylcarbonyl)amino]methyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B138). and (2Z,4S)—N-[(2R,3R,5S,6S)-6-{(2E, 4E)-5-[(3R,5S,7S)-7-(aminomethyl)-1,6-dioxaspiro[2.5]oct-5-yl]-3-methylpenta-2,4-dien-1-yl}-2,5-dimethyltetrahydro-2H-pyran-3-yl]-4-hydroxypent-2-enamide, acetate salt (#B139) and (2S,3Z)-5-{[(2R,3R,5S,6S)-6-{(2E,4E)-5-[(3R,5S,7S)-7-(aminomethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate, acetate salt (#B140)

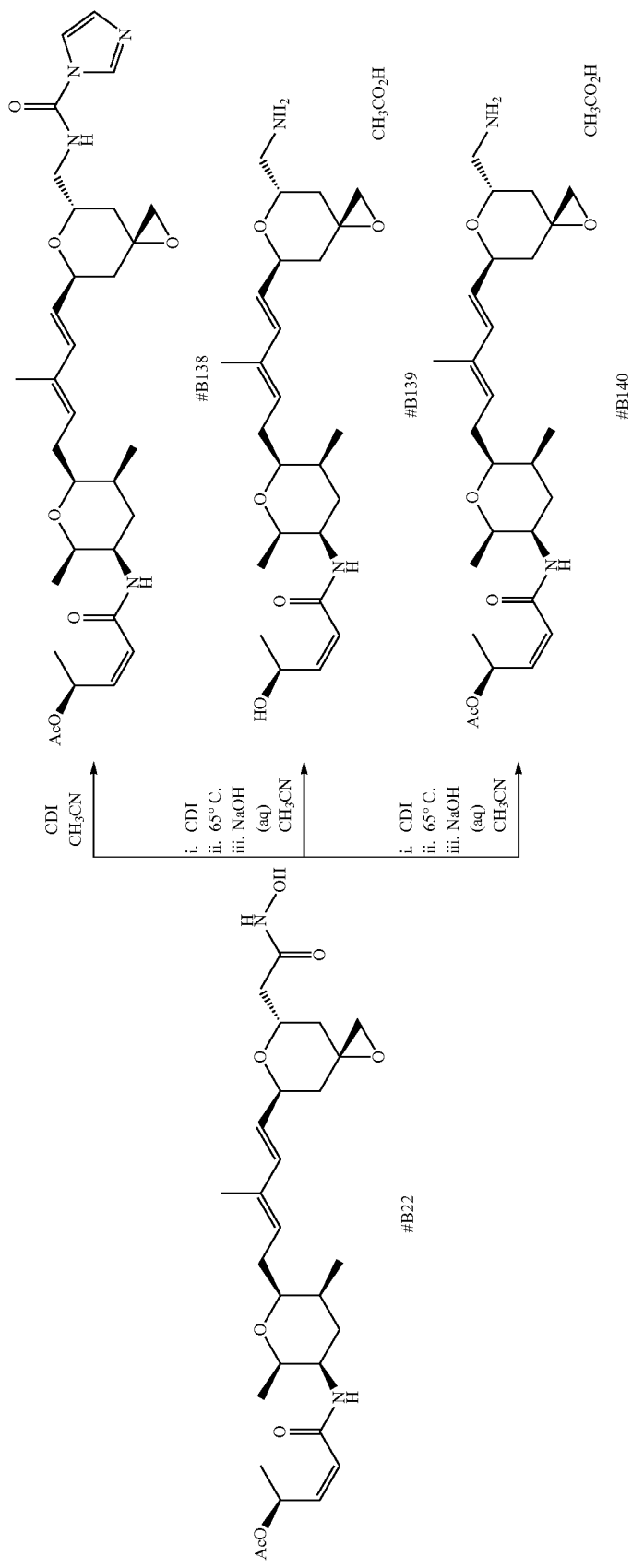

Step 1a.

Synthesis of (2S,3Z)-5-{[(2R,3R,5S,6S)-6-{(2E,4E)-5-[(3R,5S,7S)-7-{[(1H-imidazol-1-ylcarbonyl)amino]methyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B138): To a solution of #B22 (15.9 mg, 0.030 mmol, 1 eq.) in acetonitrile (0.6 mL) at rt was added carbonyl diimidazole (7.4 mg, 0.045 mmol, 1.5 eq.), and the reaction was allowed to stir for 10 min. The reaction was then heated to 60° C. for 5.5 hours and cooled to rt. Water and dichloromethane were added, and the aqueous layer was extracted. The combined organic extracts were dried over sodium sulfate and filtered, and the solvents were removed in vacuo. The crude desired material was purified by reverse phase chromatography (Method A) to give #B138 as a white solid. Yield: 3.4 mg, 0.0059 mmol, 20%. LCMS (Protocol C): m/z 585.4 [M+H]$^+$, retention time=1.40 minutes. HPLC (Protocol A$^A$) retention time=7.426 minutes (purity 83%).

Step 1b.

Synthesis of (2Z,4S)—N-[(2R,3R,5S,6S)-6-{(2E,4E)-5-[(3R,5S,7S)-7-(aminomethyl)-1,6-dioxaspiro[2.5]oct-5-yl]-3-methylpenta-2,4-dien-1-yl}-2,5-dimethyltetrahydro-2H-pyran-3-yl]-4-hydroxypent-2-enamide, acetate salt (#B139): To a solution of #B22 (35.2 mg, 0.066 mmol, 1 eq.) in acetonitrile (2.2 mL) at rt was added carbonyl diimidazole (16.2 mg, 0.099 mmol, 1.5 eq.), and the reaction was allowed to stir for 30 min. The reaction was then heated to 60° C. for 5 hours. The reaction was cooled to rt, added to a solution of acetonitrile (33 mL), water (17 mL), and 1 N NaOH (17 mL) and allowed to stir at rt for 15 min. The reaction was diluted with water and the acetonitrile removed in vacuo. The aqueous solution was extracted with dichloromethane, neutralized with acetic acid (0.5 mL) and concentrated in vacuo. The residue was taken up in acetonitrile, dried over sodium sulfate, filtered and concentrated in vacuo. The crude desired material was purified by reverse phase chromatography (Method A) to give #B139 as a white solid. Yield: 7.7 mg, 0.015 mmol, 23%. LCMS (Protocol C): m/z 449.3 [M+H]$^+$, retention time=0.93 minutes. $^1$H NMR (400 MHz, DMSO-d$_6$, mult, J in Hz) δ7.76 (d, J=8.2 Hz, 1H), 6.26 (d, J=15.6 Hz, 1H), 5.97 (d, J=11.7 Hz, 1H), 5.86 (dd, J=11.7 and 7.0 Hz, 1H), 5.67 (dd, J=15.6 and 5.8 Hz, 1H), 5.56-5.49 (m, 1H), 5.21-5.13 (m, 1H), 4.54-4.46 (m, 1H), 3.79-3.71 (m, 1H), 3.70-3.60 (m, 2H), 3.54-3.46 (m, 1H), 2.80 (dd, J=12.9 and 7.4 Hz, 1H), 2.62 (s, 2H), 2.58-2.53 (m, 1H), 2.37-2.14 (m, 2H), 1.89-1.56 (m, 11H), 1.44 (dd, J=13.3 and 7.4 Hz, 1H), 1.11 (d, J=6.6 Hz, 3H), 1.07 (d, J=6.2 Hz, 3H), 0.96 (d, J=7.4 Hz, 3H).

Step 1c.

Synthesis of (2S,3Z)-5-{[(2R,3R,5S,6S)-6-{(2E,4E)-5-[(3R,5S,7S)-7-(aminomethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate, acetate salt (#B140): To a solution of #B22 (50.8 mg, 0.095 mmol, 1 eq.) in acetonitrile (3.1 mL) at rt was added carbonyl diimidazole (23.4 mg, 0.143 mmol, 1.5 eq.), and the reaction was allowed to stir for 30 min. The reaction was then heated to 65° C. for 4 hours. The reaction was cooled to rt, added to a solution of acetonitrile (83 mL), water (6 mL), and 1 N NaOH (6 mL) and allowed to stir at rt for 35 min. The reaction was neutralized with acetic acid (0.35 mL) and concentrated in vacuo. The residue was taken up in acetonitrile, dried over sodium sulfate, filtered and concentrated in vacuo. The crude desired material was purified by reverse phase chromatography (Method A) to give #B140 Yield: 15 mg, 0.030 mmol, 32%. LCMS (Protocol C): m/z 491.3 [M+H]$^+$, retention time=1.13 minutes. HPLC (Protocol A$^A$) retention time=6.969 minutes (purity 87%). $^1$H NMR (400 MHz, DMSO-d$_6$, mult, J in Hz) δ 7.78 (d, J=7.8 Hz, 1H), 6.42-6.30 (m, 1H), 6.26 (d, J=16.0 Hz, 1H), 6.11 (d, J=11.5 Hz, 1H), 5.87 (dd, J=11.5 and 7.4 Hz, 1H), 5.67 (dd, J=16.0 and 5.8 Hz, 1H), 5.56-5.49 (m, 1H), 4.54-4.46 (m, 1H), 3.81-3.73 (m, 1H), 3.69-3.61 (m, 2H), 3.54-3.46 (m, 1H), 2.80 (dd, J=12.9 and 7.4 Hz, 1H), 2.63 (s, 2H), 2.58-2.53 (m, 1H), 2.37-2.14 (m, 2H), 1.98 (s, 3H), 1.84-1.56 (m, 8H), 1.44 (dd, J=13.3 and 7.4 Hz, 1H), 1.25 (d, J=6.2 Hz, 3H), 1.07 (d, J=6.6 Hz, 3H), 0.96 (d, J=7.0 Hz, 3H).

Example A47

Preparation of (2S,3Z)-5-{[(2R,3R,5S,6S)-6-{(2E,4E)-5-[(3R,4R,5R,7S)-4-hydroxy-7-{2-[(trans-4-hydroxycyclohexyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B141). and (2S,3Z)-5-{[(2R,3R,5S,6S)-6-{(2E,4E)-5-[(3R,4R,5R,7S)-4-hydroxy-7-{2-[(cis-3-hydroxycyclobutyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B142). and (2S,3Z)-5-({(2R,3R,5S,6S)-6-[(2E,4E)-5-{(3R,4R,5R,7S)-4-hydroxy-7-[2-(2-methylhydrazinyl)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B143). and (2S,3Z)-5-({(2R,3R,5S,6S)-6-[(2E,4E)-5-{(3R,4R,5R,7S)-4-hydroxy-7-[2-(1-methylhydrazinyl)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B144). and (2S,3Z)-5-({(2R,3R,5S,6S)-6-[(2E,4E)-5-{(3R,4R,5R,7S)-7-[2-(1,2-dimethylhydrazinyl)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B145)

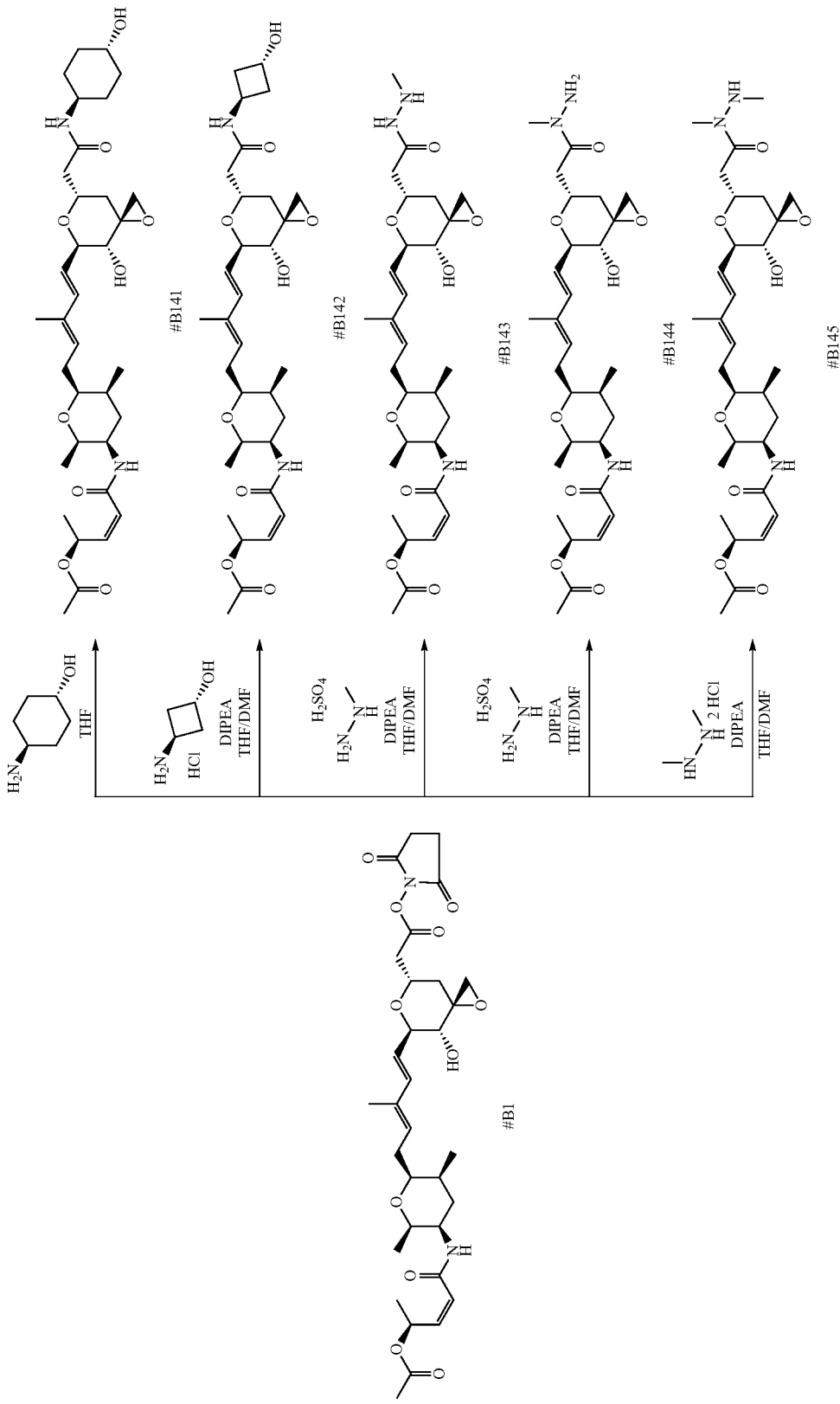

Step 1a.

Synthesis of (2S,3Z)-5-{[(2R,3R,5S,6S)-6-{(2E,4E)-5-[(3R,4R,5R,7S)-4-hydroxy-7-{2-[(trans-4-hydroxycyclohexyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B141). To a solution of #B1 (19.7 mg, 0.031 mmol, 1 eq.) dissolved in tetrahydrofuran (0.5 mL) was added trans-4-aminocyclohexanol (5.7 mg, 0.049 mmol, 1.6 eq.) After stirring for 1.5 hour, the reaction was diluted with water, extracted with dichloromethane, and the combined organics were dried over sodium sulfate and filtered. The solvents were removed in vacuo. The crude desired material was purified by reverse phase chromatography (Method A) to give #B141 as a white solid. Yield: 11.8 mg, 0.019 mmol, 60%. HPLC (Protocol $A^4$) retention time=7.408 minutes (purity 94%). LCMS (Protocol D): m/z 633.3 $[M+H]^+$, retention time=0.73 minutes. $^1$H NMR (400 MHz, DMSO-$d_6$) δ 7.79 (d, J=8.2 Hz, 1H), 7.68 (d, J=7.8 Hz, 1H), 6.42-6.32 (m, 1H), 6.28 (d, J=16.0 Hz, 1H), 6.11 (d, J=11.5 Hz, 1H), 5.87 (dd, J=11.5 and 7.4 Hz, 1H), 5.59 (dd, J=16.0 and 5.5 Hz, 1H), 5.54-5.45 (m, 1H), 5.00 (d, J=5.1 Hz, 1H), 4.49 (d, J=4.3 Hz, 1H), 4.30-4.15 (m, 2H), 3.70-3.60 (m, 2H), 3.54-3.39 (m, 2H), 3.26-3.20 (m, 1H), 2.74 (d, J=5.1 Hz, 1H), 2.58 (d, J=5.1 Hz, 1H), 2.37-2.10 (m, 3H), 1.98 (s, 3H), 1.89-1.59 (m, 10H), 1.51-1.41 (m, 1H), 1.25 (d, J=6.6 Hz, 3H), 1.20-1.10 (m, 4H), 1.07 (d, J=6.2 Hz, 3H), 0.95 (d, J=7.4 Hz, 3H).

Step 1b.

Synthesis of (2S,3Z)-5-{[(2R,3R,5S,6S)-6-{(2E,4E)-5-[(3R,4R,5R,7S)-4-hydroxy-7-{2-[(cis-3-hydroxycyclobutyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B142). To a solution of #B1 (16.2 mg, 0.026 mmol, 1 eq.) in tetrahydrofuran/N,N-dimethylformamide (5:1, 0.6 mL) at rt was added N,N-diisopropylethylamine (13.7 μL, 0.078 mmol, 3 eq.) and trans-3-aminocyclobutanol hydrochloride (4.8 mg, 0.039 mmol, 1.5 eq.) (12:48 pm), and the reaction was stirred for 2 hours. Additional N,N-dimethylformamide (100 uL), N,N-diisopropylethylamine (13 uL, 0.078 mmol, 3 eq.) and trans-3-aminocyclobutanol hydrochloride (3 mg, 0.024 mmol, 0.9 eq.) were added, and the reaction was stirred for an additional 30 min. The reaction was diluted with dimethyl sulfoxide and concentrated in vacuo to remove the tetrahydrofuran. The crude desired material was purified by reverse phase chromatography (Method A) to give #B142 as a white solid. Yield: 9.5 mg, 0.016 mmol, 61%. HPLC (Protocol $A^4$) retention time=7.057 minutes (purity 91%). LCMS (Protocol D): m/z 627.1 $[M+Na]^+$, retention time=0.72 minutes. $^1$H NMR (400 MHz, DMSO-$d_6$) δ 8.03 (d, J=7.8 Hz, 1H), 7.79 (d, J=8.2 Hz, 1H), 6.42-6.32 (m, 1H), 6.28 (d, J=16.0 Hz, 1H), 6.11 (d, J=11.7 Hz, 1H), 5.87 (dd, J=11.7 and 7.4 Hz, 1H), 5.59 (dd, J=16.0 and 5.5 Hz, 1H), 5.55-5.48 (m, 1H), 5.07-4.97 (m, 2H), 4.30-4.17 (m, 2H), 3.81-3.71 (m, 1H), 3.70-3.59 (m, 3H), 3.54-3.46 (m, 1H), 3.27-3.20 (m, 1H), 2.75 (d, J=4.9 Hz, 1H), 2.58 (d, J=4.9 Hz, 1H), 2.48-2.39 (m, 2H), 2.36-2.13 (m, 3H), 1.98 (s, 3H), 1.89-1.61 (m, 9H), 1.49-1.41 (m, 1H), 1.25 (d, J=6.6 Hz, 3H), 1.07 (d, J=6.2 Hz, 3H), 0.95 (d, J=7.4 Hz, 3H).

Step 1c.

Synthesis of (2S,3Z)-5-({(2R,3R,5S,6S)-6-[(2E,4E)-5-{(3R,4R,5R,7S)-4-hydroxy-7-[2-(2-methylhydrazinyl)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B143) and (2S,3Z)-5-({(2R,3R,5S,6S)-6-[(2E,4E)-5-{(3R,4R,5R,7S)-4-hydroxy-7-[2-(1-methylhydrazinyl)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B144): To a solution of #B1 (32.4 mg, 0.051 mmol, 1 eq.) in tetrahydrofuran/N,N-dimethylformamide (2:1, 0.75 mL) was added at rt was added N,N-diisopropylethylamine (71.8 μL, 0.408 mmol, 8 eq.) and N-methylhydrazine sulfate (22.1 mg, 0.15 mmol, 3 eq.), and the reaction was stirred for 20 min. Additional N,N-dimethylformamide (250 uL) was added. After an additional 30 min, more N,N-diisopropylethylamine (35 uL, 0.20 mmol, 4 eq.) and N-methylhydrazine sulfate were added (15 mg, 0.10 mmol, 2 eq), and the reaction was stirred for 45 min. The reaction was diluted with water and ethyl acetate, and the aqueous layer was extracted. The combined organic layers were washed with brine, dried over sodium sulfate, filtered and concentrated in vacuo. The crude desired material was purified by reverse phase chromatography (Method A) to give #B143 and #B144 as a white solids.

B143 Yield: 1.9 mg, 0.0034 mmol, 7%. LCMS (Protocol D): m/z 564.2 $[M+H]^+$, retention time=0.73 minutes. $^1$H NMR (500 MHz, DMSO-$d_6$) δ 9.31 (d, J=5.9 Hz, 1H), 7.81 (d, J=8.1 Hz, 1H), 6.41-6.32 (m, 1H), 6.29 (d, J=16.0 Hz, 1H), 6.11 (d, J=11.6 Hz, 1H), 5.87 (dd, J=11.6 and 7.6 Hz, 1H), 5.59 (dd, J=16.0 and 5.6 Hz, 1H), 5.54-5.48 (m, 1H), 5.04 (d, J=5.4 Hz, 1H), 4.80-4.72 (m, 2H), 4.29-4.20 (m, 2H), 3.69-3.61 (m, 2H), 3.53-3.46 (m, 1H), 3.27-3.21 (m, 1H), 2.75 (d, J=5.1 Hz, 1H), 2.58 (d, J=5.1 Hz, 1H), 2.45-2.13 (m, 7H), 1.98 (s, 3H), 1.89-1.74 (m, 3H), 1.72-1.58 (m, 4H), 1.53-1.45 (m, 1H), 1.25 (d, J=6.6 Hz, 3H), 1.07 (d, J=6.4 Hz, 3H), 0.95 (d, J=7.3 Hz, 3H).

B144 Yield: 2.3 mg, 0.0040 mmol, 8%. LCMS (Protocol D): m/z 564.2 $[M+H]^+$, retention time=0.76 minutes. $^1$H NMR (500 MHz, DMSO-$d_6$) δ 7.81 (d, J=7.8 Hz, 1H), 6.41-6.27 (m, 2H), 6.11 (d, J=11.5 Hz, 1H), 5.87 (dd, J=11.5 and 7.3 Hz, 1H), 5.60 (dd, J=16.1 and 5.9 Hz, 1H), 5.56-5.48 (m, 1H), 4.94 (d, J=6.4 Hz, 1H), 4.67 (s, 1H), 4.32-4.20 (m, 2H), 3.69-3.62 (m, 2H), 3.53-3.47 (m, 1H), 3.26-3.21 (m, 1H), 3.06 (dd, J=154 and 7.3 Hz, 1H), 2.98 (s, 2H), 2.75 (d, J=4.9 Hz, 1H), 2.62-2.53 (m, 2H), 2.35-2.13 (m, 3H), 1.98 (s, 3H), 1.89-1.74 (m, 3H), 1.72-1.58 (m, 5H), 1.25 (d, J=6.4 Hz, 3H), 1.07 (d, J=6.4 Hz, 3H), 0.95 (d, J=7.3 Hz, 3H).

Step 1d.

Synthesis of (2S,3Z)-5-({(2R,3R,5S,6S)-6-[(2E,4E)-5-{(3R,4R,5R,7S)-7-[2-(1,2-dimethylhydrazinyl)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B145): To a solution of #B1 (29.7 mg, 0.047 mmol, 1 eq.) in tetrahydrofuran/N,N-dimethylformamide (1:1, 1 mL) at rt was added N,N-diisopropylethylamine (116 μL, 0.658 mmol, 14 eq.) followed by N,N'-dimethylhydrazine dihydrochloride (31.3 mg, 0.235 mmol, 5 eq.), and the reaction was stirred for 30 min. The reaction was diluted with water and ethyl acetate, and the aqueous layer extracted. The combined organic layers were washed with brine, dried over sodium sulfate, filtered and concentrated in vacuo. The crude desired material was purified by reverse phase chromatography (Method A) to give #B145 as a white solid. Yield: 2.2 mg, 0.0038 mmol, 8%. LCMS (Protocol D): m/z 578.2 $[M+H]^+$, retention time=0.82 minutes. $^1$H NMR (500 MHz, DMSO-$d_6$) δ 7.81 (d, J=8.1 Hz, 1H), 6.41-6.27 (m, 2H), 6.11 (d, J=11.7 Hz, 1H), 5.87 (dd, J=11.7 and 7.6 Hz, 1H), 5.60 (dd, J=15.9 and 5.4 Hz, 1H), 5.56-5.48 (m, 1H), 4.94 (d, J=6.6 Hz, 1H), 4.79 (q, J=5.7 Hz, 1H), 4.32-4.19 (m, 2H), 3.68-3.61 (m, 2H), 3.53-3.47 (m, 1H), 3.26-3.21 (m, 1H), 3.01 (d, J=15.2 and 7.3 Hz, 1H), 2.93 (s, 3H), 2.76-2.73 (m, 1H), 2.60-2.53 (m, 2H), 2.44 (d, J=5.7 Hz, 3H), 2.35-2.15 (m, 3H), 1.98 (s, 3H), 1.87-1.75 (m, 3H), 1.72-1.56 (m, 5H), 1.25 (d, J=6.4 Hz, 3H), 1.07 (d, J=6.4 Hz, 3H), 0.95 (d, J=7.3 Hz, 3H).

Example A48

Preparation of N-{6-[(bromoacetyl)amino]hexanoyl}-D-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N~5~-carbamoyl-L-ornithinamide (#B146)

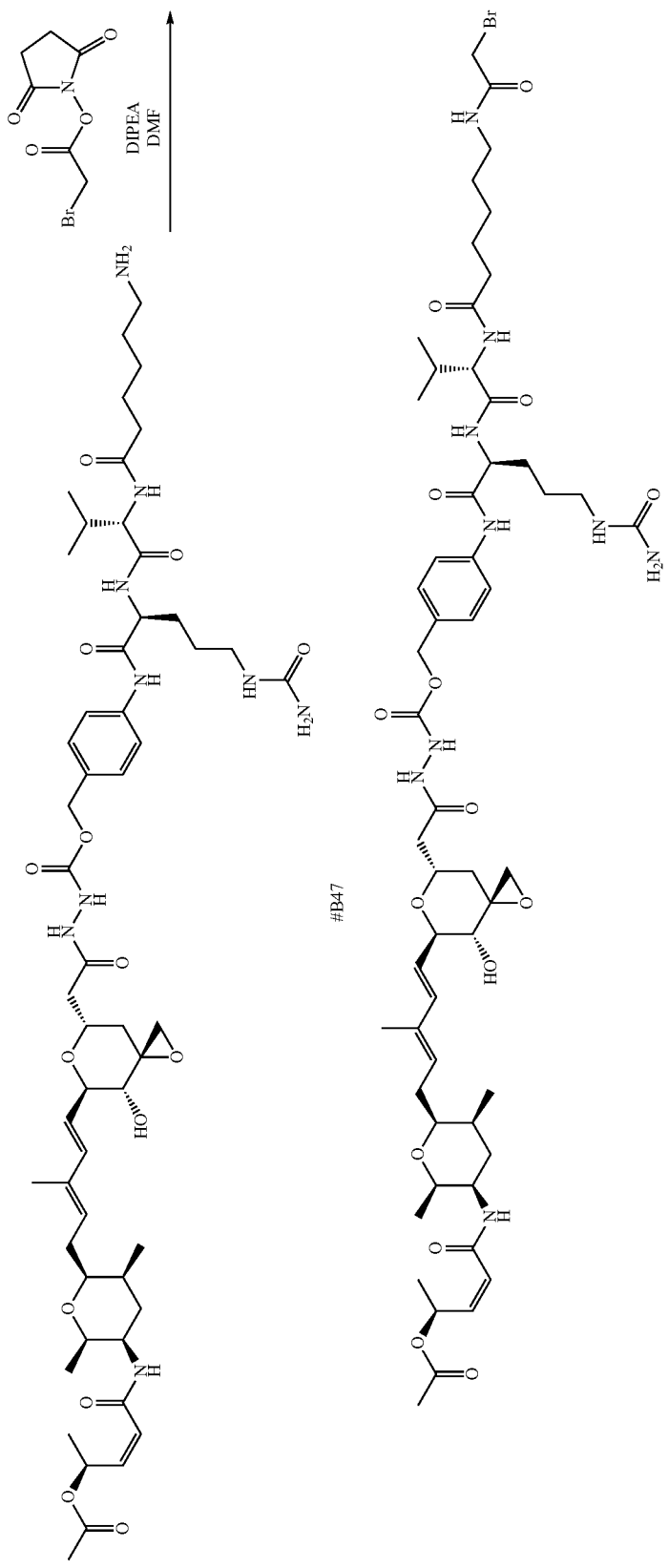

Step 1:

Synthesis of N-{6-[(bromoacetyl)amino]hexanoyl}-D-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N~5~-carbamoyl-L-ornithinamide (#B146). To a solution of #B47 (10.4 mg, 0.009 mmol, 1 eq.) in N,N-dimethylformamide (0.3 mL) at rt was added N,N-diisopropylethylamine (6.3 µL, 0.036 mmol, 4 eq.) followed by 1-[(bromoacetyl)oxy]pyrrolidine-2,5-dione (4.2 mg, 0.017 mmol, 1.9 eq.) and was stirred for 15 minutes and then purified by reverse phase chromatography (Method A) to afford #B146 as a white solid. Yield: 4.6 mg, 0.004 mmol, 43%. HPLC (Protocol $A^4$): retention time=7.597 minutes (purity 87%). LCMS (Protocol C): m/z 1188.6 [M+H]$^+$ retention time=1.37 minutes. $^1$H NMR (400 MHz, DMSO-d$_6$) δ 9.99 (s, 1H), 9.68 (s, 1H), 9.12 (s, 1H), 8.26-8.18 (m, 1H), 8.11-8.04 (m, 1H), 7.84-7.74 (m, 2H), 7.64-7.54 (m, 2H), 7.34-7.21 (m, 2H), 6.41-6.27 (m, 2H), 6.11 (d, J=11.7 Hz, 1H), 6.00-5.93 (m, 1H), 5.87 (dd, J=11.7 and 7.4 Hz, 1H), 5.65-5.47 (m, 2H), 5.40 (s, 2H), 5.04 (d, J=5.5 Hz, 1H), 5.02-4.96 (m, 2H), 4.43-4.34 (m, 1H), 4.30-4.16 (m, 3H), 3.81 (s, 2H), 3.69-3.60 (m, 2H), 3.54-3.45 (m, 1H), 3.26-3.20 (m, 1H), 3.09-2.88 (m, 4H), 2.77-2.73 (m, 1H), 2.62-2.55 (m, 1H), 2.36-2.07 (m, 5H), 1.98 (s, 3H), 1.84-1.76 (m, 1H), 1.73-1.61 (m, 5H), 1.54-1.33 (m, 5H), 1.29-1.21 (m, 5H), 1.07 (d, J=6.2 Hz, 3H), 0.95 (d, J=7.4 Hz, 3H), 0.84 (dd, J=11.3 and 6.6 Hz, 6H).

Example A49

Preparation of (2S,3Z)-5-{[(2R,3R,5S,6S)-6-{(2E,4E)-5-[(3R,4R,5R,7S)-7-(aminomethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate, acetate salt (#B147)

Step 1:

Synthesis of (2S,3Z)-5-{[(2R,3R,5S,6S)-6-{(2E,4E)-5-[(3R,4R,5R,7S)-7-(aminomethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B147): To a solution of #B14 (40 mg, 0.073 mmol, 1 eq.) in acetonitrile (2.3 mL) was added CDI (29.8 mg, 0.182 mmol, 2.5 eq.) at rt, and the reaction was stirred for 40 min. The reaction was then heated to 65° C. for 4 hours. After cooling to rt, the reaction mixture was added to a solution of acetonitrile (63 mL), water (4.5 mL), and 1 N NaOH (4.5 mL) and stirred for 30 min. Acetic acid (270 uL) was added, and the mixture concentrated in vacuo. The obtained residue was taken up in acetonitrile, dried over sodium sulfate, filtered and concentrated in vacuo. The crude desired material was purified by reverse phase chromatography (Method A) to give #B147 as a white solid. Yield: 5.1 mg, 0.0088 mmol, 12%. HPLC (Protocol $A^4$) retention time=6.778 minutes (purity 89%). LCMS (Protocol C): m/z 507.2 [M+H]$^+$, retention time=0.98 minutes. $^1$H NMR (400 MHz, DMSO-d$_6$) δ 7.77 (d, J=7.4 Hz, 1H), 6.41-6.24 (m, 2H), 6.11 (d, J=11.7 Hz, 1H), 5.87 (dd, J=11.7 and 7.4 Hz, 1H), 5.65 (dd, J=16.0 and 6.2 Hz, 1H), 5.56-5.48 (m, 1H), 5.00-4.91 (m, 1H), 4.27-4.20 (m, 1H), 3.78-3.60 (m, 3H), 3.55-3.46 (m, 1H), 3.22-3.18 (m, 1H), 2.80-2.71 (m, 2H), 2.62-2.53 (m, 2H), 2.33-2.15 (m, 3H), 1.98 (s, 3H), 1.89-1.77 (m, 5H), 1.73-1.61 (m, 4H), 1.48-1.41 (m, 1H), 1.25 (d, J=6.2 Hz, 3H), 1.07 (d, J=6.2 Hz, 3H), 0.95 (d, J=7.0 Hz, 3H).

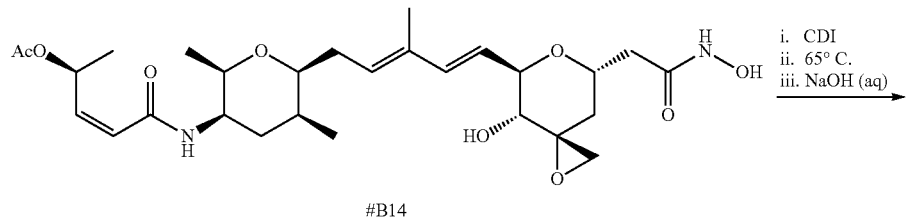

B14

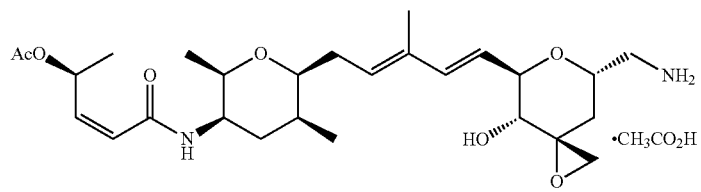

B147

Example A50

Preparation of methyl [(3S,5S,7S)-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B148)

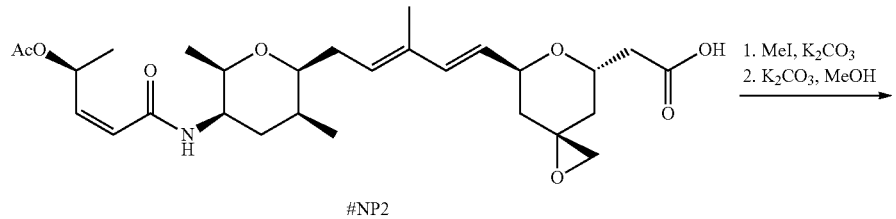

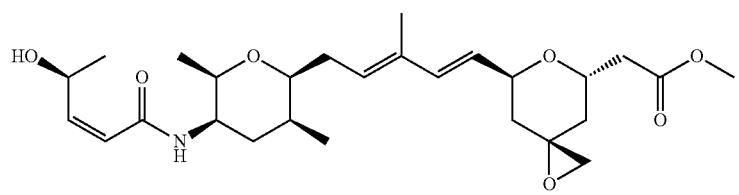

Step 1:
Synthesis of methyl [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B148): To a solution of #NP2 (204 mg, 0.393 mmol, 1 eq.) in N,N-dimethylformamide (4.5 mL) at rt was added potassium carbonate (272 mg, 1.96 mmol, 5 eq.) and iodomethane (740 μL, 11.8 mmol, 30 eq.), and the reaction was stirred for 1.5 hours. The reaction was filtered, washed with water ((3×)), dried over sodium sulfate, filtered and concentrated in vacuo. LCMS (protocol D): m/z 534.42 [M+H]$^+$, retention time=0.89 min. The crude material was used in next step without further purification.

Step 2:
Synthesis of methyl [(3S,5S,7S)-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B148). To a solution of the crude material from Step 1 of example A#50 in methanol (3.5 mL) at rt was added potassium carbonate (136 mg, 0.056 mmol, 2.5 eq.), and the reaction was stirred for 2 hours. The reaction was filtered with methanol, diluted with dimethyl sulfoxide (2 mL), and concentrated in vacuo.

Purification by reverse phase medium pressure liquid chromatography eluted with 0.02% acetic acid in water (v/v) and 0.02% acetic acid in acetonitrile (v/v) (10% to 90%) provided #B148 as a white solid. Yield: 91.6 mg, 0.18 mmol, 48%. LCMS (Protocol D): m/z 492.47 [M+H]$^+$, retention time=0.80 minutes. $^1$H NMR (400 MHz, DMSO-d$_6$) δ 7.76 (d, J=7.8 Hz, 1H), 6.25 (d, J=16.0 Hz, 1H), 5.97 (d, J=11.9 Hz, 1H), 5.87 (d, J=11.9 and 7.0 Hz, 1H), 5.65-5.48 (m, 2H), 5.22-5.13 (m, 1H), 5.10 (d, J=4.7 Hz, 1H), 4.56-4.48 (m, 1H), 4.36-4.25 (m, 1H), 3.69-3.61 (m, 2H), 3.60 (s, 3H), 3.55-3.46 (m, 1H), 2.74-2.56 (m, 4H), 2.38-2.13 (m, 2H), 1.90-1.60 (m, 9H), 1.44 (dd, J=13.2 and 7.0 Hz, 1H), 1.11 (d, J=6.2 Hz, 3H), 1.06 (d, J=6.2 Hz, 3H), 0.96 (d, J=7.0 Hz, 3H).

Example A51

Preparation of (2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl 4-(methylsulfanyl)butanoate (#B149)

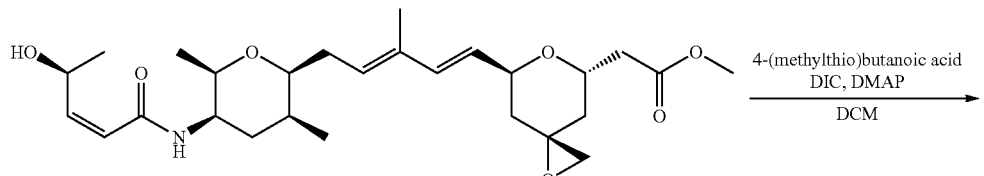

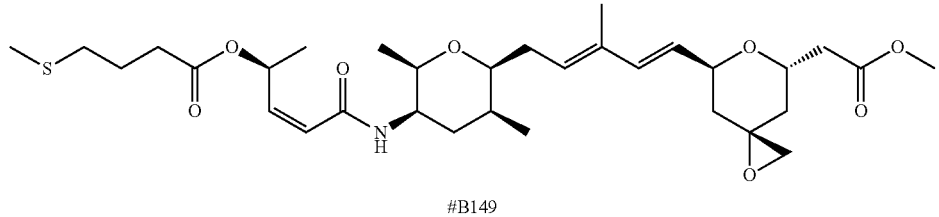

B149

Step 1:

Synthesis of (2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl 4-(methylsulfanyl)butanoate (#B149). To a solution of #B148 (12 mg, 0.024 mmol, 1 eq.) in dichloromethane (0.5 mL) was added 4-(methylthio)butanoic acid (32.2 mg, 0.24 mmol, 10 eq.), 4-N,N-dimethylamino pyridine (2.9 mg, 0.023 mmol, 1 eq.), and DIC (41.3 µL, 0.264 mmol, 11 eq.), and the reaction was allowed to stir for 1 hour. The reaction was diluted with dimethylsulfoxide (0.8 mL) and concentrated in vacuo. The crude desired material was purified by reverse phase chromatography (Method A) to give #B149 as a gum. Yield: 9.7 mg, 0.016 mmol, 66%. LCMS (Protocol D): m/z 608.2 [M+H]$^+$, retention time=1.05 minutes. $^1$H NMR (400 MHz, DMSO-d$_6$) δ 7.79 (d, J=7.8 Hz, 1H), 6.44-6.32 (m, 1H), 6.25 (d, J=16.0 Hz, 1H), 6.12 (d, J=11.7 Hz, 1H), 5.87 (dd, J=11.7 and 7.4 Hz, 1H), 5.62-5.50 (m, 2H), 4.57-4.48 (m, 1H), 4.36-4.25 (m, 1H), 3.70-3.62 (m, 2H), 3.60 (s, 3H), 3.55-3.47 (m, 1H), 2.74-2.56 (m, 4H), 2.48-2.43 (m, 2H), 2.41-2.15 (m, 4H), 2.02 (s, 3H), 1.88-1.60 (m, 11H), 1.44 (dd, J=12.9 and 6.6 Hz, 1H), 1.26 (d, J=6.6 Hz, 3H), 1.07 (d, J=6.2 Hz, 3H), 0.96 (d, J=7.4 Hz, 3H).

Example A52

Preparation of (2S,3Z)-5-{[(2R,3R,5S,6S)-6-{(2E,4E)-5-[(3R,4R,5R,7S)-7-{[(bromoacetyl)amino]methyl}-4-hydroxy-1,6-dioxaspiro[22.5]oct-5-yl]-3-methylpenta-2,4-dien-1-yl}-2,5-dimethyltetrahydro-2H-pyran-3-yl]amino}-5-oxopent-3-en-2-yl acetate (#B150)

Step 1:

Synthesis of (2S,3Z)-5-{[(2R,3R,5S,6S)-6-{(2E,4E)-5-[(3R,4R,5R,7S)-7-{[(bromoacetyl)amino]methyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B150): To a solution of #B147 (7 mg, 0.01 mmol, 1 eq.) in N,N-dimethylformamide (0.4 mL) at rt was added N,N-diisopropylethylamine (8.5 µL, 0.048 mmol, 4 eq.) and 1-[(bromoacetyl)oxy]pyrrolidine-2,5-dione (4.2 mg, 0.018 mmol, 1.5 eq.), and the reaction was stirred for 10 min. The crude desired material was purified by reverse phase chromatography (Method A) to give #B150 as white solid. Yield: 2.9 mg, 0.005 mmol, 40%. LCMS (Protocol D): m/z 649.2 [M+Na]$^+$, retention time=0.81 minutes. $^1$H NMR (400 MHz, DMSO-d$_6$) δ 8.42-8.32 (m, 1H), δ 7.79 (d, J=7.8 Hz, 1H), 6.44-6.32 (m, 1H), 6.28 (d, J=16.0 Hz, 1H), 6.11 (d, J=11.3 Hz, 1H), 5.87 (dd, J=11.3 and 7.4 Hz, 1H), 5.61 (dd, J=16.0 and 5.5 Hz, 1H), 5.56-5.49 (m, 1H), 5.02 (d, J=5.9 Hz, 1H), 4.33-4.26 (m, 1H), 3.95-3.83 (m, 3H), 3.72-3.59 (m, 2H), 3.55-3.45 (m, 1H), 3.40-3.32 (m, 1H), 3.28-3.14 (m, 2H), 2.77 (d, J=5.1 Hz, 1H), 2.61 (d, J=5.1 Hz, 1H), 2.31-2.12 (m, 2H), 1.98 (s, 3H), 1.88-1.75 (m, 3H), 1.73-1.61 (m, 4H), 1.51-1.41 (m, 1H), 1.25 (d, J=6.2 Hz, 3H), 1.07 (d, J=6.2 Hz, 3H), 0.95 (d, J=7.0 Hz, 3H).

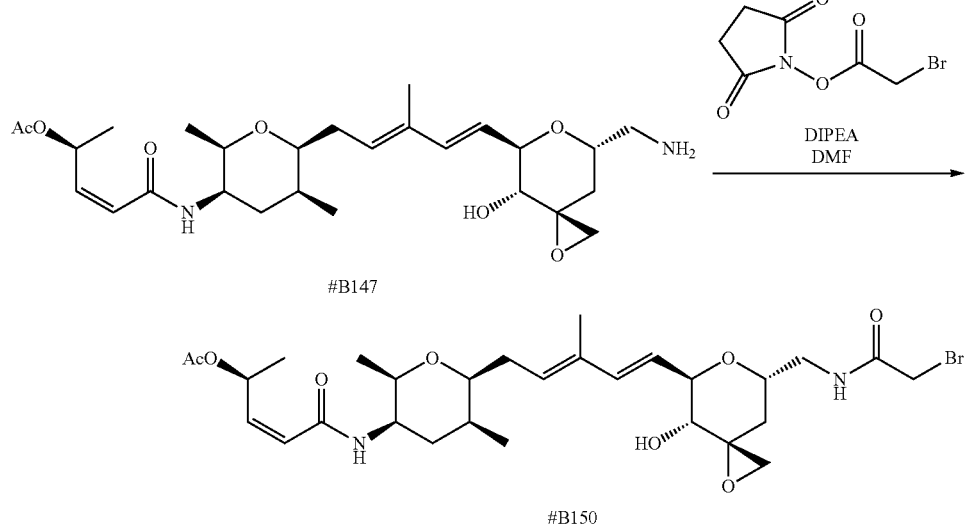

Example A53

Preparation of N-{6-[(bromoacetyl)amino]hexanoyl}-L-valyl-N-(4-{[({[(3R,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]methyl}carbamoyl)oxy]methyl}phenyl)-N~5~-carbamoyl-L-ornithinamide (#B151)

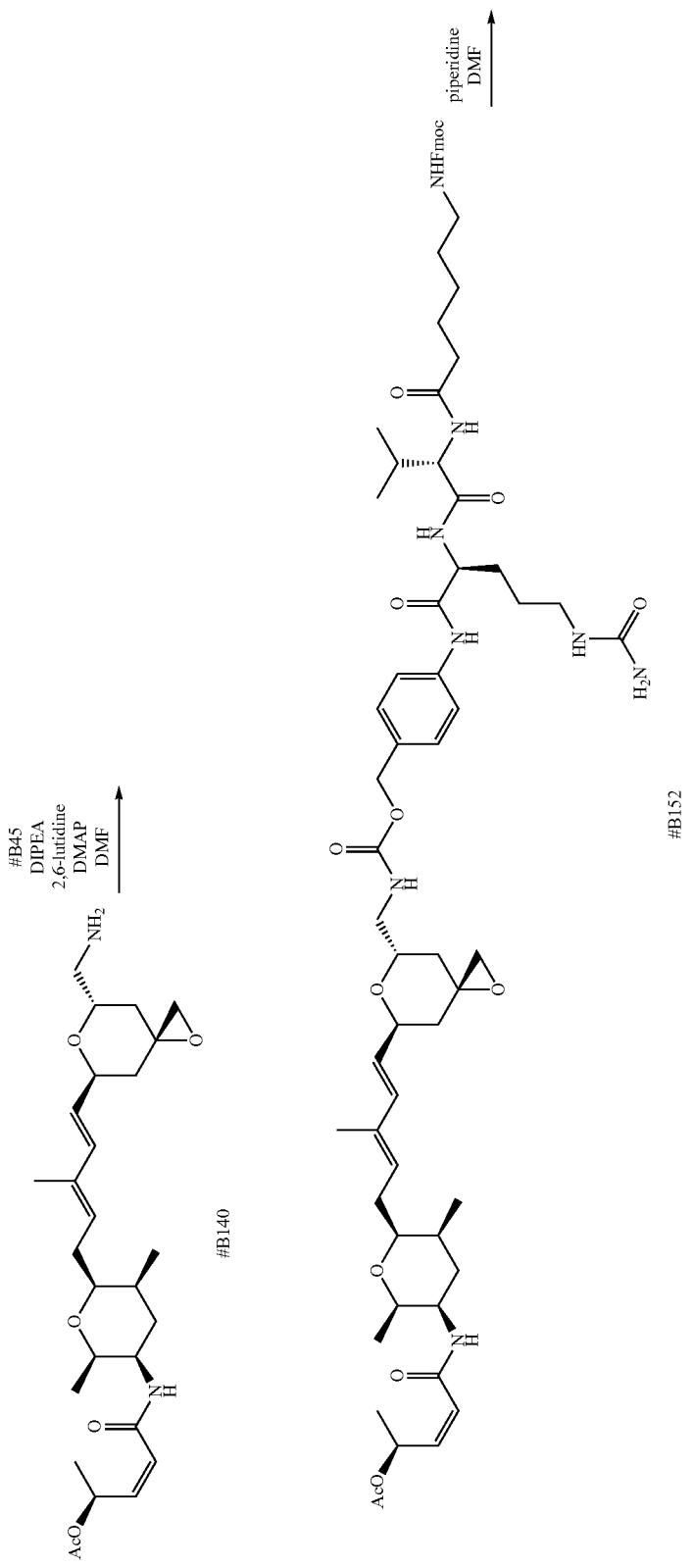

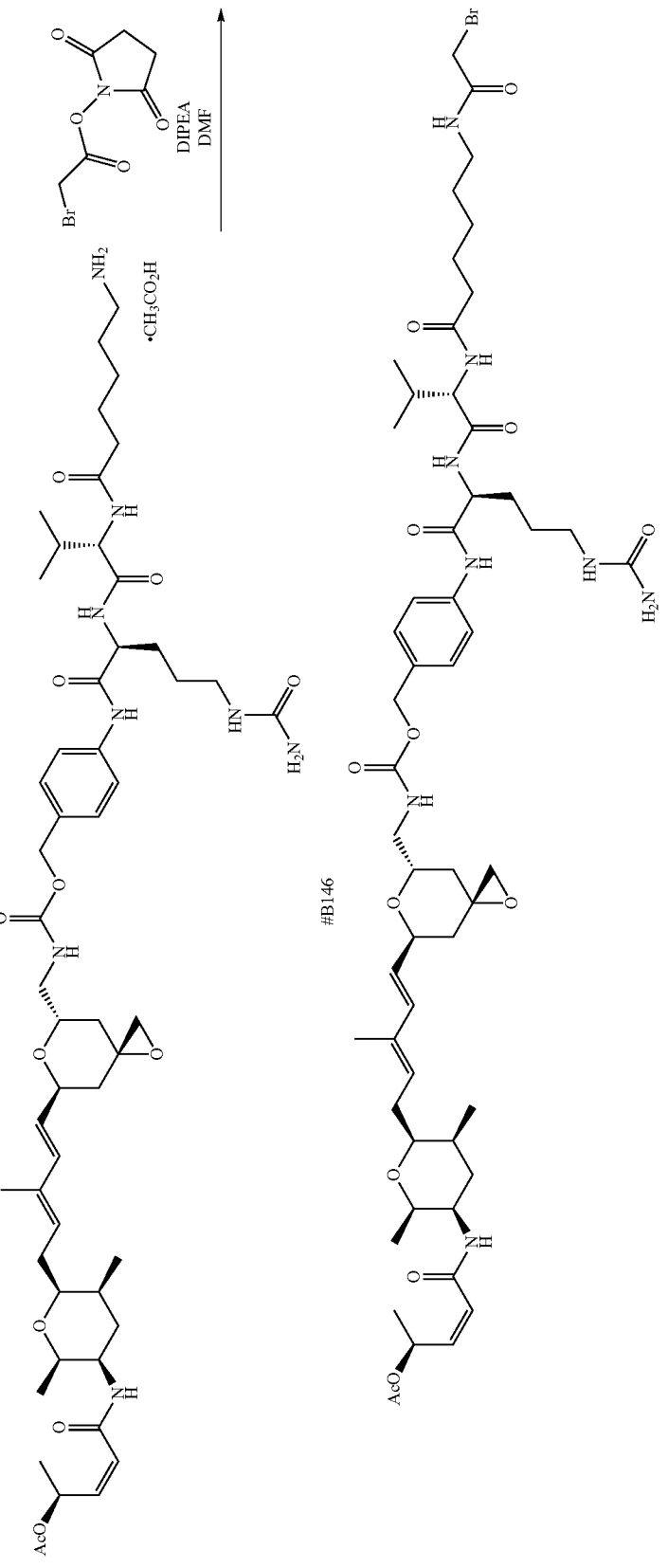

Step 1:

Synthesis of N-(6-{[(9H-fluoren-9-ylmethoxy)carbonyl] amino}hexanoyl)-L-valyl-N-(4-{[({[(3R,5S,7S)-7-{(1E, 3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl] methyl}carbamoyl)oxy]methyl}phenyl)-N~5~-carbamoyl-L-ornithinamide (#B152). To a solution of #B140 (10.7 mg, 0.022 mmol, 1 eq.) in N,N-dimethylformamide at rt was added 2,6-lutidine (10.2 µL, 0.088 mmol, 4 eq.), N,N-diisopropylethylamine (15.5 µL, 0.088 mmol, 4 eq.), 4-N, N-dimethylamino pyridine (2.7 mg, 0.022 mmol, 1 eq.), and #B45 (22.9 mg, 0.026 mmol, 1.2 eq.), and the reaction was stirred for 40 min. The crude desired material was purified by reverse phase chromatography (Method A) to give #B152 as white solid. Yield: 14.9 mg, 0.012 mmol, 55%. LCMS (Protocol C): m/z 1231.6 [M+H]$^+$, retention time=1.97 minutes.

Step 2:

Synthesis of N-(6-aminohexanoyl)-L-valyl-N-(4-{[({[(3R,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]methyl}carbamoyl)oxy]methyl}phenyl)-N-5-carbamoyl-L-ornithinamide, acetate salt (#B153): The title compound was prepared in 86% yield from 14.9 mg (0.012 mmol, 1.0 eq) of #B152 and 20.4 mg (0.24 mmol, 20.0 eq) of Piperidine using the procedure described for preparation of compound #B47. LCMS (Protocol C): m/z 1009.83 [M+H]$^+$, retention time=1.35 minutes.

Step 3:

Synthesis of N-{6-[(bromoacetyl)amino]hexanoyl}-L-valyl-N-(4-{[({[(3R,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1, 6-dioxaspiro[2.5]oct-5-yl]methyl}carbamoyl)oxy] methyl}phenyl)-N~5~-carbamoyl-L-ornithinamide (#B151). The title compound was prepared in 70% yield from 11 mg (0.01 mmol, 1.0 eq), of #B153 and 3.5 mg (0.015 mmol, 1.5 eq), 1-[(bromoacetyl)oxy]pyrrolidine-2,5-dione and 5.2 mg (0.04 mmol, 4.0 eq) of N,N-diisopropylethylamine using the procedure described for preparation of compound #B150. HPLC (Protocol A$^A$) retention time=8.413 minutes (purity 87%). LCMS (Protocol C): m/z 1151.5 [M+Na]$^+$, retention time=1.61 minutes. $^1$H NMR (400 MHz, DMSO-d$_6$) δ 9.96 (s, 1H), 8.25-8.18 (m 1H), 8.06 (d, J=7.4 Hz, 1H), 7.83-7.74 (m, 2H), 7.62-7.54 (m, 2H), 7.31-7.20 (m, 3H), 6.41-6.31 (m, 1H), 6.25 (d, J=15.8 Hz, 1H), 6.11 (d, J=11.7 Hz, 1H), 6.00-5.92 (m, 1H), 5.87 (dd, J=11.7 and 7.4 Hz, 1H), 5.61 (dd, J=15.8 and 5.9 Hz, 1H), 5.55-5.47 (m, 1H), 5.39 (s, 2H), 5.00-4.88 (m, 2H), 4.59-4.49 (m, 1H), 4.43-4.34 (m, 1H), 4.24-4.15 (m, 2H), 3.99-3.88 (m, 1H), 3.81 (s, 2H), 3.69-3.58 (m, 2H), 3.53-3.36 (m, 2H), 3.10-2.88 (m, 5H), 2.63 (s, 2H), 2.31-2.08 (m, 4H), 2.02-1.92 (m, 4H), 1.83-1.56 (m, 10H), 1.55-1.29 (m, 7H), 1.28-1.20 (m, 5H), 1.05 (d, J=6.6 Hz, 3H), 0.94 (d, J=7.4 Hz, 3H), 0.85 (dd, J=11.3 and 6.6 Hz, 6H).

Example A54

Preparation of N-{6-[(bromoacetyl)amino] hexanoyl}-L-valyl-N-(4-{[({[(3R,5S,7R,8R)-7-{(1E, 3E)-5-[(2S,3S,5R,6R)-5-{[(2Z,4S)-4-(acetyloxy) pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl] methyl}carbamoyl)oxy]methyl}phenyl)-N~5~-carbamoyl-L-ornithinamide (#B154)

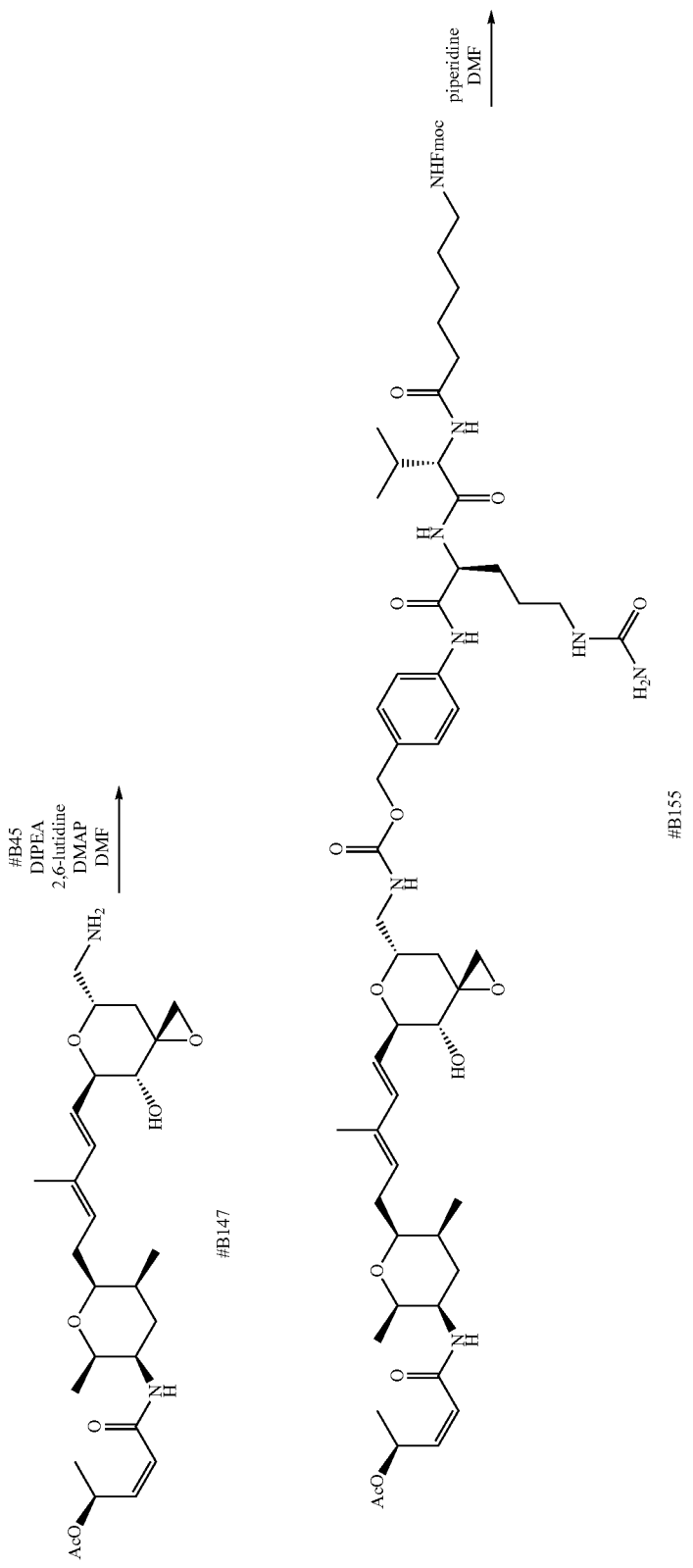

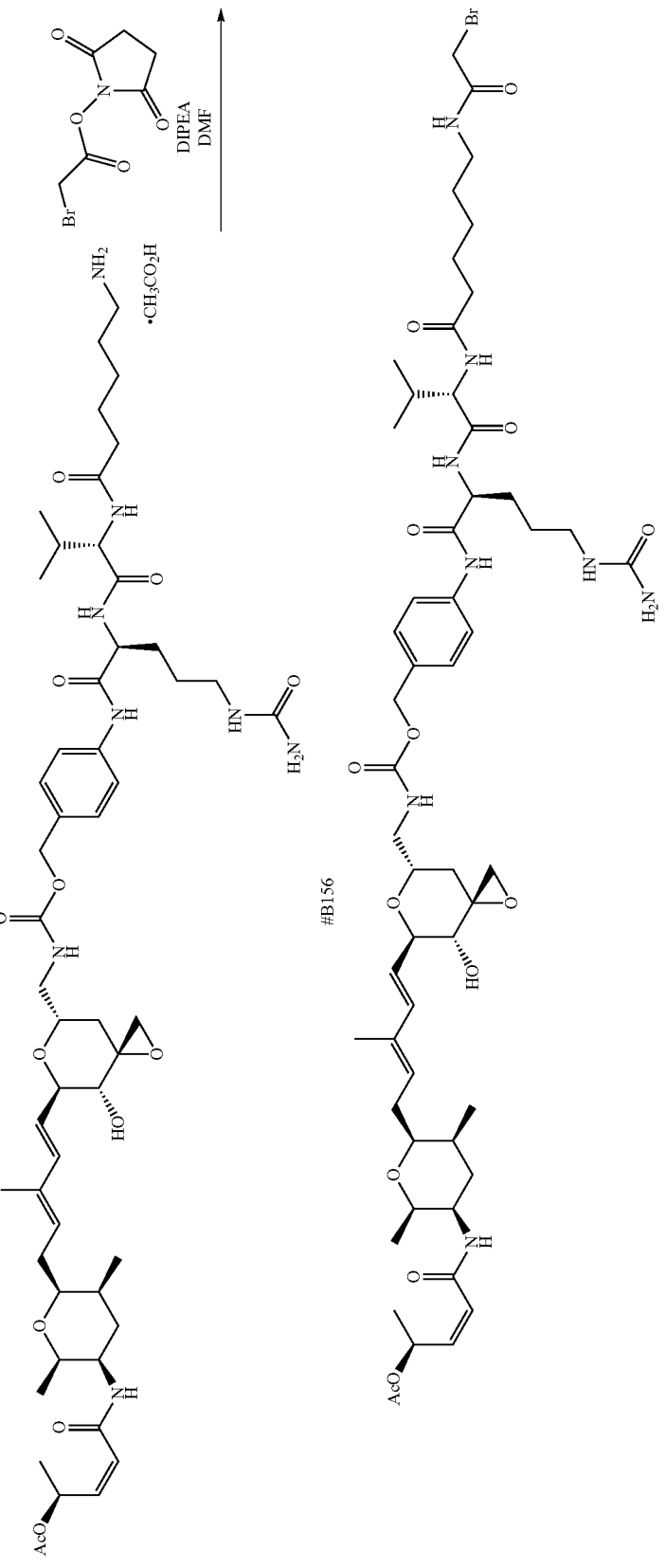

Step 1:

Synthesis of N-(6-{[(9H-fluoren-9-ylmethoxy)carbonyl]amino}hexanoyl)-L-valyl-N-(4-{[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]methyl}carbamoyl)oxy]methyl}phenyl)-N~5~-carbamoyl-L-ornithinamide (#B155). The title compound was prepared in 41% yield from 13 mg (0.023 mmol) of #B147, 9.9 mg, (0.092 mmol, 4 eq.) of 2,6-lutidine, 12.0 mg (0.092 mmol, 4 eq.), of N,N-diisopropylethylamine, 2.8 mg, (0.023 mmol, 1 eq.) of 4-N,N-dimethylamino pyridine and 24.6 mg (0.028 mmol, 4 eq) of #B45 (22.9 mg, 0.026 mmol, 1.2 eq.) using the procedure described for preparation of #B152. LCMS (Protocol D): m/z 1247.93 [M+H]+, retention time=0.91 minutes.

Step 2:

Synthesis of N-(6-aminohexanoyl)-L-valyl-N-(4-{[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]methyl}carbamoyl)oxy]methyl}phenyl)-N~5~-carbamoyl-L-ornithinamide, acetate salt (#B156). The title compound was prepared in 66% yield from 11.9 mg (0.01 mmol, 1.0 eq) of ##B155 and 17.0 mg (0.2 mmol, 20.0 eq) of piperidine using the procedure described in for preparation of #B153. HPLC (Protocol A$^A$) retention time=7.001 minutes (purity 82%). LCMS (Protocol D): m/z 1025.4 [M+H]+, retention time=0.69 minutes.

Step 3:

Synthesis of N-{6-[(bromoacetyl)amino]hexanoyl}-L-valyl-N-(4-{[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]methyl}carbamoyl)oxy]methyl}phenyl)-N~5~-carbamoyl-L-ornithinamide (#B154). The title compound was prepared in 46% yield from 6.1 mg (0.006 mmol, 1.0 eq.) of #B156, 5.0 mg (0.015 mmol, 7.0 eq) of N,N-diisopropylethylamine and 3.5 mg, 0.015 mmol, 1.5 eq.) of 1-[(bromoacetyl)oxy]pyrrolidine-2,5-dione using the procedure described for preparation of compound #B150. HPLC (Protocol A$^A$) retention time=7.669 minutes (purity 84%). LCMS (Protocol D): m/z 1151.5 [M+Na]+, retention time=0.79 minutes. $^1$H NMR (400 MHz, DMSO-d$_6$) δ 9.99 (s, 1H), 8.27-8.19 (m 1H), 8.16-8.06 (m, 1H), 7.89-7.73 (m, 2H), 7.62-7.54 (m, 2H), 7.31-7.20 (m, 3H), 6.41-6.31 (m, 1H), 6.27 (d, J=16.4 Hz, 1H), 6.11 (d, J=10.9 Hz, 1H), 6.05-5.94 (m, 1H), 5.86 (dd, J=10.9 and 7.0 Hz, 1H), 5.67-5.56 (m, 1H), 5.55-5.47 (m, 1H), 5.40 (s, 2H), 5.02-4.88 (m, 3H), 4.44-4.33 (m, 2H), 4.30-4.23 (m, 1H), 4.22-4.15 (m, 2H), 3.96-3.84 (m, 1H), 3.81 (s, 2H), 3.69-3.58 (m, 2H), 3.53-3.43 (m, 2H), 3.10-2.89 (m, 5H), 2.79-2.71 (m, 1H), 2.61-2.56 (m, 1H), 2.31-2.10 (m, 4H), 2.04-1.91 (m, 4H), 1.84-1.32 (m, 15H), 1.30-1.18 (m, 4H), 1.06 (d, J=6.2 Hz, 3H), 0.94 (d, J=7.4 Hz, 3H), 0.84 (dd, J=10.9 and 6.6 Hz, 6H).

Example A55

Preparation of (2S,3Z)-5-{[(2R,3R,5S,6S)-6-{(2E,4E)-5-[(3R,4R,5R,7S)-7-{2-[(2E)-2-{1-[4-({5-[(bromoacetyl)amino]pentyl}oxy)phenyl]ethylidene}hydrazinyl]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B157)

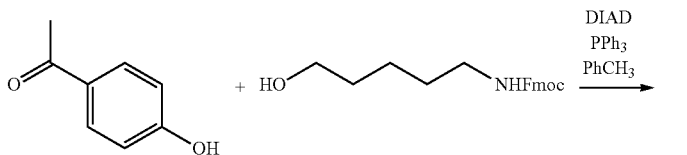

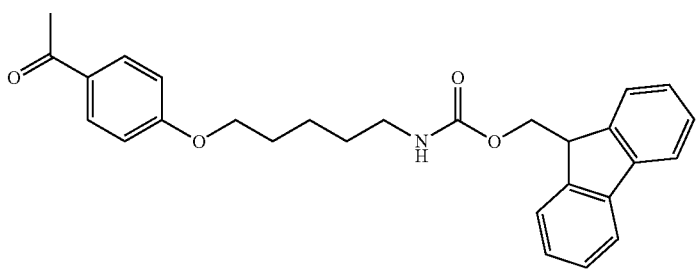

B158

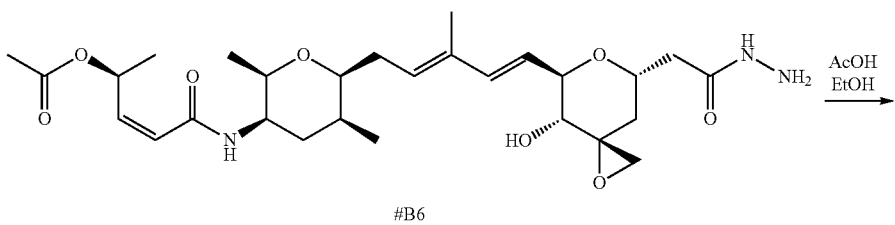

B6

-continued

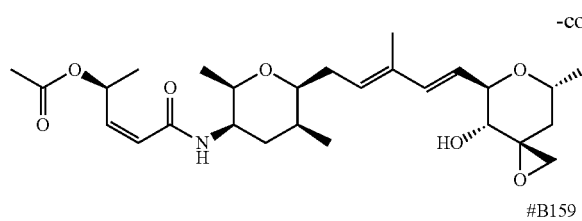 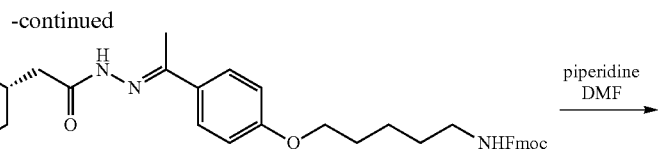

B159 piperidine
DMF
→

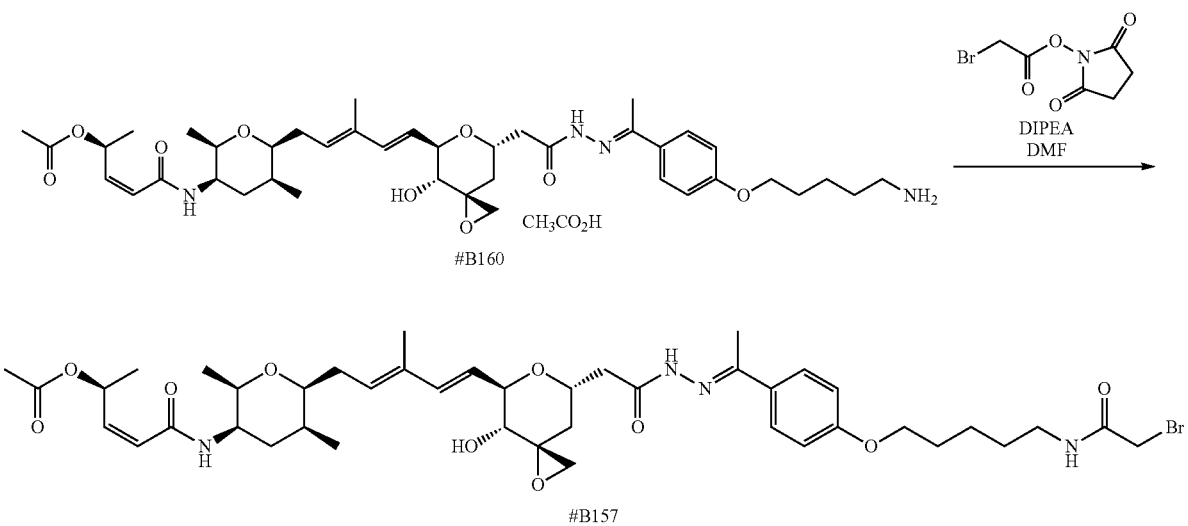

B160

DIPEA
DMF
→

B157

Step 1:

Synthesis of 9H-fluoren-9-ylmethyl [5-(4-acetylphenoxy) pentyl]carbamate (#B158): To a solution of (9H-fluoren-9-yl)methyl 5-hydroxypentylcarbamate (5 g, 15.4 mmol, 1 eq.), 1-(4-hydroxyphenyl)ethanone (2.1 g, 15.4 mmol, 1 eq.), and triphenylphosphine (4.53 g, 16.9 mmol, 1.1 eq.) in toluene (50 mL) was added DIAD (3.43 g, 16.9 mmol, 1.1 eq.) dropwise at 0-10° C. The solution was stirred at rt for 1 hour, diluted with ethyl acetate, and washed with aqueous saturated ammonium chloride and brine. The organic layers were dried over sodium sulfate, filtered and concentrated in vacuo. The residue was purified by silica gel chromatography eluted with petroleum ether: ethyl acetate from 10:1 to 7:1 and further purified by reverse phase chromatography to afford #B158 (3.6 g, 53%) as white solid. $^1$H NMR (400 MHz, CDCl$_3$): δ 7.93 (d, 2H), 7.76 (d, 2H), 7.59 (d, 2H), 7.42 (m, 2H), 7.33 (m, 2H), 6.92 (d, 2H), 4.79 (m, 1H), 4.43 (m, 2H), 4.23 (m, 1H), 4.04 (m, 2H), 3.25 (m, 2H), 2.55 (s, 3H), 1.84 (m, 2H), 1.58-1.52 (m, 4H).

Step 2:

Synthesis of (2S,3Z)-5-{[(2R,3R,5S,6S)-6-{(2E,4E)-5-[(3R,4R,5R,7S)-7-{2-[(2E)-2-(1-{4-[(5-{[(9H-fluoren-9-lmethoxy)carbonyl]amino}pentyl)oxy]phenyl}ethylidene) hydrazinyl]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B159). The title compound was prepared in 33% yield from 30.8 mg (0.056 mmol, 1.0 eq.) of #B6 and 124.0 mg (0.28 mmol, 5.0 eq) of #B158 using the procedure described for preparation of compound #B20. LCMS (Protocol D): m/z 975.4 [M+H]$^+$, retention time=1.05 minutes.

Step 3:

Synthesis of (2S,3Z)-5-{[(2R,3R,5S,6S)-6-{(2E,4E)-5-[(3R,4R,5R,7S)-7-{2-[(2E)-2-(1-{4-[(5-aminopentyl)oxy] phenyl}ethylidene)hydrazinyl]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate, acetate salt (#B160). The title compound was prepared in 64% yield from 17.8 mg (0.018 mmol, 1.0 eq)) of #B159 and 30.7 mg (0.36 mmol, 20.0 eq.) of piperidine using the procedure described for preparation of #B47. LCMS (Protocol D): m/z 753.62 [M+H]$^+$, retention time=0.66 minutes.

Step 4:

Synthesis of (2S,3Z)-5-{[(2R,3R,5S,6S)-6-{(2E,4E)-5-[(3R,4R,5R,7S)-7-{2-[(2E)-2-{1-[4-({5-[(bromoacetyl) amino]pentyl}oxy)phenyl]ethylidene}hydrazinyl]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B157): The title compound was prepared in 46% yield from 6.2 mg (0.008 mmol, 1.0 eq) of #B160 and 2.8 mg (0.012 mmol, 1.5 eq) of 1-[(bromoacetyl)oxy]pyrrolidine-2,5-dione and 4.2 mg (0.032 mmol, 4.0 eq) of N,N-diisopropylethylamine using the procedure described for preparation of compound #B150. HPLC (Protocol A$^4$) retention time=8.668 minutes (purity 53%). LCMS (Protocol D): m/z 873.3 [M+H]$^+$, retention time=0.88 minutes. $^1$H NMR (400 MHz, DMSO-d$_6$, mult, J in Hz) δ 10.39-10.25 (m, 1H), 8.30-8.20 (m, 1H), 7.82-7.66 (m, 3H), 6.99-6.90 (m, 2H), 6.42-6.22 (m, 2H), 6.16-6.06 (m, 1H), 5.92-5.81 (m, 1H), 5.68-5.34 (m, 3H), 5.09-4.92 (m, 1H), 4.51-4.25 (m, 3H), 4.03-3.94 (m, 2H), 3.82 (s, 2H), 3.70-3.55 (m, 2H), 3.50-3.40 (m, 1H), 3.15-3.05 (m, 2H), 2.90-2.71 (m, 2H), 2.64-2.56 (m, 2H), 2.30-2.10 (m, 5H), 1.98 (s, 3H), 1.94-1.84 (m, 1H), 1.83-1.55 (m, 8H), 1.53-1.33 (m, 4H), 1.29-1.20 (m, 3H), 1.12-1.00 (m, 3H), 0.98-0.88 (m, 3H).

Example A56
Preparation of (2S,3Z)-5-{[(2R,3R,5S,6S)-6-{(2E,4E)-5-[(3R,4R,5R,7S)-7-({[N-(bromoacetyl)-beta-alanyl]amino}methyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B161)
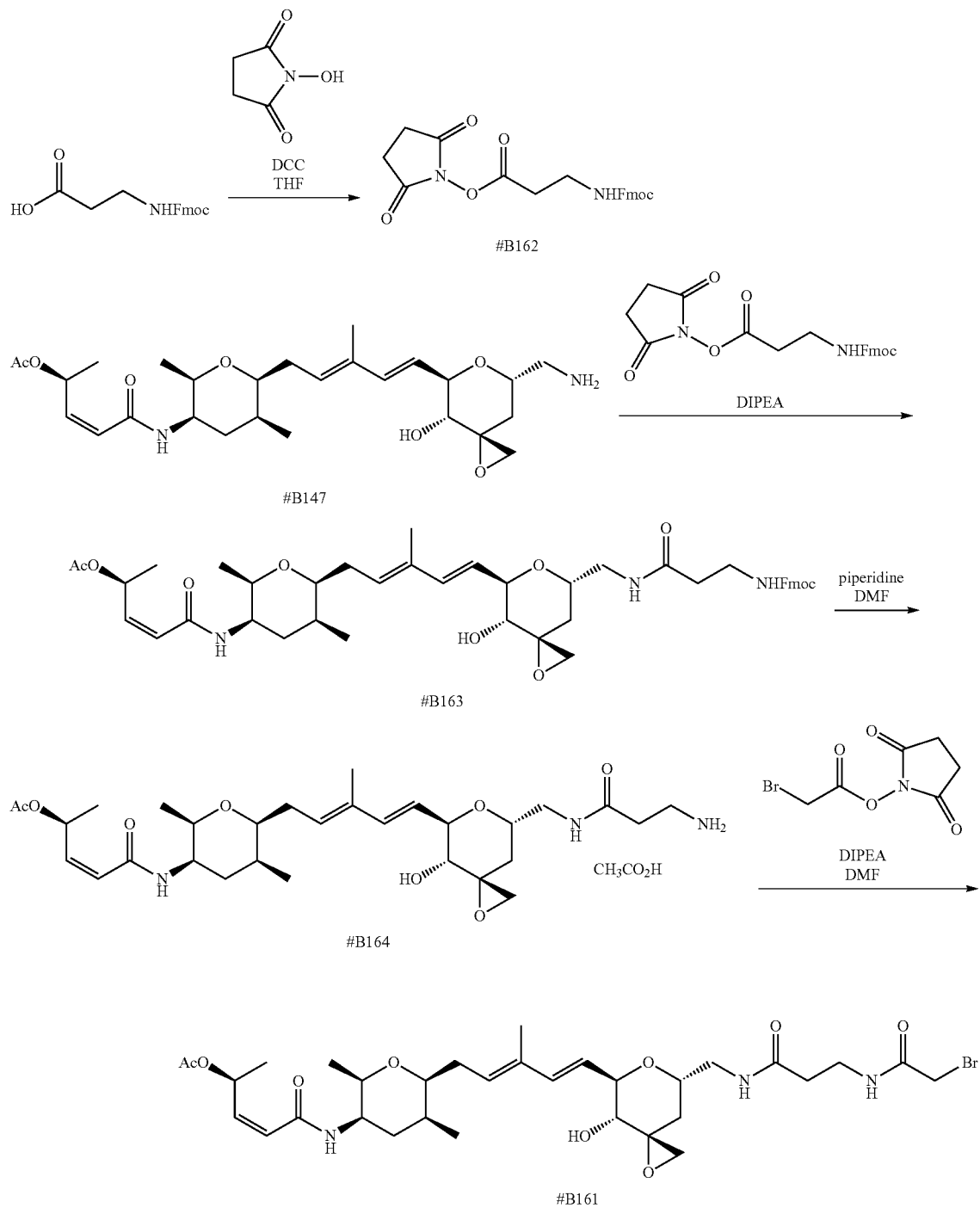

Step 1:

Synthesis of 2,5-dioxopyrrolidin-1-yl N-[(9H-fluoren-9-ylmethoxy)carbonyl]-beta-alaninate (#B162). To a solution of N-[(9H-fluoren-9-ylmethoxy)carbonyl]-β-alanine (297 mg, 0.95 mmol, 1 eq.) in tetrahydrofuran (3.5 mL) at rt was added N-hydroxysuccinimide (112 mg, 0.954 mmol, 1 eq.) and N,N'-Dicyclohexylcarbodiimide (228 mg, 1.05 mmol, 1.1 eq.), and the reaction was allowed to stir for 4 hours. The reaction was filtered washing with ethyl acetate and concentrated in vacuo. The crude desired material was purified by reverse phase medium pressure liquid chromatography eluted with 0.02% acetic acid in water (v/v) and 0.02% acetic acid in acetonitrile (v/v) (10% to 95%) to give #B162 as a white solid. Yield: 320 mg, 0.78 mmol, 82%. LCMS (Protocol D): m/z 431.0 [M+Na]$^+$, retention time=0.91 minutes.

Step 2:

Synthesis of (2S,3Z)-5-({(2R,3R,5S,6S)-6-[(2E,4E)-5-{(3R,4R,5R,7S)-7-[({N-[(9H-fluoren-9-ylmethoxy)carbonyl]-beta-alanyl}amino)methyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B163). To a solution of #B147 (15.1 mg, 0.027 mmol, 1 eq.) in N,N-dimethylformamide (0.5 mL) was added N,N-diisopropylethylamine (14.3 µL, 0.081 mmol, 3 eq.) and #B162 (22.1 mg, 0.054 mmol, 2 eq.), and the reaction was allowed to stir for 30 min. The reaction was purified by reverse phase chromatography (Method A) to give a mixture of the desired #B163 and unreacted #B162 LCMS (Protocol D): m/z 800.4 [M+H]$^+$, retention time=0.97 minutes. This material was used in next step without further purification.

Step 3:

Synthesis of (2S,3Z)-5-({(2R,3R,5S,6S)-6-[(2E,4E)-5-{(3R,4R,5R,7S)-7-[(beta-alanylamino)methyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate, acetate salt (#B164). The title compound was prepared in 63% yield from 15.7 mg (0.02 mmol, 1.0 eq) of #B163 and 34.1 mg (0.4 mmol, 20.0 eq) of piperidine using the procedure described for preparation of compound #B47. LCMS (Protocol D): m/z 578.41 [M+H]$^+$, retention time=0.62 minutes.

Step 4:

Synthesis of (2S,3Z)-5-{[(2R,3R,5S,6S)-6-{(2E,4E)-5-[(3R,4R,5R,7S)-7-({[N-(bromoacetyl)-beta-alanyl]amino}methyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B161). The title compound was prepared in 43% yield from 7.3 mg (0.013 mmol, 1.0 eq) of #B164 and 4.5 mg (0.019 mmol, 1.5 eq) of 1-[(bromoacetyl)oxy]pyrrolidine-2,5-dione and 6.8 mg (0.052 mmol, 4.0 eq) of N,N-diisopropylethylamine using the procedure described for preparation of compound #B150. HPLC (Protocol A$^A$) retention time=6.564 minutes (purity 72%). LCMS (Protocol D): m/z 698.1 [M+H]$^+$, retention time=0.79 minutes. $^1$H NMR (400 MHz, DMSO-d$_6$) δ 8.31-8.23 (m, 1H), 8.02-7.93 (m, 1H), δ 7.78 (d, J=7.8 Hz, 1H), 6.41-6.32 (m, 1H), 6.28 (d, J=15.8 Hz, 1H), 6.11 (d, J=11.7 Hz, 1H), 5.87 (dd, J=11.7 and 7.4 Hz, 1H), 5.61 (dd, J=15.8 and 5.5 Hz, 1H), 5.56-5.45 (m, 1H), 5.00 (d, J=6.2 Hz, 1H), 4.31-4.24 (m, 1H), 3.93-3.79 (m, 3H), 3.72-3.59 (m, 2H), 3.55-3.45 (m, 1H), 3.27-3.08 (m, 3H), 3.28-3.14 (m, 2H), 2.77 (d, J=5.1 Hz, 1H), 2.61 (d, J=5.1 Hz, 1H), 2.36-2.14 (m, 4H), 1.98 (s, 3H), 1.88-1.75 (m, 3H), 1.73-1.61 (m, 4H), 1.51-1.41 (m, 1H), 1.25 (d, J=6.6 Hz, 3H), 1.07 (d, J=6.2 Hz, 3H), 0.95 (d, J=7.0 Hz, 3H).

Example A57

Preparation of N-{6-[(bromoacetyl)amino]hexanoyl}-L-valyl-N-{4-[({[4-({[(2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}carbonyl)piperazin-1-yl]carbonyl}oxy)methyl]phenyl}-N~5~-carbamoyl-L-ornithinamide (#B165)

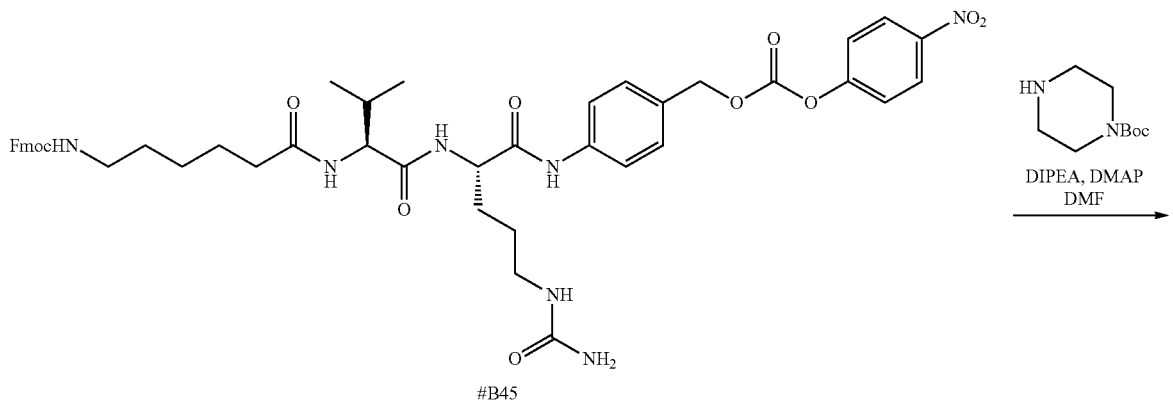

B45

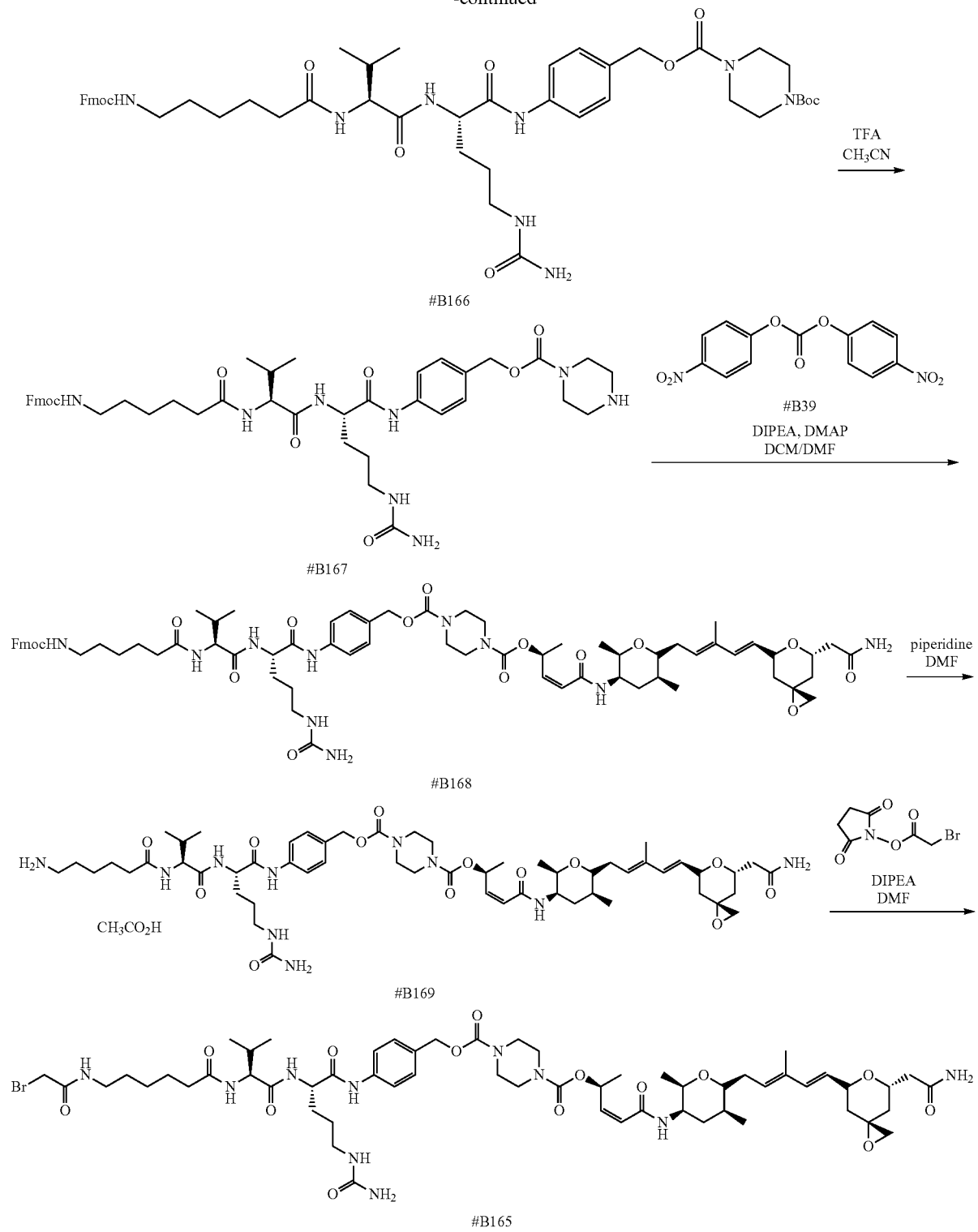

Step 1:

Synthesis of N-(6-{[(9H-fluoren-9-ylmethoxy)carbonyl]amino}hexanoyl)-L-valyl-N-{4-[({[4-(tert-butoxycarbonyl)piperazin-1-yl]carbonyl}oxy)methyl]phenyl}-N~5~-carbamoyl-L-ornithinamide (#B166). To a solution of tert-butyl piperazine-1-carboxylate (32 mg, 0.17 mmol, 1 eq.) in N,N-dimethylformamide (0.9 mL) was added N,N-diisopropylethylamine (90.8 μL, 0.52 mmol, 3 eq.) and 4-N,N-dimethylamino pyridine (4.2 mg, 0.034 mmol, 0.2 eq.) followed by #B45 (151 mg, 0.17 mmol, 1 eq.), and the reaction was stirred for 30 min. The reaction was diluted with DMSO (2.5 mL) and purified by reverse phase medium pressure liquid chromatography eluted with 0.02% acetic acid in water (v/v) and 0.02% acetic acid in acetonitrile (v/v)

(10% to 95%) to give #B166 as a white solid. Yield: 114 mg, 0.12 mmol, 71%. LCMS (Protocol C): m z 927.5 [M+H]$^+$, retention time=1.89 minutes.

Step 2:

Synthesis of N-(6-{[(9H-fluoren-9-ylmethoxy)carbonyl] amino}hexanoyl)-L-valyl-N-5-carbamoyl-N-(4-{[(piperazin-1-ylcarbonyl)oxy]methyl}phenyl)-L-ornithinamide (#B167). In two separate vessels, a suspension of #B166 (106 mg total, 0.11 mmol, 1 eq.) in acetonitrile (6 mL) at rt was added TFA (800 µL), and the reactions were stirred for 1.5-2 hours. The reactions were concentrated in vacuo, rediluted with acetonitrile, and concentrated ((3×)) in vacuo. The crude desired material was purified by reverse phase medium pressure liquid chromatography eluted with 0.02% acetic acid in water (v/v) and 0.02% acetic acid in acetonitrile (v/v) (10% to 100%) to give #B167 as a white solid. Yield: 62 mg, 0.066 mmol, 57%. LCMS (Protocol D): m z 827.4 [M+H]$^+$, retention time=0.72 minutes.

Step 3:

Synthesis of N-(6-{[(9H-fluoren-9-ylmethoxy)carbonyl] amino}hexanoyl)-L-valyl-N-{4-[({[4-({[(2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}carbonyl)piperazin-1-yl]carbonyl}oxy)methyl]phenyl}-N~5~-carbamoyl-L-ornithinamide (#B168). To a solution of #B39 (13.5 mg, 0.028 mmol, 1 eq.) in dichloromethane (0.4 mL) at rt was added 4-N,N-dimethylamino pyridine (3.4 mg, 0.028 mmol, 1 eq.), N,N-diisopropylethylamine (24.7 µL, 0.14 mmol, 5 eq.) and bis(4-nitrophenyl)carbonate (10.6 mg, 0.034 mmol, 1.2 eq.), and the reaction was allowed to stir for 6 hours. A solution of #B167 (34.5 mg, 0.037 mmol, 1.3 eq.) and N,N-diisopropylethylamine (12 uL, 0.07 mmol, 2.5 eq.) in N,N-dimethylformamide (500 uL) was added, and the reaction was allowed to stir for 1 hour. The reaction was diluted with DMSO (500 ul), and the dichloromethane was removed in vacuo. The crude desired material was purified by reverse phase chromatography (Method A) to give #B168 as a white solid. Yield: 13 mg, 0.01 mmol, 35%. LCMS (Protocol C): m/z 1329.6 [M+H]$^+$, retention time=1.81 minutes.

Step 4:

Synthesis of N-(6-aminohexanoyl)-L-valyl-N-{4-[({[4-({[(2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}carbonyl)piperazin-1-yl]carbonyl}oxy)methyl]phenyl}-N~5~-carbamoyl-L-ornithinamide, acetate salt (#B169). The title compound was prepared in 80% yield from 13 mg (0.01 mmol, 1.0 eq.) of #B168 and 17.0 mg (0.2 mmol, 20.0 eq) of piperidine using the procedure described for preparation of compound #B47. LCMS (Protocol D): m/z 1107.5 [M+H]$^+$, retention time=0.69 minutes.

Step 5:

Synthesis of N-{6-[(bromoacetyl)amino]hexanoyl}-L-valyl-N-{4-[({[4-({[(2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}carbonyl)piperazin-1-yl]carbonyl}oxy)methyl]phenyl}-N~5~-carbamoyl-L-ornithinamide (#B165). The title compound was prepared in 69% yield from 9.4 mg (0.008 mmol, 1.0 eq) of #B169 and 2.8 mg (0.012 mmol, 1.5 eq) of 1-[(bromoacetyl)oxy]pyrrolidine-2,5-dione and 4.2 mg (0.032 mmol, 4.0 eq) of N,N-diisopropylethylamine using the procedure described for preparation of compound #B150. HPLC (Protocol A$^4$) retention time=7.741 minutes (purity 91%). LCMS (Protocol C): m/z 1229.4 [M+H]$^+$, retention time=1.48 minutes. $^1$H NMR (400 MHz, DMSO-d$_6$) δ 9.99 (s, 1H), 8.27-8.19 (m 1H), 8.13-8.04 (m, 1H), 7.85-7.73 (m, 2H), 7.64-7.55 (m, 2H), 7.35-7.26 (m, 3H), 6.77 (s, 1H), 6.32-6.21 (m, 2H), 6.10 (d, J=12.1 Hz, 1H), 6.01-5.85 (m, 2H), 5.59 (dd, J=16.0 and 5.5 Hz, 1H), 5.55-5.47 (m, 1H), 5.40 (s, 2H), 5.02 (s, 2H), 4.58-4.49 (m, 1H), 4.45-4.25 (m, 2H), 4.24-4.14 (m, 2H), 3.81 (s, 2H), 3.69-3.60 (m, 2H), 3.53-3.45 (m, 2H), 3.43-3.33 (m, 6H), 3.10-2.89 (m, 4H), 2.64-2.53 (m, 2H), 2.38-2.09 (m, 5H), 2.03-1.92 (m, 1H), 1.87-1.56 (m, 11H), 1.55-1.31 (m, 7H), 1.30-1.19 (m, 5H), 1.07 (d, J=6.2 Hz, 3H), 0.95 (d, J=7.0 Hz, 3H), 0.84 (dd, J=10.9 and 6.6 Hz, 6H).

Example A58

Preparation of N-{6-[(bromoacetyl)amino] hexanoyl}-L-valyl-N-[4-({[(4-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl] acetyl}piperazin-1-yl)carbonyl]oxy}methyl)phenyl]-N~5~-carbamoyl-L-ornithinamide (#B170)

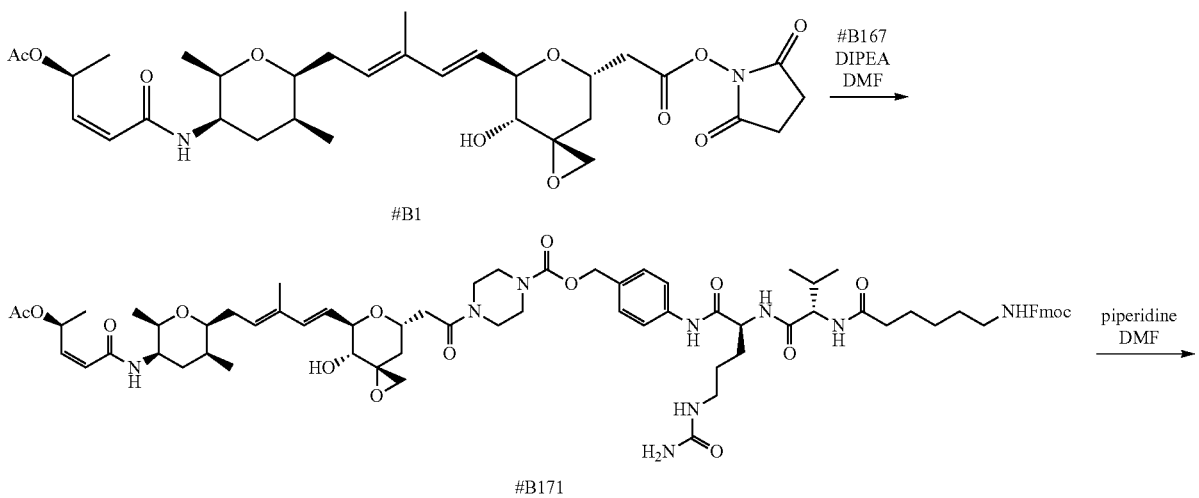

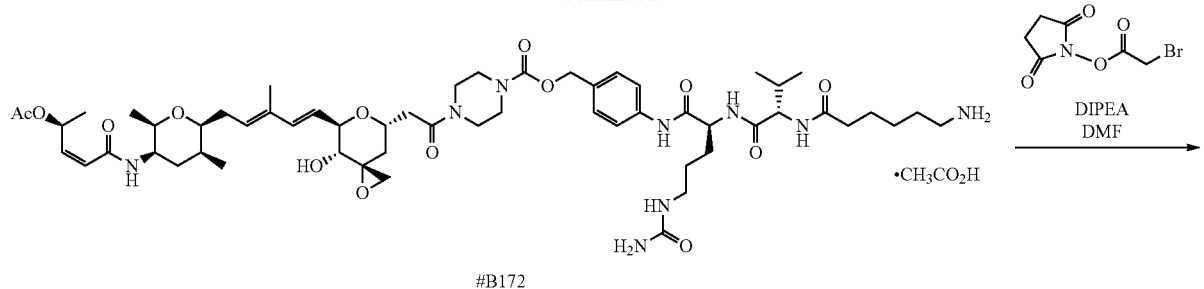

B172

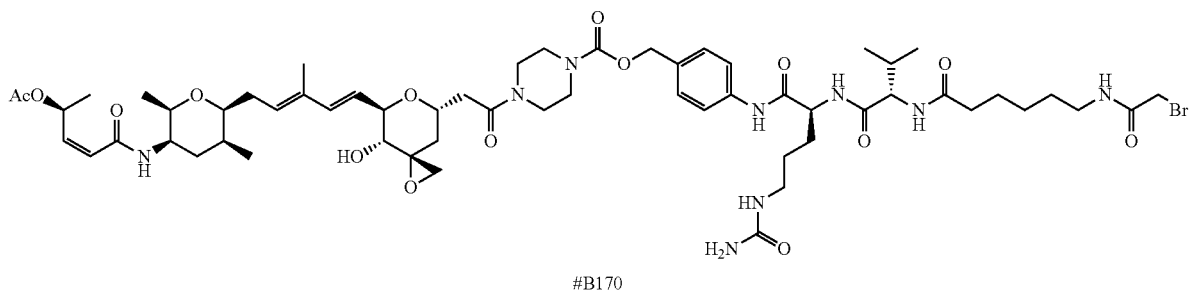

B170

Step 1:

Synthesis of N-(6-{[(9H-fluoren-9-ylmethoxy)carbonyl]amino}hexanoyl)-L-valyl-N-[4-({[4-{[(3R,5S,7R,8R)-7-{(1E,3E)-5-[2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}piperazin-1-yl)carbonyl]oxy}methyl)phenyl]-N~5~-carbamoyl-L-ornithinamide (B171): To a solution of #B1 (15 mg, 0.024 mmol, 1 eq.) in N,N-dimethylformamide (0.1 mL) at rt was added a solution of #B167 (28.2 mg, 0.03 mol, 1.25 eq.) and N,N-diisopropylethylamine (16.8 µL, 0.096 mmol, 4 eq.) in N,N-dimethylformamide (0.6 mL), and the reaction was stirred for 1.5 hours. The reaction was diluted with dimethyl sulfoxide and purified by reverse phase chromatography (Method A) to give #B171 as a white solid. Yield: 17.8 mg, 0.013 mmol, 55%. LCMS (Protocol D): m/z 1345.8 M+H, retention time=0.92 minutes.

Step 2:

Synthesis of N-(6-aminohexanoyl)-L-valyl-N-[4-({[(4-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}piperazin-1-yl)carbonyl]oxy}methyl)phenyl]-N~5~-N-carbamoyl-L-ornithinamide (B172): The title compound was prepared in 79% yield from 17.8 mg (0.013 mmol) of #B171 and 22.1 mg (0.26 mmol, 20.0 eq) of piperidine using the procedure described for preparation of compound #B47. LCMS (Protocol C): m/z 1122.6 [M+H]+, retention time=1.23 minutes.

Step 3:

Synthesis of N-{6-[(bromoacetyl)amino]hexanoyl}-L-valyl-N-[4-({[(4-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}piperazin-1-yl)carbonyl]oxy}methyl)phenyl]-N~5~-carbamoyl-L-ornithinamide (#B170). The title compound was prepared in 57% yield from 12.1 mg (0.01 mmol) of #B172 and 3.5 mg (0.015 mmol, 1.5 eq) of 1-[(bromoacetyl)oxy]pyrrolidine-2,5-dione and 5.2 mg (0.04 mmol, 4.0 eq) of N,N-diisopropylethylamine using the procedure described for preparation of compound #B15. HPLC (Protocol A$^A$) retention time=7.925 minutes (purity 81%). LCMS (Protocol C): m/z 1244.4 [M+H]+, retention time=1.45 minutes. $^1$H NMR (400 MHz, DMSO-d$_6$) δ 9.99 (s, 1H), 8.27-8.19 (m 1H), 8.13-8.04 (m, 1H), 7.85-7.73 (m, 2H), 7.64-7.55 (m, 2H), 7.35-7.26 (m, 2H), 6.44-6.24 (m, 2H), 6.10 (d, J=11.7 Hz, 1H), 6.03-5.93 (m, 1H), 5.87 (dd, J=11.7 and 7.4 Hz, 1H), 5.61 (dd, J=15.6 and 5.5 Hz, 1H), 5.55-5.47 (m, 1H), 5.40 (s, 2H), 5.02 (s, 2H), 4.98 (d, J=5.9 Hz, 1H), 4.43-4.33 (m, 2H), 4.30-4.16 (m, 3H), 3.81 (s, 2H), 3.69-3.60 (m, 2H), 3.55-3.34 (m, 6H), 3.26-3.22 (m, 1H), 3.09-2.89 (m, 4H), 2.75 (d, J=5.1 Hz, 1H), 2.63-2.55 (m, 2H), 2.31-2.09 (m, 4H), 1.98 (s, 3H), 1.92-1.78 (m, 3H), 1.73-1.31 (m, 12H), 1.30-1.19 (m, 5H), 1.07 (d, J=6.6 Hz, 3H), 0.95 (d, J=7.4 Hz, 3H), 0.84 (dd, J=10.9 and 6.6 Hz, 6H).

Example A59

Preparation of (2S,3Z)-5-({(2R,3R,5S,6S)-6-[(2E,4E)-5-{(3R,5S,7S)-7-[(butanoylamino)methyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B173)

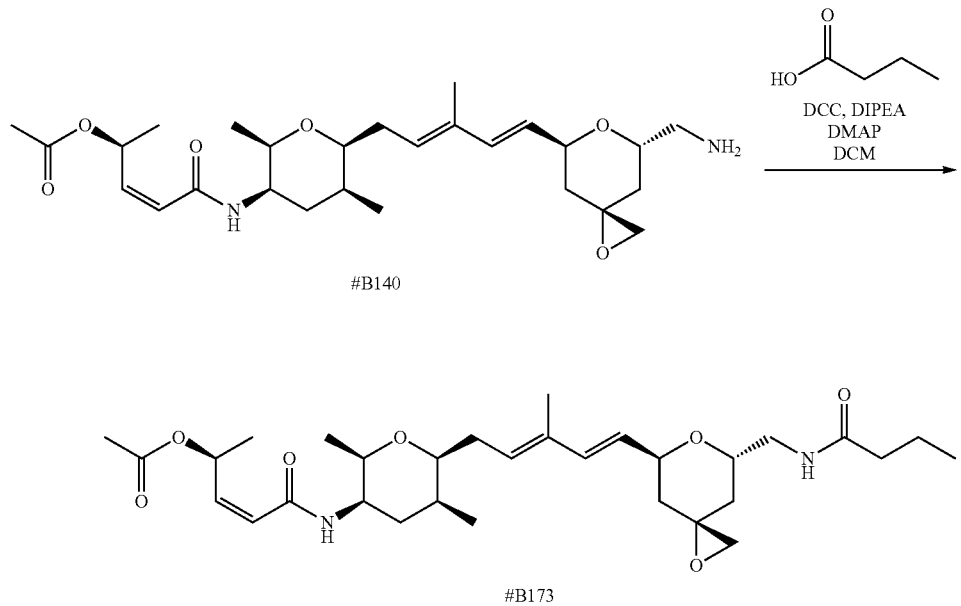

Step 1:

Synthesis of (2S,3Z)-5-({(2R,3R,5S,6S)-6-[(2E,4E)-5-{(3R,5S,7S)-7-[(butanoylamino)methyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B173). To a solution of #B140 (6.7 mg, 0.014 mmol, 1 eq.) in dichloromethane (0.4 mL) at 0° C. was added 4-N,N-dimethylamino pyridine (0.4 mg, 0.003 mmol, 0.2 eq.), N,N-diisopropylethylamine (12.3 μL, 0.07 mmol, 5 eq.) and butyric acid (6.8 μL, 0.074 mmol, 5.3 eq.), and the reaction was allowed to stir for 2 hours at rt. To the reaction was added DCC (8 mg, 0.042 mmol, 3 eq.), and the reaction was stirred for 45 min. The reaction was diluted with ethyl acetate and saturated sodium bicarbonate, extracted, washed with brine, dried over sodium sulfate, filtered, and concentrated in vacuo. The crude desired material was purified by reverse phase chromatography (Method A) to give #B173 as white solid. Yield: 3.4 mg, 0.006 mmol, 43%. HPLC (Protocol $A^d$): retention time=8.927 minutes (purity 87%).

LCMS (Protocol D): m/z 583.2 [M+Na]$^+$, retention time=0.88 minutes. $^1$H NMR (400 MHz, DMSO-d$_6$) δ 7.84-7.75 (m, 2H), 6.42-6.32 (m, 1H), 6.23 (d, J=16.0 Hz, 1H), 6.11 (d, J=11.5 Hz, 1H), 5.87 (dd, J=11.5 and 7.4 Hz, 1H), 5.65-5.45 (m, 3H), 4.60-4.51 (m, 1H), 3.96-3.85 (m, 1H), 3.70-3.60 (m, 2H), 3.54-3.46 (m, 1H), 3.12-3.01 (m, 1H), 2.63 (s, 2H), 2.32-2.12 (m, 2H), 2.09-2.01 (m, 2H), 1.98 (s, 3H), 1.75-1.56 (m, 7H), 1.55-1.45 (m, 2H), 1.41-1.33 (m, 1H), 1.25 (d, J=6.6 Hz, 3H), 1.07 (d, J=6.6 Hz, 3H), 0.95 (d, J=7.4 Hz, 3H), 0.88-0.80 (m, 3H).

Example A60

Preparation of [(3R,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-5-hydroxy-1,6-dioxaspiro[2.5]oct-5-yl]acetic acid (#B174) by biocatalysis with recombinant Fr9P

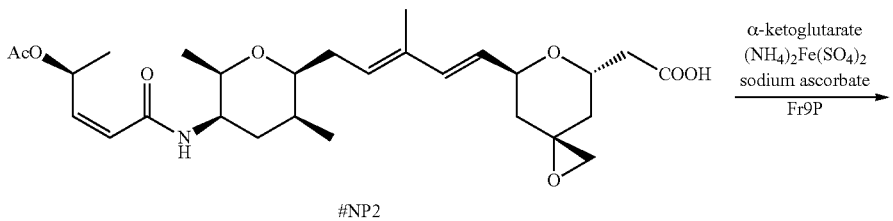

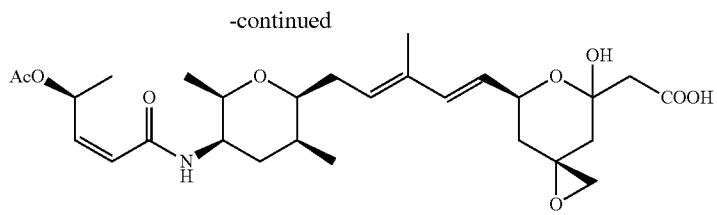

B174

Step 1:
Production of recombinant Fr9P enzyme in and purification from *Escherichia coli*. The codon-optimized Fr9P gene (as described in step 1 of example 4) was synthesized and ligated into the NcoI-HindIII sites of pGS-21a (GenScript) to generate pAE-PF16. Recombinant, His$_6$-GST tagged Fr9P protein was produced in and purified from *E. coli* BL21 (DE3) after transformation with plasmid pAE-PF16. Two 2.8-L Fernbach flasks containing 0.5 L medium (Terrific broth with 100 mg/L ampicillin) were each inoculated with 20 ml of an overnight LB culture and incubated at 200 rpm, 25° C. When the OD$_{600}$ reached ~0.9, cells were induced with 0.2 mM IPTG and incubation was resumed at 25° C. and 200 rpm. After 18-20 h, cells were harvested by centrifugation and frozen at −80° C. The cell pellet was resuspended in ~50 ml ice-cold lysis buffer [10 mM phosphate buffer pH 7.4; 500 mM NaCl; 20 mM imidazole; 10% glycerol; lysozyme 1 mg/ml; 0.5% (v/v) Tween 20; 20 mM β-mercaptoethanol] and incubated on ice for 30 min. Following sonication on ice, the cell lysate was centrifuged at 14,000 rpm and 4° C. for 45 min. The supernatant was transferred to a new tube and centrifuged again at 14,000 rpm and 4° C. for 30 min. 5 ml Ni-NTA resin slurry (Qiagen) were added to the supernatant fraction (clear lysate) contained in a small beaker on ice and gently stirred for 1 hour. The suspension was transferred to a falcon tube and centrifuged at 3,000 rpm and 4° C. for 10 min. The supernatant was discarded and the resin washed three times, each with 30 ml ice-cold wash buffer [10 mM phosphate buffer pH 7.4; 500 mM NaCl; 40 mM imidazole; 10% glycerol; 20 mM β-ME] followed by centrifugation at 3,000 rpm and 4° C. for 10 min. The resin was transferred to a disposable column and washed three more times, each with 2.5 ml wash buffer. The enzyme was eluted with 3×2.5 ml elution buffer [10 mM phosphate buffer pH 7.4; 500 mM NaCl; 250 mM imidazole; 10% glycerol; 20 mM β-ME]. The buffer was exchanged to 50 mM MOPS pH 7.5 using a PD-10 column and the solution concentrated using a Vivaspin column with molecular weight cut off of 30 kDa. Storage buffer contained 50 mM MOPS pH 7.5, 2 mM DTT and 10% glycerol (for storage at −80° C.) or 50% glycerol (for storage at −20° C.). The yield of purified enzyme was ~25 mg per liter culture.

Step 2:
Synthesis of [(3R,7S)-7-{(1E,3E)-5-[(2S,3S,5R,6R)-5-{[(2Z,4S)-4-(acetyloxy)pent-2-enoyl]amino}-3,6-dimethyl-tetrahydro-2H-pyran-2-yl]-3-methylpenta-1,3-dien-1-yl}-5-hydroxy-1,6-dioxaspiro[2.5]oct-5-yl]acetic acid (#B174) using recombinant Fr9P. To an aqueous solution of #NP2 (1 mg, 0.4 mM, 1 eq.) in 50 mM MOPS buffer pH 7.5 were added α-ketoglutarate (0.8 mM final concentration, 2 eq.), sodium ascorbate (0.08 mM, 0.2 eq.), NH$_4$Fe(II)SO$_4$ (0.04 mM, 0.1 eq.) and recombinant Fr9P from step 1 of example #A60 (1.2 µM, 0.003 eq.). After incubation at room temperature for 2 hours, the reaction was acidified to pH ~4-5 with acetic acid and extracted three times with equal volume of ethylacetate. The solvent was evaporated under reduced pressure, the residue resuspended in 0.25 ml acetonitrile, filtered and purified by reverse phase chromatography (Method H). The fraction with retention time of 18.5 min was collected and neutralized with ammonium hydroxide before it was concentrated under reduced pressure. The aqueous concentrate was acidified to pH ~4 with acetic acid and extracted twice with equal volume of ethylacetate. The solvent was removed under reduced pressure to afford #B174 as a white solid. Yield: 0.2 mg. HPLC (Protocol P): retention time=10.39 minutes. HRESIMS m/z 536.286 [M+H]$^+$; $^1$H NMR (400 MHz, DMSO-d$_6$, mult, J in Hz) δ 12.24 (brs, OH), 8.00 (d, J=8.0 Hz, 1H), 6.37 (m, 1H), 6.23 (d, J=15.9, 1H), 6.12 (dd, J=0.7, 11.5, 1H), 5.88 (dd, J=11.6, 7.5 Hz, 1H), 5.54 (m, 1H), 5.50 (m, 1H), 4.67 (m, 1H), 3.66 (m, 2H), 3.51 (m, 1H), 2.60 (m, 1H), 2.53 (m, 1H), 2.33 (m, 1H), 2.31 (m, 1H), 2.20 (m, 1H), 2.00 (s, 3H), 1.84 (m, 1H), 1.81 (m, 2H), 1.70 (s, 3H), 1.67 (m, 1H), 1.39 (m, 1H), 1.26 (d, J=6.6 Hz, 3H), 1.16 (m, 1H), 1.08 (d, J=6.4 Hz, 3H), 0.96 (d, J=7.2 Hz, 3H). $^{13}$C NMR (100 MHz, DMSO-d$_6$) δ 171.7, 170.5, 165.0, 142.7, 134.4, 133.3, 128.5, 127.3, 122.6, 95.3, 79.9, 74.8, 67.9, 67.2, 46.7, 46.1, 38.9, 37.7, 35.0, 31.5, 28.7, 20.8, 19.7, 17.6, 14.2, 12.2.

Example A61

Preparation of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl methyl [2-(pyridin-2-yldisulfanyl)ethyl]carbamate (#B175)

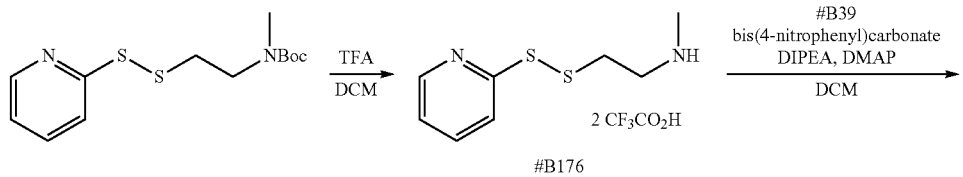

B176

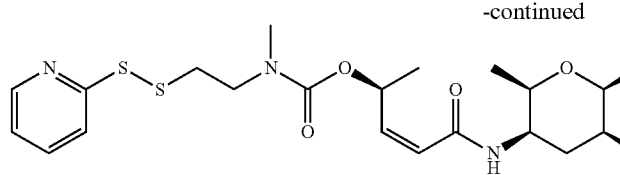
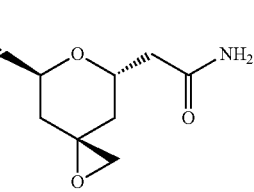

B175

Step 1:

Synthesis of N-methyl-2-(pyridin-2-yldisulfanyl)ethanamine, trifluoroacetate salt (#B176). To a solution of tert-butyl methyl[2-(pyridin-2-yldisulfanyl)ethyl]carbamate (*Angew. Chem. Int. Ed.* 2007, 46, 6469) (90 mg, 0.3 mmol, 1 eq.) in dichloromethane (1 mL) at rt was added TFA (1 mL), and the reaction was stirred for 1 hours. The reaction was concentrated in vacuo and azeotroped with acetonitrile (3×) to give #B176 as an oil. LCMS (protocol D): m/z 201.1 [M+H]$^+$, retention time=0.43 min. The crude material was used in next step without further purification.

Step 2.

Synthesis of (2S,3Z)-5-{[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl methyl [2-(pyridin-2-yldisulfanyl)ethyl]carbamate (#B175): To a solution of the #B39 (19.5 mg, 0.041 mmol, 1 eq.) in dichloromethane (0.5 mL) at rt was added 4-N,N-dimethylamino pyridine (5 mg, 0.041 mmol, 1 eq.), N,N-diisopropylethylamine (21.7 µL, 0.123 mmol, 3 eq.) and bis(4-nitrophenyl)carbonate (18.9 mg, 0.62 mmol, 1.5 eq.), and the reaction was allowed to stir for 2.5 hours. Additional bis(4-nitrophenyl)carbonate (3.1 mg, 0.008 mmol, 0.2 eq.) was added, and the reaction stirred for a further 1.5 hours. A solution of #B176 (44.1 mg, 0.103 mmol, 2.5 eq.) and N,N-diisopropylethylamine (54 µL, 0.31 mmol, 7.5 eq.) in dichloromethane (0.4 mL) was added, and the reaction was stirred for 1 hours. Additional solution of #B176 (17 mg, 0.04 mmol, 1 eq.) and N,N-diisopropylethylamine (44 µL, 0.25 mmol, 6 eq.) in dichloromethane (0.2 mL) was added, and the reaction was stirred for another 15 minutes. The reaction mixture was diluted with DMSO (1 mL), and the dichloromethane removed in vacuo. The crude desired material was purified by reverse phase medium pressure liquid chromatography eluted with 0.02% acetic acid in water (v/v) and 0.02% acetic acid in acetonitrile (v/v) (10% to 100%) to afford #B175 as a white solid. Yield: 7.6 mg, 0.011 mmol, 26%. LCMS (Protocol D): m/z 703.6 [M+H]$^+$, retention time=0.91 minutes. $^1$H NMR (400 MHz, DMSO-d$_6$, mult, J in Hz) δ 8.49-8.43 (m, 1H), 7.87-7373 (m, 2H), 7.32 (s, 1H), 7.28-7.21 (m, 1H), 6.78 (s, 1H), 6.32 (d, J=16.0 Hz, 1H), 6.26 (d, J=16.4 Hz, 1H), 6.23-6.13 (m, 1H), 6.11-5.98 (m, 1H), 5.93-5.84 (m, 1H), 5.76-5.67 (m, 1H), 5.59 (dd, J=15.9 and 5.6 Hz, 1H)

Example A#62

Preparation of (2S,3Z)-5-({(2R,3R,5S,6S)-6-[(2E,4E)-5-{(3R,4R,5R,7S)-7-[2-(2,2-dimethylhydrazinyl)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B177)

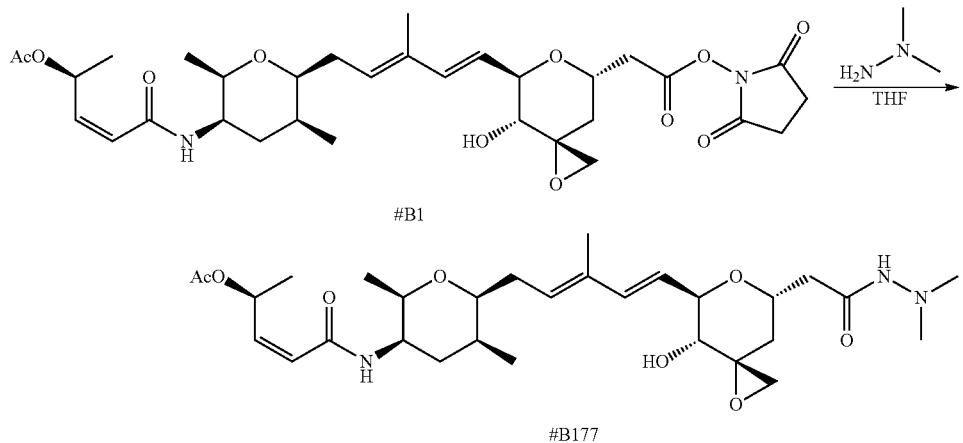

Step 1.

Synthesis of (2S,3Z)-5-({(2R,3R,5S,6S)-6-[(2E,4E)-5-{(3R,4R,5R,7S)-7-[2-(2,2-dimethylhydrazinyl)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B177). To a solution of #B1 (26.8 mg, 0.042 mmol, 1 eq.) dissolved in tetrahydrofuran (1 mL) at rt was added N,N-dimethyl hydrazine (16µ, 0.21 mmol, 5 eq.) After stirring for 40 min, more N,N-dimethyl hydrazine (6.4 µL, 0.084 mmol, 2 eq.) was added, and the reaction was stirred for 5 min. The reaction was diluted with water, extracted with ethyl acetate, and the combined organics were dried over sodium sulfate and filtered. The solvents were removed in vacuo. The crude desired material was purified by reverse phase chromatography (Method A) to give #B177 as a white solid. Yield: 14.5 mg, 0.025 mmol, 60%. LCMS (Protocol D): m/z 578.5 [M+H]$^+$, retention time=0.72 minutes. $^1$H NMR (500 MHz, DMSO-d$_6$) δ 8.85 (s, 0.6H), 8.33 (s, 0.4H), 7.93-7.84 (m, 1H), 6.40-6.27 (m, 2H), 6.10 (d, J=11.6 Hz, 1H), 5.87 (dd, J=11.6 and 7.6 Hz, 1H), 5.63-5.54 (m, 1H), 5.53-5.46 (m, 1H), 5.09 (d, J=5.1 Hz, 0.6H), 5.01 (d, J=6.6 Hz, 0.4H), 4.35-4.16 (m, 2H), 3.68-3.60 (m, 2H), 3.53-3.46 (m, 1H), 3.27-3.21 (m, 1H), 2.99-2.90 (m, 0.6H), 2.76 (d, J=5.4 Hz, 1H), 2.60-2.53 (m, 1H), 2.47-2.38 (m, 6.4H), 2.34-2.26 (m, 1H), 2.25-2.15 (m, 1H), 2.06 (dd, J=14.2 and 4.9 Hz, 1H), 1.98 (s, 3H), 1.87-1.72 (m, 3H), 1.71-1.58 (m, 4H), 1.51-1.43 (m, 1H), 1.24 (d, J=6.4 Hz, 3H), 1.07 (d, J=6.4 Hz, 3H), 0.94 (d, J=7.3 Hz, 3H).

Example A#63

Preparation of (2S,3Z)-5-({(2R,3R,5S,6S)-6-[(2E,4E)-5-{(3R,4R,5R,7S)-4-hydroxy-7-[2-({trans-3-[(1H-imidazol-1-ylcarbonyl)amino]cyclobutyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B178)

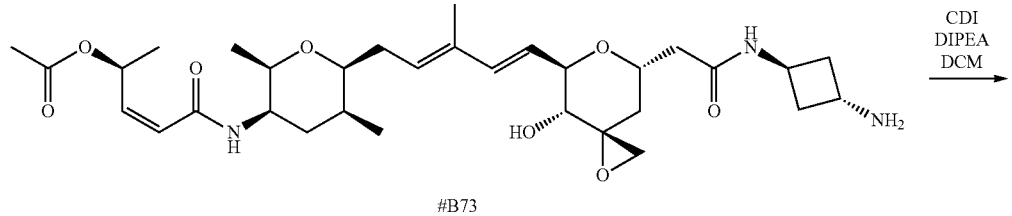

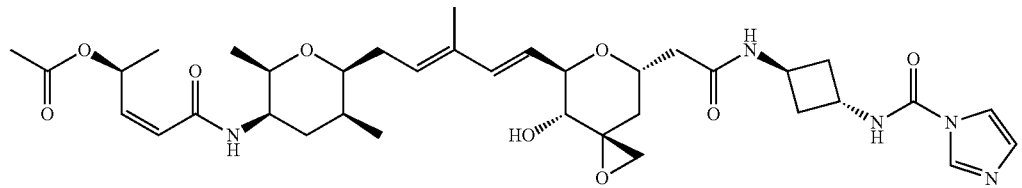

Step 1:

Synthesis of (2S,3Z)-5-({(2R,3R,5S,6S)-6-[(2E,4E)-5-{(3R,4R,5R,7S)-4-hydroxy-7-[2-({trans-3-[(1H-imidazol-1-ylcarbonyl)amino]cyclobutyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B178). To a solution of #B73 (15.3 mg, 0.025 mmol, 1 eq.) in dichloromethane (0.5 mL) at rt was added N,N-diisopropylethylamine (8.8 μL, 0.05 mmol, 2 eq.) and carbonyldimidazole (4.9 mg, 0.03 mmol, 1.2 eq.), and the reaction was stirred for 25 min. The reaction was diluted with dichloromethane, washed with water, dried over sodium sulfate, filtered, diluted with DMSO (0.8 mL) and concentrated to remove the dichloromethane. The crude desired material was purified by reverse phase chromatography (Method A) to give #B178 as a white solid. Yield: 3.2 mg, 0.0045 mmol, 18%. LCMS (Protocol D): m/z 698.6 [M+H]$^+$, retention time=0.68 minutes. $^1$H NMR (500 MHz, DMSO-d$_6$) δ 8.67 (d, J=6.9 Hz, 1H), 8.37 (d, J=7.1 Hz, 1H), 8.24 (s, 1H), 7.78 (d, J=8.1 Hz, 1H), 7.70-7.67 (m, 1H), 7.02 (s, 1H), 6.40-6.27 (m, 2H), 6.10 (dd, 11.6 and 1.5 Hz, 1H), 5.87 (dd, J=11.6 and 7.3 Hz, 1H), 5.60 (dd, J=15.7 and 5.6 Hz, 1H), 5.52-5.45 (m, 1H), 5.01 (d, J=5.4 Hz, 1H), 4.43-4.34 (m, 1H), 4.33-4.21 (m, 2H), 3.67-3.54 (m, 2H), 3.48-3.43 (m, 1H), 3.30-3.26 (m, 1H), 2.78 (d, J=5.1 Hz, 1H), 2.60-2.54 (m, 2H), 2.39-2.13 (m, 7H), 1.98 (s, 3H), 1.83-1.74 (m, 3H), 1.69 (s, 3H), 1.65-1.53 (m, 3H), 1.25 (d, J=6.4 Hz, 3H), 1.04 (d, J=6.4 Hz, 3H), 0.93 (d, J=7.3 Hz, 3H).

Example A#64

Preparation of (2S,3Z)-5-({(2R,3R,5S,6S)-6-[(2E,4E)-5-{(3R,4R,5R,7S)-4-hydroxy-7-[2-oxo-2-(tetrahydropyridazin-1(2H)-yl)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B179)

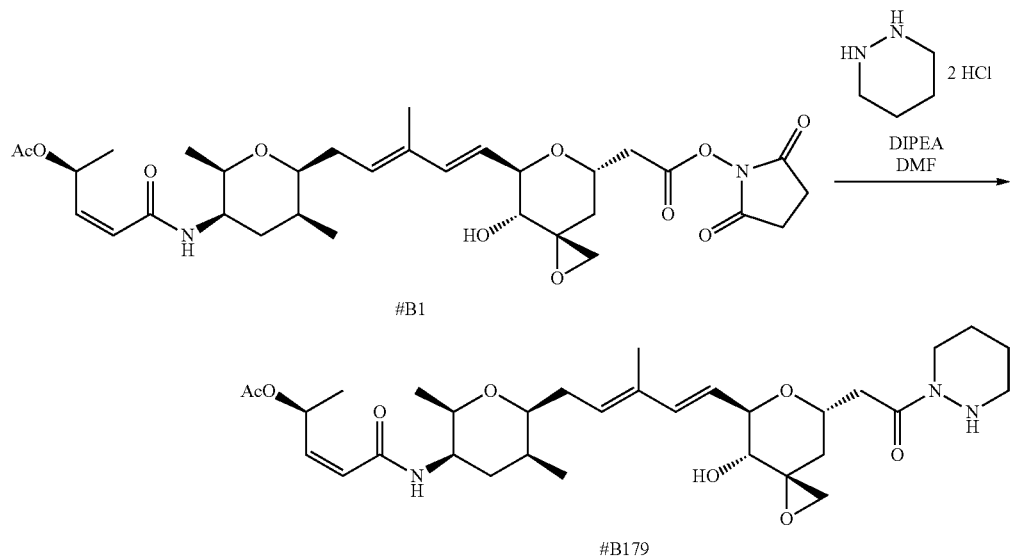

Step 1:

Synthesis of (2S,3Z)-5-({(2R,3R,5S,6S)-6-[(2E,4E)-5-{(3R,4R,5R,7S)-4-hydroxy-7-[2-oxo-2-(tetrahydropyridazin-1(2H)-yl)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B179). To a solution of #B1 (18.1 mg, 0.029 mmol, 1 eq.) in N,N-dimethylformamide (0.6 mL) at rt was added N,N-diisopropylethylamine (51.1 µL, 0.29 mmol, 10 eq.) and Hexahydropyridazine dihydrochloride (18.5 mg, 0.12 mmol, 4 eq.), and the reaction was stirred for 30 min. The reaction was purified by reverse phase chromatography (Method A) to give #B179 as a white solid. Yield: 10.7 mg, 0.018 mmol, 61%. LCMS (Protocol D): m/z 604.6 [M+H]$^+$, retention time=0.80 minutes. $^1$H NMR (400 MHz, DMSO-d$_6$) δ 7.79 (d, J=8.2 Hz, 1H), 6.42-6.27 (m, 2H), 6.11 (d, J=11.7 Hz, 1H), 5.87 (dd, J=11.7 and 7.4 Hz, 1H), 5.61 (dd, J=16.0 and 5.9 Hz, 1H), 5.55-5.47 (m, 1H), 4.92 (d, J=6.2 Hz, 1H), 4.76 (app t, J=7.0 Hz, 1H), 4.34-4.18 (m, 2H), 3.70-3.60 (m, 2H), 3.54-3.40 (m, 3H), 3.27-3.21 (m, 1H), 3.03 (dd, J=15.2 and 7.4 Hz, 1H), 2.81-2.70 (m, 3H), 2.55 (d, J=5.5 Hz, 1H), 2.33-2.15 (m, 2H), 1.98 (s, 3H), 1.85-1.74 (m, 3H), 1.71-1.56 (m, 5H), 1.55-1.48 (m, 4H), 1.25 (d, J=6.2 Hz, 3H), 1.07 (d, J=6.2 Hz, 3H), 0.95 (d, J=7.4 Hz, 3H).

Example A#65

Preparation of N-{6-[(bromoacetyl)amino]hexanoyl}-L-valyl-N-{4-[({[({[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)methyl]carbamoyl}oxy)methyl]phenyl}-N-5-carbamoyl-L-ornithinamide (#B180)

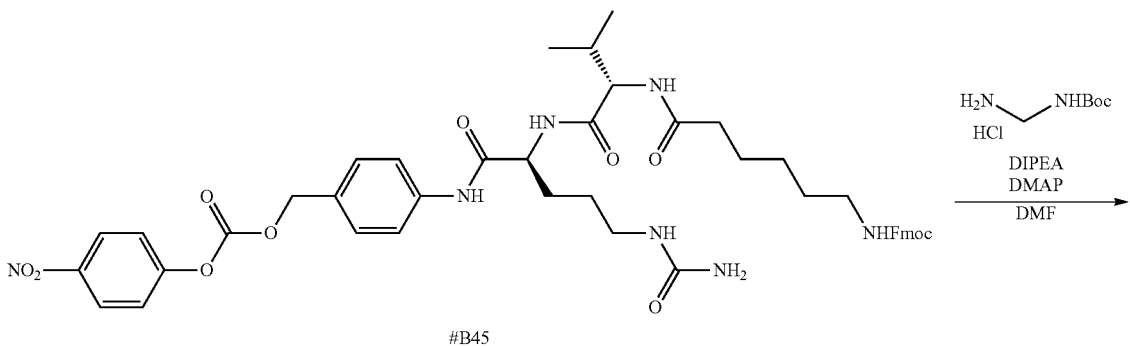

-continued
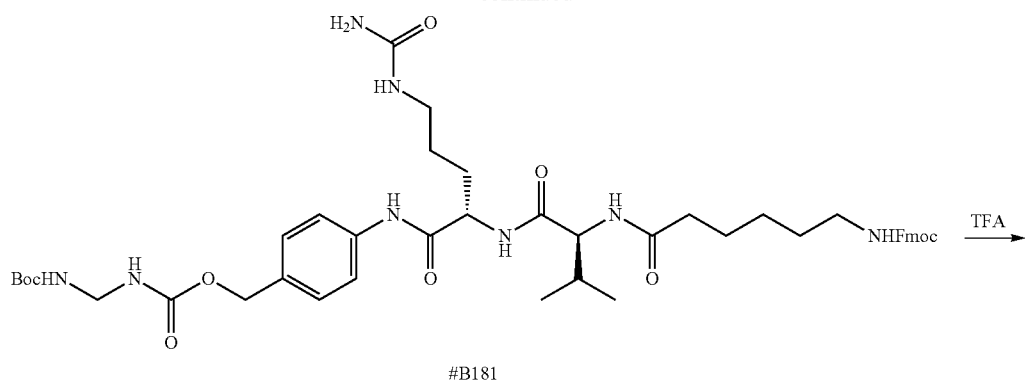
B181
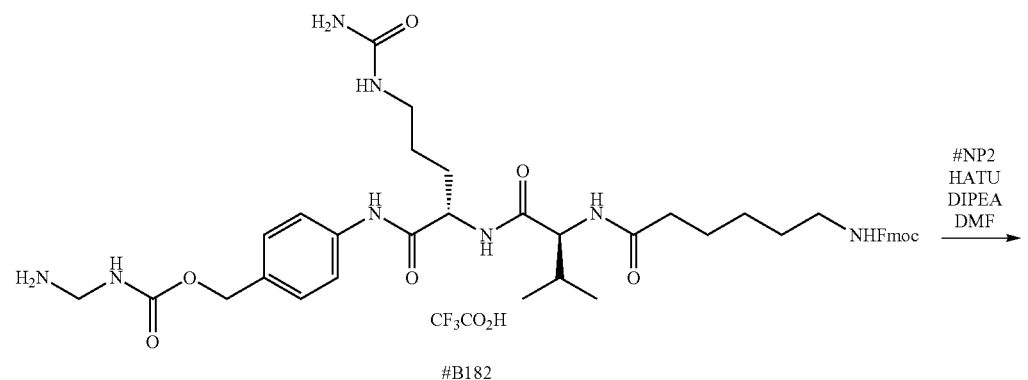
B182
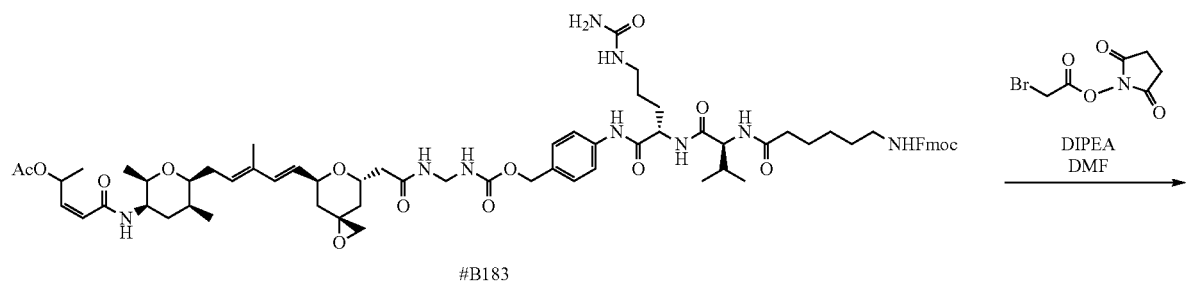
B183
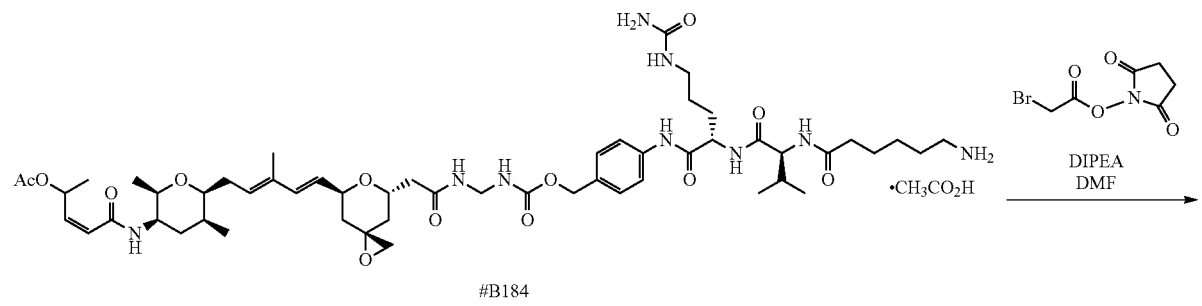
B184

-continued

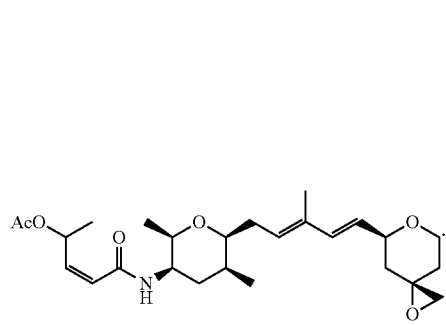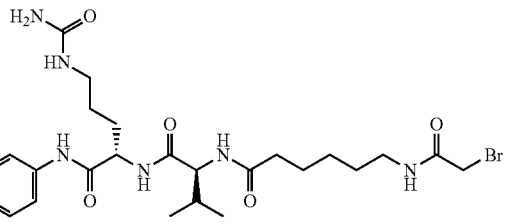

B180

Step 1:

Synthesis of N-(6-{[(9H-fluoren-9-ylmethoxy)carbonyl]amino}hexanoyl)-L-valyl-$N^5$-carbamoyl-N-[4-(9,9-dimethyl-3,7-dioxo-2,8-dioxa-4,6-diazadec-1-yl)phenyl]-L-ornithinamide (#B181). A solution of tert-butyl aminomethylcarbamate hydrochloride (*J. Org. Chem.*, 1980, 45, 1703, 32.9 mg, 0.18 mmol, 1 eq.) and N,N-diisopropylethylamine (47 µL, 0.27 mmol, 3 eq.) in N,N-dimethylformamide (1 mL) was added dropwise to a solution of #B45 (161.5 mg, 0.18 mmol, 1 eq.) in N,N-dimethylformamide (2 mL) at 0° C. 4-N,N-dimethylamino pyridine (2 mg, 0.016 mmol, 0.1 eq.) was added, and the resulting solution was stirred at room temperature for one hour. The reaction mixture was diluted with tert-butyl methyl ether and filtered. The filter cake was purified by prep-HPLC to afford #B181 as a white solid. Yield: 20 mg, 0.00023 mmol, 13%. $^1$H NMR (400 MHz, MeOD-$d_4$) δ 7.82 (d, 2H), 7.67 (d, 2H), 7.58 (d, 2H), 7.42 (m, 6H), 5.04 (br, 3H), 4.63 (s, 4H), 4.52 (m, 5H), 4.36 (m, 2H), 3.20 (m, 4H), 2.32 (m, 2H), 2.10 (m, 1H), 1.90 (m, 1H), 1.77 (m, 1H), 1.65 (m, 4H), 1.44 (m, 7H), 1.35 (m, 3H), 0.98 (m, 6H).

Step 2:

Synthesis of N-(6-{[(9H-fluoren-9-ylmethoxy)carbonyl]amino}hexanoyl)-L-valyl-N-[4-({[(aminomethyl)carbamoyl]oxy}methyl)phenyl]-$N^5$-carbamoyl-L-ornithinamide trifluoroacetate salt (#B182). To #B181 (20 mg, 0.00023 mmol) was added pre-chilled trifluoroacetic acid (1.3 mL) at 0° C., and the reaction was allowed to stir for 10 min. The reaction was concentrated, taken up in acetonitrile and reconcentrated three times to give #B182 as a gum which was used in next step without further purification: Yield: 25 mg, 0.028 mmol, 100%. LCMS (Protocol D): m/z 787.6 [M+H]$^+$, retention time=0.75 minutes.

Step 3:

Synthesis of N-(6-{[(9H-fluoren-9-ylmethoxy)carbonyl]amino}hexanoyl)-L-valyl-N-{4-[({[({[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)methyl]carbamoyl}oxy)methyl]phenyl}-$N^5$-carbamoyl-L-ornithinamide (#B183). To a solution of #NP2 (14.5 mg, 0.028 mmol, 1 eq.) in N,N-dimethylformamide (0.4 mL) at rt was added N,N-diisopropylethylamine (19.7 µL, 0.11 mmol, 4 eq.) and O-(7-azabenzotriazol-1-yl)-N,N,N'N'-tetramethyluronium hexafluorophosphate (12 mg, 0.031 mmol, 1.1 eq.). #B182 (25.2 mg, 0.028 mmol, 1 eq.) in DMF (0.6 mL) was added, and the reaction was allowed to stir for 45 min. The reaction was purified by reverse phase chromatography (Method A) to give #B183 as a white solid. Yield: 9.8 mg, 0.0076 mmol, 27%. LCMS (Protocol D): m/z 1288.94 [M+H]$^+$, retention time=0.94 minutes.

Step 4:

Synthesis of N-(6-aminohexanoyl)-L-valyl-N-{4-[({[({[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)methyl]carbamoyl}oxy)methyl]phenyl}-$N^5$-carbamoyl-L-ornithinamide acetate salt (#B184). The title compound was prepared in 75% yield from 11.9 mg (0.009 mmol, 1.0 eq) of #B183 and 15.3 mg (0.18 mmol, 20.0 eq) of piperidine using the procedure described for preparation of compound #B47. LCMS (Protocol D): m/z 1066.8 [M+H]$^+$, retention time=0.73 minutes.

Step 5:

Synthesis of N-{6-[(bromoacetyl)amino]hexanoyl}-L-valyl-N-{4-[({[({[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)methyl]carbamoyl}oxy)methyl]phenyl}-N-5-carbamoyl-L-ornithinamide (#B180). The title compound was prepared in 61% yield from 7.6 mg (0.01 mmol) of #B184 and 2.6 mg (0.011 mmol, 1.5 eq.) of 1-[(bromoacetyl)oxy]pyrrolidine-2,5-dione and 3.7 mg (0.028 mmol, 4.0 eq) of N,N-diisopropylethylamine using the procedure described for preparation of compound #B150. LCMS (Protocol D): m/z 1188.8 [M+H]$^+$, retention time=0.81 minutes. $^1$H NMR (500 MHz, DMSO-$d_6$) δ 9.98 (s, 1H), 8.45-8.37 (m, 1H), 8.27-8.20 (m, 1H), 8.14-8.05 (m, 1H), 7.85-7.73 (m, 2H), 7.61-7.55 (m, 2H), 7.30-7.24 (m, 2H), 6.40-6.32 (m, 1H), 6.25 (d, J=16.1 Hz, 1H), 6.10 (dd, J=11.5 and 1.2 Hz, 1H), 6.01-5.93 (m, 1H), 5.87 (dd, J=11.7 and 7.6 Hz, 1H), 5.60 (dd, J=15.6 and 5.4 Hz, 1H), 5.56-5.49 (m, 1H), 5.41 (s, 2H), 5.02 (s, 2H), 4.56-4.50 (m, 1H), 4.42-4.23 (m, 3H), 4.22-4.16 (m, 1H), 3.81 (s, 2H), 3.69-3.60 (m, 3H), 3.52-3.45 (m, 2H), 3.09-2.89 (m, 5H), 2.66-2.53 (m, 3H), 2.34-2.09 (m, 6H), 2.01-1.92 (m, 4H), 1.85-1.55 (m, 10H), 1.54-1.31 (m, 7H), 1.27-1.20 (m, 4H), 1.06 (d, J=6.4 Hz, 3H), 0.94 (d, J=7.3 Hz, 3H), 0.86 (d, J=6.9 Hz, 3H), 0.83 (d, J=6.9 Hz, 3H).

Example A#66
Preparation of N-{6-[(bromoacetyl)amino]hexanoyl}-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}-2-methylhydrazinyl)carbonyl]oxy}methyl)phenyl]-N$^5$-carbamoyl-L-ornithinamide (#B185)
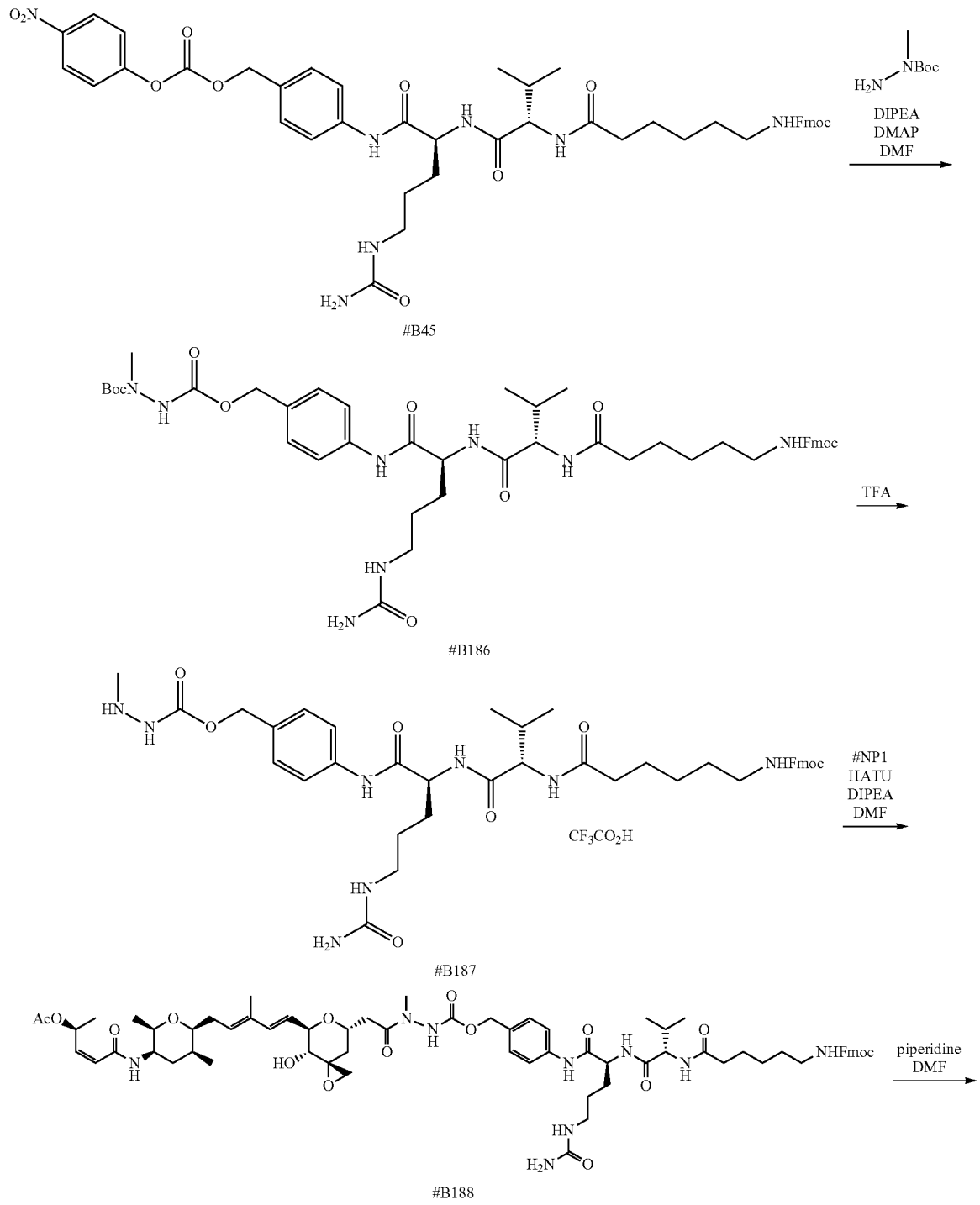

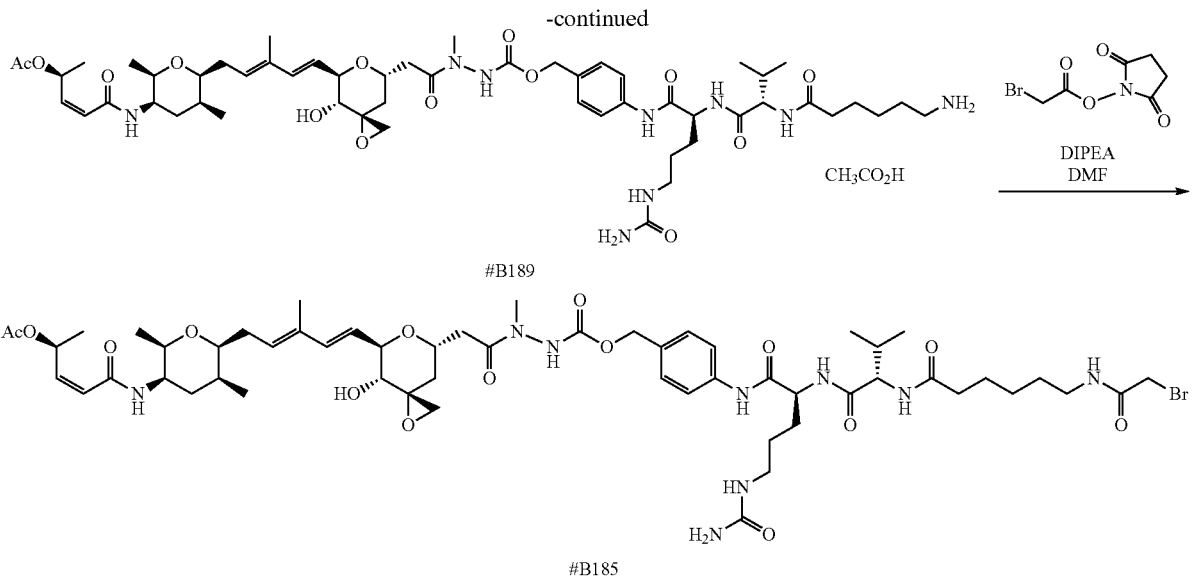

B189

B185

Step 1:

Synthesis of N-(6-{[(9H-fluoren-9-ylmethoxy)carbonyl]amino}hexanoyl)-L-valyl-N-{4-[({[2-(tert-butoxycarbonyl)-2-methylhydrazinyl]carbonyl}oxy)methyl]phenyl}-$N^5$-carbamoyl-L-ornithinamide (#B186). To a solution tert-butyl 1-methylhydrazinecarboxylate (34.8 mg, 0.24 mmol, 1.3 eq.) in N,N-dimethylformamide (1 mL) at rt was added N,N-diisopropylethylamine (64.4 μL, 0.37 mmol, 2 eq.) and 4-N,N-dimethylamino pyridine (11.1 mg, 0.091 mmol, 0.5 eq.) followed by #B45 (161 mg, 0.18 mmol, 1 eq.), and the reaction was allowed to stir. After 4 h, more tert-butyl 1-methylhydrazinecarboxylate (14 mg, 0.096 mmol, 0.5 eq.) in N,N-dimethylformamide (0.2 mL) was added, and the reaction was stirred for 1.5 h. The reaction was diluted with DMSO (1 mL) and purified by reverse phase medium pressure liquid chromatography eluted with 0.02% acetic acid in water (v/v) and 0.02% acetic acid in acetonitrile (v/v) (10% to 100%) to give #B186 as a white solid. Yield: 26.1 mg, 0.029 mmol, 16%. LCMS (Protocol D): m/z 887.6 $[M+H]^+$, retention time=0.92 minutes.

Step 2:

Synthesis of N-(6-{[(9H-fluoren-9-ylmethoxy)carbonyl]amino}hexanoyl)-L-valyl-$N^5$-carbamoyl-N-[4-({[(2-methylhydrazinyl)carbonyl]oxy}methyl)phenyl]-L-ornithinamide trifluoroacetate salt (#B187). To #B186 (16.5 mg, 0.019 mmol, 1 eq.) was added trifluoroacetic acid (1 mL) at rt, and the reaction was allowed to stir for 20 min. The reaction was concentrated, taken up in acetonitrile and reconcentrated three times to give #B187 as a gum which was used in next step without further purification. LCMS (Protocol D): m/z 809.6 $[M+Na]^+$, retention time=0.80 minutes.

Step 3:

Synthesis of N-(6-{[(9H-fluoren-9-ylmethoxy)carbonyl]amino}hexanoyl)-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}-2-methylhydrazinyl)carbonyl]oxy}methyl)phenyl]-$N^5$-carbamoyl-L-ornithinamide (#B188). To a solution of #NP1 (8.7 mg, 0.016 mmol, 1 eq.) in N,N-dimethylformamide (0.2 mL) at rt was added N,N-diisopropylethylamine (11.3 μL, 0.064 mmol, 4 eq.) and O-(7-azabenzotriazol-1-yl)-N,N,N',N''-tetramethyluronium hexafluorophosphate (7.4 mg, 0.019 mmol, 1.2 eq.) followed by a solution of #B187 (17.1 mg, 0.019 mmol, 1.2 eq.) and N,N-diisopropylethylamine (5.7 μL, 0.032 mmol, 2 eq.) in N,N-dimethylformamide (0.4 mL), and the reaction was allowed to stir for 30 min. The reaction was purified by reverse phase chromatography (Method A) to give #B188 as a white solid. Yield: 8.3 mg, 0.0064 mmol, 40%. LCMS (Protocol D): m/z 1304.9 $[M+H]^+$, retention time=0.93 minutes.

Step 4:

Synthesis of N-(6-aminohexanoyl)-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}-2-methylhydrazinyl)carbonyl]oxy}methyl)phenyl]-$N^5$-carbamoyl-L-ornithinamide acetate salt (#B189). The title compound was prepared in 80% yield from 8.3 mg (0.006 mmol, 1.0 eq.) of #B188 and 10.2 mg (0.12 mmol, 20.0 eq) of piperidine using the procedure described for preparation of compound #B47. LCMS (Protocol D): m/z 1082.81 $[M+H]^+$, retention time=0.66 minutes.

Step 5:

Synthesis of N-{6-[(bromoacetyl)amino]hexanoyl}-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}-2-methylhydrazinyl)carbonyl]oxy}methyl)phenyl]-$N^5$-carbamoyl-L-ornithinamide (#B185). The title compound was prepared in 63% yield from 5.5 mg (0.005 mmol, 1 eq.) of #B189, 1.7 mg (0.011 mmol, 1.5 eq) of 1-[(bromoacetyl)oxy]pyrrolidine-2,5-dione and 2.6 mg (0.02 mmol, 4.0 eq) of N,N-diisopropylethylamine using the procedure described for preparation of compound #B150. LCMS (Protocol D): m/z 1204.86 $[M+H]^+$, retention time=0.77 minutes. $^1$H NMR (500 MHz, DMSO-$d_6$) δ 10.01 (s, 1H), 9.94-9.81 (m, 1H), 8.28-8.20 (m, 1H), 8.13-8.05 (m, 1H), 7.86-7.76 (m, 2H), 7.66-7.55 (m, 2H), 7.37-7.25 (m, 2H), 6.59-6.46 (m, 1H), 6.40-6.29 (m, 2H), 6.10 (dd, J=11.6 and 1.5 Hz, 1H), 6.01-5.95 (m, 1H), 5.87 (dd, J=11.6 and 7.6 Hz, 1H), 5.65-5.57 (m, 1H), 5.56-5.50 (m, 1H), 5.41 (m, 2H), 5.12-4.96 (m, 4H), 4.42-4.33 (m, 1H), 4.32-4.24 (m, 1H), 4.23-4.16 (m, 2H), 3.81 (s, 2H), 3.69-3.60 (m, 2H), 3.52-3.47 (m, 1H), 3.07-2.89 (m, 5H), 2.77-2.73 (m, 1H), 2.60-2.54 (m, 1H), 2.34-2.08 (m, 4H), 2.01-1.92 (m, 4H), 1.86-1.31 (m, 14H), 1.27-1.20 (m, 4H), 1.06 (d, J=6.1 Hz, 3H), 0.94 (d, J=7.3 Hz, 3H), 0.86 (d, J=6.9 Hz, 3H), 0.83 (d, J=6.6 Hz, 3H).
Example A#67
Preparation of N-{7-[(2,5-dioxopyrrolidin-1-yl)oxy]-7-oxoheptanoyl}-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N^5-carbamoyl-L-ornithinamide (#B190)
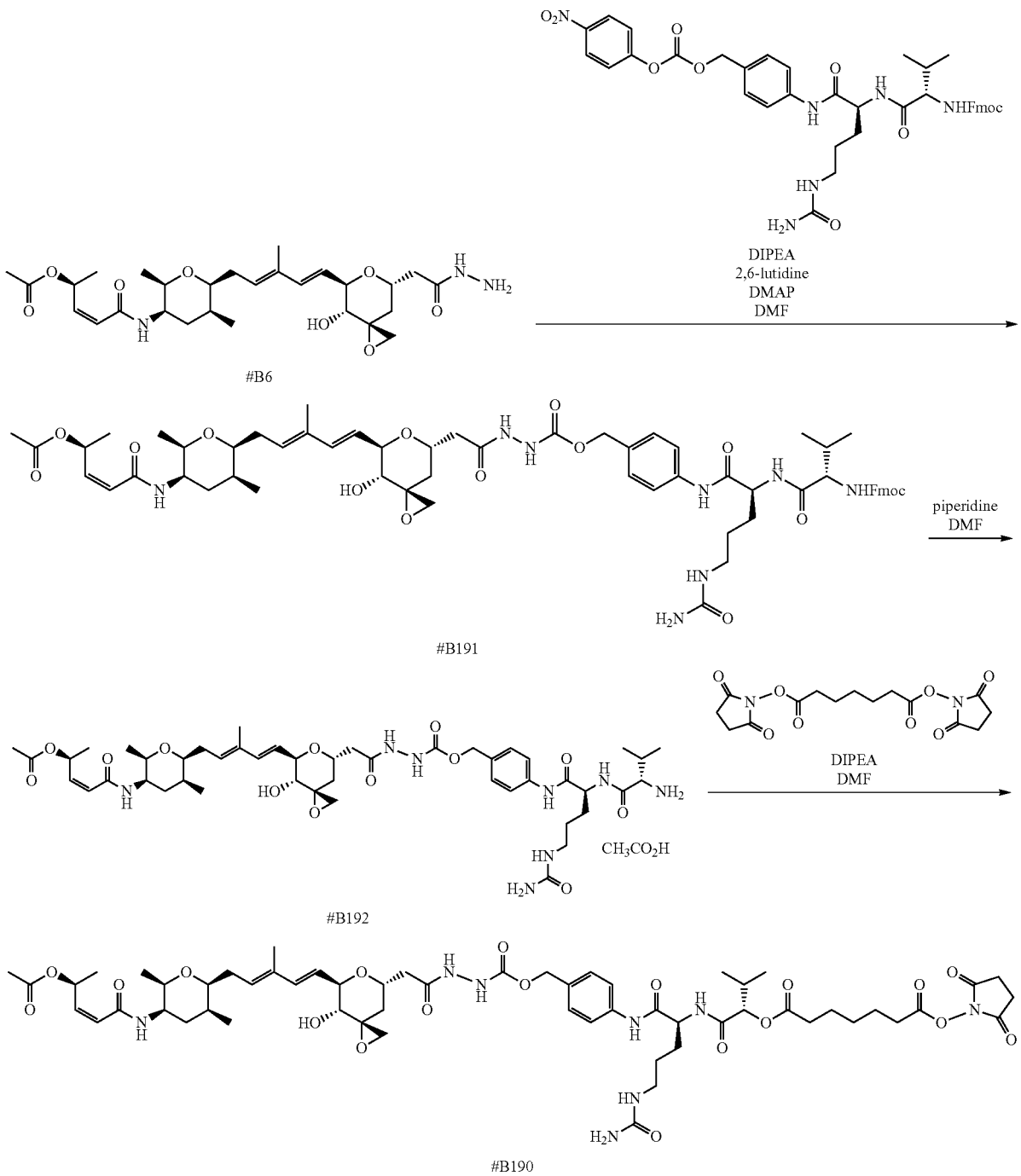

Step 1:

Synthesis of N-[(9H-fluoren-9-ylmethoxy)carbonyl]-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N⁵-carbamoyl-L-ornithinamide (#B191). To a solution of #B6 (19.4 mg, 0.035 mmol, 1 eq.) in N,N-dimethylformamide (0.5 mL) at rt was added N,N-diisopropylethylamine (24.7 µL, 0.14 mmol, 4 eq.), 2,6-lutidine (16.3 µL, 0.14 mmol, 4 eq.), 4-N,N-dimethylamino pyridine (4.3 mg, 0.035 mmol, 1 eq.) and N-[(9H-fluoren-9-ylmethoxy)carbonyl]-L-valyl-N⁵-carbamoyl-N-[4-({[(4-nitrophenoxy)carbonyl]oxy}methyl)phenyl]-L-ornithinamide (40.6 mg, 0.053 mmol, 1.5 eq.), and the reaction was stirred for 2.5 h. More N-[(9H-fluoren-9-ylmethoxy)carbonyl]-L-valyl-N⁵-carbamoyl-N-[4-({[(4-nitrophenoxy)carbonyl]oxy}methyl)phenyl]-L-ornithinamide (13.5 mg, 0.018 mmol, 0.5 eq.) was added, and the reaction was stirred for another 1 h. The reaction was purified by reverse phase chromatography (Method A) to give #B191 as a white solid. Yield: 9.4 mg, 0.0081 mmol, 23%. LCMS (Protocol D): m/z 1177.8 [M+H]⁺, retention time=0.90 minutes.

Step 2:

Synthesis of L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N⁵-carbamoyl-L-ornithinamide acetate salt (#B192). The title compound was prepared in 56% yield from 9.4 mg (0.008 mmol, 1.0 eq) of #B191 and 13.6 mg (0.16 mmol, 20.0 eq) of piperidine using the procedure described for preparation of compound #B47. LCMS (Protocol D): m/z 955.8 [M+H]⁺, retention time=0.65 minutes.

Step 3:

Synthesis of N-{7-[(2,5-dioxopyrrolidin-1-yl)oxy]-7-oxoheptanoyl}-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N⁵-carbamoyl-L-ornithinamide (#B190). To a solution of #B192 (4.5 mg, 0.004 mmol, 1 eq.) in N,N-dimethylformamide (0.3 mL) at rt was added N,N-diisopropylethylamine (3.5 µL, 0.02 mmol, 5 eq.) followed by 1,1'-[(1,7-dioxoheptane-1,7-diyl)bis(oxy)]dipyrrolidine-2,5-dione (prepared as in *J. Am. Chem. Soc.* 2006, 128, 2802, 8.9 mg, 0.025 mmol) 6.2 eq.), and the reaction was allowed to stir for 35 min. The reaction was purified by reverse phase chromatography (Method A) to give #B190 as a white solid. Yield: 1.65 mg, 0.0014 mmol, 34%. LCMS (Protocol D): m/z 1194.80 [M+H]⁺, retention time=0.75 minutes. ¹H NMR (500 MHz, CD₃CN) δ 9.06 (s, 1H), 8.17 (s, 1H), 7.71-7.63 (m, 2H), 7.35-7.25 (m, 2H), 7.19 (d, J=7.6 Hz, 1H), 6.73 (d, J=6.6 Hz, 1H), 6.47 (d, J=8.8 Hz, 1H), 6.41-6.30 (m, 2H), 5.96-5.85 (m, 2H), 5.67-5.50 (m, 2H), 5.33-5.24 (m, 1H), 5.08-4.99 (m, 2H), 4.74 (s, 1H), 4.57-4.48 (m, 1H), 4.39-4.25 (m, 2H), 4.15-4.08 (m, 1H), 3.82-3.75 (m, 1H), 3.67-3.59 (m, 1H), 3.55-3.47 (m, 1H), 3.35-3.20 (m, 2H), 3.12-2.99 (m, 2H), 2.82-2.73 (m, 5H), 2.66-2.52 (m, 6H), 2.46-2.38 (m, 2H), 2.36-2.20 (m, 4H), 1.98 (s, 3H), 1.77-1.57 (m, 11H), 1.53-1.36 (m, 6H), 1.30 (d, J=6.6 Hz, 3H), 1.06 (d, J=6.6 Hz, 3H), 1.00-0.91 (m, 9H).

Example A#68

Preparation of N-{6-[(bromoacetyl)amino]hexanoyl}-L-valyl-N-[2-(3-{[(2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}-3-oxopropyl)phenyl]-L-alaninamide (#B193)

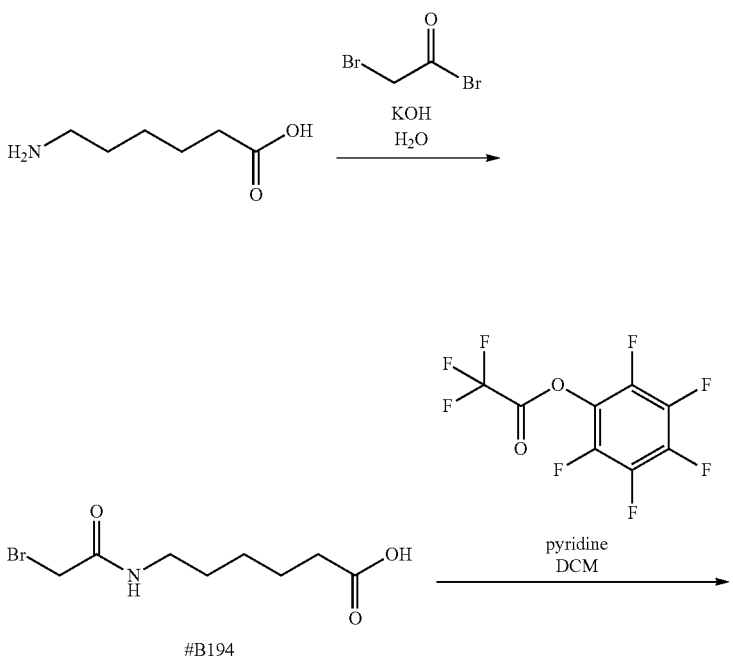

B194

-continued
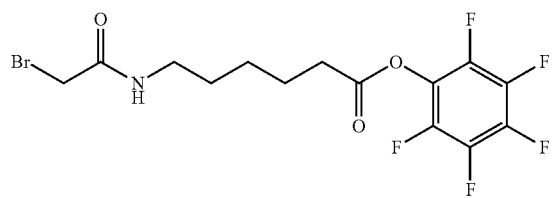
B195
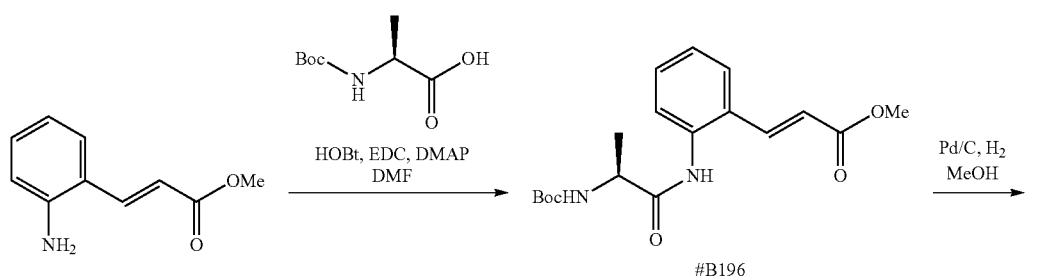
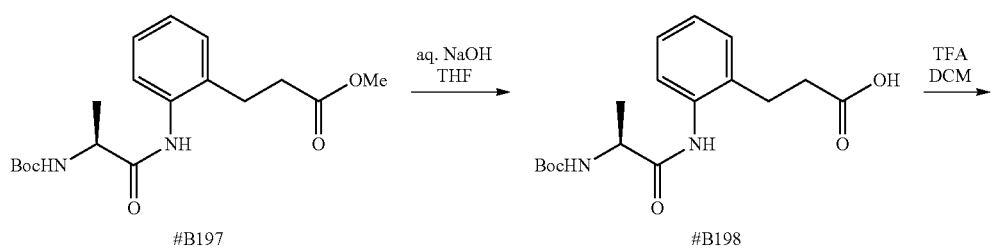
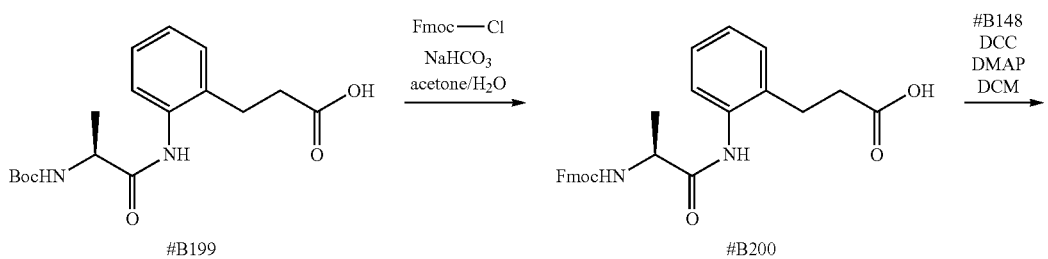
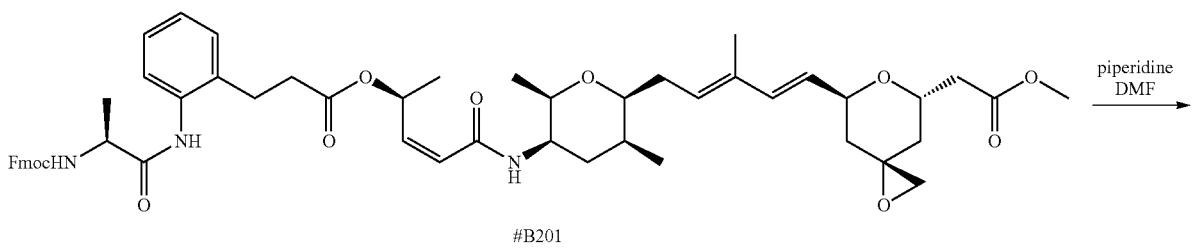
B201
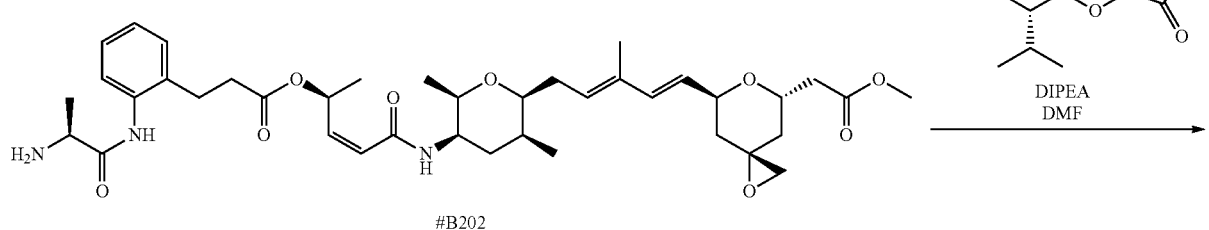
B202

-continued

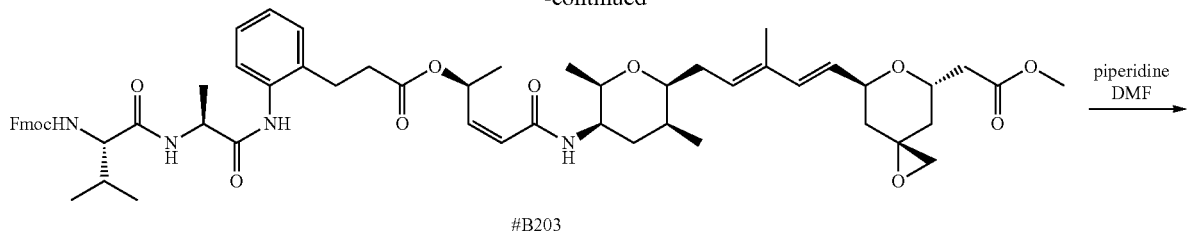

B203

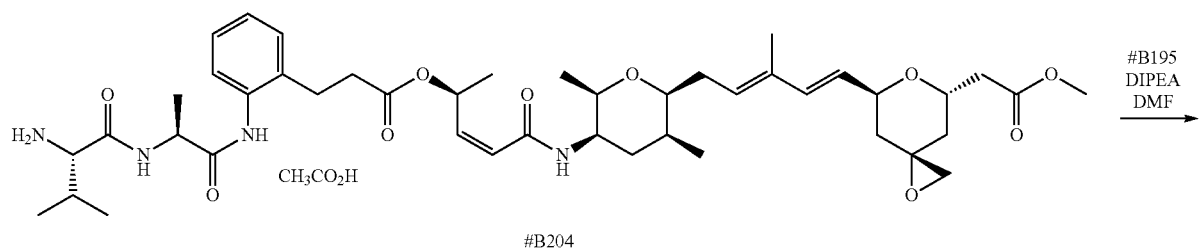

B204

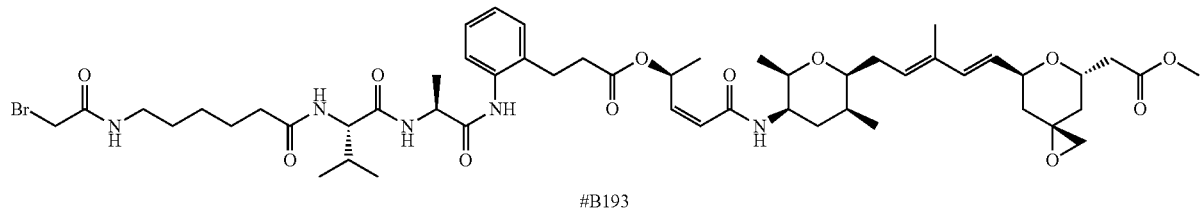

B193

Step 1:

Synthesis of 6-[(bromoacetyl)amino]hexanoic acid (#B194). 6-aminohexanoic acid (14.2 g, 0.11 mol, 1 eq.)) was added to KOH (6.2 g, 0.11 mol, 1 eq.) in water (30 mL) at 0° C. Bromoacetyl bromide (26.1 g, 0.13 mol, 1.2 eq.) was added dropwise while potassium carbonate solution (2.8 N) was added dropwise to adjust pH >7.8. After the addition, the solution was stirred at 0° C. for one hour. The reaction mixture was acidified by 0.5 M HCl to adjust pH to 1 and extracted with ethyl acetate. The organic phase was dried over sodium sulfate and concentrated in vacuo. The residue was purified by silica column chromatography eluted with dichloromethane:methanol 50:1 to afford #B194 (10.2 g, 38%) as a white solid.

Step 2:

Synthesis of pentafluorophenyl 6-[(bromoacetyl)amino] hexanoate (#B195). To a solution of #B194 (8 g, 31.7 mmol, 1 eq.) in dichloromethane (400 mL) was added pentafluorophenyl trifluoroacetate (13.3 g, 45.7 mmol, 1.45 eq.) and pyridine (10 g, 127 mmol, 4 eq.) at 0° C. The reaction mixture was stirred at 0° C. for 10 minutes. The reaction mixture was washed with 0.5 M HCl and concentrated in vacuo. The residue was purified by flash chromatography eluted with ethyl acetate (49.2% in PE) to afford #B195 (9.5 g, 71.7%) as white solid. $^1$H NMR (400 MHz, CDCl$_3$) D6.53 (br, 1H), 3.89 (s, 2H), 3.35 (m, 2H), 2.70 (m, 2H), 1.83 (m, 2H), 1.64 (m, 2H), 1.48 (m, 2H).

Step 3:

Synthesis of methyl (2E)-3-(2-{[N-(tert-butoxycarbonyl)-L-alanyl]amino}phenyl)prop-2-enoate (#B196). A mixture of methyl (2E)-3-(2-aminophenyl)prop-2-enoate (14 g, 79.1 mmol, 1 eq.), N-(tert-butoxycarbonyl)-L-alanine (22.4 g, 119 mmol, 1.5 eq.), 1-hydroxybenzotriazole (16.1 g, 119 mmol, 1.5 eq.), 1-[3-(dimethylamino)propyl]-3-ethylcarbodiimide hydrochloride (22.8 g, 119 mmol, 1.5 eq.), and 4-N,N-dimethylamino pyridine (1.93 g, 15.8 mmol, 0.2 eq.) in N,N-dimethylformamide (600 mL) was stirred at 50° C. for 3 d. The reaction mixture was diluted with ethyl acetate (1500 mL) and water (500 mL). The organic layer was separated and washed with water (300 mL×2), dried over sodium sulfate and concentrated to dryness. The residue was purified by silica column chromatography eluted with petroleum ether:ethyl acetate from 20:1 to 5:1 to afford crude #B196 (21 g, 76.4%) as a yellow oil that was used without further purification.

Step 4:

Synthesis of methyl 3-(2-{[N-(tert-butoxycarbonyl)-L-alanyl]amino}phenyl)propanoate (#B197). To a solution of crude #B196 (21 g, 60.3 mmol, 1 eq.) in methanol (1 L) was added Pd/C (4 g) at 20° C., and the reaction mixture was stirred at rt under hydrogen (35 psi) for 12 h. The reaction mixture was filtered and concentrated to dryness to afford crude #B197 (19 g, 90.5%) as yellow oil which was used without further purification.

Step 5:

Synthesis of 3-(2-{[N-(tert-butoxycarbonyl)-L-alanyl] amino}phenyl)propanoic acid (#B198). To a solution of crude #B197 (19 g, 54.2 mmol, 1 eq.) in tetrahydrofuran (150 mL) was added sodium hydroxide (110 mL, 2 M) at 0° C., and the reaction was stirred at 50° C. for 3 h. The tetrahydrofuran was removed in vacuo, and the resulting solution was adjusted to pH=3-4 by 1 M HCl and extracted with ethyl acetate (100 mL×3). The extract was washed with brine (20 mL×1), dried over sodium sulfate and concentrated to dryness to afford crude #B198 (16 g, 88.9%) as brown oil.

Step 3:

Synthesis of 3-[2-(L-alanylamino)phenyl]propanoic acid trifluoroacetate salt (#B199). To a solution of #B198 (16 g, 47.5 mmol, 1 eq.) in dichloromethane (150 mL) was added TFA (100 mL) at 0° C., and the reaction was stirred at 25° C. for 12 h. The reaction mixture was concentrated to dryness, and the residue was used directly in next step without further purification.

Step 4:

Synthesis of 3-[2-({N-[(9H-fluoren-9-ylmethoxy)carbonyl]-L-alanyl}amino)phenyl]propanoic acid (#B200). To a solution of #B199 (5 g, 21.1 mmol, 1 eq.) in acetone (50 mL) and water (100 mL) was added sodium bicarbonate (5.30 g, 63.4 mmol, 3 eq.) at 0° C. Then 9H-fluoren-9-ylmethylcarbonochloridate (4.94 g, 19.1 mmol, 0.9 eq.) in acetone (50 mL) was added dropwise at 0° C. The reaction was adjusted to pH=3-4 with 1 M HCl, and the aqueous phase was extracted ethyl acetate. The combined organic layers were dried over sodium sulfate, concentrated in vacuo, and the residue was purified by silica column chromatography eluted with methanol:dichloromethane (1.5%~2%) to afford a crude product, which was further purified by prep-HPLC to afford a white solid, that was further purified by SFC-separation to afford #B200 (560 mg, 5.8%) as a white solid. $^1$H NMR (400 Hz, DMSO-$d_6$): □9.65 (s, 1H), 7.92 (d, 2H), 7.76 (m, 3H), 7.43-7.14 (m, 8H), 4.32 (m, 4H), 2.80 (m, 2H), 2.50 (m, 2H), 1.37 (m, 3H).

Step 5:

Synthesis of (2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl 3-[2-({N-[(9H-fluoren-9-ylmethoxy)carbonyl]-L-alanyl}amino)phenyl]propanoate (#B201). To a solution of #B148 (21.2 mg, 0.043 mmol, 1 eq.) in dichloromethane (0.5 mL) at rt was added 4-N,N-dimethylamino pyridine (3.5 mg, 0.029 mmol, 0.67 eq.), a solution of #B200 (39.4 mg, 0.086 mmol, 2 eq.) in N,N-dimethylformamide (0.3 mL), and N,N'-dicyclohexylcarbodiimide (DCC) (23.2 mg, 0.107 mmol, 2.5 eq.), and the reaction was allowed to stir for 2.5 h. More DCC (23 mg, 0.107 mmol, 2.5 eq.) was added, and the reaction was allowed to stir for an additional 2 h. The reaction was diluted with DMSO (0.7 mL), and purified by reverse phase chromatography (Method A) to give #B201 as a white solid. Yield: 8.6 mg, 0.009 mmol, 21%. LCMS (Protocol D): m/z 954.57 [M+Na]$^+$, retention time=1.10 minutes.

Step 6:

Synthesis of (2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl 3-[2-(L-alanylamino)phenyl]propanoate acetate salt (#B202). The title compound was prepared in 70% yield from 15.1 mg (0.016 mmol, 1.0 eq.) of #B201 and 27.2 mg (0.32 mmol, 20.0 eq.) of piperidine using the procedure described for preparation of compound #B47. LCMS (Protocol D): m/z 955.8 [M+H]$^+$, retention time=0.65 minutes.

Step 7:

Synthesis of N-[(9H-fluoren-9-ylmethoxy)carbonyl]-L-valyl-N-[2-(3-{[(2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}-3-oxopropyl)phenyl]-L-alaninamide (#B203). To a solution of #B202 (9 mg, 0.01 mmol, 1 eq.) in N,N-dimethylformamide (0.4 mL) at rt was added N,N-diisopropylethylamine (8.5 μL, 0.048 mmol, 4 eq.) followed by 2,5-dioxopyrrolidin-1-yl-N-[(9H-fluoren-9-ylmethoxy)carbonyl]-L-valinate (10.5 mg, 0.024 mmol, 2 eq.), and the reaction was allowed to stir for 20 min. The reaction was purified by reverse phase chromatography (Method A) to give #B203 as a white solid. Yield: 7.4 mg, 0.007 mmol, 60%. LCMS (Protocol D): m/z 1031.9 [M+H]$^+$, retention time=1.11 minutes.

Step 8:

Synthesis of L-valyl-N-[2-(3-{[(2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}-3-oxopropyl)phenyl]-L-alaninamide acetate salt (#B204). The title compound was prepared in 87% yield from 7.4 mg (0.007 mmol, 1.0 eq.) of #B203 and 11.9 mg (0.14 mmol, 20.0 eq.) of piperidine using the procedure described for preparation of compound #B47. LCMS (Protocol D): m/z 809.9 [M+H]$^+$, retention time=0.81 minutes.

Step 9:

Synthesis of N-{6-[(bromoacetyl)amino]hexanoyl}-L-valyl-N-[2-(3-{[(2S,3Z)-5-{[(2R,3R,5S,6S)-6-{(2E,4E)-5-[(3S,5S,7S)-7-(2-methoxy-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl]oxy}-3-oxopropyl)phenyl]-L-alaninamide (#B193). To a solution of #B204 (5.3 mg, 0.006 mmol, 1 eq.) in N,N-dimethylformamide (0.4 mL) at rt was added N,N-diisopropylethylamine (6.3 μL, 0.036 mmol, 6 eq.) followed by #B195 (2.9 mg, 0.007 mmol, 1.2 eq.), and the reaction was allowed to stir for 10 min. The reaction was purified by reverse phase chromatography (Method A) to give #B193 as a white solid. Yield: 4.1 mg, 0.004 mmol, 65%. LCMS (Protocol D): m/z 1044.9 [M+H]$^+$, retention time=0.95 minutes. $^1$H NMR (500 MHz, DMSO-$d_6$) δ 9.42 (s, 1H), 8.26-8.19 (m, 1H), 8.14 (d, J=6.9 Hz, 1H), 7.85-7.77 (m, 2H), 7.30-7.10 (m, 4H), 6.42-6.33 (m, 1H), 6.25 (d, J=15.9 Hz, 1H), 6.10 (dd, J=11.7 and 1.2 Hz, 1H), 5.83 (dd, J=11.5 and 7.3 Hz, 1H), 5.58 (dd, J=15.9 and 5.1 Hz, 1H), 5.56-5.50 (m, 1H), 4.55-4.42 (m, 2H), 4.34-4.26 (m, 1H), 4.20 (dd, J=8.8 and 6.9 Hz, 1H), 3.81 (s, 2H), 3.68-3.62 (m, 2H), 3.60 (s, 3H), 3.54-3.46 (m, 1H), 3.07-2.99 (m, 2H), 2.87-2.56 (m, 7H), 2.35-2.08 (m, 5H), 2.02-1.92 (m, 2H), 1.88-1.61 (m, 8H), 1.53-1.35 (m, 5H), 1.33 (d, J=7.1 Hz, 3H), 1.28-1.19 (m, 4H), 1.06 (d, J=6.4 Hz, 3H), 0.95 (d, J=7.3 Hz, 3H), 0.85 (d, J=6.6 Hz, 3H), 0.82 (d, J=6.6 Hz, 3H).

Example A#69
Preparation of N-{6-[(bromoacetyl)amino]hexanoyl}-L-valyl-N-{4-[({2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}tetrahydropyridazin-1(2H)-yl]carbonyl}oxy)methyl]phenyl}-N5-carbamoyl-L-ornithinamide (#B205)
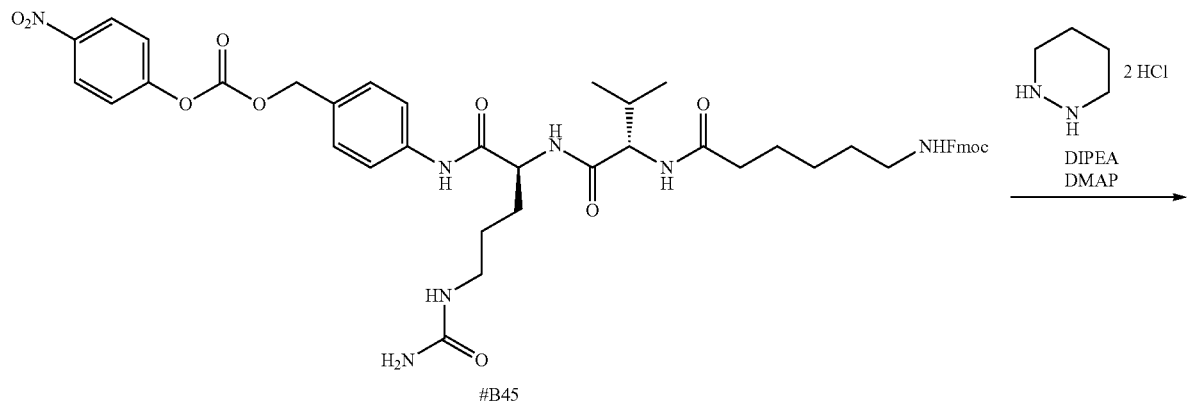
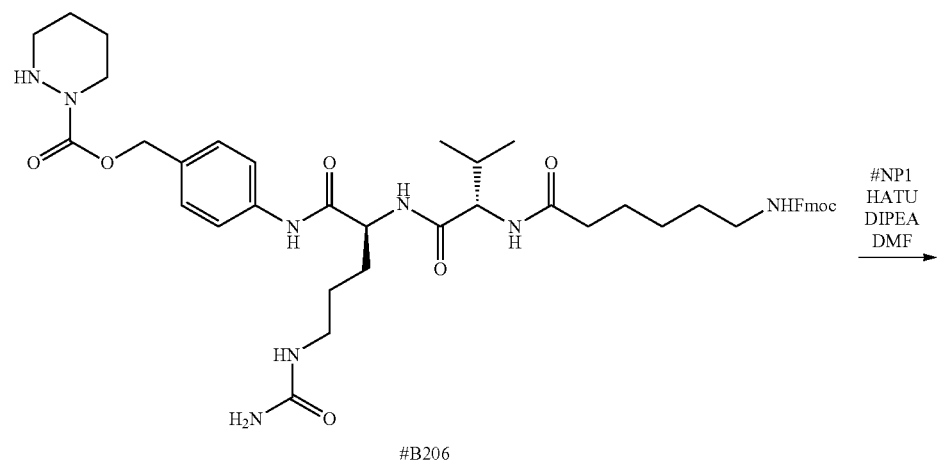
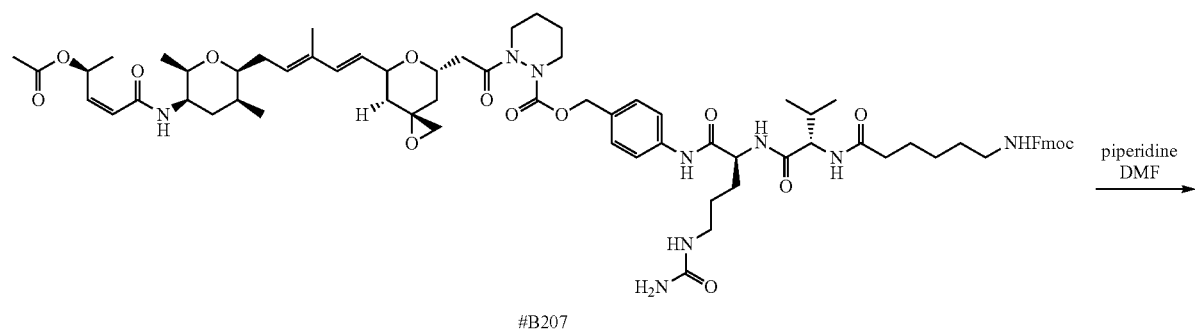

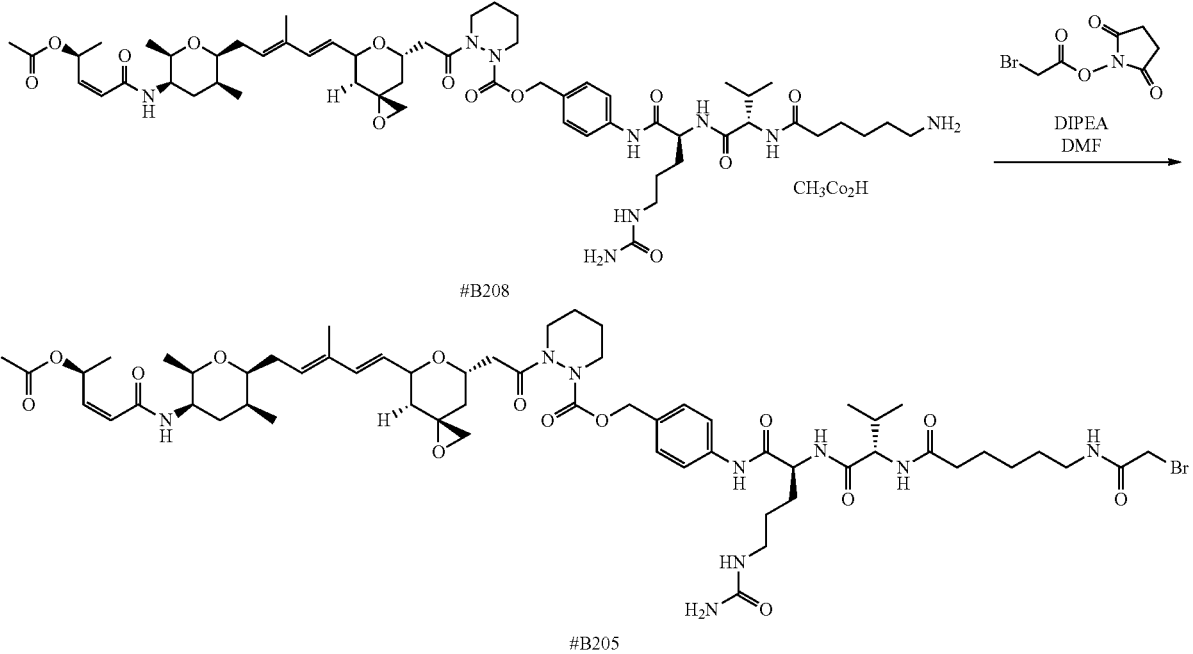

Step 1:

Synthesis of N-(6-{[(9H-fluoren-9-ylmethoxy)carbonyl]amino}hexanoyl)-L-valyl-$N^5$-carbamoyl-N-(4-{[(tetrahydropyridazin-1 (2H)-ylcarbonyl)oxy]methyl}phenyl)-L-ornithinamide (#B206). To a solution of hexahydropyridazine dihydrochloride (11.1 mg, 0.07 mmol, 1 eq.) in N,N-dimethylformamide (0.4 mL) at rt was added N,N-diisopropylethylamine (49.3 μL, 0.28 mmol, 4 eq.) and 4-N,N-dimethylamino pyridine (4.3 mg, 0.035 mmol, 0.5 eq.) followed by #B45 (61.6 mg, 0.07 mmol, 1 eq.), and the reaction was allowed to stir for 30 min. The reaction was purified by reverse phase medium pressure liquid chromatography eluted with 0.02% acetic acid in water (v/v) and 0.02% acetic acid in acetonitrile (v/v) (5% to 95%) to give #B206 as a white solid. Yield: 19.8 mg, 0.024 mmol, 34%. LCMS (Protocol D): m/z 827.63 [M+H]$^+$, retention time=0.84 minutes.

Step 2:

Synthesis of N-(6-{[(9H-fluoren-9-ylmethoxy)carbonyl]amino}hexanoyl)-L-valyl-N-{4-[({[2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}tetrahydropyridazin-1(2H)-yl]carbonyl}oxy)methyl]phenyl}-$N^5$-carbamoyl-L-ornithinamide (#B207). To a solution of #NP1 (15.5 mg, 0.029 mmol, 2 eq.) in N,N-dimethylformamide (0.15 mL) at rt was added N,N-diisopropylethylamine (19.7 μL, 0.11 mmol, 8 eq.) and O-(7-azabenzotriazol-1-yl)-N,N,N',N'-tetramethyluronium hexafluorophosphate (11.3 mg, 0.029 mmol, 2.1 eq.) followed by a solution of #B206 (11.4 mg, 0.014 mmol, 1 eq.) in N,N-dimethylformamide (0.6 mL), and the reaction was allowed to stir for 22 h. The reaction was purified by reverse phase chromatography (Method A) to give #B207 as a white solid. Yield: 4.2 mg, 0.003 mmol, 22%. LCMS (Protocol D): m/z 1345.2 [M+H]$^+$, retention time=0.97 minutes.

Step 3:

Synthesis of N-(6-aminohexanoyl)-L-valyl-N-{4-[({[2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}tetrahydropyridazin-1(2H)-yl]carbonyl}oxy)methyl]phenyl}-$N^5$-carbamoyl-L-ornithinamide acetate salt (#B208). The title compound was prepared in 67% yield from 9.8 mg (0.007 mmol, 1.0 eq.) of #B207 and 11.9 mg (0.14 mmol, 20.0 eq.) of piperidine using the procedure described for preparation of compound #B47. LCMS (Protocol D): m/z 1122.95 [M+H]$^+$, retention time=0.74 minutes.

Step 4:

Synthesis of N-{6-[(bromoacetyl)amino]hexanoyl}-L-valyl-N-{4-[({[2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}tetrahydropyridazin-1(2H)-yl]carbonyl}oxy)methyl]phenyl}-$N^5$-carbamoyl-L-ornithinamide (#B205). The title compound was prepared in 52% yield from 5.6 mg (0.005 mmol, 1 eq.) of #B208, 1.7 mg (0.007 mmol, 1.5 eq) of 1-[(bromoacetyl)oxy]pyrrolidine-2,5-dione and 2.6 mg (0.02 mmol, 4.0 eq) of N,N-diisopropylethylamine using the procedure described for preparation of compound #B150. LCMS (Protocol D): m/z 1244.9 [M+H]$^+$, retention time=0.83 minutes. $^1$H NMR (500 MHz, DMSO-d$_6$) δ 10.04 (br s, 1H), 8.24 (br s, 1H), 8.13 (br s, 1H), 7.87-7.77 (m, 2H), 7.65-7.55 (m, 2H), 7.36-7.24 (m, 2H), 6.88-6.77 (m, 1H), 6.41-6.26 (m, 2H), 6.10 (d, J=11.5 Hz, 1H), 6.04-5.95 (m, 1H), 5.86 (dd, J=11.5 and 7.3 Hz, 1H), 5.66-5.48 (m, 2H), 5.42 (br s, 1H), 5.18-5.06 (m, 1H), 5.05-4.94 (m, 1H), 4.39-4.15 (m, 5H), 4.11-3.98 (m, 1H), 3.81 (s, 2H), 3.68-3.60 (m, 2H), 3.53-3.45 (m, 1H), 3.28-3.20 (m, 2H), 3.08-2.89 (m, 4H), 2.85-2.72 (m, 2H), 2.34-2.08 (m, 5H), 2.02-1.92 (m, 4H), 1.86-1.31 (m, 18H), 1.28-1.20 (m, 4H), 1.09-1.03 (m, 3H), 0.94 (d, J=7.3 Hz, 3H), 0.85 (d, J=6.6 Hz, 3H), 0.82 (d, J=6.6 Hz, 3H).

Example A#70

Preparation of (2Z,4S)—N-[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B209)

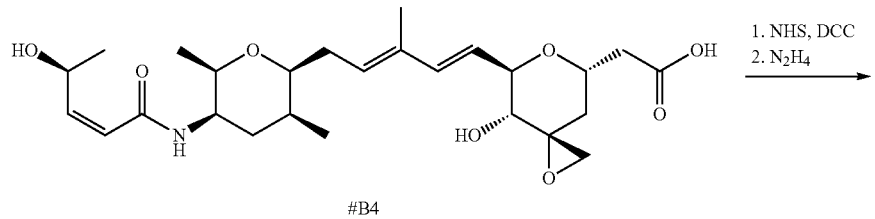

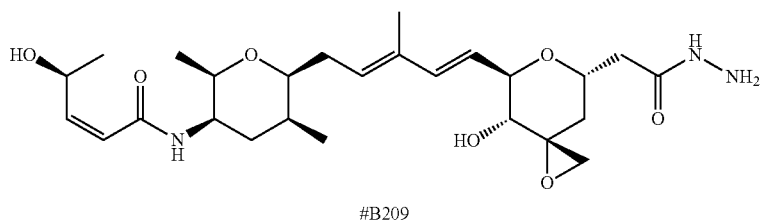

Step 1:

Synthesis of (2Z,4S)—N-[(2R,3R,5S,6S)-6-{(2E,4E)-5-[(3R,4R,5R,7S)-7-(2-hydrazinyl-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]-4-hydroxypent-2-enamide (#B209). To a solution of #B4 (13.1 mg, 0.027 mmol, 1 eq.) in tetrahydrofuran (0.4 mL) at 0° C. was added DCC (11.7 mg, 0.054 mmol, 2 eq.), and the reaction was stirred for 10 min. N-hydroxysuccinimide (6.3 mg, 0.054 mmol, 2 eq.) was added, and the reaction was allowed to stir for 5 h at rt. The reaction was diluted with acetonitrile, filtered and concentrated. The residue was taken up in dichloromethane (0.5 mL), and a solution of hydrazine (1 M in THF, 270 μL, 0.27 mmol, 10 eq.) was added. The reaction was stirred for 10 min, diluted with dimethyl sulfoxide, concentrated to remove the dichloromethane, and filtered. The crude residue was purified by reverse phase chromatography (Method A) to afford #B209 as a solid. Yield: 8.1 mg, 59%. LCMS (Protocol D): m/z 508.6 [M+H]$^+$, retention time=0.59 minutes. $^1$H NMR (400 MHz, DMSO-d$_6$) δ 9.00 (s, 1H), 7.76 (d, J=7.4 Hz, 1H), 6.29 (d, J=15.8 Hz, 1H) 5.98 (d, J=11.3 Hz, 1H), 5.86 (dd, J=11.3 and 7.4 Hz, 1H), 5.60 (dd, J=15.8 and 5.5 Hz, 1H), 5.56-5.48 (m, 1H), 5.23-5.07 (m, 2H), 5.06-4.98 (m, 1H), 4.32-4.09 (m, 3H), 3.70-3.59 (m, 2H), 3.55-3.45 (m, 1H), 3.25-3.19 (m, 1H), 2.74 (d, J=5.1 Hz, 1H), 2.58 (d, J=5.1 Hz, 1H), 2.44 (dd, J=14.4 and 8.6 Hz, 1H), 2.36-2.14 (m, 3H), 1.93-1.58 (m, 8H), 1.50-1.42 (m, 1H), 1.11 (d, J=6.2 Hz, 3H), 1.07 (d, J=6.2 Hz, 3H), 0.96 (d, J=7.0 Hz, 3H).

Example A#71

Preparation of (2S,3Z)-5-({(2R,3R,5S,6S)-6-[(2E,4E)-5-{(3R,4R,5R,7S)-7-[(6S,9S)-19-bromo-6-methyl-2,5,8,11,18-pentaoxo-9-(propan-2-yl)-3,4,7,10,17-pentaazanonadec-1-yl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B210)

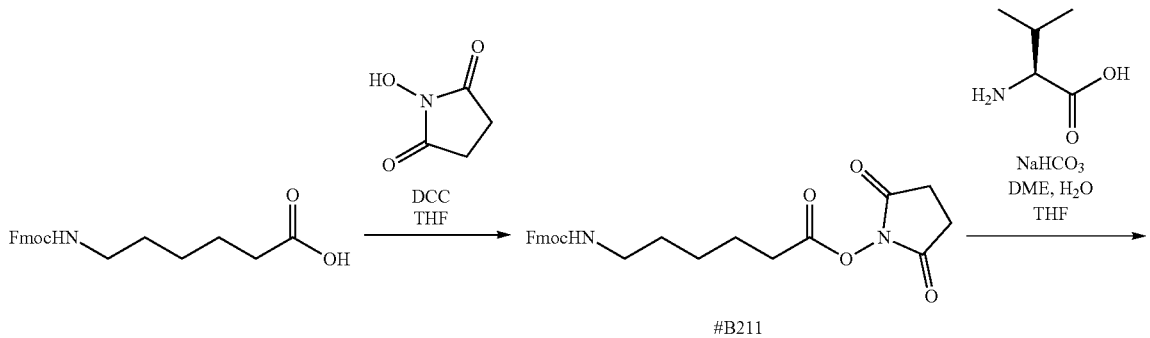

-continued
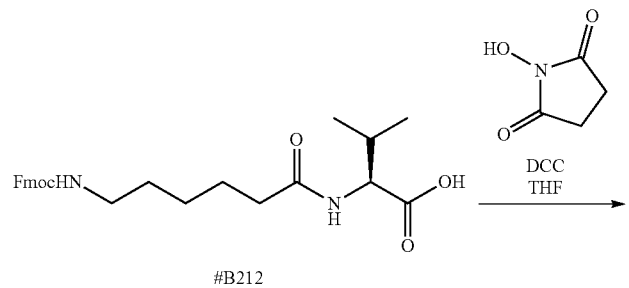
B212
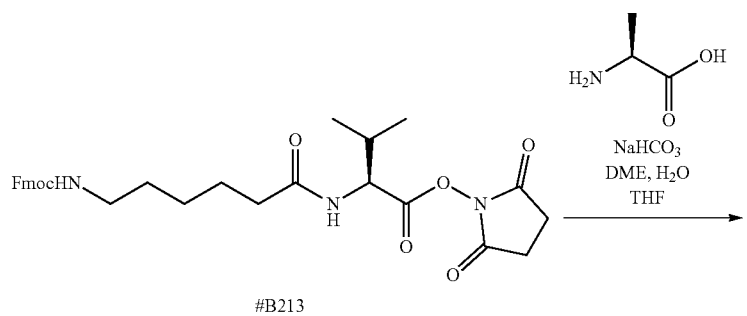
B213
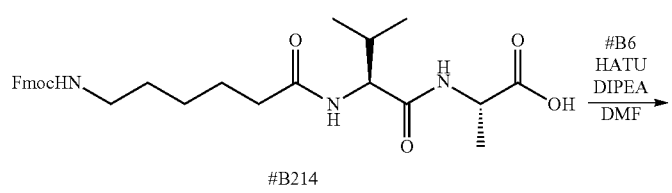
B214
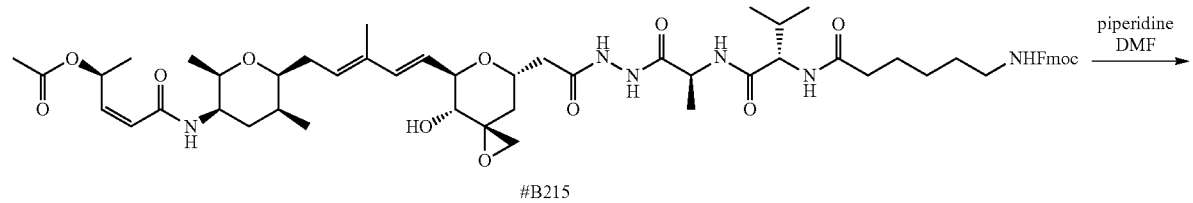
B215
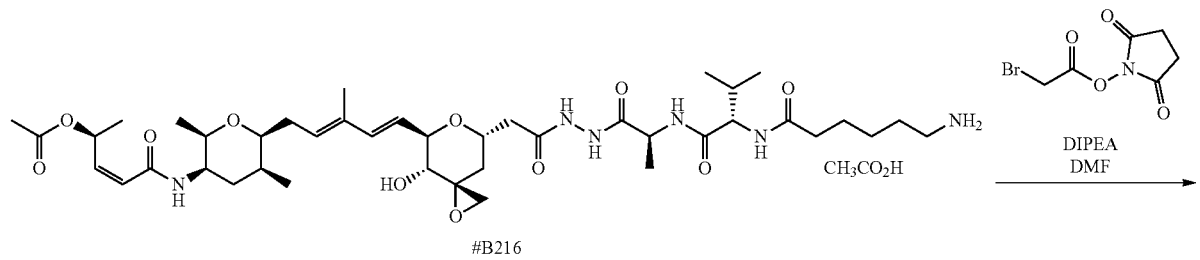
B216
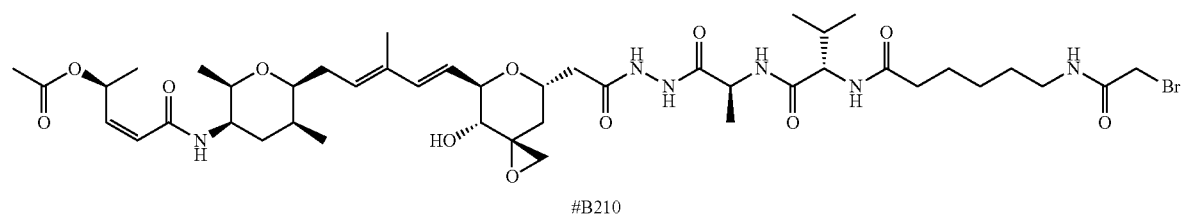 [SMILES: CC(=O)O[C@@H](C)/C=C\C(=O)N[C@@H]1C[C@H](C)[C@H](C/C=C(C)/C=C/[C@H]2O[C@H](CC(=O)NNC(=O)[C@H](C)NC(=O)[C@@H](NC(=O)CCCCCNC(=O)CBr)C(C)C)C[C@@]3(CO3)[C@@H]2O)O[C@@H]1C]
B210

Step 1:
Synthesis of 9H-fluoren-9-ylmethyl-{6-[(2,5-dioxopyrrolidin-1-yl)oxy]-6-oxohexyl}carbamate (#B211). To a solution of 6-((((9H-fluoren-9-yl)methoxy)carbonyl)amino)hexanoic acid (6 g, 16.9 mmol, 1 eq.) in tetrahydrofuran (250 mL) was added N-hydroxysuccinimide (2.13 g, 18.5 mmol, 1.1 eq.) and DCC (3.5 g, 18.59 mmol, 1.1 eq.) at 0° C., and the reaction was stirred at 20° C. overnight. The reaction mixture was cooled to −20° C., filtered and concentrated to dryness. The residue was stirred in MTBE (300 mL) for 20 min and filtered again. The filter cake was dried in vacuo to afford #B211 (5.6 g, 73%) as a white solid.

Step 2:
Synthesis of N-(6-{[(9H-fluoren-9-ylmethoxy)carbonyl]amino}hexanoyl)-L-valine (#B212). To a solution of L-valine (1.5 g, 12.8 mmol, 1 eq.) in water (60 mL) and tetrahydrofuran (30 mL) at 0° C. was added NaHCO$_3$ (1.37 g, 16.3 mmol, 1.3 eq.). Then a solution of #B211 (5.67 g, 12.6 mmol, 0.98 eq.) in dimethoxyethane (80 mL) and tetrahydrofuran (80 mL) was added dropwise at 0-10° C., and the reaction was stirred at 20° C. for 18 h. The pH of the reaction mixture was adjusted to 4 by addition of citric acid, and the reaction mixture was concentrated. Ethyl acetate (450 mL) and methanol (50 mL) were added, and the mixture was stirred for 10 min. The organic layer was separated, dried over sodium sulfate and concentrated to dryness. The residue was purified by flash column chromatography eluted with dichloromethane:methanol from 100:1 to 8:1 to afford #B212 (2.6 g, 45%) as a white solid.

Step 3:
Synthesis of 2,5-dioxopyrrolidin-1-yl-N-(6-{[(9H-fluoren-9-ylmethoxy)carbonyl]amino}hexanoyl)-L-valinate (#B213). To a solution of #B212 (2 g, 4.42 mmol, 1 eq.) in tetrahydrofuran (60 mL) at 0° C. was added N-hydroxysuccinimide (0.53 g, 4.65 mmol, 1.05 eq.) and DCC (0.88 g, 4.65 mmol, 1.05 eq.), and the reaction was stirred at 20° C. overnight. The reaction mixture was cooled to −20° C., filtered and concentrated to dryness. The residue was stirred in MTBE (300 mL) for 20 min and filtered. The filter cake was dried in vacuo to afford #B213 (1.9 g, 79%) as a white solid.

Step 4:
Synthesis of N-(6-{[(9H-fluoren-9-ylmethoxy)carbonyl]amino}hexanoyl)-L-valyl-L-alanine (#B214). To a solution of L-alanine (0.32 g, 3.6 mmol, 1.04 eq.) in water (15 mL) and tetrahydrofuran (10 mL) at 0° C. was added NaHCO$_3$ (0.44 g, 5.19 mmol, 1.5 eq.). Then a solution of #B213 (1.9 g, 3.46 mmol, 1 eq.) in dimethoxyethane (30 mL) was added dropwise at 0-10° C., and the reaction was stirred at 20° C. for 18 hours. The pH of the reaction mixture was adjusted to 4 by addition of citric acid, and the reaction mixture was concentrated. Dichloromethane (400 mL) and methanol (50 mL) were added, and the mixture was stirred for 10 min. The organic layer was separated, dried over sodium sulfate and concentrated to dryness. The residue was purified by flash column chromatography eluted with dichloromethane:methanol from 100:1 to 8:1 to afford a residue that was recrystallized with methanol/tetrahydrofuran (3:1) three times to give #B214 (490 mg, 27%) as a white solid. $^1$H NMR (400 MHz, DMSO): □ 12.48 (b, 1H), 8.21 (b, 1H), 7.91 (d, 2H), 7.77 (d, 1H), 7.68 (m, 2H), 7.41 (m, 2H), 7.33 (m, 2H), 7.31 (m, 1H), 4.29 (m, 2H), 4.18 (m, 3H), 2.94 (m, 2H), 2.16 (m, 2H), 1.93 (m, 1H), 1.47 (m, 2H), 1.37 (m, 2H), 1.25 (m, 3H), 1.21 (m, 2H), 0.86 (m, 6H).

Step 5:
Synthesis of (2S,3Z)-5-({(2R,3R,5S,6S)-6-[(2E,4E)-5-{(3R,4R,5R,7S)-7-[(12S,15S)-1-(9H-fluoren-9-yl)-15-methyl-3,10,13,16,19-pentaoxo-12-(propan-2-yl)-2-oxa-4,11,14,17,18-pentaazaicosan-20-yl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B215). To a solution of #B214 (11.5 mg, 0.022 mmol, 1.2 eq.) in N,N-dimethylformamide (0.2 mL) at rt was added N,N-diisopropylethylamine (12.7 µL, 0.072 mmol, 4 eq.) and O-(7-azabenzotriazol-1-yl)-N,N,N',N'-tetramethyluronium hexafluorophosphate (8.5 mg, 0.022 mmol, 1.2 eq.) followed by a solution of #B6 (10 mg, 0.018 mmol, 1 eq.) in N,N-dimethylformamide (0.5 mL), and the reaction was allowed to stir for 35 min. The reaction was purified by reverse phase chromatography (Method A) to give #B215 as a white solid. Yield: 14.6 mg, 0.014 mmol, 77%. LCMS (Protocol D): m/z 1056.0 [M+H]$^+$, retention time=0.94 minutes.

Step 6:
Synthesis of (2S,3Z)-5-{[(2R,3R,5S,6S)-6-{(2E,4E)-5-[(3R,4R,5R,7S)-7-(2-{2-[(2S)-2-({(2S)-2-[(6-aminohexanoyl)amino]-3-methylbutanoyl}amino)propanoyl]hydrazinyl}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate, acetate salt (#B216). The title compound was prepared in 85% yield from 20.8 mg (0.02 mmol, 1.0 eq.) of #B215 and 34.1 mg (0.4 mmol, 20.0 eq.) of piperidine using the procedure described for preparation of compound #B47. LCMS (Protocol D): m/z 833.9 [M+H]$^+$, retention time=0.65 minutes.

Step 7:
Synthesis of (2S,3Z)-5-({(2R,3R,5S,6S)-6-[(2E,4E)-5-{(3R,4R,5R,7S)-7-[(6S,9S)-19-bromo-6-methyl-2,5,8,11,18-pentaoxo-9-(propan-2-yl)-3,4,7,10,17-pentaazanonadec-1-yl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B210). The title compound was prepared in 57% yield from 15.2 mg (0.017 mmol, 1 eq.) of #B216, 6.1 mg (0.026 mmol, 1.5 eq) of 1-[(bromoacetyl)oxy]pyrrolidine-2,5-dione and 8.9 mg (0.068 mmol, 4.0 eq) of N,N-diisopropylethylamine using the procedure described for preparation of compound #B150. LCMS (Protocol D): m/z 975.68 [M+Na]$^+$, retention time=0.76 minutes. $^1$H NMR (500 MHz, DMSO-d$_6$) δ 9.93-9.80 (m, 2H), 8.26-8.19 (m, 1H), 8.14 (d, J=7.8 Hz, 1H), 7.98 (d, J=7.6 Hz, 1H), 7.85-7.73 (m, 2H), 6.56 (br s, 1H), 6.41-6.26 (m, 2H), 6.11 (d, J=11.5 Hz, 1H), 5.86 (dd, J=11.7 and 7.6 Hz, 1H), 5.61 (dd, J=15.9 and 5.6 Hz, 1H), 5.56-5.48 (m, 1H), 5.10-5.03 (m, 1H), 4.39-4.13 (m, 4H), 3.81 (s, 2H), 3.69-3.60 (m, 2H), 3.54-3.45 (m, 1H), 3.25-3.19 (m, 1H), 3.09-3.00 (m, 2H), 2.74 (d, J=5.0 Hz, 1H), 2.58 (d, J=5.0, 1 H), 2.35-2.25 (m, 2H), 2.24-2.05 (m, 3H), 1.98 (s, 3H), 1.96-1.75 (m, 4H), 1.73-1.60 (m, 4H), 1.55-1.33 (m, 5H), 1.29-1.18 (m, 7H), 1.07 (d, J=6.4 Hz, 3H), 0.95 (d, J=7.3 Hz, 3H), 0.87-0.77 (m, 6H).

Example A#72

Preparation of (2R)-2-(pyridin-2-yldisulfanyl)propyl-2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinecarboxylate (#B217)

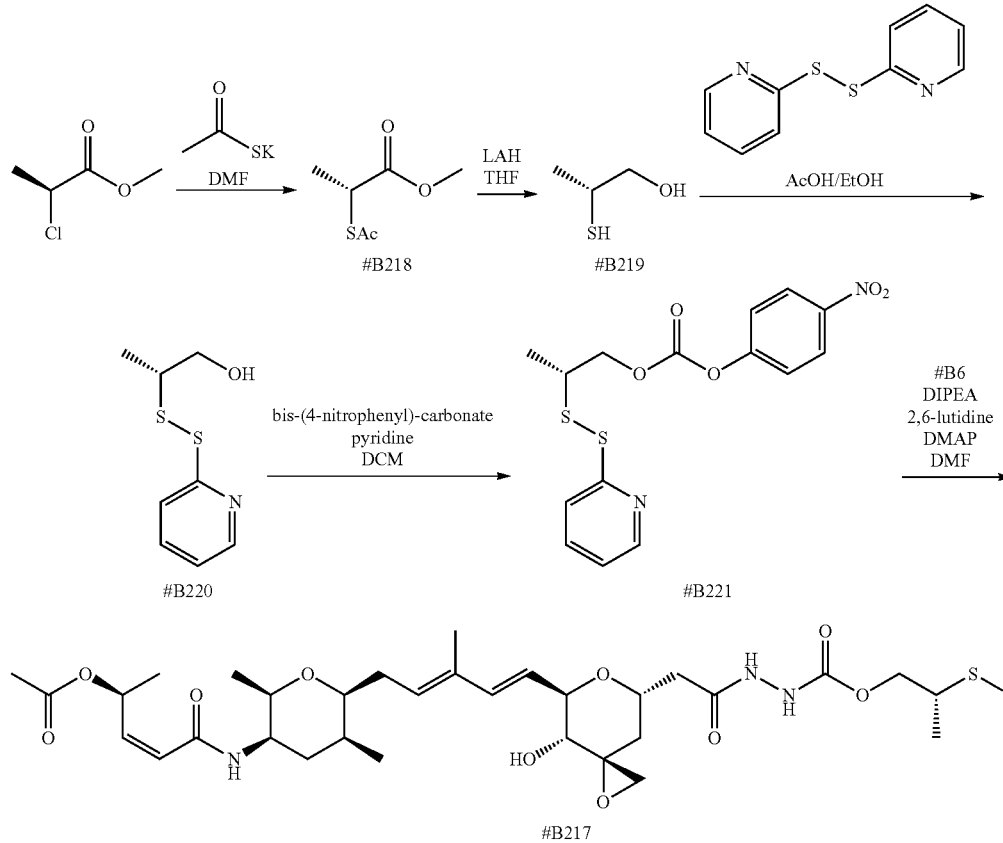

Step 1:
Synthesis of methyl (2R)-2-(acetylsulfanyl)propanoate (#B218). To a solution of potassium thioacetate (3.9 g, 34.4 mmol, 1.2 eq.) in N,N-dimethylformamide (60 mL) was added a solution of S-methyl-2-chloropropanoate (3.5 g, 28.7 mmol, 1 eq.) in N,N-dimethylformamide (10 mL) at rt, and the mixture was stirred at rt overnight. The mixture was poured into water (150 mL) and extracted with petroleum ether (100 mL) three times. The extracts were washed with brine, dried over sodium sulfate and concentrated in vacuo to afford #B218 (4.4 g, 94.8%) as a slight yellow oil.

Step 2:
Synthesis of (2R)-2-sulfanylpropan-1-ol (#B219). To a suspension of LAH (3.4 g, 89.5 mmol, 5 eq.) in tetrahydrofuran (116 mL) was added a solution of #B218 (2.9 g, 17.9 mmol, 1 eq.) in tetrahydrofuran (29 mL) at 0° C., and the mixture was stirred at rt for 1 h. The reaction was quenched with 2 N HCl (50 mL) carefully. The mixture was extracted with dichloromethane (100 mL) five times, and the extracts were dried over sodium sulfate. The solution was concentrated in vacuo to about 150 mL, and the solution was used in the next step directly without further purification.

Step 3:
Synthesis of (2R)-2-(pyridin-2-yldisulfanyl)propan-1-ol (#B220). To a solution of aldrithiol-2 (5.9 g, 26.8 mmol, 1.5 eq.) and acetic acid (1.07 g, 17.9 mmol, 1 eq.) in ethanol (120 mL) at 0° C. was added a solution of #B219 in THF (150 mL, ~17.9 mmol, 1 eq.), and the mixture was stirred at rt overnight. The mixture was concentrated in vacuo, and the residue was purified by silica gel chromatography eluted with petroleum ether:ethyl acetate (10:1 to 4:1) to afford a yellow oil that was re-purified by SFC to afford #B220 (860 mg, 24%) as a slight yellow oil. $^1$H NMR (400 Hz, CDCl$_3$): □8.50 (m, 1H), 7.59 (m, 1H), 7.40 (d, 1H), 7.16 (m, 1H), 5.98 (m, 1H), 3.70 (m, 1H), 3.41 (m, 1H), 3.12 (m, 1H), 1.31 (d, 3H).

Step 4:
Synthesis of 4-nitrophenyl-(2R)-2-(pyridin-2-yldisulfanyl)propyl carbonate (#B221). To a solution of #B220 (111 mg, 0.554 mmol, 1 eq.) in dichloromethane (0.9 mL) at rt was added pyridine (99.4 μL, 1.22 mmol, 2.2 eq.) followed by a solution of 4-nitrophenylchloroformate (140 mg, 0.665 mmol, 1.2 eq.) in dichloromethane (0.9 mL) dropwise, and the reaction was stirred overnight. The reaction was diluted with dichloromethane and water, extracted two times and washed with brine, and the combined organic extracts were dried over sodium sulfate, filtered and concentrated. The residue was purified by silica gel chromatography on eluting with dichloromethane to give #B221 as a gum. Yield: 45 mg, 0.123 mmol, 22%. LCMS (Protocol D): m/z 367.2 [M+H]$^+$, retention time=0.99 minutes.

Step 5:
Synthesis of (2R)-2-(pyridin-2-yldisulfanyl)propyl-2-{[(3R,5S,7R,8R)-7- {(1E,3E)-5-[(2S,3S,5R,6R)-5-{[(2Z, 4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinecarboxylate (#B217). To a solution of #B6 (9.8 mg, 0.018 mmol, 1 eq.) in N,N-dimethylformamide (0.1 mL) at rt was added N,N-diisopropylethylamine (12.7 µL, 0.072 mmol, 4 eq.), 2,6-lutidine (8.4 µL, 0.072 mmol, 4 eq.), 4-N,N-dimethylamino pyridine (2.2 mg, 0.018 mmol, 1 eq.) was added a solution of #B221 (10 mg, 0.027 mmol, 1.5 eq.) in N,N-dimethylformamide (0.3 mL), and the reaction was allowed to stir for 5.5 h. The reaction was purified by reverse phase chromatography (Method A) to give #B217 as a white solid. Yield: 5.9 mg, 0.0076 mmol, 42%. LCMS (Protocol D): m/z 777.51 [M+H]$^+$, retention time=0.84 minutes. $^1$H NMR (500 MHz, CD$_3$CN) δ 8.45-8.38 (m, 1H), 8.15 (br s, 1H), 7.84-7.73 (m, 2H), 7.35 (br s, 1H), 7.16 (ddd, J=7.3, 4.9, and 1.2 Hz, 1H), 6.48-6.28 (m, 3H), 5.97-5.84 (m, 2H), 5.63 (dd, J=15.7 and 5.9 Hz, 1H), 5.59-5.52 (m, 1H), 4.40-4.26 (m, 2H), 4.20-4.04 (m, 2H), 3.83-3.75 (m, 1H), 3.69-3.61 (m, 1H), 3.56-3.49 (m, 1H), 3.32 (d, J=4.7 Hz, 1H), 3.24 (br s, 1H), 2.79 (d, J=4.9 Hz, 1H), 2.65-2.53 (m, 2H), 2.47-2.38 (m, 1H), 2.36-2.19 (m, 4H), 1.97 (s, 3H), 1.77-1.67 (m, 4H), 1.66-1.58 (m, 1H), 1.35-1.26 (m, 6H), 1.07 (d, J=6.4 Hz, 3H), 0.98 (d, J=7.3 Hz, 3H).

Example A#73

Preparation of N$^2$-acetyl-L-lysyl-L-valyl-N$^5$-carbamoyl-N-[4-({[(2-{[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-L-ornithinamide, acetate salt (#B222)

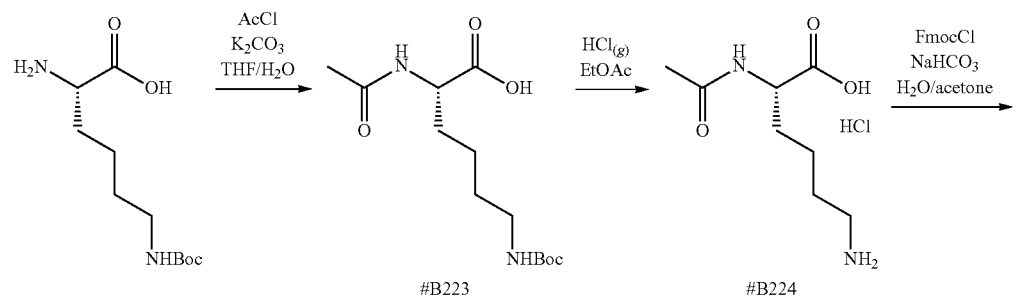

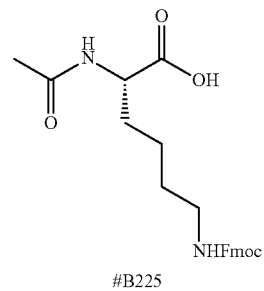

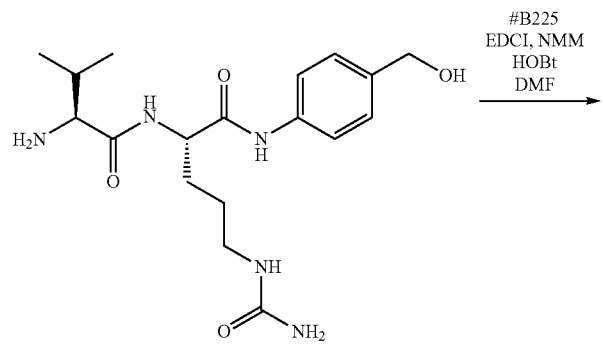

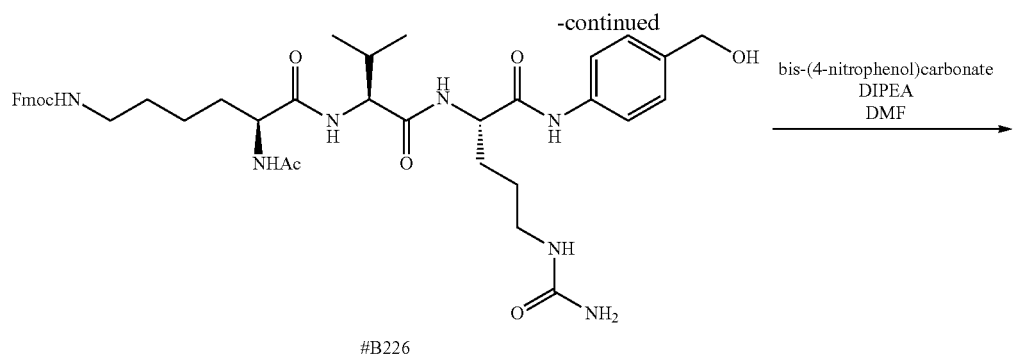

B226

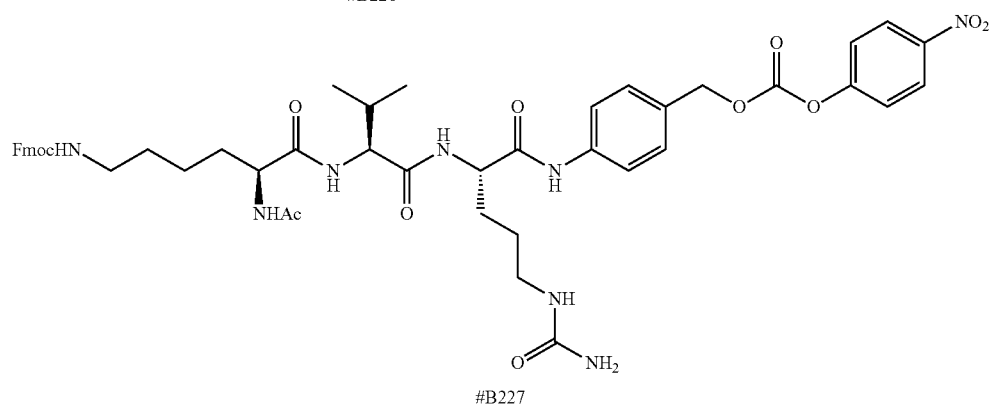

B227

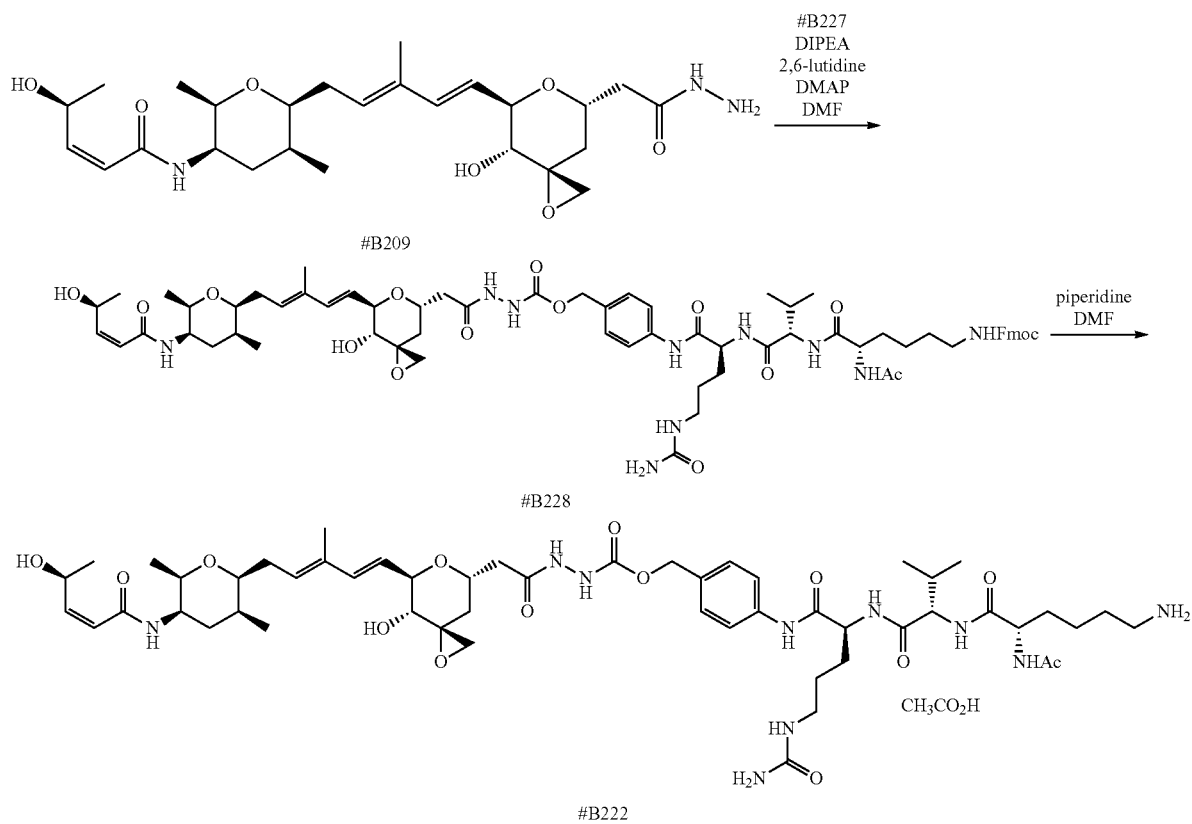

Step 1:
Synthesis of $N^2$-acetyl-$N^6$-(tert-butoxycarbonyl)-L-lysine (#B223). To a mixture of $N^6$-(tert-butoxycarbonyl)-L-lysine (22.5 g, 91.5 mmol, 1 eq.) and $K_2CO_3$ (63.1 g, 0.457 mol, 5 eq.) in tetrahydrofuran/water (200 mL/200 mL) at 0° C. was added acetyl chloride (8.62 g, 0.109 mol, 1.2 eq.), and the mixture was stirred at rt for 4 h. The mixture was concentrated in vacuo to remove the tetrahydrofuran, and the aqueous layer was adjusted to pH=1 with 2 M HCl and extracted with EtOAc (100 mL) three times. The extract was washed with brine (100 mL), dried over sodium sulfate and concentrated in vacuo to afford #B223 (23.1 g, 87.7%) as a yellow oil.

Step 2:

Synthesis of $N^2$-acetyl-L-lysine hydrochloride salt (#B224). To a solution of #B223 (23.1 g, 0.080 mmol, 1 eq.) in ethyl acetate (400 mL) at 0° C. was added HCl (g) in ethyl acetate (250 mL) under nitrogen. The mixture was stirred at rt for 4 h and filtered. The solid was washed with ethyl acetate and dried in vacuo to afford #B224 (18.5 g, >100%) as a white solid which was used without further purification.

Step 3:

Synthesis of $N^2$-acetyl-$N^6$-[(9H-fluoren-9-ylmethoxy)carbonyl]-L-lysine (#B225). To a mixture of #B224 (8 g, 35.6 mmol, 1 eq.) and $NaHCO_3$ (5.99 g, 71.3 mmol, 2 eq.) in acetone/water (80 mL/80 mL) at 0° C. was added a solution of Fmoc-Cl (9.41 g, 36.3 mmol, 1.02 eq.) in acetone (80 mL), and the mixture was stirred at rt for 2 h. The mixture was adjusted to pH=3-4 with 2 N HCl and extracted with ethyl acetate (100 mL) three times. The extracts were washed with brine (100 mL), dried over sodium sulfate and concentrated in vacuo to give the crude product (7 g) as a yellow oil. To the crude product was added dichloromethane and tert-butylmethyl ether (100 mL), and the suspension was stirred for 30 min and then filtered. The filter cake was dried in vacuo to afford #B225 (3.25 g, 22.2%) as a white solid.

Step 4:

Synthesis of $N^2$-acetyl-$N^6$-[(9H-fluoren-9-ylmethoxy)carbonyl]-L-lysyl-L-valyl-$N^5$-carbamoyl-N-[4-(hydroxymethyl)phenyl]-L-ornithinamide (#B226). To a mixture of #B225 (1.04 g, 2.54 mmol, 1 eq.) in N,N-dimethylformamide (20 mL) at 0° C. was added N-methylmorpholine (769 mg, 7.61 mmol, 3 eq.), 1-ethyl-3-(3-dimethylaminopropyl)carbodiimide-HCl (632 mg, 3.30 mmol, 1.3 eq.), 1-hydroxybenzotriazole hydrate (445 mg, 3.30 mmol, 1.3 eq.) and L-valyl-N-carbamoyl-N-[4-(hydroxymethyl)phenyl]-L-ornithinamide (From WO04010957, 1.01 g, 2.66 mmol, 1.05 eq.) under nitrogen, and the mixture was stirred at rt for 2 h. the mixture was poured into tert-butylmethyl ether (300 mL) and filtered. The solid was washed with dichloromethane (50 mL) and water (50 mL) and dried in vacuo to afford #B226 (1.87 g, 95.6%) as a white solid.

Step 5:

Synthesis of $N^2$-acetyl-$N^6$-[(9H-fluoren-9-ylmethoxy)carbonyl]-L-lysyl-L-valyl-$N^5$-carbamoyl-N-[4-({[(4-nitrophenoxy)carbonyl]oxy}methyl)phenyl]-L-ornithinamide (#B227). To a mixture of #B226 (1.87 g, 2.43 mmol, 1 eq.) and bis-(4-nitrophenyl)carbonate (2.21 g, 7.28 mmol, 3 eq.) in N,N-dimethylformamide (30 mL) at 0° C. was added N,N-diisopropylethylamine (313 mg, 2.43 mmol, 1 eq.) under nitrogen, and the mixture was stirred at rt overnight. The mixture was poured into tert-butylmethylether (50 mL) and filtered. The solid (1.95 g) was purified by prep HPLC to give #B227 (580 mg, 25.7%) as a white solid. $^1H$ NMR (400 Hz, DMSO-$d_6$): [ ]10.1 (s, 1H), 8.29 (d, 2H), 8.00 (d, 1H), 7.86 (d, 1H), 7.65 (d, 2H), 7.64 (d, 1H), 7.61 (m, 4H), 7.40 (m, 2H), 7.38 (m, 4H), 7.30 (m, 3H), 6.01 (br, 1H), 5.21 (s, 2H), 4.35 (br, 1H), 4.27-4.15 (m, 5H), 2.96 (m, 4H), 1.98 (m, 1H), 1.82 (s, 3H), 1.65 (br, 3H), 1.43-1.24 (m, 7H), 0.83 (m, 6H).

Step 6:

Synthesis of $N^2$-acetyl-$N^6$-[(9H-fluoren-9-ylmethoxy)carbonyl]-L-lysyl-L-valyl-$N^5$-carbamoyl-N-[4-({[(2-{[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-L-ornithinamide (#B228). To a solution of #B209 (8.1 mg, 0.016 mmol, 1 eq.) in N,N-dimethylformamide (0.4 mL) at rt was added 2,6-lutidine (7.5 µL, 0.064 mmol, 4 eq.), N,N-diisopropylethylamine (11.3 µL, 0.064 mmol, 4 eq.) and 4-N,N-dimethylaminopyridine (2 mg, 0.016 mmol, 1 eq.) followed by #B227 (17.8 mg, 0.019 mmol, 1.2 eq.), and the reaction was stirred for 5 h. The reaction was purified by reverse phase chromatography (Method A) to give #B228 as a white solid. Yield: 5.5 mg, 0.004 mmol, 26%. LCMS (Protocol D): m/z 1306.1 $[M+H]^+$, retention time=0.81 minutes.

Step 7:

Synthesis of $N^2$-acetyl-L-lysyl-L-valyl-$N^5$-carbamoyl-N-[4-({[(2-{[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}hydrazinyl)carbonyl]oxy}methyl)phenyl]-L-ornithinamide, acetate salt (#B222). The title compound was prepared in 79% yield from 9.5 mg (0.007 mmol, 1.0 eq.) of #B228 and 11.9 mg (0.14 mmol, 20.0 eq.) of piperidine using the procedure described for preparation of compound #B47. LCMS (Protocol D): m/z 1084.1 $[M+H]^+$, retention time=0.58 minutes. $^1H$ NMR (500 MHz, DMSO-$d_6$) δ 10.10 (s, 1H), 8.22-8.12 (m, 1H), 8.03 (d, J=7.8 Hz, 1H), 7.87-7.74 (m, 2H), 7.64-7.53 (m, 2H), 7.34-7.18 (m, 2H), 6.31 (d, J=15.9 Hz, 1H), 6.09-6.01 (m, 1H), 5.98 (d, J=11.8 Hz, 1H), 5.86 (dd, J=11.8 and 7.1 Hz, 1H), 5.66-5.56 (m, 1H), 5.55-5.49 (m, 1H), 5.44 (br s, 1H), 5.23-4.91 (m, 3H), 4.43-4.33 (m, 1H), 4.30-4.21 (m, 2H), 4.20-4.12 (m, 1H), 3.69-3.59 (m, 1H), 3.53-3.45 (m, 1H), 3.07-2.88 (m, 2H), 2.76-2.71 (m, 1H), 2.61-2.56 (m, 1H), 2.35-2.14 (m, 4H), 2.04-1.53 (m, 18H), 1.52-1.18 (m, 10H), 1.11 (d, J=6.4 Hz, 3H), 1.06 (d, J=6.4 Hz, 3H), 0.95 (d, J=7.3 Hz, 3H), 0.85 (d, J=6.9 Hz, 3H), 0.82 (d, J=6.9 Hz, 3H).

Example A#74

Preparation of methyl [(3R,5S,7R,8R)-8-hydroxy-7-{(1E,3E)-5-[(2S,3S,5R,6R)-5-{[(2Z,4S)-4-methoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B229)

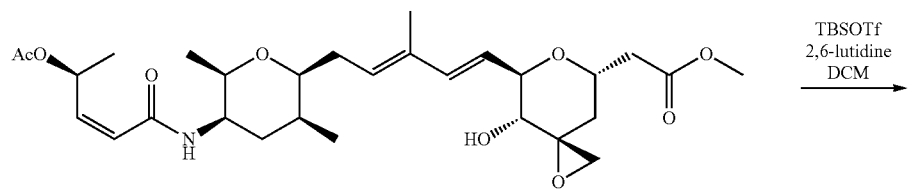

B55

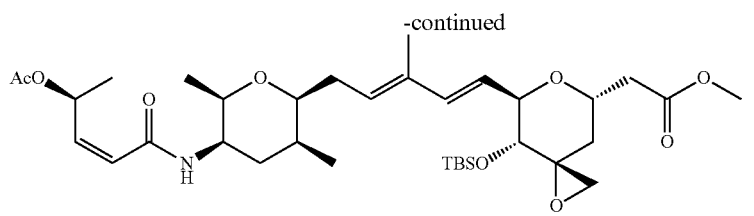

B230

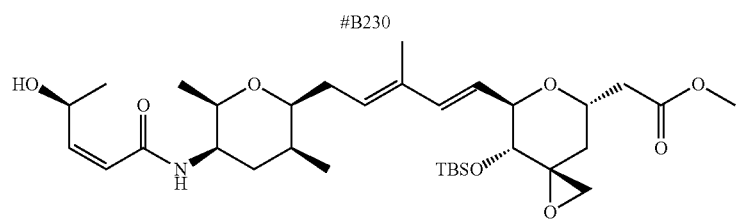

B231

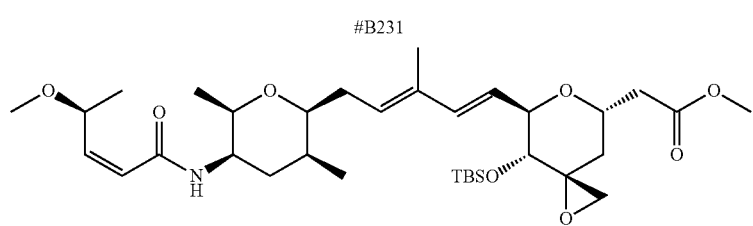

B232

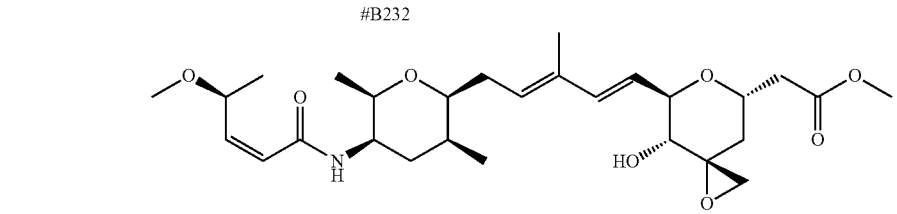

B229

Step 1:

Synthesis of methyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-{[tert-butyl(dimethyl)silyl]oxy}-1,6-dioxaspiro[2.5]oct-5-yl]acetate (#B230). To a solution of the #B55 (66.8 mg, 0.122 mmol, 1 eq.) in dichloromethane at 0° C. was added 2,6-lutidine (71.1 µL, 0.61 mmol, 5 eq.) followed by tert-butyl(chloro)dimethylsilane (86.3 L, 0.366 mmol, 3 eq.), and the reaction was allowed to warm to rt. After 1 h, the reaction was cooled to 0° C., quenched with aqueous $NaHCO_3$, extracted with dichloromethane three times, dried over sodium sulfate, filtered and concentrated. The residue was purified by reverse phase medium pressure liquid chromatography eluted with 0.02% acetic acid in water (v/v) and 0.02% acetic acid in acetonitrile (v/v) (10% to 100%) to give #B230 as a gum. Yield: 68 mg, 0.001 mmol, 84%. LCMS (Protocol D): m/z 686.58 [M+Na]$^+$, retention time=1.16 minutes.

Step 2:

Synthesis of methyl [(3R,5S,7R,8R)-8-{[tert-butyl(dimethyl)silyl]oxy}-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B231). To a solution #B230 (68 mg, 0.1 mmol, 1 eq.) in methanol (1 mL) at rt was added $K_2CO_3$ (35.2 mg, 0.255 mmol, 2.5 eq.), and the reaction was allowed to stir for 1 h. The reaction was filtered washing with ethyl acetate. The organic layer was washed with water and brine, dried over sodium sulfate and concentrated. The residue was purified by reverse phase medium pressure liquid chromatography eluted with 0.02% acetic acid in water (v/v) and 0.02% acetic acid in acetonitrile (v/v) (10% to 100%) to give #B231 as a white solid. Yield: 33.2 mg, 0.053 mmol, 52%. LCMS (Protocol D): m/z 622.55 [M+H]$^+$, retention time=1.09 minutes.

Step 3:

Synthesis of methyl [(3R,5S,7R,8R)-8-{[tert-butyl(dimethyl)silyl]oxy}-7-{(1E,3E)-5-[(2S,3S,5R,6R)-5-{[(2Z,4S)-4-methoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B232). To a solution of #B231 (24.7 mg, 0.04 mmol, 1 eq.) in N,N-dimethylformamide (0.5 mL) at rt was added MeI (37.5 µL, 0.6 mmol, 15 eq.) and $Ag_2O$ (55.6 mg, 0.24 mmol, 6 eq.), and the reaction was allowed to stir for 23 h in the dark. More MeI (38 µL, 0.6 mmol, 15 eq.) and $Ag_2O$ (55 mg, 0.24 mmol, 6 eq.) were added, and the reaction was stirred for a further 25 h. The reaction was filtered over celite and purified by reverse phase chromatography (Method A) to give #B232 as a white solid. Yield: 9.4 mg, 0.015 mmol, 37%. LCMS (Protocol D): m/z 636.7 [M+H]$^+$, retention time=1.19 minutes.

Step 4:

Synthesis of methyl [(3R,5S,7R,8R)-8-hydroxy-7-{(1E,3E)-5-[(2S,3S,5R,6R)-5-{[(2Z,4S)-4-methoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B229). To a solution of #B232 (12.6 mg, 0.02 mmol, 1 eq.) in tetrahydrofuran (0.4 mL) at 0° C. was added tetrabutylammonium fluoride (1 M in tetrahydrofuran, 20.7 µL, 0.02 mmol, 1 eq.), and the reaction was allowed to warm to rt and stir for 1 h. More tetrabutylammonium fluoride (1 M in tetrahydrofuran, 10.3 uL, 0.01 mmol, 0.5 eq) was added, and the reaction was stirred for 45 min. The reaction was concentrated, taken up in DMSO, and purified by reverse phase chromatography (Method A) to give #B229 as a white solid. Yield: 4.9 mg, 0.01 mmol, 47%. LCMS (Protocol D): m/z 522.50 [M+H]$^+$, retention time=0.79 minutes. $^1$H NMR (500 MHz, DMSO-d$_6$) δ 7.75 (d, J=8.0 Hz, 1H), 6.28 (d, J=15.8 Hz, 1H), 6.16 (d, J=11.7 Hz, 1H), 5.75 (dd, J=11.7 and 8.1 Hz, 1H), 5.58 (dd, J=15.8 and 5.1 Hz, 1H), 5.55-5.47 (m, 1H), 5.10-4.99 (m, 2H), 4.31-4.21 (m, 2H), 3.69-3.62 (m, 2H), 3.60 (s, 3H), 3.54-3.47 (m, 1H), 3.28-3.22 (m, 1H), 3.14 (s, 3H), 2.76 (d, J=5.1 Hz, 1H), 2.69-2.55 (m, 3H), 2.35-2.14 (m, 2H), 1.90-1.75 (m, 3H), 1.73-1.60 (m, 4H), 1.57-1.48 (m, 1H), 1.12 (d, J=6.4 Hz, 3H), 1.07 (d, J=6.4 Hz, 3H), 0.95 (d, J=7.3 Hz, 3H).

Example A#75

Preparation of N$^2$-acetyl-L-lysyl-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N$^5$-carbamoyl-L-ornithinamide, acetate salt (#B233)

0.037 mmol, 1 eq.) followed by #B227 (45 mg, 0.048 mmol, 1.3 eq.), and the reaction was stirred for 4 h. The reaction was purified by reverse phase chromatography (Method A) to give #B234 as a white solid. Yield: 18.5 mg, 0.014 mmol, 37%. LCMS (Protocol D): m/z 1348.1 [M+H]$^+$, retention time=0.88 minutes.

Step 2:

Synthesis of N$^2$-acetyl-L-lysyl-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N$^5$-carbamoyl-L-ornithinamide, acetate salt (#B233). To a solution of #B234 (18.5 mg, 0.014 mmol, 1 eq.) in N,N-dimethylformamide (0.7 mL) at rt was added piperidine (27.6 μL, 0.28 mmol, 20 eq.), and the reaction was stirred for 20 min. The reaction was purified by reverse phase chromatography (Method A) to give a white solid which was further purified by reverse phase chromatography (Method C, Phenomenex Luna PFP(2) column) to give #B233 as a white solid. Yield: 8 mg, 0.07 mmol, 50%. LCMS (Protocol D): m/z 1125.91 [M+H]$^+$, retention time=0.63 minutes. $^1$H NMR (500 MHz, DMSO-d$_6$) δ 10.11

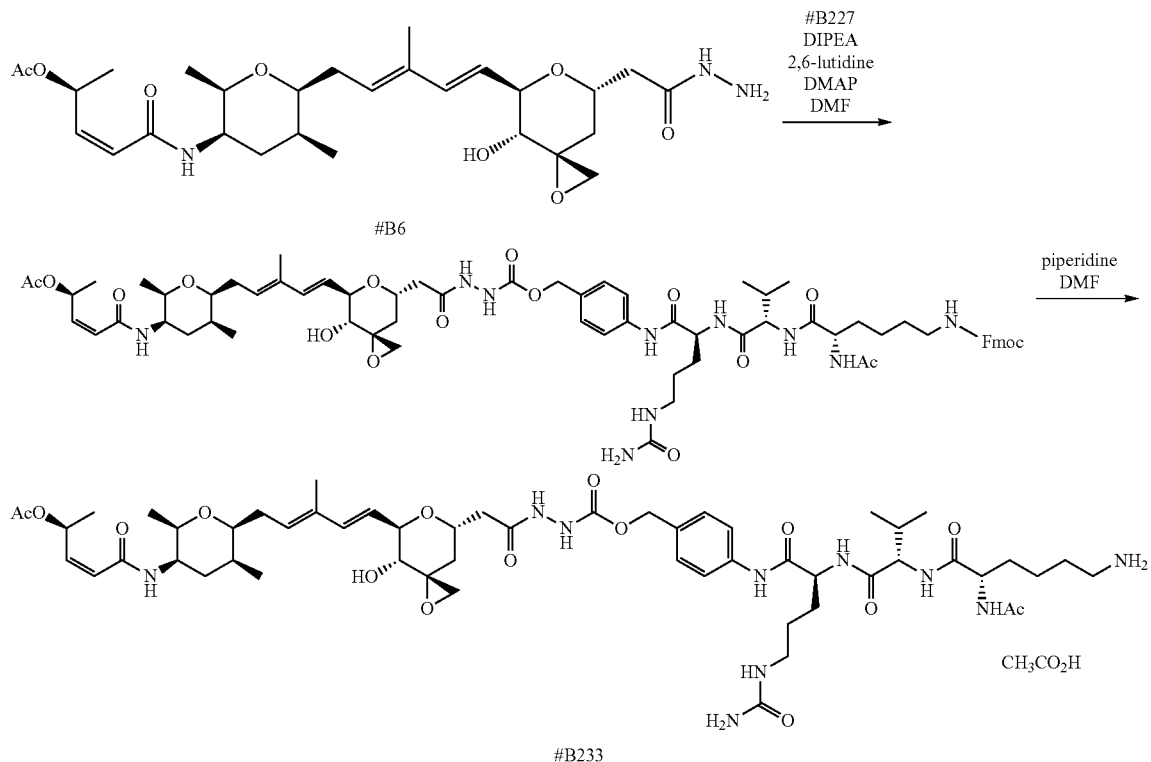

Step 1:
Synthesis of N$^2$-acetyl-N$^6$-[(9H-fluoren-9-ylmethoxy)carbonyl]-L-lysyl-L-valyl-N-[4-({[(2-{[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}hydrazinyl)carbonyl]oxy}methyl)phenyl]-N$^5$-carbamoyl-L-ornithinamide (#B234). To a solution of #B6 (20.5 mg, 0.037 mmol, 1 eq.) in N,N-dimethylformamide (0.8 mL) at rt was added 2,6-lutidine (17.3 μL, 0.148 mmol, 4 eq.), N,N-diisopropylethylamine (26 μL, 0.148 mmol, 4 eq.) and 4-N,N-dimethylamino pyridine (4.5 mg, (s, 1H), 8.43 (s, 1H), 8.19-8.11 (m, 1H), 8.05 (d, J=8.1 Hz, 1H), 7.86-7.76 (m, 2H), 7.64-7.53 (m, 2H), 7.34-7.18 (m, 2H), 6.42-6.27 (m, 2H), 6.16-6.04 (m, 2H), 5.86 (dd, J=11.5 and 7.3 Hz, 1H), 5.66-5.38 (m, 3H), 5.12-4.89 (m, 3H), 4.43-4.33 (m, 1H), 4.32-4.22 (m, 2H), 4.20-4.14 (m, 1H), 3.68-3.59 (m, 1H), 3.54-3.45 (m, 1H), 3.07-2.86 (m, 2H), 2.79-2.72 (m, 1H), 2.71-2.65 (m, 1H), 2.61-2.55 (m, 1H), 2.34-2.14 (m, 4H), 2.04-1.94 (m, 4H), 1.92-1.75 (m, 7H), 1.74-1.54 (m, 8H), 1.53-1.19 (m, 12H), 1.06 (d, J=6.4 Hz, 3H), 0.94 (d, J=7.1 Hz, 3H), 0.86 (d, J=6.8 Hz, 3H), 0.82 (d, J=6.8 Hz, 3H).

Example A#76

Preparation of methyl [(3R,5S,7R,8R)-8-hydroxy-7-{(1E,3E)-5-[(2S,3S,5R,6R)-5-{[(2Z,4S)-4-hydroxy-pent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B235)

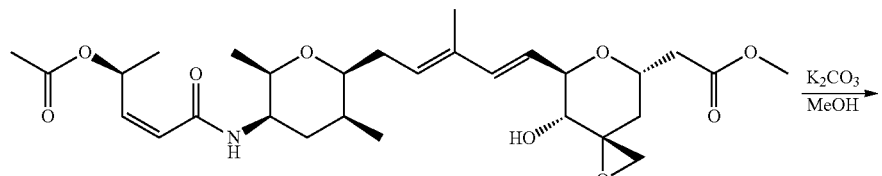

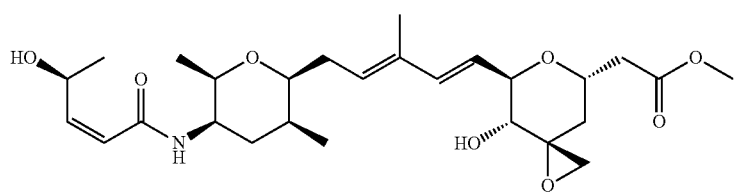

Step 1:

Synthesis of methyl [(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B235). To a solution #B55 (60 mg, 0.11 mmol, 1 eq.) in methanol (1 mL) at rt was added $K_2CO_3$ (37.7 mg, 0.273 mmol, 2.5 eq.), and the reaction was allowed to stir for 1 h. The reaction was filtered washing with ethyl acetate. The organic layer was washed with water and brine, dried over sodium sulfate and concentrated. The residue was purified by reverse phase chromatography (Method A) to give #B235 as a white solid. Yield: 31.2 mg, 0.06 mmol, 56%. LCMS (Protocol D): m/z 530.43 [M+Na]$^+$, retention time=0.72 minutes. $^1$H NMR (500 MHz, DMSO-d$_6$) δ 7.78 (d, J=7.6 Hz, 1H), 6.28 (d, J=16.0 Hz, 1H), 5.98 (d, J=11.8 Hz, 1H), 5.87 (dd, J=11.8 and 7.6 Hz, 1H), 5.58 (dd, J=16.0 and 5.2 Hz, 1H), 5.55-5.49 (m, 1H), 5.23-5.14 (m, 1H), 5.10 (d, J=4.7 Hz, 1H), 5.02 (d, J=6.1 Hz, 1H), 4.31-4.22 (m, 2H), 3.69-3.62 (m, 2H), 3.60 (s, 3H), 3.54-3.47 (m, 1H), 3.28-3.22 (m, 1H), 2.76 (d, J=5.1 Hz, 1H), 2.69-2.55 (m, 3H), 2.35-2.15 (m, 2H), 1.90-1.73 (m, 3H), 1.73-1.61 (m, 4H), 1.57-1.49 (m, 1H), 1.11 (d, J=6.5 Hz, 3H), 1.06 (d, J=6.2 Hz, 3H), 0.96 (d, J=7.5 Hz, 3H).

Example A#77

Preparation of (2R)-2-(pyridin-2-yldisulfanyl)propyl-[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetate (#B236)

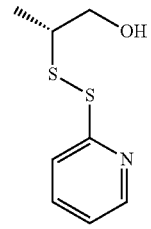

B220
DIC
DMAP
DCM

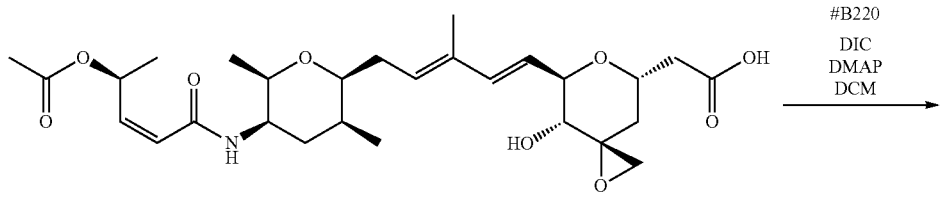

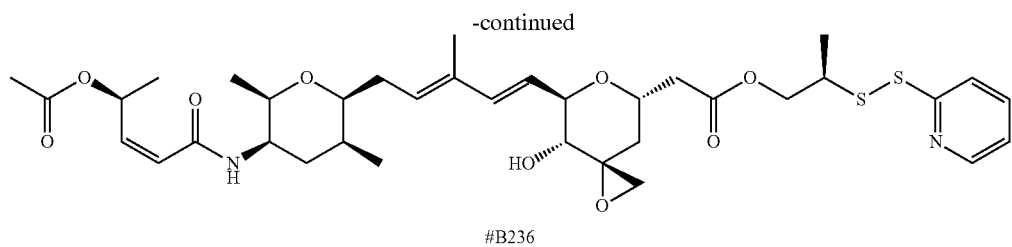

B236

Step 1:

Synthesis of (2R)-2-(pyridin-2-yldisulfanyl)propyl-[(3R, 5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetate (#B236). To a solution of #NP1 (10.4 mg, 0.019 mmol, 1 eq.) and #B220 (11.5 mg, 0.057 mmol, 3 eq.) in dichloromethane (0.3 mL) at rt was added 4-N,N-dimethylamino pyridine (2.3 mg, 0.019 mmol, 1 eq.) and N,N'-di-iso-propylcarbodiimide (8.9 L, 0.057 mmol, 3 eq.), and the reaction was allowed to stir for 75 min. The reaction was concentrated, taken up in DMSO, and purified by reverse phase chromatography (Method A) to give #B236 as a white solid. Yield: 7.6 mg, 0.011 mmol, 55%. LCMS (Protocol D): m/z 719.58 [M+H]$^+$, retention time=0.94 minutes. $^1$H NMR (500 MHz, DMSO-d$_6$) δ 8.46-8.40 (m, 1H), 7.86-7.74 (m, 3H), 7.27-7.20 (m, 1H), 6.41-6.32 (m, 1H), 6.27 (d, J=16.1 Hz, 1H), 6.10 (dd, J=11.7 and 1.5 Hz, 1H), 5.87 (dd, J=11.7 and 7.6 Hz, 1H), 5.61 (dd, J=16.1 and 5.9 Hz, 1H), 5.52-5.45 (m, 1H), 5.02 (d, J=6.1 Hz, 1H), 4.31-4.20 (m, 2H), 4.18-4.06 (m, 2H), 3.68-3.58 (m, 2H), 3.52-3.44 (m, 1H), 3.28-3.23 (m, 1H), 2.76 (d, J=4.9 Hz, 1H), 2.70 (dd, J=15.2 and 9.3 Hz, 1H), 2.62-2.53 (m, 2H), 2.34-2.14 (m, 2H), 1.98 (s, 3H), 1.86-1.72 (m, 4H), 1.70-1.59 (m, 4H), 1.29-1.21 (m, 6H), 1.06 (d, J=6.4 Hz, 3H), 0.94 (d, J=7.3 Hz, 3H).

Example A#78

Preparation of N-{6-[(bromoacetyl)amino]hexanoyl}-L-valyl-N-{4-[({[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]carbamoyl}oxy)methyl]phenyl}-N$^5$-carbamoyl-L-ornithinamide (#B237)

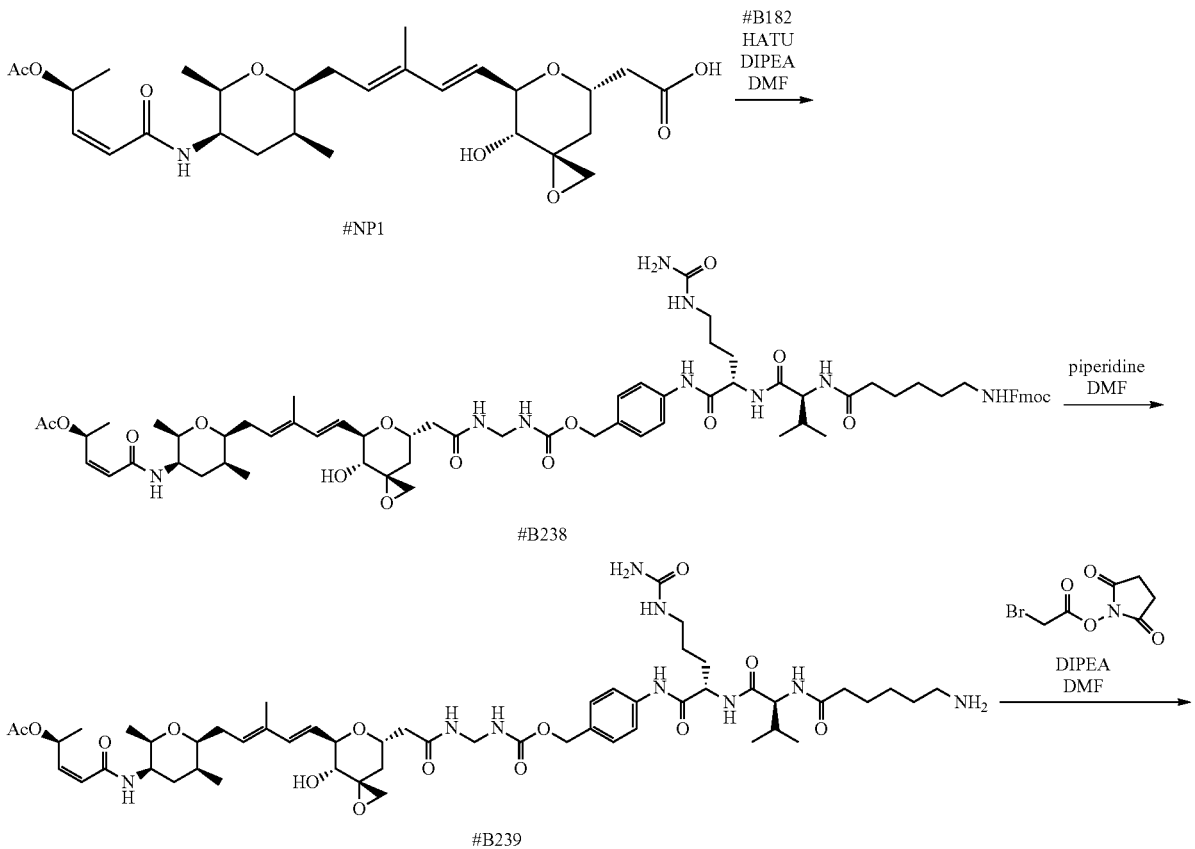

-continued

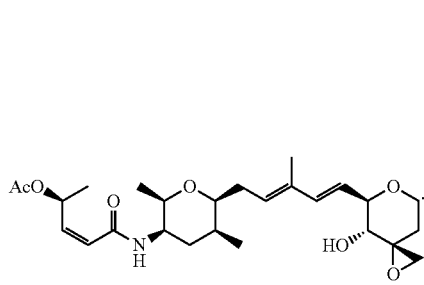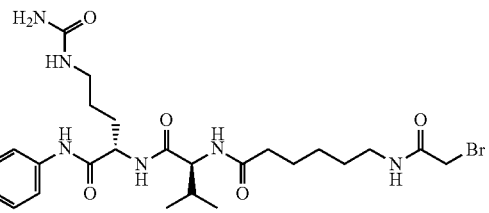

B237

Step 1:
Synthesis of N-(6-{[(9H-fluoren-9-ylmethoxy)carbonyl]amino}hexanoyl)-L-valyl-N-{4-[({[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]carbamoyl}oxy)methyl]phenyl}-N⁵-carbamoyl-L-ornithinamide (#B238). To a solution of #NP1 (20.4 mg, 0.038 mmol, 1 eq.) in N,N-dimethylformamide (0.4 mL) at rt was added N,N-diisopropylethylamine (40.2 µL, 0.228 mmol, 6 eq.) and O-(7-azabenzotriazol-1-yl)-N,N,N',N'-tetramethyluronium hexafluorophosphate (19 mg, 0.049 mmol, 1.3 eq.) followed by a solution of #B182 (34.2 mg, 0.038 mmol, 1 eq.) in N,N-dimethylformamide (0.7 mL), and the reaction was allowed to stir for 45 min. The reaction was purified by reverse phase chromatography (Method A) to give #B238 as a white solid. Yield: 16.1 mg, 0.012 mmol, 33%. LCMS (Protocol D): m/z 1305.3 [M+H]⁺, retention time=0.92 minutes.

Step 2:
Synthesis of N-(6-aminohexanoyl)-L-valyl-N-{4-[({[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]carbamoyl}oxy)methyl]phenyl}-N⁵-carbamoyl-L-ornithinamide (#B239). The title compound was prepared in 88% yield from 16.1 mg (0.012 mmol, 1.0 eq.) of #B238 and 20.4 mg (0.24 mmol, 20.0 eq.) of piperidine using the procedure described for preparation of compound #B47. LCMS (Protocol D): m/z 1083.1 [M+H]⁺, retention time=0.67 minutes.

Step 3:
Synthesis of N-{6-[(bromoacetyl)amino]hexanoyl}-L-valyl-N-{4-[({[({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)methyl]carbamoyl}oxy)methyl]phenyl}-N⁵-carbamoyl-L-ornithinamide (#B237). The title compound was prepared in 62% yield from 11.5 mg (0.011 mmol) of #B239, 4 mg (0.017 mmol, 1.5 eq) of 1-[(bromoacetyl)oxy]pyrrolidine-2,5-dione and 5.7 mg (0.044 mmol, 4.0 eq) of N,N-diisopropylethylamine using the procedure described for preparation of compound #B150. LCMS (Protocol D): m/z 1203.2 [M+H]⁺, retention time=0.77 minutes. ¹H NMR (500 MHz, DMSO-d₆) δ 9.99 (s, 1H), 8.45-8.37 (m, 1H), 8.28-8.20 (m, 1H), 8.15-8.05 (m, 1H), 7.86-7.73 (m, 2H), 7.62-7.54 (m, 2H), 7.31-7.22 (m, 2H), 6.41-6.33 (m, 1H), 6.30 (d, J=15.9 Hz, 1H), 6.11 (dd, J=11.6 and 1.5 Hz, 1H), 6.02-5.94 (m, 1H), 5.86 (dd, J=11.6 and 7.6 Hz, 1H), 5.60 (dd, J=15.9 and 5.6 Hz, 1H), 5.56-5.48 (m, 1H), 5.41 (s, 2H), 5.04 (d, J=5.4 Hz, 1H), 4.95 (s, 2H), 4.43-4.15 (m, 5H), 3.81 (s, 2H), 3.69-3.60 (m, 2H), 3.53-3.45 (m, 1H), 3.25-3.18 (m, 1H), 3.09-2.88 (m, 4H), 2.73 (d, J=5.0 Hz, 1H), 2.57 (d, J=5.0 Hz, 1H), 2.34-2.08 (m, 5H), 2.03-1.91 (m, 4H), 1.91-1.74 (m, 4H), 1.73-1.30 (m, 12H), 1.29-1.18 (m, 4H), 1.06 (d, J=6.4 Hz, 3H), 0.94 (d, J=7.3 Hz, 3H), 0.86 (d, J=6.6 Hz, 3H), 0.83 (d, J=6.9 Hz, 3H).

Example A#79

Preparation of methyl [(3R,5S,7R,8R)-8-methoxy-7-{(1E,3E)-5-[(2S,3S,5R,6R)-5-{[(2Z,4S)-4-methoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B240)

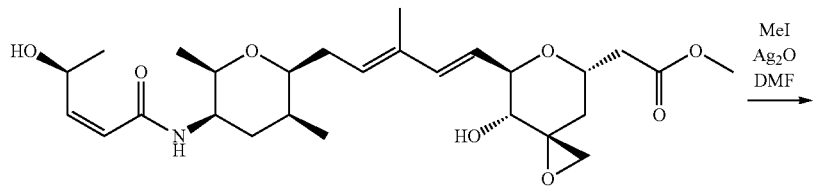

B235

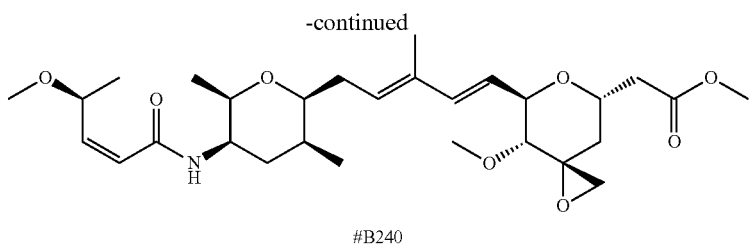

B240

Step 1:

Synthesis of methyl [(3R,5S,7R,8R)-8-methoxy-7-{(1E,3E)-5-[(2S,3S,5R,6R)-5-{[(2Z,4S)-4-methoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetate (#B240). To a solution of #B235 (24.2 mg, 0.048 mmol, 1 eq.) in N,N-dimethylformamide (0.5 mL) at rt was added MeI (45 µL, 0.7 mmol, 15 eq.) and Ag$_2$O (66.7 mg, 0.29 mmol, 6 eq.), and the reaction was allowed to stir for 23 h in the dark. More MeI (45 µL, 0.7 mmol, 15 eq.) and Ag$_2$O (67 mg, 0.29 mmol, 6 eq.) were added, and the reaction was stirred for a further 24 h. The reaction was filtered over celite and purified by reverse phase chromatography (Method A) to give #B240 as a white solid. Yield: 12.2 mg, 0.023 mmol, 48%. LCMS (Protocol D): m/z 536.7 [M+H]$^+$, retention time=0.90 minutes. $^1$H NMR (500 MHz, DMSO-d$_6$) δ 7.75 (d, J=8.0 Hz, 1H), 6.36 (d, J=15.8 Hz, 1H), 6.16 (d, J=11.7 Hz, 1H), 5.75 (dd, J=11.7 and 8.1 Hz, 1H), 5.62-5.50 (m, 2H), 5.10-4.99 (m, 1H), 4.58-4.51 (m, 1H), 4.28-4.18 (m, 1H), 3.70-3.62 (m, 2H), 3.60 (s, 3H), 3.55-3.47 (m, 1H), 3.32 (s, 3H), 3.14 (s, 3H), 2.96-2.91 (m, 1H), 2.70-2.63 (m, 2H), 2.58-2.52 (m, 1H), 2.35-2.16 (m, 2H), 2.06-1.97 (m, 1H), 1.88-1.75 (m, 2H), 1.73-1.60 (m, 4H), 1.18-1.09 (m, 4H), 1.07 (d, J=6.4 Hz, 3H), 0.96 (d, J=7.3 Hz, 3H).

Example A#80

Preparation of (2S,3Z)-5-({(2R,3R,5S,6S)-6-[(2E,4E)-5-{(3R,4R,5R,7S)-7-[(carbamoylamino)methyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B241). and (2S,3Z)-5-{[(2R,3R,5S,6S)-6-{(2E,4E)-5-[(3R,4R,5R,7S)-4-hydroxy-7-{[(propylcarbamoyl)amino]methyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B242)

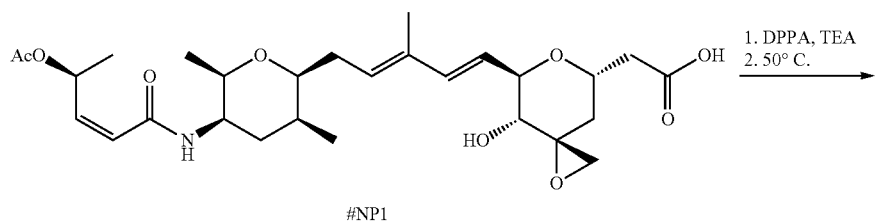

NP1

1. DPPA, TEA
2. 50° C.

B243

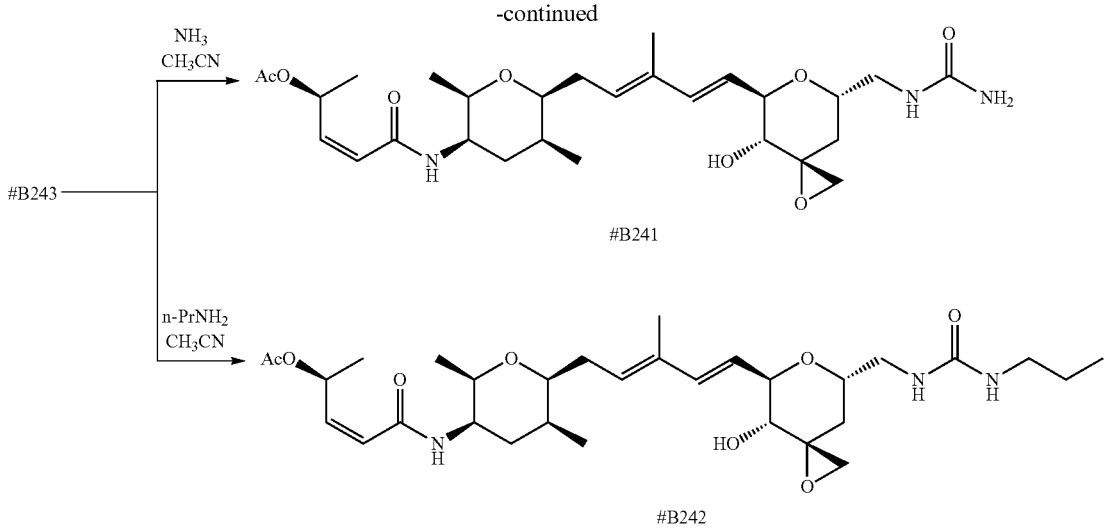

Step 1:

Synthesis of (2S,3Z)-5-{[(2R,3R,5S,6S)-6-{(2E,4E)-5-[(3R,4R,5R,7S)-4-hydroxy-7-(isocyanatomethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B243). To a solution of #NP1 (25.6 mg, 0.048 mmol, 1 eq.) in dichloromethane (1 mL) at rt was added triethylamine (7.3 mg, 0.072 mmol, 1.5 eq.) followed by diphenylphosphoryl azide (11.7 μL, 0.053 mmol, 1.1 eq.)), and the reaction was allowed to stir for 20 h. The reaction was diluted with dichloromethane, washed with 5% NaHCO$_3$ (aq.) three times, dried over sodium sulfate and concentrated in vacuo to give a yellow oil. The oil was dissolved acetonitrile (1 mL) and heated to 50° C. for 1 h. The reaction was cooled to give #B243 as a solution in acetonitrile which was used without further purification. Full conversion assumed. LCMS (Protocol D): m/z 533.6 [M+H]$^+$, retention time=0.88 minutes.

Step 2.

Synthesis of (2S,3Z)-5-({(2R,3R,5S,6S)-6-[(2E,4E)-5-{(3R,4R,5R,7S)-7-[(carbamoylamino)methyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B241). To a solution of #B243 (12.8 mg, 0.024 mmol, 1 eq.) in acetonitrile (0.5 mL) at rt was added NH$_3$ (7 M in methanol, 34.3 μL, 0.24 mmol, 10 eq.), and the reaction was allowed to stir for 30 min. The reaction was concentrated, diluted with DMSO and purified by reverse phase chromatography (Method A) to give #B241 as a white solid. Yield: 6.7 mg, 0.012 mmol, 51%. LCMS (Protocol D): m/z 550.6 [M+H]$^+$, retention time=0.72 minutes. $^1$H NMR (400 MHz, DMSO-d$_6$) δ 7.79 (d, J=8.2 Hz, 1H), 6.41-6.25 (m, 2H), 6.11 (d, J=11.7 Hz, 1H), 6.02-5.94 (m, 1H), 5.87 (dd, J=11.7 and 7.4 Hz, 1H), 5.64 (dd, J=16.0 and 5.9 Hz, 1H), 5.57-5.50 (m, 1H), 5.46 (br s, 1H), 5.01 (d, J=5.9 Hz, 1H), 4.32-4.23 (m, 1H), 3.88-3.77 (m, 1H), 3.70-3.60 (m, 2H), 3.55-3.46 (m, 1H), 3.25-3.04 (m, 3H), 2.75 (d, J=5.1 Hz, 1H), 2.60 (d, J=5.1 Hz, 1H), 2.35-2.13 (m, 2H), 1.98 (s, 3H), 1.88-1.59 (m, 8H), 1.46-1.37 (m, 1H), 1.25 (d, J=6.2 Hz, 3H), 1.07 (d, J=6.2 Hz, 3H), 0.95 (d, J=7.0 Hz, 3H).

Step 3.

Synthesis of (2S,3Z)-5-{[(2R,3R,5S,6S)-6-{(2E,4E)-5-[(3R,4R,5R,7S)-4-hydroxy-7-{[(propylcarbamoyl)amino]methyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B242). To a solution of #B243 (9 mg, 0.02 mmol, 1 eq.) in acetonitrile (0.4 mL) at rt was added n-propylamine (7 μL, 0.085 mmol, 5 eq.), and the reaction was stirred for 10 min. The reaction was diluted with DMSO (0.7 ml), concentrated in vacuo and purified by reverse phase chromatography (Method A) to give #B242 as a white solid. Yield: 8 mg, 0.014 mmol, 80%. LCMS (Protocol D): m/z 592.7 [M+H]$^+$, retention time=0.80 minutes. $^1$H NMR (500 MHz, DMSO-d$_6$) δ 7.80 (0 (d, J=8.1 Hz, 1H), 6.41-6.32 (m, 1H), 6.28 (d, J=16.0 Hz, 1H), 6.11 (d, J=11.7 Hz, 1H), 6.00-5.93 (m, 1H), 5.91-5.81 (m, 2H), 5.62 (dd, J=16.0 and 5.6 Hz, 1H), 5.54-5.46 (m, 1H), 5.02 (d, J=5.6 Hz, 1H), 4.31-4.25 (m, 1H), 3.86-3.77 (m, 1H), 3.69-3.59 (m, 2H), 3.53-3.45 (m, 1H), 3.26-3.08 (m, 3H), 2.97-2.88 (m, 2H), 2.75 (d, J=5.1 Hz, 1H), 2.60 (d, J=5.1 Hz, 1H), 2.35-2.15 (m, 2H), 1.98 (s, 3H), 1.88-1.75 (m, 3H), 1.73-1.60 (m, 4H), 1.44-1.30 (m, 3H), 1.25 (d, J=6.6 Hz, 3H), 1.07 (d, J=6.4 Hz, 3H), 0.95 (d, J=7.3 Hz, 3H), 0.82 (app t, J=7.3 Hz, 3H).

Example A#81

Preparation of (2S,3Z)-5-{[(2R,3R,5S,6S)-6-{(2E,4E)-5-[(3R,4R,5R,7S)-4-hydroxy-7-{[({[(2R)-2-(pyridin-2-yldisulfanyl)propyl]oxy}carbonyl)amino]methyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B244)

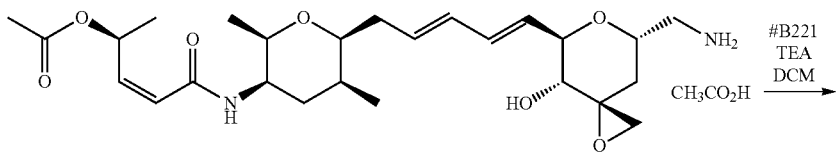

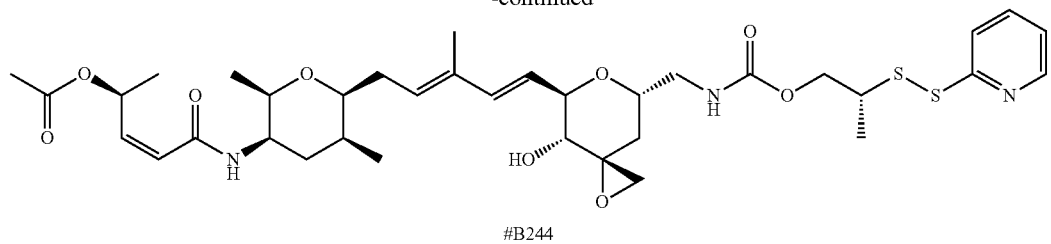

B244

Step 1:

Synthesis of (2S,3Z)-5-{[(2R,3R,5S,6S)-6-{(2E,4E)-5-[(3R,4R,5R,7S)-4-hydroxy-7-{[({[(2R)-2-(pyridin-2-yldisulfanyl)propyl]oxy}carbonyl)amino]methyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B244). To a solution of #B147 (8.2 mg, 0.014 mmol, 1 eq.) in dichloromethane (0.4 mL) at rt was added triethylamine (12.3 µL, 0.088 mmol, 6.3 eq.) followed by #B221 (9.4 mg, 0.026 mmol, 1.9 eq.) in dichloromethane (0.3 mL), and the reaction was stirred for 30 min. 4-N,N-dimethylamino pyridine (1 mg, 0.008 mmol, 0.6 eq.) was added, and the reaction was allowed to stir for 2 h. The reaction was concentrated, taken up in DMSO (800 uL) and purified by reverse phase chromatography (Method A) to give #B244 as a white solid. Yield: 4 mg, 0.005 mmol, 40%. LCMS (Protocol D): m/z 734.33 [M+H]$^+$, retention time=0.91 minutes. $^1$H NMR (500 MHz, DMSO-d$_6$) δ 8.46-8.40 (m, 1H), 7.85-7.76 (m, 2H), 7.36-7.29 (m, 1H), 7.26-7.20 (m, 1H), 6.41-6.32 (m, 1H), 6.25 (d, J=15.8 Hz, 1H), 6.11 (d, J=11.6 Hz, 1H), 5.87 (dd, J=11.6 and 7.6 Hz, 1H), 5.61 (dd, J=15.8 and 6.0 Hz, 1H), 5.50-5.43 (m, 1H), 4.98 (d, J=6.2 Hz, 1H), 4.29-4.22 (m, 1H), 4.10-4.03 (m, 1H), 4.01-3.85 (m, 2H), 3.67-3.57 (m, 2H), 3.52-3.44 (m, 1H), 3.28-3.21 (m, 1H), 3.02-2.93 (m, 1H), 2.76 (d, J=5.1 Hz, 1H), 2.57 (d, J=5.1 Hz, 1H), 2.34-2.13 (m, 2H), 1.98 (s, 3H), 1.85-1.53 (m, 9H), 1.28-1.20 (m, 6H), 1.05 (d, J=6.2 Hz, 3H), 0.93 (d, J=7.3 Hz, 3H).

Example A#82

Preparation of N-(24-bromo-23-oxo-4,7,10,13,16,19-hexaoxa-22-azatetracosan-1-oyl)-L-valyl-N-{4-[({[2-({[(3R,5S,7R,8R)-7-{(1E,3E)-5-[(2S,3S,5R,6R)-5-{(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)ethyl]carbamoyl}oxy)methyl]phenyl}-N$^5$-carbamoyl-L-ornithinamide (#B245)

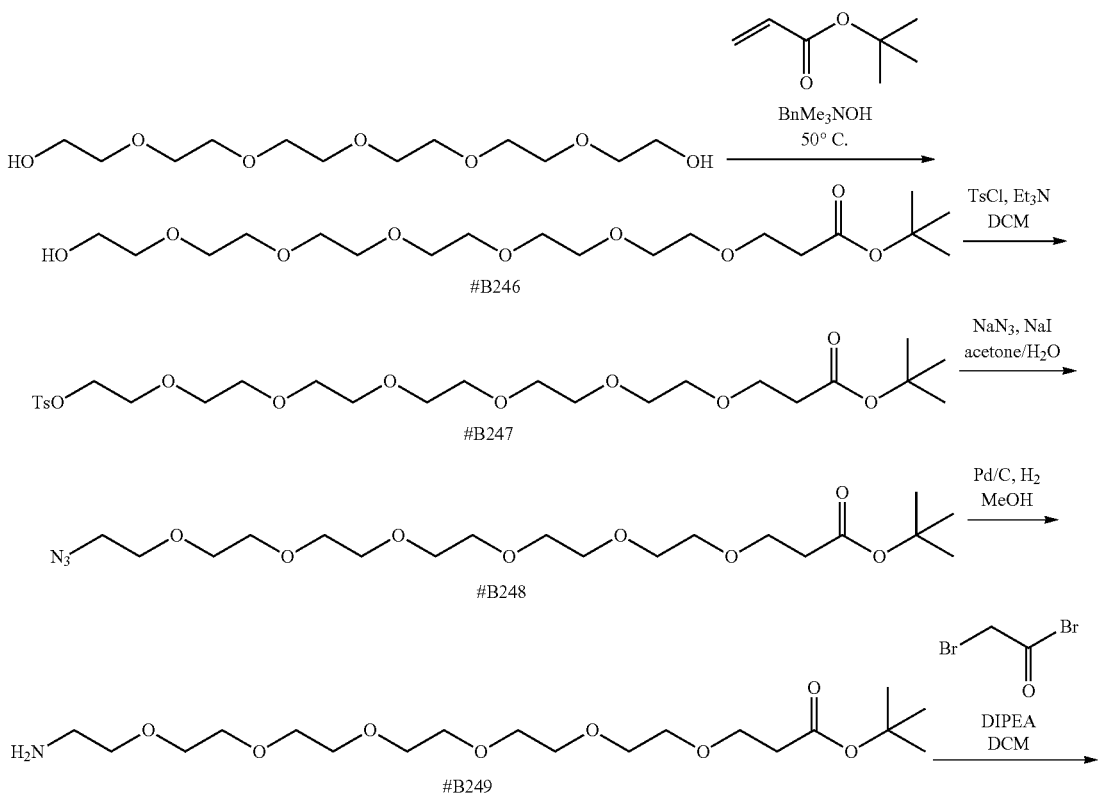

-continued
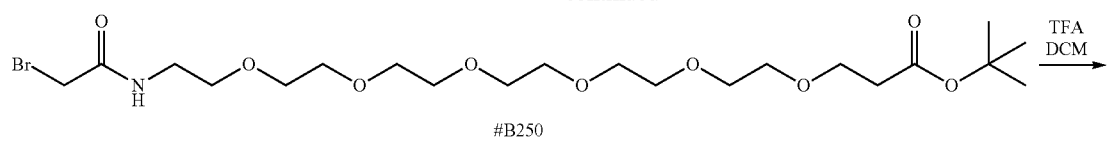
B250
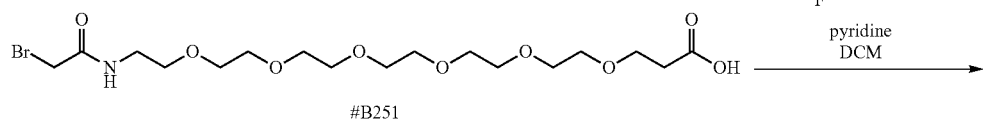
B251
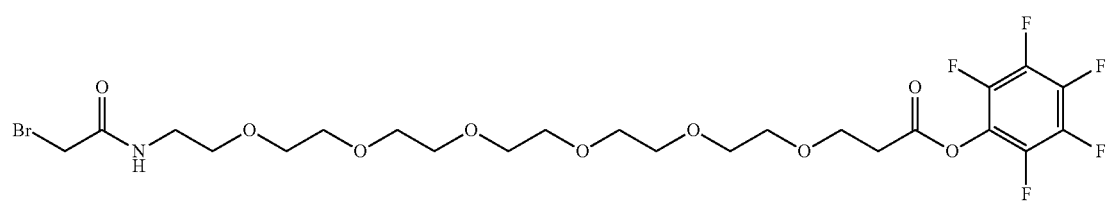
B252
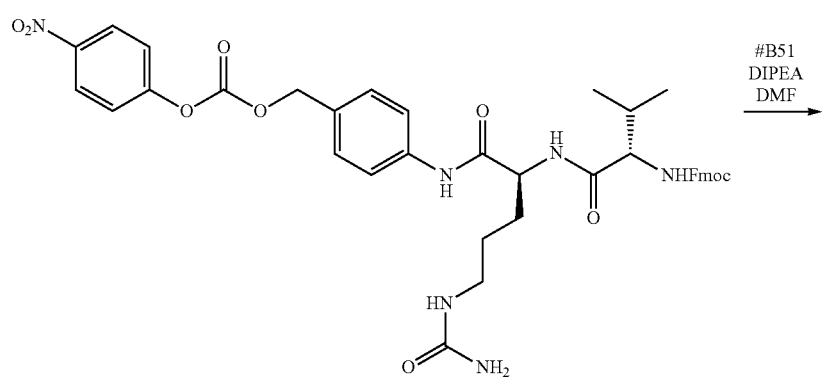
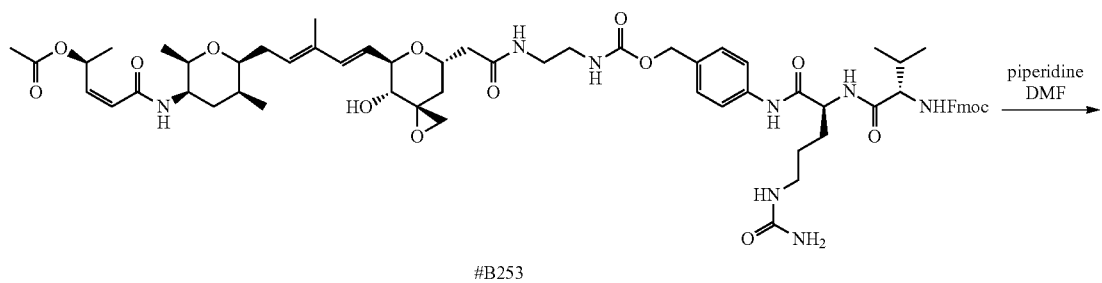
B253
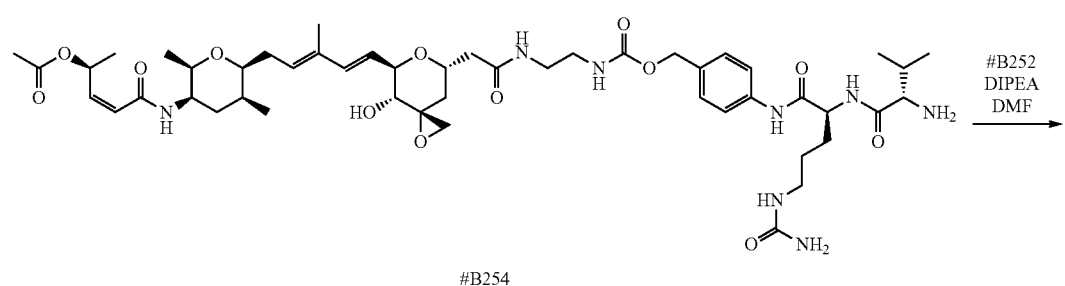
B254

-continued

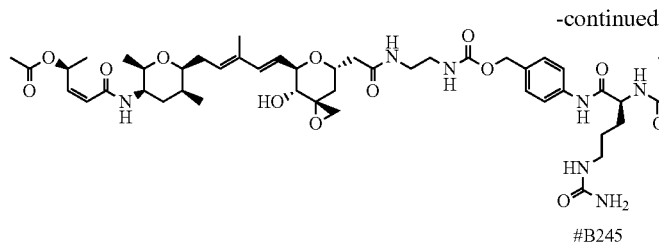
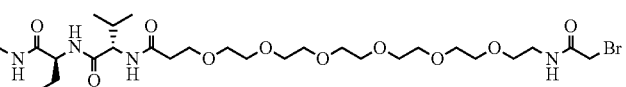

B245

Step 1:

Synthesis of tert-butyl 1-hydroxy-3,6,9,12,15,18-hexaoxahenicosan-21-oate (#B246). A mixture of 3,6,9,12,15-pentaoxaheptadecane-1,17-diol (25 g, 88.7 mmol, 1 eq.), tert-butyl prop-2-enoate (11.3 g, 88.7 mmol, 1 eq.) and benzyltrimethylammonium hydroxide (2.5 mL) was stirred at 50° C. overnight. The reaction mixture was purified by silica gel chromatography eluting with ethyl acetate:dichloromethane (4%-10%) to afford #B246 (9.63 g, 25.7%) as a yellow oil.

Step 2:

Synthesis of tert-butyl 1-{[(4-methylphenyl)sulfonyl]oxy}-3,6,9,12,15,18-hexaoxahenicosan-21-oate (#B247). To a solution of #B246 (9.63 g, 23.5 mmol, 1 eq.) and triethylamine (3.56 g, 35.2 mmol, 1.5 eq.) in dichloromethane (150 mL) was added 4-methylbenzenesulfonyl chloride (6.69 g, 35.2 mmol, 1.5 eq.) at 0° C., and the solution was stirred at rt overnight. The reaction mixture was washed with aqueous $NaHCO_3$ (150 mL), and the aqueous phase was re-extracted with ethyl acetate (200 mL×3). The combined organic layers were dried over sodium sulfate and concentrated in vacuo, and the residue was purified by silica column chromatography eluting with methanol:dichloromethane (0.5%-0.8%) to afford #B247 (9.21 g, 69.7%) as a yellow oil.

Step 3:

Synthesis of tert-butyl 1-azido-3,6,9,12,15,18-hexaoxahenicosan-21-oate (#B248). To a solution of #B247 (13.0 g, 23.0 mmol, 1 eq.) in acetone/water (150 mL/150 mL) was added sodium azide (3.20 g, 49.2 mmol, 2.1 eq.) and sodium iodide (621 mg, 3.45 mmol, 0.15 eq.), and the reaction was stirred at reflux overnight. The reaction mixture was extracted with ethyl acetate (150 mL×3), and the organic phases were concentrated in vacuo. The residue was purified by silica column chromatography eluting with ethyl acetate:petroleum ether (12-35%) to afford #B248 (8.30 g, 83.1%) as a yellow oil.

Step 4:

Synthesis of tert-butyl 1-amino-3,6,9,12,15,18-hexaoxahenicosan-21-oate (#B249). A suspension of #B248 (8.30 g, 19.1 mmol, 1 eq.) and Pd/C (1.0 g) in methanol was stirred under hydrogen balloon at rt overnight. The reaction mixture was filtered, and the filtrate was concentrated in vacuo to afford #B249 (7.80 g, 100%) as a yellow oil, which was directly used for the next step.

Step 5:

Synthesis of tert-butyl 1-bromo-2-oxo-6,9,12,15,18,21-hexaoxa-3-azatetracosan-24-oate (#B250). To a solution of #B249 (5.80 g, 14.1 mmol, 1 eq.) in dichloromethane (300 mL) was added N,N-diisopropylethylamine (5.50 g, 42.6 mmol, 3 eq.) and bromoacetyl bromide (4.24 g, 21.3 mmol, 1.5 eq.) at 0° C., and the reaction was stirred at 0° C. for 15 min. The reaction mixture was concentrated to dryness, and the residue was purified by silica column chromatography eluting with methanol:dichloromethane (0.5-0.8%) to afford #B250 (5.20 g, 69.3%) as a yellow solid.

Step 6:

Synthesis of 1-bromo-2-oxo-6,9,12,15,18,21-hexaoxa-3-azatetracosan-24-oic acid (#B251). To a solution of #B250 (5.20 g, 9.80 mmol, 1 eq.) in dichloromethane (100 mL) was added trifluoroacetic acid (100 mL) at 0° C., and the solution was stirred at rt for 3 h. The reaction mixture was concentrated in vacuo to afford #B251 (6.00 g, 100%) as a yellow oil.

Step 7:

Synthesis of pentafluorophenyl 1-bromo-2-oxo-6,9,12,15,18,21-hexaoxa-3-azatetracosan-24-oate (#B252). To a solution of #B251 (4.65 g, 9.80 mmol, 1 eq.) and pentafluorophenyl trifluoroacetate (4.12 g, 14.7 mmol, 1.5 eq.) in dichloromethane (150 mL) was added dropwise pyridine (4.65 g, 9.80 mmol, 1.5 eq.) at 0° C., and the solution was stirred at for 30 min. The reaction mixture was washed with 2 M HCl (150 mL×2), and the aqueous phase was extracted dichloromethane (150 mL×2). The combined organic layers were dried over sodium sulfate and concentrated in vacuo, and the residue was purified by silica column chromatography eluting with methanol:dichloromethane (1.5-2%) to afford a yellow oil, which was further purified by prep-HPLC to afford #B252 (1.20 g, 19.1%) as a yellow oil. $^1H$ NMR (400 MHz, $CDCl_3$) ☐7.06 (br, 1H), 3.89 (m, 4H), 3.69-3.59 (m, 22H), 3.58 (m, 2H), 2.96 (m, 2H).

Step 8:

Synthesis of N-[(9H-fluoren-9-ylmethoxy)carbonyl]-L-valyl-N-{4-[({[2-({[(3R,5S,7R,8R)-7-{(E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)ethyl]carbamoyl}oxy)methyl]phenyl}-$N^5$-carbamoyl-L-ornithinamide (#B253). To a solution of #B51 (18.5 mg, 0.032 mmol, 1 eq.) in N,N-dimethylformamide (0.8 mL) at rt was added N,N-diisopropylethylamine (22.5 µL, 0.128 mmol, 4 eq.) followed by N-[(9H-fluoren-9-ylmethoxy)carbonyl]-L-valyl-$N^5$-carbamoyl-N-[4-({[(4-nitrophenoxy)carbonyl]oxy}methyl)phenyl]-L-ornithinamide (29.1 mg, 0.038 mmol, 1.2 eq.), and the reaction was stirred for 70 min. More N-[(9H-fluoren-9-ylmethoxy)carbonyl]-L-valyl-$N^5$-carbamoyl-N-[4-({[(4-nitrophenoxy)carbonyl]oxy}methyl)phenyl]-L-ornithinamide (4.9 mg, 0.006 mmol, 0.2 eq.) was added, and the reaction was stirred for a further 30 min. The reaction was purified by reverse phase chromatography (Method A) to give #B253 as a white solid. Yield: 13.1 mg, 0.011 mmol, 34%. LCMS (Protocol D): m/z 1206.2 $[M+H]^+$, retention time=0.91 minutes.

Step 9:

Synthesis of L-valyl-N-{4-[({[2-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)ethyl]carbamoyl}oxy)methyl]

phenyl}-N⁵-carbamoyl-L-ornithinamide (#B254). The title compound was prepared in 76% yield from 13.1 mg (0.011 mmol, 1.0 eq.) of #B253 and 18.7 mg (0.22 mmol, 20.0 eq.) of piperidine using the procedure described for preparation of compound #B47. LCMS (Protocol D): m/z 984.0 [M+H]⁺, retention time=0.67 minutes.

Step 10:

Synthesis of N-(24-bromo-23-oxo-4,7,10,13,16,19-hexaoxa-22-azatetracosan-1-oyl)-L-valyl-N-{4-[({[2-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)ethyl]carbamoyl}oxy)methyl]phenyl}-N⁵-carbamoyl-L-ornithinamide (#B245). To a solution of #B254 (8.2 mg, 0.008 mmol, 1 eq.) in N,N-dimethylformamide (0.15 mL) at rt was added N,N-diisopropylethylamine (5.7 µL, 0.032 mmol, 4 eq.) followed by #B252 (7.5 mg, 0.012 mmol, 1.5 eq.) in N,N-dimethylformamide (0.3 mL), and the reaction was allowed to stir at rt for 30 min. The reaction was purified by reverse phase chromatography (Method A) to give #B245 as a white solid. Yield: 5.4 mg, 0.0038 mmol, 47%. LCMS (Protocol D): m/z 1440.72 [M+H]⁺, retention time=0.75 minutes. ¹H NMR (500 MHz, DMSO-d₆) δ 9.98 (s, 1H), 8.38-8.28 (m, 1H), 8.17-8.07 (m, 1H), 7.96-7.90 (m, 1H), 7.90-7.84 (m, 1H), 7.83-7.76 (m, 1H), 7.64-7.54 (m, 2H), 7.32-7.23 (m, 2H), 7.21-7.12 (m, 1H), 6.41-6.32 (m, 1H), 6.28 (d, J=15.8 Hz, 1H), 6.11 (dd, J=11.7 and 1.2 Hz, 1H), 6.02-5.94 (m, 1H), 5.87 (dd, J=11.7 and 7.6 Hz, 1H), 5.60 (dd, J=15.8 and 5.6 Hz, 1H), 5.56-5.46 (m, 1H), 5.41 (s, 2H), 5.03 (d, J=5.6 Hz, 1H), 4.93 (s, 2H), 4.41-4.34 (m, 1H), 4.29-4.18 (m, 2H), 3.85 (s, 2H), 3.69-3.55 (m, 4H), 3.54-3.45 (m, 22H), 3.43-3.39 (m, 2H), 3.27-3.19 (m, 2H), 3.16-2.89 (m, 6H), 2.74 (d, J=5.2 Hz, 1H), 2.58 (d, J=5.2 Hz, 1H), 2.42-2.14 (m, 5H), 2.01-1.91 (m, 4H), 1.88-1.75 (m, 3H), 1.73-1.53 (m, 6H), 1.52-1.30 (m, 4H), 1.25 (d, J=6.4 Hz, 3H), 1.06 (d, J=6.1 Hz, 3H), 0.94 (d, J=7.3 Hz, 3H), 0.86 (d, J=6.9 Hz, 3H), 0.83 (d, J=6.9 Hz, 3H).

Example A#83

Preparation of N-(24-bromo-23-oxo-4,7,10,13,16,19-hexaoxa-22-azatetracosan-1-oyl)-L-valyl-N-[2-(3-{[trans-4-({[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)cyclohexyl]oxy}-3-oxopropyl)phenyl]-L-alaninamide (#B255)

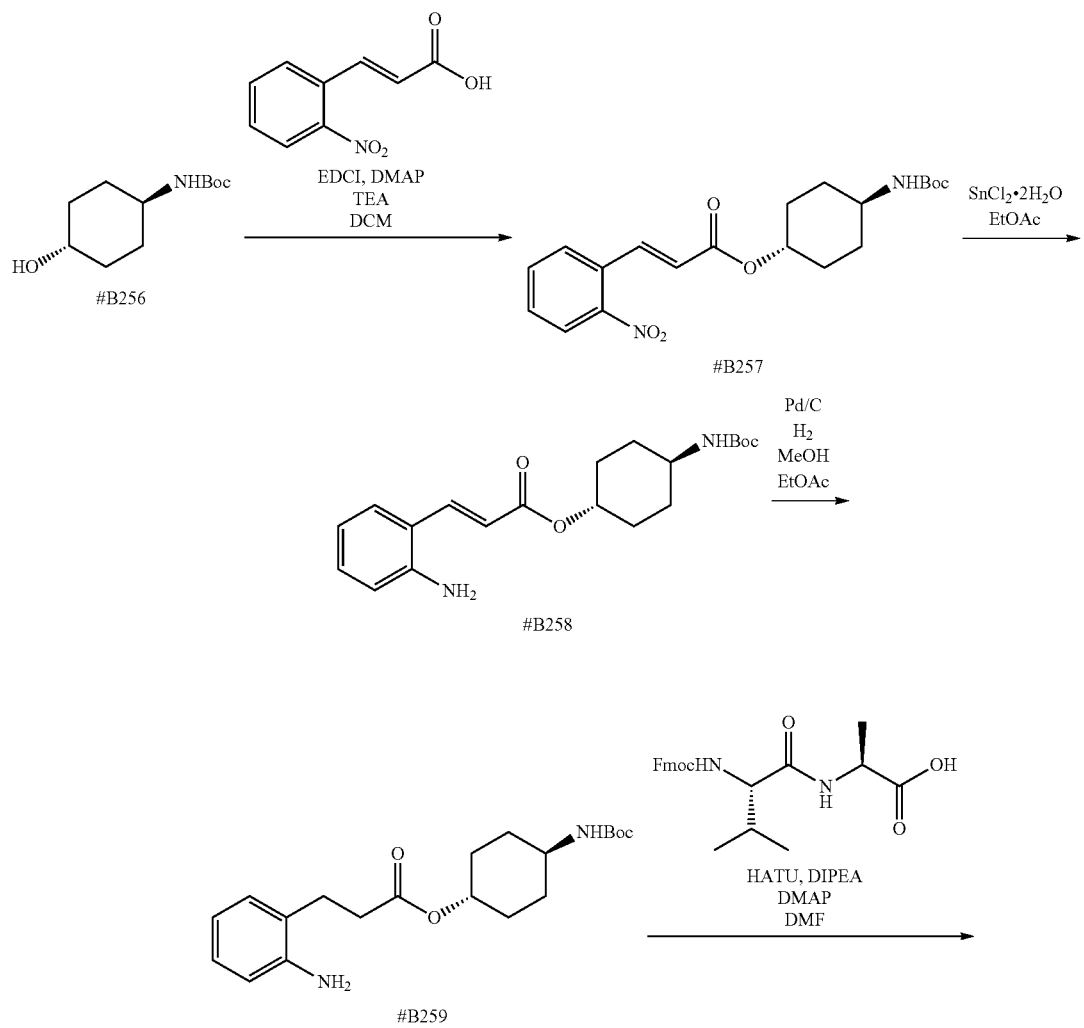

-continued
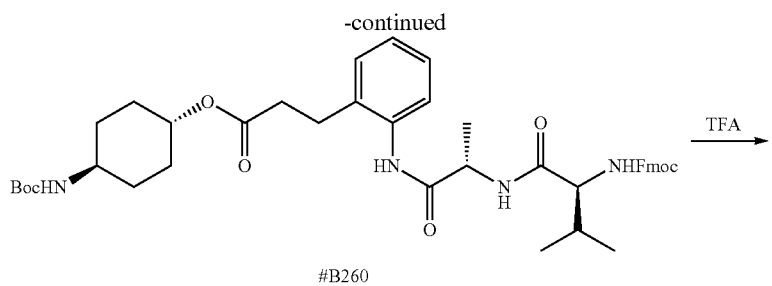
B260
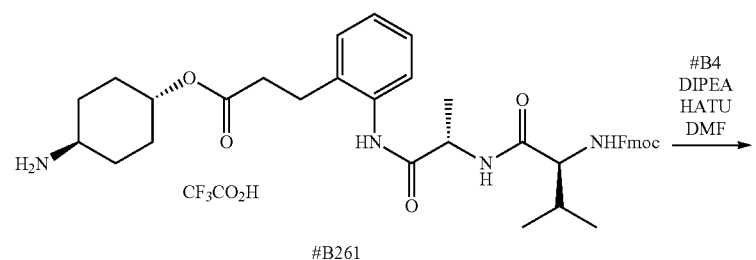
B261
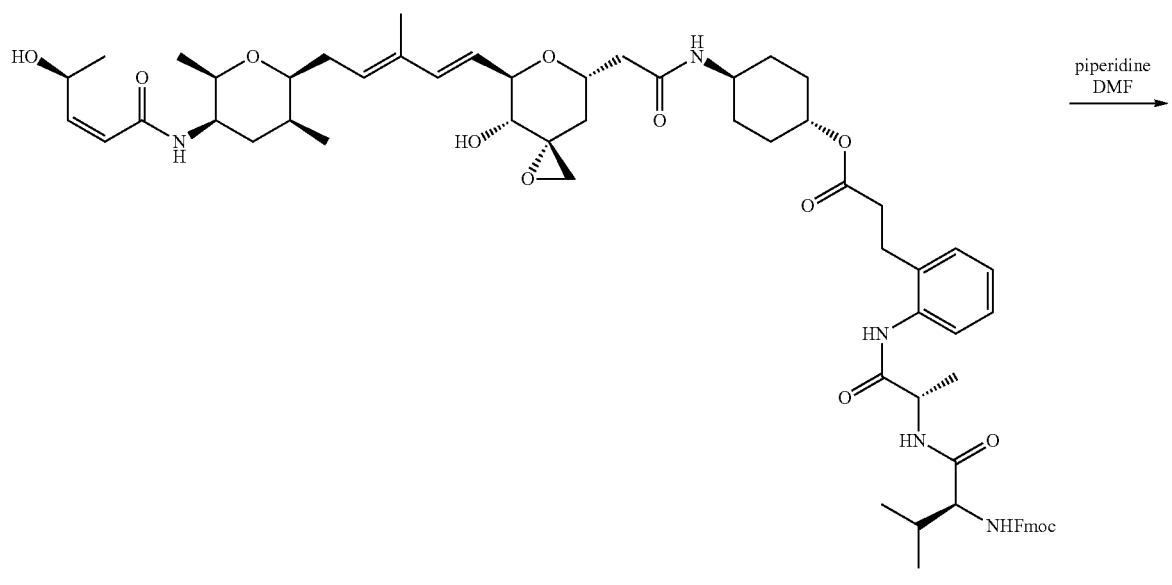
B262
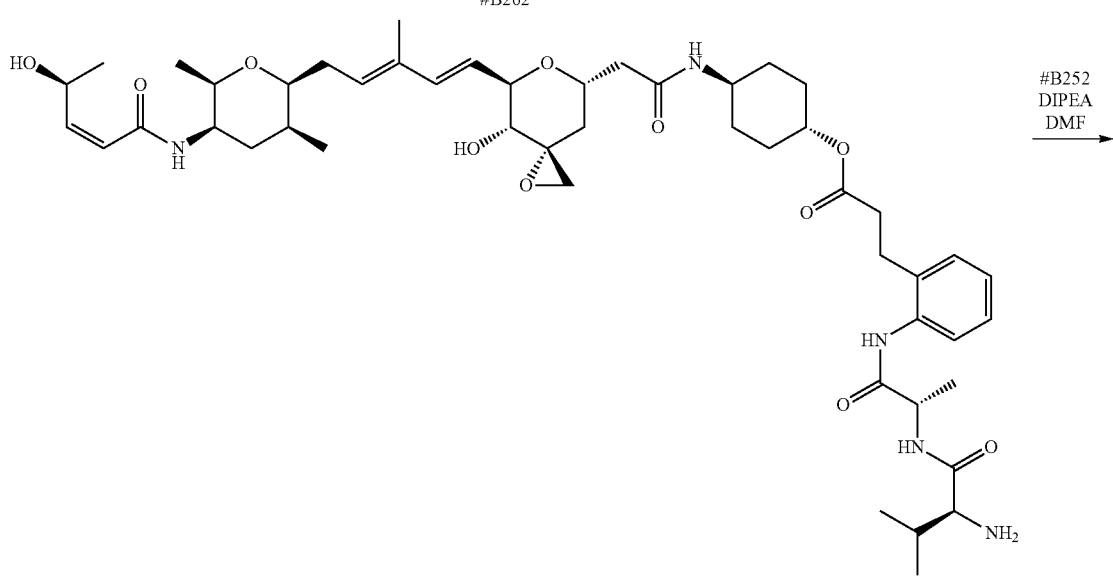
B263

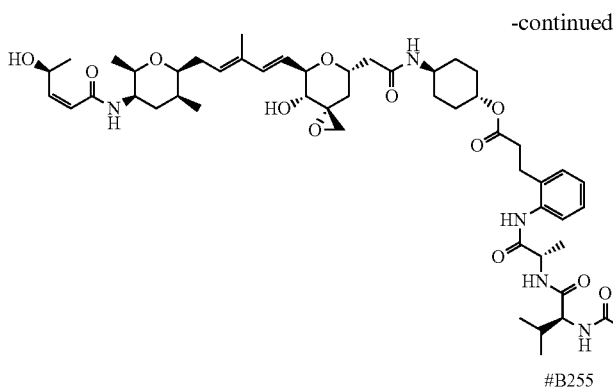
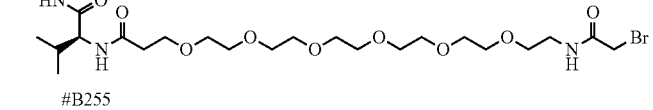

B255

Step 1:
Synthesis of trans-4-[(tert-butoxycarbonyl)amino]cyclohexyl (2E)-3-(2-nitrophenyl)prop-2-enoate (#B257). To a solution of (2E)-3-(2-nitrophenyl)prop-2-enoic acid (8.26 g, 55.8 mmol, 1 eq.) in dichloromethane (100 mL) was added #B256 (12 g, 55.8 mmol, 1 eq.) followed by 1-ethyl-3-(3-dimethylaminopropyl) carbodiimide-HCl (10.9 g, 55.8 mmol, 1 eq.), 4-N,N-dimethylamino pyridine (680 mg, 5.58 mmol, 0.1 eq.) and triethylamine (23 mL, 167.7 mmol, 3 eq.), and the reaction was stirred for 17 h at rt. The reaction was concentrated and purified by flash column chromatography eluting with petroleum ether/ethyl acetate (4:1) to afford #B257 (8.8 g, 40%) as a white solid.

Step 2:
Synthesis of trans-4-[(tert-butoxycarbonyl)amino]cyclohexyl (2E)-3-(2-aminophenyl)prop-2-enoate (#B258). To a solution of #B257 (7.8 g, 20 mmol, 1 eq.) in ethyl acetate (150 mL) was added SnCl₂ dihydrate (25 g, 0.11 mol, 5.5 eq.), and the reaction was stirred for 16 h. The solution pH was adjusted to pH=8-9 with aqueous NaHCO₃ and filtered. The filter cake was washed with ethyl acetate/methanol three times, and the combined organic layers were washed with brine, dried over sodium sulfate and concentrated in vacuo. The residue was purified by flash column chromatography eluting with petroleum ether/ethyl acetate (4:1) and ethyl acetate/methanol (20:1) to afford #B258 (850 mg, 12%) as a yellow solid.

Step 3:
Synthesis of trans-4-[(tert-butoxycarbonyl)amino]cyclohexyl 3-(2-aminophenyl)propanoate (#B259). To a solution of #B258 (800 mg, 2.2 mmol, 1 eq.) in ethyl acetate (10 mL) at rt was added Pd/C (1 g), and the mixture was stirred under hydrogen (35 psi) for 30 min. The reaction was filtered and concentrated in vacuo to give crude #B259 (500 mg, 63%) as a white solid that was used without further purification.

Step 4:
Synthesis of N-[(9H-fluoren-9-ylmethoxy)carbonyl]-L-valyl-N-{2-[3-({trans-4-[(tert-butoxycarbonyl)amino]cyclohexyl}oxy)-3-oxopropyl]phenyl}-L-alaninamide (#B260). To a solution of #B259 (400 mg, 1.1 mmol, 1 eq.) in N,N-dimethylformamide (20 mL) at rt was added N-[(9H-fluoren-9-ylmethoxy)carbonyl]-L-valyl-L-alanine (453 mg, 1.1 mmol, 1 eq.), 4-N,N-dimethylamino pyridine (12 mg, 0.1 mmol, 0.1 eq.) and O-(7-azabenzotriazol-1-yl)-N,N,N',N'-tetramethyluronium hexafluorophosphate (460 mg, 1.2 mmol, 1.1 eq.), and the reaction was stirred for 3 d. The reaction mixture was poured into water and extracted with ethyl acetate three times. The combined organic layers were dried over sodium sulfate and concentrated. The residue was purified by flash column chromatography eluting with dichloromethane/methanol (20:1 to 10:1) to afford #B260 (110 mg, 13%) as a white solid. ¹H NMR (500 MHz, CDCl₃) δ 9.18 (s, 1H), 7.77 (m, 3H), 7.61 (d, 2H), 7.40 (m, 4H), 7.15 (m, 3H), 6.77 (m, 1H), 5.47 (d, 1H), 4.73 (m, 2H), 4.45 (m, 4H), 4.24 (m, 1H), 3.11 (q, 1H), 2.85 (m, 2H), 2.69 (m, 2H), 2.17 (m, 2H), 1.97 (m, 4H), 1.65 (m, 1H), 1.56 (m, 3H), 1.43 (m, 11H), 1.25 (m, 4H), 0.98 (m, 6H).

Step 5:
Synthesis of N-[(9H-fluoren-9-ylmethoxy)carbonyl]-L-valyl-N-(2-{3-[(trans-4-aminocyclohexyl)oxy]-3-oxopropyl}phenyl)-L-alaninamide trifluoroacetate salt (#B261). To #B260 (34.8 mg, 0.046 mmol, 1.0 eq) was added pre-chilled trifluoroacetic acid (0.8 mL) at 0° C., and the reaction was allowed to stir for 10 min as it warmed to rt. The reaction was concentrated, taken up in acetonitrile and reconcentrated three times to give #B261 as a gum which was used in next step without further purification. Assume full conversion. LCMS (Protocol D): m/z 655.8 [M+H]⁺, retention time=0.81 minutes.

Step 6:
Synthesis of N-[(9H-fluoren-9-ylmethoxy)carbonyl]-L-valyl-N-[2-(3-{[trans-4-({[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)cyclohexyl]oxy}-3-oxopropyl)phenyl]-L-alaninamide (#B262). To a solution of #B4 (14.1 mg, 0.029 mmol, 1 eq.) in N,N-dimethylformamide (0.2 mL) at rt was added N,N-diisopropylethylamine (30.6 µL, 0.17 mmol, 6 eq.) and O-(7-azabenzotriazol-1-yl)-N,N,N',N'-tetramethyluronium hexafluorophosphate (13.6 mg, 0.035 mmol, 1.2 eq.), and the reaction was stirred for five minutes. A solution of #B261 (35.4 mg, 0.046 mmol, 1.6 eq.) in N,N-dimethylformamide (0.6 mL) was added, and the reaction was allowed to stir for 30 min. The reaction was purified by reverse phase chromatography (Method A) to give #B262 as a white solid. Yield: 22.8 mg, 0.02 mmol, 70%. LCMS (Protocol D): m/z 1131.2 [M+H]⁺, retention time=0.96 minutes.

Step 7:
Synthesis of L-valyl-N-[2-(3-{[trans-4-({[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)cyclohexyl]oxy}-3-oxopropyl)phenyl]-L-alaninamide (#B263). The title compound was prepared in 88% yield from 22.8 mg (0.02 mmol, 1.0 eq.) of #B262 and 34.1 mg (0.40 mmol, 20.0 eq.)

of piperidine using the procedure described for preparation of compound #B47. LCMS (Protocol D): m/z 908.54 [M+H]+, retention time=0.64 minutes.

Step 8:

Synthesis of N-(24-bromo-23-oxo-4,7,10,13,16,19-hexaoxa-22-azatetracosan-1-oyl)-L-valyl-N-[2-(3-{[trans-4-({[(3R,5S,7R,8R)-8-hydroxy-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)cyclohexyl]oxy}-3-oxopropyl)phenyl]-L-alaninamide (#B255). To a solution of #B263 (16.1 mg, 0.018 mmol, 1 eq.) in N,N-dimethylformamide (0.2 mL) at rt was added N,N-diisopropylethylamine (12.7 μL, 0.072 mmol, 4 eq.)

Example A#84

Preparation of methyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-methoxy-1,6-dioxaspiro[2.5]oct-5-yl]acetate (#B265) and methyl [(3R,5S,7R,8R)-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-8-methoxy-1,6-dioxaspiro[2.5]oct-5-yl] acetate (#B264)

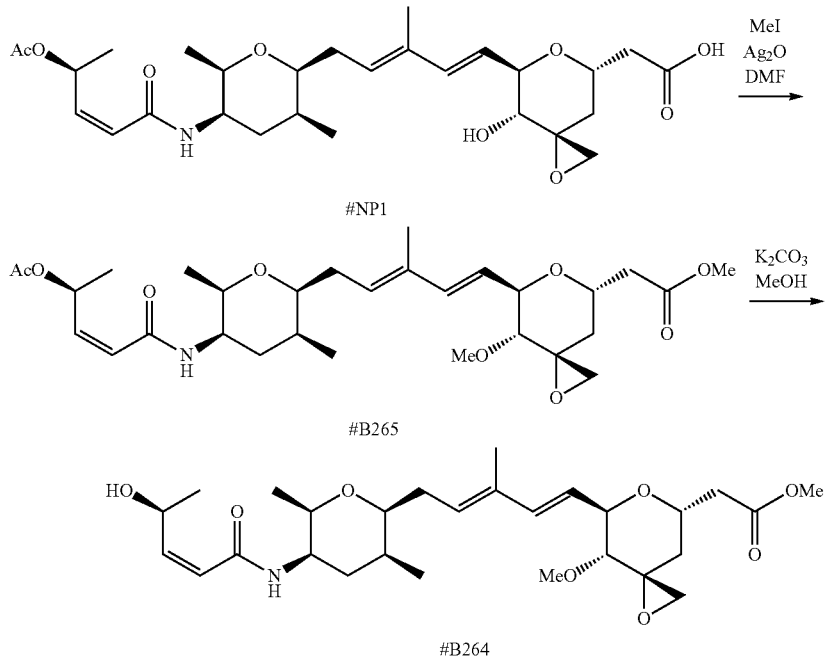

followed by #B252 (9.4 mg, 0.034 mmol, 1.9 eq.) in N,N-dimethylformamide (0.5 mL), and the reaction was allowed to stir at rt for 15 min. More #B252 (8.8 mg, 0.014 mmol, 0.75 eq.) in N,N-dimethylformamide (0.3 mL) was added, and the reaction was stirred for another 15 min. The reaction was purified by reverse phase chromatography (Method A) to give #B255 as a white solid. Yield: 14.4 mg, 0.011 mmol, 59%. LCMS (Protocol D): m/z 1365.75 [M+H]+, retention time=0.78 minutes. $^1$H NMR (500 MHz, DMSO-$d_6$) δ 9.40 (s, 1H), 8.37-8.29 (m, 1H), 8.15 (d, J=7.1 Hz, 1H), 7.87 (d, J=8.8 Hz, 1H), 7.82-7.74 (m, 2H), 7.29-7.09 (m, 4H), 6.28 (d, J=15.9 Hz, 1H), 5.98 (d, J=10.5 Hz, 1H), 5.87 (dd, J=11.7 and 7.1 Hz, 1H), 5.60 (dd, J=15.9 and 5.6 Hz, 1H), 5.54-5.46 (m, 1H), 5.22-5.13 (m, 1H), 5.11 (d, J=4.7 Hz, 1H), 5.02 (d, J=5.1 Hz, 1H), 4.61-4.52 (m, 1H), 4.51-4.42 (m, 1H), 4.30-4.17 (m, 3H), 3.85 (s, 2H), 3.69-3.37 (m, 25H), 3.27-3.19 (m, 3H), 2.88-2.72 (m, 3H), 2.57 (d, J=5.1 Hz, 1H), 2.42-2.13 (m, 5H), 2.01-1.91 (m, 2H), 1.88-1.59 (m, 10H), 1.53-1.43 (m, 1H), 1.40-1.16 (m, 7H), 1.11 (d, J=6.4 Hz, 3H), 1.06 (d, J=6.4 Hz, 3H), 0.96 (d, J=7.3 Hz, 3H), 0.86 (d, J=6.9 Hz, 3H), 0.83 (d, J=6.9 Hz, 3H).

Step 1:

Synthesis of methyl [(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-methoxy-1,6-dioxaspiro[2.5]oct-5-yl]acetate (#B265). To a solution of #NP1 (32.9 mg, 0.061 mmol, 1 eq.) in N,N-dimethylformamide (0.7 mL) at rt was added MeI (114 μL, 1.83 mmol, 30 eq.) and Ag$_2$O (170 mg, 0.73 mmol, 12 eq.), and the reaction was allowed to stir for 72 h in the dark. The reaction was filtered over celite washing with N,N-dimethylformamide (0.8 mL) and split into two parts. One part was carried forward to step two while the other was purified by reverse phase chromatography (Method A) to give #B265 as a white solid. Yield: 4.66 mg, 0.008 mmol, 14%. LCMS (Protocol D): m/z 564.39 [M+H]+, retention time=0.90 minutes. $^1$H NMR (400 MHz, DMSO-$d_6$) δ 7.79 (d, J=7.8 Hz, 1H), 6.41-6.31 (m, 2H), 6.11 (dd, J=11.7 and 1.2 Hz, 1H), 5.87 (dd, J=11.7 and 7.8 Hz, 1H), 5.63-5.51 (m, 2H), 4.58-4.51 (m, 1H), 4.28-4.18 (m, 1H), 3.70-3.57 (m, 5H), 3.55-3.47 (m, 1H), 3.33 (s, 3H), 2.96-2.91 (m, 1H), 2.71-2.63 (m, 2H), 2.37-2.15 (m, 2H), 2.07-1.94 (m, 4H), 1.88-1.75 (m, 2H), 1.73-1.60 (m, 4H), 1.25 (d, J=6.2 Hz, 3H), 1.19-1.11 (m, 1H), 1.07 (d, J=6.2 Hz, 3H), 0.96 (d, J=7.0 Hz, 3H).

Step 2:

Synthesis of methyl [(3R,5S,7R,8R)-7-{(1E,3E)-5-[(2S,3S,5R,6R)-5-{[(2Z,4S)-4-hydroxypent-2-enoyl]amino}-3,6-dimethyltetrahydro-2H-pyran-2-yl]-3-methylpenta-1,3-dien-1-yl}-8-methoxy-1,6-dioxaspiro[2.5]oct-5-yl]acetate (#B264). To a solution #B265 (20 mg, 0.035 mmol, 1 eq.) in methanol (0.6 mL) at rt was added K$_2$CO$_3$ (12.2 mg, 0.088 mmol, 2.5 eq.), and the reaction was allowed to stir for 45 min. The reaction was filtered washing with ethyl acetate. The organic layer was washed with water and brine, dried over sodium sulfate and concentrated. The residue was purified by reverse phase chromatography (Method A) to give #B264 as a white solid. Yield: 4.2 mg, 0.008 mmol, 23%. LCMS (Protocol D): m/z 522.40 [M+Na]$^+$, retention time=0.81 minutes. $^1$H NMR (400 MHz, DMSO-d$_6$) δ 7.76 (d, J=7.8 Hz, 1H), 6.36 (d, J=14.4 Hz, 1H), 5.98 (d, J=11.7 Hz, 1H), 5.87 (dd, J=11.7 and 7.0 Hz, 1H), 5.63-5.50 (m, 2H), 5.22-5.08 (m, 2H), 4.58-4.52 (m, 1H), 4.28-4.18 (m, 1H), 3.70-3.57 (m, 5H), 3.55-3.47 (m, 1H), 3.32 (s, 3H), 2.96-2.91 (m, 1H), 2.71-2.63 (m, 2H), 2.37-2.16 (m, 2H), 2.06-1.96 (m, 1H), 1.89-1.59 (m, 6H), 1.20-1.02 (m, 7H), 0.96 (d, J=7.4 Hz, 3H).

Example A#85

Preparation of (2S,3Z)-5-{[(2R,3R,5S,6S)-6-{(2E,4E)-5-[(3R,4R,5R,7S)-7-{2-[(4-carbamoylbenzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B266)

Step 1:

Synthesis of (2S,3Z)-5-{[(2R,3R,5S,6S)-6-{(2E,4E)-5-[(3R,4R,5R,7S)-7-{2-[(4-carbamoylbenzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B266). To a solution of #B1 (18.7 mg, 0.03 mmol, 1 eq.) in N,N-dimethylformamide (0.5 mL) at rt was added N,N-diisopropylethylamine (21.2 μL, 0.12 mmol, 2 eq.) and 4-(aminomethyl)benzamide hydrochloride salt (11.2 mg, 0.06 mmol, 2 eq.), and the reaction was stirred for 1 h. The reaction was purified by reverse phase chromatography (Method A) to give #B266 as a white solid. Yield: 15.4 mg, 0.023 mmol, 77%. LCMS (Protocol D): m/z 668.37 [M+Na]$^+$, retention time=0.71 minutes. $^1$H NMR (500 MHz, DMSO-d$_6$) δ 8.50-8.43 (m, 1H), 7.88 (s, 1H), 7.82-7.74 (m, 3H), 7.33-7.25 (m, 3H), 6.41-6.27 (m, 2H), 6.10 (d, J=11.6 Hz, 1H), 5.87 (dd, J=11.6 and 7.5 Hz, 1H), 5.62 (dd, J=15.8 and 5.5 Hz, 1H), 5.50-5.43 (m, 1H), 5.04 (d, J=5.4 Hz, 1H), 4.43-4.20 (m, 3H), 3.68-3.59 (m, 2H), 3.53-3.45 (m, 1H), 3.29-3.23 (m, 1H), 2.78 (d, J=5.3 Hz, 1H), 2.68-2.56 (m, 2H), 2.35-2.13 (m, 3H), 1.98 (s, 3H), 1.90-1.72 (m, 4H), 1.70 (s, 3H), 1.66-1.58 (m, 1H), 1.57-1.49 (m, 1H), 1.25 (d, J=6.5 Hz, 3H), 1.04 (d, J=6.2 Hz, 3H), 0.93 (d, J=7.3 Hz, 3H).

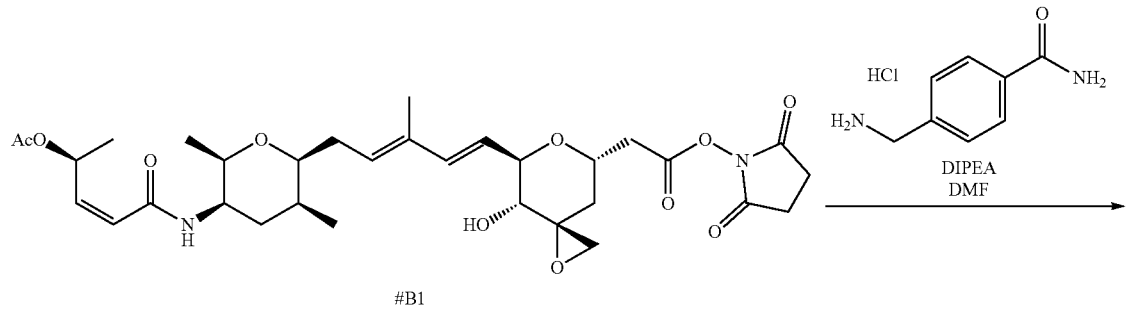

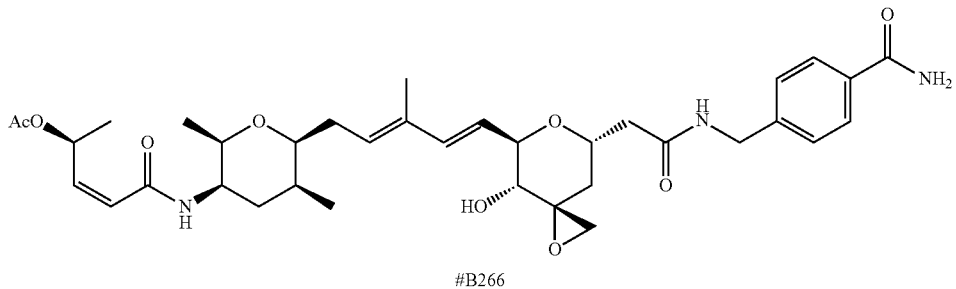

Example A#86

Preparation of (2S,3Z)-5-{[(2R,3R,5S,6S)-6-{(2E,4E)-5-[(3R,4R,5R,7S)-7-{2-[(4-carbamoylphenyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B267)

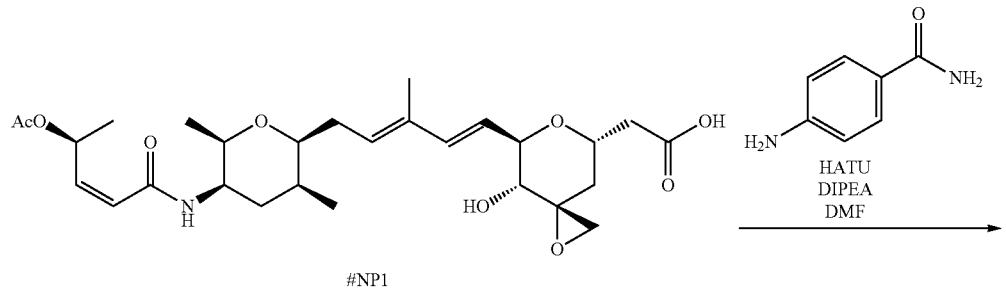

Step 1:

Synthesis of (2S,3Z)-5-{[(2R,3R,5S,6S)-6-{(2E,4E)-5-[(3R,4R,5R,7S)-7-{2-[(4-carbamoylphenyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B267). To a solution of #NP1 (12.4 mg, 0.023 mmol, 1 eq.) in N,N-dimethylformamide (0.5 mL) at rt was added N,N-diisopropylethylamine (20.2 µL, 0.12 mmol, 5 eq.) and O-(7-azabenzotriazol-1-yl)-N,N,N'N'-tetramethyluronium hexafluorophosphate (10.9 mg, 0.028 mmol, 1.2 eq.), and the reaction was stirred for five minutes. 4-Aminobenzamide (6.3 mg, 0.046 mmol, 2 eq.) was added, and the reaction was allowed to stir for 1 h. The reaction was purified by reverse phase chromatography (Method A) to give #B267 as a white solid. Yield: 4.5 mg, 0.007 mmol, 30%. LCMS (Protocol D): m/z 654.37 [M+H]$^+$, retention time=0.73 minutes. $^1$H NMR (500 MHz, DMSO-d$_6$) δ 10.21 (s, 1H), 7.88-7.75 (m, 3H), 7.70-7.62 (m, 2H), 7.23 (s, 1H), 6.41-6.32 (m, 1H), 6.26 (d, J=16.1 Hz, 1H), 6.10 (d, J=11.6 Hz, 1H), 5.87 (dd, J=11.6 and 7.6 Hz, 1H), 5.58 (dd, J=16.1 and 5.3 Hz, 1H), 5.43-5.34 (m, 1H), 5.08 (d, J=5.4 Hz, 1H), 4.42-4.29 (m, 2H), 3.70-3.59 (m, 2H), 3.48-3.40 (m, 1H), 3.30-3.26 (m, 1H), 2.81-2.73 (m, 2H), 2.62 (d, J=5 Hz, 1H), 2.31-2.12 (m, 2H), 1.98 (s, 3H), 1.96-1.88 (m, 1H), 1.87-1.74 (m, 2H), 1.68 (s, 3H), 1.63-1.50 (m, 2H), 1.25 (d, J=6.5 Hz, 3H), 1.06 (d, J=6.2 Hz, 3H), 0.93 (d, J=7.5 Hz, 3H).

Example A#87

Preparation of (2S,3Z)-5-({(2R,3R,5S,6S)-6-[(2E,4E)-5-{(3R,4R,5R,7S)-7-[(6S,9S)-19-bromo-6-methyl-2,5,8,11,18-pentaoxo-9-(propan-2-yl)-3,4,7,10,17-pentaazanonadec-1-yl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B268)

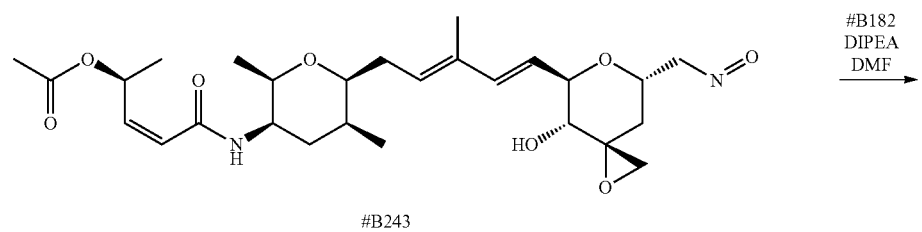

-continued

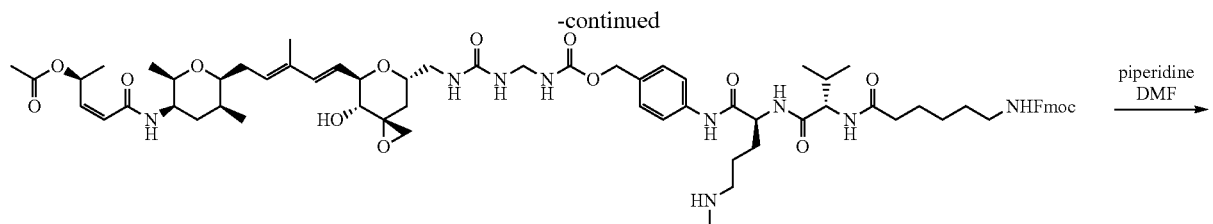

B269

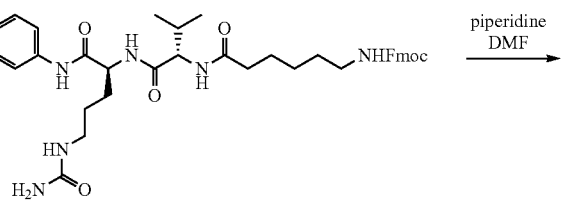

B270

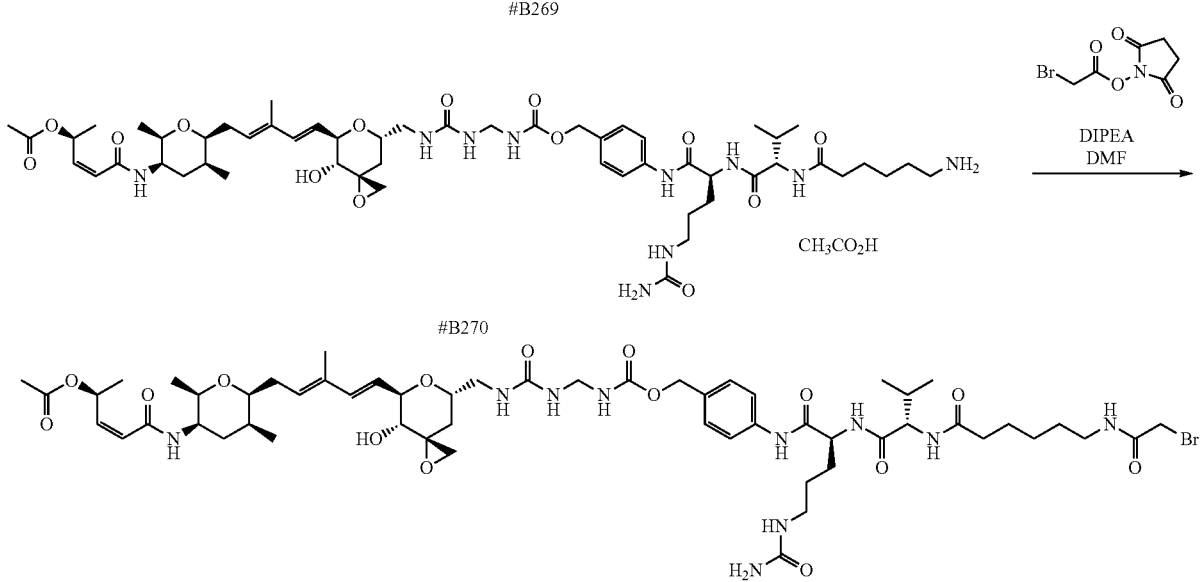

B268

Step 1:

Synthesis of N-(6-{[(9H-fluoren-9-ylmethoxy)carbonyl]amino}hexanoyl)-L-valyl-N-(4-{9-[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]-3,7-dioxo-2-oxa-4,6,8-triazanon-1-yl}phenyl)-N⁵-carbamoyl-L-ornithinamide (#B269). To a solution of #B243 (19.7 mg, 0.037 mmol, 1 eq.) in acetonitrile (1 mL) was added N,N-dimethylformamide (0.5 mL), and the acetonitrile was removed in vacuo. To this solution was added N,N-diisopropylethylamine (32.6 μL, 0.19 mmol, 5 eq.) followed by a solution of #B182 (40.5 mg, 0.045 mmol, 1.22 eq.), and the reaction was stirred for 30 min. More N,N-diisopropylethylamine (32.6 μL, 0.19 mmol, 5 eq.) was added, and the reaction was stirred for another 70 min. The reaction was purified by reverse phase chromatography (Method A) to give #B269 as a white solid. Yield: 12 mg, 0.009 mmol, 25%. LCMS (Protocol D): m/z 1320.4 [M+H]⁺, retention time=0.91 minutes.

Step 2:

Synthesis of N-(6-aminohexanoyl)-L-valyl-N-(4-{9-[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]-3,7-dioxo-2-oxa-4,6,8-triazanon-1-yl}phenyl)-N⁵-carbamoyl-L-ornithinamide acetate salt (#B270). The title compound was prepared in 69% yield from 19.8 mg (0.015 mmol, 1.0 eq.) of #B269 and 25.5 mg (0.3 mmol, 20.0 eq.) of piperidine using the procedure described for preparation of compound #B47. LCMS (Protocol D): m/z 1097.78 [M+H]⁺, retention time=0.64 minutes.

Synthesis of (2S,3Z)-5-({(2R,3R,5S,6S)-6-[(2E,4E)-5-{(3R,4R,5R,7S)-7-[(6S,9S)-19-bromo-6-methyl-2,5,8,11,18-pentaoxo-9-(propan-2-yl)-3,4,7,10,17-pentaazanonadec-1-yl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B268). The title compound was prepared in 64% yield from 12 mg (0.01 mmol, 1 eq.) of #B270, 3.5 mg (0.015 mmol, 1.5 eq) of 1-[(bromoacetyl)oxy]pyrrolidine-2,5-dione and 5.2 mg (0.04 mmol, 4.0 eq) of N,N-diisopropylethylamine using the procedure described for preparation of compound #B150. LCMS (Protocol D): m/z 1217.43 [M+H]⁺, retention time=0.75 minutes. ¹H NMR (500 MHz, DMSO-d₆) δ 9.98 (s, 1H), 8.27-8.20 (m, 1H), 8.08 (d, J=7.3 Hz, 1H), 7.84-7.73 (m, 2H), 7.62-7.54 (m, 2H), 7.30-7.23 (m, 2H), 6.65-6.57 (m, 1H), 6.41-6.32 (m, 1H), 6.29 (d, J=15.9 Hz, 1H), 6.16-6.07 (m, 2H), 6.01-5.93 (m, 1H), 5.86 (dd, J=11.5 and 7.6 Hz, 1H), 5.63 (dd, J=15.9 and 5.6 Hz, 1H), 5.55-5.47 (m, 1H), 5.41 (s, 2H), 5.01 (d, J=5.9 Hz, 1H), 4.94 (s, 1H), 4.43-4.16 (m, 4H), 3.81 (s, 2H), 3.69-3.59 (m, 2H), 3.54-3.45 (m, 1H), 3.26-3.10 (m, 3H), 3.08-2.88 (m, 4H), 2.74 (d, J=5.0 Hz, 1H), 2.60 (d, J=5.0 Hz, 1H), 2.35-2.09 (m, 6H), 2.01-1.92 (m, 4H), 1.87-1.75 (m, 4H), 1.74-1.30 (m, 14H), 1.29-1.19 (m, 4H), 1.06 (d, J=6.4 Hz, 3H), 0.95 (d, J=7.3 Hz, 3H), 0.86 (d, J=6.6 Hz, 3H), 0.83 (d, J=6.9 Hz, 3H).

Example #A88

Preparation of (2E)-4-amino-N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]pent-2-enamide (#B271) and (2Z)-4-amino-N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]pent-2-enamide (#B272)

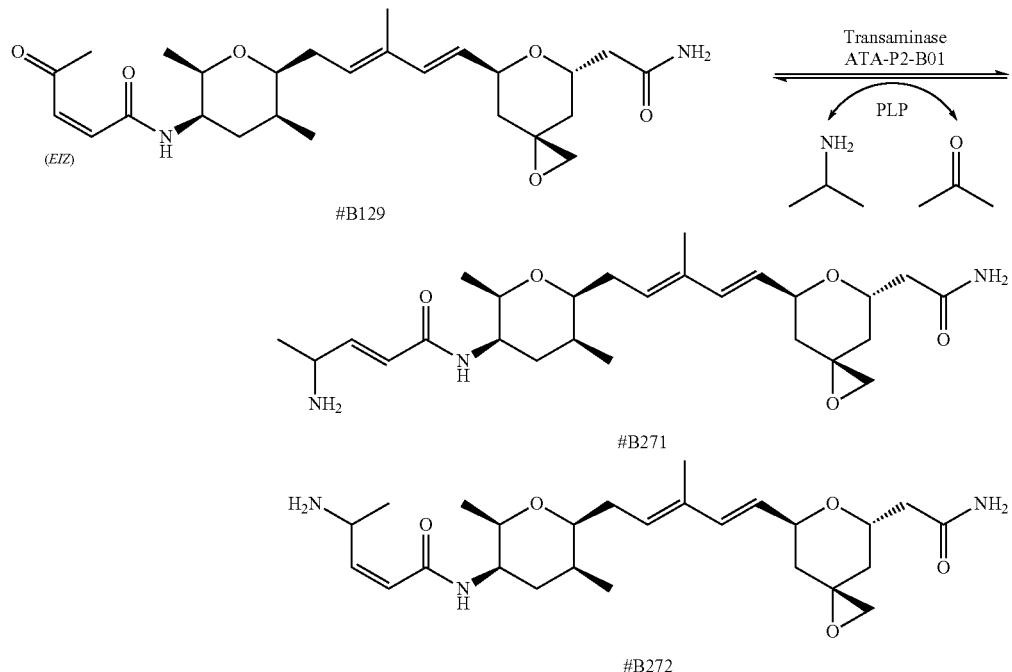

Step 1:

Synthesis of (2E)-4-amino-N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]pent-2-enamide (#B271) and (2Z)-4-amino-N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]pent-2-enamide (#B272): To 100 mM sodium phosphate buffer pH 7.4 (3.57 ml) were added #B129 (7 mg, in 0.23 ml DMSO, 1 eq.), isopropylamine (1.475 ml of a 1 M solution made in phosphate buffer pH 3, giving a solution of pH ~7, 100 eq.), pyridoxal phosphate (0.295 ml of a 50 mM solution in phosphate buffer pH 7.4, 1 eq.), and ATA-P2-B01 enzyme preparation (33 mg, in 0.33 ml phosphate buffer pH 7.4, Codexis, lot #D11134, R-selective for acetophenone). After incubation at 30° C., 200 rpm for 19 hours, pH was adjusted to ~12 with sodium hydroxide and the reaction was extracted seven times with equal volume of ethylacetate. The solvent was evaporated under reduced pressure, the residue resuspended in 0.25 ml acetonitrile/water 1:1, filtered and purified by reverse phase chromatography in a total of 10 runs (Method I). The fractions with retention time of 10 and 13 min were collected and neutralized with ammonium hydroxide before freeze-drying to afford #B271 and #B272, respectively, as white solids.

B271; (Yield 1.6 mg). HPLC (Protocol P): retention time=6.5 minutes; HRESIMS m/z observed 476.3124 [M+H]$^+$ (predicted for $C_{26}H_{42}N_3O_5$ is m/z 476.3124); $^1$H NMR (400 MHz, DMSO-$d_6$, mult, J in Hz) δ 7.55 (d, J=8.2 Hz, 1H), 7.32 (br s, 1H), 6.77 (br s, 1H), 6.54 (dd, J=15.6 and 6.2 Hz, 1H), 6.27 (d, J=16.0 Hz, 1H), 6.21 (dd, J=15.4 and 1.2 Hz, 1H), 5.59 (dd, J=16.0 and 5.5 Hz, 1H), 5.51 (br t, J=7.0 Hz, 1H), 4.54 (br q, J=5.5 Hz, 1H), 4.30 (m, 1H), 3.69 (m, 1H), 3.64 (m, 1H), 3.50 (m, 1H), 3.42 (m, 1H), 2.62 (m, 2H), 2.58-2.52 (m, 1H), 2.34-2.27 (m, 2H), 2.24-2.17 (m, 2H), 1.85-1.73 (m, 4H), 1.70 (s, 3H), 1.64 (m, 2H), 1.37 (dd, J=13.1 and 6.2 Hz, 1H), 1.07 (d, J=6.6 Hz, 3H), 1.05 (d, J=6.2 Hz, 3H), 0.96 (d, J=7.4 Hz, 3H).

B272 (Yield 1.1 mg) HPLC (Protocol P): retention time=6.85 minutes; HRESIMS m/z 476.3131 [M+H]$^+$ (predicted for $C_{26}H_{42}N_3O_5$ is m/z 476.3124); $^1$H NMR (400 MHz, DMSO-$d_6$, mult, J in Hz) δ 7.76 (d, J=7.8 Hz, 1H), 7.32 (br s, 1H), 6.77 (br s, 1H), 6.27 (d, J=15.6 Hz, 1H), 5.88 (br d, J=11.7, 1H), 5.73 (dd, J=11.5 and 8.4 Hz, 1H), 5.59 (dd, J=16.0 and 5.5 Hz, 1H), 5.51 (br t, J=6.6 Hz, 1H), 4.54 (br q, J=5.5 Hz, 1H), 4.47 (m, J=7.0 Hz, 1H), 4.30 (m, 1H), 3.65 (m, 2H), 3.50 (m, 1H), 2.62 (m, 2H), 2.55 (m, 1H), 2.34-2.27 (m, 2H), 2.24-2.18 (m, 2H), 1.83-1.75 (m, 2H), 1.70 (s, 3H), 1.65 (m, 3H), 1.38 (dd, J=13.3 and 6.2 Hz, 1H), 1.24 (br s, 1H), 1.07 (d, J=6.2 Hz, 3H), 1.02 (d, J=6.6 Hz, 3H), 0.95 (d, J=7.4 Hz, 3H).

Example #A89

Preparation of (2E)-4-amino-N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]pent-2-enamide (#B273)

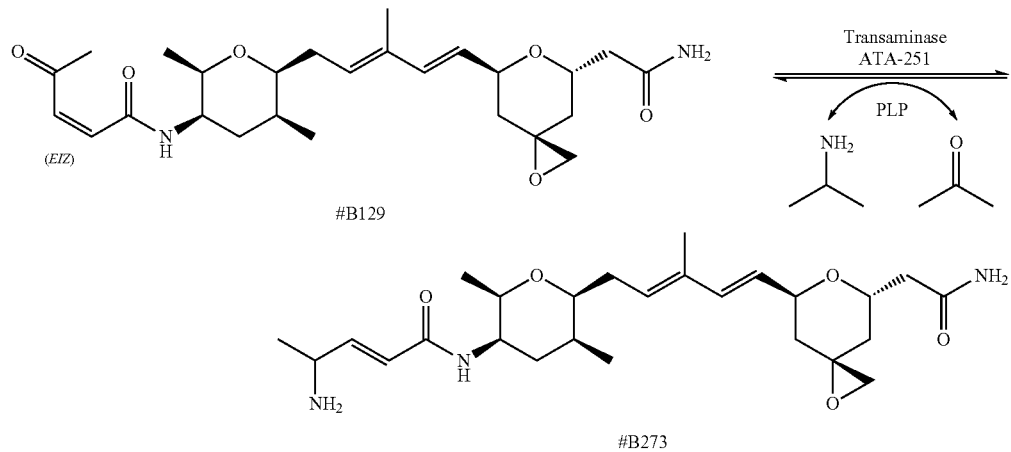

Step 1:

Synthesis (2E)-4-amino-N-[(2R,3R,5S,6S)-6-{(2E,4E)-5-[(3S,5S,7S)-7-(2-amino-2-oxoethyl)-1,6-dioxaspiro[2.5]oct-5-yl]-3-methylpenta-2,4-dien-1-yl}-2,5-dimethyltetrahydro-2H-pyran-3-yl]pent-2-enamide (#B273). To #B129 (2.9 mg, in 0.1 ml DMSO, 1 eq.) were added pyridoxal phosphate (0.125 ml of a 50 mM solution in phosphate buffer pH 7.4, 1 eq.), and a mixture of isopropylamine (0.625 ml of a 1 M solution made in phosphate buffer pH 3, giving a solution of pH ~7, 100 eq.), ATA-251 enzyme preparation (15 mg, in 0.15 ml phosphate buffer pH 7.4, Codexis, lot #D11140, S-selective for acetophenone) and 100 mM sodium phosphate buffer pH 7.4 (1.6 ml) that had been pre-incubated at 45° C., 200 rpm for 1 hour. After incubation at 37° C., 200 rpm for 22 hours, pH was adjusted to ~12 with sodium hydroxide and the reaction was extracted seven times with equal volume of ethylacetate. The solvent was evaporated under reduced pressure, the residue resuspended in 0.25 ml acetonitrile/water 1:1, filtered and purified by reverse phase chromatography in a total of 4 runs (Method J). The fraction with retention time of 9 min was collected and neutralized with ammonium hydroxide before freeze-drying to afford #B273 as white solid. Yield: 0.7 mg. HPLC (Protocol P): retention time=6.6 minutes; HRESIMS m/z 476.3126 [M+H]$^+$ (predicted for $C_{26}H_{42}N_3O_5$ is m/z 476.3124); $^1$H NMR (500 MHz, DMSO-d$_6$, mult, J in Hz) δ 7.57 (d, J=8.3 Hz, 1H), 7.33 (br s, 1H), 6.78 (br s, 1H), 6.54 (dd, J=15.4 and 6.1 Hz, 1H), 6.27 (d, J=15.9 Hz, 1H), 6.22 (br d, J=15.4 Hz, 1H), 5.59 (dd, J=15.9 and 5.4 Hz, 1H), 5.51 (br t, J=7.1 Hz, 1H), 4.54 (q, J=5.3 Hz, 1H), 4.30 (m, 1H), 3.69 (m, 1H), 3.64 (dq, J=6.8 and 2.2 Hz, 1H), 3.49 (dt, J=7 and 2.2 Hz, 1H), 3.42 (m, 1H), 2.62 (m, 2H), 2.58-2.53 (m, 1H), 2.33-2.28 (m, 1H), 2.23-2.18 (m, 2H), 1.85-1.74 (m, 4H), 1.70 (s, 3H), 1.64 (m, 2H), 1.37 (dd, J=13.3 and 6.2 Hz, 1H), 1.07 (d, J=6.6 Hz, 3H), 1.05 (d, J=6.3 Hz, 3H), 0.96 (d, J=7.3 Hz, 3H).

Example #A90

Preparation of (2S,3Z)-5-({(2R,3R,5S,6S)-6-[(2E,4E)-5-{(3R,5S)-7-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B274)

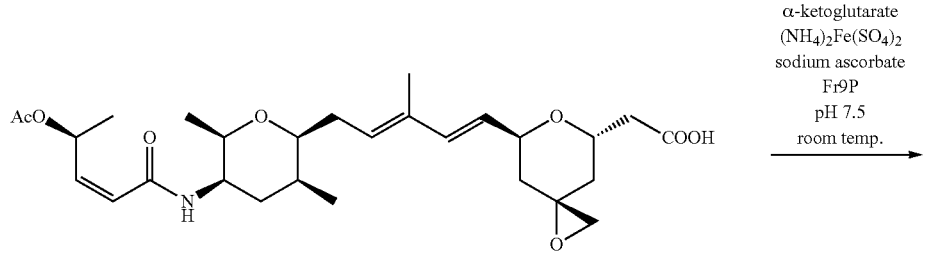

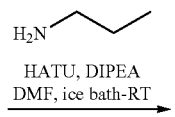
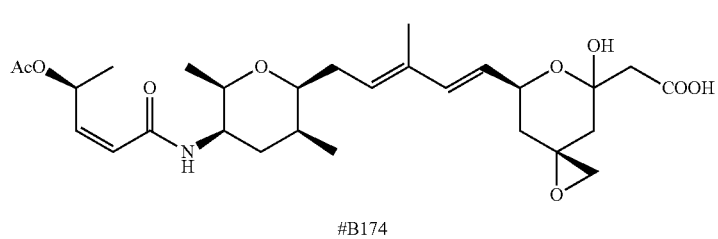
B174

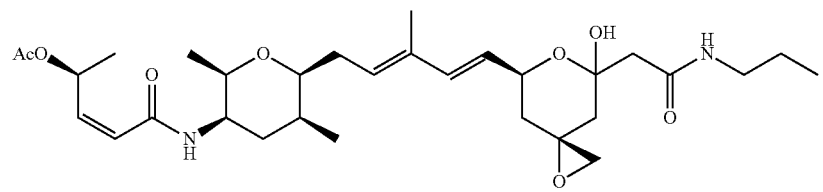
B274

Step 1:

Synthesis of [(3R,7S)-7-{(1E,3E)-5-[(2S,3S,5R,6R)-5-{[(2Z,4S)-4-(acetyloxy)pent-2-enoyl]amino}-3,6-dimethyl-tetrahydro-2H-pyran-2-yl]-3-methylpenta-1,3-dien-1-yl}-5-hydroxy-1,6-dioxaspiro[2.5]oct-5-yl]acetic acid (#B174). To an aqueous solution of #NP2 (4 mg, 0.4 mM, 1 eq.) in 50 mM MOPS buffer pH 7.5 were added α-ketoglutarate (0.8 mM final concentration, 2 eq.), sodium ascorbate (0.08 mM, 0.2 eq.), NH$_4$Fe(II)SO$_4$ (0.04 mM, 0.1 eq.) and recombinant Fr9P from step 1 of example #A60 (1.6 µM, 0.004 eq.). After incubation at room temperature for 2 hours, the reaction was acidified to pH ~4-5 with acetic acid and extracted three times with equal volume of ethylacetate. The solvent was evaporated under reduced pressure, to provide #B174 which was used without further purification. LCMS m/z 536 [M+H]+.

Step 2:

Synthesis of (2S,3Z)-5-({(2R,3R,5S,6S)-6-[(2E,4E)-5-{(3R,5S,7S)-7-hydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B274)

To #B174 (4.0 mg; 0.0075 mmol) in DMF (0.05M), at 0° C. To this was added HATU (1.4 eq) and the mixture was stirred for 5 min. DIPEA (1 eq), followed by propylamine (1.5 eq) in DMF were added and. the mixture stirred at RT for 2 h. The reaction was diluted with acetonitrile and purified by reverse phase HPLC (Protocol K): retention time=10.8 minutes; The fraction containing the product was immediately frozen and lyophilized to afford #B274 as a white solid (2.4 mg; Yield 60%). LCMS m/z 577 [M+H]+ $^1$H NMR (400 MHz, DMSO-d$_6$, mult, J in Hz) δ 7.99 (dd, J=5.5, 5.5 Hz, 1H), 7.80 (d, J=8.0 Hz, 1H), 6.36 (m, 1H), 6.21 (d, J=15.7 Hz, 1H), 6.11 (dd, J=11.7, 0.9 Hz, 1H), 5.86 (dd, J=11.6, 7.6 Hz, 1H), 5.53 (dd, 15.7, 6.0 Hz, 1H), 5.47 (m, 1H), 4.65 (m, 1H), 3.65 (m, 1H), 3.64 (m, 1H), 3.48 (m, 1H), 3.05 (m, 1H), 3.01 (m, 1H), 2.47 (m, 2H), 2.40 (m, 2H), 2.29 (m, 1H), 2.19 (m, 1H), 2.11 (m, 1H), 1.98 (s, 3H), 1.80 (m, 3H), 1.68 (s, 3H), 1.64 (m, 1H), 1.41 (m, 2H), 1.29 (m, 1H), 1.25 (d, J=6.4 Hz, 3H), 1.17 (m, 1H), 1.07 (d, J=6.7 Hz, 3H), 0.94 (d, J=7.2 Hz, 3H), 0.84 (dd, J=7.6, 7.6 Hz, 3H). $^{13}$C NMR (100 MHz, DMSO-d$_6$) δ 170.0, 169.7, 164.4, 142.6, 133.9, 133.6, 128.4, 127.3, 122.6, 95.9, 79.7, 74.7, 66.8, 67.7, 54.2, 49.2, 46.0, 45.5, 39.8, 39.7, 37.8, 35.0, 31.4, 28.5, 22.0, 19.5, 17.4, 13.9, 12.6, 12.0, 10.9.

Example #A91

Preparation of (2S,3Z)-5-({(2R,3R,5S,6S)-6-[(2E,4E)-5-{(3R,4R,5R,7S)-4,7-dihydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B275)

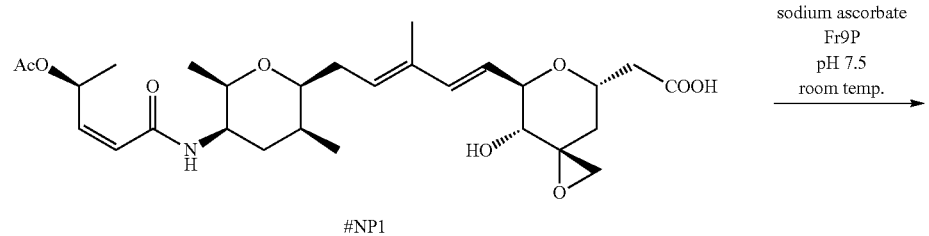
NP1

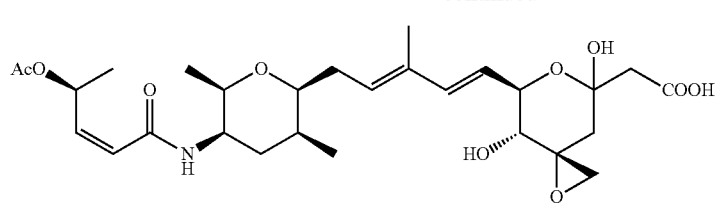
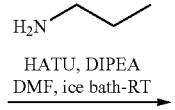

B276

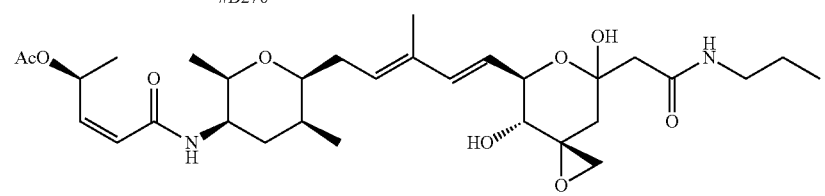

B275

Step 1:

Synthesis of [(3R,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-5,8-dihydroxy-1,6-dioxaspiro[2.5]oct-5-yl]acetic acid (#B276): To an aqueous solution of #NP1 (4 mg, 0.4 mM, 1 eq.) in 50 mM MOPS buffer pH 7.5 were added α-ketoglutarate (0.8 mM final concentration, 2 eq.), sodium ascorbate (0.08 mM, 0.2 eq.), NH$_4$Fe(II)SO$_4$ (0.04 mM, 0.1 eq.) and recombinant Fr9P from step 1 of example #A60 (1.2 μM, 0.003 eq.). After incubation at room temperature for 1 hour 30 min, the reaction was acidified to pH ~4-5 with acetic acid and extracted three times with equal volume of ethylacetate. The solvent was evaporated under reduced pressure, and the obtained crude #B276 was used without further purification. LCMS m/z 552 [M+H]$^+$.

Step 2:

Synthesis of (2S,3Z)-5-({(2R,3R,5S,6S)-6-[(2E,4E)-5-{(3R,4R,5R,7S)-4,7-dihydroxy-7-[2-oxo-2-(propylamino)ethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate (#B275)

To #B276 (4.3 mg; 0.0080 mmol) in DMF (0.05M), and at 0° C. was added HATU (1.4 eq) and allowed stirred for 5 min. DIPEA (1 eq), followed by propylamine (1.5 eq) in DMF were added, and the reaction was allowed to stir at RT 1 h. An additional amount of HATU (0.7 eq), DIPEA (1 eq) and propylamine (1 eq) were added, and the mixture was stirred for an additional 30 min. The crude product was diluted with acetonitrile and purified by reverse phase HPLC (Protocol K): retention time=8.60 minutes. The fraction containing the product was immediately frozen and lyophilized to afford #B275 as a white solid (2.3 mg; Yield 49%). LCMS m/z 593 [M+H]+; $^1$H NMR (400 MHz, DMSO-d$_6$, mult, J in Hz) δ 8.01 (dd, J=5.6, 5.6 Hz, 1H), 7.81 (d, J=8.0 Hz, 1H), 6.36 (m, 1H), 6.24 (d, J=16.1 Hz, 1H), 6.11 (dd, J=12.1 Hz, 1H), 5.88 (dd, J=11.7, 7.7 Hz, 1H), 5.67 (dd, 16.1, 4.4 Hz, 1H), 5.44 (m, 1H), 4.55 (d, 8.7 Hz, 1H), 4.33 (m, 1H), 3.65 (m, 1H), 3.64 (m, 1H), 3.48 (m, 1H), 3.33 (m, 1H), 3.07 (m, 1H), 3.00 (m, 1H), 2.73 (m, 1H), 2.39 (m, 2H), 2.31 (m, 1H), 2.29 (m, 1H), 2.27 (m, 1H), 2.19 (m, 1H), 1.98 (s, 3H), 1.80 (m, 2H), 1.69 (s, 3H), 1.64 (m, 1H), 1.49 (m, 1H), 1.41 (m, 2H), 1.25 (d, J=6.3 Hz, 3H), 1.07 (d, J=6.3 Hz, 3H), 0.95 (d, J=7.2 Hz, 3H), 0.84 (m, 3H). $^{13}$C NMR (100 MHz, DMSO-d$_6$) δ 170.4, 169.6, 164.7, 143.4, 135.5, 134.0, 128.9, 126.3, 123.4, 95.7, 80.6, 75.4, 71.4, 68.4 (×2), 56.7, 46.7, 46.2, 45.9, 41.3, 40.6, 35.6, 32.1, 29.1, 22.8, 21.4, 20.2, 18.1, 14.6, 12.8, 11.8.

Example #A92

Preparation of N-[6-(2,5-dioxo-2,5-dihydro-1H-pyrrol-1-yl)hexanoyl]-L-valyl-N-{4-[({[trans-4-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)cyclohexyl]carbamoyl}oxy)methyl]phenyl}-N5-carbamoyl-L-ornithinamide (#B277)

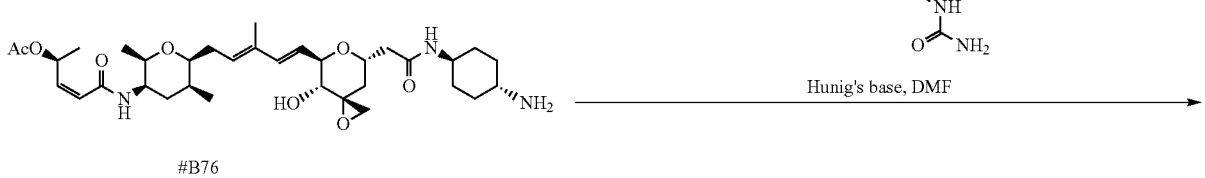

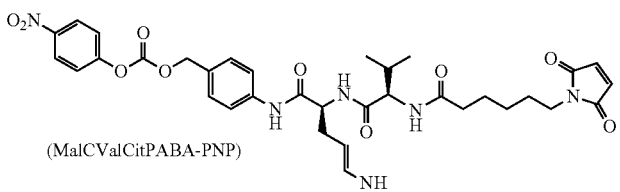

B76

-continued

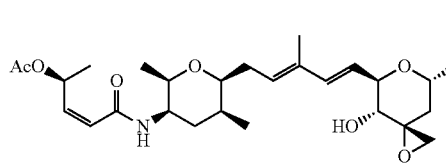

B#277

Step 1:

Synthesis of N-[6-(2,5-dioxo-2,5-dihydro-1H-pyrrol-1-yl)hexanoyl]-L-valyl-N-{4-[({[trans-4-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)cyclohexyl]carbamoyl}oxy)methyl]phenyl}-N5-carbamoyl-L-ornithinamide (#B277) To a solution of N-[6-(2,5-dioxo-2,5-dihydro-1H-pyrrol-1-yl)hexanoyl]-L-valyl-N5-carbamoyl-N-{4-[({[(4 nitrobenzyl)oxy]carbonyl}oxy)methyl]phenyl}-L-ornithinamide (Mal-CValCitPABC-PNP, prepared as in *Bioconjugate Chem.* 2002, 13, 855-869, 16.5 mg, 0.022 mmol, 1.1 eq.) and B76 (11.9 mg, 83% purity, 0.019 mmol, 1.0 eq.) in anhydrous N,N-dimethylformamide (1.5 ml) was added N,N-diisopropylethylamine (30 µL). The resulting mixture was stirred at ambient temperature for 0.5 hour. The reaction mixture was purified using reverse phase chromatography (Method B*) to afford #B277 as a white powder. Yield: 9.3 mg, 40%. HPLC (Protocol N): retention time=9.5 minutes (purity 94%). LCMS (Protocol M): m/z 1229.5 [M+H]$^+$.

Example #A93

Preparation of (2S,3Z)-5-{[(2R,3R,5S,6S)-6-{(2E,4E)-5-[(3R,4R,5R,7S)-7-{2-[(trans-4-{[6-(2,5-dioxo-2,5-dihydro-1H-pyrrol-1-yl)hexanoyl]amino}cyclohexyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B278)

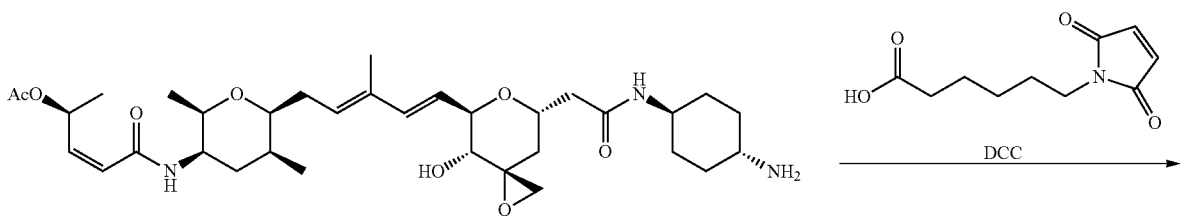

B76

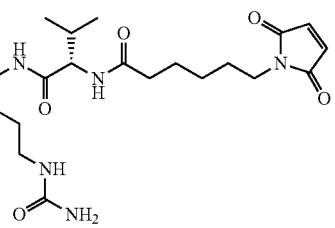

DCC →

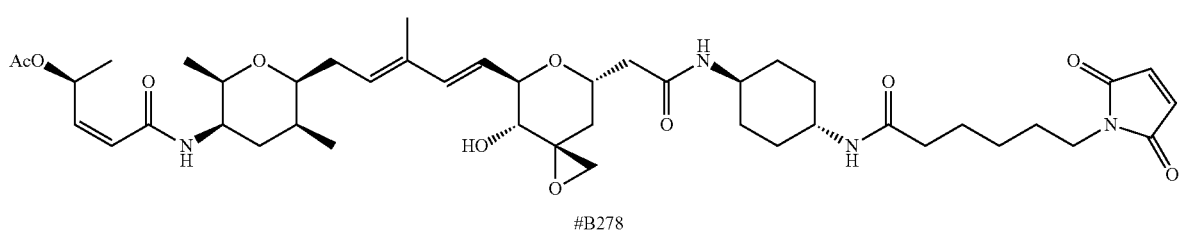

B278

Step 1:
Synthesis of (2S,3Z)-5-{[(2R,3R,5S,6S)-6-{(2E,4E)-5-[(3R,4R,5R,7S)-7-{2-[(trans-4-{[6-(2,5-dioxo-2,5-dihydro-1H-pyrrol-1-yl)hexanoyl]amino}cyclohexyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B278) A solution 6-maleimidohexanoic acid (24.2 mg, 0.11 mmol, 5 eq.) and dicyclohexylcarbodiimide (DCC, 49.5 mg, 0.24 mmol, 11 eq.) in anhydrous N,N-dimethylformamide (1.0 mL) was stirred at ambient temperature for 30 min. #B76 (13.0 mg, 83% purity, 0.021 mmol, 1.0 eq.) in N,N-dimethylformamide (0.5 ml) was added and the resulting mixture stirred for 2 hours. The reaction mixture was purified using reverse phase chromatography (Method B*) to afford #B278 as a white powder. Yield: 8.6 mg, 49%. HPLC (Protocol N): retention time=9.6 minutes (purity 96%). LCMS (Protocol M): m/z 824.4 [M+H]$^+$.

Example #A94

Preparation of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,5-anhydro-1-(carboxymethyl)-3-C-(chloromethyl)-2-deoxy-D-erythro-pentitol (#NP5) [PF-06739239]

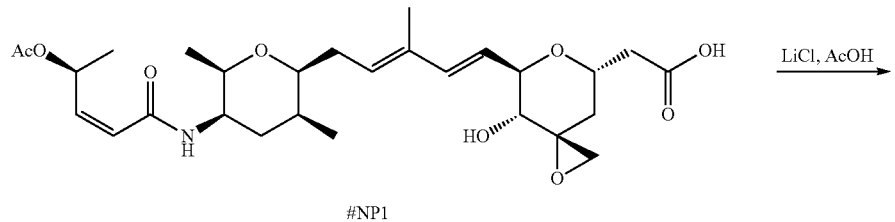

NP1

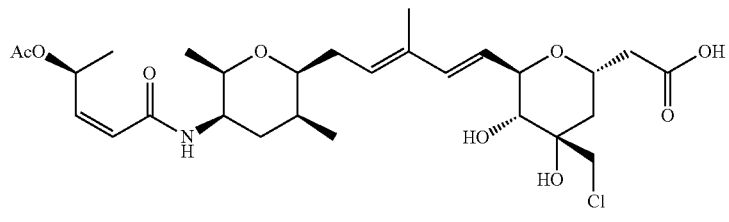

NP5

Step 1:
Synthesis of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,5-anhydro-1-(carboxymethyl)-3-C-(chloromethyl)-2-deoxy-D-erythro-pentitol (#NP5) A solution of #NP1 (101 mg, ~70% pure, ~0.19 mmol, 1 eq.) in anhydrous tetrahydrofuran (1.0 mL) was mixed with a solution of lithium chloride (61 mg, 1.4 mmol, 7 eq.) in anhydrous acetic acid (1.0 mL) at 0° C. The resulting solution was stirred at ambient temperature for 1.5 hours. The reaction mixture was purified using reverse phase chromatography (Method B*) to afford #NP5 as a white powder. Yield: 54.6 mg, ~76%. HPLC (Protocol N): retention time=10.5 minutes (purity 96%). LCMS (Protocol M): m/z 572.5 [M+H]$^+$. $^1$H NMR (400 MHz, DMSO-d$_6$, mult, J in Hz) δ 12.00 (br s, D$_2$O exchangeable), 7.80 (d, J=8.2, 1H, D$_2$O exchangeable), 6.36 (dq, J=6.0, 6.0, 1H), 6.22 (br d, J=15.6, 1H), 6.11 (d, J=11.7, 1H), 5.87 (dd, J=11.7, 7.4, 1H), 5.62 (dd, J=15.6, 5.4, 1H), 5.47 (br dd, J=7.0, 7.0, 1H), 5.02 (d, J=7.0, 1H, D$_2$O exchangeable), 4.78 (br s, 1H, D$_2$O exchangeable), 4.27 (m, 1H), 4.09 (dd, 8.1, 6.3, 1H), 3.65 (m, 2H), 3.63 (d, J=10.9, 1H), 3.50 (m, 1H), 3.46 (d, J=10.9, 1H), 3.22 (dd, J=8.6, 7.4, 1H), 2.97 (dd, J=15.6, 9.0, 1H), 2.60 (dd, J=15.6, 5.5, 1H), 2.28 (m, 1H), 2.21 (m, 1H), 1.98 (s, 3H), 1.92 (dd, J=14.7, 6.6, 1H), 1.80 (m, 3H), 1.70 (s, 3H), 1.65 (m, 2H), 1.25 (d, J=6.6, 3H), 1.07 (d, J=6.5, 3H), 0.95 (d, J=7.0, 3H).

Example #A95

Preparation of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methyl-penta-1,3-dien-1-yl}-1,5-anhydro-3-C-(chloromethyl)-2-deoxy-1-[2-oxo-2-(pentafluorophenoxy)ethyl]-D-erythro-pentitol (#B279)

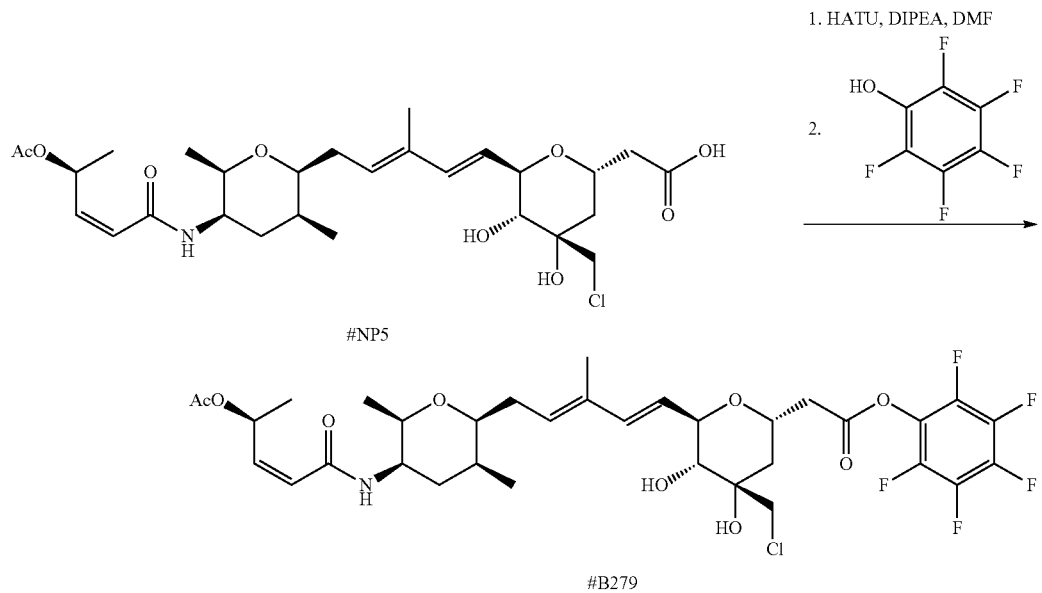

Step 1:

Synthesis of (1S,5R)-5-{(1E,3E)-5-[(2S,3S,5R,6R)-5-{[(2Z,4S)-4-(acetyloxy)pent-2-enoyl]amino}-3,6-dimethyl-tetrahydro-2H-pyran-2-yl]-3-methylpenta-1,3-dien-1-yl}-1,5-anhydro-3-C-(chloromethyl)-2-deoxy-1-[2-oxo-2-(pentafluorophenoxy)ethyl]-D-erythro-pentitol (#B279) To a solution of #NP5 (18.2 mg, 0.032 mmol, 1 eq.) and HATU (16.8 mg) in dry N,N-dimethylformamide (200 uL) was added with N,N-diisopropylethylamine (20 uL) and the solution was stirred for 5 min at ambient temperature and then mixed with pentafluorophenol (25 mg, 0.13 mmol, 4 eq.) in N,N-dimethylformamide (150 ul). The reaction mixture was stirred for 20 minutes and then purified using reverse phase chromatography (Method B*) to afford #B279 as a white powder. Yield: 15.1 mg, 74%. HPLC (Protocol N): retention time=14.8 minutes (purity 94%). LCMS (Protocol M): m/z 738.3 [M+H]+. $^1$H NMR (400 MHz, DMSO-$d_6$, mult, J in Hz) δ 7.80 (d, J=7.8, 1H, $D_2O$ exchangeable), 6.36 (dq, J=6.0, 6.0, 1H), 6.24 (br d, J=15.6, 1H), 6.11 (d, J=11.3, 1H), 5.87 (dd, J=11.3, 7.4, 1H), 5.66 (dd, J=15.9, 5.5, 1H), 5.44 (br dd, J=6.6, 6.6, 1H), 5.16 (d, J=7.0, 1H, $D_2O$ exchangeable), 4.97 (br s, 1H, $D_2O$ exchangeable), 4.46 (m, 1H), 4.16 (dd, 9.0, 5.8, 1H), 3.70-3.63 (m, 3H), 3.68 (d, J=10.6, 1H), 3.51 (d, J=10.9, 1H), 3.49 (m, 1H), 3.27 (dd, J=9.0, 7.0, 1H), 3.10 (dd, J=15.6, 4.3, 1H), 2.30 (m, 1H), 2.19 (m, 1H), 2.01 (dd, J=15.1, 7.0, 1H), 1.97 (s, 3H), 1.81 (m, 2H), 1.77 (d, J=14.8, 1H), 1.70 (s, 3H), 1.64 (m, 1H), 1.25 (d, J=6.4, 3H), 1.07 (d, J=6.5, 3H), 0.95 (d, J=7.0, 3H).

Example #A96

Preparation of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methyl-penta-1,3-dien-1-yl}-1,5-anhydro-1-[2-({2-[(bromoacetyl)amino]ethyl}amino)-2-oxoethyl]-3-C-(chloromethyl)-2-deoxy-D-erythro-pentitol (#B280)

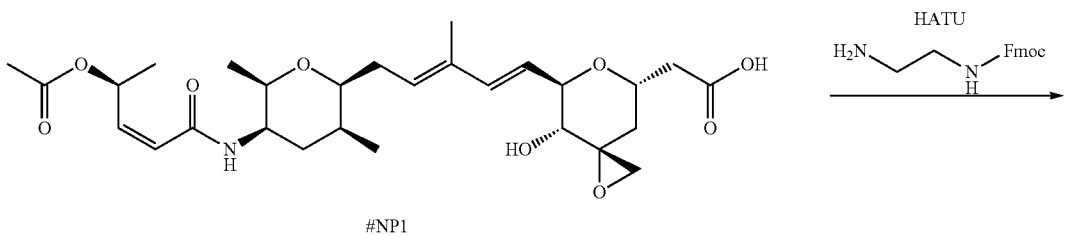

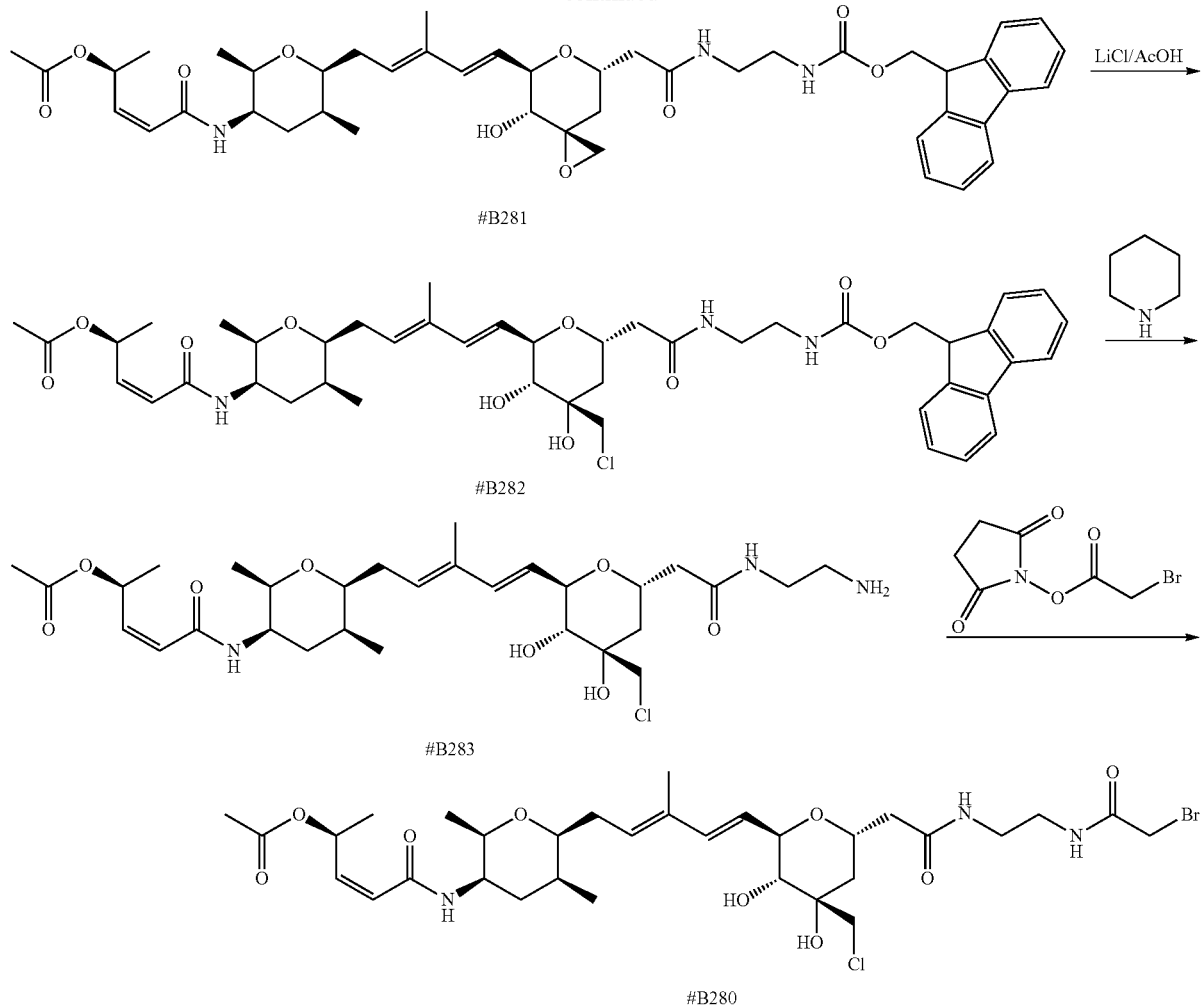

Step 1:

Synthesis of (2S,3Z)-5-{[(2R,3R,5S,6S)-6-{(2E,4E)-5-[(3R,4R,5R,7S)-7-{2-[(2-{[(9H-fluoren-9-ylmethoxy)carbonyl]amino}ethyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B281). To a solution of #NP1 (122.1 mg, ~67% purity, 0.22 mmol, 1.2 eq.) and O-(7-azabenzotriazol-1-yl)-N,N,N',N'-tetramethyluronium hexafluorophosphate (HATU, 151 mg, 0.30 mmol, 1.7 eq.) in N,N-dimethylformamide (3 mL) was added N,N-diisopropylethylamine (Hunig's base, 60 uL) and the resulting solution was stirred at ambient temperature for 10 min. N-fluorenylmethyloxycarbonyl-1,2-diaminoethane hydrobromide (73 mg, 0.2 mmol, 1 eq.) in N,N-dimethylformamide (0.5 mL) was then added and resulting solution was stirred for 10 min. The reaction mixture was filtered and then purified using reversed phase chromatography (Method F*) to afford #B281 as a white powder. Yield: 114.5 mg, 64% yield. HPLC (Protocol N): retention time=12.7 minutes (purity 99%). ESIMS (positive) m/z 800.7 [M+H]$^+$.

Step 2:

Synthesis of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1-5-anhydro-3-C-(chloromethyl)-2-deoxy-1-{2-[(2-{[(9H-fluoren-9-ylmethoxy)carbonyl]amino}ethyl)amino]-2-oxoethyl}-D-erythro-pentitol (#B282) A solution of #B281 (44.5 mg, 0.056 mmol) in anhydrous tetrahydrofuran (0.4 mL) was mixed with a solution of lithium chloride (30.0 mg, 0.71 mmol) in dry acetic acid (0.2 mL). The reactant was stirred at ambient temperature for 1.5 hours and then purified using reversed phase chromatography (Method F*) to afford #B282 as a white powder. Yield: 48.0 mg, 100% yield. HPLC (Protocol N): retention time=16.0 minutes (purity 96%). ESIMS (positive) m/z 836.7 [M+H]$^+$.

Step 3:

Synthesis of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1-{2-[(2-aminoethyl)amino]-2-oxoethyl}-1,5-anhydro-3-C-(chloromethyl)-2-deoxy-D-erythro-pentitol (#B283) To a solution of #B282 (48 mg, 0.057 mmol) in DMF (2 mL) was added piperidine (20 uL). The solution was stirred at ambient temperature for 1 hour and then purified using reversed phase chromatography (Method F*) to afford #B283 as a white powder. Yield: 26.4 mg, 92% yield. HPLC (Protocol N): retention time=6.8 minutes (purity 91%). ESIMS (positive) m/z 614.6 [M+H]$^+$.

Step 4:

Synthesis of (1S,5R)-5-{(1E,3E)-5-[(2S,3S,5R,6R)-5-{[(2Z,4S)-4-(acetyloxy)pent-2-enoyl]amino}-3,6-dimethyl-tetrahydro-2H-pyran-2-yl]-3-methylpenta-1,3-dien-1-yl}-1,5-anhydro-1-[2-({2-[(bromoacetyl)amino]ethyl}amino)-2-oxoethyl]-3-C-(chloromethyl)-2-deoxy-D-erythro-pentitol (#B280) To a solution of #B283 (9.1 mg, 0.015 mmol) and 1-[(bromoacetyl)oxy]pyrrolidine-2,5-dione (6.2 mg, 0.024 mmol) in DMF (0.5 ml) was added N,N'-diisopropylethylamine (Hunig's base, 5.0 uL). The resulting solution was stirred at ambient temperature for 30 minutes and then purified using reversed phase chromatography (Method F*) to afford #B280 as a white powder. Yield: 5.8 mg, 53% yield.

HPLC (Protocol N): retention time=10.0 minutes (purity 99%). ESIMS (positive) m/z 736.6 [M+H]$^+$.

Example #A97

Preparation of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,5-anhydro-3-C-(chloromethyl)-2-deoxy-1-(2-methoxy-2-oxoethyl)-D-erythro-pentitol (#B284)

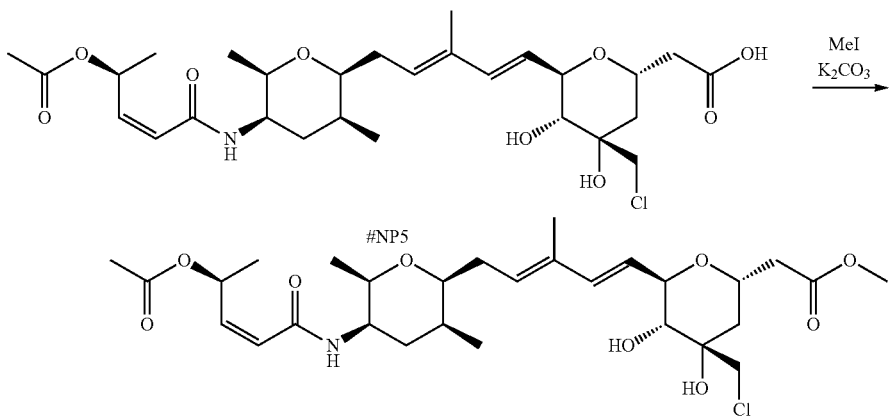

Step 1:

Synthesis of (1S,5R)-5-{(1E,3E)-5-[(2S,3S,5R,6R)-5-{[(2Z,4S)-4-(acetyloxy)pent-2-enoyl]amino}-3,6-dimethyl-tetrahydro-2H-pyran-2-yl]-3-methylpenta-1,3-dien-1-yl}-1,5-anhydro-3-C-(chloromethyl)-2-deoxy-1-(2-methoxy-2-oxoethyl)-D-erythro-pentitol (#B284) To a suspension of #NP5 (6.2 mg, 0.011 mmol, 1 eq.) and potassium carbonate (20.0 mg, 0.14 mmol, 12 eq.) in N,N-dimethylformamide (0.5 mL) was added methyl iodide (20 uL, 0.32 mmol, 29 eq.). The resulting mixture was stirred at 0 deg for 30 minutes. The solid was removed by filtration and the filtrate was purified using reversed phase chromatography (Method F*) to afford #B284 as a white powder. Yield: 5.6 mg, 90% yield. HPLC (Protocol N): retention time=12.7 minutes (purity 97%). ESIMS (positive) m/z 586.4 [M+H]$^+$.

Example #A98

Preparation of (2S,3Z)-5-({(2R,3R,5S,6S)-6-[(2E,4E)-5-{(2S,4S,6S)-4-(chloromethyl)-4-hydroxy-6-[2-oxo-2-(propylamino)ethyl]tetrahydro-2H-pyran-2-yl}-3-methylpenta-2,4-dien-1-yl]-2,5-dimethyltetrahydro-2H-pyran-3-yl}amino)-5-oxopent-3-en-2-yl acetate (#B285)

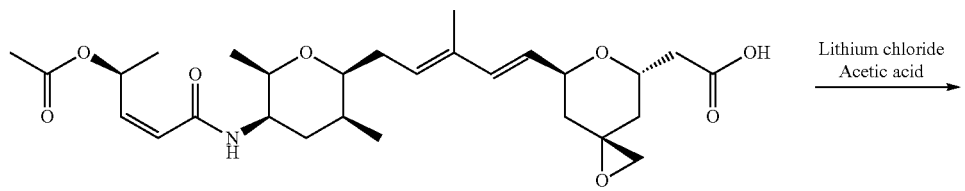

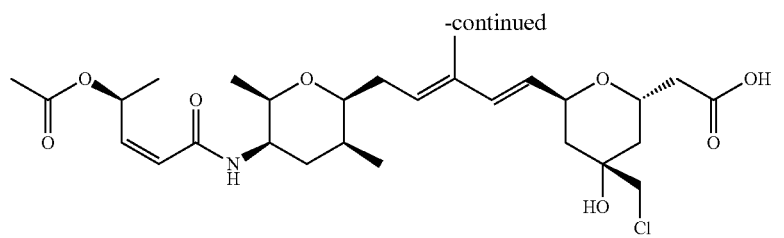

NP8

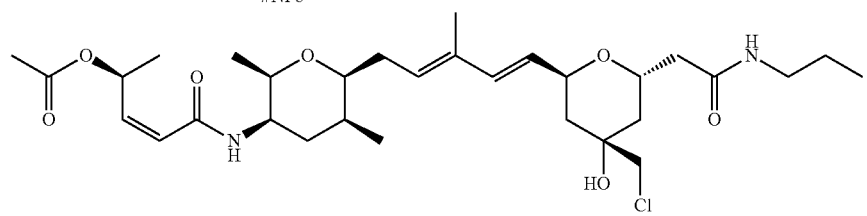

B285

Step 1:

Synthesis of [(2S,4S,6S)-6-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-4-(chloromethyl)-4-hydroxytetrahydro-2H-pyran-2-yl] acetic acid (#NP8) A solution of #NP2 (70.4 mg, 90% purity, 0.19 mmol, 1 eq.) in anhydrous tetrahydrofuran (1.0 mL) was mixed with a solution of lithium chloride (50 mg, 1.2 mmol, 6 eq.) in dry acetic acid (1.0 mL) at 0° C. The solution was stirred at ambient temperature for 1.5 hours and then at 40 deg for 2 hours. The reactant was purified using reversed phase chromatography (Method F*) to afford #NP8 as a white powder. Yield: 52.0 mg, 72% yield. HPLC (Protocol N): retention time=11.4 minutes (purity 98%). ESIMS (positive) m/z 556.2 [M+H]$^+$.

Step 2:

Synthesis of (2S,3Z)-5-({(2R,3R,5S,6S)-6-[(2E,4E)-5-{(2S,4S,6S)-4-(chloromethyl)-4-hydroxy-6-[2-oxo-2-(propylamino)ethyl]tetrahydro-2H-pyran-2-yl}-3-methylpenta-2,4-dien-1-yl]-2,5-dimethyltetrahydro-2H-pyran-3-yl}amino)-5-oxopent-3-en-2-yl acetate. (#B285) A solution of #NP8 (5.0 mg, 0.009 mmol, 1 eq.), O-(7-azabenzotriazol-1-yl)-N,N,N',N'-tetramethyluronium hexafluorophosphate (HATU, 5.2 mg, 0.014 mmol, 1.5 eq.), and diisopropylethylamine (Hunig's base, 5.0 uL) in anhydrous N,N-dimethylformamide (0.5 ml) was stirred at ambient temperature for 10 minutes. Neat propylamine (5.0 uL, 0.08, 9 eq.) was then added and the solution stirred for 1 hour and then purified using reversed phase chromatography (Method F*) to afford #B285 as a white powder. Yield: 4.2 mg, 90% yield. HPLC (Protocol N): retention time=11.8 minutes (purity 95%). ESIMS (positive) m/z 597.4 [M+H]$^+$.

Example #A99

Preparation of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,5-anhydro-3-C-(chloromethyl)-2-deoxy-1-[2-oxo-2-(propylamino)ethyl]-D-erythro-pentitol (#B286)

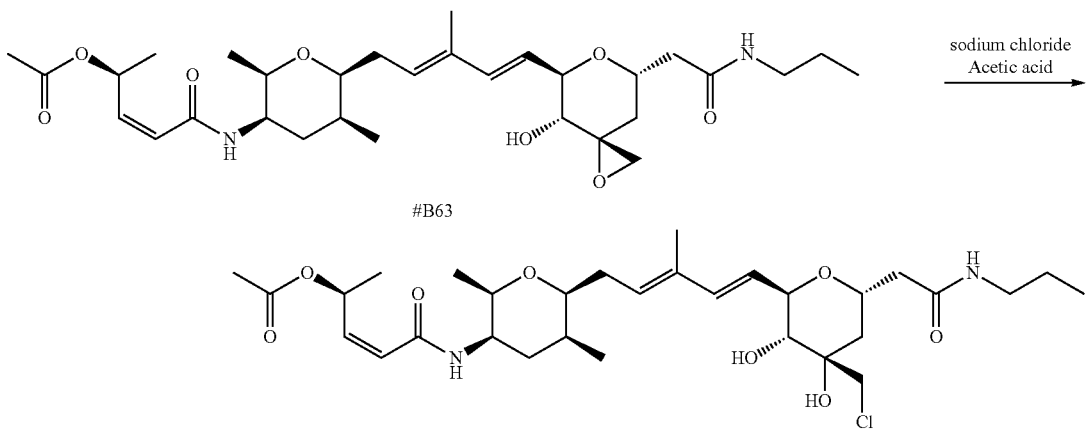

B63

B286

Step 1:

Synthesis of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1, 5-anhydro-3-C-(chloromethyl)-2-deoxy-1-[2-oxo-2-(propylamino)ethyl]-D-erythro-pentitol (#B286) A solution of #B63 (18.4 mg, 0.032 mmol, 1 eq.) in anhydrous tetrahydrofuran (1.0 ml) was mixed with a suspension of sodium chloride (50.0 mg) in dry acetic acid (0.5 mL). The solution was then stirred at 50° C. for 5 hours and purified using reversed phase chromatography (Method F*) to afford #B286 as a white powder. Yield: 17.5 mg, 94% yield. HPLC (Protocol N): retention time=10.9 minutes (purity 97%). ESIMS (positive) m/z 613.6 [M+H]+.

Example #A100

Preparation of (2S,3Z)-5-{[(2R,3R,5S,6S)-6-{(2E,4E)-5-[(3R,4R,5R,7S)-7-(2-{[trans-3-(2,5-dioxo-2,5-dihydro-1H-pyrrol-1-yl)cyclobutyl]amino}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B287) and (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,5-anhydro-3-C-(chloromethyl)-2-deoxy-1-(2-{[trans-3-(2,5-dioxo-2,5-dihydro-1H-pyrrol-1-yl)cyclobutyl]amino}-2-oxoethyl)-D-erythro-pentitol (#B288)

bonylmaleimide (45 mg, 0.29 mmol, 6 eq.). The suspension was then stirred at OC for 1 hour. The products were extracted with ethyl acetate (10 mL). The organic layer was dried over anhydrous magnesium chloride and then evaporated to dryness under reduced pressure. The residue was re-dissolved in dichloromethane (2 mL), and triethylamine (90 uL) was added and then stirred at 40° C. for 2 hours. The reaction mixture was neutralized with acetic acid and purified using reversed phase chromatography (Method F*) to afford #B287 as a white powder. Yield: 4.3 mg, 11% yield. HPLC (Protocol N): retention time=10.1 minutes (purity 97%). ESIMS (positive) m/z 684.4 [M+H]+.

Step 2:
Synthesis of (1S,5R)-5-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,5-anhydro-3-C-(chloromethyl)-2-deoxy-1-(2-{[trans-3-(2,5-dioxo-2,5-dihydro-1H-pyrrol-1-yl)cyclobutyl]amino}-2-oxoethyl)-D-erythro-pentitol (#B288) A solution of #B287 (2.7 mg) in anhydrous tetrahydrofuran (200 uL) was mixed with a solution of lithium chloride (13 mg) in dry acetic acid (200 uL) at 0 deg. The solution was stirred at ambient temperature for 0.5 hour and then purified using reversed phase chromatography (Method F*) to afford #B288 as a white powder. Yield: 0.8 mg, 26% yield. HPLC (Protocol N): retention time=10.6 minutes (purity 92%). ESIMS (positive) m/z 720.7 [M+H]+.

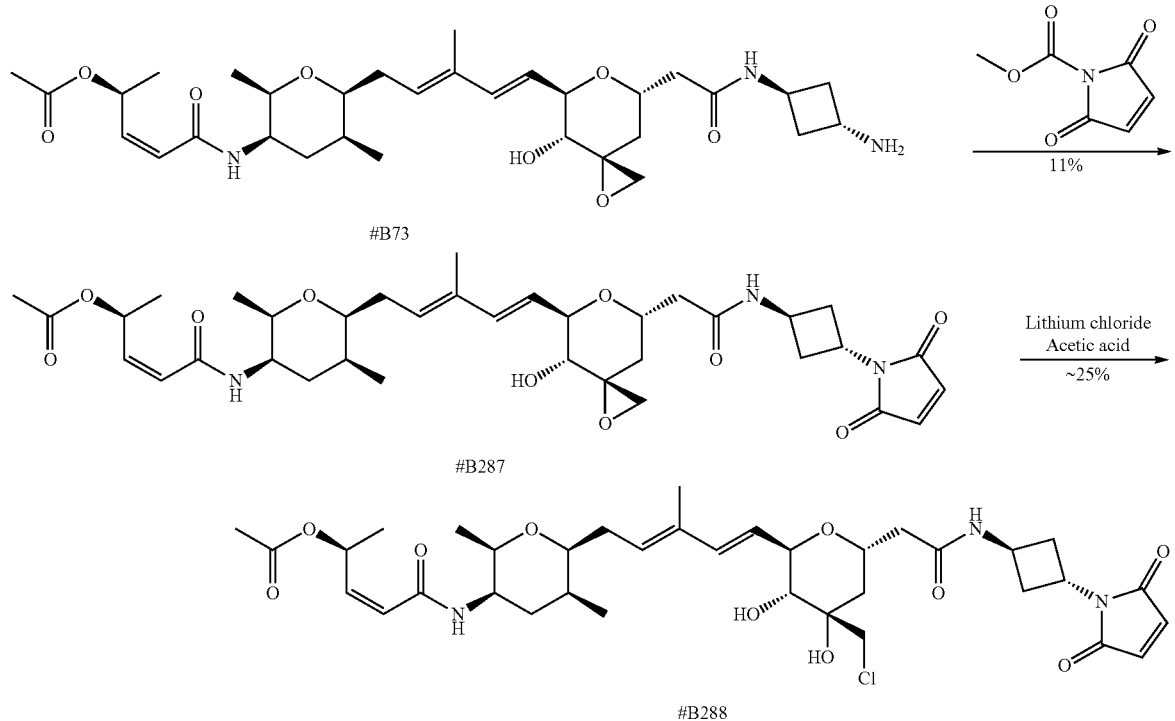

Step 1:
Synthesis of (2S,3Z)-5-{[(2R,3R,5S,6S)-6-{(2E,4E)-5-[(3R,4R,5R,7S)-7-(2-{[trans-3-(2,5-dioxo-2,5-dihydro-1H-pyrrol-1-yl)cyclobutyl]amino}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate (#B287). To a solution of #B73 (32.5 mg, 0.05 mmol, 1 eq.) in 1:2:3 dimethylsulfoxide/saturated sodium bicarbonate/water (6 mL total) was added N-methoxycar- Conjugation Procedures
General Conjugation Procedure A:
Commercially available Herceptin antibody (Genentech Inc) is dialyzed into Dulbecco's Phosphate Buffered Saline (DPBS, Lonza). The dialyzed antibody (5-10 mg/mL) is then reacted with PL (3-12) equivalents linker-payload (10 mM in dimethyl sulfoxide (DMSO)) containing the reactive N-hydroxysuccinimide ester at room temperature for 2 h in 50 mM borate buffer pH 8.7. In some cases, 50 mM borate buffer pH 8.7 is substituted by Dulbecco's Phosphate Buffered Saline (DPBS, Lonza). In some cases, to improve the solubility/reactivity of the linker-payload, dimethylacetamide (DMA) or DMSO is added to achieve 10-15% (v/v) total organic solvent component in final reaction mixture. The reaction mixture is then buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated and buffer exchanged in to 10 mM Sodium succinate buffer, 5.4% trehalose pH 5.1 using GE Healthcare Sephadex G-25 M buffer exchange columns per manufacturer's instructions. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure B:

Commercially available Herceptin antibody (Genentech Inc) or therapeutic antibodies are dialyzed into 50 mM phosphate buffer pH 6.8. The dialyzed antibody (5-10 mg/mL) is reacted with PL (4-12) equivalents linker-payload (5-30 mM in dimethylacetamide (DMA) or dimethyl sulfoxide (DMSO)) containing the reactive pentafluorophenyl ester at room temperature for 2-20 h in 50 mM phosphate buffer pH 6.8. In some cases, to improve the solubility/reactivity of the linker-payload, DMA or DMSO is added to achieve 10-15% (v/v) total organic solvent component in final reaction mixture. The reaction mixture is then buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated and buffer exchanged in to 10 mM Sodium succinate buffer, 5.4% trehalose pH 5.1 using GE Healthcare Sephadex G-25 M buffer exchange columns per manufacturer's instructions. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure C:

Commercially available Herceptin antibody (Genentech Inc) or therapeutic antibodies are dialyzed into Dulbecco's Phosphate Buffered Saline (DPBS, Lonza). The dialyzed antibody is reduced with addition of y(1-7) equivalents of tris(2-carboxyethyl)phosphine hydrochloride (TCEP, 5 mM in distilled water) and diluted to 15 mg/mL final antibody concentration using DPBS, 5 mM 2,2',2'',2'''-(Ethane-1,2-diyldinitrilo)tetraacetic acid (EDTA), pH 7.0 (Buffer A). The reaction is incubated at 37° C. for 2 h and then cooled to room temperature. Conjugation was performed by addition of PL (2 to 15) equivalents of linker-payload (5-10 mM in dimethylacetamide (DMA) or dimethyl sulfoxide (DMSO)). In some cases, to improve the solubility/reactivity of the linker-payload, DMA or DMSO is added to achieve 10-15% (v/v) total organic solvent in final reaction mixture, and Buffer A added to achieve 10 mg/mL final antibody concentration. The reaction is then incubated for 2 h at room temperature. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure D:

Therapeutic antibody is dialyzed into Dulbecco's Phosphate Buffered Saline (DPBS, Lonza). The dialyzed antibody is reduced with addition of y(1-7) equivalents of tris(2-carboxyethyl)phosphine hydrochloride (TCEP, 5 mM in distilled water) and diluted to 15 mg/mL final antibody concentration using DPBS, 5 mM 2,2',2'',2'''-(Ethane-1,2-diyldinitrilo)tetraacetic acid (EDTA), pH 7.0 (Buffer A). The reaction is incubated at 37° C. for 2 h and then cooled to room temperature. Conjugation was performed by addition of PL (2 to 15) equivalents of linker-payload (5-10 mM in dimethylacetamide (DMA). In some cases, to improve the solubility/reactivity of the linker-payload, DMA or DMSO is added to achieve 10-15% (v/v) total organic solvent in final reaction mixture, and 20× borate buffer and DPBS is added to achieve 10 mg/mL final antibody concentration in 50 mM borate buffer pH 8.7. The reaction is incubated for 3 h at 37° C. or for 16 h at room temperature. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure E:

Therapeutic antibody carrying extra cysteine residues relative to native antibody is dialyzed into Dulbecco's Phosphate Buffered Saline (DPBS, Lonza). The dialyzed antibody is reduced with addition of 100 equivalents of tris(2-carboxyethyl)phosphine hydrochloride (TCEP, 5 mM in distilled water) and diluted to 15 mg/mL final antibody concentration using DPBS, 5 mM 2,2',2'',2'''-(Ethane-1,2-diyldinitrilo)tetraacetic acid (EDTA), pH 7.0 (Buffer A). The reaction is then incubated at room temperature for 2 h and then cooled to room temperature. After the reduction, TCEP is removed from the reaction mixture using a Millipore Amicon Ultra 4 mL 50KD MWCO ultrafiltration device. The reaction mixture is concentrated to 1/10nth the original volume four times and re diluted to original volume each time using Buffer A. In some cases, reaction mixture is subsequently buffer exchanged into Buffer A using GE Healthcare Sephadex G-25 M buffer exchange columns per manufacturer's instructions. Alternative methods such as Tangential Flow Filteration (TFF) or dialysis are also useful in particular circumstances. Following the reduction, the reduced hinge/internal disulfides of the Antibody is re-oxidized using 1-1.5 mM dehydroascorbate (DHA) at room temperature overnight in Buffer A. After the oxidation, DHA is removed from the reaction mixture using a Millipore Amicon Ultra 4 mL 50KD MWCO ultrafiltration device.

The reaction mixture is concentrated to ⅒th the original volume four times and re-diluted to original volume each time using 50 mM Borate buffer pH 8.7. In some cases, reaction mixture is subsequently buffer exchanged into 50 mM Borate buffer pH 8.7 using GE Healthcare Sephadex G-25 M buffer exchange columns per manufacturer's instructions. Alternative methods such as TFF or dialysis are also useful in particular circumstances. Conjugation is performed by addition of PL (3 to 12) equivalents of linker-payload (10 mM in dimethylacetamide (DMA)). In some cases, to improve the solubility/reactivity of the linker-payload, DMA or DMSO is added to achieve 10-15% (v/v) total organic solvent in final reaction mixture, and 20× borate buffer and DPBS is added to achieve 5-10 mg/mL final antibody concentration in 50 mM borate buffer pH 8.7. The reaction is incubated for 3 h at 37° C. or 16 h at room temperature. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure F:

Therapeutic antibody carrying extra cysteine residues relative to native antibody is dialyzed into Dulbecco's Phosphate Buffered Saline (DPBS, Lonza). The dialyzed antibody is reduced with addition of 100 equivalents of tris(2-carboxyethyl)phosphine hydrochloride (TCEP, 5 mM in distilled water) and diluted to 15 mg/mL final antibody concentration using DPBS, 5 mM 2,2',2'',2'''-(Ethane-1,2-diyldinitrilo)tetraacetic acid (EDTA), pH 7.0 (Buffer A). The reaction is then incubated at room temperature for 2 h and then cooled to room temperature. After the reduction, TCEP is removed from the reaction mixture using a Millipore Amicon Ultra 4 mL 50KD MWCO ultrafiltration device. The reaction mixture is concentrated to ⅒th the original volume four times and re-diluted to original volume each time using Buffer A. In some cases, reaction mixture is subsequently buffer exchanged into Buffer A using GE Healthcare Sephadex G-25 M buffer exchange columns per manufacturer's instructions. Alternative methods such as Tangential Flow Filteration (TFF) or dialysis are also useful in particular circumstances. Following the reduction, the reduced hinge/internal disulfides of the Antibody is re-oxidized using 1-1.5 mM dehydroascorbate (DHA) at room temperature overnight in Buffer A. After the oxidation, DHA is removed from the reaction mixture using a Millipore Amicon Ultra 4 mL 50KD MWCO ultrafiltration device. The reaction mixture is concentrated to ⅒th the original volume four times and re-diluted to original volume each time using Buffer A. In some cases, reaction mixture is subsequently buffer exchanged into Buffer A using GE Healthcare Sephadex G-25 M buffer exchange columns per manufacturer's instructions. Alternative methods such as Tangential Flow Filteration (TFF) or dialysis are also useful in particular circumstances. Conjugation is performed by addition of PL (2 to 15) equivalents of linker-payload (5-10 mM in dimethylacetamide (DMA) or dimethyl sulfoxide (DMSO)). In some cases, to improve the solubility/reactivity of the linker-payload, DMA or DMSO is added to achieve 10-15% (v/v) total organic solvent in final reaction mixture, and Buffer A added to achieve 5-10 mg/mL final antibody concentration. The reaction is incubated for 1-2 h at room temperature. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure G:

Conjugation reactions is performed in the upper portion of a centrifugal ultrafiltration device such as Amicon Ultra 50 k Ultracel filters (part #UFC805096, GE). A 132 mM stock solution of L-cysteine is prepared in Dulbecco's Phosphate Buffered Saline (DPBS, Lonza) 5 mM 2,2',2'',2'''-(Ethane-1,2-diyldinitrilo)tetraacetic acid (EDTA), pH 7.0 (Buffer A). This solution (50 uL) is added to a mixture of the respective mutant antibody carrying extra cysteine residues (5 mg) in 950 uL of Buffer A. The final cysteine concentration in the reaction mixture is 6.6 mM. After allowing the reaction to stand at room temperature for 1.5 hour, the reaction tube is centrifuged to concentrate the material to approximately 100 uL. The mixture is diluted to 1 mL with Buffer A. This process is repeated 4 times in order to remove all the cysteine reductant. The resulting material is diluted to 1 mL in Buffer A and treated with 16 uL of a 5 mM solution of the maleimide linker-payload (in dimethyl acetamide (DMA) (approximately 5 equivalents). After standing at room temperature for 1.5 hour the reaction tube is centrifuged to concentrate the material to approximately 100 μL. The mixture is diluted to 1 mL with DPBS. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure H:

Therapeutic antibody carrying transglutamine enzyme-reactive glutamine residues is dialyzed into Dulbecco's Phosphate Buffered Saline (DPBS, Lonza). The transglutaminase mediated conjugation is carried by mixing 0.5-5.0 mg/mL transglutaminase reactive glutamine containing antibody in 25 mM Tris Buffer pH 8.0, 150 mM NaCl, 0.31 mM reduced glutathione with 5.0-20.0-fold molar excess of amino alkyl linker carrying payload (5-10 mM in dimethylacetamide (DMA) or dimethyl sulfoxide (DMSO)) and 2% w/v transglutaminase (Ajinomot Activa TI). The reaction is then incubated from 4-16 h at room temperature. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

General Conjugation Procedure I:

Therapeutic antibody mutant carrying extra cysteine residues relative to native antibody is dialyzed into Dulbecco's Phosphate Buffered Saline (DPBS, Lonza). The dialyzed antibody is reduced with addition of ×(25-100) equivalents of tris(2-carboxyethyl)phosphine hydrochloride (TCEP, 5 mM in distilled water) and diluted to 15 mg/mL final antibody concentration using DPBS, 5 mM 2,2',2'',2'''-(Ethane-1,2-diyldinitrilo)tetraacetic acid (EDTA), pH 6.5-7.4 (Buffer A). The reaction is then incubated at room temperature for 1-2 h and then cooled to room temperature. After the reduction, TCEP is removed from the reaction mixture using a Millipore Amicon Ultra 4 mL 50KD MWCO ultrafiltration device. The reaction mixture is concentrated to $^1\!/_{10}$nth the original volume four times and re diluted to original volume each time using Buffer A. In some cases, reaction mixture is subsequently buffer exchanged into Buffer A using GE Healthcare Sephadex G-25 M buffer exchange columns per manufacturer's instructions. Following the reduction, the reduced hinge/internal disulfides of the Antibody is re-oxidized using 1 mM dehydroascorbate (DHA) at room temperature overnight in Buffer A. After the oxidation, DHA is removed from the reaction mixture using a Millipore Amicon Ultra 4 mL 50KD MWCO ultrafiltration device. The reaction mixture is concentrated to $^1\!/_{10}$nth the original volume four times and re-diluted to original volume each time using Buffer A. Conjugation is performed by addition of PL (2 to 10) equivalents of linker-payload (5-10 mM in dimethylacetamide (DMA) or dimethyl sulfoxide (DMSO)). In some cases, to improve the solubility/reactivity of the linker-payload, DMA or DMSO is added to achieve 10-15% (v/v) total organic solvent in final reaction mixture, and Buffer A added to achieve 5-10 mg/mL final antibody concentration. The reaction is incubated for 1-4 h at room temperature. The reaction mixture is subsequently buffer exchanged into DPBS (pH7.4) using GE Healthcare Sephadex G-25 M buffer exchange columns per manufacturer's instructions. Crude material is purified by size exclusion chromatography (SEC) using a GE AKTA Explorer system with a GE Superdex 200 column and DPBS (pH7.4) eluent. The pooled monomer fraction from AKTA is then concentrated if required. The ADC is further characterized via size exclusion chromatography (SEC) for purity and liquid chromatography electrospray ionization tandem mass spectrometry (LC-ESI MS) to calculate drug-antibody ratio (loading). The protein concentration is determined via UV spectrophotometer.

SEC and HPLC-ESI MS Conditions Used for Analysis of Conjugates:

Protocol 1:

Protocol 1 (SEC):

Column: Column: TSK-gel G3000SWxl, 300×7.8 mm, 10 µm; Mobile phase: Phosphate buffer saline (PBS, 1×), pH 7.4 with 2% acetonitrile; Isocratic; Flow rate: 1 mL/minute. Temperature: room temperature; Injection Volume: 5 µL; Instrument: Agilent 1100 HPLC.

Protocol 1b:

Column: Superdex 200 5/150 GL, 5×150 mm, 13 µm; Mobile phase: Phosphate buffer saline (PBS, 1×), pH 7.4 with 2% acetonitrile; Isocratic; Flow rate: 1 mL/minute. Temperature: room temperature; Injection Volume: 5 µL; Instrument: Agilent 1100 HPLC.

Protocol 2:

Protocol 2 (HPLC): Column: Column: Agilent Poroshell 300SB-C8, 75×2.1 mm, 2.6 µm; Mobile phase A: 0.1% formic acid in water (v/v); Mobile phase B: 0.1% formic acid in acetonitrile (v/v); Gradient: 20% B to 45% B over 4 minutes; Flow rate: 1.0 mL/minute. Temperature: 60° C.; Detection: 220 nm; MS (+) range 400-2000 Da; Injection volume: 10 µL; Instrument: Agilent 1100 LC, Waters MicromassZQ MS. Deconvolution was performed using MaxEnt1. Samples were treated with 100 fold excess Tris(2-carboxyethyl)phosphine hydrochloride (TCEP) or Dithiothreitol (DTT) and incubated for 15 min at room temperature prior to injection.

Protocol 3:

Column: Aquity UPLC BEH 200 SEC 1.7 um; Mobile phase: 450 mM NaCl; Flow rate: 0.5 mL/minute. Temperature: 35 C; Injection Volume: 10 µL.

Trastuzumab In Vitro and In Vivo Studies

It is noted that for the following studies trastuzumab in the absence of conjugated cytotoxic agents shows no significant in vitro potency or in vivo efficacy at equivalent antibody concentrations.

In Vitro Cell Assay Procedure

Target expressing (BT474 (breast cancer), N87 (gastric cancer), HCC1954 (breast cancer), MDA-MB-361-DYT2 (breast cancer)) or non-expressing (MDA-MB-468) cells were seeded in 96-well cell culture plates for 24 hours before treatment. Cells were treated with 3-fold serially diluted antibody-drug conjugates or free compounds (i.e., no antibody conjugated to the drug) in duplicate at 10 concentrations. Cell viability was determined by CellTiter 96® AQ$_{ue}$-$_{ous}$ One Solution Cell Proliferation MTS Assay (Promega, Madison Wis.) 96 hours after treatment. Relative cell viability was determined as percentage of untreated control. IC$_{50}$ values were calculated using a four parameter logistic model #203 with XLfit v4.2 (IDBS, Guildford, Surry, UK). Results are shown in Tables 4 and 9. The potency ranged upward from 0.0002 nm. Testing in other cell lines is reported in Table 9A. Similar procedures and techniques were employed.

Figure 3:
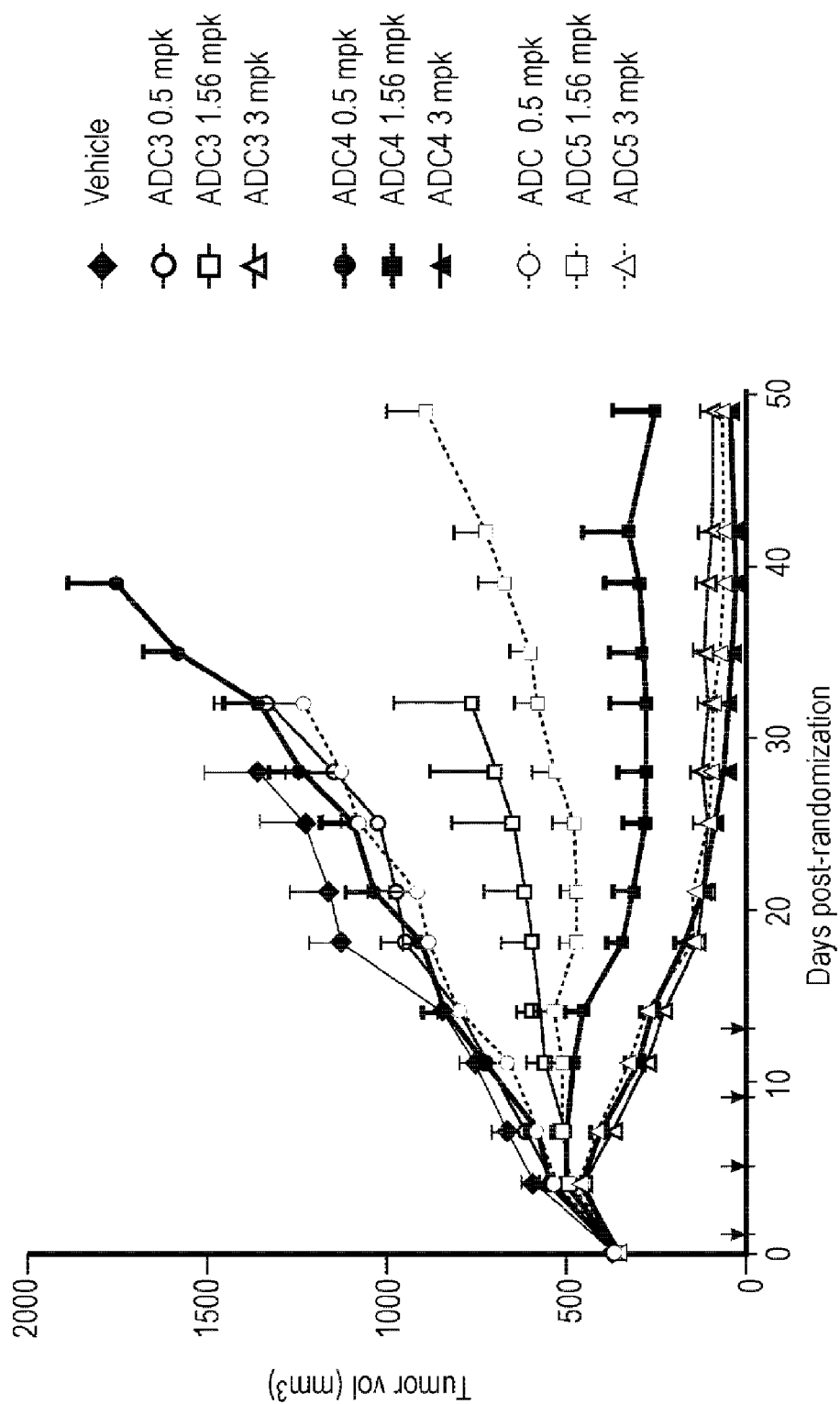
FIG. 3 is a graph showing the in vivo efficacy of ADCs 3, 4 and 5 in N87 mouse xenograft in vivo model.
Figure 4:
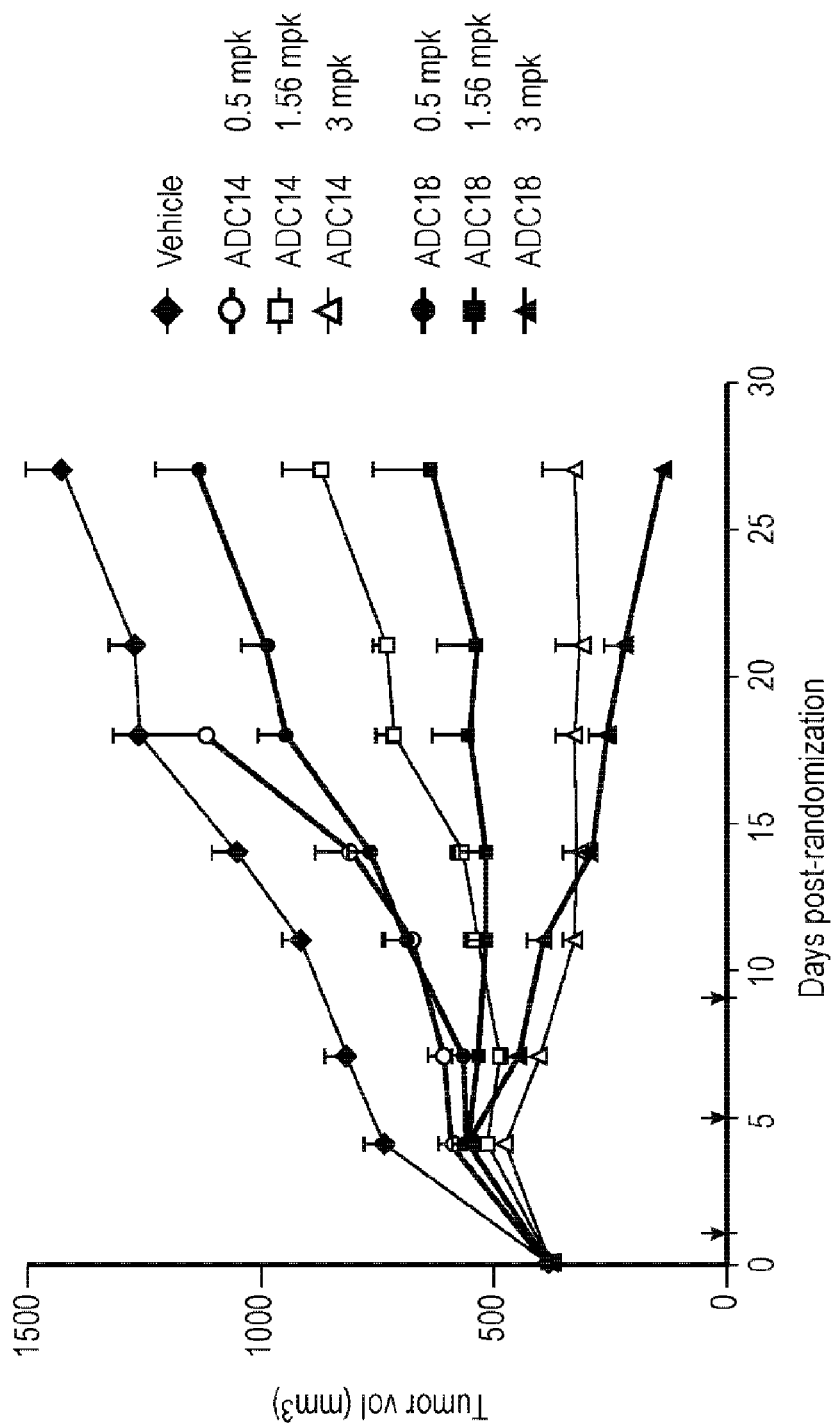
FIG. 4 is a graph showing the in vivo efficacy of ADCs 14, 18 in N87 mouse xenograft in vivo model.

In Vivo N87 Tumor Xenograft Model (FIGS. 3 and 4)

In vivo efficacy studies of antibody-drug conjugates were performed with target-expressing xenograft models using the N87 cell lines. For efficacy study, 7.5 million tumor cells in 50% matrigel are implanted subcutaneously into 6-8 weeks old nude mice until the tumor sizes reach between 250 and 350 mm$^3$. Dosing is done through bolus tail vein injection. Depending on the tumor response to treatment, animals are injected with 1-10 mg/kg of antibody drug conjugates treated four times every four days. All experimental animals are monitored for body weight changes weekly. Tumor volume is measured twice a week for the first 50 days and once weekly thereafter by a Caliper device and calculated with the following formula: Tumor volume=(length×width$^2$)/2. Animals are humanely sacrificed before their tumor volumes reach 2500 mm$^3$. The tumor size is observed to decrease after the first week of treatment. Animals may be monitored continuously for tumor regrowth after the treatment has discontinued.

Results of the testing of ADC's 3, 4 and 5 and ADC's 14 and 15 in the N87 mouse xenograft in vivo screening model are shown in FIGS. 3 and 4.

Table 1 provides the preparation Details for Examples #B82-#B108.

Table 2 provides characterization data for Examples #B82-#B108.
Table 3 provides the preparation of Payload-Linkers #B109-#B117.
Table 4 shows in vitro Cytotoxicity data for Natural products and synthetic analogs.
Table 5 provides the characterization data for Payload-Linkers #B109-#B117.
Table 6 provides structure of ADCs and the payload linkers used to prepare them.
Table 7 provides general methods of preparation of exemplified ADCs.
Table 8 provides analytical data for exemplified ADCs.
Table 9 shows Table 9: In vitro cytotoxicity data for ADCs.
Tables

TABLE 1

Preparation Details for Examples #B82-#B108

| EX# | R$^{1'}$ | R$^{2'}$ | Starting Amine | Method of Preparation; Non-commercial Starting Materials | Purification Method; Amount made; Yield |
|---|---|---|---|---|---|
| #B82 | OH | (N-methyl-N-(2-methylthioethyl)amide) | HN(Me)CH$_2$CH$_2$SMe | General Procedure F; (#B1) | Method D*; 1.5 mg; 67% |
| #B83 | OH | (3-(methylamino)benzylamide) | H$_2$N-CH$_2$-C$_6$H$_4$-NHMe | General Procedure F; (#B1) | Method D*; 8.4 mg; 40% |
| #B84 | OH | (4-amino-2-fluorobenzylamide) | H$_2$N-CH$_2$-C$_6$H$_3$(F)-NH$_2$ | General Procedure F; (#B1) | Method D*; 9 mg; 40% |
| #B85 | OH | (4-amino-3-fluorobenzylamide) | H$_2$N-CH$_2$-C$_6$H$_3$(F)-NH$_2$ | General Procedure F; (#B1) | Method D*; 14.6 mg; 69% |
| #B86 | OH | (trans-4-(dimethylamino)cyclohexylamide) | H$_2$N-C$_6$H$_{10}$-NMe$_2$ | General Procedure B$^1$; (#B1) | Method E; 5.9 mg; 22% |
| #B87 | H | (trans-4-(dimethylamino)cyclohexylamide) | H$_2$N-C$_6$H$_{10}$-NMe$_2$ | General Procedure B$^1$; (#B2) | Method A; 14 mg; 56% |
| #B88 | OH | (4-amino-3-trifluoromethylbenzylamide) | H$_2$N-CH$_2$-C$_6$H$_3$(CF$_3$)-NH$_2$ | General Procedure F; (#B1) | Method D*; 17.7 mg; 77% |
| #B89 | OH | (3-aminobenzylamide) | H$_2$N-CH$_2$-C$_6$H$_4$-NH$_2$ | General Procedure F; (#B1) | Method D*; 9.6 mg; 48% |

TABLE 1-continued

Preparation Details for Examples #B82-#B108

| EX# | R$^{1'}$ | R$^{2'}$ | Starting Amine | Method of Preparation; Non-commercial Starting Materials | Purification Method; Amount made; Yield |
|---|---|---|---|---|---|
| #B90 | H | | | General Procedure B$^2$; (#B2) | Method A; 17 mg; 29% |
| #B91 | OH | | | General Procedure D; (#B1) | Method D*; 19 mg; 63% |
| #B92 | OH | | | General Procedure D; (#B1) | Method D*; 11.2 mg; 53% |
| #B93 | OH | | | General Procedure D; (#B1) | Method D*; 9.6 mg; 33% |
| #B94 | OH | | | General Procedure D; (#B1) | Method D*; 9.7 mg; 33% |
| #B95 | H | | | General Procedure E; (#NP2) | Method D*; 1.6 mg; 3.7% |
| #B96 | H | | | General Procedure D; (#B2) | Method D*; 18.3 mg; 60% |
| #B97 | H | | | General Procedure D; (#B2) | Method D*; 15.3 mg; 53% |
| #B98 | H | | | General Procedure D; (#B2) | Method D*; 14.7 mg; 49% |

TABLE 1-continued

Preparation Details for Examples #B82-#B108

| EX# | R$^{1'}$ | R$^{2'}$ | Starting Amine | Method of Preparation; Non-commercial Starting Materials | Purification Method; Amount made; Yield |
|---|---|---|---|---|---|
| #B99 | H | -NH-C6H4-SO2-NHMe | H2N-CH2-C6H4-SO2-NHMe | General Procedure D; (#B2) | Method D*; 16.4 mg; 55% |
| #B100 | H | -NH-CH2-C6H4-NH2 | H2N-CH2-C6H4-NH2 | General Procedure D; (#B2) | Method D*; 2.0 mg; 8 % |
| #B101 | H | -NH-CH2-C6H5 | H2N-CH2-C6H5 | General Procedure D; (#B2) | Method D* 5.7 mg; 22 % |
| #B102 | H | -N(Me)-CH2CH2-SMe | HN(Me)-CH2CH2-SMe | General Procedure E; (#NP2) | Method D*; 20 mg; 42 % |
| #B103 | H | -NH-CH2CH2-S-Me | H2N-CH2CH2-S-Me | General Procedure E; (#NP2) | Method A 26 mg; 68% |
| #B104 | H | -NH-CH2CH2-S(O)2-Me | H2N-CH2CH2-S(O)2-Me | General Procedure B; (#B2) | Method A 11.3 mg; 58% |
| #B105 | OH | -NH-(CH2)4-COOH | H2N-(CH2)4-COOH | General Procedure A; (#B1) | Method A; 14 mg; 65% |
| #B106 | OH | -NH-CH2CH2-O-CH2CH2-O-CH2CH2-COOH | H2N-CH2CH2-O-CH2CH2-O-CH2CH2-COOH | General Procedure B; (#B1) | Method A$^3$ 15.3 mg; 63% |
| #B107 | H | -NH-CH2CH2-O-CH2CH2-O-CH2CH2-COOH | H2N-CH2CH2-O-CH2CH2-O-CH2CH2-COOH | General Procedure B; (#B2) | Method A; 32 mg; 66% |

TABLE 1-continued

Preparation Details for Examples #B82-#B108

| EX# | R[1'] | R[2'] | Starting Amine | Method of Preparation; Non-commercial Starting Materials | Purification Method; Amount made; Yield |
|---|---|---|---|---|---|
| #B108 | H | OH | OH | General Procedure B; (#B2) | Method A; 17 mg; 73% |

[1] Amine was dissolved into methanol and free based with excess N,N-diisopropylethylamine. Entire mixture added to reaction.
[2] Starting amine prepared as described in Eur. Pat. Appl. (1996), EP 694536 A1 19960131
[3] HPL C fractions were neutralized with ammonia hydroxide and then lyophilized

TABLE 2

Characterization data for Examples #B82-#B108

| EX# | Mass spectrum: LC-MS or HPLC observed m/z and retention time in minutes | IUPAC Name |
|---|---|---|
| #B82 | HPLC (Protocol G); m/z 623.6 [M + H]+; (2.56 minutes) | (2S,3Z)-5-{[(2R,3R,5S,6S)-6-{(2E,4E)-5-[(3R,4R,5R,7S)-4-hydroxy-7-(2-{methyl[2-(methylsulfanyl)ethyl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B83 | HPLC (Protocol B); m/z 654.6 [M + H]+; (1.91 minutes) | (2S,3Z)-5-{[(2R,3R,5S,6S)-6-{(2E,4E)-5-[(3R,4R,5R,7S)-4-hydroxy-7-(2-{[3-(methylamino)benzyl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B84 | HPLC (Protocol B); m/z 658.6 [M + H]+; (2.29 minutes) | (2S,3Z)-5-{[(2R,3R,5S,6S)-6-{(2E,4E)-5-[(3R,4R,5R,7S)-7-{2-[(4-amino-2-fluorobenzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B85 | HPLC (Protocol B); m/z 658.34 [M + H]+; (2.35 minutes) | (2S,3Z)-5-{[(2R,3R,5S,6S)-6-{(2E,4E)-5-[(3R,4R,5R,7S)-7-{2-[(4-amino-3-fluorobenzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B86 | HPLC (Protocol G); m/z 660.65 [M + H]+; (1.96 minutes) | (2S,3Z)-5-{[(2R,3R,5S,6S)-6-{(2E,4E)-5-[(3R,4R,5R,7S)-7-(2-{[trans-4-(dimethylamino)cyclohexyl]amino}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B87 | HPLC (Protocol A[4]); (7.036 minutes); LCMS (Protocol D); m/z 644.9 [M + H]+; (0.65 minutes) | (2S,3Z)-5-{[(2R,3R,5S,6S)-6-{(2E,4E)-5-[(3S,5S,7S)-7-(2-{[trans-4-(dimethylamino)cyclohexyl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B88 | HPLC (Protocol B); m/z 708.66 [M + H]+; (3.41 minutes) | (2S,3Z)-5-{[(2R,3R,5S,6S)-6-{(2E,4E)-5-[(3R,4R,5R,7S)-7-(2-{[4-amino-3-(trifluoromethyl)benzyl]amino}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B89 | HPLC (Protocol B); m/z 640.62 [M + H]+; (1.89 minutes) | (2S,3Z)-5-{[(2R,3R,5S,6S)-6-{(2E,4E)-5-[(3R,4R,5R,7S)-7-{2-[(3-aminobenzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |

TABLE 2-continued

Characterization data for Examples #B82-#B108

| EX# | Mass spectrum: LC-MS or HPLC observed m/z and retention time in minutes | IUPAC Name |
|---|---|---|
| #B90 | HPLC (Protocol A[A]); (6.892 minutes); LCMS (Protocol D); m/z 644.2 [M + H]+; (0.68 minutes) | (2S,3Z)-5-{[(2R,3R,5S,6S)-6-{(2E,4E)-5-[(3S,5S,7S)-7-(2-{[cis-4-(dimethylamino)cyclohexyl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B91 | HPLC (Protocol B); m/z 746.5 [M + H]+; (2.79 minutes) | (2S,3Z)-5-{[(2R,3R,5S,6S)-6-{(2E,4E)-5-[(3R,4R,5R,7S)-7-(2-{[4-(dimethylsulfamoyl)benzyl](methyl)amino}-2-oxoethyl)-4-hydroxy-1,6-dioxaspiro[2.5]oct-5-yl]-3-methylpenta-2,4-dien-1-yl}-2,5-dimethylahydro-2H-pyran-3-yl]amino}-5-oxopent-3-en-2-yl acetate |
| #B92 | HPLC (Protocol B); m/z 658.62 [M + H]+; (1.98 minutes) | (2S,3Z)-5-{[(2R,3R,5S,6S)-6-{(2E,4E)-5-[(3R,4R,5R,7S)-7-{2-[(5-amino-2-fluorobenzyl)amino]-2-oxoethyl}-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B93 | HPLC (Protocol B); m/z 732.4 [M + H]+; (2.65 minutes) | (2S,3Z)-5-{[(2R,3R,5S,6S)-6-{(2E,4E)-5-[(3R,4R,5R,7S)-7-(2-{[4-(dimethylsulfamoyl)benzyl]amino}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B94 | HPLC (Protocol B); m/z 718.4 [M + H]+; (2.48 minutes) | (2S,3Z)-5-{[(2R,3R,5S,6S)-6-{(2E,4E)-5-[(3R,4R,5R,7S)-4-hydroxy-7-(2-{[4-(methylsulfamoyl)benzyl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B95 | HPLC (Protocol K); (5.27 minutes); m/z 563.4 [M + H]+ | ((2S,3Z)-5-{[(2R,3R,5S,6S)-6-{(2E,4E)-5-[(3S,5S,7S)-7-{2-[(2-hydroxyethyl)amino]-2-oxoethy}l-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B96 | HPLC (Protocol B); m/z 730.5 [M + H]+; (3.17 minutes) | (2S,3Z)-5-{[(2R,3R,5S,6S)-6-{(2E,4E)-5-[(3S,5S,7S)-7-(2-{[4-(dimethylsulfamoyl)benzyl](methyl)amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B97 | HPLC (Protocol B); m/z 688.5 [M + H]+; (2.67 minutes) | (2S,3Z)-5-{[(2R,3R,5S,6S)-2,5-dimethyl-6-{(2E,4E)-3-methyl-5-[(3S,5S,7S)-7-{2-oxo-2-[(4-sulfamoylbenzyl)amino]ethyl}-1,6-dioxaspiro[2.5]oct-5-yl]penta-2,4-dien-1-yl}tetrahydro-2H-pyran-3-yl]amino}-5-oxopent-3-en-2-yl acetate |
| #B98 | HPLC (Protocol B); m/z 716.5 [M + H]+; (2.97 minutes) | (2S,3Z)-5-{[(2R,3R,5S,6S)-6-{(2E,4E)-54(3S,5S,7S)-7-(2-{[4-(dimethylsulfamoyl)benzyl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B99 | HPLC (Protocol B); m/z 702.4 [M + H]+; (2.79 minutes) | (2S,3Z)-5-{[(2R,3R,5S,6S)-2,5-dimethyl-6-{(2E,4E)-3-methyl-5-[(3S,5S,7S)-7-(2-{[2-(methylsulfonyl)ethyl]amino}-2-oxoethyl)-1,6-dioxaspiro[2.5]oct-5-yl]penta-2,4-dien-1-yl}tetrahydro-2H-pyran-3-yl]amino}-5-oxopent-3-en-2-yl acetate |
| #B100 | HPLC (Protocol B); m/z 624.4 [M + H]+; (2.10 minutes) | (2S,3Z)-5-{[(2R,3R,5S,6S)-6-{(2E,4E)-5-[(3S,5S,7S)-7-{2-[(4-aminobenzyl)amino]-2-oxoethyl}-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B101 | HPLC (Protocol B); m/z 609.4 [M + H]+; (3.1 minutes) | (2S,3Z)-5-({(2R,3R,5S,6S)-6-[(2E,4E)-5-{(3S,5S,7S)-7-[2-(benzylamino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate |
| #B102 | HPLC (Protocol K); (6.6 minutes); m/z 607.5 [M + H]+ | (2S,3Z)-5-{[(2R,3R,5S,6S)-2,5-dimethyl-6-{(2E,4E)-3-methyl-5-[(3S,5S,7S)-7-(2-{methyl[2-(methylsulfanyl)ethyl]amino}-2-oxoethyl)-1,6-dioxaspiro[2.5]oct-5-yl]penta-2,4-dien-1-yl}tetrahydro-2H-pyran-3-yl]amino}-5-oxopent-3-en-2-yl acetate |
| #B103 | LCMS (Protocol D); m/z 593.1 [M + H]+; (0.88 minutes) | (2S,3Z)-5-{[(2R,3R,5S,6S)-2,5-dimethyl-6-{(2E,4E)-3-methyl-5-[(3S,5S,7S)-7-(2-{methyl[2-(methylsulfanyl)ethyl]amino}-2-oxoethyl)-1,6-dioxaspiro[2.5]oct-5-yl]penta-2,4-dien-1-yl}tetrahydro-2H-pyran-3-yl]amino}-5-oxopent-3-en-2-yl acetate |
| #B104 | LCMS (Protocol D) m/z 625.5 [M + H]+; (0.80 minutes) | (2S,3Z)-5-{[(2R,3R,5S,6S)-2,5-dimethyl-6-{(2E,4E)-3-methyl-5-{(3S,5S,7S)-7-(2-{[2-(methylsulfonyl)ethyl]amino}-2-oxoethyl)-1,6-dioxaspiro[2.5]oct-5-yl]penta-2,4-dien-1-yl}tetrahydro-2H-pyran-3-yl]amino}-5-oxopent-3-en-2-yl acetate |

TABLE 2-continued

Characterization data for Examples #B82-#B108

| EX# | Mass spectrum: LC-MS or HPLC observed m/z and retention time in minutes | IUPAC Name |
|---|---|---|
| #B105 | HPLC (Protocol A[4]); (5.75 minutes); LCMS (Protocol L); m/z 649.6 [M + H]+; (2.52 minutes) | 6-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)hexanoic acid |
| #B106 | HPLC (Protocol A[4]); (7.514 minutes); LCMS (Protocol D); m/z 695.2 [M + H]+; (0.74 minutes) | 3-{2-[2-({[(3R,5S,7R,8R)-7-{(1E,3E)-5-[(2S,3S,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-8-hydroxy-1,6-dioxaspiro[2.5]octyl]acetyl}amino)ethoxy]ethoxy} propanoic acid |
| #B107 | HPLC (Protocol A[4]); (8.084 minutes); LCMS (Protocol D); m/z 679.2 [M + H]+; (0.79 minutes) | 3-{2-[2-({[(3S,5S,7S)-7-{(1E,3E)-5-[(2S,3S,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)ethoxy]ethoxy}propanoic acid |
| #B108 | HPLC (Protocol A[4]); (7.603 minutes); LCMS (Protocol D); m/z 633.1 [M + H]+; (0.81 minutes) | 6-({[(3S,5S,7S)-7-{(1E,3E)-5-[(2S,3S,5R,6R)-5-{[(2Z,4S)-4-acetoxypent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)hexanoic acid |

TABLE 3

Preparation of Payload-Linkers #B109-#B117

| Ex. # | R1' | R2' | Starting Material | Method of Preparation | Purification Method; Amount made; Yield |
|---|---|---|---|---|---|
| #B109 | H | pentafluorophenyl ester | NP2 | General Procedure C | Method A; 47 mg; 89% |
| #B110 | OH | 6-aminohexanoic acid pentafluorophenyl ester | #B105 | General Procedure C | Method A; 8.9 mg; 48% |
| #B111 | OH | 6-aminohexanoic acid N-hydroxysuccinimide ester | #B105 | General Procedure A | Method A; 9.0 mg; 70% |

TABLE 3-continued

Preparation of Payload-Linkers #B109-#B117

| Ex. # | R1' | R2' | Starting Material | Method of Preparation | Purification Method; Amount made; Yield |
|---|---|---|---|---|---|
| #B112 | OH | ~NH-CH2CH2-O-CH2CH2-O-CH2CH2-C(O)O-C6F5 | #B106 | General Procedure C[1] | Method A; 9.9 mg; 52% |
| #B113 | H | ~NH-(CH2)4-C(O)O-C6F5 | #B108 | General Procedure C | Method C*; 11 mg; 44% |
| #B114 | H | ~NH-(CH2)4-C(O)O-NHS | #B108 | General Procedure A | Method A; 4.5 mg; 16% |
| #B115 | OH | ~NH-CH2CH2-O-CH2CH2-O-CH2CH2-C(O)O-NHS | #B106 | General Procedure A | Method A; 16 mg; 60% |
| #B116 | H | ~NH-CH2CH2-O-CH2CH2-O-CH2CH2-C(O)O-NHS | #B107 | General Procedure A | Method A; 10.6 mg; 62% |
| #B117 | H | ~NH-CH2CH2-O-CH2CH2-O-CH2CH2-C(O)O-C6F5 | #B107 | General Procedure C | Method C*; 12 mg; 42% |

[1]Reaction was neutralized with TEA before HPLC purification.

TABLE 4

In vitro Cytotoxicity data for Natural products and synthetic analogs

| EX# | N87 IC$_{50}$ (nM) | BT474 IC$_{50}$ (nM) | MDA-MB-361-DYT2 IC$_{50}$ (nM) | MDA-MB-468 IC$_{50}$ (nM) |
|---|---|---|---|---|
| #NP1 | 61.646 | 144.997 | 160.284 | 141.671 |
| #NP2 | 2.51 | 5.12 | 8.496 | 3.388 |
| #NP5 | >100 | >100 | | >100 |
| #NP6 | >100 | >100 | | >100 |
| #NP7 | >100 | >100 | | >100 |
| #NP8 | 0.643 | 1.941 | | 1.351 |
| #NP9 | 74.291 | 65.78 | | 59.246 |
| #NP11 | 3.665 | 3.719 | 4.156 | 1.555 |
| #NP12 | 13.85 | 5.02 | 4.91 | |
| #B4 | >100 | >100 | >100 | >100 |
| #B6 | 5.66 | 16.5 | 25.4 | 7.97 |
| #B7 | 0.344 | 1.12 | 1.88 | |
| #B8 | 10.7 | 14.1 | 25.5 | |
| #B9 | 1.34 | 3.26 | 5.26 | |
| #B10 | 12.1 | 43.5 | 77.5 | |
| #B11 | 1.61 | 3.42 | 6.71 | |
| #B12 | 54.57 | 55.52 | 87.84 | |
| #B13 | 0.99 | 0.68 | 1.93 | |
| #B15 | 0.203 | 0.522 | 0.537 | 0.363 |
| #B16 | 16.8 | 76.1 | >100 | 36.8 |
| #B22 | 4.23 | 1.76 | 7.46 | |
| #B39 | 4.65 | 3.4 | 7.67 | |
| #B40 | 6.76 | 1.86 | 5.84 | |
| #B55 | 0.822 | 0.879 | 1.256 | |
| #B63 | 1.103 | 0.651 | 0.293 | 0.348 |
| #B64 | 24.82 | 5.26 | | 1.38 |
| #B66 | 1.578 | 0.18 | | 0.27 |
| #B71 | 0.451 | 1.076 | 1.362 | |
| #B72 | 0.481 | 0.607 | 1.156 | |
| #B73 | 173.983 | 296.342 | 442.575 | 275.769 |
| #B76 | 330.871 | 340.877 | 884.901 | 271.599 |
| #B79 | 0.423 | 0.723 | 1.313 | |
| #B81 | 70.686 | >100 | >100 | >100 |
| #B82 | 0.12 | 0.288 | 0.251 | |
| #B83 | 1.05 | 1.45 | 2.59 | |
| #B84 | 2.54 | 2.53 | 8.27 | |
| #B85 | 1.56 | 1.47 | 5.5 | |
| #B86 | 14 | 20.1 | 73.3 | |
| #B87 | 0.744 | 1.21 | 3.47 | |
| #B88 | 0.73 | 1.8 | 2.96 | |
| #B89 | 1.91 | 3.56 | 7.99 | |
| #B90 | 0.87 | 1.26 | 3.9 | |
| #B91 | 0.783 | 3.02 | 3.78 | |
| #B92 | 1.5 | 2.28 | 6.18 | |
| #B93 | 0.647 | 2.27 | 3.96 | |
| #B94 | 4.9 | 18.6 | 37.4 | |
| #B95 | 1.06 | 1.28 | 11.1 | |
| #B96 | 12.3 | 22.9 | 31.5 | |
| #B97 | 5.09 | 8.83 | 41.6 | |
| #B98 | 2.55 | 5.75 | 8.7 | |
| #B99 | 3.28 | 7.87 | 21.5 | |
| #B100 | 5.05 | 10.6 | 16.9 | |
| #B101 | 10.4 | 25.6 | 34.8 | |
| #B102 | 7.79 | 10.7 | 32.9 | |
| #B103 | 1.6 | 4.03 | 4.25 | |
| #B104 | 1.41 | 4.02 | 9.13 | |
| #B129 | >100.000 | >100.000 | >100.000 | |
| #B130 | 2.984 | 1.5 | 4.503 | |
| #B134 | 1.799 | 1.181 | 2.023 | |
| #B136 | 90.149 | 25.451 | >100.000 | |
| #B137 | 5.589 | 1.796 | 10.266 | |
| #B139 | 6.511 | 5.491 | 13.366 | |
| #B140 | 1.012 | 0.517 | 0.632 | |
| #B141 | 10.981 | 10.864 | 12.75 | |
| #B142 | 11.228 | | 55.54 | |
| #B143 | 2.428 | | 9.508 | |
| #B144 | 0.982 | | 6.1 | |
| #B145 | 0.408 | | 2.026 | |
| #B147 | 9.918 | 6.812 | 17.166 | |
| #B148 | 47.42 | 40.779 | >100.000 | 64.434 |
| #B149 | >100.000 | | >100.000 | |
| #B173 | 6.377 | 3.642 | 29.134 | 7.851 |
| #B177 | 1.609 | | 5.646 | |
| #B179 | 0.299 | | 1.286 | |
| #B209 | 60.555 | | >100.000 | |
| #B229 | 3.597 | | 9.143 | |
| #B235 | 16.421 | | 36.822 | |
| #B240 | 9.794 | | 5.054 | |
| #B241 | 21.341 | | 43.617 | |
| #B242 | 0.570 | | 3.761 | |
| #B264 | >100.000 | | >100.000 | |
| #B265 | 10.200 | | 8.669 | |
| #B266 | 28.389 | | >100.000 | |
| #B267 | 3.438 | | 23.780 | |
| #B271 | >100.000 | | >100.000 | |
| #B272 | >100.000 | | >100.000 | |
| #B273 | 600.376 | | >1000.000 | |
| #B275 | 5.335 | | 22.231 | |
| #B284 | 1.301 | | 2.032 | |
| #B285 | 7.608 | | 11.666 | |
| #B286 | 0.387 | | 1.109 | |

TABLE 5

Characterization data for Examples #B109-#B117

| Ex# | Mass spectrum: LC-MS or HPLC observed m/z and retention time in minutes | IUPAC Name |
|---|---|---|
| #B109 | HPLC (Protocol E); (8.993 minutes); LCMS (Protocol D); m/z 686.2 [M + H]$^+$; (1.11 minutes) | pentafluorophenyl [(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetate |
| #B110 | HPLC (Protocol A$^A$); (9.930 minutes); LCMS (Protocol D); m/z 815.2 [M + H]$^+$; (0.99 minutes) | pentafluorophenyl 6-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]oct-5-yl]acetyl}amino)hexanoate |
| #B111 | HPLC (Protocol A$^B$); (11.19 minutes); LCMS (Protocol D); m/z 746.2 [M + H]$^+$; (0.80 minutes) | (2S,3Z)-5-({(2R,3R,5S,6S)-6-[(2E,4E)-5-{(3R,4R,5R,7S)-7-[2-({6-[(2,5-dioxopyrrolidin-1-yl)oxy]-6-oxohexyl}amino)-2-oxoethyl]-4-hydroxy-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate |

TABLE 5-continued

Characterization data for Examples #B109-#B117

| Ex# | Mass spectrum: LC-MS or HPLC observed m/z and retention time in minutes | IUPAC Name |
| --- | --- | --- |
| #B112 | HPLC (Protocol A[A]); (9.564 minutes); LCMS (Protocol D); m/z 883.1 [M + Na]+; (0.94 minutes) | pentafluorophenyl 3-{2-[2-({[(3R,5S,7R,8R)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-8-hydroxy-1,6-dioxaspiro[2.5]octyl]acetyl}amino)ethoxy]ethoxy}propanoate |
| #B113 | HPLC (Protocol A[A]); (10.652 minutes); LCMS (Protocol D); m/z 799.1 [M + H]+; (1.03 minutes) | pentafluorophenyl 6-({[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)hexanoate |
| #B114 | LCMS (Protocol D); m/z 730.3 [M + H]+; (0.88 minutes) | (2S,3Z)-5-({(2R,3R,5S,6S)-6-[(2E,4E)-5-{(3S,5S,7S)-7-[2-({6-[(2,5-dioxopyrrolidin-1-yl)oxy]-6-oxohexyl}amino)-2-oxoethyl]-1,6-dioxaspiro[2.5]oct-5-yl}-3-methylpenta-2,4-dien-1-yl]-2,5-dimethyltetrahydro-2H-pyran-3-yl}amino)-5-oxopent-3-en-2-yl acetate |
| #B115 | HPLC (Protocol A[A]); (8.082 minutes); LCMS (Protocol D); m/z 792.1 [M + H]+; (0.81 minutes) | (2S,3Z)-5-{[(2R,3R,5S,6S)-6-{(2E,4E)-5-[(3R,4R,5R,7S)-7-(2-{[2-(2-{3-[(2,5-dioxopyrrolidin-1-yl)oxy]-3-oxopropoxy}ethoxy)ethyl]amino}-2-oxoethyl)-4-hydroxy-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B116 | HPLC (Protocol A[A]); (8.580 minutes); LCMS (Protocol D); m/z 776.1 [M + H]+; (0.83 minutes) | (2S,3Z)-5-{[(2R,3R,5S,6S)-6-{(2E,4E)-5-[(3S,5S,7S)-7-(2-{[2-(2-{3-[(2,5-dioxopyrrolidin-1-yl)oxy]-3-oxopropoxy}ethoxy)ethyl]amino}-2-oxoethyl)-1,6-dioxaspiro[2.5]oct-5-yl]-3-methylpenta-2,4-dien-1-yl}-2,5-dimethyltetrahydro-2H-pyran-3-yl]amino}-5-oxopent-3-en-2-yl acetate |
| #B117 | HPLC (Protocol A[A]); (10.282 minutes); LCMS (Protocol D); m/z 845.9 [M + H]+; (1.0 minutes) | pentafluorophenyl 3-{2-[2-({[(3S,5S,7S)-7-{(1E,3E)-5-[(2S,3S,5R,6R)-5-{[(2Z,4S)-4-(acetyloxy)pent-2-enoyl]amino}-3,6-dimethyltetrahydro-2H-pyran-2-yl]-3-methylpenta-1,3-dien-1-yl}-1,6-dioxaspiro[2.5]oct-5-yl]acetyl}amino)ethoxy]ethoxy}propanoate |

TABLE 6

Structure of ADC and Payload Linkers used to prepare them

| ADC# | Structure | LP used for synthesis of ADC |
|---|---|---|
| ADC1 | 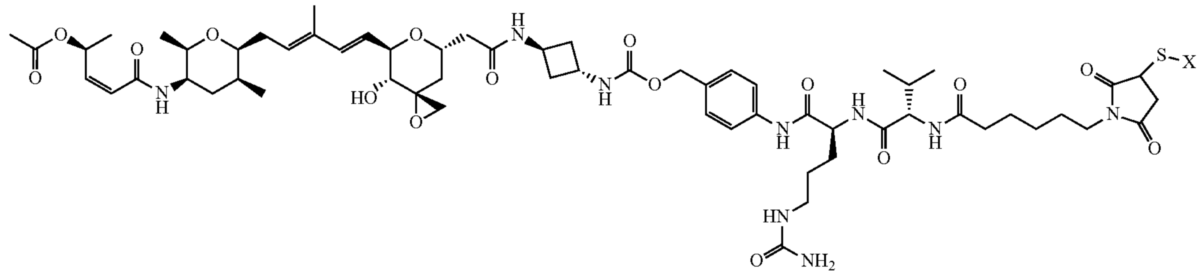 | #B75 |
| ADC2 | 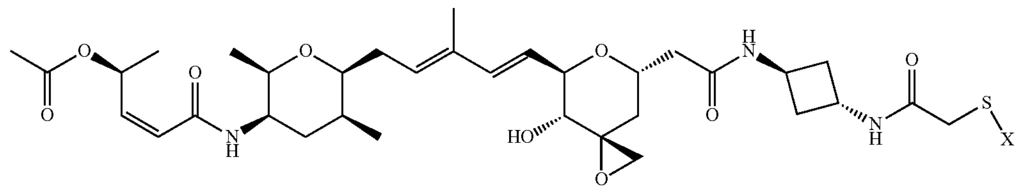 | #B74 |
| ADC3 | 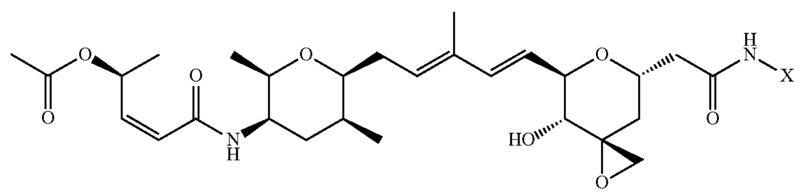 | #B1 |
| ADC4 | 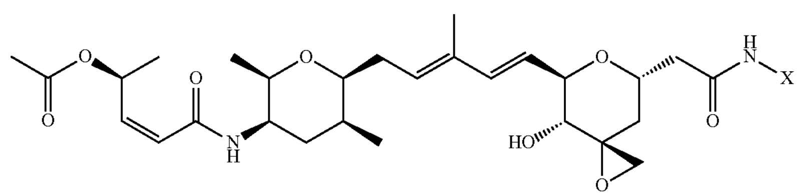 | #B1 |

TABLE 6-continued

Structure of ADC and Payload Linkers used to prepare them

| ADC# | Structure | LP used for synthesis of ADC |
|---|---|---|
| ADC5 | 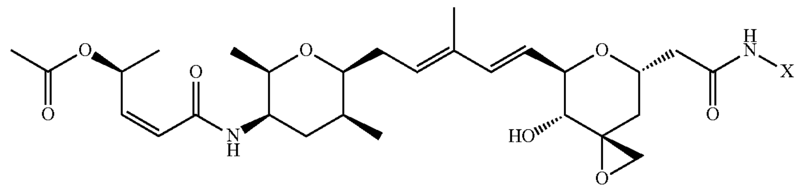 | #B1 |
| ADC6 | 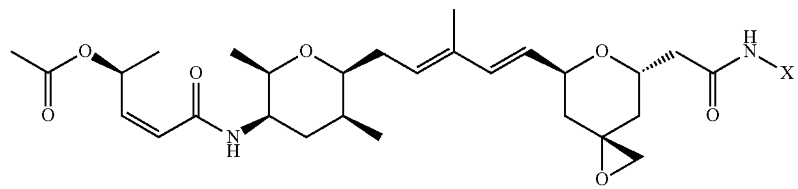 | #B2 |
| ADC7 | 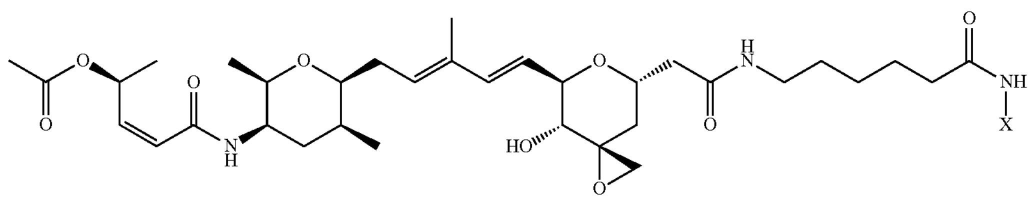 | #B111 |
| ADC8 | 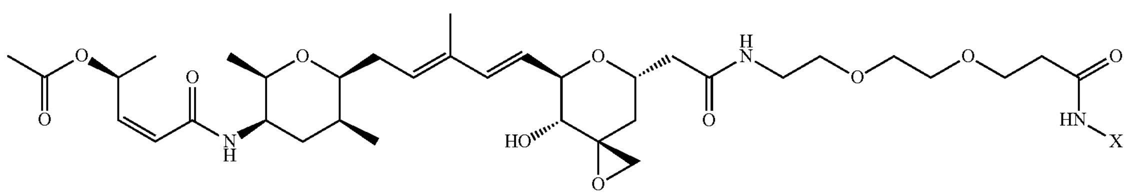 | #B115 |
| ADC9 | 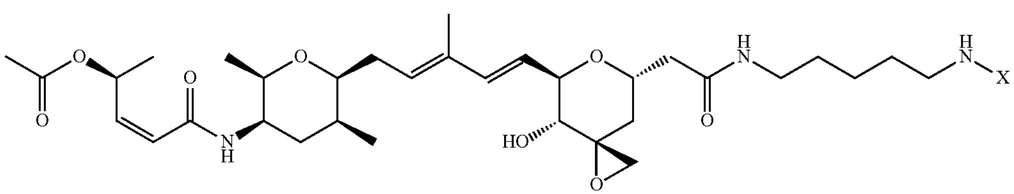 | #B77 |

TABLE 6-continued

Structure of ADC and Payload Linkers used to prepare them

| ADC# | Structure | LP used for synthesis of ADC |
|---|---|---|
| ADC10 | 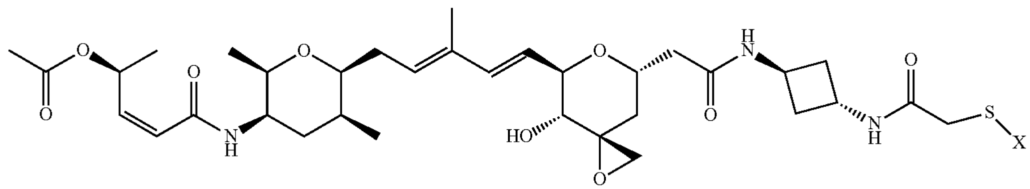 | #B74 |
| ADC11 | 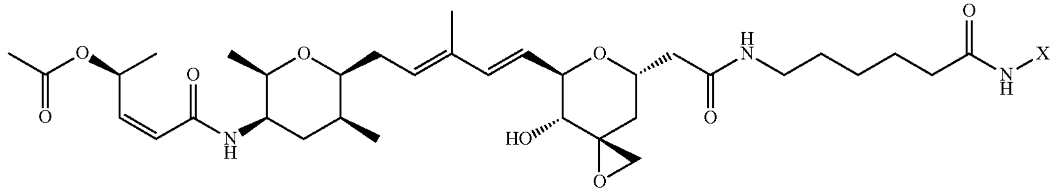 | #B110 |
| ADC12 | 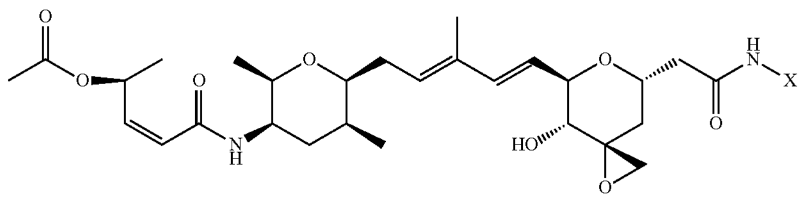 | #B3 |
| ADC13 | 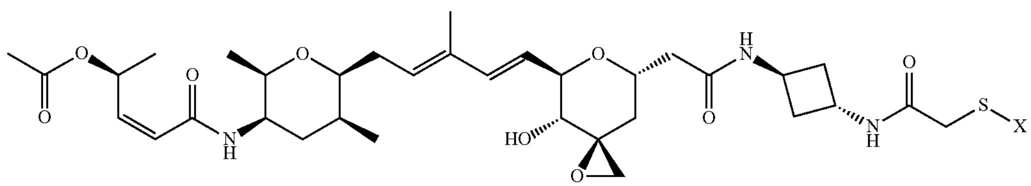 | #B74 |
| ADC14 | 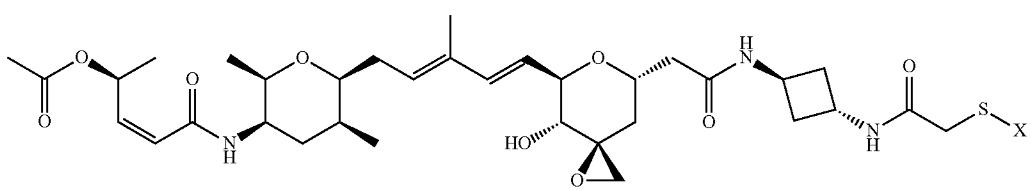 | #B74 |

TABLE 6-continued

Structure of ADC and Payload Linkers used to prepare them

| ADC# | Structure | LP used for synthesis of ADC |
|---|---|---|
| ADC15 | 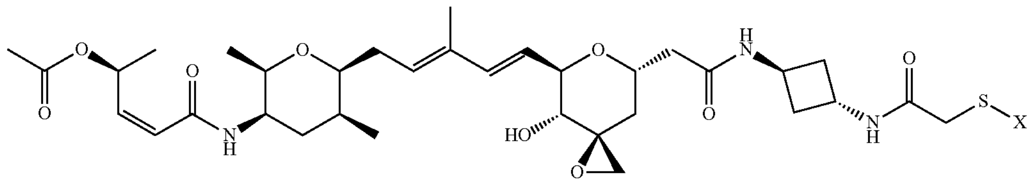 | #B74 |
| ADC16 | 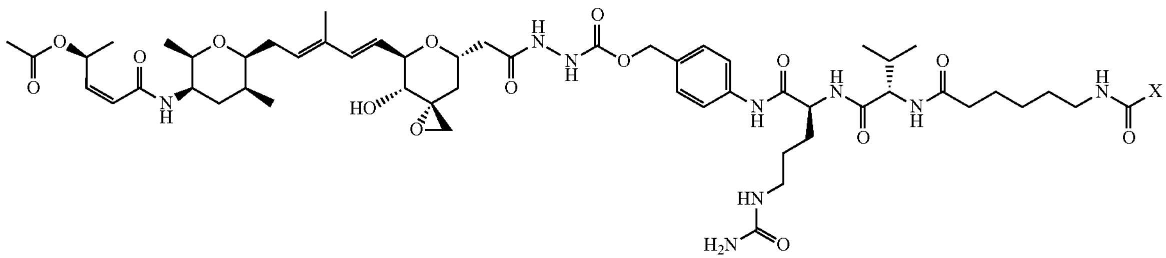 | #B47 |
| ADC17 | 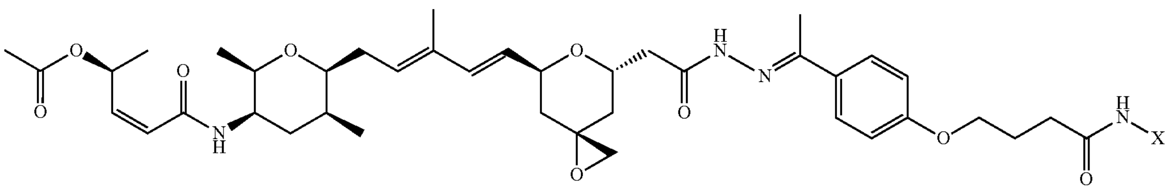 | #B19 |
| ADC18 | 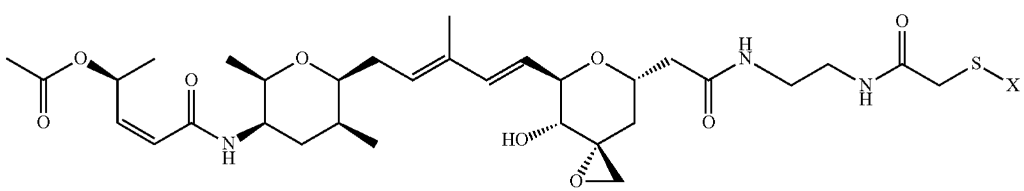 | #B52 |

TABLE 6-continued

Structure of ADC and Payload Linkers used to prepare them

| ADC# | Structure | LP used for synthesis of ADC |
|---|---|---|
| ADC19 | 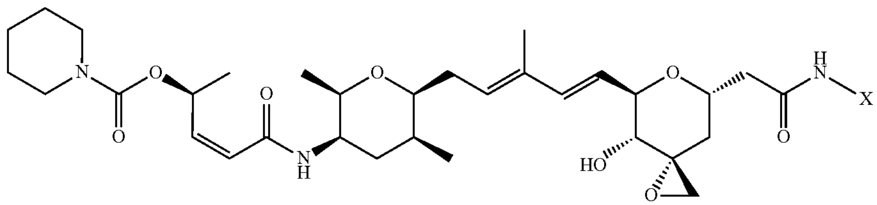 | #B67 |
| ADC20 | 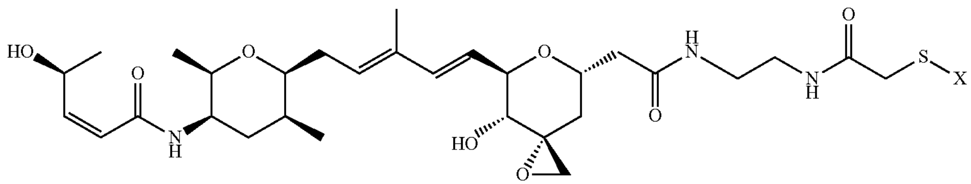 | #B54 |
| ADC21 | 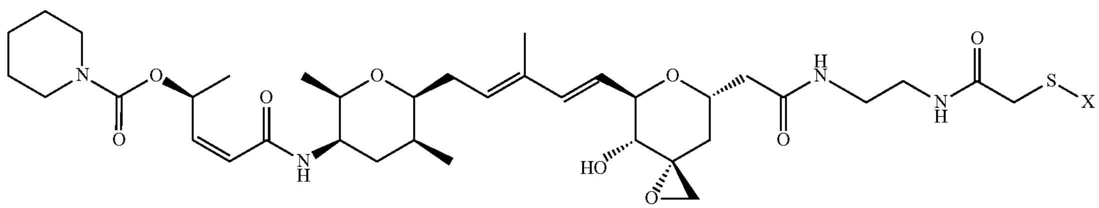 | #B62 |
| ADC22 | 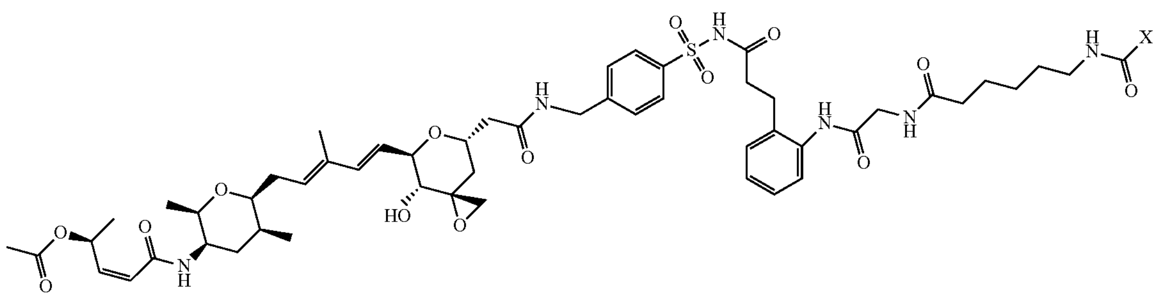 | #B36 |

TABLE 6-continued

Structure of ADC and Payload Linkers used to prepare them

| ADC# | Structure | LP used for synthesis of ADC |
|---|---|---|
| ADC23 | 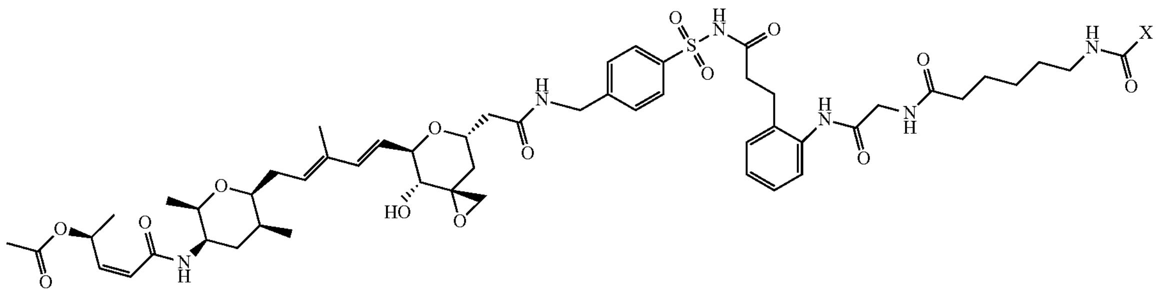 | #B36 |
| ADC24 | 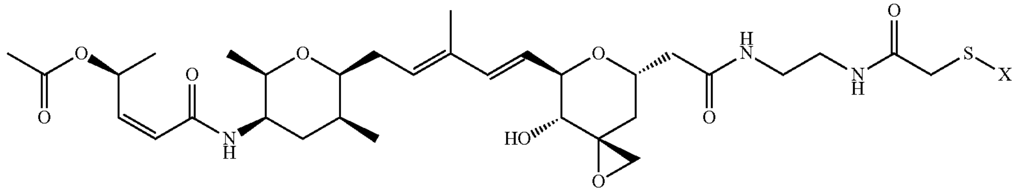 | #B52 |
| ADC25 | 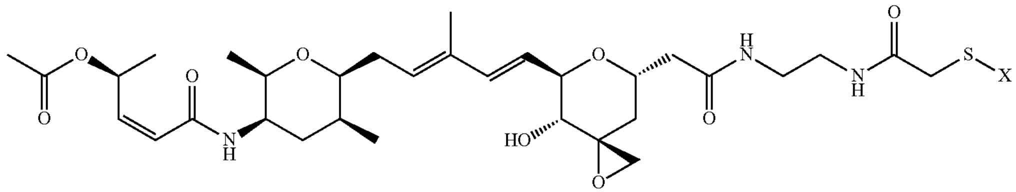 | #B52 |
| ADC26 | 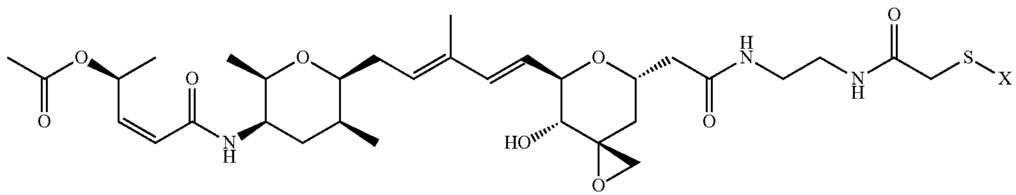 | #B52 |

TABLE 6-continued

Structure of ADC and Payload Linkers used to prepare them

| ADC# | Structure | LP used for synthesis of ADC |
|---|---|---|
| ADC27 | 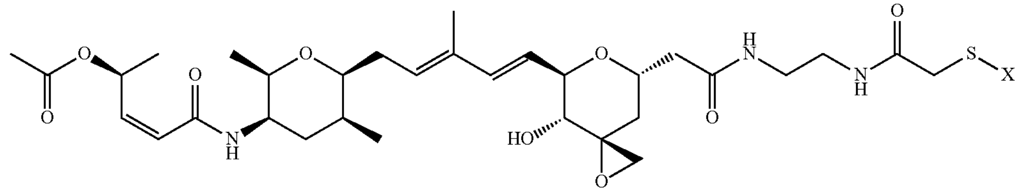 | #B52 |
| ADC28 | 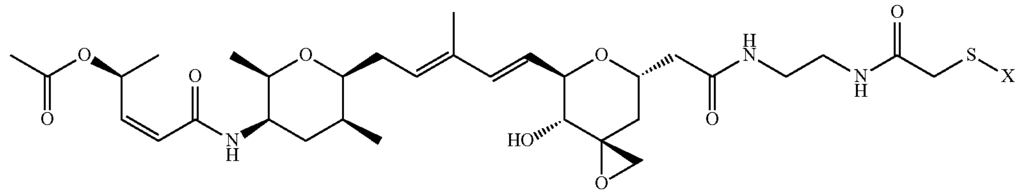 | #B52 |
| ADC29 | 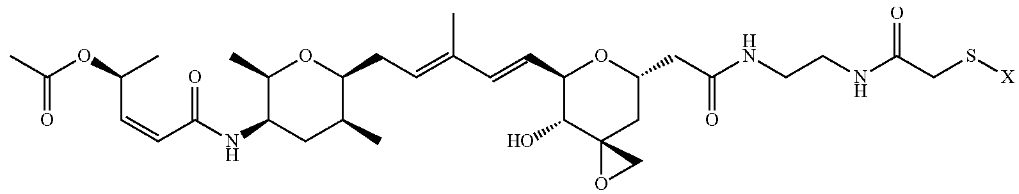 | #B52 |
| ADC30 | 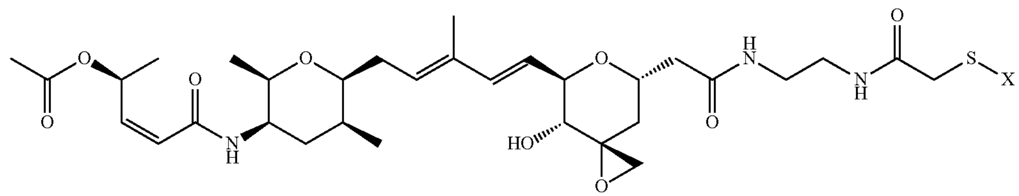 | #B52 |
| ADC31 | 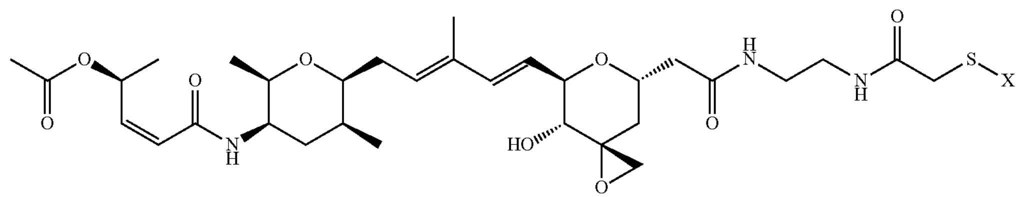 | #B52 |

TABLE 6-continued

Structure of ADC and Payload Linkers used to prepare them

| ADC# | Structure | LP used for synthesis of ADC |
|---|---|---|
| ADC32 | 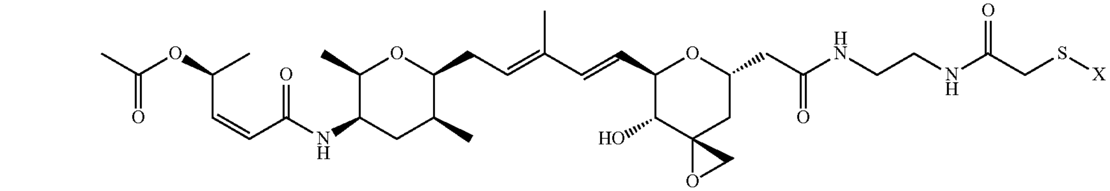 | #B52 |
| ADC33 | 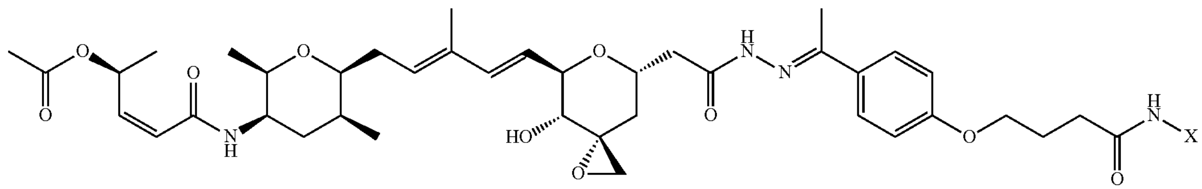 | #B21 |
| ADC34 | 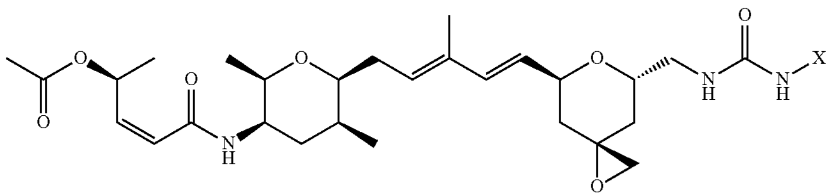 | #B138 |
| ADC35 | 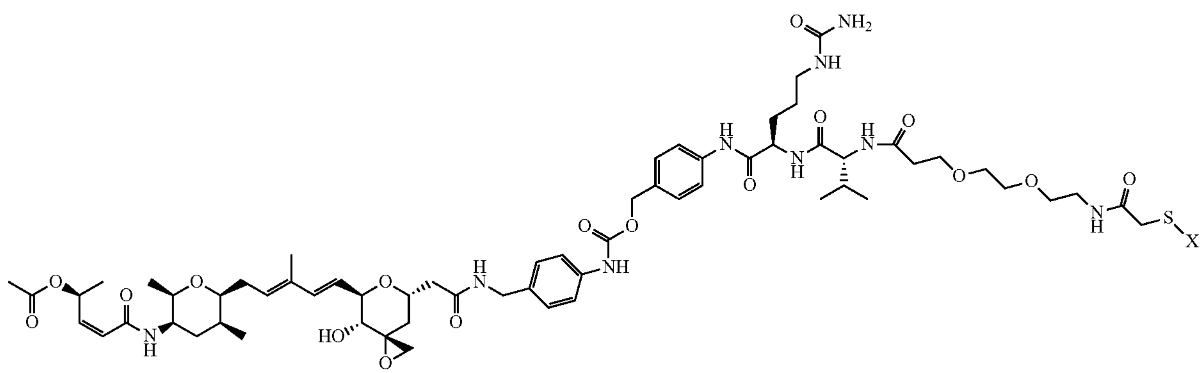 | #B27 |

TABLE 6-continued

Structure of ADC and Payload Linkers used to prepare them

| ADC# | Structure | LP used for synthesis of ADC |
|---|---|---|
| ADC36 | 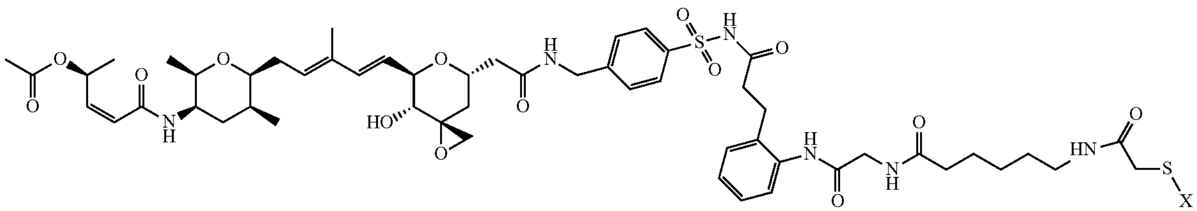 | #B37 |
| ADC37 | 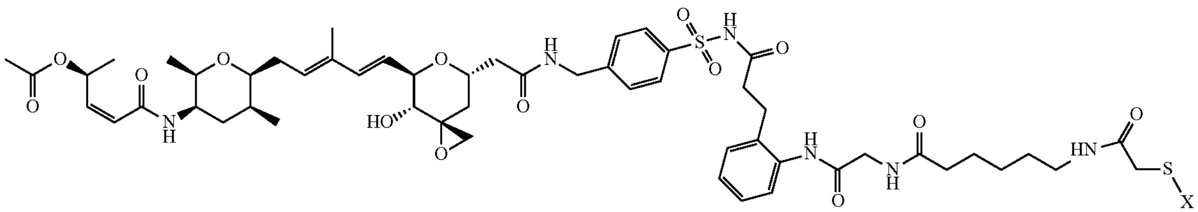 | #B37 |
| ADC38 | 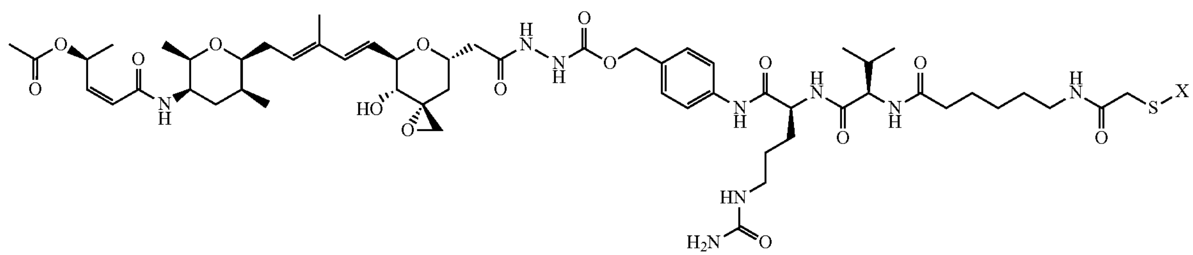 | #B146 |
| ADC39 | 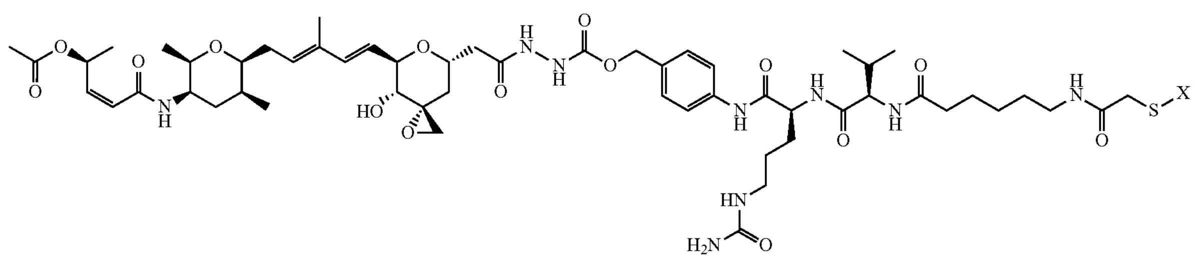 | #B146 |

TABLE 6-continued

Structure of ADC and Payload Linkers used to prepare them

| ADC# | Structure | LP used for synthesis of ADC |
|---|---|---|
| ADC40 | 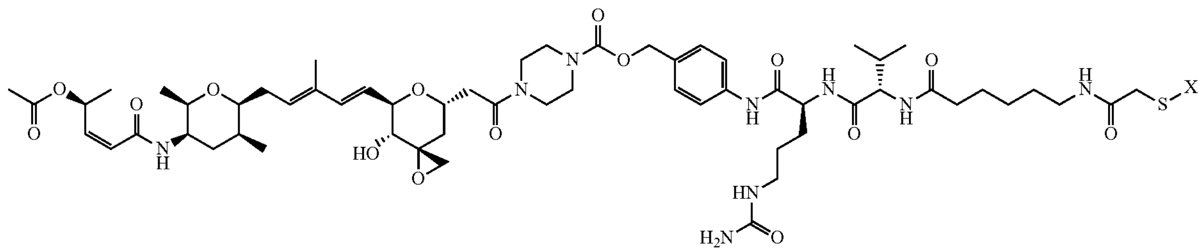 | #B170 |
| ADC41 | 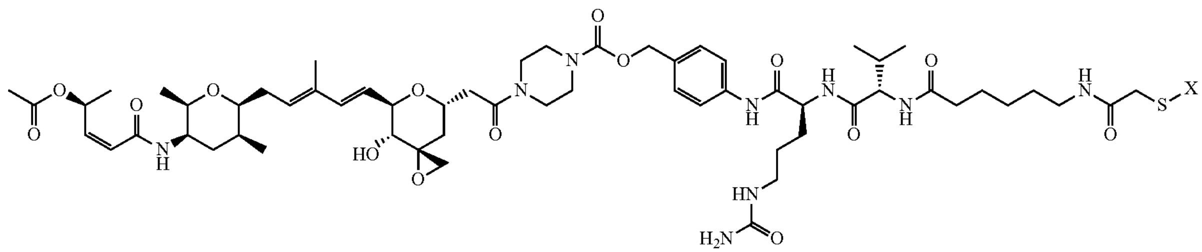 | #B170 |
| ADC42 | 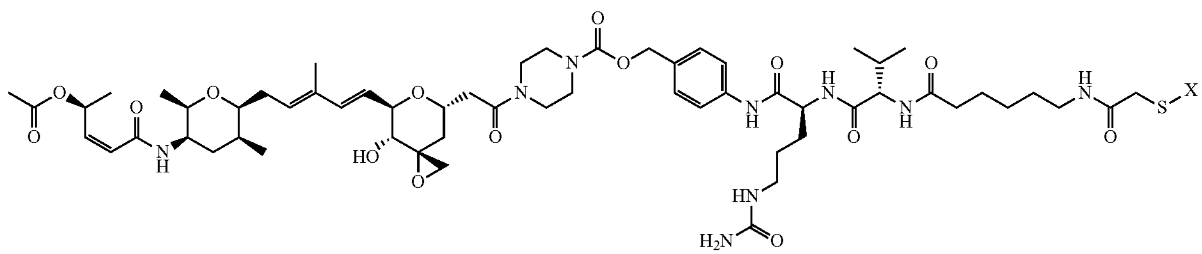 | #B170 |

TABLE 6-continued

Structure of ADC and Payload Linkers used to prepare them

| ADC# | Structure | LP used for synthesis of ADC |
|---|---|---|
| ADC43 | 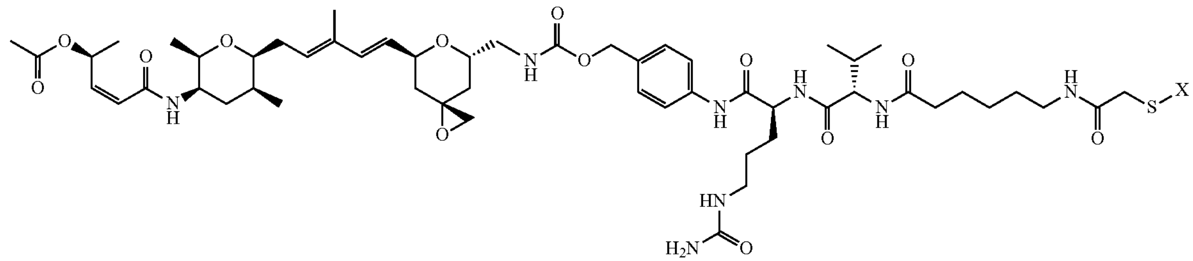 | #B151 |
| ADC44 | 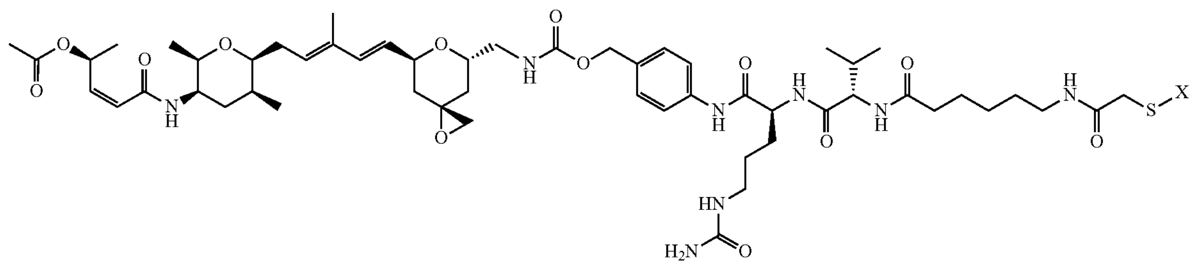 | #B151 |
| ADC45 | 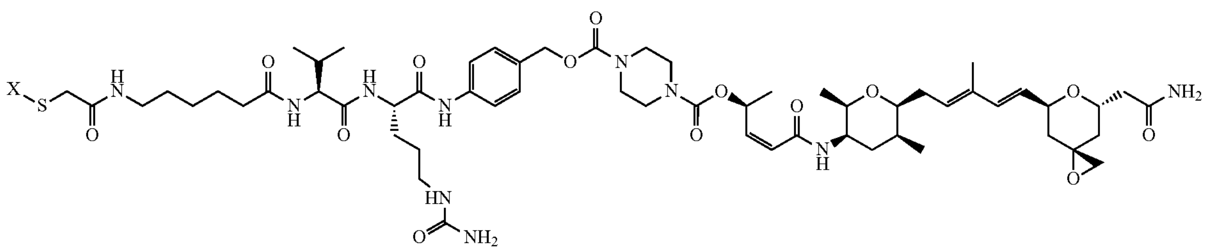 | #B165 |

TABLE 6-continued

Structure of ADC and Payload Linkers used to prepare them

| ADC# | Structure | LP used for synthesis of ADC |
|---|---|---|
| ADC46 | 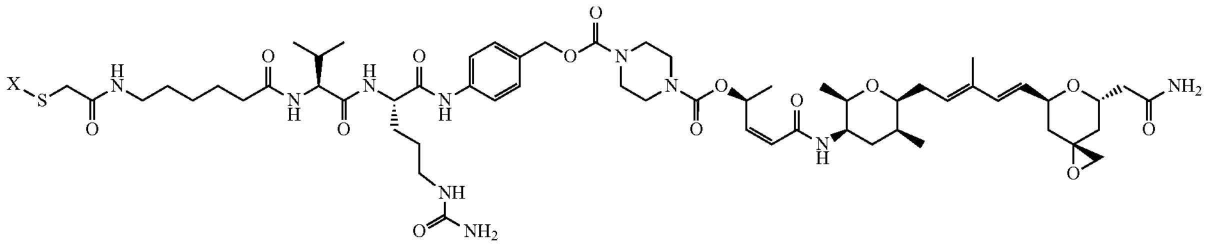 | #B165 |
| ADC47 | 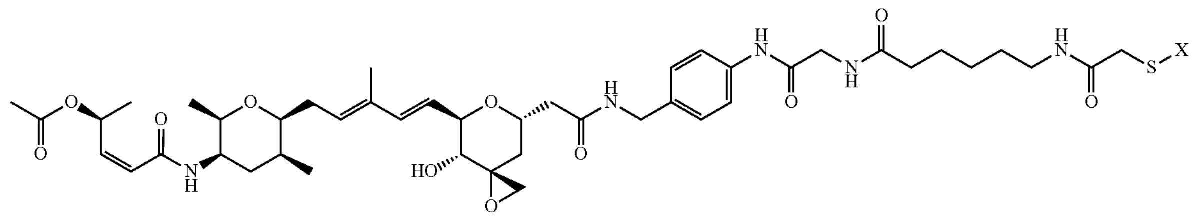 | #B123 |
| ADC48 | 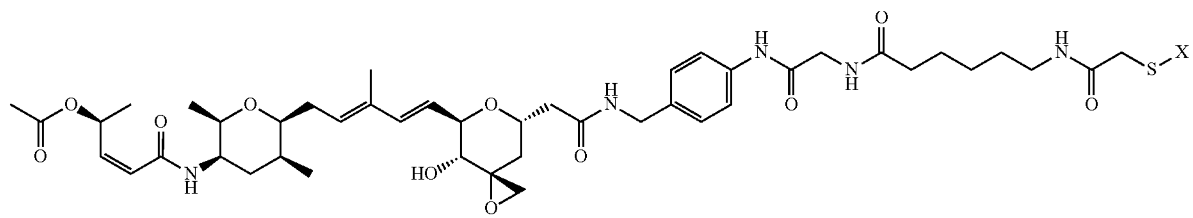 | #B123 |
| ADC49 | 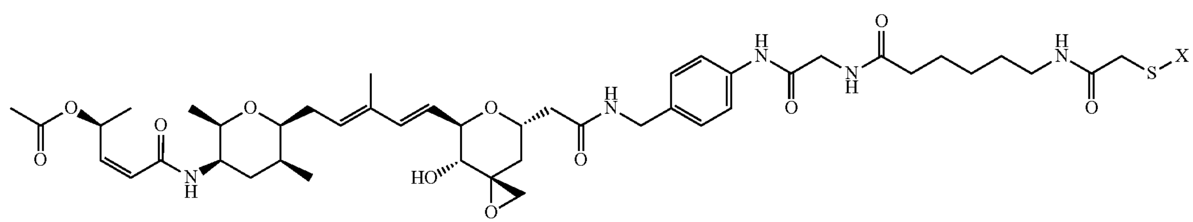 | #B123 |

TABLE 6-continued

Structure of ADC and Payload Linkers used to prepare them

| ADC# | Structure | LP used for synthesis of ADC |
|---|---|---|
| ADC50 | 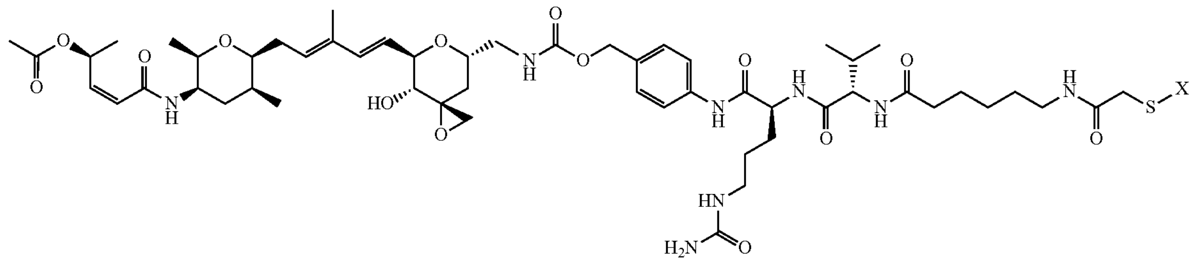 | #B154 |
| ADC51 | 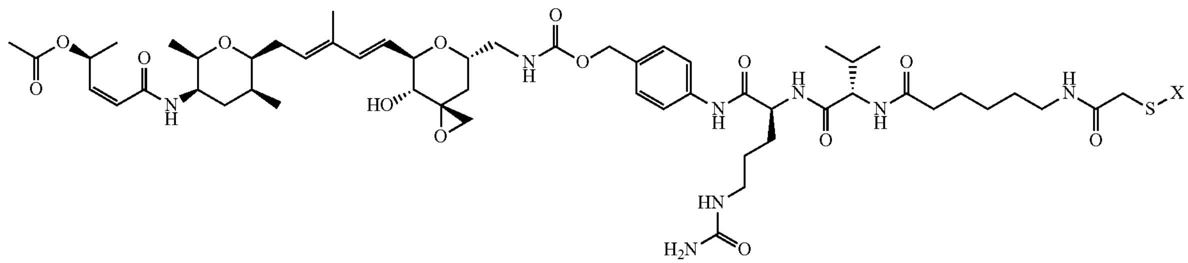 | #B154 |
| ADC52 | 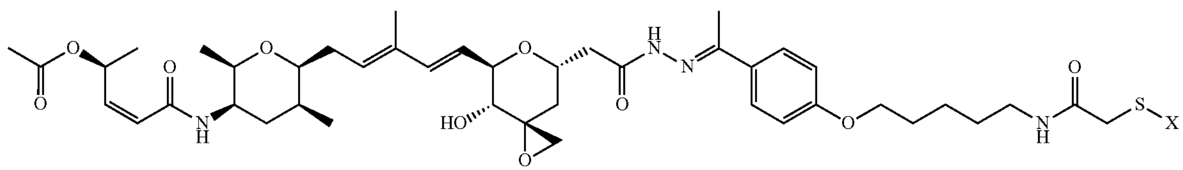 | #B157 |
| ADC53 | 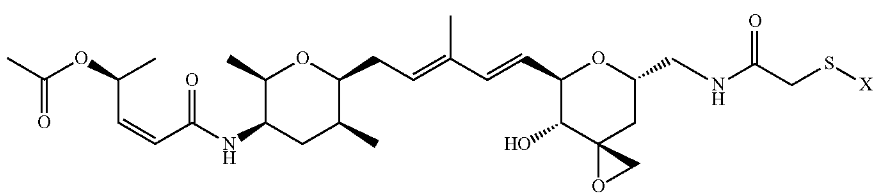 | #B150 |

TABLE 6-continued

Structure of ADC and Payload Linkers used to prepare them

| ADC# | Structure | LP used for synthesis of ADC |
|---|---|---|
| ADC54 | 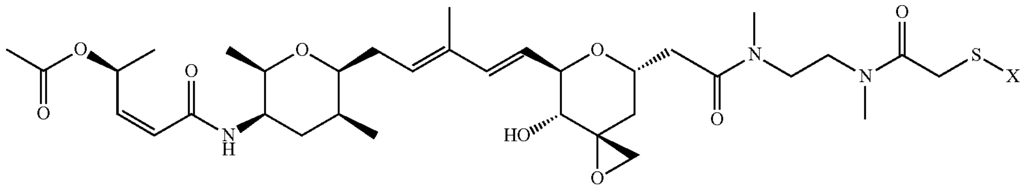 | #B128 |
| ADC55 | 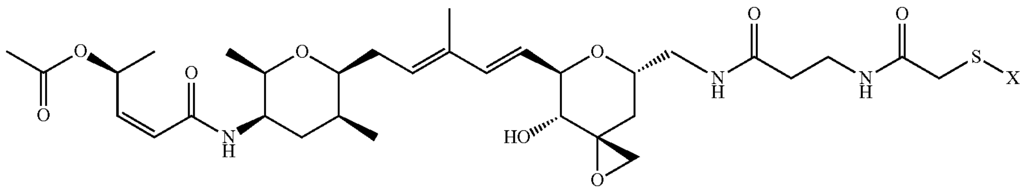 | #B161 |
| ADC56 | 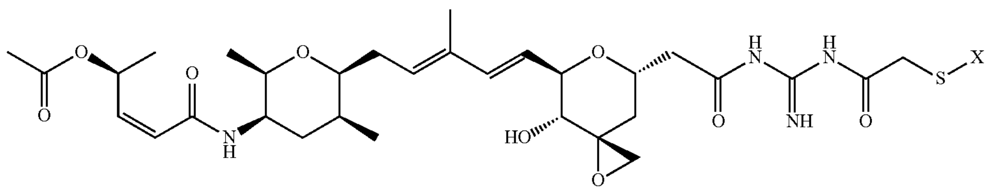 | #B126 |
| ADC57 | 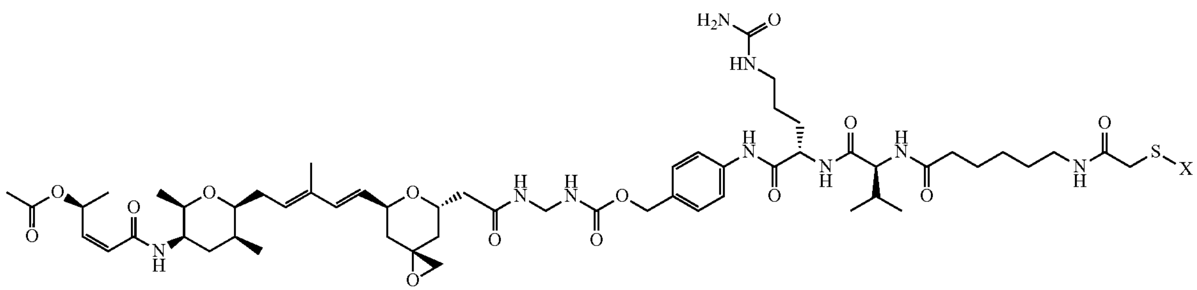 | #B180 |

TABLE 6-continued

Structure of ADC and Payload Linkers used to prepare them

| ADC# | Structure | LP used for synthesis of ADC |
|---|---|---|
| ADC58 | 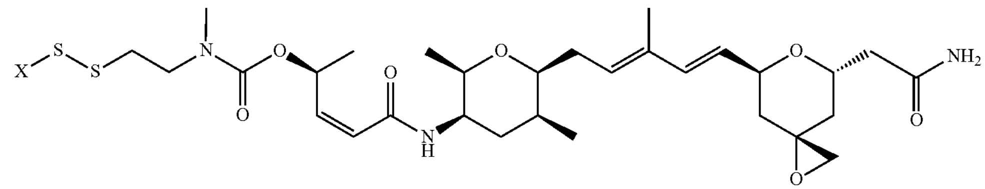 | #B175 |
| ADC59 | 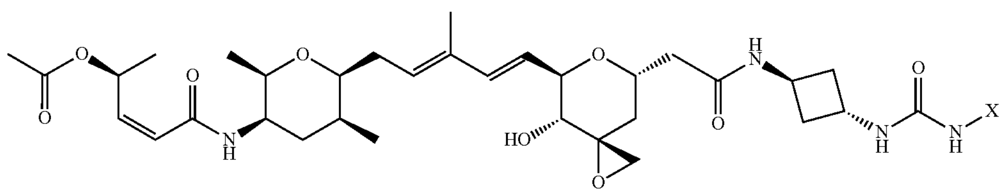 | #B178 |
| ADC60 | 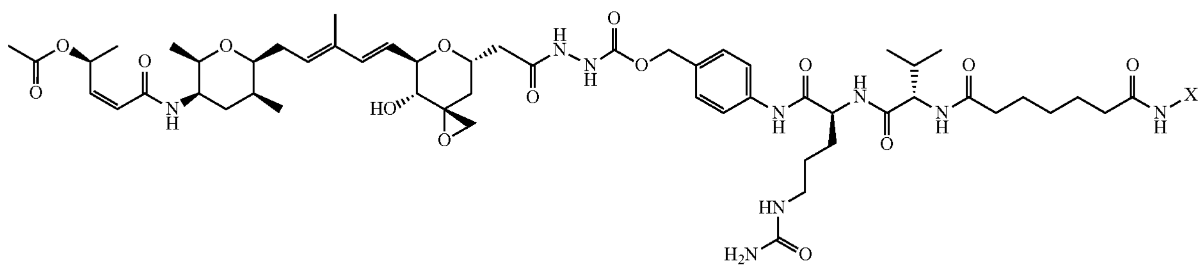 | #B190 |
| ADC61 | 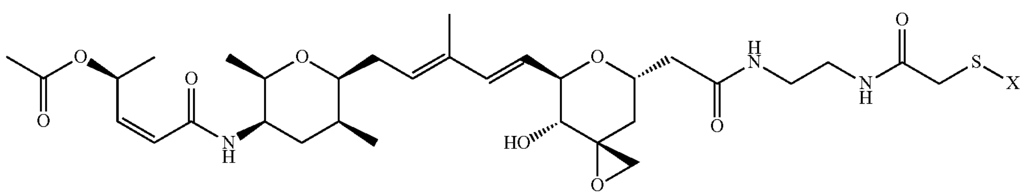 | #B52 |

TABLE 6-continued

Structure of ADC and Payload Linkers used to prepare them

| ADC# | Structure | LP used for synthesis of ADC |
|---|---|---|
| ADC62 | 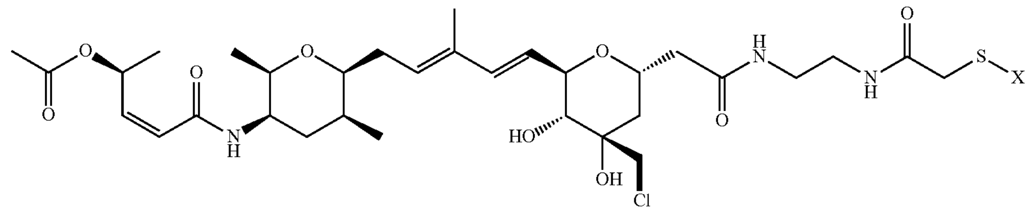 | #B280 |
| ADC63 | 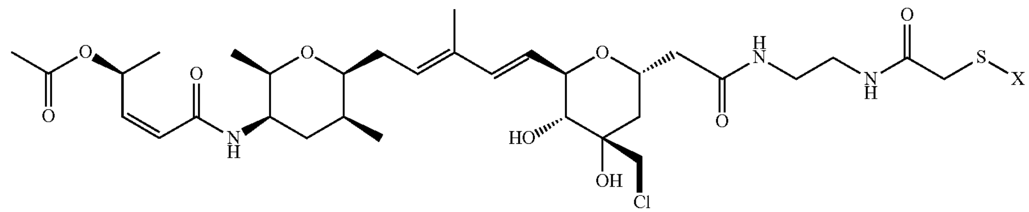 | #B280 |
| ADC64 | 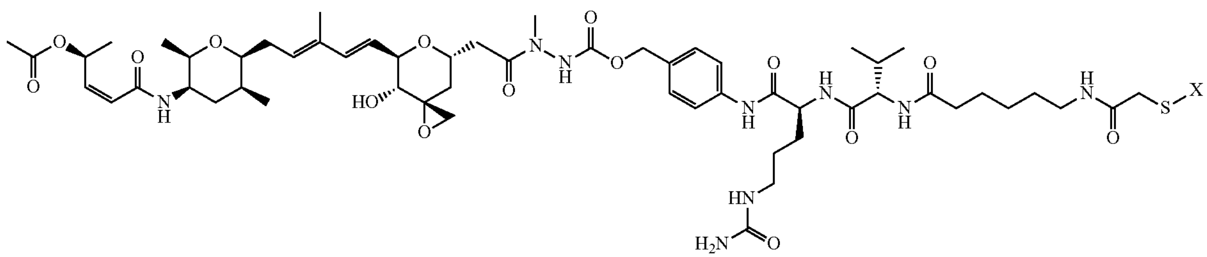 | #B185 |
| ADC65 | 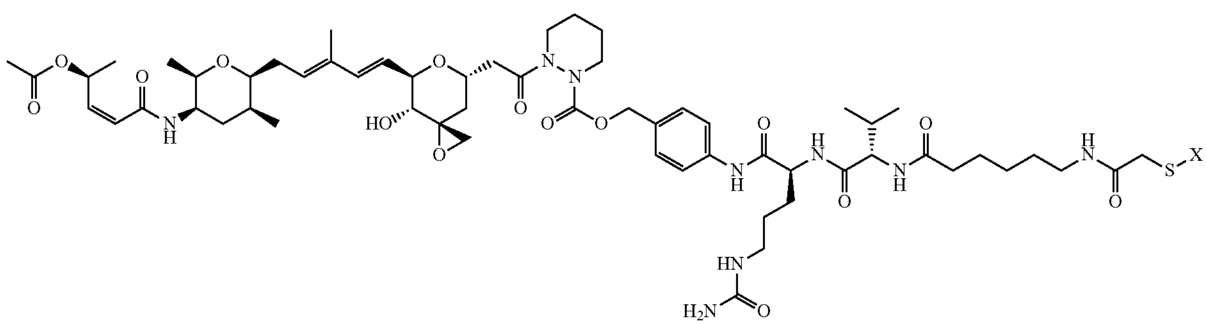 | #B205 |

TABLE 6-continued

Structure of ADC and Payload Linkers used to prepare them

| ADC# | Structure | LP used for synthesis of ADC |
|---|---|---|
| ADC66 | 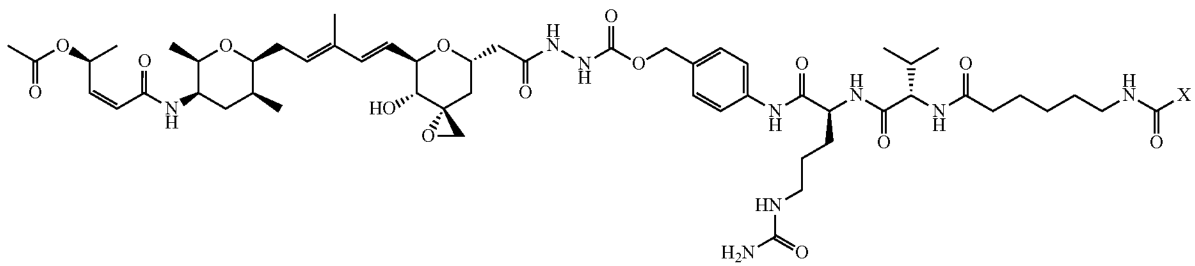 | #B47 |
| ADC67 | 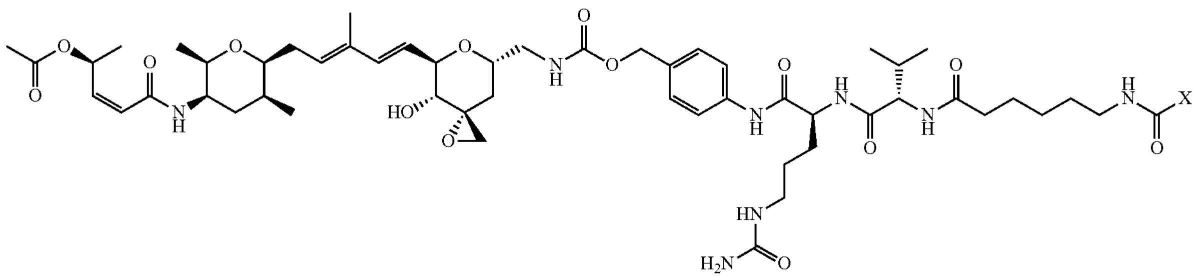 | #B156 |
| ADC68 | 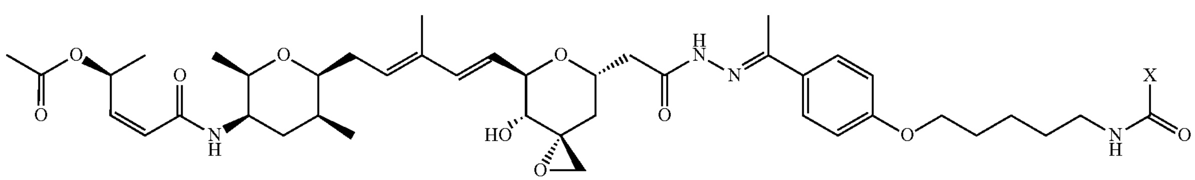 | #B160 |
| ADC69 | 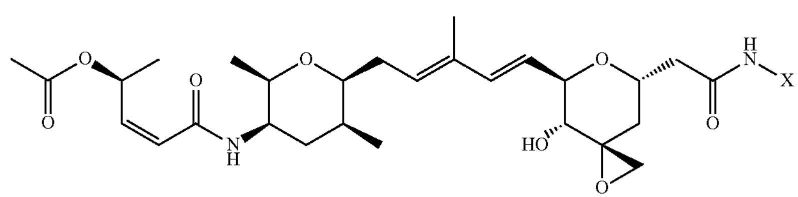 | #B1 |

TABLE 6-continued

Structure of ADC and Payload Linkers used to prepare them

| ADC# | Structure | LP used for synthesis of ADC |
|---|---|---|
| ADC70 | 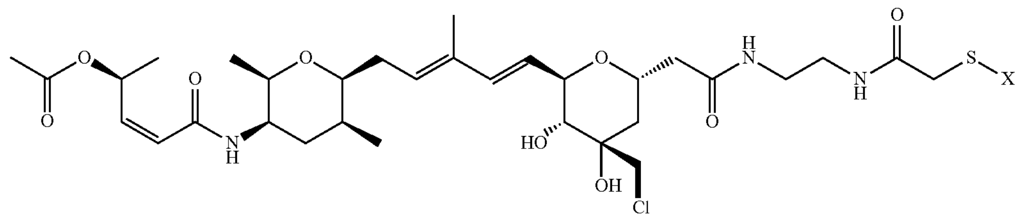 | #B280 |
| ADC71 | 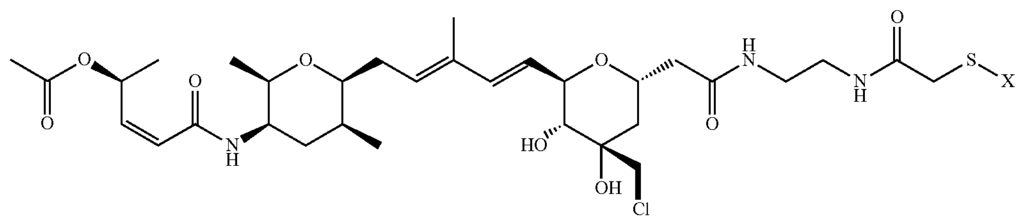 | #B280 |
| ADC72 | 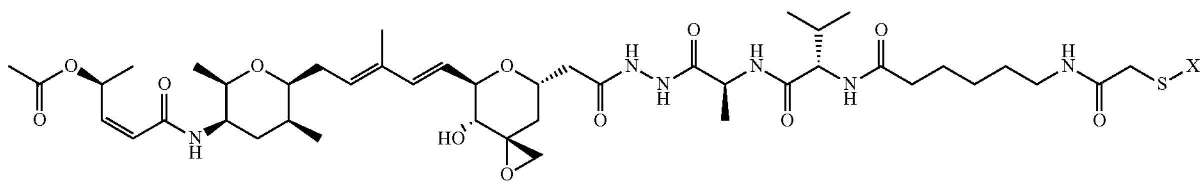 | #B210 |
| ADC73 | 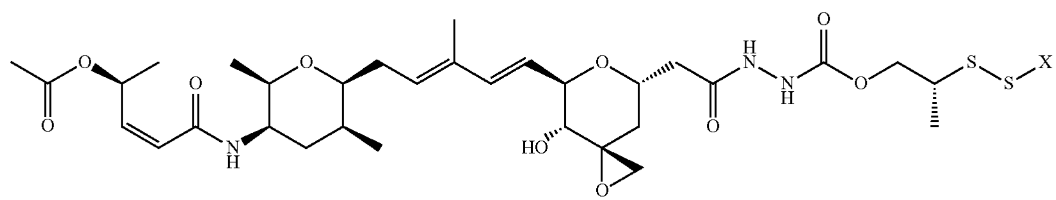 | #B217 |

TABLE 6-continued

Structure of ADC and Payload Linkers used to prepare them

| ADC# | Structure | LP used for synthesis of ADC |
|---|---|---|
| ADC74 | 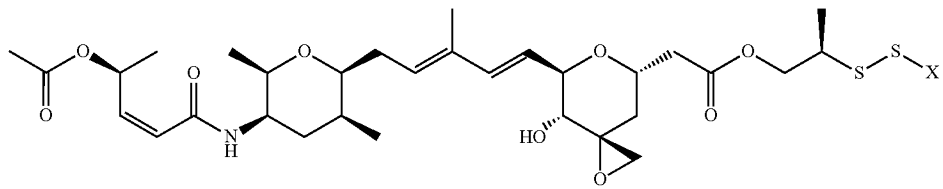 | #B236 |
| ADC75 | 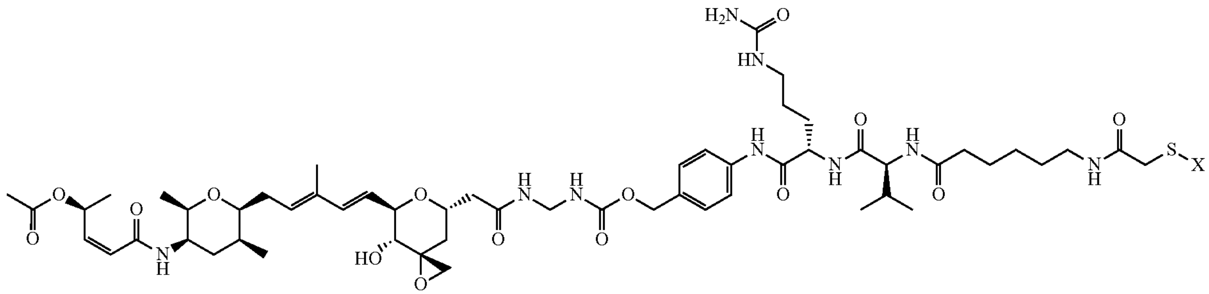 | #B237 |
| ADC76 | 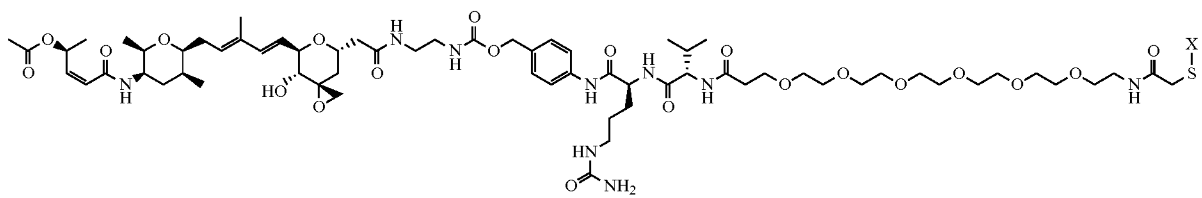 | #B245 |
| ADC77 | 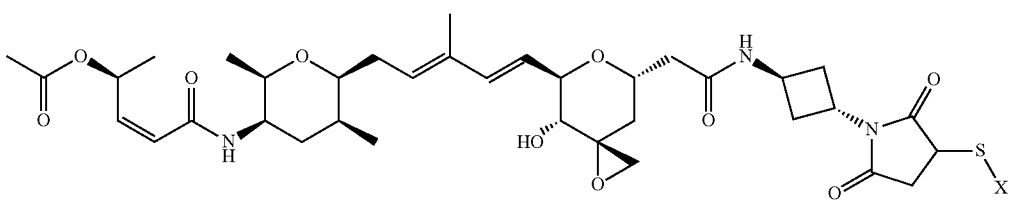 | #B287 |

TABLE 6-continued

Structure of ADC and Payload Linkers used to prepare them

| ADC# | Structure | LP used for synthesis of ADC |
|---|---|---|
| ADC78 | 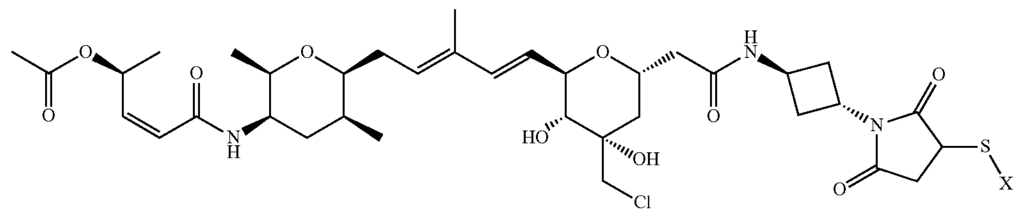 | #B288 |
| ADC79 | 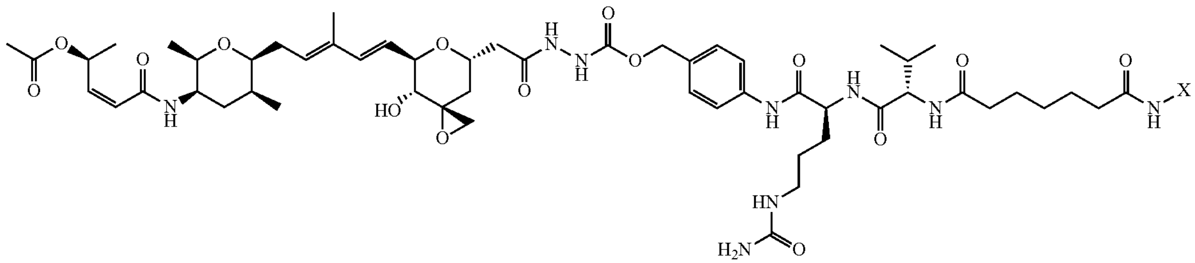 | #B190 |
| ADC80 | 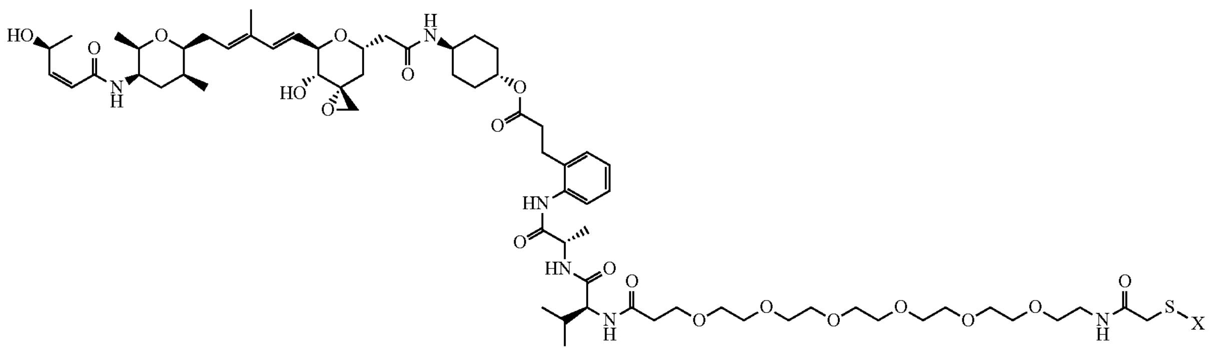 | #B255 |

TABLE 6-continued

Structure of ADC and Payload Linkers used to prepare them

| ADC# | Structure | LP used for synthesis of ADC |
|---|---|---|
| ADC81 | 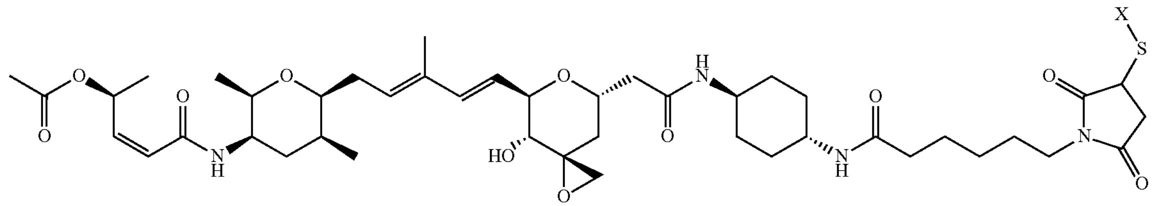 | #B278 |
| ADC82 | 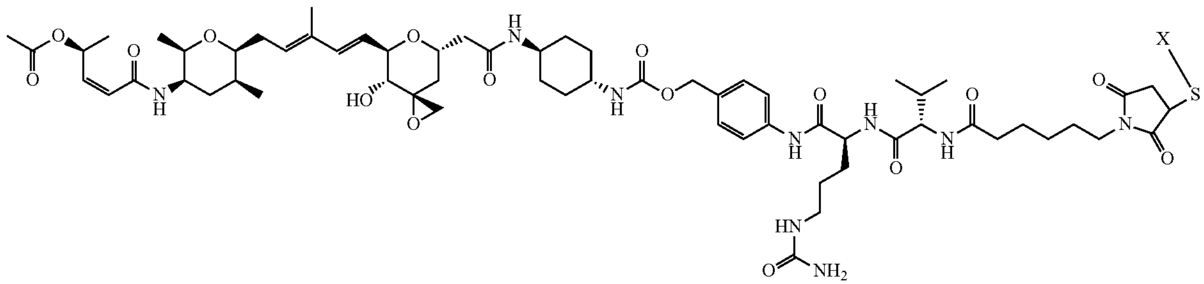 | #B277 |
| ADC83 | 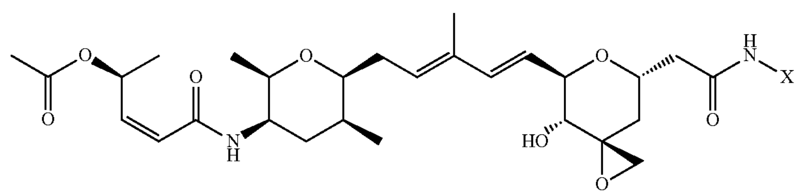 | #B1 |
| ADC84 | 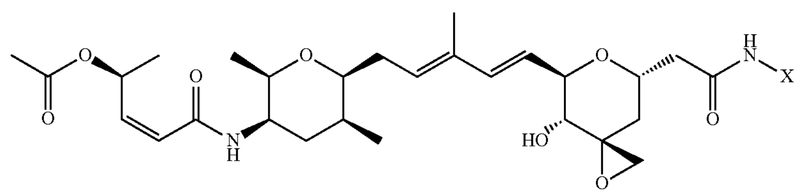 | #B1 |

TABLE 7

General method of Preparation of ADCs

| ADC# | General Method for preparation | Antibody used/ Conjuagting Amino acid | Antibody concentration (or) Amount of 2,2',2"- phosphane- triyltripropanoic acid (TCEP) = y[a] | Amount of equivalent of Linker/ Payload (PL) used | Theoretical MW increase |
|---|---|---|---|---|---|
| ADC1 | F | H-A114C/C114 | 7 | 7 | 1201 |
| ADC2 | E | H-A114C/C114 | 7 | 7 | 643 |
| ADC3 | A | H/K | 10 | 4 | 518 |
| ADC4 | A | H/K | 10 | 5.5 | 518 |
| ADC5 | A | H/K | 10 | 7 | 518 |
| ADC6 | A | H/K | 10 | 7 | 501 |
| ADC7 | A | H/K | 5 | 4.5 | 631 |
| ADC8 | A | H/K | 5 | 5 | 678 |
| ADC9 | H[1] | H/TG1-(Q)_1 | 4.8 | 20 | 1051 |
| ADC10 | D | H-A114C/C114 | 5[a] | 12 | 643 |
| ADC11 | B | H/kK188 | 10[3] | 5.5 | 631 |
| ADC12 | B | H/kK188 | 10[3] | 6.5 | 518 |
| ADC13 | D | H/C | 4[a] | 10 | 643 |
| ADC14 | D | H-L398C + L443C/C | 6[a] | 14 | 643 |
| ADC15 | D | H-K392C + L443C/C | 6[a] | 14 | 643 |
| ADC16 | H[2] | H/TG1-(Q) | 0.5 | 50 | 602 |
| ADC17 | A | H/K | 10 | 8 | 721 |
| ADC18 | E | H-K392C + L443C/ (C392 + C443) | 10 | 12 | 617 |
| ADC19 | A | H/K | 10 | 8 | 586 |
| ADC20 | E | H-K392C + L443C/ (C392 + C443) | 10 | 12 | 575 |
| ADC21 | E | H-K392C + L443C/ (C392 + C443) | 10 | 12 | 686 |
| ADC22 | H | H/TG1-(Q) | 7.2 | 31 | 1003 |
| ADC23 | H | | | | |
| ADC24 | E | H-A114C/C114 | 8.25 | 5 | 617 |
| ADC25 | D | H/C | 10 | 11 | 617 |
| ADC26 | E | H-K392C + L443C/ (C392 + C443) | 8 | 12 | 617 |
| ADC27 | E | H-E388C + N421C/ (C388 + C421) | 10 | 12 | 617 |
| ADC28 | E | H-Q347C + K392C/ (C347 + C392) | 10 | 12 | 617 |
| ADC29 | E | H-L443C + kK183C/ (C443 + kC183) | 10 | 12 | 617 |
| ADC30 | E | H-Q347C + L443C/ (C347 + C443) | 10 | 12 | 617 |
| ADC31 | E | H-kK183C/kC183 | 10 | 5 | 617 |
| ADC32 | E | H-N421C/C421 | 10 | 5 | 617 |
| ADC33 | A | H/K | 10 | 8 | 736 |
| ADC34 | A | H/K | 10 | 8 | 517 |
| ADC35 | E | H-A114C/C114 | 8.5 | 7 | 1245 |
| ADC36 | E | H-A114C/C114 | 8.5 | 7 | 1062 |
| ADC37 | E | H-K392C + L443C/ (C392 + C443) | 8 | 16 | 1062 |
| ADC38 | E | H-A114C/C114 | 8.5 | 7 | 1109 |
| ADC39 | E | H-K392C + L443C/ (C392 + C443) | 8 | 16 | 1109 |
| ADC40 | E | H-A114C/C114 | 9.1 | 7 | 1163 |
| ADC41 | D | H/C | 2.5[a] | 8.4 | 1163 |
| ADC42 | E | H-K392C + L443C/ (C392 + C443) | 8 | 16 | 1163 |
| ADC43 | E | H-A114C/C114 | 9.1 | 7 | 1050 |
| ADC44 | D | H/C | 2.5[a] | 8.4 | 1050 |
| ADC45 | E | H-A114C/C114 | 9.1 | 7 | 1148 |
| ADC46 | D | H/C | 2.5[a] | 8.4 | 1148 |
| ADC47 | E | H-A114C/C114 | 9.1 | 7 | 849 |
| ADC48 | D | H/C | 2.5[a] | 8.4 | 849 |
| ADC49 | E | H-K392C + L443C/ (C392 + C443) | 8 | 16 | 849 |
| ADC50 | E | H-A114C/C114 | 9 | 5 | 1066 |
| ADC51 | E | H-K392C + L443C/ (C392 + C443) | 8 | 16 | 1066 |
| ADC52 | E | H-A114C/C114 | 9 | 5 | 793 |
| ADC53 | E | H-K392C + L443C/ (C392 + C443) | 5.9 | 12 | 548 |
| ADC54 | E | H-K392C + L443C/ (C392 + C443) | 5.9 | 12 | 645 |
| ADC55 | E | H-K392C + L443C/ (C392 + C443) | 6.9 | 12 | 619 |

TABLE 7-continued

General method of Preparation of ADCs

| ADC# | General Method for preparation | Antibody used/ Conjuagting Amino acid | Antibody concentration (or) Amount of 2,2',2"- phosphane- triyltripropanoic acid (TCEP) = y$^a$ | Amount of equivalent of Linker/ Payload (PL) used | Theoretical MW increase |
|---|---|---|---|---|---|
| ADC56 | E | H-A114C/C114 | 12.4 | 9 | 616 |
| ADC57 | E | H-C114 | 9.25 | 5.5 | 1107 |
| ADC58 | E | H-C114 | 9.25 | 5.5 | 593 |
| ADC59 | A | H/K | 10 | 6 | 631 |
| ADC60 | A | H/K | 10 | 6 | 1080 |
| ADC61 | E | H-C392 + C443 + kC183 | 5 | 12 | 617 |
| ADC62 | E | H-C114 | 9.2 | 7.5 | 653 |
| ADC63 | E* | H-C392 + C443 | 8 | 14 | 653 |
| ADC64 | E | H-C392 + C443 | 8 | 10 | 1123 |
| ADC65 | E | H-C392 + C443 | 8 | 10 | 1163 |
| ADC66 | H | H/TG1-(Q)Q | 10 | 15 | 1051 |
| ADC67 | H | H/TG1-(Q)Q | 10 | 15 | 1009 |
| ADC68 | H | H/TG1-(Q) | 10 | 15 | 737 |
| ADC69 | A** | AntibodyY/K | 1.86 | 7.5 | 518 |
| ADC70 | D* | H/C | 4$^a$ | 15 | 653 |
| ADC71 | E* | H-C443 | 10 | 8 | 653 |
| ADC72 | E | H-C392 + C443 | 8 | 12.9 | 874 |
| ADC73 | E | H-C114 | 9 | 5 | 665 |
| ADC74 | E | H-C114 | 9 | 5 | 609 |
| ADC75 | E | H-C114 | 9 | 5 | 1123 |
| ADC76 | E | H-C114 | 9 | 5 | 1360 |
| ADC77 | F | H-C392 + C443 | 8.3 | 10 | 683 |
| ADC78 | F | H-C392 + C443 | 8.3 | 10 | 720 |
| ADC79 | A | H/K | 10 | 10 | 1080 |
| ADC80 | E | H-C114 | 9.1 | 5.9 | 1285 |
| ADC81 | G | 5T4-A1-C443 | 2.5 | 21 | 825 |
| ADC82 | G | 5T4-A1-C443 | 2.5 | 21 | 1230 |
| ADC83 | A** | M1/70/K | 3.23 | 6.5 | 518 |
| ADC84 | A** | AntibodyX/K | 2.9 | 7.5 | 518 |

$^1$Reaction time = 16 hours,
$^2$Reaction time = 4 hours
$^3$Reaction time = 20 hours
$^a$Amount of 2,2',2"-phosphanetriyltripropanoic acid (TCEP) = y used
*Reaction Buffer used is DPBS, 5 mM EDTA pH 7.0 instead of 50 mM borate buffer.
**Reaction Buffer used is 180 mM HEPES buffer pH 8.8 instead of 50 mM borate buffer.

TABLE 8

Analytical Data of ADCs

| ADC# | Mass spectra: HPLC-SEC retention time and HPLC Δ mass for the Heavy Chain (HC) portion (up to 6 Da difference with theoritical Δ mass) | Loading or Drug per Antibody ratio (DAR) |
|---|---|---|
| ADC1 | SEC (Protocol 1): 7.694 min; HPLC (Protocol 2): HC Δ mass = 1203 | 1.6 |
| ADC2 | SEC (Protocol 1): 7.556 min; HPLC (Protocol 2): HC Δ mass = 646 | 1.3 |
| ADC3 | SEC (Protocol 1): 7.598 min; HPLC (Protocol 2): HC Δ mass = 517 | 2.2 |
| ADC4 | SEC (Protocol 1): 7.603 min; HPLC (Protocol 2): HC Δ mass = 518 | 3.2 |
| ADC5 | SEC (Protocol 1): 7.605 min; HPLC (Protocol 2): HC Δ mass = 520 | 4.2 |
| ADC6 | SEC (Protocol 1): 7.723 min; HPLC (Protocol 2): HC Δ mass = 500 | 3.6 |
| ADC7 | SEC (Protocol 1): 7.151 min; HPLC (Protocol 2): HC Δ mass = 631 | 1.9 |
| ADC8 | SEC (Protocol 1): 7.290 min; HPLC (Protocol 2): HC Δ mass = 678 | 2.1 |
| ADC9 | SEC (Protocol 1): 7.093 min; HPLC (Protocol 2): HC Δ mass = 1049 | 1.8 |
| ADC10 | SEC (Protocol 1): 7.399 min; HPLC (Protocol 2): HC Δ mass = 644 | 3.1 |
| ADC11 | SEC (Protocol 1): 7.38 min; HPLC (Protocol 2): HC Δ mass = 629 | 2.5 |
| ADC12 | SEC (Protocol 1): 7.37 min; HPLC (Protocol 2): HC Δ mass = 517 | 1.8 |
| ADC13 | SEC (Protocol 1): 7.566 min; HPLC (Protocol 2): HC Δ mass = 644 | 7.3 |
| ADC14 | SEC (Protocol 1): 7.598 min; HPLC (Protocol 2): HC Δ mass = 640 | 6.6 |
| ADC15 | SEC (Protocol 1): 7.547 min; HPLC (Protocol 2): HC Δ mass = 644 | 6.7 |
| ADC16 | SEC (Protocol 1): 7.425 min; HPLC (Protocol 2): HC Δ mass = 603 | 1.8 |
| ADC17 | SEC (Protocol 1): 7.297 min; HPLC (Protocol 2): HC Δ mass = 721 | 2.3 |
| ADC18 | SEC (Protocol 1): 7.549 min; HPLC (Protocol 2): HC Δ mass = 620 | 4 |
| ADC19 | SEC (Protocol 1): 8.161 min; HPLC (Protocol 2): HC Δ mass = 590 | 2.9 |
| ADC20 | SEC (Protocol 1): 7.806 min; HPLC (Protocol 2): HC Δ mass = 577 | 4 |
| ADC21 | SEC (Protocol 1): 8.679_11.628 min; HPLC (Protocol 2): HC Δ mass = 688 | 4 |

TABLE 8-continued

Analytical Data of ADCs

| ADC# | Mass spectra: HPLC-SEC retention time and HPLC Δ mass for the Heavy Chain (HC) portion (up to 6 Da difference with theoritical Δ mass) | Loading or Drug per Antibody ratio (DAR) |
|---|---|---|
| ADC22 | SEC (Protocol 1b): 5.95 min; HPLC (Protocol 2): HC Δ mass = 1001 | 2 |
| ADC23 | | |
| ADC24 | SEC (Protocol 1b): 7.136 min; HPLC (Protocol 2): HC Δ mass = 618 | 1.9 |
| ADC25 | SEC (Protocol 1b): 7.119 min; HPLC (Protocol 2): HC Δ mass = 618 | 6.3 |
| ADC26 | SEC (Protocol 1b): 7.948 min; HPLC (Protocol 2): HC Δ mass = 618 | 3.9 |
| ADC27 | SEC (Protocol 1b): 8.358 min; HPLC (Protocol 2): HC Δ mass = 622 | 3.6 |
| ADC28 | SEC (Protocol 1b): 7.921 min; HPLC (Protocol 2): HC Δ mass = 619 | 3.8 |
| ADC29 | SEC (Protocol 1b): 8.046 min; HPLC (Protocol 2): HC Δ mass = 618 | 4 |
| ADC30 | SEC (Protocol 1b): 7.933 min; HPLC (Protocol 2): HC Δ mass = 618 | 4 |
| ADC31 | SEC (Protocol 1b): 7.982 min; HPLC (Protocol 2): HC Δ mass = 618 | 2 |
| ADC32 | SEC (Protocol 1b): 7.765 min; HPLC (Protocol 2): HC Δ mass = 618 | 2 |
| ADC33 | SEC (Protocol 1b): 5.821 min; HPLC (Protocol 2): HC Δ mass = 736 | 3 |
| ADC34 | SEC (Protocol 1b): 5.766 min; HPLC (Protocol 2): HC Δ mass = 517 | 1.4 |
| ADC35 | SEC (Protocol 1b): 8.414 min; HPLC (Protocol 2): HC Δ mass = 1243 | 1.8 |
| ADC36 | SEC (Protocol 1b): 8.074 min; HPLC (Protocol 2): HC Δ mass = 1062 | 2.2 |
| ADC37 | SEC (Protocol 1b): 5.964 min; HPLC (Protocol 2): HC Δ mass = 1060 | 2.9 |
| ADC38 | SEC (Protocol 1b): 8.314 min; HPLC (Protocol 2): HC Δ mass = 1109 | 2 |
| ADC39 | SEC (Protocol 1b): 6.031 min; HPLC (Protocol 2): HC Δ mass = 1106 | 3.2 |
| ADC40 | SEC (Protocol 1b): 6.031 min; HPLC (Protocol 2): HC Δ mass = 1164 | 2 |
| ADC41 | SEC (Protocol 1b): 5.925 min; HPLC (Protocol 2): HC Δ mass = 1163 | 5.7 |
| ADC42 | SEC (Protocol 1b): 6.009 min; HPLC (Protocol 2): HC Δ mass = 1160 | 4.1 |
| ADC43 | SEC (Protocol 1b): 6.079 min; HPLC (Protocol 2): HC Δ mass = 1051 | 2 |
| ADC44 | SEC (Protocol 1b): 5.953 min; HPLC (Protocol 2): HC Δ mass = 1050 | 4.3 |
| ADC45 | SEC (Protocol 1b): 6.059 min; HPLC (Protocol 2): HC Δ mass = 1149 | 2 |
| ADC46 | SEC (Protocol 1b): 5.963 min; HPLC (Protocol 2): HC Δ mass = 1147 | 3.8 |
| ADC47 | SEC (Protocol 1b): 6.026 min; HPLC (Protocol 2): HC Δ mass = 852 | 2.3 |
| ADC48 | SEC (Protocol 1b): 5.943 min; HPLC (Protocol 2): HC Δ mass = 850 | 5.8 |
| ADC49 | SEC (Protocol 1b): 6.008 min; HPLC (Protocol 2): HC Δ mass = 852 | 4.3 |
| ADC50 | SEC (Protocol 1b): 6.031 min; HPLC (Protocol 2): HC Δ mass = 1068 | 2 |
| ADC51 | SEC (Protocol 1b): 6.05 min; HPLC (Protocol 2): HC Δ mass = 1066 | 3.1 |
| ADC52 | SEC (Protocol 1b): 6.036 min; HPLC (Protocol 2): HC Δ mass = 796 | 1.8 |
| ADC53 | SEC (Protocol 1b): 6.432 min; HPLC (Protocol 2): HC Δ mass = 544 | 4 |
| ADC54 | SEC (Protocol 1b): 6.425 min; HPLC (Protocol 2): HC Δ mass = 643 | 4 |
| ADC55 | SEC (Protocol 1b): 6.443 min; HPLC (Protocol 2): HC Δ mass = 617 | 3.6 |
| ADC56 | SEC (Protocol 1b): 6.463 min; HPLC (Protocol 2): HC Δ mass = 616 | 1.6 |
| ADC57 | SEC (Protocol 1b): 6.475 min; HPLC (Protocol 2): HC Δ mass = 1107 | 1.8 |
| ADC58 | SEC (Protocol 1b): 6.474 min; HPLC (Protocol 2): HC Δ mass = 589 | 1.9 |
| ADC59 | SEC (Protocol 1b): 6.409 min; HPLC (Protocol 2): HC Δ mass = 630 | 2.4 |
| ADC60 | SEC (Protocol 1b): 6.454 min; HPLC (Protocol 2): HC Δ mass = 1078 | 1.8 |
| ADC61 | SEC (Protocol 1b): 6.437 min; HPLC (Protocol 2): HC Δ mass = 618 | 5.1 |
| ADC62 | SEC (Protocol 1b): 6.48 min; HPLC (Protocol 2): HC Δ mass = 653 | 1.7 |
| ADC63 | SEC (Protocol 1b): 6.452 min; HPLC (Protocol 2): HC Δ mass = 651 | 1.8 |
| ADC64 | SEC (Protocol 1b): 6.502 min; HPLC (Protocol 2): HC Δ mass = 1126 | 4.2 |
| ADC65 | SEC (Protocol 1b): 6.495 min; HPLC (Protocol 2): HC Δ mass = 1162 | 4.2 |
| ADC66 | SEC (Protocol 1b): 6.362 min; HPLC (Protocol 2): HC Δ mass = 1052 | 3.3 |
| ADC67 | SEC (Protocol 1b): 6.414 min; HPLC (Protocol 2): HC Δ mass = 1006 | 2.9 |
| ADC68 | SEC (Protocol 1b): 6.377 min; HPLC (Protocol 2): HC Δ mass = 736 | 2.1 |
| ADC69 | SEC (Protocol 3): 2.396 min; HPLC (Protocol 2): HC Δ mass = 518 | 4.2 |
| ADC70 | SEC (Protocol 1b): 6.285 min; HPLC (Protocol 2): HC Δ mass = 653 | 7.8 |
| ADC71 | SEC (Protocol 1b): 6.376 min; HPLC (Protocol 2): HC Δ mass = 656 | 1.4 |
| ADC72 | SEC (Protocol 1b): 6.332 min; HPLC (Protocol 2): HC Δ mass = 873 | 3.1 |
| ADC73 | SEC (Protocol 1b): 6.38 min; HPLC (Protocol 2): HC Δ mass = 665 | 1.9 |
| ADC74 | SEC (Protocol 1b): 6.379 min; HPLC (Protocol 2): HC Δ mass = 608 | 1.8 |
| ADC75 | SEC (Protocol 1b): 6.378 min; HPLC (Protocol 2): HC Δ mass = 1123 | 2 |
| ADC76 | SEC (Protocol 1b): 6.355 min; HPLC (Protocol 2): HC Δ mass = 1359 | 1.9 |
| ADC77 | SEC (Protocol 1b): 6.332 min; HPLC (Protocol 2): HC Δ mass = 689 | 4 |
| ADC78 | SEC (Protocol 1b): 6.369 min; HPLC (Protocol 2): HC Δ mass = 721 | 3.2 |
| ADC79 | SEC (Protocol 1b): 6.454 min; HPLC (Protocol 2): HC Δ mass = 1078 | 3 |
| ADC80 | SEC (Protocol 1b): 6.372 min; HPLC (Protocol 2): HC Δ mass = 1283 | 2.0 |
| ADC81 | SEC (Protocol 1): 9.183 min; HPLC (Protocol 2): HC Δ mass = 825 | 1.9 |
| ADC82 | SEC (Protocol 1): 9.367 min; HPLC (Protocol 2): HC Δ mass = 1231 | 1.9 |
| ADC83 | SEC (Protocol 3): 2.26 min; HPLC (Protocol 2): HC Δ mass = 518 | 3.4 |
| ADC84 | SEC (Protocol 3): 2.306 min; HPLC (Protocol 2): HC Δ mass = 518 | 4.4 |

TABLE 9

In vitro cytotoxicity data for ADCs

| ADC# | N87 IC$_{50}$ (nM) | BT474 IC$_{50}$ (nM) | MDA-MB-361-DYT2 IC$_{50}$ (nM) | MDA-MB-468 IC$_{50}$ (nM) |
|---|---|---|---|---|
| ADC1 | 0.48 | 1.1 | >1000 | >1000 |
| ADC2 | 1.26 | 2.02 | >1000 | >1000 |
| ADC3 | 0.62 | 0.75 | 506.44 | >1000 |
| ADC4 | 0.73 | 0.83 | 9 | >1000 |
| ADC5 | 0.85 | 0.93 | 0.77 | >1000 |
| ADC6 | 0.52 | 1.03 | 123.00 | 580.3 |
| ADC7 | 0.37 | 1.32 | >1000 | >1000 |

TABLE 9-continued

In vitro cytotoxicity data for ADCs

| ADC# | N87 IC$_{50}$ (nM) | BT474 IC$_{50}$ (nM) | MDA-MB-361-DYT2 IC$_{50}$ (nM) | MDA-MB-468 IC$_{50}$ (nM) |
|---|---|---|---|---|
| ADC8 | 0.38 | 1.69 | >850 | >1000 |
| ADC9 | 0.57 | 38.7 | 734 | 626 |
| ADC10 | 0.44 | 1.13 | 645 | >1000 |
| ADC11 | 0.64 | 3.26 | >1000 | >1000 |
| ADC12 | 0.21 | 0.65 | 796 | >1000 |
| ADC13 | 500.49 | 501.26 | 367.92 | >1000 |
| ADC14 | 0.564 | 1.18 | 0.92 | >1000 |
| ADC15 | 0.56 | 1.04 | 1.13 | 749 |
| ADC16 | 0.36 | 0.85 | 836 | 646 |
| ADC17 | 1.15 | 2.48 | 16.1 | 6.27 |
| ADC18 | 0.76 | 0.99 | 1.22 | >1000 |
| ADC19 | 1.01 | 1.05 | 0.78 | >1000 |
| ADC20 | 1.41 | 1.68 | 14.72 | >1000 |
| ADC21 | 1.1 | 1.35 | 1.15 | >1000 |
| ADC22 | <0.082 | 0.543 | >1000.000 | >1000.000 |
| ADC23 | 0.388 | 0.712 | >1000.000 | >1000.000 |
| ADC24 | 0.43 | 1.13 | >1000.000 | >1000.000 |
| ADC25 | 1.166 | 3.524 | >1000.000 | >1000.000 |
| ADC26 | 0.326 | 0.939 | 0.905 | >1000.000 |
| ADC27 | 5.535 | 7.295 | >1000.000 | >1000.000 |
| ADC28 | 0.792 | 1.337 | >517.927 | >1000.000 |
| ADC29 | 0.936 | 1.394 | 220.984 | >1000.000 |
| ADC30 | 1.216 | 1.882 | >1000.000 | >1000.000 |
| ADC31 | 1.295 | 1.652 | >1000.000 | >1000.000 |
| ADC32 | 4.229 | 3.104 | >1000.000 | >1000.000 |
| ADC33 | 1.089 | 0.968 | 25.123 | 55.117 |
| ADC34 | 2.956 | 1.333 | 29.445 | 13.28 |
| ADC35 | >1000.000 | 7.52 | >1000.000 | >1000.000 |
| ADC36 | 5.057 | 1.487 | >1000.000 | >1000.000 |
| ADC37 | 0.438 | 0.727 | >1000.000 | >1000.000 |
| ADC38 | 0.92 | 0.684 | >971.382 | 678.881 |
| ADC39 | 0.253 | 0.814 | 539.318 | >652.881 |
| ADC40 | 292.352 | 1.374 | >1000.000 | >1000.000 |
| ADC41 | 1.124 | 1.289 | >1000.000 | >1000.000 |
| ADC42 | 0.387 | 3.55 | >1000.000 | >1000.000 |
| ADC43 | >517.760 | 162.752 | >1000.000 | >1000.000 |
| ADC44 | 311.476 | >1000.000 | >1000.000 | >1000.000 |
| ADC45 | >507.594 | >502.150 | >1000.000 | >1000.000 |
| ADC46 | 27.266 | 33.941 | >1000.000 | >1000.000 |
| ADC47 | >500.464 | 2.644 | >1000.000 | >1000.000 |
| ADC48 | 0.948 | 1.387 | >1000.000 | >1000.000 |
| ADC49 | 0.666 | 1.713 | >1000.000 | >1000.000 |
| ADC50 | 7.011 | 2.956 | >1000.000 | >1000.000 |
| ADC51 | 3.613 | 3.282 | >1000.000 | >1000.000 |
| ADC52 | 0.732 | 0.441 | 297.62 | 78.288 |
| ADC53 | 0.46 | 0.733 | 1.761 | >1000.000 |
| ADC54 | 0.387 | 0.682 | 38.177 | >1000.000 |
| ADC55 | 0.775 | 1.181 | 2.827 | >1000.000 |
| ADC56 | 1.583 | 2.697 | 253.894 | 166.107 |
| ADC57 | 525.654 | 17.021 | >1000.000 | >1000.000 |
| ADC58 | 40.988 | 8.516 | >1000.000 | >1000.000 |
| ADC59 | 1.180 | 1.903 | 704.928 | >1000.000 |
| ADC60 | 0.387 | 0.803 | 467.403 | 977.305 |
| ADC61 | 1.458 | 1.433 | 17.826 | >1000.000 |
| ADC62 | 1.321 | 1.042 | >1000.000 | >1000.000 |
| ADC63 | 0.752 | 0.785 | 650.252 | 909.588 |
| ADC64 | 0.860 | 1.582 | 329.206 | 180.131 |
| ADC65 | 1.198 | 2.364 | 86.588 | 44.689 |
| ADC66 | 1.097 | 1.103 | >1000.000 | >1000.000 |
| ADC67 | 95.434 | 10.354 | >1000.000 | >1000.000 |
| ADC68 | 17.622 | 14.213 | 697.158 | 369.898 |
| ADC70 | 1.909 | 3.325 | 19.619 | >1000.000 |
| ADC71 | 0.595 | 1.032 | >1000.000 | >1000.000 |
| ADC72 | 0.640 | 1.274 | >1000.000 | >1000.000 |
| ADC73 | 0.906 | 0.940 | >1000.000 | 323.986 |
| ADC74 | 68.249 | 13.402 | >1000.000 | >1000.000 |
| ADC75 | 1.066 | 1.088 | >1000.000 | >1000.000 |
| ADC76 | 1.164 | 1.355 | >1000.000 | >1000.000 |
| ADC77 | 1.071 | 2.292 | 180.278 | >1000.000 |
| ADC78 | 0.760 | 1.215 | 247.494 | >1000.000 |
| ADC79 | 0.158 | 0.534 | 0.380 | 762.235 |
| ADC80 | 7.878 | 13.050 | >1000 | >1000 |

TABLE 9A

In vitro cytotoxicity data for ADCs

| ADC# | (MDA-MB-435) IC$_{50}$ (nM) | MDA-MB-468 IC$_{50}$ (nM) | Peritoneal Macrophage IC$_{50}$ (nM) | Cell 3 IC$_{50}$ (nM) | Cell 4 IC$_{50}$ (nM) | Cell 5 IC$_{50}$ (nM) | Cell 6 IC$_{50}$ (nM) | Cell 7 IC$_{50}$ (nM) |
|---|---|---|---|---|---|---|---|---|
| ADC69 | | | | 17.182 | 1.851 | 2.177 | 0.971 | |
| ADC81 | 162.737 | 35.578 | | | | | | |
| ADC82 | 370.545 | 9.978 | | | | | | |
| ADC83 | | | 0.0002 | | | | | |
| ADC84 | | | 1.522 | | | | | |

SEQUENCE LISTING

SEQ ID NO: 1    AGAGTTTGATCCTGGCTCAG

SEQ ID NO: 2    GGTTACCTTGTTACGACTT

SEQ ID NO: 3    CTACGGGAGGCAGCAGTGGG

SEQ ID NO: 4    CCCACTGCTGCCTCCCGTAG

SEQ ID NO: 5    CAGCAGCCGCGGTAATAC

SEQ ID NO: 6    GTATTACCGCGGCTGCTG

SEQ ID NO: 7    CATGGCTGTCGTCAGCTCGT

| SEQUENCE LISTING |
| --- |

SEQ ID NO: 8    ACGAGCTGACGACAGCCATG

SEQ ID NO: 9    AGAGTTTGATCCTGGCTCAGATTGAACGCTGGCGGCATGCCTTACACATGCAAGT
CGAACGGCAGCACGGGTGCTTGCACCTGGTGGCGAGTGGCGAACGGGTGAGTAAT
ACATCGGAACATGTCCTGTAGTGGGGATAGCCCGGCGAAAGCCGGATTAATACC
GCATACGATCTACGGATGAAAGCGGGGGATCTTCGGACCTCGCGCTATAGGGTTG
GCCGATGGCTGATTAGCTAGTTGGTGGGGTAAAGGCCTACCAAGGCGACGATCAG
TAGCTGGTCTGAGAGGACGATCAGCCACACTGGGACTGAGACACGGCCCAGACTC
CTACGGGAGGCAGCAGTGGGGAATTTTGGACAATGGGGGAAACCCTGATCCAGCA
ATGCCGCGTGTGTGAAGAAGGCCTTCGGGTTGTAAAGCACTTTTGTCCGGAAAGA
AATCCTTTGGGCTAATACCCCGGGGGATGACGGTACCGGAAGAATAAGCACCGG
CTAACTACGTGCCAGCAGCCGCGGTAATACGTAGGGTGCGAGCGTTAATCGGAAT
TACTGGGCGTAAAGCGTGCGCAGGCGGTTTGTTAAGACAGATGTGAAATCCCCGG
GCTTAACCTGGGAACTGCATTTGTGACTGGCAAGCTAGAGTATGGCAGAGGGGGG
TAGAATTCCACGTGTAGCAGTGAAATGCGTAGAGATGTGGAGGAATACCGATGGC
GAAGGCAGCCCCCTGGGCCAATACTGACGCTCATGCACGAAAGCGTGGGGAGCAA
ACAGGATTAGATACCCTGGTAGTCCACGCCCTAAACGATGTCAACTAGTTGTTGG
GGATTCATTTCCTTAGTAACGTAGCTAACGCGTGAAGTTGACCGCCTGGGGAGTA
CGGTCGCAAGATTAAAACTCAAAGGAATTGACGGGGACCCGCACAAGCGGTGGAT
GATGTGGATTAATTCGATGCAACGCGAAAAACCTTACCTACCCTTGACATGGTCG
GAATCCTGAAGAGATTCGGGAGTGCTCGAAAGAGAACCGATACACAGGTGCTGCA
TGGCTGTCGTCAGCTCGTGTCGTGAGATGTTGGGTTAAGTCCCGCAACGAGCGCA
ACCCTTGTCCTTAGTTGCTACGCAAGAGCACTCTAAGGAGACTGCCGGTGACAAA
CCGGAGGAAGGTGGGGATGACGTCAAGTCCTCATGGCCCTTATGGGTAGGGCTTC
ACACGTCATACAATGGTCGGAACAGAGGGTTGCCAACCCGCGAGGGGGAGCTAAT
CCCAGAAAACCGATCGTAGTCCGGATTGCACTCTGCAACTCGAGTGCATGAAGCT
GGAATCGCTAGTAATCGCGGATCAGCATGCCGCGGTGAATACGTTCCCGGGTCTT
GTACACACCGCCCGTCACACCATGGGAGTGGGTTTTACCAGAAGTGGCTAGTCTA
ACCGCAAGGAGGACGGTCACCACGGTAGGATTCATGACTGGGGTGAAGTCGTAAC
AAGGTAACC

SEQ ID NO: 10    TGG CGA ACA GAT CGA GTT TG

SEQ ID NO: 11    CTT GCG GAG AAC TGT GAA TGC GCA ATA GAA GCG CTG TCA TGG
AAT G

SEQ ID NO: 12    CCG AAA AGT GCC ACC TGA CGT CTA AGA TAA CTC GTG GAT ATT
CGG CAA G

SEQ ID NO: 13    AGA ATC CCG CGA TCC CAA C

SEQ ID NO: 14    TTG CGC ATT CAC AGT TCT C

SEQ ID NO: 15    TCT TAG ACG TCA GGT GGC AC

SEQ ID NO: 16    GGA CGA ATC GAA CTC AGG AAC TTG

SEQ ID NO: 17    CGA AGA GCG ATT GAG GAA AAG G

SEQ ID NO: 18    GTT GGT TTG CGC ATT CAC AGT TCT CCG CAA GAA TTG ATT GCA
AGG GCT GCT AAA GGA AG

SEQ ID NO: 19    TCT TCC GCT TCC TCG CTC ACT GAC TCG CTG CGC TCG GTC ACG
GAA ATG TTG AAT ACT CAT ACT C

SEQ ID NO: 20    GCT CTA GAC ATC GAT TTA TTA TGA CAA CTT GAC

SEQ ID NO: 21    CCC AAA AAA ACG GGT ATG G

SEQ ID NO: 22    CTA CTG TTT CTC CAT ACC CGT TTT TTT GGG GGG TTG TTG GTT
TTT GAA ATT GC

SEQ ID NO: 23    ATG GTG AAG CTT AAG TCG ACA ACC GGC ATT CC

SEQ ID NO: 24    GCA TTC ACA GTT CTC CGC AAG

SEQ ID NO: 25    CTC GCT CAC TGA CTC GCT G

SEQ ID NO: 26    GCA ATT AAC CCT CAC TAA AGG

SEQ ID NO: 27    CTA TAG GGC GAA TTG GGT AC

SEQ ID NO: 28    GCA TCC AAT CAC TTG AAC AGG

SEQ ID NO: 29    CTT GCG GAG AAC TGT GAA TGC GCA AGC CAT CAT TCT CGA CAT
TTC C

-continued

| SEQUENCE LISTING |
|---|
| SEQ ID NO: 30   CCG AAA AGT GCC ACC TGA CGT CTA AGA AGA TTG TGA CGG TAC TGA AGC |
| SEQ ID NO: 31   AGA GAA CGA TCG CTC CAC AG |
| SEQ ID NO: 32   TTG CGC ATT CAC AGT TCT C |
| SEQ ID NO: 33   TCT TAG ACG TCA GGT GGC AC |
| SEQ ID NO: 34   GGA CGA ATC GAA CTC AGG AAC TTG |
| SEQ ID NO: 35   CGA AGA GCG ATT GAG GAA AAG G |

We claim:

1. A compound of formula (II):

L-P     (II)

or a pharmaceutically acceptable salt thereof, wherein:
L is the linker moiety $L^1$-$L^2$-$L^3$, where $L^3$ is bound to P;
P is a radical of formula (I):

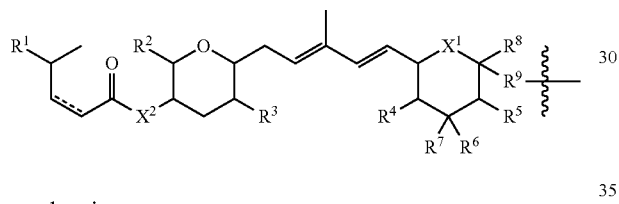

wherein:
a dashed line represents an optional bond;
each $X^1$ is independently selected from the group consisting of: —O—, —S— and —NR—;
each $X^2$ is independently selected from the group consisting of: —O—, —S— and —NR—;
each X' is CR or N;
each X″ is CH—, CR—$(C(R)_2)_m$—NR—, CR—$(C(R)_2)_m$—O—; CR—$(C(R)_2)_m$—C(O)NR—, CR—(C(R)$_2$)$_m$—C(O)NR—NR—, CR—$(C(R)_2)_m$—SO$_2$NR—, CR—$(C(R)_2)_m$—NR—NR—, CR—$(C(R)_2)_m$—NR—C(O)— or N— if X″ binds to $L^2$ or an additional $L^3$, or otherwise is O, S, CRR, CR—$(C(R)_2)_m$—NRR or NRR;
each X‴ is —$(C(R)_2)_m$—NR— or CR—$(C(R)_2)_m$—O— if X‴ binds to $L^2$, or otherwise is R;
Y is —$C(R)_2$—, —O—, —NR— or —S—;
$R^1$ is selected from the group consisting of: —R, —OR, —OCOR$^{13}$, —OCONR$^{14}$R$^{15}$, —OCON(R$^{14}$)NR(R$^{15}$), =O (double bond to oxygen) and —NR$^{14}$R$^{15}$;
$R^2$ and $R^3$ are independently selected from the group consisting of: hydrogen and $C_{1-6}$alkyl;
$R^4$ and $R^5$ are independently selected from the group consisting of: hydrogen, —OR, —NR$^{14}$R$^{15}$ and oxo;
$R^6$ and $R^7$ are independently selected from the group consisting of: hydrogen, halogen, hydroxyl and $C_{1-6}$alkyl optionally substituted with 1-3 substituents independently selected from hydroxyl and halogen;
$R^6$ and $R^7$, together with the carbon atom to which they are bound, form a $C_{2-5}$alkylidene optionally substituted with 1-3 substituents independently selected from R,
$R^6$ and $R^7$ together are oxo, or
$R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;
$R^8$ is hydrogen, $C_{1-6}$alkyl or —OR;
$R^9$ is —$(C(R)_2)_m$—C(O)— or —$(C(R)_2)_m$—;
$L^1$ is selected from: -acid, —NR-acid and

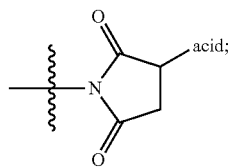

$L^2$ is $L^{2A}$-$L^{2B}$-$L^{2C}$ or $L^{2C}$-$L^{2B}$-$L^{2A}$ where:
$L^{2A}$ comprises one or more components selected from: —O—, —C(O)—, —C(O)NR—, —C(O)—$C_{1-6}$alkyl-, —C(O)NR$C_{1-6}$alkyl-, —$C_{1-6}$alkyl(OCH$_2$CH$_2$)$_{1-6}$—, —C(O)—$C_{1-6}$alkyl-NRC(O)—, —C(O)—$C_{1-6}$alkyl (OCH$_2$CH$_2$)$_{1-6}$—, —$C_{1-6}$alkyl(OCH$_2$CH$_2$)$_{1-6}$—C(O)—, —$C_{1-6}$alkyl-S—S—$C_{1-6}$alkyl-NRC(O)CH$_2$—, —$C_{1-6}$alkyl-(OCH$_2$CH$_2$)$_{1-6}$—NRC(O)CH$_2$—, —C(O)—$C_{1-6}$alkyl-NRC(O)$C_{1-6}$alkyl-, —N=CR-phenyl-O—$C_{1-6}$alkyl-, —N=CR-phenyl-O—$C_{1-6}$alkyl-C(O)—, —C(O)—$C_{1-6}$alkyl(OCH$_2$CH$_2$)$_{1-6}$—NRC(O)—, —C(O)—$C_{1-6}$alkyl-phenyl-(NR—C(O)—$C_{1-6}$alkyl)$_{1-4}$-, —C(O)—$C_{1-6}$alkyl-(OCH$_2$CH$_2$)$_{1-6}$—NRC(O)$C_{1-6}$alkyl-, —$C_{1-6}$alkyl-, —S—, —C(O)—$C_{1-6}$alkyl-phenyl-NR—, —O—$C_{1-6}$alkyl-S—, —C(O)—O—$C_{1-6}$alkyl-S— and (—CH$_2$—CH$_2$—O—)$_{1-20}$, or $L^{2A}$ is absent;
$L^{2B}$ is selected from AA$_{0-aa}$, where AA is a natural or non-natural amino acid and aa is 12; and
$L^{2C}$ comprises one or more components selected from: —PABA- and —PABC—, or $L^{2C}$ is absent;
$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)—NR— where the two R groups optionally join to form a 4-10 membered ring, —NR—$C_{1-6}$alkyl-phenyl-NR—, —NR—$C_{1-6}$alkyl-phenyl-SO$_2$—NR—, —SO$_2$—, —NR—$C_{1-6}$alkyl-phenyl-C(O)—,

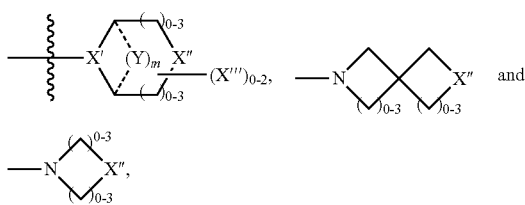

or $L^3$ is absent;

$R^{13}$ is selected from the group consisting of hydrogen, $C_{1-6}$alkyl, $C_{3-8}$carbocyclyl, $C_{3-8}$heterocyclyl, $C_{1-6}$alkyl-$C_{6-14}$aryl, $C_{1-6}$alkyl-$C_{5-14}$heteroaryl, wherein $R^{13}$ is optionally substituted with —NRR or —SO$_2$NRR;

each $R^{14}$ and $R^{15}$ is independently selected from the group consisting of: hydrogen, hydroxyl, —NRR, —NRNR$_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —(CH$_2$CH$_2$O)$_{1-6}$CH$_2$CH$_2$C(O)OR, —(CH$_2$CH$_2$O)$_{1-6}$CH$_2$CH$_2$NRR, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —(C(R)$_2$)$_m$—R$^{18}$ where each $R^{18}$ is independently selected from (i) —NRR, (ii) —C(NRR)(C(O)OR), (iii) —S—R, (iv) aryl or heteroaryl optionally substituted with one or more of halogen, —CF$_3$, —(C(R)$_2$)$_m$—NRR or —(C(R)$_2$)$_m$—SO$_2$NRR, (v) —SO$_2$R, (vi) —S—S—$C_{1-6}$alkyl-C(O)OR, (vii) —SO$_2$NRR, (viii) —C(O)NRR, (ix) —C(O)OR, (x) —$C_{4-6}$cycloalkyl optionally substituted with —NRR, —SO$_2$NRR or —NR—C(O)(CH$_2$)$_{0-6}$NRR, (xi) —R, (xii) —OR, (xiii) —N(R)NRR, (xiv) —C(O)N(R)NRR, (xv) —(C(R)$_2$)$_m$—O—NRR and (xiv) —S—S—$C_{1-6}$alkyl-NRR;

acid is an amino acid residue selected from —SCH$_2$CH(COOH)(NH$_2$), —NH(CH$_2$)$_4$CH(COOH)(NH$_2$) and —C(O)(CH$_2$)$_2$CH(COOH)(NH$_2$);

each R is independently selected from the group consisting of: hydrogen and —$C_{1-6}$alkyl; and each m is independently 0, 1, 2 or 3.

2. Additionally, a compound or compounds of formula (II'):

L-P'  (II')

or a pharmaceutically acceptable salt thereof, wherein:
L is the linker moiety $L^1$-$L^2$-$L^3$, where $L^3$ is bound to P';
P' is a radical of formula (I'):

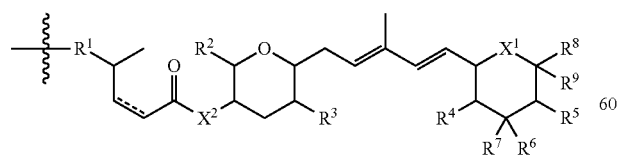

wherein:
a dashed line represents an optional bond;
each $X^1$ is independently selected from the group consisting of: —O—, —S— and —NR—;

each $X^2$ is independently selected from the group consisting of: —O—, —S— and —NR—;
each X' is CR or N;
each X" is CH—, CR—(C(R)$_2$)$_m$—NR—, CR—(C(R)$_2$)$_m$—O—; CR—(C(R)$_2$)$_m$—C(O)NR—, CR—(C(R)$_2$)$_m$—C(O)NR—NR—, CR—(C(R)$_2$)$_m$—SO$_2$NR—, CR—(C(R)$_2$)$_m$—NR—NR—, CR—(C(R)$_2$)$_m$—NR—C(O)— or N— if X" binds to $L^2$ or an additional $L^3$, or otherwise is O, S, CRR, CR—(C(R)$_2$)$_m$—NRR or NRR;
each X''' is —(C(R)$_2$)$_m$—NR— or CR—(C(R)$_2$)$_m$—O— if X''' binds to $L^2$, or otherwise is R;
Y is —C(R)$_2$—, —O—, —NR— or —S—;
$R^1$ is selected from the group consisting of: —(C(R)$_2$)$_m$—, —OR", —OCOR$^{13'}$, —OC(O)NRR$^{4'}$, —OCON(R)N(R)—, and —NR—
$R^2$ and $R^3$ are independently selected from the group consisting of: hydrogen and $C_{1-6}$alkyl;
$R^4$ and $R^5$ are independently selected from the group consisting of: hydrogen, —OR, —NR$^{14}$R$^{15}$ and oxo;
$R^6$ and $R^7$ are independently selected from the group consisting of: hydrogen, halogen, hydroxyl and $C_{1-6}$alkyl optionally substituted with 1-3 substituents independently selected from hydroxyl and halogen,
$R^6$ and $R^7$, together with the carbon atom to which they are bound, form a $C_{2-5}$alkylidene optionally substituted with 1-3 substituents independently selected from R,
$R^6$ and $R^7$ together are oxo, or
$R^6$ and $R^7$, together with the carbon atom to which they are bound, form a 3- to 5-membered heterocycloalkyl moiety comprising 1 or 2 heteroatoms independently selected from the group consisting of oxygen, nitrogen and sulfur, wherein said heterocycloalkyl moiety may be optionally substituted with one to three substituents independently selected from R;
$R^8$ is hydrogen, $C_{1-6}$alkyl or —OR;
$R^9$ is independently selected from hydrogen, —$C_{1-6}$alkyl, —(C(R)$_2$)$_m$—C(O)OR, —(C(R)$_2$)$_m$—C(O)NR$^{14}$R$^{15}$, —(C(R)$_2$)$_m$—NR$^{14}$R$^{15}$, —(C(R)$_2$)$_m$—C(O)—SR, —(C(R)$_2$)$_m$—C(O)NR$^{14}$N(R)R$^{15}$, —(C(R)$_2$)$_m$—NR—C(O)—NR$^{14}$R$^{15}$, —(C(R)$_2$)$_m$—N(R)COR$^{13}$ and —(C(R)$_2$)$_m$—NR$^{14}$N(R)R$^{15}$;
$L^1$ is selected from: -acid, —NR-acid and

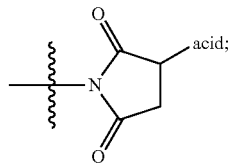

$L^2$ is $L^{2A}$-$L^{2B}$-$L^{2C}$ or $L^{2C}$-$L^{2B}$-$L^{2A}$ where:
$L^{2A}$ comprises one or more components selected from: —O—, —C(O)—, —C(O)NR—, —C(O)—$C_{1-6}$alkyl-, —C(O)NRC$_{1-6}$alkyl-, —$C_{1-6}$alkyl(OCH$_2$CH$_2$)$_{1-6}$—, —C(O)—$C_{1-6}$alkyl-NRC(O)—, —C(O)—$C_{1-6}$alkyl(OCH$_2$CH$_2$)$_{1-6}$—, —$C_{1-6}$alkyl(OCH$_2$CH$_2$)$_{1-6}$—C(O)—, —$C_{1-6}$alkyl-S—S—$C_{1-6}$alkyl-NRC(O)CH$_2$—, —$C_{1-6}$alkyl-(OCH$_2$CH$_2$)$_{1-6}$—NRC(O)CH$_2$—, —C(O)—$C_{1-6}$alkyl-NRC(O)$C_{1-6}$alkyl-, —N=CR-phenyl-O—$C_{1-6}$alkyl-, —N=CR-phenyl-O—$C_{1-6}$alkyl-C(O)—, —C(O)—$C_{1-6}$alkyl(OCH$_2$CH$_2$)$_{1-6}$—NRC(O)—, —C(O)—$C_{1-6}$alkyl-phenyl-(NR—C(O)—$C_{1-6}$alkyl)$_{1-4}$-, —C(O)—$C_{1-6}$alkyl-(OCH$_2$CH$_2$)$_{1-6}$—NRC(O)$C_{1-6}$alkyl-, —$C_{1-6}$alkyl-, —S—, —C(O)—

$C_{1-6}$alkyl-phenyl-NR—, —O—$C_{1-6}$alkyl-S—, —C(O)—O—$C_{1-6}$alkyl-S— and (—$CH_2$—$CH_2$—O—)$_{1-20}$, or $L^{2A}$ is absent;

$L^{2B}$ is selected from $AA_{0-aa}$, where AA is a natural or non-natural amino acid and aa is 12; and $L^{2C}$ comprises one or more components selected from: —PABA- and —PABC—, or $L^{2C}$ is absent;

$L^3$ is selected from one or more of: —$C_{1-6}$alkyl-, —NR—$C_3$-$C_8$heterocyclyl-NR—, —NR—$C_3$-$C_8$carbocyclyl-NR—, —NR—$C_{1-6}$alkyl-NR—, —NR—$C_{1-6}$alkyl-, —S—, —NR—, —NR—NR— and —NR—C(O)NR— where the two R groups optionally join to form a 4-10 membered ring, —NR—$C_{1-6}$alkyl-phenyl-NR—, —NR—$C_{1-6}$alkyl-phenyl-$SO_2$—NR—, —$SO_2$—, —NR—$C_{1-6}$alkyl-phenyl-C(O)—,

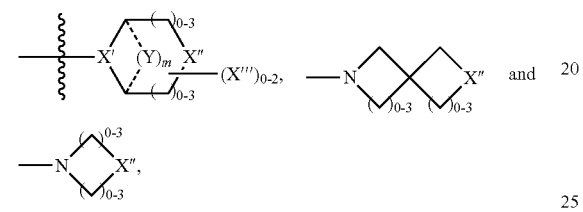

or $L^3$ is absent:

$R^{13'}$ is selected from the group consisting of a bond, —$C_{1-6}$alkylene-, —$C_{3-8}$carbocyclyl-, —$C_{3-8}$heterocyclyl-, —$C_{1-6}$alkyl-$C_{6-14}$aryl-, —$C_{1-6}$alkyl-$C_{5-14}$heteroaryl-;

each $R^{14}$ and $R^{15}$ is independently selected from the group consisting of: hydrogen, hydroxyl, —NRR, —$NRNR_2$, —$C_{3-10}$carbocyclyl, —$C_{1-6}$alkylene-$C_{3-10}$carbocyclyl, —$C_{3-10}$heterocyclyl, —$C_{1-6}$alkylene-$C_{3-10}$heterocyclyl, —($CH_2CH_2O)_{1-6}CH_2CH_2C(O)OR$, —($CH_2CH_2O)_{1-6}CH_2CH_2NRR$, —$C_{1-6}$alkyl, $C_{6-14}$aryl, —$C_{1-6}$alkylene-$C_{6-14}$aryl and —$C_{5-14}$heteroaryl;

or $R^{14}$ and $R^{15}$, together with the atom or atoms to which they are joined, form a $C_{3-10}$heterocyclyl ring, wherein $R^{14}$, $R^{15}$, or both, or a ring formed with $R^{14}$ and $R^{15}$, are optionally substituted with —$(C(R)_2)_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —$CF_3$, —$(C(R)_2)_m$—NRR or —(C(R)_2)_m$—$SO_2$NRR, (v) —$SO_2$R, (vi) —S—S—$C_{1-6}$alkyl-C(O)OR, (vii) —$SO_2$NRR, (viii) —C(O)NRR, (ix) —C(O)OR, (x) —$C_{4-6}$ cycloalkyl optionally substituted with —NRR, —$SO_2$NRR or —NR—C(O)($CH_2)_{0-6}$NRR, (xi) —R, (xii) —OR, (xiii) —N(R)NRR, (xiv) —C(O)N(R)NRR, (xv) —$(C(R)_2)_m$—O—NRR and (xiv) —S—S—$C_{1-6}$alkyl-NRR;

each $R^{14'}$ is independently selected from the group consisting of: a bond, —NR—, —$C_{3-10}$carbocyclyl-, —$C_{3-10}$heterocyclyl-, —($CH_2CH_2O)_{1-6}CH_2CH_2C(O)OR'$, —($CH_2CH_2O)_{1-6}CH_2CH_2NR$—, and —$C_{1-6}$alkylene-;

wherein $R^{14'}$ is optionally substituted with —$(C(R)_2)_m$—$R^{18}$ where each $R^{18}$ is independently selected from (i) —NRR, (ii) —C(NRR)(C(O)OR), (iii) —S—R, (iv) aryl or heteroaryl optionally substituted with one or more of halogen, —$CF_3$, —NRR or —$SO_2$NRR, (v) —$SO_2$R, (vi) —S—S—$C_{1-6}$alkyl-C(O)OR, (vii) —$SO_2$NRR, (viii) —C(O)NRR, (ix) —C(O)OR, (x) —$C_{4-6}$ cycloalkyl optionally substituted with —NRR, —$SO_2$NRR or —NR—C(O)($CH_2)_{0-6}$NRR, (xi) —R, (xii) —OR, (xiii) —N(R)NRR, (xiv) —C(O)N(R)NRR, (xv) —$(C(R)_2)_m$—O—NRR and (xiv) —S—S—$C_{1-6}$alkyl-NRR;

acid is an amino acid residue selected from —$SCH_2CH(COOH)(NH_2)$, —$NH(CH_2)_4CH(COOH)(NH_2)$ and —$C(O)(CH_2)_2CH(COOH)(NH_2)$;

each R is independently selected from the group consisting of: hydrogen and —$C_{1-6}$alkyl;

each R' is independently selected from —H, $C_1$-$C_8$ alkyl, $C_1$-$C_8$ heteroalkyl and aryl;

each R" is independently selected from the group consisting of: a bond and —$C_{1-6}$alkylene-; and each m is independently 0, 1, 2 or 3.

* * * * *

SEQUENCE LISTING

<160> NUMBER OF SEQ ID NOS: 35

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
agagtttgat cctggctcag                                              20

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
ggttaccttg ttacgactt                                               19

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
ctacgggagg cagcagtggg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
cccactgctg cctcccgtag                                              20

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5

| | |
|---|---|
| cagcagccgc ggtaatac | 18 |

<210> SEQ ID NO 6
<211> LENGTH: 18
<212> TYPE: DNA
<213> ORGANISM: Artificial Sequence
<220> FEATURE:
<223> OTHER INFORMATION: Synthetic Construct

<400> SEQUENCE: 6

| | |
|---|---|
| gtattaccgc ggctgctg | 18 |

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7

| | |
|---|---|
| catggctgtc gtcagctcgt | 20 |

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| acgagctgac gacagccatg | 20 |

<210> SEQ ID NO 9
<211> LENGTH: 1494
<212> TYPE: DNA
<213> ORGANISM: Burkholderia sp. FERM BP-3421

<400> SEQUENCE: 9

| | |
|---|---|
| agagtttgat cctggctcag attgaacgct ggcggcatgc cttacacatg caagtcgaac | 60 |
| ggcagcacgg gtgcttgcac ctggtggcga gtggcgaacg ggtgagtaat acatcggaac | 120 |
| atgtcctgta gtgggggata gcccggcgaa agccggatta ataccgcata cgatctacgg | 180 |
| atgaaagcgg gggatcttcg gacctcgcgc tatagggttg gccgatggct gattagctag | 240 |
| ttggtggggt aaaggcctac caaggcgacg atcagtagct ggtctgagag gacgatcagc | 300 |
| cacactggga ctgagacacg gcccagactc ctacgggagg cagcagtggg gaattttgga | 360 |
| caatggggga accctgatc cagcaatgcc gcgtgtgtga agaaggcctt cgggttgtaa | 420 |
| agcacttttg tccggaaaga atcctttgg gctaataccc ggggggatg acggtaccgg | 480 |
| aagaataagc accggctaac tacgtgccag cagccgcggt aatacgtagg gtgcgagcgt | 540 |
| taatcggaat tactgggcgt aaagcgtgcg caggcggttt gttaagacag atgtgaaatc | 600 |
| cccgggctta acctgggaac tgcatttgtg actggcaagc tagagtatgg cagagggggg | 660 |
| tagaattcca cgtgtagcag tgaaatgcgt agagatgtgg aggaataccg atggcgaagg | 720 |
| cagcccctg ggccaatact gacgctcatg cacgaaagcg tggggagcaa acaggattag | 780 |
| ataccctggt agtccacgcc ctaaacgatg tcaactagtt gttggggatt catttcctta | 840 |
| gtaacgtagc taacgcgtga agttgaccgc ctggggagta cggtcgcaag attaaaactc | 900 |
| aaaggaattg acgggaccc gcacaagcgg tggatgatgt ggattaattc gatgcaacgc | 960 |

-continued

```
gaaaaacctt acctacccctt gacatggtcg gaatcctgaa gagattcggg agtgctcgaa    1020
agagaaccga tacacaggtg ctgcatggct gtcgtcagct cgtgtcgtga gatgttgggt    1080
taagtcccgc aacgagcgca acccttgtcc ttagttgcta cgcaagagca ctctaaggag    1140
actgccggtg acaaaccgga ggaaggtggg gatgacgtca agtcctcatg gcccttatgg    1200
gtagggcttc acacgtcata caatggtcgg aacagagggt tgccaacccg cgaggggag    1260 ctaatcccag aaaaccgatc gtagtccgga ttgcactctg caactcgagt gcatgaagct    1320
ggaatcgcta gtaatcgcgg atcagcatgc cgcggtgaat acgttccgg gtcttgtaca    1380 caccgcccgt cacaccatgg gagtgggttt taccagaagt ggctagtcta accgcaagga    1440
ggacggtcac cacggtagga ttcatgactg gggtgaagtc gtaacaaggt aacc           1494
```

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10

```
tggcgaacag atcgagtttg                                                    20
```

<210> SEQ ID NO 11
<211> LENGTH: 46
<212> TYPE: DNA
<213> ORGANISM: Artificial Sequence
<220> FEATURE:
<223> OTHER INFORMATION: Synthetic Construct

<400> SEQUENCE: 11

```
cttgcggaga actgtgaatg cgcaatagaa gcgctgtcat ggaatg                       46
```

<210> SEQ ID NO 12
<211> LENGTH: 49
<212> TYPE: DNA
<213> ORGANISM: Artificial Sequence
<220> FEATURE:
<223> OTHER INFORMATION: Synthetic Construct

<400> SEQUENCE: 12

```
ccgaaaagtg ccacctgacg tctaagataa ctcgtggata ttcggcaag                    49
```

<210> SEQ ID NO 13
<211> LENGTH: 19
<212> TYPE: DNA
<213> ORGANISM: Artificial Sequence
<220> FEATURE:
<223> OTHER INFORMATION: Synthetic Construct

<400> SEQUENCE: 13

```
agaatcccgc gatcccaac                                                     19
```

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14

```
ttgcgcattc acagttctc                                                     19
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
tcttagacgt caggtggcac                                              20

<210> SEQ ID NO 16
<211> LENGTH: 24
<212> TYPE: DNA
<213> ORGANISM: Artificial Sequence
<220> FEATURE:
<223> OTHER INFORMATION: Synthetic Construct

<400> SEQUENCE: 16
ggacgaatcg aactcaggaa cttg                                         24

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
cgaagagcga ttgaggaaaa gg                                           22

<210> SEQ ID NO 18
<211> LENGTH: 59
<212> TYPE: DNA
<213> ORGANISM: Artificial Sequence
<220> FEATURE:
<223> OTHER INFORMATION: Synthetic Construct

<400> SEQUENCE: 18
gttggtttgc gcattcacag ttctccgcaa gaattgattg caagggctgc taaaggaag   59

<210> SEQ ID NO 19
<211> LENGTH: 64
<212> TYPE: DNA
<213> ORGANISM: Artificial Sequence
<220> FEATURE:
<223> OTHER INFORMATION: Synthetic Construct

<400> SEQUENCE: 19
tcttccgctt cctcgctcac tgactcgctg cgctcggtca cggaaatgtt gaatactcat   60
actc                                                               64

<210> SEQ ID NO 20
<211> LENGTH: 33
<212> TYPE: DNA
<213> ORGANISM: Artificial Sequence
<220> FEATURE:
<223> OTHER INFORMATION: Synthetic Construct

<400> SEQUENCE: 20
gctctagaca tcgatttatt atgacaactt gac                               33

<210> SEQ ID NO 21
<211> LENGTH: 19
<212> TYPE: DNA
<213> ORGANISM: Artificial Sequence
<220> FEATURE:
```

<223> OTHER INFORMATION: Synthetic Construct

<400> SEQUENCE: 21
cccaaaaaaa cgggtatgg                                                    19

<210> SEQ ID NO 22
<211> LENGTH: 53
<212> TYPE: DNA
<213> ORGANISM: Artificial Sequence
<220> FEATURE:
<223> OTHER INFORMATION: Synthetic Construct

<400> SEQUENCE: 22
ctactgtttc tccatacccg ttttttggg gggttgttgg tttttgaaat tgc               53

<210> SEQ ID NO 23
<211> LENGTH: 32
<212> TYPE: DNA
<213> ORGANISM: Artificial Sequence
<220> FEATURE:
<223> OTHER INFORMATION: Synthetic Construct

<400> SEQUENCE: 23
atggtgaagc ttaagtcgac aaccggcatt cc                                    32

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
gcattcacag ttctccgcaa g                                                21

<210> SEQ ID NO 25
<211> LENGTH: 19
<212> TYPE: DNA
<213> ORGANISM: Artificial Sequence
<220> FEATURE:
<223> OTHER INFORMATION: Synthetic Construct

<400> SEQUENCE: 25
ctcgctcact gactcgctg                                                    19

<210> SEQ ID NO 26
<211> LENGTH: 21
<212> TYPE: DNA
<213> ORGANISM: Artificial Sequence
<220> FEATURE:
<223> OTHER INFORMATION: Synthetic Construct

<400> SEQUENCE: 26
gcaattaacc ctcactaaag g                                                21

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
ctatagggcg aattgggtac                                                   20

```
<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
gcatccaatc acttgaacag g                                            21

<210> SEQ ID NO 29
<211> LENGTH: 46
<212> TYPE: DNA
<213> ORGANISM: Artificial Sequence
<220> FEATURE:
<223> OTHER INFORMATION: Synthetic Construct

<400> SEQUENCE: 29
cttgcggaga actgtgaatg cgcaagccat cattctcgac atttcc                 46

<210> SEQ ID NO 30
<211> LENGTH: 48
<212> TYPE: DNA
<213> ORGANISM: Artificial Sequence
<220> FEATURE:
<223> OTHER INFORMATION: Synthetic Construct

<400> SEQUENCE: 30
ccgaaaagtg ccacctgacg tctaagaaga ttgtgacggt actgaagc               48

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
agagaacgat cgctccacag                                              20

<210> SEQ ID NO 32
<211> LENGTH: 19
<212> TYPE: DNA
<213> ORGANISM: Artificial Sequence
<220> FEATURE:
<223> OTHER INFORMATION: Synthetic Construct

<400> SEQUENCE: 32
ttgcgcattc acagttctc                                               19

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
tcttagacgt caggtggcac                                              20

<210> SEQ ID NO 34
<211> LENGTH: 24
<212> TYPE: DNA
<213> ORGANISM: Artificial Sequence
<220> FEATURE:
<223> OTHER INFORMATION: Synthetic Construct
```

```
<400> SEQUENCE: 34
ggacgaatcg aactcaggaa cttg                                          24

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
cgaagagcga ttgaggaaaa gg                                            22
```